(12) United States Patent
Qin et al.

(10) Patent No.: US 7,893,056 B2
(45) Date of Patent: Feb. 22, 2011

(54) PEPTIDE DEFORMYLASE INHIBITORS

(75) Inventors: Donghui Qin, Collegeville, PA (US); Beth Norton, Research Triangle Park, NC (US); Andrew Nicholas Knox, Collegeville, PA (US); Siegfried B. Christensen, Collegeville, PA (US); Kelly M. Aubart, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 175 days.

(21) Appl. No.: 12/265,983

(22) Filed: Nov. 6, 2008

(65) Prior Publication Data

US 2009/0306066 A1 Dec. 10, 2009

Related U.S. Application Data

(60) Provisional application No. 60/986,631, filed on Nov. 9, 2007.

(51) Int. Cl.
*C07D 498/04* (2006.01)
*A61K 31/5383* (2006.01)

(52) U.S. Cl. .................................. 514/230.5; 544/105
(58) Field of Classification Search ................ 544/105; 514/230.5
See application file for complete search history.

(56) References Cited

U.S. PATENT DOCUMENTS

| 5,691,382 | A | 11/1997 | Crimmin et al. | |
|---|---|---|---|---|
| 6,013,792 | A | 1/2000 | Castelhano et al. | |
| 6,028,110 | A | 2/2000 | Miller et al. | |
| 6,037,472 | A | 3/2000 | Castelhano et al. | |
| 7,019,003 | B2 | 3/2006 | Xiang et al. | |
| 7,332,485 | B2 | 2/2008 | Aubart et al. | |
| 2002/0119962 | A1 | 8/2002 | Jacobs et al. | 514/210.17 |
| 2007/0197512 | A1 | 8/2007 | Inoue et al. | 514/224.2 |

FOREIGN PATENT DOCUMENTS

| WO | WO02/16315 | 2/2002 |
|---|---|---|
| WO | WO03/101442 | 12/2003 |
| WO | WO2004/050638 | 6/2004 |
| WO | WO2004/056751 | 7/2004 |
| WO | WO2005/005456 | 1/2005 |
| WO | WO2006/055663 | 5/2006 |
| WO | WO 2006055663 A2 * | 5/2006 |

OTHER PUBLICATIONS

Groche, et al., "Isolation and Crystallization of Functionally Competent *Escherichia coli* Peptide Deformylase forms Containing either Iron or Nickel in the Active Site," *Biochemical and Biophysical Research Communications* 246: 342-346 (1998) Article No. RC988616.
Chen, et al., "Actinonin, a Naturally Occurring Antibacterial Agent, Is a Potent Deformylase Inhibitor," *Biochemistry* 39: 1256-1263 (2000).
Giglione, et al., "Peptide Deformylase as a target for new generation, broad spectrum antimicrobial agents," *Molecular Microbiology* 36(6): 1197-1205 (2000).
Huntington, et al., "Synthesis and Antibacterial Activity of Peptide Deformylase Inhibitors," *Biochemistry* 39: 4543-4551 (2000).
Apfel, et al, "Hydroxamic Acid Derivatives as Potent Peptide Deformylase Inhibitors and Antibacterial Agents," *J. Med. Chem.* 43: 2324-2331 (2000).
Clements, John M., "Antibiotic Activity and Characterization of BB-3497, a Novel Peptide Deformylase Inhibitor," *Antimicrobial Agents and Chemotherapy* 45(2): 563-570 (Feb. 2001).
Ray, et al. "Wildcatters Welcome: The need for new antimicrobial agents." *Therapy*, 1(1): 1-5 (2004).

* cited by examiner

*Primary Examiner*—Kahsay T Habte
(74) *Attorney, Agent, or Firm*—Grace C. Hsu; John Lemanowicz

(57) ABSTRACT

The present invention is directed to certain {2-(alkyl)-3-[2-(5-fluoro-4-pyrimidinyl)hydrazino]-3-oxopropyl}hydroxyformamide derivatives, compositions containing them, the use of such compounds in the inhibition of bacterial peptide deformylase (PDF) activity, and in the treatment of bacterial infections. Specifically, the invention is directed to compounds of formula (I):

wherein R1, R2 and R3 are defined herein and to pharmaceutically acceptable salts thereof. The compounds of this invention are bacterial peptide deformylase inhibitors and can be useful in the treatment of bacterial infections.

70 Claims, 14 Drawing Sheets

PEPTIDE DEFORMYLASE INHIBITORS

This application claims the benefit of U.S. Provisional App. No. 60/986,631 filed 9 Nov. 2007.

FIELD OF THE INVENTION

The present invention relates to certain {2-(alkyl)-3-[2-(5-fluoro-4-pyrimidinyl)hydrazino]-3-oxopropyl}hydroxyformamide compounds, compositions containing them, the use of such compounds in the inhibition of bacterial peptide deformylase (PDF) activity, and in the treatment of bacterial infections.

BACKGROUND OF THE INVENTION

Bacterial protein synthesis starts with N-formyl-methionyl-tRNA (f-Met-tRNA$_i$) and, as a consequence, all newly synthesized polypeptides contain an N-formyl-methionine terminus (f-Met-pp) (Scheme I). Peptide deformylase (PDF) is a metalloenzyme that removes the N-formyl group of the polypeptides as they emerge from the ribosome during the elongation process [Adams, J. M. (1968) J. Mol. Biol. 33, 571-589; Livingston, D. M. and Leder, P. (1969) Biochemistry 8, 435-443; Ball, L. A. and Kaesberg, P. (1973) J. Mol. Biol. 79, 531-537]. Depending on the nature of their second amino acid, polypeptides are further processed by methionine amino peptidase (MAP) to yield the mature protein. Deformylation plays an indispensable role in protein maturation as MAP, an essential enzyme for bacterial growth, cannot hydrolyze N-blocked peptides.

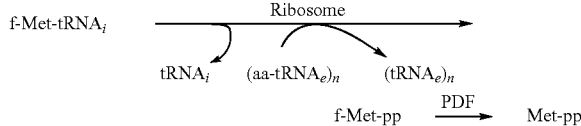

Scheme I. Role of PDF in protein synthesis

PDF is ubiquitous in bacteria, with at least one pdf gene present in all bacterial genomes sequenced to date.

PDF does not play a role in eukaryotic cytoplasmic protein synthesis which does not involve N-formylation, but nuclear-encoded PDF proteins, containing a chloroplast/mitochondria localization signal, have been identified in parasites, plants and mammals, including humans. PDF is essential in plant and parasite organelles since their genomes encode for a number of proteins which require deformylation for activity, but there is evidence to suggest that this is not the case in animals. In fact, characterization of human mitochondrial PDF has shown that it is much less active than its bacterial counterpart. Furthermore, PDF inhibitors which are active against the human PDF enzyme in vitro have no effect on the growth of normal human cell lines [Nguyen, K. T., Hu, X., Colton, C., Chakrabarti, R., Zhu, M. X. and Pei, D. (2003) Biochemistry 42, 9952-9958].

Thus, PDF inhibitors represent a promising new class of antibacterial agents with a novel mode of action covering a broad-spectrum of pathogens.

PDF inhibitors have been described in the art. Patent applications have been filed on hydrazine-3-oxopropyl hydroxyformamide derivatives of the following formula, see WO 03/101442 and WO2006/055663.

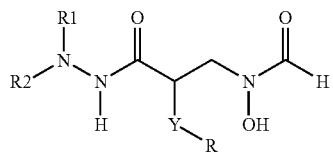

Thus, attempts have been made to prepare compounds that inhibit PDF activity and a number of such compounds have been disclosed in the art. However, there remains a continuing need for inhibitors of PDF which can be used in the treatment of bacterial infections.

SUMMARY OF THE INVENTION

The present invention is directed to certain {2-(alkyl)-3-[2-(5-fluoro-4-pyrimidinyl)hydrazino]-3-oxopropyl}hydroxyformamide derivatives, compositions containing them, the use of such compounds in the inhibition of bacterial peptide deformylase (PDF) activity, and in the treatment of bacterial infections. Specifically, the invention is directed to compounds of Formula (I):

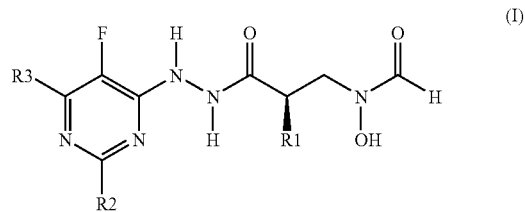

wherein R1, R2 and R3 are defined below and to pharmaceutically acceptable salts thereof. The compounds of this invention are bacterial peptide deformylase inhibitors and can be useful in the treatment of bacterial infections.

Figure 6:
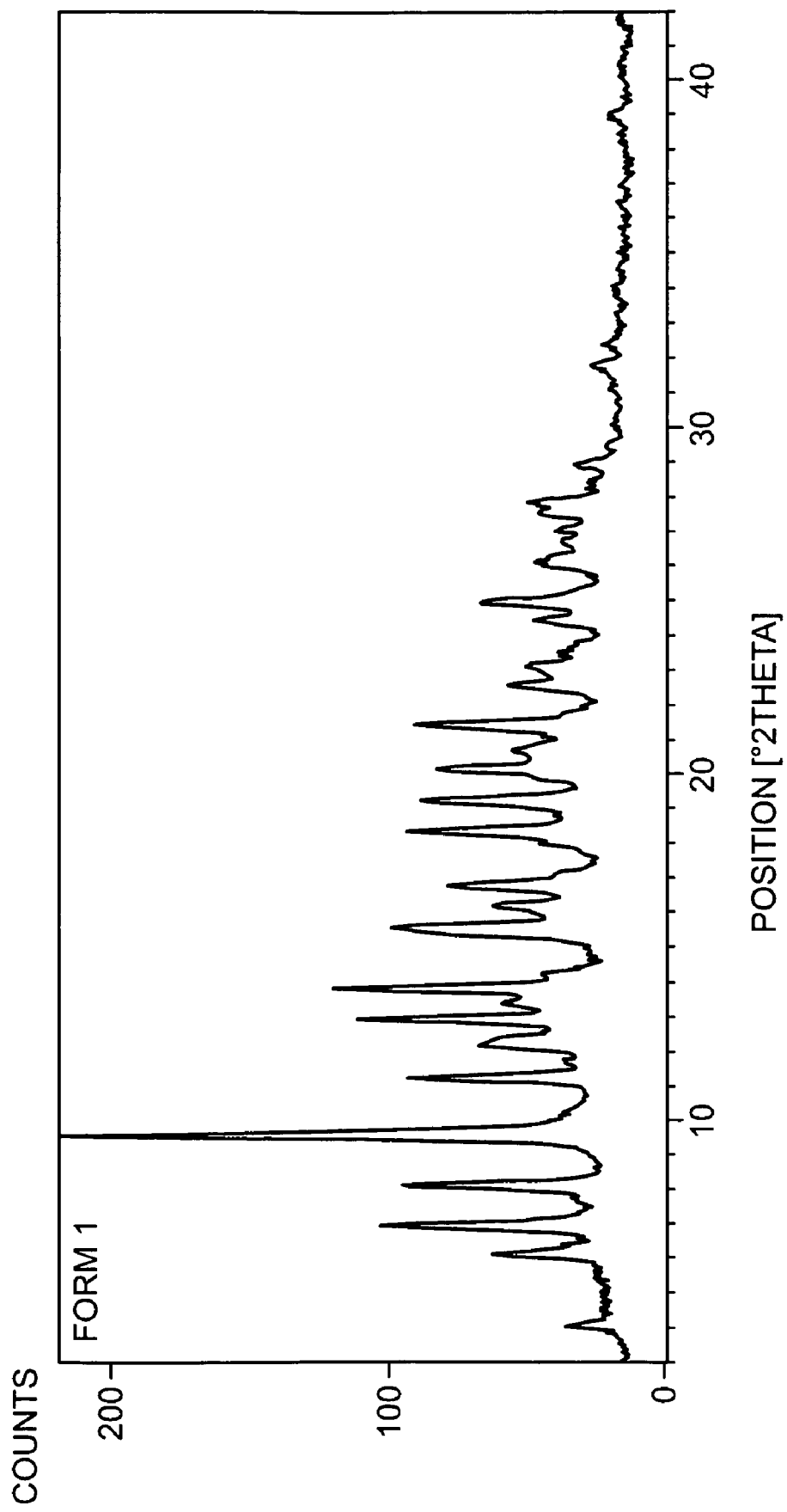

FIG. 6 provides an X-ray powder diffraction pattern of polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in degrees 2 theta and the y-axis is intensity.

Figure 7:
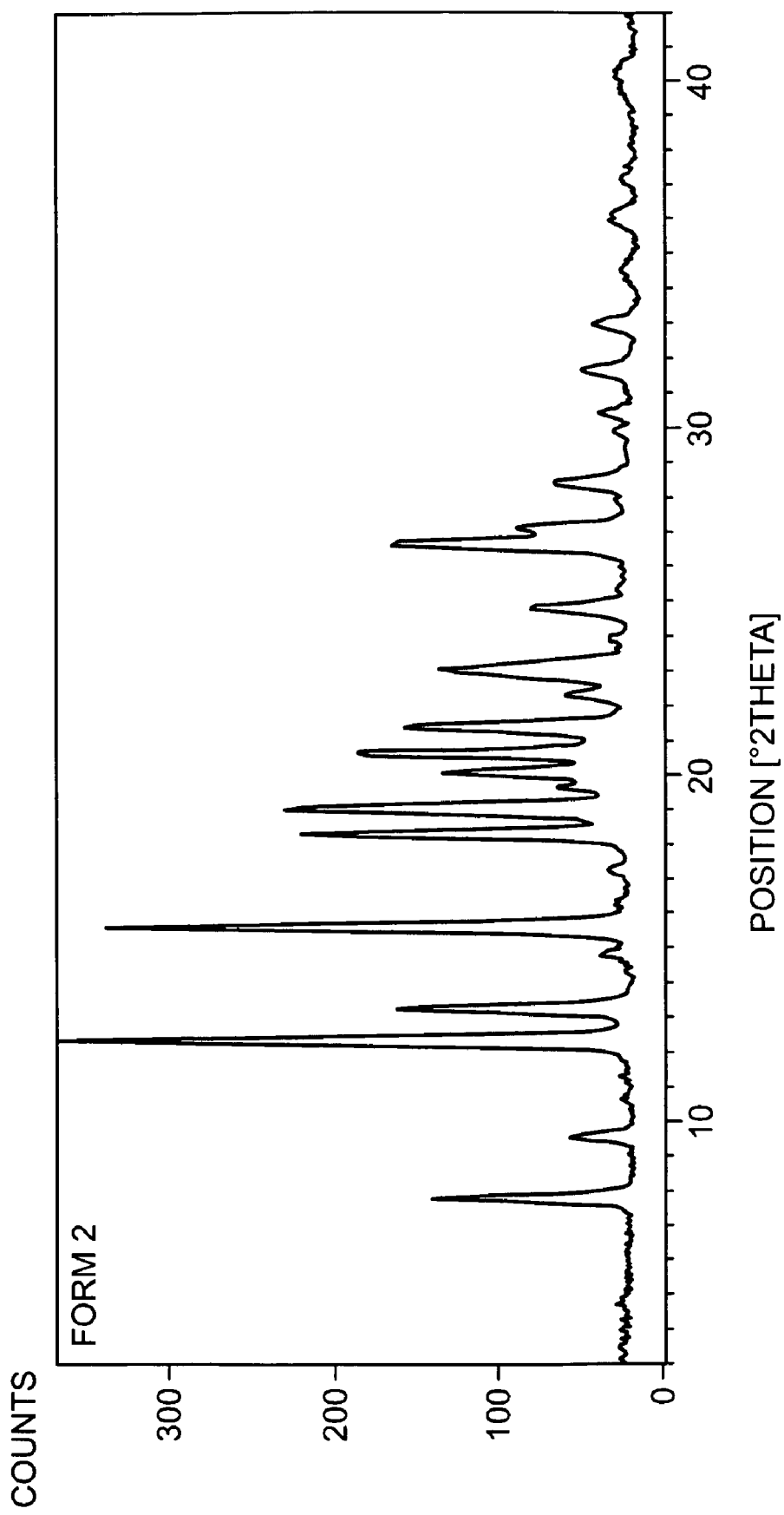

FIG. 7 provides an X-ray powder diffraction pattern of polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in degrees 2 theta and the y-axis is intensity.

Figure 8:
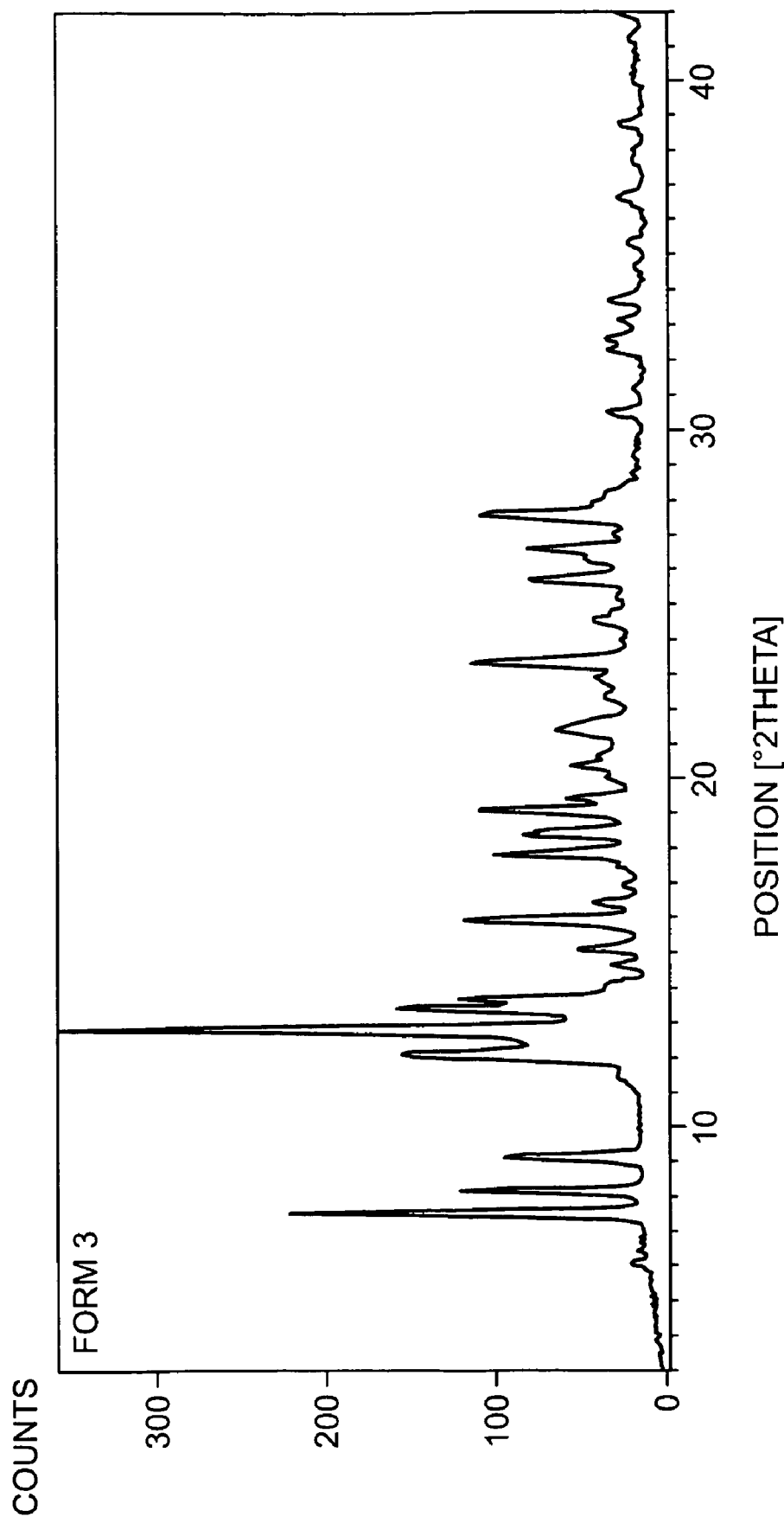

FIG. 8 provides an X-ray powder diffraction pattern of polymorphic Form 3 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in degrees 2 theta and the y-axis is intensity.

Figure 9:
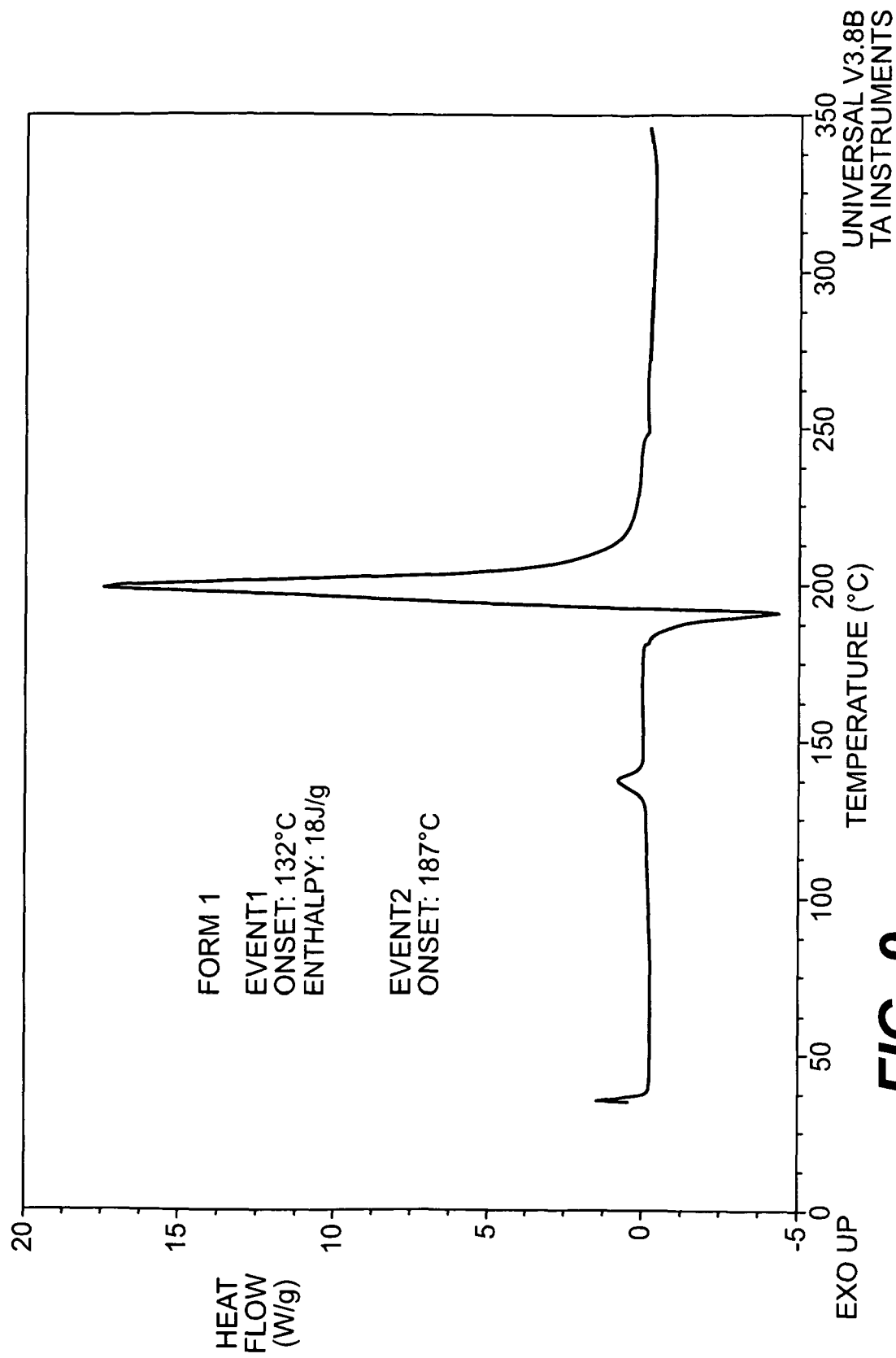

FIG. 9 provides a differential scanning calorimitry (DSC) thermogram of polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is heat flow (Watts/gram). The thermal event at 132° C. corresponds to exothermic solid state form conversion of Form 1 to Form 3.

Figure 10:
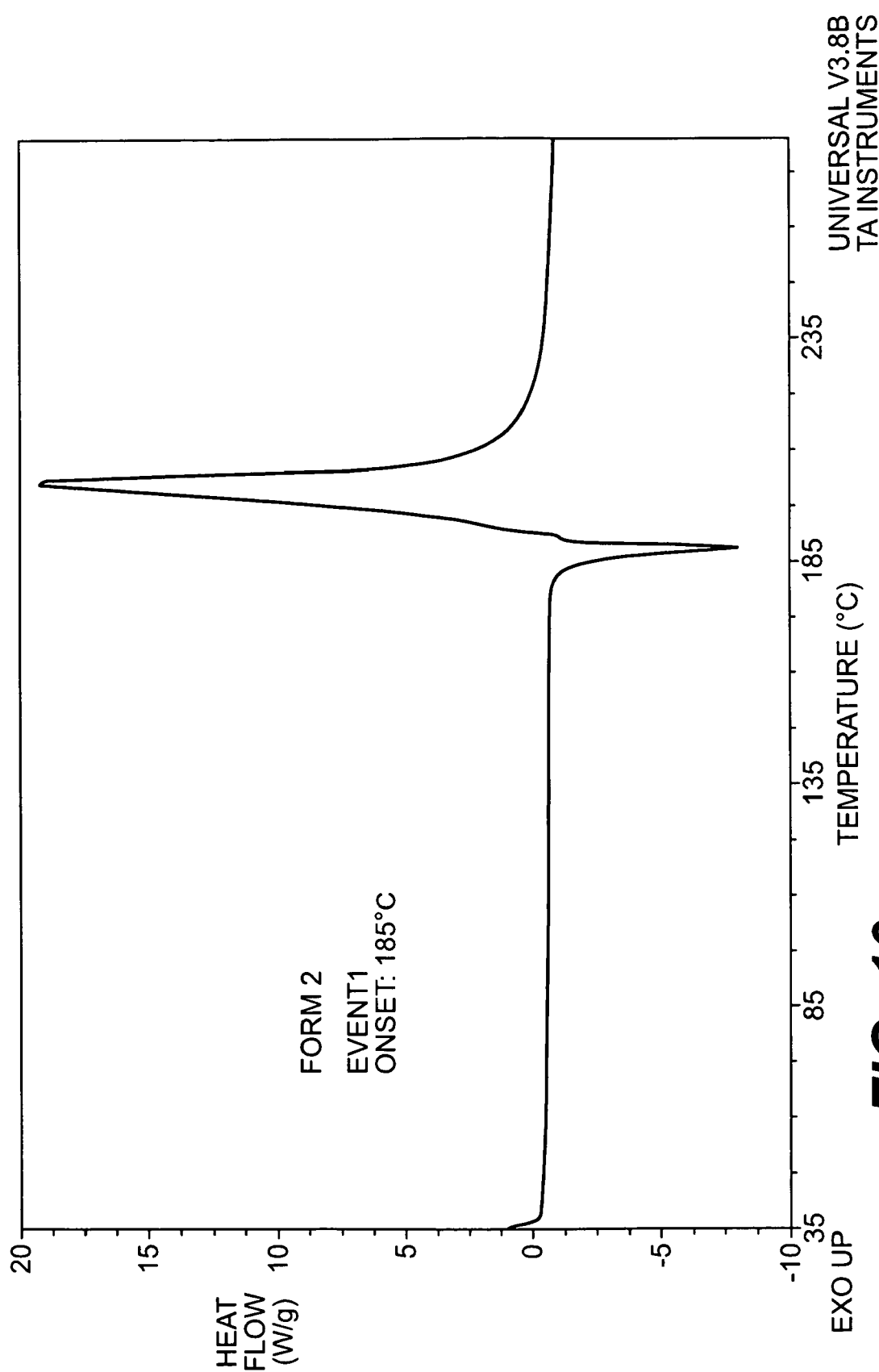

FIG. 10 provides a differential scanning calorimitry (DSC) thermogram of polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is heat flow (Watts/gram).

Figure 11:
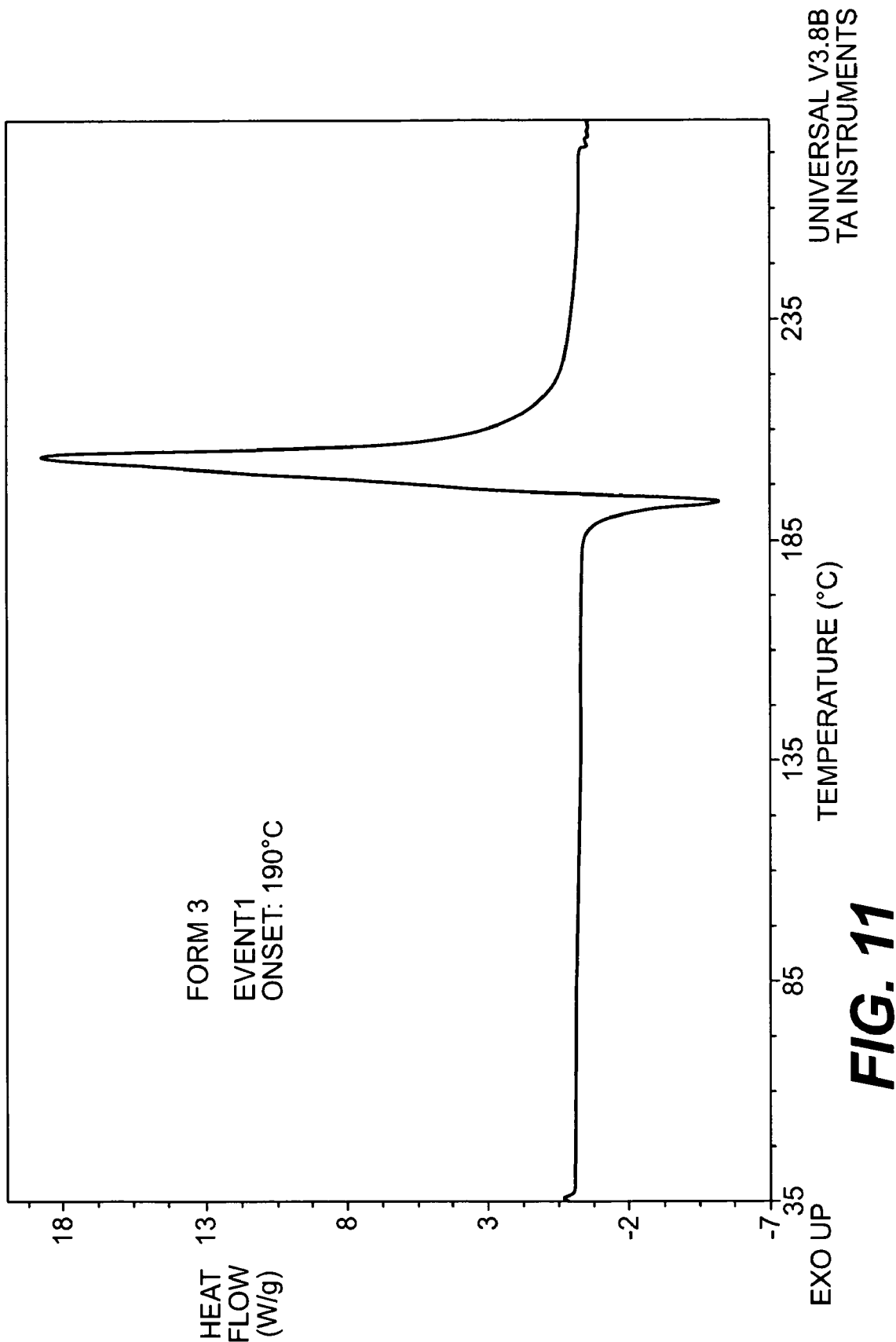

FIG. 11 provides a differential scanning calorimitry (DSC) thermogram of polymorphic Form 3 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is heat flow (Watts/gram).

Figure 12:
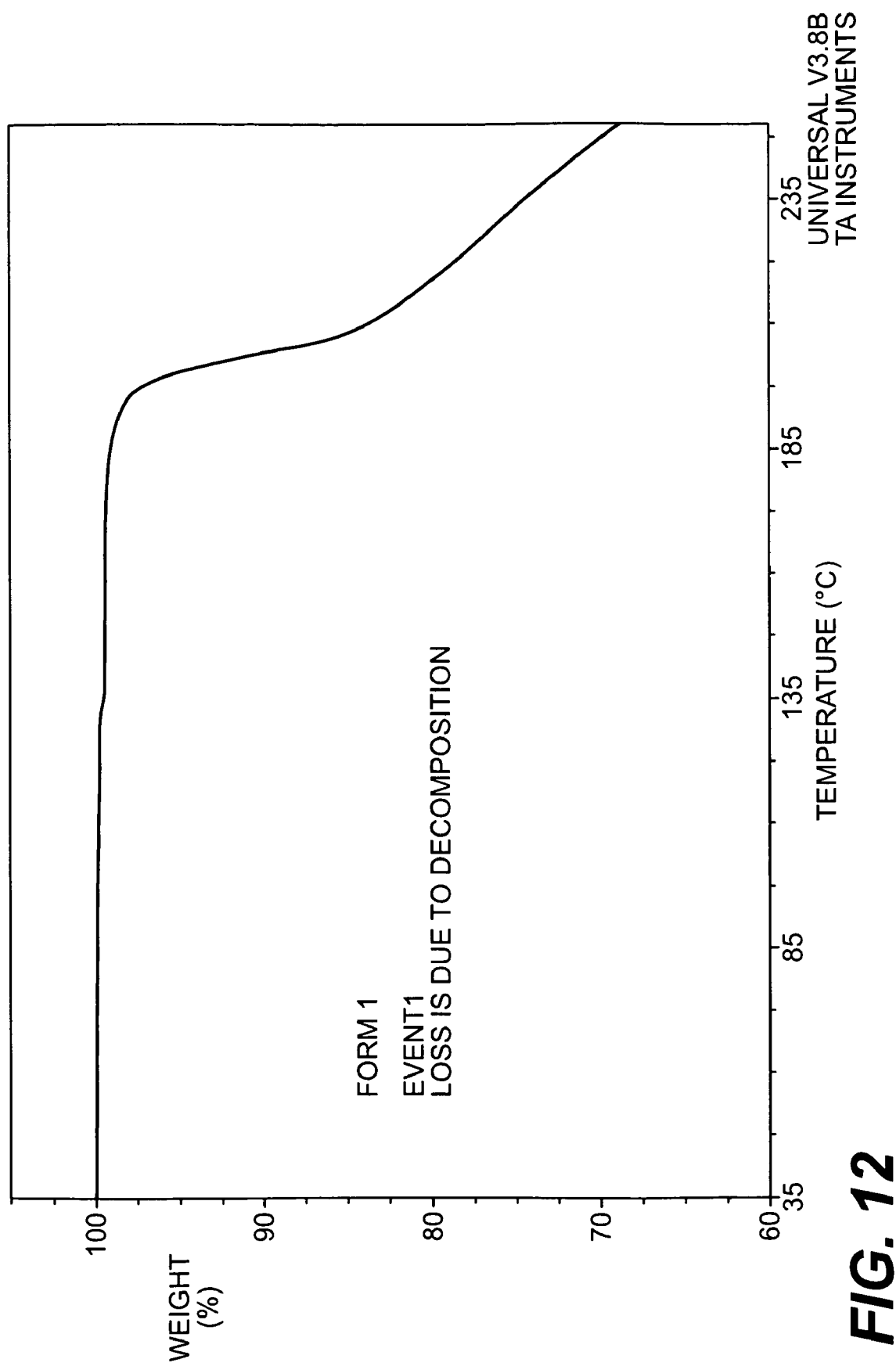

FIG. 12 provides a thermogravimetric analysis (TGA) trace of polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is percent weight change.

Figure 13:
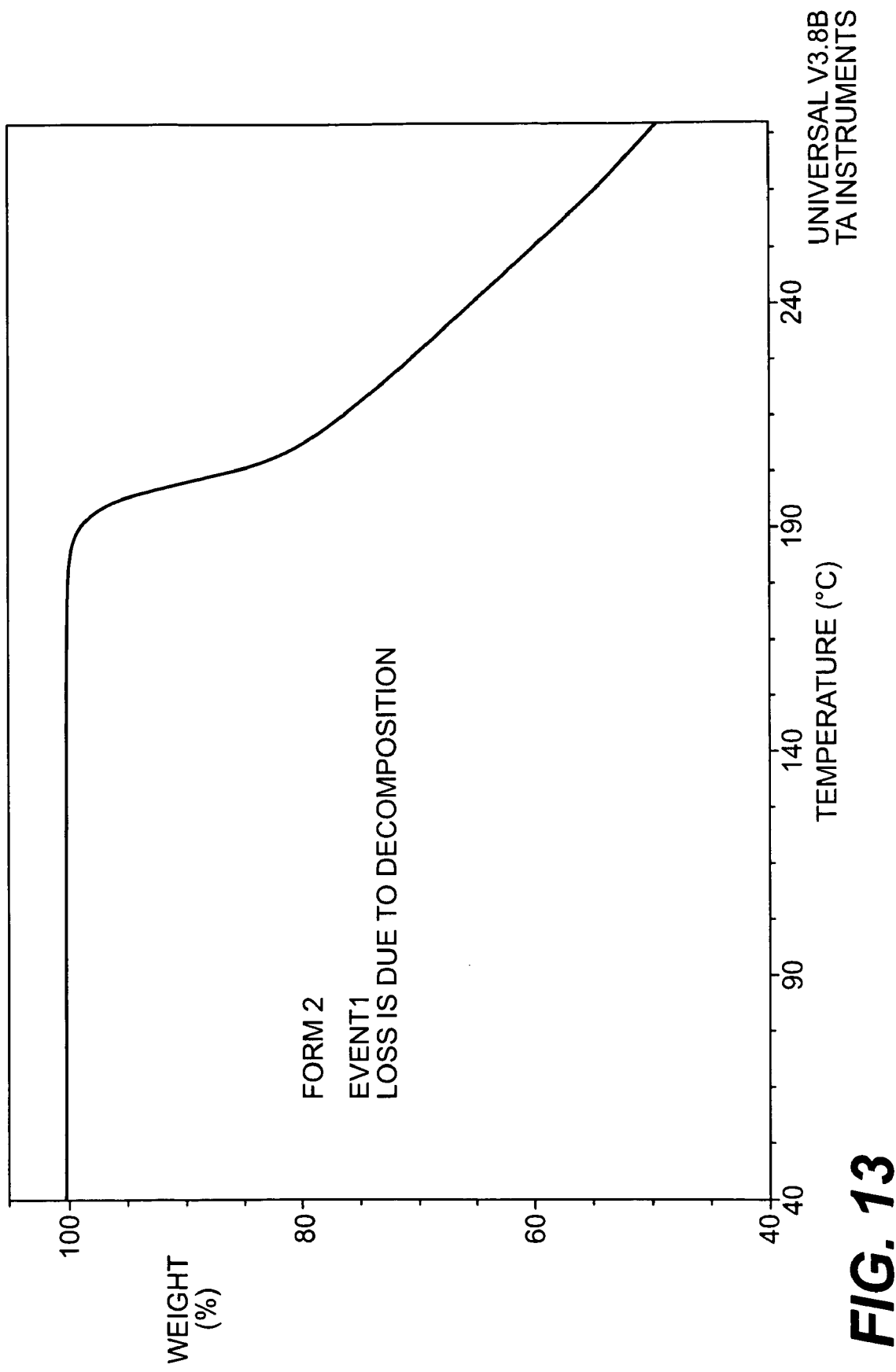

FIG. 13 provides a thermogravimetric analysis (TGA) trace of polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is percent weight change.

Figure 14:
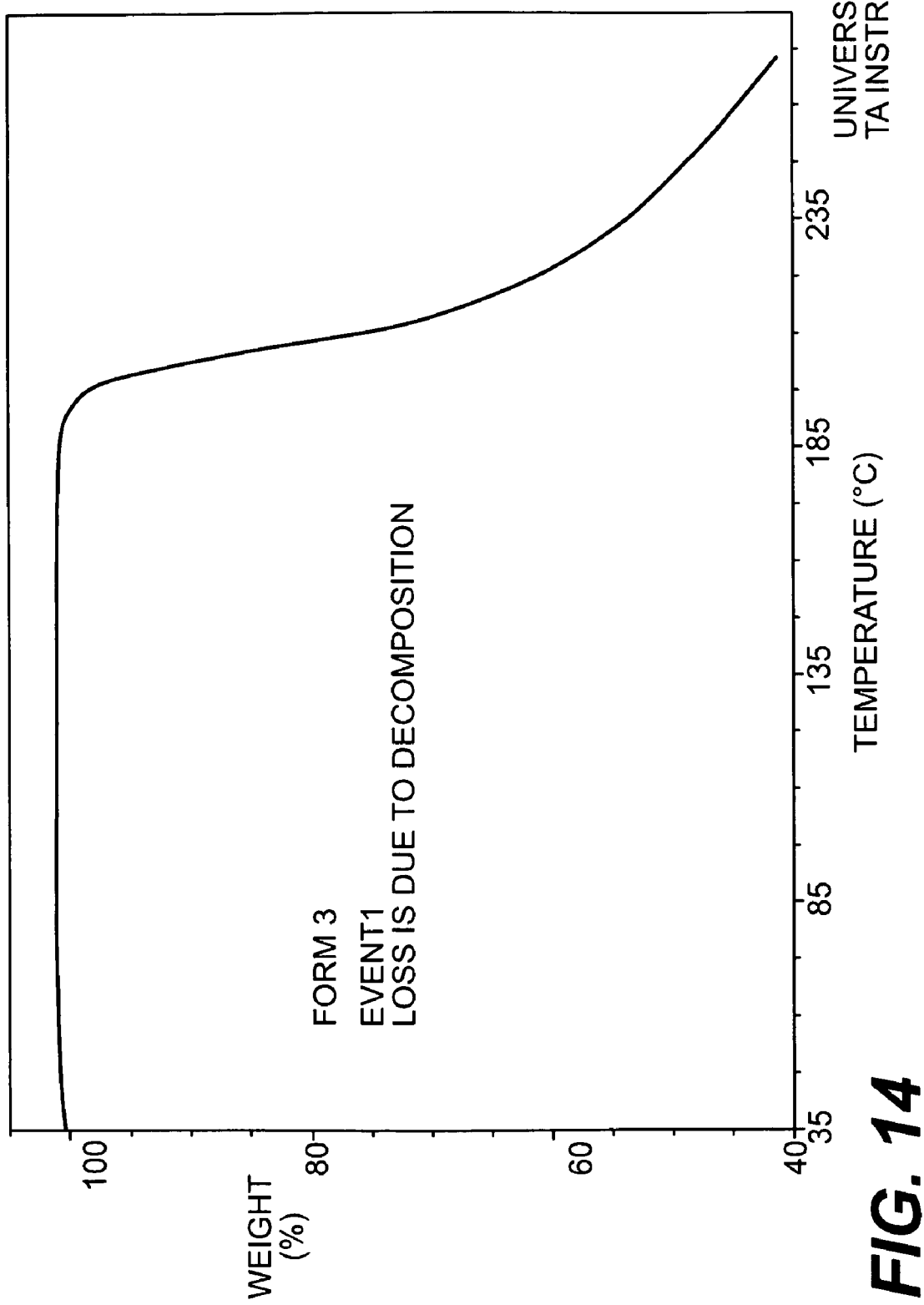

FIG. 14 provides a thermogravimetric analysis (TGA) trace of polymorphic Form 3 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is temperature (° C.) and the y-axis is percent weight change.

DETAILED DESCRIPTION OF THE INVENTION

In describing the invention, chemical elements are identified in accordance with the Periodic Table of the Elements. Abbreviations and symbols utilized herein are in accordance with the common usage of such abbreviations and symbols by those skilled in the chemical and biological arts. Specifically, the following abbreviations may be used in the examples and throughout the specification:

g (grams); mg (milligrams);
kg (kilograms); μg (micrograms);
L (liters); mL (milliliters);
μL (microliters); psi (pounds per square inch);
M (molar); mM (millimolar);
μM (micromolar); nM (nanomolar);
pM (picomolar); nm (nanometers);
mm (millimeters); wt (weight);
N (Normal); CFU (colony forming units);
I. V. (intravenous); Hz (Hertz);
MHz (megahertz); mol (moles);
mmol (millimoles); RT (room temperature);
min (minutes); h (hours);
b.p. (boiling point); TLC (thin layer chromatography);
T$_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); AcOH (acetic acid);
HOAt (1-hydroxy-7-azabenzotriazole);
THP (tetrahydropyran); NMM (N-methylmorpholine);
Pd/C (Palladium on Carbon); MTBE (tert-butyl methyl ether);
HOBT (1-hydroxybenzotriazole); mCPBA (meta-chloroperbenzoic acid;
EDC (1-[3-dimethylamino)propyl]-3-ethylcarbodiimide hydrochloride);
Boc (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
NAD (nicotinamide adenine dinucleotide);
HPLC (high pressure liquid chromatography);
LC/MS (liquid chromatography/mass spectrometry);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide); LAH (Lithium aluminum hydride);
fHNO$_3$ (fuming HNO$_3$); NaOMe (sodium methoxide);
EDTA (ethylenediaminetetraacetic acid);
TMEDA (N,N,N',N'-tetramethyl-1,2-ethanediamine);
NBS (N-bromosuccinimide); DIPEA (diisopropylethylamine);
dppf (1,1'-bis(diphenylphosphino)ferrocene); and
NIS (N-iodsuccinimide).

All references to ether are to diethyl ether and brine refers to a saturated aqueous solution of NaCl.

Terms and Definitions

"Alkyl" refers to a monovalent saturated hydrocarbon chain having the specified number of member carbon atoms. For example, C1-C7 alkyl refers to an alkyl group having from 1 to 7 member carbon atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkenyl" refers to an unsaturated hydrocarbon chain having the specified number of member carbon atoms and having one or more carbon-carbon double bonds within the chain. For example, C2-C6 alkenyl refers to an alkenyl group having from 2 to 6 member carbon atoms. In certain embodiments, alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Representative branched alkenyl groups have one, two, or three branches. Alkenyl includes ethylenyl, propenyl, butenyl, pentenyl, and hexenyl.

"Alkoxy" refers to an alkyl moiety attached through an oxygen bridge (i.e. a —O—C1-C6 alkyl group wherein C1-C6 is defined herein). Examples of such groups include methoxy, ethoxy, propoxy, butoxy, pentoxy and hexoxy.

"Alkynyl" refers to an unsaturated hydrocarbon chain having the specified number of member carbon atoms and having one or more carbon-carbon triple bonds within the chain. For example, C2-C6 alkynyl refers to an alkynyl group having from 2 to 6 member atoms. In certain embodiments alkynyl groups have one carbon-carbon triple bond within the chain. In other embodiments, alkynyl groups have more than one carbon-carbon triple bond within the chain. For the sake of clarity, unsaturated hydrocarbon chains having one or more carbon-carbon triple bond within the chain and one or more carbon-carbon double bond within the chain are referred to as alkynyl groups. Alkynyl groups may be optionally substituted with one or more substituents as defined herein. Representative branched alkynyl groups have one, two, or three branches. Alkynyl includes ethynyl, propynyl, butynyl, pentynyl, and hexynyl.

"Aryl" refers to an aromatic hydrocarbon ring system. Aryl groups are monocyclic ring systems or bicyclic ring systems. Monocyclic aryl ring refers to phenyl. Bicyclic aryl rings refer to napthyl and to rings wherein phenyl is fused to a cycloalkyl or cycloalkenyl ring having 5, 6, or 7 member carbon atoms. Aryl groups may be optionally substituted with one or more substituents as defined herein.

"Cycloalkyl" refers to a saturated hydrocarbon ring having the specified number of member carbon atoms. Cycloalkyl groups are monocyclic ring systems. For example, C3-C6 cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Cycloalkenyl" refers to an unsaturated hydrocarbon ring having the specified number of member carbon atoms and having a carbon-carbon double bond within the ring. For example, C3-C6 cycloalkenyl refers to a cycloalkenyl group having from 3 to 6 member carbon atoms. In certain embodiments, cycloalkenyl groups have one carbon-carbon double bond within the ring. In other embodiments, cycloalkenyl groups have more than one carbon-carbon double bonds within the ring. Cycloalkenyl rings are not aromatic. Cycloalkenyl groups are monocyclic ring systems. Cycloalkenyl groups may be optionally substituted with one or more substituents as defined herein. Cycloalkenyl includes cyclopropenyl, cyclobutenyl, cyclopentenyl, cyclohexenyl, and cyclohexadienyl.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess is greater than zero. For example, enantiomerically enriched refers to products whose enantiomeric excess is greater than 50% ee, greater than 75% ee, or greater than 90% ee.

"Enantiomerically pure" refers to products whose enantiomeric excess is 99% ee or greater.

"Halo" refers to the halogen radicals fluoro, chloro, bromo, and iodo.

"Haloalkyl" refers to an alkyl group wherein at least one hydrogen atom attached to a member atom within the alkyl group is replaced with halo. The number of halo substituents include but are not limited to 1, 2, 3, 4, 5, or 6 substituents. Haloalkyl includes monofluoromethyl, difluoroethyl, and trifluoromethyl.

"Heteroaryl" refers to an aromatic ring containing from 1 to 5, suitably 1 to 4, more suitably 1 or 2 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems, or are fused bicyclic ring systems. Monocyclic heteroaryl rings have from 5 to 6 member atoms. Bicyclic heteroaryl rings have from 8 to 10 member atoms. Bicyclic heteroaryl rings include those rings wherein the primary heteroaryl and the secondary monocyclic cycloalkyl, cycloalkenyl, heterocycloalkyl, aryl or heteroaryl ring are attached, forming a fused bicyclic ring system. Heteroaryl includes, among others, pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, napthyridinyl, pyrazolopyridyl, pyrazolopyrimidinyl, 3H-[1,2,3]triazolo[4,5-d]pyrimidinyl, and 3H-[1,2,3]triazolo[4,5-b]pyridinyl.

"Heteroatom" refers to a nitrogen, sulfur, or oxygen atom.

"Heterocycloalkyl" refers to a saturated or unsaturated ring containing from 1 to 4 heteroatoms as member atoms in the ring. Heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. In certain embodiments, heterocycloalkyl is saturated. In other embodiments, heterocycloalkyl is unsaturated, but not aromatic. Heterocycloalkyl includes, among others, pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1-pyrazolidinyl, azepinyl, 1,3-dioxanyl, 1,4-dioxanyl, 1,3-oxathiolanyl, 1,3-dithianyl, azetidinyl, isoxazolidinyl,3-azabicyclo[3.1.0]hexyl; azabicylo[3.2.1]octyl, azabicylo[3.3.1]nonyl, azabicylo[4.3.0]nonyl, 2,5-diazabicyclo[2.2.1]heptanyl, octahydropyrrolo[1,2-a]pyrazinyl, octahydropyrazino[2,1-c][1,4]oxazinyl, oxabicylo[2.2.1]heptyl, hexahydro-1H-azepinyl, 2,3,4,7-tetrahydro-1H-azepinyl, tetrahydro-5H-[1,3]dioxolo[4,5-c]pyrrolyl; tetrahydro-1H-furo[3,4-c]pyrrol-(3H)-yl; hexahydropyrrolo[1,2-a]pyrazin-(1H)-yl; octahydropyrazino[1,2-a]azepin-(1H)-yl; hexahydropyrazino[2,1-c][1,4]oxazin-(1H)-yl; hexahydropyrrolo[3,4-c]pyrrol-(1H)-yl; 10-oxa-4-azatricyclo[5.2.1.02,6]decyl; octahydro-1(2H)-quinoxalinyl; octahydro-1H-cyclopenta[b]pyrazinyl; hexahydrofuro[3,4-b]pyrazin-(2H)-yl; octahydro-6H-pyrrolo[3,4-b]pyridinyl; 4,7-diazaspiro[2.5]octyl; and 5-azaspiro[2.4]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituents as defined herein.

"Pharmaceutically acceptable" refers to those compounds, materials, compositions, and dosage forms which are, within the scope of sound medical judgment, suitable for use in contact with the tissues of human beings or animals without excessive toxicity, irritation, or other problem or complication, commensurate with a reasonable benefit/risk ratio.

"Substituted" in reference to a group indicates that one or more hydrogen atoms attached to a member atom within the group is replaced with a substituent selected from the group of defined substituents. It should be understood that the term "substituted" includes the implicit provision that such substitution be in accordance with the permitted valence of the substituted atom and the substituent, and that the substitution results in a stable compound (i.e. one that does not spontaneously undergo transformation such as by hydrolysis, rearrangement, cyclization, or elimination, and that is sufficiently robust to survive isolation from a reaction mixture). When it is stated that a group may contain one or more substituents, one or more (as appropriate) member atom within the group may be substituted. In addition, a single member atom within the group may be substituted with more than one substituent as long as such substitution is in accordance with the permitted valence of the atom. Suitable substituents are defined herein for each substituted or optionally substituted group.

"Sulfanyl" refers to an alkyl moiety attached through a sulphur bridge (i.e —S—C1-C6 alkyl group wherein C1-C6 alkyl is as defined herein). Examples of sulfanyl groups include thiomethyl and thioethyl.

Compounds

The present invention is directed to compounds according to Formula I:

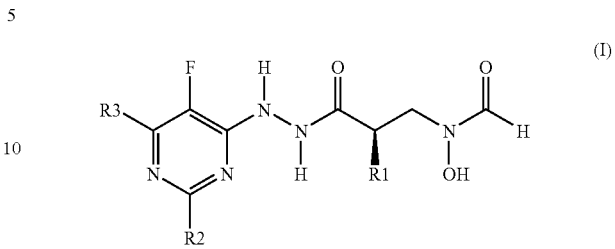

wherein

R1 is selected from the group consisting of C2-C7 alkyl and —(CH$_2$)$_n$—C3-C6 cycloalkyl;

R2 is selected from the group consisting of C1-C3 alkyl; cyclopropyl; C1-C3 alkoxy; C1-C3 haloalkyl; C1-C3 sulfanyl; 5-membered heteroaryl; 5-membered heterocycloalkyl; halo; hydroxymethyl; and —NRaRb;

R3 is selected from the group consisting of —NR4R5; halo; phenyl, optionally substituted by one to three R6 groups; and heteroaryl, optionally substituted by one to three R6 groups;

R4 is selected from the group consisting of H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

R5 is selected from H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

or R4 and R5 are joined together with the N-atom to which they are attached, forming a heterocycloalkyl group optionally substituted with one to three R6 groups;

each R6 is independently selected from the group consisting of C1-C6 alkyl, optionally substituted with one to three R7 groups; hydroxy; C1-C3 alkoxy; —C(O)NRaRb; —C(O)Rc; —C(O)ORc; heterocycloalkyl; C3-C6 cycloalkyl optionally substituted with one —NRaRb or pyrrolidinyl; oxo; cyano; —NRaRb; phenyl; heteroaryl; and halo;

each R7 is independently selected from the group consisting of hydroxy; C1-C3 alkoxy; halo; phenyl; cyano; —NRaRb; —C(O)NRaRb; —C(O)Rc; C3-C6 cycloalkyl, optionally substituted with one hydroxy, heterocycloalkyl or —NRaRb group; heterocycloalkyl; and heteroaryl optionally substituted with one methyl, —NRaRb or hydroxy;

each Ra is each independently selected from the group consisting of H and C1-C3 alkyl optionally substituted with one hydroxy, methoxy, or dimethylamine;

each Rb is independently selected from the group consisting of H and C1-C3 alkyl;

each Rc is independently selected from the group consisting of C1-C3 alkyl optionally substituted with one methoxy group; phenyl; heterocycloalkyl; and heteroaryl; and n is an integer from 0 to 2.

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified, the structure is intended to encompass all individual stereoisomers and all mixtures thereof. Thus, compounds according to Formula I containing one or more chiral centers may be used as racemic mixtures, diastereomeric mixtures, enantiomerically enriched mixtures, diastereomerically enriched mixtures, or as enantiomerically and diastereomerically pure individual stereoisomers.

Individual stereoisomers of a compound according to Formula I which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into a diastereomeric salt, complex or derivative, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group. In certain other embodiments, compounds according to Formula I may contain a basic functional group. Thus, the skilled artisan will appreciate that salts of the compounds according to Formula I may be prepared. Indeed, in certain embodiments of the invention, salts of the compounds according to Formula I may be preferred over the respective free base or free acid because, for example, such salts may impart greater stability or solubility to the molecule thereby facilitating formulation into a dosage form. Accordingly, the invention is further directed pharmaceutically acceptable salts of the compounds according to Formula I. For a review on suitable salts see Berge et al, J. Pharm. Sci., 1977, 66, 1-19.

Acid salts: Suitable addition salts are formed from acids which form non-toxic salts and examples are hydrochloride, hydrobromide, hydroiodide, sulphate, bisulphate, nitrate, phosphate, hydrogen phosphate, acetate, maleate, malate, fumarate, malonate, lactate, tartrate, citrate, formate, gluconate, succinate, piruvate, oxalate, oxaloacetate, trifluoroacetate, saccharate, benzoate, methanesulphonate, ethanesulphonate, benzenesulphonate, p-toluenesulphonate, methanesulphonic, ethanesulphonic, p-toluenesulphonic, and isethionate.

Base salts: Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, the term "compounds of the invention" means both the compounds according to Formula I and salts thereof, including pharmaceutically acceptable salts. The term "a compound of the invention" also appears herein and refers to both a compound according to Formula I and its salts, including pharmaceutically acceptable salts.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents used in making the compound, or by using different isolation or purification procedures. For example, changes in temperature, pressure, or solvent may result in polymorphs. In addition, one polymorph may spontaneously convert to another polymorph under certain conditions.

In one embodiment of the present invention R1 is —$(CH_2)_n$—C3-C6 cycloalkyl. Suitably, R1 is —$(CH_2)_n$—C3-C6 cycloalkyl wherein n is 1. Suitably R1 is —$CH_2$-cyclopentyl.

In another embodiment of the present invention R2 is C1-C3 alkyl; C1-C3 alkoxy; C1-C3 haloalkyl; C1-C3 sulfanyl; or halo. Suitably R2 is methyl; ethyl; thiomethyl; thioethyl; fluoromethyl; difluoromethyl; 1-fluoromethyl; chloro; cyclopropyl; or methoxy. Suitably R2 is methyl; ethyl; thiomethyl; or chloro.

In another embodiment of the present invention R3 is —NR4R5; C1-C6 alkoxy; or heteroaryl, optionally substituted by one to three R6 groups. Suitably R3 is —NR4R5 wherein R4 is C1-C6 alkyl, optionally substituted with one or two R7 groups; or C3-C6 cycloalkyl, optionally substituted by one to three R6 groups; and R5 is H, C1-C6 alkyl, or C1-C6 alkoxy.

In another embodiment of the present invention R4 is cyclopropyl; cyclobutyl; cyclopentyl; tetrahydro-2H-pyranyl; 2-oxohexahydro-1H-azepinyl; 2-oxo-2,3,4,7-tetrahydro-1H-azepinyl; 5-fluoro-pyridinyl; or C1-C6 alkyl optionally substituted with one of the following R7 groups selected from the group consisting of hydroxyl; methoxy; cyano; —C(O)NRaRb; —C(O)Rc; morpholinyl; pyridinyl; 1,3-thiazolyl; 2-amino-1,3-thiazoyl; thienyl; furanyl; phenyl; and 1-hydroxy-1H-imidazolyl; and R5 is H; C1-C3 alkyl; cyclopropyl; or piperazinyl optionally substituted with one R6 group.

In another embodiment R4 is methyl; ethyl optionally substituted with one substituent selected from the group consisting of: hydroxyl, methoxy and —NRaRb; propyl; isopropyl; cyclopropyl; cyclobutyl; and cyclopentyl.

In another embodiment of the present invention R5 is selected from the group consisting of H; C1-C6 alkyl; C1-C6 alkoxy; and C3-C6 cycloalkyl. Suitably R5 is H; methyl; or methoxy. Suitably R5 is H; C1-C3 alkyl; cyclopropyl; or piperazinyl optionally substituted with one R6 group.

In another embodiment of the present invention R3 is —NR4R5 wherein R4 and R5 are joined together with the N-atom to which they are attached to form a heterocycloalkyl group optionally substituted with one to three R6 groups. Suitably R3 is —NR4R5 wherein R4 and R5 are joined together with the N-atom to which they are attached forming azetidinyl; pyrrolidinyl; piperazinyl; morpholinyl; 2,5-dihydro-1H-pyrrolyl; hexahydropyrazino[2,1-c][1,4]oxazin-(1H)-yl; isoxazolidinyl; hexahydropyrrolo[1,2-a]pyrazin-(1H)-yl; or 2,5-diazabicyclo[2.2.1]heptyl each of which may be optionally substituted with one to three R6 groups.

In another embodiment of the present invention R3 is —NR4R5 wherein R4 and R5 are joined together with the N-atom to which they are attached forming 1-piperidinyl; 4-thiomorpholinyl; 1-pyrazolidinyl; tetrahydro-5H-[1,3]dioxolo[4,5-c]pyrrolyl; tetrahydro-1H-furo[3,4-c]pyrrol-(3H)-yl; hexahydropyrrolo[3,4-c]pyrrol-(1H)-yl; hexahydropyrrolo[1,2-a]pyrazin-(1H)-yl; hexahydropyrazino[2,1-c][1,4]oxazin-(1H)-yl; hexahydrofuro[3,4-b]pyrazin-(2H)-yl; octahydro-2H-pyrido[1,2-a]pyrazinyl; octahydropyrazino[1,2-a]azepin-(1H)-yl; octahydropyrazino[2,1-c][1,4]oxazinyl; octahydro-1H-cyclopenta[b]pyrazinyl; octahydro-1(2H)-quinoxalinyl; octahydro-6H-pyrrolo[3,4-b]pyridinyl; 3-azabicyclo[3.1.0]hexyl; 2,5-diazabicyclo[2.2.1]heptyl; 4,7-diazaspiro[2.5]octyl; 5-azaspiro[2.4]heptyl; or 10-oxa-4-azatricyclo[5.2.1.0$^{2,6}$]decyl.

Suitably R3 is —NR4R5 wherein R4 and R5 are joined together with the N-atom to which they are attached forming azetidinyl optionally substituted with one or two R6 groups each independently selected from the group consisting of methyl; ethyl; fluoro; methoxy; hydroxyl; hydroxymethyl; cyclopropyl; dimethylamino; ethylmethylamino; —CH$_2$-dimethylamino; morpholinyl; pyrrolidinyl; —CH$_2$-pyrrolidinyl; and pyridinyl.

Suitably R3 is —NR4R5 wherein R4 and R5 are joined together with the N-atom to which they are attached forming pyrrolidinyl optionally substituted with one to three R6 groups each independently selected from the group consisting of methyl; methoxy; —CH$_2$-methoxy; hydroxyl; hydroxymethyl; hydroxyethyl; dimethylamino; ethylmethylamino; —CH$_2$-dimethylamino; —CH$_2$-pyrrolidinyl; —CH$_2$-morpholinyl; pyridinyl; 2-(dimethylamino)-1,1-dimethylethyl; fluoromethyl; —CH$_2$-2-hydroxyethylmethylamino; —CH$_2$-2-methoxyethylamino; cyano; —C(O)N(CH$_3$)$_2$; 1-(dimethyamino)cyclopropyl; —CH$_2$-ethylemethylamino; —CH$_2$-diethylamino; —C(O)N(CH$_2$CH$_3$)$_2$; —CH$_2$-piperidinyl; —CH$_2$-isopropylmethylamino; —CH$_2$-propylmethylamino; —NHCOOCH$_3$; —CH$_2$-3H-[1,2,3]triazolo[4,5-d]pyrimidin-3-yl; and (cis)-10-oxa-4-azatricyclo[5.2.1.0$^{2,6}$]dec-4-yl.

Suitably R3 is —NR4R5 wherein R4 and R5 are joined together with the N-atom to which they are attached forming piperazinyl optionally substituted with one to three R6 groups each independently selected from the group consisting of methyl; ethyl; isopropyl; hydroxymethyl; hydroxyethyl; —CH$_2$—O—CH$_3$; and —COOCH$_3$.

Suitably R3 is —NR4R5 wherein R4 and R5 are joined together with the N-atom to which they are attached forming (9aS)-octahydropyrazino[2,1-c][1,4]oxazinyl.

In another embodiment of the present invention R6 is C1-C3 alkyl, optionally substituted with one to three R7 groups; hydroxy; C1-C3 alkoxy; —C(O)NRaRb; or —NRaRb. Suitably R6 is methyl; ethyl; isopropyl; methoxy; hydroxyl; diethylamino; or N,N-dimethylacetamido.

In another embodiment R6 is heteroaryl. Suitably R6 is a 6-membered heteroaryl. Suitably R6 is pyridinyl.

In another embodiment of the present invention R7 is C1-C3 alkoxy; hydroxyl; or —NRaRb. Suitably R7 is methoxy.

In another embodiment R7 is heterocycloalkyl. Suitably R7 is a 6-membered heterocycloalkyl. Suitably R7 is morpholinyl.

In another embodiment R7 is heteroaryl. Suitably R7 is pyridinyl; 1,3-thiazolyl; thienyl; furanyl; imidazolyl; 1H-benzamidazolyl; 3H-[1,2,3]triazolo[4,5-d]pyrimidin-3-yl; or 3H-[1,2,3]triazolo[4,5-b]pyridin-3-yl.

In another embodiment of the present invention Ra and Rb are both methyl.

In another embodiment of the present invention Rc is heterocycloalkyl. Suitably Rc is pyrrolidinyl.

Another embodiment of the present invention is a compound according to Formula (I) wherein:

R1 is selected from the group consisting of C2-C7 alkyl and —(CH$_2$)$_n$—C3-C6 cycloalkyl;

R2 is selected from the group consisting of C1-C3 alkyl; cyclopropyl; C1-C3 alkoxy; C1-C3 haloalkyl; C1-C3 sulfanyl; 5-membered heteroaryl; 5-membered heterocycloalkyl; halo; hydroxymethyl; and —NRaRb;

R3 is selected from the group consisting of —NR4R5; halo; phenyl, optionally substituted by one to three R6 groups; and heteroaryl, optionally substituted by one to three R6 groups;

R4 is selected from the group consisting of H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

R5 is selected from the group consisting of H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

or R4 and R5 are joined together with the N-atom to which they are attached, forming a heterocycloalkyl group optionally substituted with one to three R6 groups;

each R6 is independently selected from the group consisting of C1-C6 alkyl, optionally substituted with one to three R7 groups; hydroxy; C1-C3 alkoxy; —C(O)NRaRb; —C(O)Rc; heterocycloalkyl; C3-C6 cycloalkyl; oxo; cyano; —NRaRb; phenyl; heteroaryl; and halo;

each R7 is independently selected from the group consisting of hydroxy; C1-C3 alkoxy; halo; phenyl; cyano; —NRaRb; —C(O)NRaRb; —C(O)Rc; C3-C6 cycloalkyl, optionally substituted with one hydroxy, heterocycloalkyl or —NRaRb group; heterocycloalkyl; and heteroaryl;

each Ra is independently selected from the group consisting of H and C1-C3 alkyl;

each Rb is independently selected from the group consisting of H and C1-C3 alkyl;

each Rc is independently selected from the group consisting of C1-C3 alkyl; phenyl; heterocycloalkyl; and heteroaryl; and n is an integer from 0 to 2.

Another embodiment of the present invention is a compound according to Formula (I) wherein:

R1 is —CH$_2$-cyclopentyl;

R2 is selected from the group consisting of methyl; ethyl; thiomethyl; thioethyl; fluoromethyl; difluoromethyl; 1-fluoromethyl; chloro; cyclopropyl; or methoxy;

R3 is —NR4R5;

R4 is selected from the group consisting of H; C1-C3 alkyl; cyclopropyl; and piperazinyl optionally substituted with one R6 group;

R5 is selected from the group consisting of H; C1-C6 alkyl, optionally substituted with one or two R7 groups; C1-C6 alkoxy; C3-C6 cycloalkyl, optionally substituted with one to three R6 groups; heterocycloalkyl, optionally substituted by one to three R6 groups; heteroaryl, optionally substituted by one to three R6 groups; and phenyl, optionally substituted by one to three R6 groups;

or R4 and R5 are joined together with the N-atom to which they are attached, forming a heterocycloalkyl group optionally substituted with one to three R6 groups;

each R6 is independently selected from the group consisting of C1-C6 alkyl, optionally substituted with one to three R7 groups; hydroxy; C1-C3 alkoxy; —C(O)NRaRb; —C(O)Rc; C(O)ORc; heterocycloalkyl; C3-C6 cycloalkyl optionally substituted with one —NRaRb or pyrrolidinyl; oxo; cyano; —NRaRb; phenyl; heteroaryl; and halo;

each R7 is independently selected from the group consisting of hydroxy; C1-C3 alkoxy; halo; phenyl; cyano; —NRaRb; —C(O)NRaRb; —C(O)Rc; C3-C6 cycloalkyl, optionally substituted with one hydroxy, heterocycloalkyl or —NRaRb group; heterocycloalkyl; and heteroaryl optionally substituted with one methyl, —NRaRb or hydroxy;

each Ra is each independently selected from H and C1-C3 alkyl optionally substituted with one hydroxy, methoxy group or dimethylamine;

each Rb is independently selected from H and C1-C3 alkyl; and each Rc is independently selected from C1-C3 alkyl optionally substituted with one methoxy group; phenyl; heterocycloalkyl; and heteroaryl.

Specific examples of compounds of the present invention include the following:

((2R)-2-(Cyclopentylmethyl)-3-{2-[5-fluoro-2-methyl-6-(1-pyrrolidinyl)-4-pyrimidinyl]hydrazino}-3-oxopropyl)hydroxyformamide;

[(2R)-3-{2-[6-(1-Azetidinyl)-2-ethyl-5-fluoro-4-pyrimidinyl]hydrazino}-2-(cyclopentylmethyl)-3-oxopropyl]hydroxyformamide;

[(2R)-3-{2-[6-(1-Azetidinyl)-5-fluoro-2-(methylthio)-4-pyrimidinyl]hydrazino}-2-(cyclopentylmethyl)-3-oxopropyl]hydroxyformamide;

[(2R)-3-{2-[2-Chloro-5-fluoro-6-(4-methyl-1-piperazinyl)-4-pyrimidinyl]hydrazino}-2-(cyclopentylmethyl)-3-oxopropyl]hydroxyformamide;

[(2R)-3-(2-{2-Chloro-5-fluoro-6-[(1-methylethyl)amino]-4-pyrimidinyl}hydrazino)-2-(cyclopentylmethyl)-3-oxopropyl]hydroxyformamide;

[(2R)-3-{2-[6-(1-Azetidinyl)-5-fluoro-2-methyl-4-pyrimidinyl]hydrazino}-2-(cyclopentylmethyl)-3-oxopropyl]hydroxyformamide;

((2R)-2-(Cyclopentylmethyl)-3-{2-[5-fluoro-2-methyl-6-(4-morpholinyl)-4-pyrimidinyl]hydrazino}-3-oxopropyl)hydroxyformamide;

[(2R)-2-(Cyclopentylmethyl)-3-(2-{5-fluoro-2-methyl-6-[methyl(methyloxy)amino]-4-pyrimidinyl}hydrazino)-3-oxopropyl]hydroxyformamide;

((2R)-2-(Cyclopentylmethyl)-3-{2-[6-(2,5-dihydro-1H-pyrrol-1-yl)-5-fluoro-2-methyl-4-pyrimidinyl]hydrazino}-3-oxopropyl)hydroxyformamide;

((2R)-2-(Cyclopentylmethyl)-3-{2-[5-fluoro-2-methyl-6-(1,3-thiazolidin-3-yl)-4-pyrimidinyl]hydrazino}-3-oxopropyl)hydroxyformamide;

[(2R)-2-(Cyclopentylmethyl)-3-(2-{5-fluoro-2-methyl-6-[3-(methyloxy)-1-azetidinyl]-4-pyrimidinyl}hydrazino)-3-oxopropyl]hydroxyformamide;

[(2R)-2-(Cyclopentylmethyl)-3-(2-{5-fluoro-2-methyl-6-[(3R)-3-(methyloxy)-1-pyrrolidinyl]-4-pyrimidinyl}hydrazino)-3-oxopropyl]hydroxyformamide;

[(2R)-2-(Cyclopentylmethyl)-3-(2-{5-fluoro-2-methyl-6-[(3S)-3-(methyloxy)-1-pyrrolidinyl]-4-pyrimidinyl}hydrazino)-3-oxopropyl]hydroxyformamide;

[(2R)-2-(Cyclopentylmethyl)-3-(2-{5-fluoro-2-methyl-6-[(1-methylethyl)amino]-4-pyrimidinyl}hydrazino)-3-oxopropyl]hydroxyformamide;

{(2R)-2-(Cyclopentylmethyl)-3-[2-(5-fluoro-2-methyl-6-{methyl[2-(methyloxy)ethyl]amino}-4-pyrimidinyl)hydrazino]-3-oxopropyl}hydroxyformamide;

[(2R)-2-(Cyclopentylmethyl)-3-(2-{6-[ethyl(methyl)amino]-5-fluoro-2-methyl-4-pyrimidinyl}hydrazino)-3-oxopropyl]hydroxyformamide;

[(2R)-2-(Cyclopentylmethyl)-3-(2-{5-fluoro-6-[(2S)-2-(hydroxymethyl)-1-pyrrolidinyl]-2-methyl-4-pyrimidinyl}hydrazino)-3-oxopropyl]hydroxyformamide;

[(2R)-3-{2-[6-(Cyclobutylamino)-5-fluoro-2-methyl-4-pyrimidinyl]hydrazino}-2-(cyclopentylmethyl)-3-oxopropyl]hydroxyformamide;

[(2R)-3-{2-[6-(Cyclopentylamino)-5-fluoro-2-methyl-4-pyrimidinyl]hydrazino}-2-(cyclopentylmethyl)-3-oxopropyl]hydroxyformamide;

[(2R)-2-(Cyclopentylmethyl)-3-(2-{5-fluoro-6-[(3R)-3-(hydroxymethyl)-1-pyrrolidinyl]-2-methyl-4-pyrimidinyl}hydrazino)-3-oxopropyl]hydroxyformamide;

[(2R)-2-(Cyclopentylmethyl)-3-(2-{5-fluoro-6-[(3S)-3-(hydroxymethyl)-1-pyrrolidinyl]-2-methyl-4-pyrimidinyl}hydrazino)-3-oxopropyl]hydroxyformamide;

[(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide;

((2R)-2-(Cyclopentylmethyl)-3-{2-[2-ethyl-5-fluoro-6-(4-methyl-1-piperazinyl)-4-pyrimidinyl]hydrazino}-3-oxopropyl)hydroxyformamide;

N-[(2R)-2-(Cyclopentylmethyl)-3-{2-[2-ethyl-5-fluoro-6-(2-isoxazolidinyl)-4-pyrimidinyl]hydrazino}-3-oxopropyl]-N-hydroxyformamide;

N-[(2R)-2-(Cyclopentylmethyl)-3-(2-{6-[(3R)-3-(dimethylamino)-1-pyrrolidinyl]-2-ethyl-5-fluoro-4-pyrimidinyl}hydrazino)-3-oxopropyl]-N-hydroxyformamide;

N-[(2R)-2-(Cyclopentylmethyl)-3-(2-{6-[(3S)-3-(dimethylamino)-1-pyrrolidinyl]-2-ethyl-5-fluoro-4-pyrimidinyl}hydrazino)-3-oxopropyl]-N-hydroxyformamide;

N-[(2R)-2-(Cyclopentylmethyl)-3-(2-{2-ethyl-5-fluoro-6-[(3S)-3-hydroxy-1-pyrrolidinyl]-4-pyrimidinyl}hydrazino)-3-oxopropyl]-N-hydroxyformamide;

N-[(2R)-2-(Cyclopentylmethyl)-3-(2-{2-ethyl-5-fluoro-6-[(3R)-3-hydroxy-1-pyrrolidinyl]-4-pyrimidinyl}hydrazino)-3-oxopropyl]-N-hydroxyformamide;

N-[(2R)-2-(Cyclopentylmethyl)-3-{2-[6-(cyclopropylamino)-2-ethyl-5-fluoro-4-pyrimidinyl]hydrazino}-3-oxopropyl]-N-hydroxyformamide;

N-[(2R)-2-(Cyclopentylmethyl)-3-{2-[2-ethyl-6-(4-ethyl-1-piperazinyl)-5-fluoro-4-pyrimidinyl]hydrazino}-3-oxopropyl]-N-hydroxyformamide;

N-[(2R)-2-(Cyclopentylmethyl)-3-(2-{2-ethyl-5-fluoro-6-[4-(2-hydroxyethyl)-1-piperazinyl]-4-pyrimidinyl}hydrazino)-3-oxopropyl]-N-hydroxyformamide;

N-[(2R)-2-(Cyclopentylmethyl)-3-{2-[2-ethyl-5-fluoro-6-(methylamino)-4-pyrimidinyl]hydrazino}-3-oxopropyl]-N-hydroxyformamide;

N-[(2R)-2-(Cyclopentylmethyl)-3-{2-[2-ethyl-6-(ethylamino)-5-fluoro-4-pyrimidinyl]hydrazino}-3-oxopropyl]-N-hydroxyformamide;

N-[(2R)-2-(Cyclopentylmethyl)-3-(2-{2-ethyl-5-fluoro-6-[4-(1-methylethyl)-1-piperazinyl]-4-pyrimidinyl}hydrazino)-3-oxopropyl]-N-hydroxyformamide;

1-(6-{2-[(2R)-3-Cyclopentyl-2-{[formyl(hydroxy)amino]methyl}propanoyl]hydrazino}-2-ethyl-5-fluoro-4-pyrimidinyl)-N,N-dimethyl-L-prolinamide;

N-{(2R)-2-(Cyclopentylmethyl)-3-[2-(6-{[2-(dimethylamino)ethyl](methyl)amino}-2-ethyl-5-fluoro-4-pyrimidinyl)hydrazino]-3-oxopropyl}-N-hydroxyformamide;

N-[(2R)-2-(Cyclopentylmethyl)-3-(2-{6-[(3S)-3,4-dimethyl-1-piperazinyl]-2-ethyl-5-fluoro-4-pyrimidinyl}hydrazino)-3-oxopropyl]-N-hydroxyformamide;

N-[(2R)-2-(Cyclopentylmethyl)-3-(2-{6-[(3R)-3,4-dimethyl-1-piperazinyl]-2-ethyl-5-fluoro-4-pyrimidinyl}hydrazino)-3-oxopropyl]-N-hydroxyformamide;

((2R)-2-(Cyclopentylmethyl)-3-{2-[5-fluoro-6-(4-methyl-1-piperazinyl)-2-(methylthio)-4-pyrimidinyl]hydrazino}-3-oxopropyl)hydroxyformamide;

((2R)-2-(Cyclopentylmethyl)-3-{2-[6-(ethylamino)-5-fluoro-2-(methylthio)-4-pyrimidinyl]hydrazino}-3-oxopropyl)hydroxyformamide;

((2R)-2-(Cyclopentylmethyl)-3-{2-[5-fluoro-6-(methylamino)-2-(methylthio)-4-pyrimidinyl]hydrazino}-3-oxopropyl)hydroxyformamide;

((2R)-2-(Cyclopentylmethyl)-3-{2-[5-fluoro-6-[(3S)-3-hydroxy-1-pyrrolidinyl]-2-(methylthio)-4-pyrimidinyl]hydrazino}-3-oxopropyl)hydroxyformamide;

((2R)-2-(Cyclopentylmethyl)-3-{2-[6-(dimethylamino)-5-fluoro-2-(methylthio)-4-pyrimidinyl]hydrazino}-3-oxopropyl)hydroxyformamide;

((2R)-2-(Cyclopentylmethyl)-3-{2-[5-fluoro-2-(methylthio)-6-(propylamino)-4-pyrimidinyl]hydrazino}-3-oxopropyl)hydroxyformamide;

((2R)-2-(Cyclopentylmethyl)-3-{2-[5-fluoro-6-{[2-(methyloxy)ethyl]amino}-2-(methylthio)-4-pyrimidinyl]hydrazino}-3-oxopropyl)hydroxyformamide;

1-[6-[2-((2R)-3-Cyclopentyl-2-{[formyl(hydroxy)amino]methyl}propanoyl)hydrazino]-5-fluoro-2-(methylthio)-4-pyrimidinyl]-N,N-dimethyl-L-prolinamide;

((2R)-2-(Cyclopentylmethyl)-3-{2-[5-fluoro-6-[(3R)-3-hydroxy-1-pyrrolidinyl]-2-(methylthio)-4-pyrimidinyl]hydrazino}-3-oxopropyl)hydroxyformamide;

((2R)-2-(Cyclopentylmethyl)-3-{2-[6-[(3R)-3-(dimethylamino)-1-pyrrolidinyl]-5-fluoro-2-(methylthio)-4-pyrimidinyl]hydrazino}-3-oxopropyl)hydroxyformamide;

((2R)-2-(Cyclopentylmethyl)-3-{2-[6-(4-ethyl-1-piperazinyl)-5-fluoro-2-(methylthio)-4-pyrimidinyl]hydrazino}-3-oxopropyl)hydroxyformamide;

[(2R)-3-{2-[2-Chloro-5-fluoro-6-(4-morpholinyl)-4-pyrimidinyl]hydrazino}-2-(cyclopentylmethyl)-3-oxopropyl]hydroxyformamide;

[(2R)-3-{2-[6-(1-Azetidinyl)-2-chloro-5-fluoro-4-pyrimidinyl]hydrazino}-2-(cyclopentylmethyl)-3-oxopropyl]hydroxyformamide;

[(2R)-3-{2-[2-Chloro-6-(4-ethyl-1-piperazinyl)-5-fluoro-4-pyrimidinyl]hydrazino}-2-(cyclopentylmethyl)-3-oxopropyl]hydroxyformamide;

[(2R)-3-(2-{2-Chloro-5-fluoro-6-[(2-hydroxyethyl)(methyl)amino]-4-pyrimidinyl}hydrazino)-2-(cyclopentylmethyl)-3-oxopropyl]hydroxyformamide;

[(2R)-3-(2-{2-Chloro-5-fluoro-6-[3-(methyloxy)-1-azetidinyl]-4-pyrimidinyl}hydrazino)-2-(cyclopentylmethyl)-3-oxopropyl]hydroxyformamide;

[(2R)-3-[2-(2-Chloro-5-fluoro-6-{methyl[2-(methyloxy)ethyl]amino}-4-pyrimidinyl)hydrazino]-2-(cyclopentylmethyl)-3-oxopropyl]hydroxyformamide;

[(2R)-3-(2-{2-Chloro-5-fluoro-6-[(8aS)-hexahydropyrrolo[1,2-a]pyrazin-2(1H)-yl]-4-pyrimidinyl}hydrazino)-2-(cyclopentylmethyl)-3-oxopropyl]hydroxyformamide;

[(2R)-3-(2-{2-Chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl]hydroxyformamide;

1-{6-Chloro-2-[2-((2R)-3-cyclopentyl-2-{[formyl(hydroxy)amino]methyl}propanoyl)hydrazino]-5-fluoro-4-pyrimidinyl}-N,N-dimethyl-L-prolinamide;

[(2R)-3-{2-[2-Chloro-5-fluoro-6-(propylamino)-4-pyrimidinyl]hydrazino}-2-(cyclopentylmethyl)-3-oxopropyl]hydroxyformamide;

[(2R)-3-(2-{2-Chloro-6-[(3S)-3,4-dimethyl-1-piperazinyl]-5-fluoro-4-pyrimidinyl}hydrazino)-2-(cyclopentylmethyl)-3-oxopropyl]hydroxyformamide;

[(2R)-3-(2-{2-Chloro-6-[(3R)-3,4-dimethyl-1-piperazinyl]-5-fluoro-4-pyrimidinyl}hydrazino)-2-(cyclopentylmethyl)-3-oxopropyl]hydroxyformamide;

[(2R)-3-(2-{2-Chloro-6-[(2S)-2,4-dimethyl-1-piperazinyl]-5-fluoro-4-pyrimidinyl}hydrazino)-2-(cyclopentylmethyl)-3-oxopropyl]hydroxyformamide;

[(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide; and

[(2R)-3-(2-{2-Chloro-5-fluoro-6-[(9aS)-hexahydropyrazino[2,1-c][1,4]oxazin-8(1H)-yl]-4-pyrimidinyl}hydrazino)-2-(cyclopentylmethyl)-3-oxopropyl]hydroxyformamide; or a salt thereof.

One embodiment of the present invention is a compound which is [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide or a salt thereof.

Another embodiment of the present invention is a compound which is [(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide or a salt thereof.

Another embodiment of the present invention is a compound which is [(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide or a salt thereof.

Another embodiment of the present invention is a compound which is [(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide or a salt thereof.

Another embodiment of the present invention is a compound which is ((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide or a salt thereof.

Compound Preparation

The compounds according to Formula I are prepared using conventional organic syntheses. Suitable synthetic routes are depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

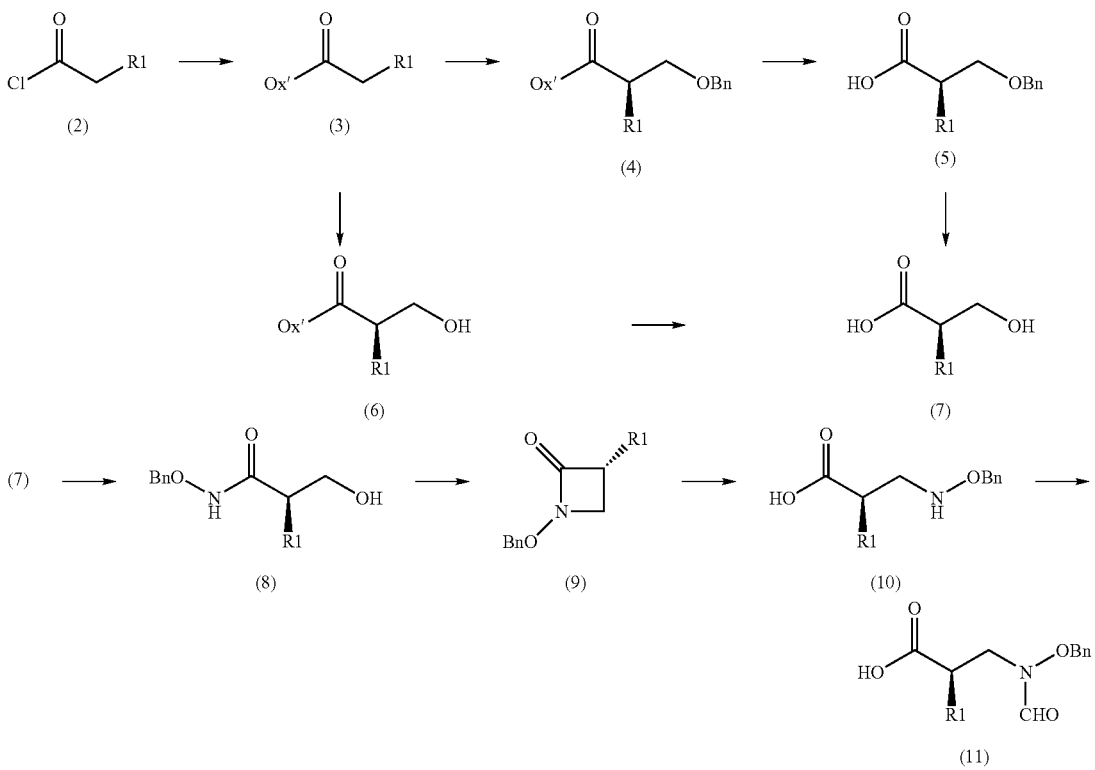

Scheme 1

As shown in Scheme 1, (11) can be prepared by reacting an appropriate acid chloride (2) with a chiral agent, such as (S)-(−)-4-benzyl-2-oxazolidinone (Evans' chiral oxazolidinone), in the presence of a base, such as n-butyl lithium, to afford the chiral intermediate (3). Treatment of the compound (3) with a base, such as diisopropylethylamine, in the presence of a chelating agent, such as titanium tetrachloride, in a solvent, such as tetrahydrofuran, followed by addition of an electrophile, such as benzyloxymethylchloride, provides compound (4). Conversion of compound (4) to the corresponding hydroxyacid (7) can be achieved by a sequence comprising oxidative cleavage of the chiral oxazolidinone, using, for example $H_2O_2$ and lithium hydroxide, to the respective intermediate (5), followed by hydrogenolysis, to afford intermediate (7). Compound (3) can also be converted to intermediate (7) in an alternative two-step procedure. For this transformation, (3) can be treated with a base, such as diisopropylethylamine, in the presence of a chelating agent, such as titanium tetrachloride, in a solvent, such as tetrahydrofuran, followed by addition of trioxane or a suitable alternative formaldehyde equivalent to provide compound (6), which is then submitted to oxidative cleavage of the chiral oxazolidinone, using, for example $H_2O_2$ and lithium hydroxide, to the respective acid (7).

Coupling of acid (7) with benzyloxyamine in the presence of coupling agents, such as EDC and DMAP, yields the amide (8). This can be cyclized to azetidin-2-one (9) using Mitsunobu conditions. Hydrolysis of the azetidin-2-one (9), using for example lithium hydroxide in an appropriate solvent, gives the corresponding acid (10). Conversion of compound (10) to product (11) can be achieved using an appropriate formylating agent, such as formic acid/acetic anhydride or methyl formate, in neat reagents or in an appropriate solvent, such as dichloromethane.

a catalyst, such as 10% Pd/C, in an appropriate solvent, such as ethanol to provide (12). Treatment of (12) with dihydropyran under acid catalysis, such as pyridinium p-toluenesulfonate, in an appropriate solvent, such as methylene chloride, provides THP-protected azetidin-2-one (13). Hydrolysis of azetidin-2-one (13), using for example lithium hydroxide in an appropriate solvent, gives the corresponding acid (14). Conversion of compound (14) to the product (15) can be achieved using an appropriate formylating agent, such as formic acid/acetic anhydride or methyl formate, in neat reagents or in an appropriate solvent, such as dichloromethane. Conversion of compound (14) to product (15) can also be accomplished using 5-methyl-2-thioxo-[1,3,4]thiadiazole-3-carbaldehyde (Yazawa, Hisatoyo; Goto, Shunsuke; Tetrahedron Lett. 26; 31; 1985; 3703-3706) as a formylating agent in an appropriate solvent, such as acetone.

Intermediate (15) can also be prepared according to literature procedures [Bracken, Bushell, Dean, Francavilla, Jain, Lee, Seepersaud, Shu, Sundram, Yuan; PCT Int. Appl. (2006), WO 2006127576 A2].

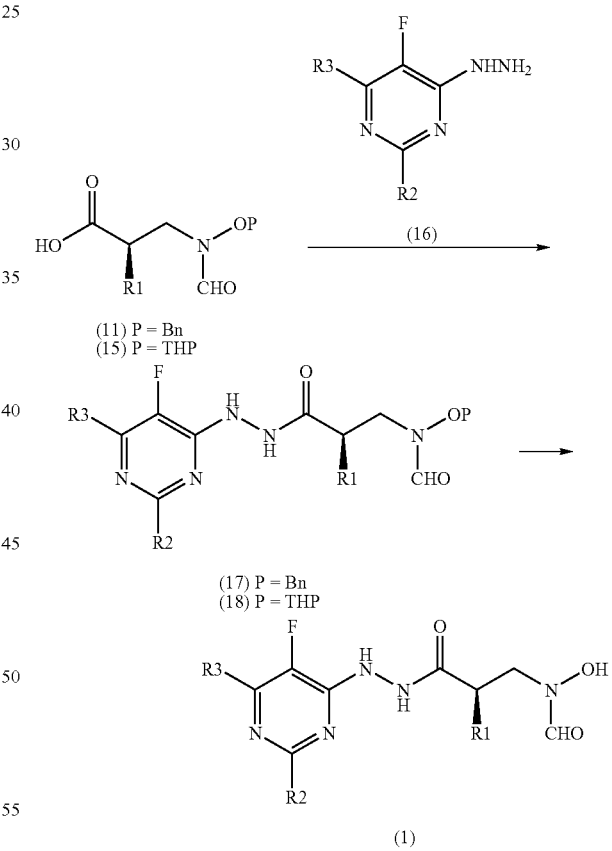

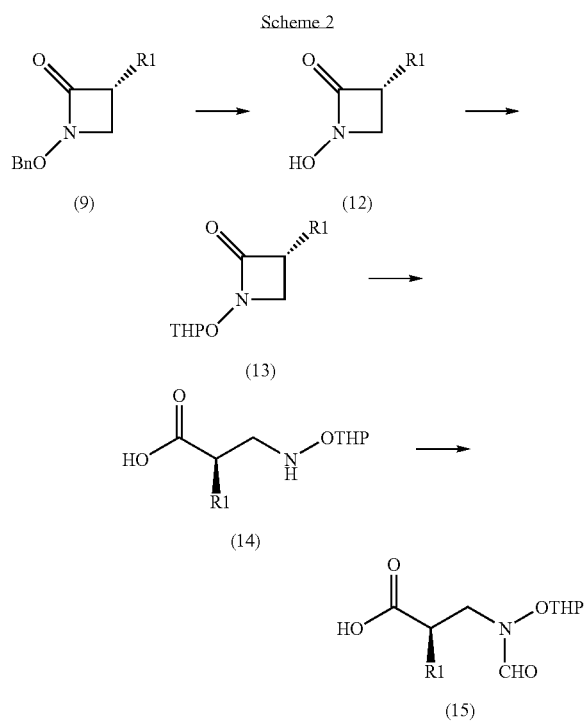

As shown in Scheme 2, THP-protected intermediate (15) can be prepared by hydrogenation of azetidin-2-one (9) using As shown in Scheme 3, coupling of the chiral acid (11 or 15) with the pyrimidinyl hydrazine (16, R2=alkyl, halo, H), using conditions such as EDC-HOAt-NMM, provides the hydrazide (17 or 18). Final deprotection (hydrogenolysis using a catalyst, such as 10% Pd/C, in an appropriate solvent, such as ethanol, in the case that P is Bn; treatment with 80% acetic acid-water at room temperature or 40° C. in the case that P is THP) gives the final desired compounds (1), where R2=alkyl, halo, H.

Hydrazines of general structure (16) may be prepared according to literature methods by those skilled in the art. The following examples of specific structures of hydrazines (16) and the synthetic methods used to generate them are merely illustrative and are not to be construed as a limitation of the scope of the present invention.

Hydrazines (24) where R2 is alkyl and R3 is an amino group (R4R5N) may be prepared from the appropriate precursors as shown in Scheme 4.

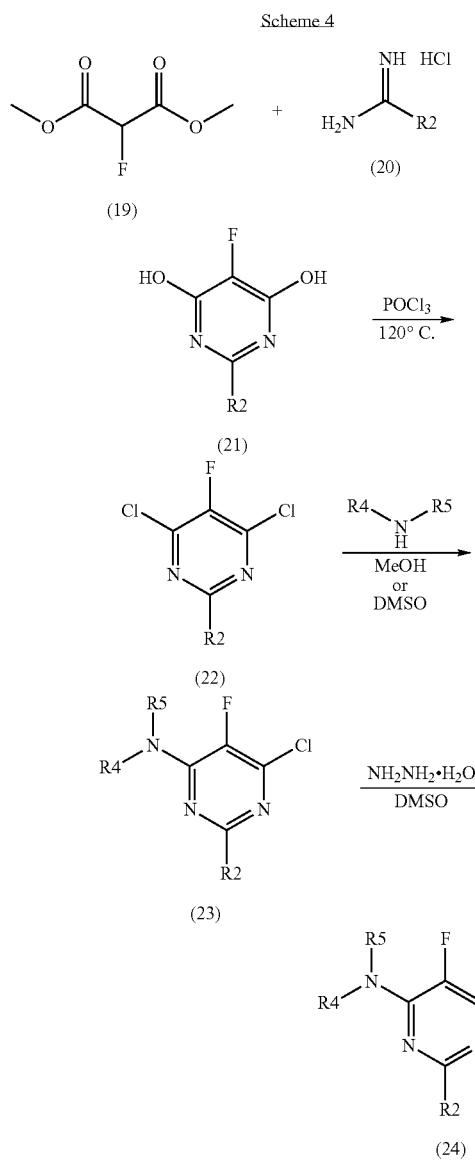

R2 = hydrogen, alkyl

As shown in Scheme 4, hydrazine (24) when R2 is hydrogen or alkyl can be prepared from the condensation of commercially-available fluoromalonate (19) and the appropriate amidine (20) under basic conditions to provide pyrimidinone (21). Amidines (20) are commercially available or may be prepared according to literature methods by those skilled in the art. Treatment of pyrimidinone (21) with POCl₃ provides dichloropyrimidine (22). Treatment of dichloropyrimidine (22) with the desired amine R4R5NH at room temperature in an appropriate solvent, such as methanol or DMSO, followed by further treatment with hydrazine monohydrate, in an appropriate solvent, such as DMSO, usually with heating, then provides the desired product (24) where R2 is hydrogen or alkyl.

Hydrazines of formula (30) [(16) in which R2=chloro] may be prepared as shown in either Schemes 5 or 6.

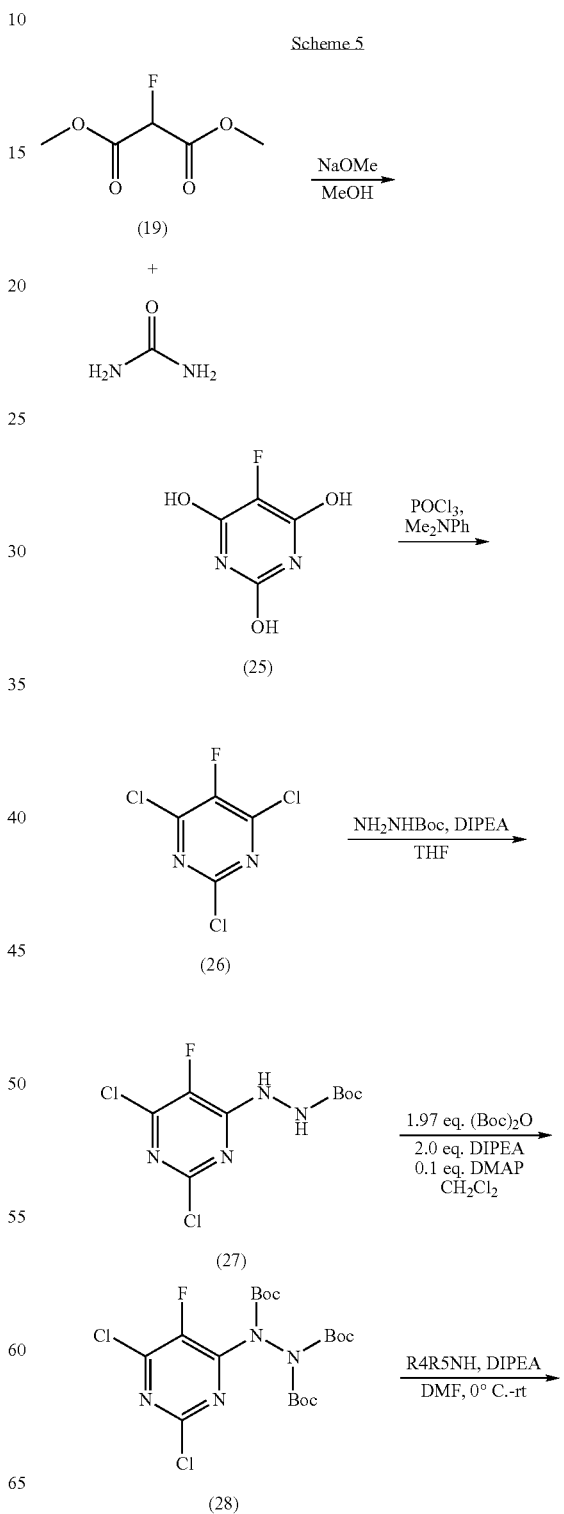

-continued

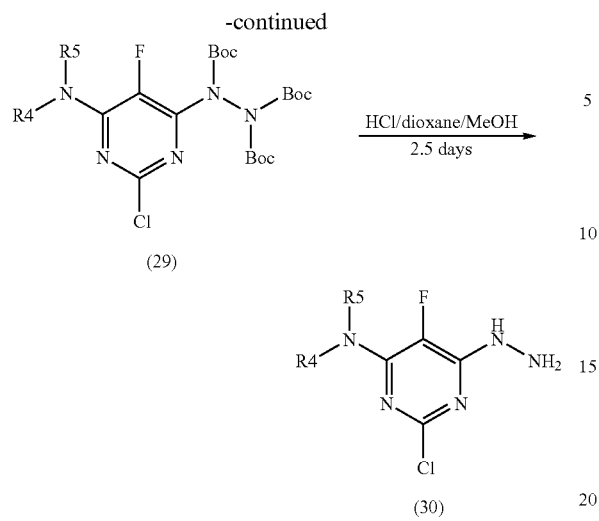

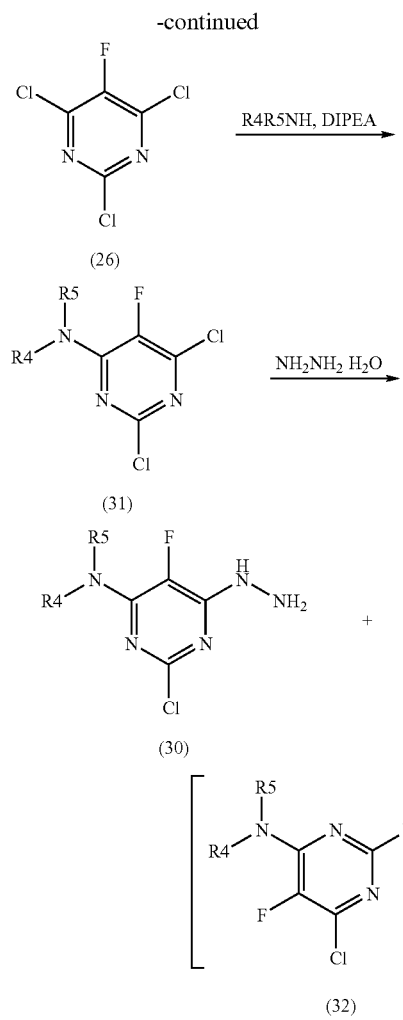

Condensation of commercially-available fluoromalonate (19) and urea under basic conditions provides pyrimidinone (25). Treatment of pyrimidinone (25) with POCl₃ provides trichloropyrimidine (26). Treatment of trichloropyrimidine (26) with Boc-protected hydrazine and diisopropylethylamine at room temperature in an appropriate solvent, such as THF, provides intermediate (27). Further treatment with di-t-butyldicarbonate in the presence of diisopropylethylamine and DMAP, in an appropriate solvent, such as methylene chloride, then provides the desired tri-Boc-protected product (28). Treatment of (28) with amine R4R5NH, in an appropriate solvent such as DMF, provides pyrimidine (29), and deprotection of (29) under acidic conditions, followed by a basic workup, provides the desired hydrazines (30).

Alternatively, hydrazines of formula (30) may be prepared as shown in Scheme 6.

Scheme 6

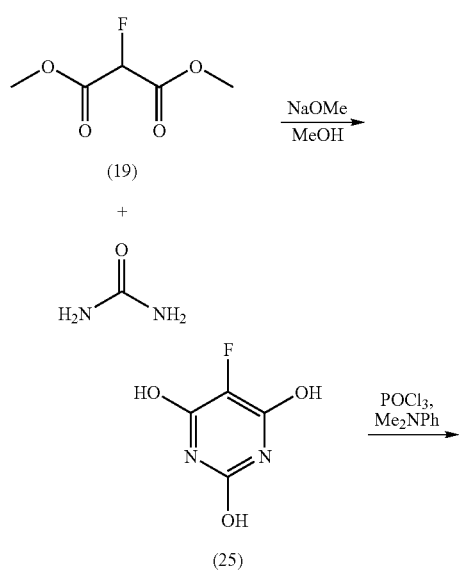

Treatment of trichloropyrimidine (26) with the desired amine R4R5NH at room temperature in an appropriate solvent, such as DMSO, followed by further treatment with hydrazine monohydrate and heating, provides the desired product (30), as well as the regioisomeric product (32). The two regioisomers can usually be separated chromatographically, such as by HPLC.

Final compounds (1) where R2 is thiomethyl or methoxy can be prepared as shown in Scheme 7.

Scheme 7

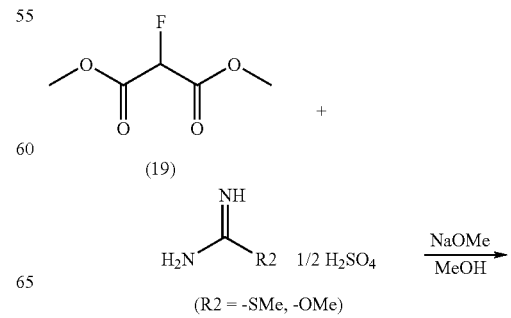

(R2 = -SMe, -OMe)

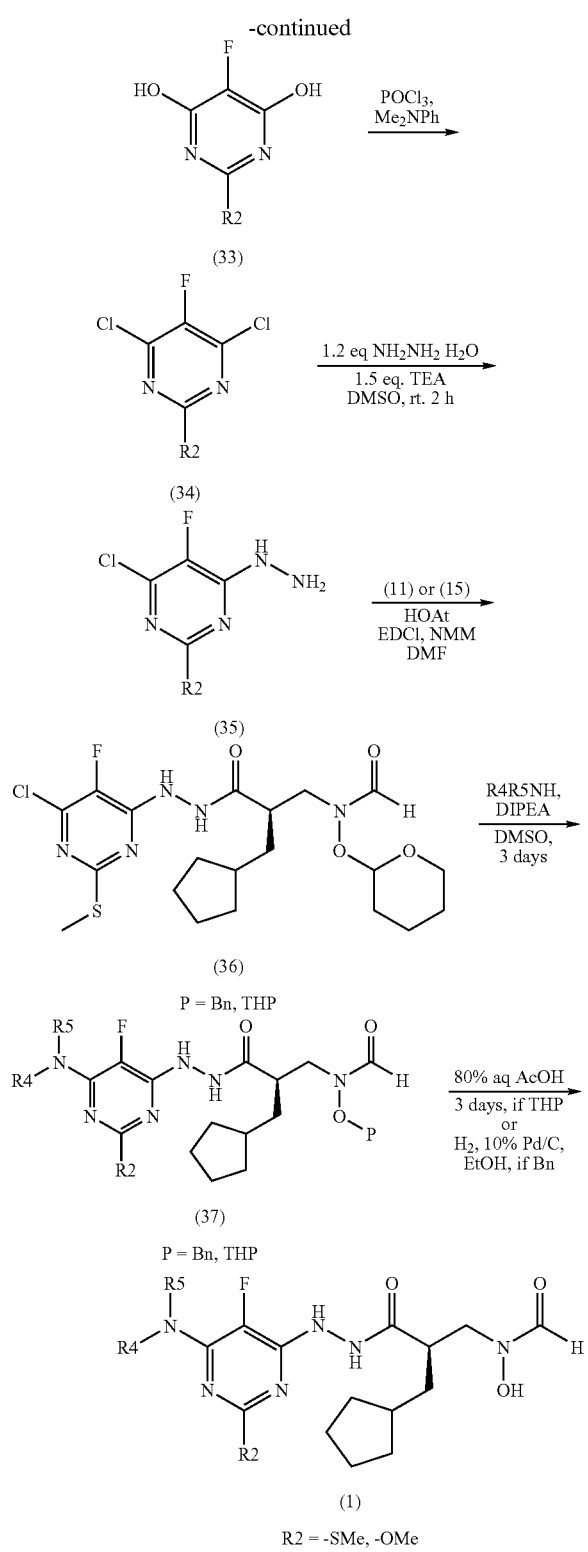

(34) with hydrazine monohydrate, in an appropriate solvent, such as methanol, provides pyrimidinylhydrazine (35), which is then coupled to acid (11) or (15) using conditions such as EDC-HOAt-NMM to provide intermediate (36). Addition of R4R5NH to intermediate (36) provides either the O-Bn-protected or O-THP-protected product (37). Final deprotection by either hydrogenolysis using a catalyst such as 10% Pd/C, in an appropriate solvent, such as ethanol, in the case that P is Bn; or treatment with 80% acetic acid-water at room temperature or 40° C. in the case that P is THP, gives the final desired compounds (1) when R2 is methoxy or thiomethyl, respectively.

Amines R4R5NH may be purchased from available commercial sources, prepared according to literature methods by those skilled in the art, or prepared as disclosed in the examples herein.

Methods of Use

The compounds of the invention are inhibitors of microbial peptide deformylase (PDF) and are, therefore, capable of preventing bacterial growth. These compounds are potentially useful in the treatment of infectious diseases wherein the underlying pathology is (at least in part) attributable to (i.e. caused by) a variety of prokaryotic organisms. Examples include, but are not limited to, Gram positive and Gram negative aerobic and anaerobic bacteria from the genera *Streptococcus*, e.g. *S. pneumoniae* and *S. pyogenes*, *Staphylococcus*, e.g. *S. aureus*, *S. epidermidis*, and *S. saprophyticus*, *Moraxella*, e.g. *M. catarrhalis*, *Haemophilus*, e.g. *H. influenzae*, *Neisseria*, *Mycoplasma*, e.g. *M. pneumoniae*, *Legionella*, e.g. *L. pneumophila*, *Chlamydia*, e.g. *C. pneumoniae*, *Bacteroides*, *Clostridium*, *Fusobacterium*, *Propionibacterium*, and *Peptostreptococcus*.

Suitably the compounds of the present invention may be useful in the treatment of bacterial infections caused by *Streptococcus*, more suitably *S. pneumoniae* or *S. pyogenes*.

Suitably the compounds of the present invention may be useful in the treatment of bacterial infections caused by *Staphylococcus*, more suitably *S. aureus*, *S. epidermidis*, or *S. saprophyticus*.

Suitably the compounds of the present invention may be useful in the treatment of bacterial infections caused by *Moraxella*, more suitably *M. catarrhalis*.

Suitably the compounds of the present invention may be useful in the treatment of bacterial infections caused by *Haemophilus*, more suitably *H. influenzae*.

Suitably the compounds of the present invention may be useful in the treatment of bacterial infections caused by *Neisseria*.

Suitably the compounds of the present invention may be useful in the treatment of bacterial infections caused by *Mycoplasma*, more suitably *M. pneumoniae*.

Suitably the compounds of the present invention may be useful in the treatment of bacterial infections caused by *Legionella*, more suitably *L. pneumophila*.

Suitably the compounds of the present invention may be useful in the treatment of bacterial infections caused by *Chlamydia*, more suitably *C. pneumoniae*.

Suitably the compounds of the present invention may be useful in the treatment of bacterial infections caused by *Bacteroides*.

Suitably the compounds of the present invention may be useful in the treatment of bacterial infections caused by *Clostridium*.

Suitably the compounds of the present invention may be useful in the treatment of bacterial infections caused by *Fusobacterium*.

Condensation of commercially-available fluoromalonate (19) and either O-methylisourea hemisulfate or S-methylisothiourea hemisulfate under basic conditions provides pyrimidinone (33), in which R2 is methoxy or thiomethyl, respectively. Treatment of pyrimidinone (33) with POCl₃ provides dichloropyrimidine (34). Treatment of dichloropyrimidine Suitably the compounds of the present invention may be useful in the treatment of bacterial infections caused by *Propionibacterium*.

Suitably the compounds of the present invention may be useful in the treatment of bacterial infections caused by *Peptostreptococcus*.

The compounds of the invention may also be useful in the treatment of bacterial infections caused by bacteria that are resistant to β-lactam, quinolone, macrolides, ketolides, glycopeptide, and oxazolidinone classes of antibiotics. Such drug resistant bacterial infections include, but are not limited to, penicillin, macrolide or levofloxacin resistant *S. pneumoniae*; methicillin or macrolide resistant, and vancomycin intermediate *S. aureus*; methicillin resistant *S. epidermidis*; and oxazolidinone resistant *S. aureus*.

The compounds of the invention may be used to treat a bacterial infection in mammals, specifically humans. Such infections include, but are not limited to, ear infections, sinusitis, upper and lower respiratory tract infections, genital infections, skin and soft tissue infections, and bacterial endocarditis. The compounds of the invention may also be used to prevent a bacterial infection in mammals, specifically humans, such as a bacterial infection that may result from medical or dental procedures.

Suitably the compounds of the invention may be used to treat ear infections.

Suitably the compounds of the invention may be used to treat sinusitis.

Suitably the compounds of the invention may be used to treat upper and lower respiratory tract infections.

Suitably the compounds of the invention may be used to treat genital infections.

Suitably the compounds of the invention may be used to treat skin and soft tissue infections.

Suitably the compounds of the invention may be used to treat bacterial endocarditis.

The methods of treatment of the invention, specifically methods for the treatment infectious diseases including bacterial infections, comprise administering an effective amount of a compound according to Formula I, or a pharmaceutically acceptable salt thereof, to a patient in need thereof.

One embodiment of the present invention provides for a method of treating a bacterial infection in humans comprising administration of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide, or a pharmaceutically acceptable salt thereof, to a human in need thereof.

Another embodiment of the present invention provides for a method of treating a bacterial infection in humans comprising administration of [(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide, or a pharmaceutically acceptable salt thereof, to a human in need thereof.

Another embodiment of the present invention provides for a method of treating a bacterial infection in humans comprising administration of [(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide, or a pharmaceutically acceptable salt thereof, to a human in need thereof.

Another embodiment of the present invention provides for a method of treating a bacterial infection in humans comprising administration of [(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide, or a pharmaceutically acceptable salt thereof, to a human in need thereof.

Another embodiment of the present invention provides for a method of treating a bacterial infection in humans comprising administration of ((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide, or a pharmaceutically acceptable salt thereof, to a human in need thereof.

As used herein, "infectious disease" refers to any disease characterized by the presence of a microbial infection, such as a bacterial infection.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "effective amount" in reference to a compound of the invention means an amount of the compound sufficient to treat the patient's condition, but low enough to avoid serious side effects (at a reasonable benefit/risk ratio) within the scope of sound medical judgment. An effective amount of a compound will vary with the particular compound chosen (e.g., consider the potency, efficacy, and half-life of the compound); the route of administration chosen; the condition being treated; the severity of the condition being treated; the age, size, weight, and physical condition of the patient being treated; the medical history of the patient being treated; the duration of the treatment; the nature of concurrent therapy; the desired therapeutic effect; and like factors, and can be routinely determined by the skilled artisan.

As used herein, "patient" refers to a human or other mammal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration, to a human weighing approximately 70 kg, would range from 50 mg to 3 g, suitably 100 mg to 2 g of a compound of the invention a day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, particularly in bacterial infections. Thus, in a further aspect, the invention is directed to the use of a compound according to Formula I or a pharmaceutically-acceptable salt thereof in the preparation of a medicament for the treatment of bacterial infections.

As stated above, compounds according to Formula I are PDF inhibitors, and may be useful in the treatment of bacterial infections. The biological activity of the compounds according to Formula I can be determined using suitable assays such as those measuring inhibition of the enzymatic activity of PDF and those evaluating the ability of the compounds to inhibit bacterial growth in vitro or in animal models of infection.

Certain Examples of the invention possess greater in vitro antibacterial activity (MIC and/or MIC90) and/or better in vivo efficacy over the examples from WO 03/101442. These Examples include, but are not limited to, the following:

[(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide;

[(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide;

[(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide;

[(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide; and ((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide.

PDF IC50 Assay

Enzymatic activity of PDF was measured using a formate dehydrogenase (FDH)-coupled assay [Lazennec and Meinnel (1997) Anal. Biochem. 244, 180-182]. Once formate is released from methionine by PDF, it is oxidized by FDH thereby reducing one molecule of NAD to NADH and resulting in an increase in absorbance at 340 nm. Reactions were initiated by adding PDF to microtiter plates containing all other reaction components and were continuously monitored for 20 min at 25° C. The final reaction composition for the *Staphylococcus aureus* PDF (SaPDF) assay was 50 mM potassium phosphate, pH 7.6, 5 units/mL FDH, 7 mM NAD, 5% DMSO, 1 nM SaPDF, and 2.9 mM formyl-Met-Ala-Ser in 50 µL total volume. Serial dilutions of inhibitors were performed in DMSO. Reagents and assay format were identical for *Haemophilus influenzae* PDF except that formyl-Met-Ala-Ser was 6 mM final. In the *Streptococcus pneumoniae* PDF assay, reaction conditions were similar but contained 30 pM enzyme, 2 mM NAD and 4 mM formyl-Met-Ala-Ser. The varying formyl-Met-Ala-Ser concentrations reflect $K_M$ values for substrate using the different PDF isozymes. $IC_{50}$s were determined by fitting to the equation: % Inhibition=100/ 1+$(IC_{50}/[I])^s$, where s is a slope factor, I is the inhibitor concentration and the $IC_{50}$ is the concentration of compound that causes 50% inhibition.

Results

Examples 1-281 inhibit *S. aureus*, *H. influenzae* and *S. pneumoniae* PDF activities with IC50s≦100 nM.

Antimicrobial Activity Assay

Whole-cell antimicrobial activity was determined by broth microdilution using the Clinical and Laboratory Standards Institute (CLSI, formerly NCCLS) recommended methodology (NCCLS Document M7-A6, "Methods for Dilution Susceptibility Tests for Bacteria that Grow Aerobically—Approved Standard Sixth Edition", 2003). Compounds were tested in serial two-fold dilutions ranging from 64 to 0.06 µg/mL. A panel of 12 strains was evaluated in the assay. This panel consisted of the following laboratory strains: *Staphylococcus aureus* Oxford, *Staphylococcus aureus* WCUH29, *Enterococcus faecalis* 1, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* Ery2, *Escherichia coli* 7623 (AcrABEFD+) and *Escherichia coli* 120 (AcrAB−). The minimum inhibitory concentration (MIC) was determined as the lowest concentration of compound that inhibited visible growth. A mirror reader was used to assist in determining the MIC endpoint.

Results

Each of the Examples 1-281 have a minimal inhibitory concentration (MIC)≦4 µg/mL against at least one of the organisms listed above. For at least one strain of every organism listed above, at least one example had an MIC≦4 µg/mL, with the exception of *Enterococcus faecalis* 1, and *Enterococcus faecalis* 7, for which most examples had MICs≧16 µg/mL.

Antimicrobial Activity data (MIC's in µg/mL) for specific Examples is given in Table 2.

TABLE 2

| Organism | Example 24* μg/ml | Example 63* μg/ml | Example 109 μg/ml | Example 172 μg/ml | Example 275 μg/ml |
|---|---|---|---|---|---|
| S. aureus Oxford | 2 | 1 | 2 | 1, 2 | 2, 4 |
| S. aureus WCUH29 | 0.375 | 0.5 | 0.5 | 0.5 | 0.5, 1 |
| E. faecalis I | 48 | 16 | 64, >64 | 16 | 32, 64 |
| E. faecalis 7 | 32 | 64 | >64 | 8, 64 | 16, 64 |
| H. influenzae Q1 | 0.5 | 0.25 | 0.5 | 1, 2 | 0.5, 1 |
| H. influenzae NEMC1 | 1 | 0.5 | 1 | 1, 2 | 1 |
| M. catarrhalis 1502 | 0.375 | 0.125 | 0.25 | ≦0.06, 0.125 | 0.25 |
| S. pneumoniae 1629 | 0.75 | 0.5 | 0.5 | 0.5 | 1 |
| S. pneumoniae N1387 | 0.5 | 0.25 | 0.25 | 0.125 | 0.5 |
| S. pneumoniae ERY2 | 0.375 | 0.25 | 0.25 | 0.125-0.25 | 0.5 |
| E. coli 7623 AcrABEFD+ | 16 | 4 | 8 | 4, 16 | 4, 16 |
| E. coli 120 AcrAB− | 0.1875 | 0.25 | ≦0.06, 0.125 | 0.125-0.5 | ≦0.06, 0.5 |
| Number of times entire panel of 12 strains was run | 6 | 13 | 2 | 2 | 2 |

*MIC data is expressed as the median of all results obtained

Animal Models of Infection

All procedures were performed in accordance with protocols approved by the GSK Institutional Animal Care and Use Committee, and meet or exceed the standards of the American Association for the Accreditation of Laboratory Animal Care (AAALAC), the United States Department of Health and Human Services and all local and federal animal welfare laws.

Rat respiratory tract infection (RTI) model with *H. influenzae* or *S. pneumoniae*. In this model, anesthetized rats (male Sprague Dawley [Cr1:CD (SD] 100 g) (Charles River) were infected by intrabronchial instillation of 2–3×10$^6$ bacterial CFU/rat in 100 μL of agar directly into the lungs [G. Smith (1991) Lab Animals vol 25, 46-49]. Animals (n=6 per group) were dosed with different amounts of compound (2-fold dilution ranging from 37.5 to 300 mg/kg) by oral gavage twice daily for 4 days starting 1 h after infection. Control animals were dosed with diluent on the same schedule. The rats were euthanized 96 h post infection and the lungs removed aseptically and homogenized in 1 mL of sterile saline with a stomacher machine. Ten fold serial dilutions were done in sterile saline to enumerate viable bacteria numbers. This rat lung infection model has been shown to be able to predict human efficacy in community-acquired pneumonia (CAP) caused by *S. pneumoniae* [Hoover J. L., C. Mininger, R. Page, R. Straub, S. Rittenhouse, and D. Payne. (2007). Abstract A-17. Proceedings of the 47th ICAAC, Chicago, Ill.].

Murine groin *S. aureus* abscess model of skin and soft tissue infection (SSTI). In this model, anesthetized mice (male CD1, 20 g) (Charles River) were infected with *S. aureus* in semi-solid agar (1×10$^6$ CFU/mouse) subcutaneously in the groin area (Jarvest, R. L., Berge, J. M., Berry, V., Boyd, H. F., Brown, M. J., Elder, J. S., Forrest, A. K., Fosberry, A. P., Gentry, D. R., Hibbs, M. J., Jaworski, D. D., O'Hanlon, P. J., Pope, A. J., Rittenhouse, S. Sheppard, R. J., Slater-Radosti, C. and Worby, A. (2002) J. Med Chem., 45, 1959-1962). The animals (n=6 per group) were dosed with different amounts of compound (2-fold dilution ranging from 37.5 to 300 mg/kg) by oral gavage twice daily starting 1 h after infection. Control animals were dosed with diluent on the same schedule. Mice are euthanized 96 h post infection and the abscesses are aseptically removed and homogenized. Ten fold serial dilutions were done in sterile saline to enumerate viable bacteria numbers.

Results

Some of the Examples described herein have demonstrated oral efficacy in one or more of the above animal models of infection, reducing the amount of bacteria recovered from lungs or abscesses, with respect to the untreated control animals, by ≧3 log$_{10}$ CFU/mL.

Compositions

The compounds of the invention will normally, but not necessarily, be formulated into pharmaceutical compositions prior to administration to a patient. Accordingly, in another aspect, the invention is directed to pharmaceutical compositions comprising a compound of the invention and one or more pharmaceutically acceptable excipients.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 25 mg to 1.5 g, suitably 100 to 500 mg, of compound of the invention.

The pharmaceutical compositions of the invention typically contain one compound of the invention. However, in certain embodiments, the pharmaceutical compositions of the invention may contain more than one compound of the invention. For example, in certain embodiments the pharmaceutical compositions of the invention may contain two compounds of the invention. In addition, the pharmaceutical compositions of the invention may optionally further comprise one or more additional pharmaceutically active compounds.

As used herein, "pharmaceutically acceptable excipient" means a pharmaceutically acceptable material, composition or vehicle that, for example, are involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically acceptable excipients may be chosen for a particular function that they may serve in the composition. For example, certain pharmaceutically-acceptable excipients may be chosen for their ability to facilitate the production of uniform dosage forms. Certain pharmaceutically acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or another portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to parenteral administration. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

In another aspect, the invention is directed to a pharmaceutical composition comprising [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide, or a pharmaceutically acceptable salt thereof, and a pharmaceutically acceptable excipient. Suitably [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide, or a pharmaceutically acceptable salt thereof, may be formulated for oral administration, suitably in a liquid or tablet form, or for patenteral administration.

In another aspect, the invention is directed to a pharmaceutical composition comprising [(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide, or a pharmaceutically acceptable salt thereof, and a pharmaceutically acceptable excipient. Suitably [(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide, or a pharmaceutically acceptable salt thereof, may be formulated for oral administration, suitably in a liquid or tablet form, or for patenteral administration.

In another aspect, the invention is directed to a pharmaceutical composition comprising [(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide, or a pharmaceutically acceptable salt thereof, and a pharmaceutically acceptable excipient. Suitably [(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide, or a pharmaceutically acceptable salt thereof, may be formulated for oral administration, suitably in a liquid or tablet form, or for patenteral administration.

In another aspect, the invention is directed to a pharmaceutical composition comprising [(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide, or a pharmaceutically acceptable salt thereof, and a pharmaceutically acceptable excipient. Suitably [(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide, or a pharmaceutically acceptable salt thereof, may be formulated for oral administration, suitably in a liquid or tablet form, or for patenteral administration.

In another aspect, the invention is directed to a pharmaceutical composition comprising ((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide, or a pharmaceutically acceptable salt thereof, and a pharmaceutically acceptable excipient Suitably ((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide, or a pharmaceutically acceptable salt thereof, may be formulated for oral administration, suitably in a liquid or tablet form, or for patenteral administration.

Polymorphic Forms

There have been found to be 3 characterized and reproducible polymorphic solid state forms of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. These three forms are Form 1, Form 2, and Form 3.

Form 1 is a crystalline form which may be produced from a slurry of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide in ethers, acetates, ketones, longer chain alcohols, and other solvent systems (for example, nitromethane, acetonitrile, 2-butanone, methyl acetate, ethyl acetate, diethyl ether, heptane, dimethyl carbonate, t-butyl ethyl ether, 1-methoxy-2-propanol, 2-methoxyethyl ether, chloroform, chlorobenzene, tetrahydrofuran, toluene, cyclohexane, and cyclohexanone).

A solvated form has been analytically observed for [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide in ethyl acetate. Desolvation of the ethyl acetate solvate may be accomplished by vacuum filtration, and results in Form 1.

Form 2 is a crystalline form which may be produced from a slurry of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide in water.

Form 3 is a crystalline form which may be produced from a slurry of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide in neat, small alcohol solvent systems, such as methanol, 1-propanol, and 1-butanol. These alcohols must contain little to no water content to avoid production of Form 2, although the exact water content threshold has not been established. Heating Form 1 to above 132° C. (but not greater than ~185° C. which would lead to decomposition of the compound) causes an exothermic solid state form conversion of Form 1 to Form 3.

The invention provides [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide Form 1, Form 2, or Form 3 in substantially pure form. The invention further provides for mixtures of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide which comprise two or more of Form 1, Form 2, and Form 3. In one embodiment the mixture may include both Form 1 and Form 2. The composition may comprise from 1, 2, 3, 4, 5, 10, 15, 20, 25, 30, 35, 40, 45, 50, 55, 60, 70, 75, 80, 85, 90, 95, 97 or greater than about 99 percent of either Form 1 or Form 2. In another embodiment the mixture may comprise both Form 2 and Form 3. The composition may comprise from 1, 2, 3, 4, 5, 10, 15, 20, 25, 30, 35, 40, 45, 50, 55, 60, 70, 75, 80, 85, 90, 95, 97 or greater than about 99 percent of either Form 2 or Form 3. In another embodiment the mixture may comprise both Form 1 and Form 3. In another embodiment the mixture may comprise 1, 2, 3, 4, 5, 10, 15, 20, 25, 30, 35, 40, 45, 50, 55, 60, 70, 75, 80, 85, 90, 95, 97 or greater than about 99 percent of either Form 1 or Form 3.

In one embodiment of the invention a composition may comprise from 1, 2, 3, 4, 5, 10, 15, 20, 25, 30, 35, 40, 45, 50, 55, 60, 70, 75, 80, 85, 90, 95, 97 or greater than about 99 percent of an individual polymorphic form, be it Form 1, Form 2, or Form 3.

Another embodiment of the invention is the polymorph Form 1, Form 2, or Form 3 in substantially pure crystalline form.

As is known, the crystalline state of a compound can be described by several crystallographic parameters: unit cell dimensions, space groups, and atomic position of the atoms in the compound relative to the origin of its unit cell. These parameters are experimentally determined by crystal x-ray analysis. It is possible for a compound to form more than one type of crystal. These different crystalline forms are called polymorphs.

Form 1, Form 2, and Form 3 may be differentiated by X-Ray powder diffraction (XRPD) of the solid state forms, as shown herein in FIGS. 6 to 8 for Forms 1 to 3 respectively. FT-IR, FT-Raman, Differential Scanning Calorimetry (DSC), and Thermogravimetric Analysis (TGA) data may also be used to assist in differentiation of the solid state forms as are shown and described herein.

Characteristic powder X-ray diffraction pattern peak positions are reported for polymorphs in terms of the angular positions (two theta) with an allowable variability, generally of about 0.1+/−°2-theta. The entire pattern, or most of the pattern peaks may also shift by about 0.1+/−° due to difference in calibration, setting, and other variations from instrument to instrument and from operator to operator.

The XRPD data described herein was acquired on a Bruker AXS PXRD General Area Detector Diffraction system using methods as described herein. Characteristic XRPD angles and d-spacings are recorded in Table 1 below.

Polymorphic Form 1 may therefore be characterized by any one, any two, any three, any four, or any five or more of the 2-theta angle peaks.

Polymorphic Form 2 may therefore be characterized by any one, any two, any three, any four, or any five or more of the 2-theta angle peaks.

Polymorphic Form 3 may therefore be characterized by any one, any two, any three, any four, or any five or more of the 2-theta angle peaks.

Similar characterizations of any one, any two, any three, any four, or any five or more may also be attributed to the d-spacing/angstroms as shown in Table 1 below.

TABLE 1

| Form 1 | | Form 2 | | Form 3 | |
|---|---|---|---|---|---|
| 2θ | d-spacing/Å | 2θ | d-spacing/Å | 2θ | d-spacing/Å |
| 4.1 | 21.8 | 7.8 | 11.3 | 6.1 | 14.5 |
| 6.1 | 14.5 | 9.5 | 9.3 | 7.5 | 11.7 |
| 6.9 | 12.8 | 12.3 | 7.2 | 8.2 | 10.8 |
| 8.1 | 10.9 | 13.2 | 6.7 | 9.1 | 9.7 |
| 9.5 | 9.3 | 15.6 | 5.7 | 12.0 | 7.4 |
| 11.2 | 7.9 | 18.3 | 4.8 | 12.8 | 6.9 |
| 12.9 | 6.9 | 19.0 | 4.7 | 13.4 | 6.6 |
| 13.8 | 6.4 | 20.6 | 4.3 | 16.0 | 5.6 |
| 15.6 | 5.7 | 21.4 | 4.1 | 23.3 | 3.8 |
| 18.3 | 4.8 | 26.7 | 3.3 | 27.6 | 3.2 |

The FT-IR spectrum of the solid forms was recorded using a Thermo Magna MidIR system using methods as described herein. Slight variations in observed peaks are expected based on the specific spectrometer employed and the analyst's sample preparation technique. Some margin of error is present in each of the peak assignments reported below. The margin of error in the peak assignments is approximately +/−1 cm$^{-1}$.

Form 1 IR peaks were observed at: 1035+/−1 cm$^{-1}$, 1059+/−1 cm$^{-1}$, 1114+/−1 cm$^{-1}$, 1155+/−1 cm$^{-1}$, 1173+/−1 cm$^{-1}$, 1347+/−1 cm$^{-1}$, 1416+/−1 cm$^{-1}$, 1443+/−1 cm$^{-1}$, 1603+/−1 cm$^{-1}$, and 1656+/−1 cm$^{-1}$. Suitably, Form 1 exhibits these characteristic peaks of any one, any two, any three, any four, or any five or more peaks.

Form 2 IR peaks were observed at: 1036+/−1 cm$^{-1}$, 1114+/−1 cm$^{-1}$, 1152+/−1 cm$^{-1}$, 1172+/−1 cm$^{-1}$, 1310+/−1 cm$^{-1}$, 1414+/−1 cm$^{-1}$, 1441+/−1 cm$^{-1}$, 1570+/−1 cm$^{-1}$, 1601+/−1 cm$^{-1}$, and 1662+/−1 cm$^{-1}$. Suitably, Form 2 exhibits these characteristic peaks of any one, any two, any three, any four, or any five or more peaks.

Figure 1:
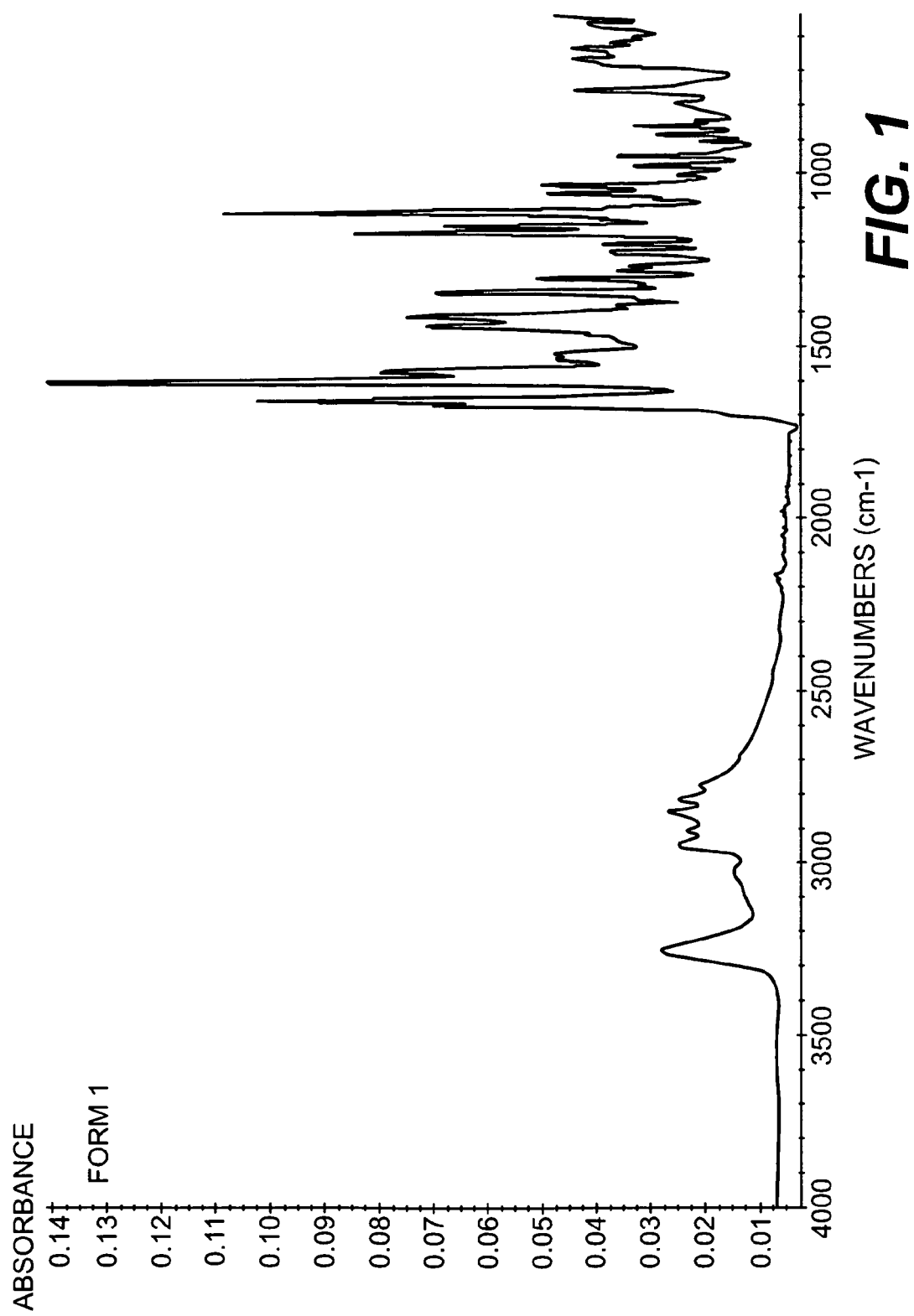
FIG. 1 provides a FT-IR spectrum of polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in cm$^{-1}$ and the y-axis is absorbance.
Figure 2:
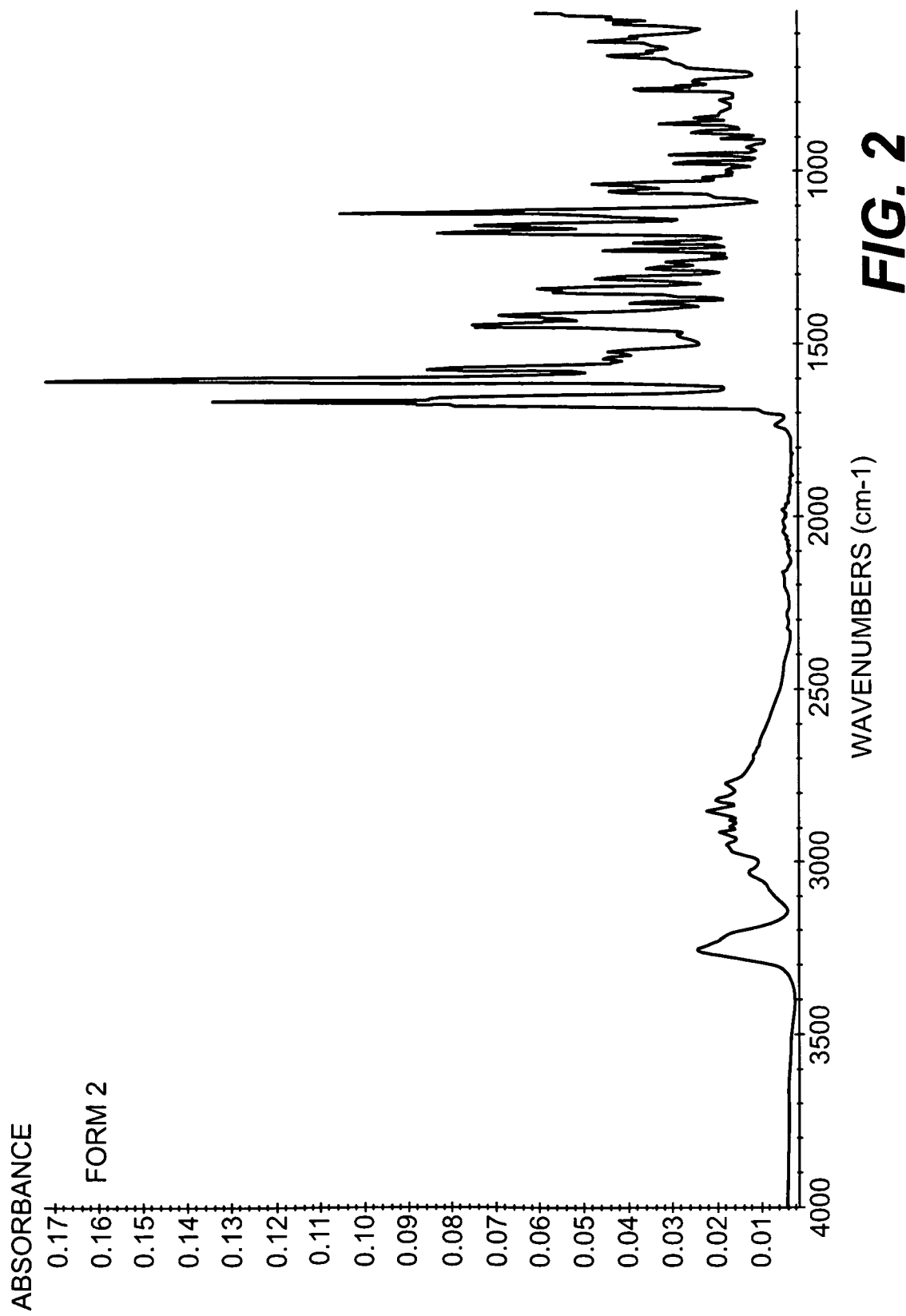
FIG. 2 provides a FT-IR spectrum of polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in cm$^{-1}$ and the y-axis is absorbance.

The IR data for Forms 1 and 2 are illustrated in FIGS. 1 and 2 respectively.

The FT-Raman spectrum of the solid forms was recorded using a Thermo FT-Raman System 960 Spectrometer using methods as described herein. Slight variations in observed peaks are expected based on the specific spectrometer employed and the analyst's sample preparation technique. Some margin of error is present in each of the peak assignments reported below. The margin of error in the peak assignments is approximately +/−1 cm$^{-1}$.

Form 1 Raman peaks were observed at: 506+/−1 cm$^{-1}$, 760+/−1 cm$^{-1}$, 796+/−1 cm$^{-1}$, 884+/−1 cm$^{-1}$, 1180+/−1 cm$^{-1}$, 1305+/−1 cm$^{-1}$, 1449+/−1 cm$^{-1}$, 1606+/−1 cm$^{-1}$, 1674+/−1 cm$^{-1}$, and 2935+/−1 cm$^{-1}$. Suitably, Form 1 exhibits these characteristic peaks of any one, any two, any three, any four, or any five or more peaks.

Form 2 Raman peaks were observed at: 273+/−1 cm$^{-1}$, 483+/−1 cm$^{-1}$, 507+/−1 cm$^{-1}$, 764+/−1 cm$^{-1}$, 847+/−1 cm$^{-1}$, 1179+/−1 cm$^{-1}$, 1228+/−1 cm$^{-1}$, 1446+/−1 cm$^{-1}$, 1673+/−1 cm$^{-1}$, and 2932+/−1 cm$^{-1}$. Suitably, Form 2 exhibits these characteristic peaks of any one, any two, any three, any four, or any five or more peaks.

Form 3 Raman peaks were observed at: 273+/−1 cm$^{-1}$, 506+/−1 cm$^{-1}$, 766+/−1 cm$^{-1}$, 797+/−1 cm$^{-1}$, 1176+/−1 cm$^{-1}$, 1228+/−1 cm$^{-1}$, 1302+/−1 cm$^{-1}$, 1446+/−1 cm$^{-1}$, 1672+/−1 cm$^{-1}$, and 2934+/−1 cm$^{-1}$. Suitably, Form 3 exhibits these characteristic peaks of any one, any two, any three, any four, or any five or more peaks.

Figure 3:
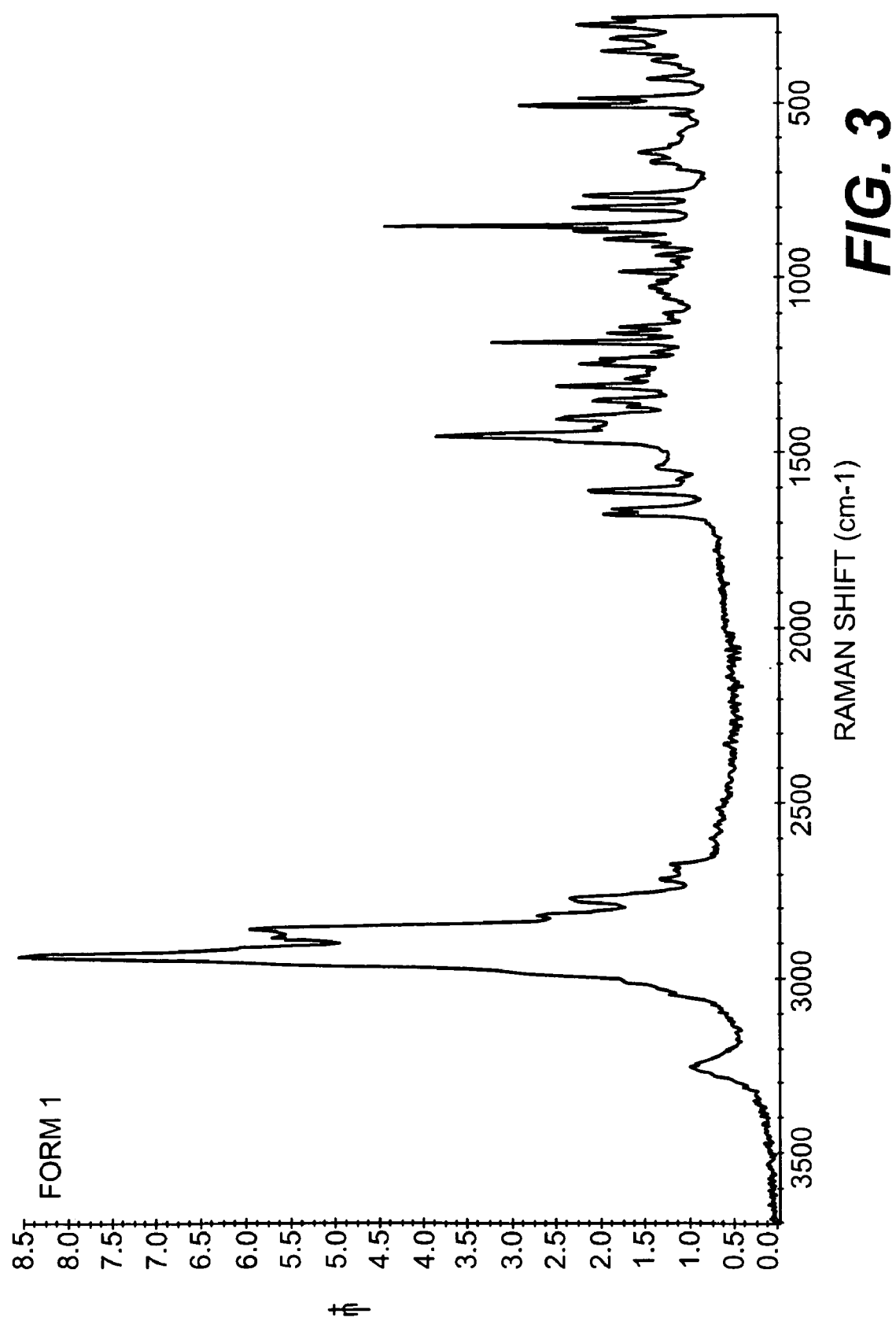
FIG. 3 provides a FT-Raman spectrum of polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in cm$^{-1}$ and the y-axis is intensity.
Figure 4:
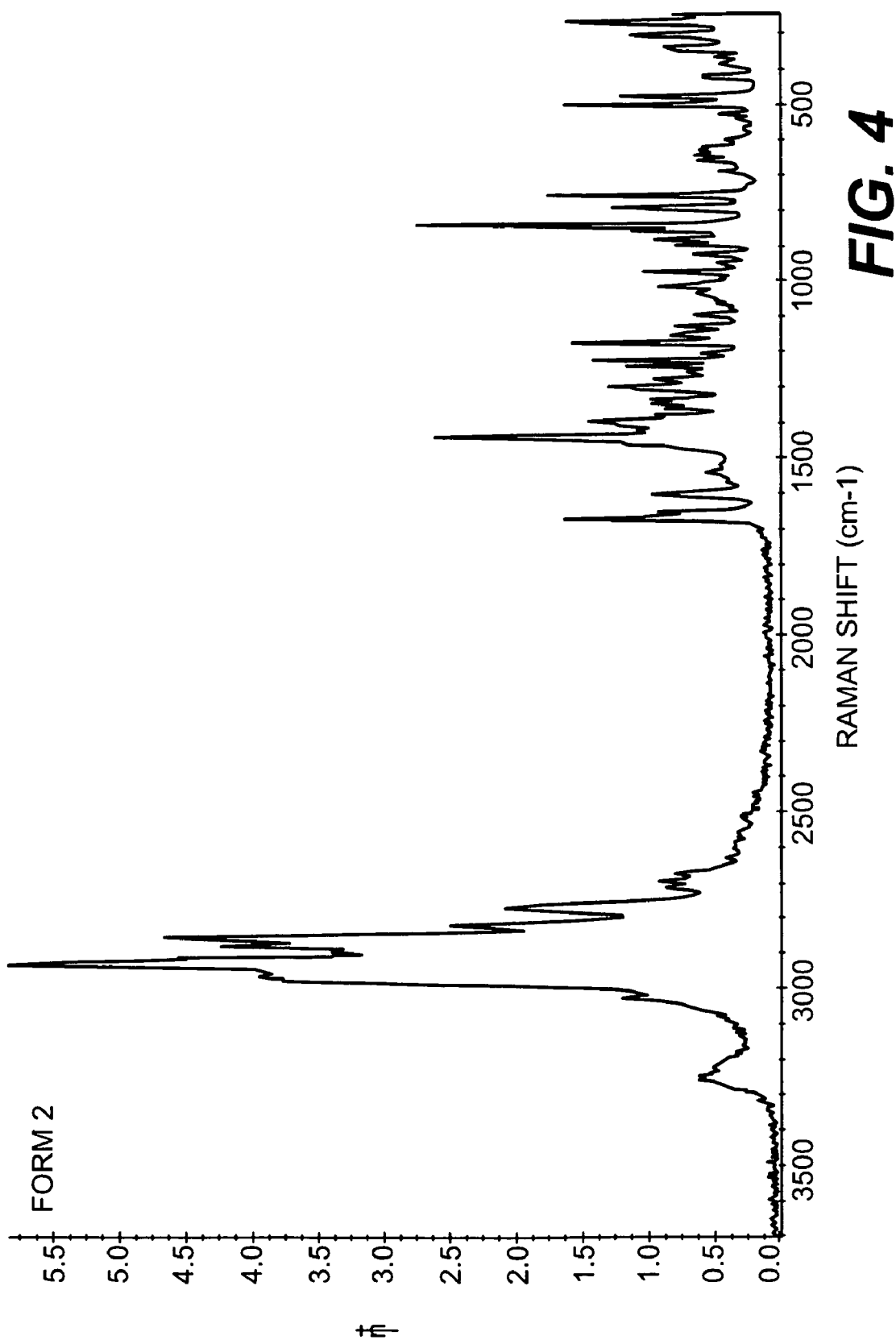
FIG. 4 provides a FT-Raman spectrum of polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide. The x-axis is in cm$^{-1}$ and the y-axis is intensity.
Figure 5:
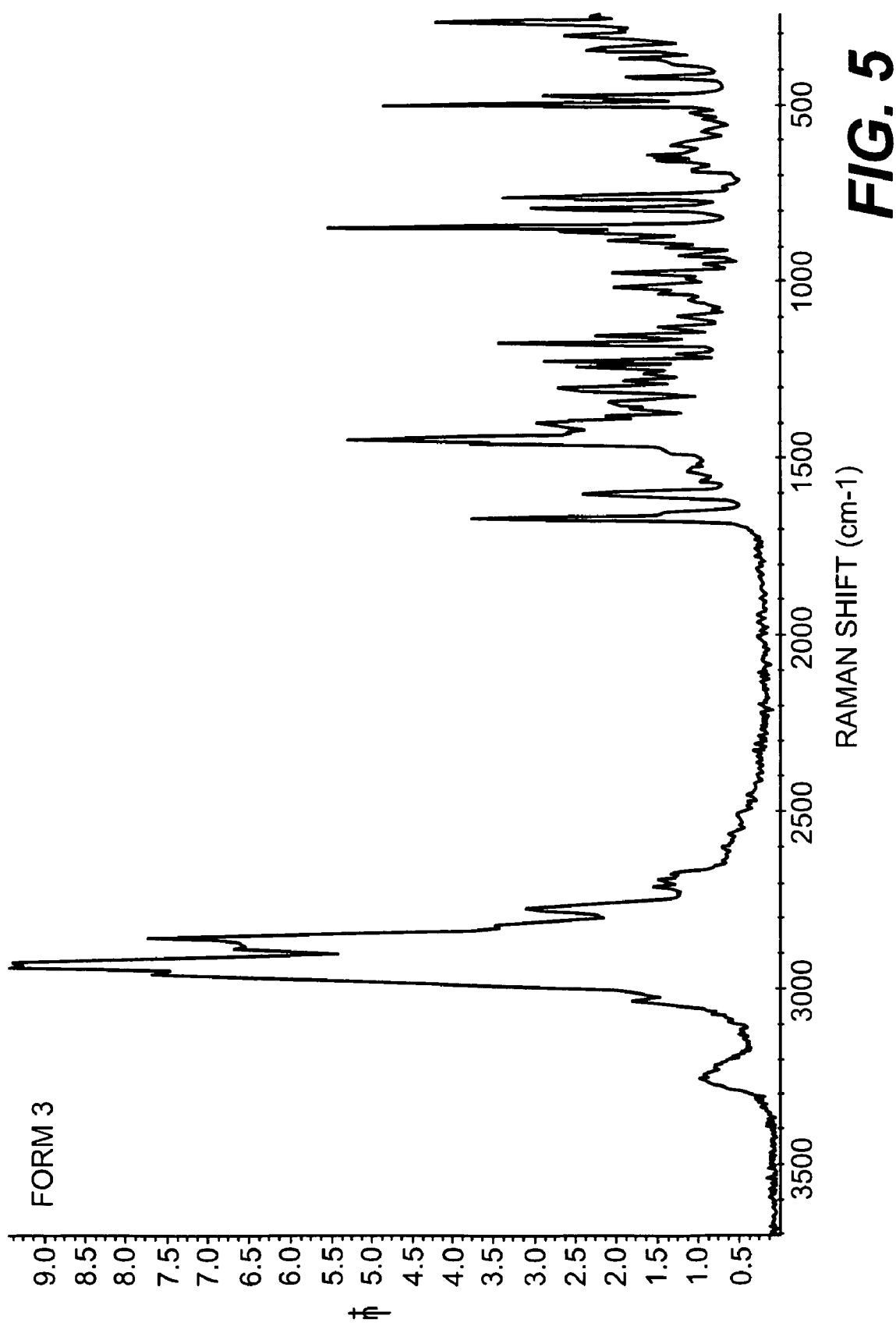
FIG. 5 provides a FT-Raman spectrum of polymorphic Form 3 of [(2R)-2-(Cyclopentylmethyl)-3-(2-{5-fluoro-6-[(9aS)-hexahydropyrazino[2,1-c][1,4]oxazin-8(1H)-yl]-2- methyl-4-pyrimidinyl}hydrazino)-3-oxopropyl]hydroxyformamide. The x-axis is in cm$^{-1}$ and the y-axis is intensity.

The Raman data for Forms 1 to 3 are illustrated in FIGS. 3 to 5 respectively.

The DSC thermogram of the forms was obtained using a TA Instruments Thermal Analysis System, Model DSC Q100 using methods as described herein. The data are illustrated herein as FIGS. 9 to 11 for Forms 1 to 3 respectively.

Forms 1, 2, and 3 had a melt onset measured by DSC at approximately 187° C., 185° C., and 190° C. respectively. With respect to Form 1 (FIG. 9) there was a melt at 132° C. which corresponds to exothermic solid state form conversion of Form 1 to Form 3.

The TGA trace of the forms was obtained using a TA Instruments Thermal Analysis System, Model TGA Q500 using methods described herein. The data are illustrated herein as FIGS. 12-14 for Forms 1 to 3 respectively.

One embodiment of the present invention is the polymorphic form, Form 1, substantially as shown in the X-ray diffraction pattern of FIG. 6, the FT-IR spectrum of FIG. 1, the FT-Raman spectrum of FIG. 3, the DSC thermogram of FIG. 9, and the TGA trace of FIG. 12.

Another embodiment of the present invention is the polymorph Form 1 characterized by an X-ray diffraction pattern comprising peaks expressed in terms of two theta angles wherein the x-ray diffraction pattern comprises peaks at 4.1+/−0.1°, 6.1+/−0.1°, 6.9+/−0.1°, 8.1+/−0.1°, 9.5+/−0.1°, 11.2+/−0.1°, 12.9+/−0.1°, 13.8+/−0.1°, 15.6+/−0.1°, and 18.3+/−0.1°. Suitably Form 1 is characterized by an X-ray diffraction pattern comprising of peaks at 8.1+/−0.1°, 9.5+/−0.1°, 11.2+/−0.1°, 12.9+/−0.1°, 13.8+/−0.1°, and 15.6+/−0.1°.

Another embodiment of the present invention is the polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl] hydroxyformamide wherein said polymorphic form is characterized by an X-ray diffraction pattern comprising peaks expressed in terms of 2 theta angles, wherein:

a. said X-ray diffraction pattern comprises a peak at 4.1+/−0.1°; or b. said X-ray diffraction pattern comprises a peak at 4.1+/−0.1° and 6.1+/−0.1°; or
c. said X-ray diffraction pattern comprises a peak at 4.1+/−0.1°, 6.1+/−0.1°, and 6.9+/−0.1°; or
d. said X-ray diffraction pattern comprises a peak at 4.1+/−0.1°, 6.1+/−0.1°, 6.9+/−0.1°, and 8.1+/−0.1°; or
e. said X-ray diffraction pattern comprises a peak at 4.1+/−0.1°, 6.1+/−0.1°, 6.9+/−0.1°, 8.1+/−0.1°, and 9.5+/−0.1°; or
f. said X-ray diffraction pattern comprises a peak at 4.1+/−0.1°, 6.1+/−0.1°, 6.9+/−0.1°, 8.1+/−0.1°, 9.5+/−0.1°, and 11.2+/−0.1°; or
g. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, and 12.9+/−0.1°; or
h. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, and 13.8+/−0.1°; or
i. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, 13.8+/−0.1°, and 15.6+/−0.1°; or
j. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, 13.8+/−0.1°, 15.6+/−0.1°, and 18.3+/−0.1°.

Another embodiment of the present invention is a pharmaceutical composition comprising Form 1 and a pharmaceutically acceptable excipient.

Another embodiment of the present invention is the polymorphic form, Form 2, substantially as shown in the X-ray diffraction pattern of FIG. 7, the FT-IR spectrum of FIG. 2, the FT-Raman spectrum of FIG. 4, the DSC thermogram of FIG. 10, and the TGA trace of FIG. 13.

Another embodiment of the present invention is the polymorph Form 2 characterized by an X-ray diffraction pattern comprising peaks expressed in terms of two theta angles wherein the x-ray diffraction pattern comprises peaks at 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, 21.4+/−0.1°, and 26.7+/−0.1°. Suitably Form 2 is characterized by an X-ray diffraction pattern comprising of peaks at 7.8+/−0.1°, 9.5+/−0.1°, 12.3+/−0.1°, 13.2+/−0.1°, 15.6+/−0.1°, 18.3+/−0.1°, and 19.0+/−0.1°.

Another embodiment of the present invention is the polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks expressed in terms of 2 theta angles, wherein:
a. said X-ray diffraction pattern comprises a peak at 7.8+/−0.1°; or
b. said X-ray diffraction pattern comprises a peak at 7.8+/−0.1° and 9.5+/−0.1°; or
c. said X-ray diffraction pattern comprises a peak at 7.8+/−0.1°, 9.5+/−0.1°, and 12.3+/−0.1°; or
d. said X-ray diffraction pattern comprises a peak at 7.8+/−0.1°, 9.5+/−0.1°, 12.3+/−0.1°, and 13.2+/−0.1°; or
e. said X-ray diffraction pattern comprises a peak at 7.8+/−0.1°, 9.5+/−0.1°, 12.3+/−0.1°, 13.2+/−0.1°, and 15.6+/−0.1°; or
f. said X-ray diffraction pattern comprises a peak at 7.8+/−0.1°, 9.5+/−0.1°, 12.3+/−0.1°, 13.2+/−0.1°, 15.6+/−0.1°, and 18.3+/−0.1°; or
g. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, and 19.0+/−0.1°; or
h. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, and 20.6+/−0.1°; or
i. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, and 21.4+/−0.1°; or
j. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, 21.4+/−0.1°, and 26.7+/−0.1°.

Another embodiment of the present invention is a pharmaceutical composition comprising Form 2 and a pharmaceutically acceptable excipient.

Another embodiment of the present invention is the polymorphic form, Form 3, substantially as shown in the X-ray diffraction pattern of FIG. 8, the FT-Raman spectrum of FIG. 5, the DSC thermogram of FIG. 11, and the TGA trace of FIG. 14.

Another embodiment of the present invention is the polymorph Form 3 characterized by an X-ray diffraction pattern comprising peaks expressed in terms of two theta angles wherein the x-ray diffraction pattern comprises peaks at 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, 23.3+/−0.1°, and 27.6+/−0.1°. Suitably Form 3 is characterized by an X-ray diffraction pattern comprising of peaks at 7.5+/−0.1°, 8.2+/−0.1°, 9.1+/−0.1°, 12.8+/−0.1°, 13.4+/−0.1°, and 16.0+/−0.1°.

Another embodiment of the present invention is the polymorphic form, Form 3, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks expressed in terms of 2 theta angles, wherein:
a. said X-ray diffraction pattern comprises a peak at 6.1+/−0.1°; or
b. said X-ray diffraction pattern comprises a peak at 6.1+/−0.1° and 7.5+/−0.1°; or
c. said X-ray diffraction pattern comprises a peak at 6.1+/−0.1°, 7.5+/−0.1°, and 8.2+/−0.1°; or
d. said X-ray diffraction pattern comprises a peak at 6.1+/−0.1°, 7.5+/−0.1°, 8.2+/−0.1°, and 9.1+/−0.1°; or
e. said X-ray diffraction pattern comprises a peak at 6.1+/−0.1°, 7.5+/−0.1°, 8.2+/−0.1°, 9.1+/−0.1°, and 12.0+/−0.1°; or
f. said X-ray diffraction pattern comprises a peak at 6.1+/−0.1°, 7.5+/−0.1°, 8.2+/−0.1°, 9.1+/−0.1°, 12.0+/−0.1°, and 12.8+/−0.1°; or
g. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, and 13.4+/−0.1°; or
h. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, and 16.0+/−0.1°; or
i. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, and 23.3+/−0.1°; or
j. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, 23.3+/−0.1°, and 27.6+/−0.1°.

Another embodiment of the present invention is a pharmaceutical composition comprising Form 3 and a pharmaceutically acceptable excipient.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 10% to 80% CH$_3$CN (0.018% TFA) in 3.0 min with a 1.25 min hold and 0.5 min re-equilibration; detection by MS, UV at 214 nm, and a light scattering detector (ELS). Column: 2.1×50 mm Zorbax SB-C8.

For preparative (prep) HPLC; ca. 100 mg of the final products were injected in 1000 µL of MeOH, DMSO, or DMF onto a SunFire Prep C18 OBD 5 um 30×75 mm column at 35 mL/min with a 10 min gradient from 5% CH$_3$CN to 95% CH$_3$CN in H$_2$O, followed by a 90% CH$_3$CN in H$_2$O hold for 1.9 min. Flash chromatography was run over Merck Silica gel 60 (230-400 mesh), or using a Teledyne Isco Combiflash Companion with normal phase, disposable Redi-Sep flash columns.

Intermediate A (2R)-3-Cyclopentyl-2-({formyl[(phenylmethyl)oxy]amino}methyl)propanoic acid

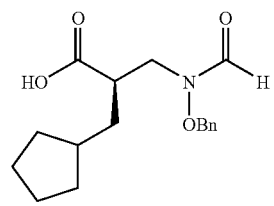

Part A:

(4S)-Benzyl-3-(3-cyclopentylpropanoyl)oxazolidin-2-one

To a solution of (S)-(−)-4-benzyl-2-oxazolidinone (25 g, 141 mmol) in THF (350 mL) at −78° C. was added dropwise n-BuLi (56.4 mL, 2.5M solution in hexane, 141 mmol). After stirring for 60 min at the same temperature, the reaction mixture was then treated with 3-cyclopentylpropionyl chloride (21.6 mL, 141 mmol) over 0.25 h. The reaction mixture was allowed to warm to room temperature and stirred overnight. The reaction was quenched with saturated aqueous NH$_4$Cl solution (320 mL). The aqueous layer was extracted with EtOAc (3×200 mL). The combined organic layers were dried (MgSO$_4$) and evaporated to yield (4S)-benzyl-3-(3-cyclopentylpropanoyl)oxazolidin-2-one as a white solid (42.4 g, 100%). LCMS: (M+H)$^+$: 302.3.

Part B:

(4S)-3-((2R)-3-Cyclopentyl-2-{[(phenylmethyl)oxy]methyl}propanoyl)-4-(phenylmethyl)-1,3-oxazolidin-2-one To a solution of (4S)-benzyl-3-(3-cyclopentylpropanoyl)oxazolidin-2-one (42.4 g, 141 mmol) in dichloromethane (500 mL) at 0° C. under nitrogen was added titanium (IV) chloride (1 M in DCM, 155 mL, 155 mmol) in a slow steady stream. After 5 min, diisopropylethylamine (27 mL, 155 mmol) was added dropwise. After stirring at 0° C. for 1 h, benzyloxymethylchloride (TCI-America) (39 mL, 280 mmol) was added in a slow steady stream to the resulting titanium enolate, and the mixture was maintained at 0° C. for 3.5 h. The reaction mixture was then quenched with water (400 mL). The aqueous layer was extracted with dichloromethane (150 mL×2). The organic extracts were washed with saturated NaHCO$_3$, were dried (MgSO$_4$) and were evaporated. The residue was washed with ether (2×), and then was triturated with hexanes/ether to provide 2 crops of (4S)-3-((2R)-3-cyclopentyl-2-{[(phenylmethyl)oxy]methyl}propanoyl)-4-(phenylmethyl)-1,3-oxazolidin-2-one as a pale yellow solid (42.7 g, 72%). LCMS: (M+H)$^+$: 422.2.

Part C:

(4S)-3-[(2R)-3-Cyclopentyl-2-(hydroxymethyl)propanoyl]-4-(phenylmethyl)-1,3-oxazolidin-2-one A solution of (4S)-3-((2R)-3-cyclopentyl-2-{[(phenylmethyl)oxy]methyl}propanoyl)-4-(phenylmethyl)-1,3-oxazolidin-2-one (42.7 g, 0.1 mol) in ethanol (800 mL) and DMF (180 mL) was subjected to catalytic hydrogenation using 10% Pd/C (4 g) and a balloon of hydrogen. The reaction was 50% complete by LCMS after 24 h. The reaction was purged with nitrogen and a fresh balloon of hydrogen was introduced. After an additional 60 h, the reaction was again purged with nitrogen, was filtered, and the filtrate solvents were removed to provide (4S)-3-[(2R)-3-cyclopentyl-2-(hydroxymethyl)propanoyl]-4-(phenylmethyl)-1,3-oxazolidin-2-one (33.1 g, 100%). LCMS: (M+H)$^+$: 332.3.

Part D:

(2R)-3-Cyclopentyl-2-(hydroxymethyl)propanoic acid (4S)-3-[(2R)-3-Cyclopentyl-2-(hydroxymethyl)propanoyl]-4-(phenylmethyl)-1,3-oxazolidin-2-one (33.1 g, 0.1 mol) was stirred in a mixture of THF (330 mL) and water (55 mL) and cooled to 0° C. 30% Hydrogen peroxide (96 mL, 1 mol) was added, followed by lithium hydroxide monohydrate (8.4 g, 0.2 mol). The reaction was warmed to room temperature, and then stirred overnight. The THF was removed by rotary evaporation. The aqueous residue was washed with dichloromethane (3×100 mL), was acidified with 6N HCl, and was extracted with ethyl acetate (4×100 mL). The organic extracts were dried (MgSO$_4$) and were evaporated to provide (2R)-3-cyclopentyl-2-(hydroxymethyl)propanoic acid as a clear, colorless oil (18.5 g, >100%). LCMS: (M+H)$^+$: not detected. $^1$H NMR (400 MHz, CDCl$_3$): δ 7.3 (br s, 1H), 3.79 (d, J=5.83 Hz, 2H), 2.64-2.71 (m, 1H), 1.45-1.87 (m, 9H), 1.05-0.14 (m, 2H).

Part E:

(2R)-3-Cyclopentyl-2-(hydroxymethyl)-N-[(phenylmethyl)oxy]propanamide

To a mixture of (2R)-3-cyclopentyl-2-(hydroxymethyl) propanoic acid (18.3 g, 106 mmol), O-benzyl hydroxyamine hydrochloride (18.62 g, 117 mmol) and 4-(dimethylamino) pyridine (28.5 g, 233 mmol) in dichloromethane (110 mL) at 0° C. was added 1-[3-(dimethylamino)propyl]-3-ethylcarbodiimide hydrochloride (22.3 g, 117 mmol). The mixture was maintained at 0° C. for 3 h. After this time, 500 mL of 1N cold, aqueous HCl solution was added, and the mixture was stirred for another 30 min. The resulting white solid precipitate was collected by filtration. The precipitate was washed with 1N HCl, with water, and with cold DCM. Drying overnight in a vacuum dessicator provided (2R)-3-cyclopentyl-2-(hydroxymethyl)-N-[(phenylmethyl)oxy]propanamide (19.1 g, 65%). LCMS: (M+H)$^+$: 278.1.

Part F:

(3R)-3-(Cyclopentylmethyl)-1-[(phenylmethyl)oxy]-2-azetidinone

To a mixture of (2R)-3-cyclopentyl-2-(hydroxymethyl)-N-[(phenylmethyl)oxy]propanamide (22.5 g, 81 mmol) and triphenylphosphine (22.5 g, 97 mmol) in THF (800 mL) at 0° C. was added dropwise diisopropyl azodicarboxylate (18.9 mL, 97 mmol). The reaction mixture was maintained at 0° C. for 45 min and was then evaporated. Purification by chromatography on silica gel using an eluting system of hexane/EtOAc (95:5) provided (3R)-3-(cyclopentylmethyl)-1-[(phenylmethyl)oxy]-2-azetidinone (16.9 g, 81%). LCMS: (M+H)$^+$: 260.1.

Part G:

(2R)-3-Cyclopentyl-2-({[(phenylmethyl)oxy] amino}methyl)propanoic acid

A mixture of (3R)-3-(cyclopentylmethyl)-1-[(phenylmethyl)oxy]-2-azetidinone (20 g, 77.1 mmol) and LiOH.H$_2$O (32.4 g, 0.77 mol) in THF/water (500 mL/170 mL) was stirred at room temperature for 36 h. To the reaction mixture was added 6M HCl (130 mL), and then 1 N NaOH was added until a neutral pH was obtained. The layers were separated, and the aqueous layer was extracted once with EtOAc. The combined organics were dried (MgSO$_4$) and concentrated to provide (2R)-3-cyclopentyl-2-({[(phenylmethyl)oxy] amino}methyl)propanoic acid (22.85 g, >100%) as a clear, colorless oil. LCMS: (M+H)$^+$: 277.9.

Part H:

(2R)-3-Cyclopentyl-2-({formyl[(phenylmethyl)oxy] amino}methyl)propanoic acid

Under a nitrogen atmosphere, formic acid (192 mL, 5 mol) was dissolved in CH$_2$Cl$_2$ (450 mL) and cooled to 0° C. Acetic anhydride (73 mL, 0.77 mol) was then added, and the reaction mixture was stirred for 45 min. After this time, a solution of (2R)-3-cyclopentyl-2-({[(phenylmethyl)oxy] amino}methyl)propanoic acid (22.85 g crude material, assumed 77.1 mmol) in CH$_2$Cl$_2$ (450 mL) was added, and the resulting mixture was stirred for 1.5 h at 0° C. The volatiles were then removed, the crude residue was dissolved in EtOAc (500 mL), and the mixture was washed with brine (4×100 mL). The organics were dried (MgSO$_4$) and concentrated to provide (2R)-3-cyclopentyl-2-({formyl[(phenylmethyl)oxy] amino}methyl)propanoic acid (23.5 g, 100%) as a thick syrup. LCMS: (M+H)$^+$: 306.1.

The (2R)-3-cyclopentyl-2-({formyl[(phenylmethyl)oxy] amino}methyl)propanoic acid, diisopropylethylamine salt, isopropanol solvate can be prepared in the following manner:

To a solution of (2R)-3-cyclopentyl-2-({formyl[(phenylmethyl)oxy]amino}methyl)propanoic acid (25.9 h, 85 mmol) in diethyl ether (85 mL) was added diisopropylethylamine (19.7 mL, 113 mmol), and the mixture was stirred at room temperature for approximately 3 h. The reaction mixture was then diluted with additional diethyl ether (85 mL) and water (400 mL). The layers were separated, and the organic layer was extracted two more times with a water/brine mixture (250 mL water with 30 mL brine added and 200 mL water with 30 mL brine added). The combined aqueous layers were then extracted with 40% isopropanol in chloroform (3×300 mL). The combined isopropanol/chloroform layers were dried (Na$_2$SO$_4$), filtered and evaporated to provide the 2(R)-3-cyclopentyl-2-({formyl[(phenylmethyl)oxy]amino}methyl) propanoic acid, diisopropylethylamine salt, isopropanol solvate (30.29 g) as a clear beige oil. LCMS: (M+H)$^+$: 306.2.

Intermediate B (2R)-3-Cyclopentyl-2-{[formyl(tetrahydro-2H-pyran-2-yloxy)amino]methyl}propanoic acid

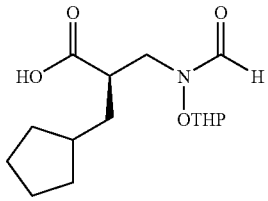

Part A:

(3R)-3-(Cyclopentylmethyl)-1-(tetrahydro-2H-pyran-2-yloxy)-2-azetidinone (3R)-3-(Cyclopentylmethyl)-1-[(phenylmethyl)oxy]-2-azetidinone (100 g, 386 mmol) was dissolved in ethanol (1.2 L), and the solution was degassed. Pd on C (10%, dry, 8 g) was added and the suspension was purged with hydrogen and stirred under a hydrogen atmosphere (balloon) until the reaction was complete by LC-MS (approximately 6 h). The suspension was then sparged with nitrogen, filtered through Celite, and evaporated to dryness. The resulting solid was redissolved in $CH_2Cl_2$ (1 L) and dihydropyran (70 mL, 767 mmol) was added, followed by pyridinium p-toluenesulfonate (PPTS, 5%, 4.85 g). The reaction mixture was stirred 3 days at room temperature, then concentrated and chromatographed on silica gel using 10-20% ethyl acetate in hexanes to provide (3R)-3-(Cyclopentylmethyl)-1-(tetrahydro-2H-pyran-2-yloxy)-2-azetidinone as a colorless liquid (100%).

Part B:

(2R)-3-Cyclopentyl-2-{[(tetrahydro-2H-pyran-2-yloxy)amino]methyl}propanoic acid (3R)-3-(Cyclopentylmethyl)-1-(tetrahydro-2H-pyran-2-yloxy)-2-azetidinone (68 g, 268 mmol) was dissolved in THF (1 L) and placed in a 3-necked 3 L round bottomed flask that had been fitted with an internal thermocouple, reflux condenser, and a mechanical stirrer. A solution of lithium hydroxide monohydrate (56.3 g, 1.34 mol) in 400 mL $H_2O$ was prepared and added dropwise via the addition funnel, with vigorous stirring. The reaction mixture was stirred at room temperature for 36 h before being diluted with $H_2O$ (350 mL) and washed with hexanes (300 mL). The organic layer was extracted with $H_2O$ (100 mL) and the combined aqueous layers were cooled to 0° C. and carefully acidified with 2M citric acid (~525 mL) drop wise over the course of 90 min, keeping the internal temperature below 10° C. The acidified material was extracted with ethyl acetate (3×250 mL) and the combined organic layers were washed with water (2×), dried over $MgSO_4$, filtered, and evaporated. Benzene (500 mL) was added and evaporated, and the residue was dried in vacuo to obtain (2R)-3-cyclopentyl-2-{[(tetrahydro-2H-pyran-2-yloxy)amino]methyl}propanoic acid (70.9 g, 98%) as a colorless liquid.

Part C:

(2R)-3-Cyclopentyl-2-{[formyl(tetrahydro-2H-pyran-2-yloxy)amino]methyl}propanoic acid To a solution of (2R)-3-cyclopentyl-2-{[(tetrahydro-2H-pyran-2-yloxy)amino]methyl}propanoic acid (97.05 g, 358 mmol) in acetone (1.1 L) at room temperature was added 5-methyl-2-thioxo-[1,3,4]thiadiazole-3-carbaldehyde (57.3 g, 358 mmol) (Tetrahedron Lett. 1985, 26, 3703-3706). When the reaction was deemed complete, the acetone was removed in vacuo. The residue was suspended in a mixture of hexanes (320 mL) and methyl-t-butyl ether (180 mL), then sonicated. After 10 min, the white solid (presumably 5-methyl-3H-[1,3,4]thiadiazole-2-thione) was filtered off, and the filtrate was evaporated in vacuo to give (2R)-3-cyclopentyl-2-{[formyl(tetrahydro-2H-pyran-2-yloxy)amino]methyl}propanoic acid as a pale yellow gum (124 g, >100%). NMR shows the product contains a small amount of MTBE and 5-methyl-3H-[1,3,4]thiadiazole-2-thione.

(2R)-3-Cyclopentyl-2-{[formyl(tetrahydro-2H-pyran-2-yloxy)amino]methyl}propanoic acid can also be prepared according to literature procedures [Bracken, Bushell, Dean, Francavilla, Jain, Lee, Seepersaud, Shu, Sundram, Yuan; PCT Int. Appl. (2006), WO 2006127576 A2].

The (2R)-3-cyclopentyl-2-{[formyl(tetrahydro-2H-pyran-2-yloxy)amino]methyl}propanoic acid, diisopropylethylamine salt can be prepared in the following manner:

A solution of (2R)-3-cyclopentyl-2-{[(tetrahydro-2H-pyran-2-yloxy)amino]methyl}propanoic acid (39.45 g, 145 mmol) in methyl formate (300 mL) and diisopropylethylamine (27.9 mL, 160 mmol) was placed in a sealed tube and heated to 50° C. for 4 days. After cooling to room temperature, the methyl formate was removed in vacuo, and the remaining residue was dissolved in diethyl ether. The ether solution was extracted with water, and the layers were separated. The aqueous layer was then back-extracted with a solution of 40% isopropanol in chloroform (2×). The combined isopropanol/chloroform layers were then concentrated in vacuo to provide (2R)-3-cyclopentyl-2-{[formyl(tetrahydro-2H-pyran-2-yloxy)amino]methyl}propanoic acid as the diisopropylethyl amine salt (28 g, containing a residual amount of chloroform and isopropanol).

Intermediate C 4,6-Dichloro-5-fluoro-2-methylpyrimidine

Part A:

5-Fluoro-4,6-dihydroxy-2-methylpyrimidine

A solution of 200 mL of 25% wt sodium methoxide in methanol (0.84 mol) was diluted with an additional 200 mL of methanol. Acetamidine-HCl (40 g, 0.42 mol) was added to the sodium methoxide solution (white precipitate formed), followed by addition of dimethyl fluoromalonate (70 g, 0.46 mol). The contents were stirred at room temperature overnight, then concentrated in vacuo to dryness. The resulting residue was redissolved in hot water (300 mL). After cooling the aqueous solution to room temperature, concentrated HCl was added slowly until crystal formation (fine white prisms) took place at about pH 5. Concentrated HCl was added dropwise until pH 3, and then the contents were filtered. The isolated crystals were rinsed with 1M HCl and dried under vacuum to provide 5-fluoro-4,6-dihydroxy-2-methylpyrimidine (65.5 g, >100%). LCMS: (M+H)+: 145.

Part B:

4,6-Dichloro-5-fluoro-2-methylpyrimidine

5-Fluoro-4,6-dihydroxy-2-methylpyrimidine (assumed 60 g, 0.42 mol) was treated with 300 mL of POCl$_3$ at 120° C. for 3 h. The reaction mixture was then cooled to room temperature and concentrated in vacuo until the rate of solvent removal slowed to a drop rate of less than 1 drop/second. The product is somewhat volatile and excessive concentration in vacuo will reduce the yield. The crude residue was poured over crushed ice, and the resulting slurry was stirred for 1 h, during which time the solution came to room temperature. A yellow solid formed which was filtered off, washed with water, and air dried briefly until free flowing. This solid was collected and placed in a dessicator over P$_2$O$_5$ until dry, providing pure 4,6-dichloro-5-fluoro-2-methylpyrimidine (59 g, 79%). LCMS: (M+H)+: 181/183.

Intermediate D 4,6-Dichloro-2-ethyl-5-fluoropyrimidine

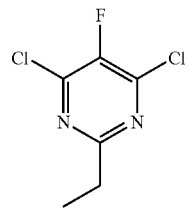

Part A:

2-Ethyl-5-fluoro-6-hydroxy-4(1H)-pyrimidinone

Propionamide hydrochloride salt (30.0 g, 276.3 mmol) and dimethyl fluoromalonate (41.4 g, 276.3 mmol) in anhydrous methanol (400 mL) were treated with solid NaOMe (45 g, 829 mmol) portion-wise at room temperature. After the addition, the white suspension was heated to 85° C. and stirred for 2 h. The solvent was then evaporated to dryness. To the residue was added 70 mL of 6 N HCl solution with vigorous stirring. The suspension was stirred for 10 min until the residue was fully neutralized. The white precipitate was collected by filtration and dried over vacuum to give 2-ethyl-5-fluoro-6-hydroxy-4(1H)-pyrimidinone as a white solid. LCMS: (M+H)+: 159.0; (M+Na)+:181.1. In some cases, this product may contain co-precipitated NaCl, causing the yield to exceed the theoretical value. In such cases, this product was carried forward through the next step with the NaCl present.

Part B:

4,6-Dichloro-2-ethyl-5-fluoropyrimidine

2-Ethyl-5-fluoro-6-hydroxy-4(1H)-pyrimidinone (20 g, 126.6 mmol) in POCl$_3$ (58 mL, 633 mmol) was heated at 125° C. (oil bath) for 2 h. An additional 68 mL of fresh POCl$_3$ was added to the hot solution. The resulting solution was heated for an additional 2 h until all the starting material was consumed. The excess POCl$_3$ was distilled (62° C.-68° C.) in vacuo to give a light brown residue. After being cooled to room temperature, the residue was diluted with 50 mL of CH$_2$Cl$_2$, then poured into ice water (200 mL). To this mixture was added 200 mL of CH$_2$Cl$_2$ and the subsequent mixture was stirred for 10 min. After separation of the two layers, the aqueous layer was further extracted with 100 mL of CH$_2$Cl$_2$. The combined organic layers were dried over Na$_2$SO$_4$, then filtered through a short silica gel pad, which was then washed with 150 mL of 1% MeOH in CH$_2$Cl$_2$. Evaporation of the solvent provided 4,6-dichloro-2-ethyl-5-fluoropyrimidine (21 g, 85%) as a light yellow liquid. LCMS: (M+H)+: not detected.

Intermediate E

[(2R)-3-{2-[6-Chloro-5-fluoro-2-(methylthio)-4-pyrimidinyl]hydrazino}-2-(cyclopentylmethyl)-3-oxopropyl](tetrahydro-2H-pyran-2-yloxy)formamide

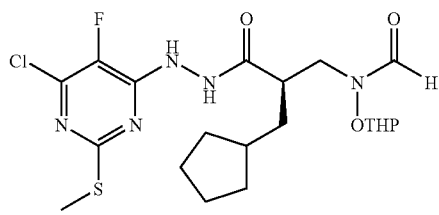

Part A:

5-Fluoro-6-hydroxy-2-methylthio-4(1H)-pyrimidinone

To a stirred solution of 2-methyl-2-thiopseudourea sulfate (41.7 g, 0.15 mol) and dimethyl fluoromalonate (45 g, 0.30 mol) in MeOH (600 mL) at 0° C. (ice bath) was added NaOMe (48.6 g, 0.90 mol) in portions. After the addition was complete, the ice bath was withdrawn and the reaction mixture was stirred at room temperature overnight. LCMS showed the formation of the desired pyrimidinone product. The reaction mixture was concentrated to near dryness under vacuum, diluted with water (50 mL), and acidified with 6N HCl (~150 mL) to ~pH 2 to precipitate the product. After filtration, the solid was washed with 1N HCl (2×10 mL) and dried under vacuum to afford 5-fluoro-6-hydroxy-2-methylthio-4(1H)-pyrimidinone (35.7 g, 68%) as a white solid. LCMS: (M+H)+: 177.3.

Part B:

4,6-Dichloro-5-fluoro-2-(methylthio)pyrimidine

A mixture of 5-fluoro-6-hydroxy-2-(methylthio)-4(1H)-pyrimidinone (35.7 g, 0.20 mol) in POCl$_3$ (150 mL) was heated at 115° C. for 3 h. After cooling to room temperature, the reaction mixture was slowly poured into an ice-water mixture (1500 mL) and stirred for 20 min. The product was extracted into ethyl acetate (3×800 mL), and the combined organic extracts were washed with water (2×1000 mL), brine (1000 mL), and dried ($Na_2SO_4$). Evaporation of the solvent provided 4,6-dichloro-5-fluoro-2-(methylthio)pyrimidine as a pale yellow solid (37.8 g, 89%). LCMS: $(M+H)^+$: not detected.

Part C:

4-Chloro-5-fluoro-6-hydrazino-2-(methylthio)pyrimidine 4,6-Dichloro-5-fluoro-2-(methylthio)pyrimidine (16.8 g, 78.85 mmol) and triethylamine (16.49 mL, 118.3 mmol) were dissolved in DMSO (200 mL) and stirred. The mixture was cooled to ~5° C. with an ice water bath. To this solution was slowly added hydrazine monohydrate (4.59 mL, 94.62 mmol). After the addition was complete, the reaction mixture was warmed up to RT and stirring was continued for 1 h. The reaction mixture was diluted with water (500 mL), and the aqueous solution was extracted with $CH_2Cl_2$ (3×300 mL). The combined organic solution was washed with water (3×250 mL) and brine (250 mL), then dried ($Na_2SO_4$) and concentrated in vacuo to afford 4-chloro-5-fluoro-6-hydrazino-2-(methylthio)pyrimidine as a red foamy solid (9.70 g, 59%). LCMS: $(M+H)^+$: 208.9.

Part D:

[(2R)-3-{2-[6-Chloro-5-fluoro-2-(methylthio)-4-pyrimidinyl]hydrazino}-2-(cyclopentylmethyl)-3-oxopropyl](tetrahydro-2H-pyran-2-yloxy)formamide A mixture of 4-chloro-5-fluoro-6-hydrazino-2-(methylthio)pyrimidine (9.70 g, 46.5 mmol), (2R)-3-cyclopentyl-2-{[formyl(tetrahydro-2H-pyran-2-yloxy)amino]methyl}propanoic acid (19.9 g, 46.5 mmol), HOAt (6.96 g, 51.2 mmol), EDCI (9.82 g, 51.2 mmol) and N-methyl morpholine (25.6 mL, 232.5 mmol) in DMF (300 mL) was stirred at room temperature overnight. The reaction mixture was diluted with ethyl acetate/hexanes (3:2, 1 L) and washed with water (3×500 mL), and the organics were dried ($Na_2SO_4$) and concentrated in vacuo. The residue was purified by Gilson RP-HPLC (35-95% acetonitrile/water, 8 min gradient time) to afford [(2R)-3-{2-[6-chloro-5-fluoro-2-(methylthio)-4-pyrimidinyl]hydrazino}-2-(cyclopentylmethyl)-3-oxopropyl](tetrahydro-2H-pyran-2-yloxy)formamide as a red glass (12.89 g, 56.0%). LCMS: $(M+H)^+$: 490.4.

Intermediate F

2,4,6-Trichloro-5-fluoropyrimidine

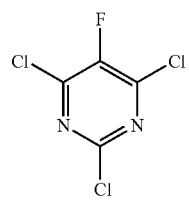

Part A:

5-Fluoro-6-hydroxy-2,4(1H,3H)-pyrimidinedione

A mechanically stirred solution of urea (60.06 g, 1 mol) and dimethyl fluoromalonate (150.11 g, 1 mol) in methanol (1 L) was treated with 25 wt % NaOMe in methanol (~4.6 M, 435 mL, 2 mol). The mixture was refluxed for 3 h and then allowed to cool to room temperature. The mixture was filtered, the wet cake was dissolved in warm water (~1.2 L), and the resulting aqueous solution was acidified with concentrated aqueous HCl (~160 mL) to pH=2 while stirring over 1 h. The mixture was allowed to cool to room temperature, and the product was filtered and washed thoroughly with water, then dried under vacuum to give 5-fluoro-6-hydroxy-2,4(1H,3H)-pyrimidinedione (80 g, 55%) as a white solid. LCMS: $(M+H)^+$: 147.0.

Part B:

2,4,6-Trichloro-5-fluoropyrimidine

Finely powdered 5-fluoro-6-hydroxy-2,4(1H,3H)-pyrimidinedione (74 g, 0.507 mol) was added portionwise over 30 min to $POCl_3$ (232 mL, 2.5 mol) with stirring (exothermic). Upon complete addition, the mixture was held at 60° C. while N,N,-dimethylaniline (65 mL) was added dropwise by syringe. After addition, the mixture was heated to 100-110° C. (internal) until the reaction was judged complete, usually in 4-8 h. The mixture was cooled and the bulk of the remaining $POCl_3$ was removed by careful vacuum distillation at 80-90° C. (some product can be detected in the $POCl_3$ distillate). The remaining residue was poured onto ice (~1 L) and stirred for 30 min, then extracted with ether (1×400 mL, 2×150 mL). The combined extracts were washed with water and brine, then dried ($MgSO_4$). Filtration and atmospheric distillation of the ether provided the crude product, which was distilled under reduced pressure to provide the product (28.8 g, 28%) as a low melting white crystalline solid (b.p. 80-85° C., 12 mm). LCMS: $(M+H)^+$: not detected.

Intermediate G

Tris(1,1-dimethylethyl)2-(2,6-dichloro-5-fluoro-4-pyrimidinyl)-1,1,2-hydrazinetricarboxylate

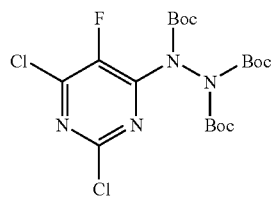

Part A:

1,1-Dimethylethyl 2-(2,6-dichloro-5-fluoro-4-pyrimidinyl)hydrazinecarboxylate 2,4,6-Trichloro-5-fluoropyrimidine (20.92 g, 104.1 mmol) was dissolved in THF (300 mL) at room temperature and stirred. To this stirring solution was added t-butyl carbazate (13.74 g, 104.1 mmol), followed by diisopropylethylamine (19.0 mL, 109.3 mmol). The reaction mixture turned light yellow, and after several minutes a precipitate formed. The reaction appeared complete after 1.5 h, as monitored by TLC (10% EtOAc/Hex). The reaction mixture was concentrated in vacuo to remove most of the THF, and the residue was dissolved in CH$_2$Cl$_2$ (~400 mL). The solution was washed with ~400 mL of sat. aq. NH$_4$Cl. The organics were dried and concentrated to give a pale yellow solid (31.37 g). LCMS: (M+H+2Na-Boc)$^+$: 241.

Part B:

Tris(1,1-dimethylethyl)2-(2,6-dichloro-5-fluoro-4-pyrimidinyl)-1,1,2-hydrazinetricarboxylate 1,1-Dimethylethyl 2-(2,6-dichloro-5-fluoro-4-pyrimidinyl)hydrazinecarboxylate (31.37 g, 104.1 mmol assumed) was suspended in CH$_2$Cl$_2$ (400 mL). Di-t-butyl dicarbonate (44.75 g, 205.0 mmol) was added to the solution, followed by diisopropylethylamine (36.3 mL, 208.2 mmol). When almost everything was dissolved, DMAP (1.27 g, 10.4 mmol) was added slowly. The reaction mixture turned reddish, and after 5 min, mild bubbling was observed. After 45 min, the reaction appeared complete by LCMS, and the mixture had turned light orange. The reaction mixture was washed with ~300 mL sat. NH$_4$Cl, and the organics were set aside. A slurry was prepared with ~1800 mL Florsil in CH$_2$Cl$_2$, which was poured onto a large fritted funnel. The entire organic solution was then poured through the Florsil pad, washing with 2 L of CH$_2$Cl$_2$. A red band was left behind on the Florsil, and TLC showed that the product had finished eluting from the pad. The filtrate was concentrated to a foamy colorless oil, which crystallized overnight in the refrigerator (37.87 g, 73% from 2,4,6-trichloro-5-fluoropyrimidine). LCMS: (M+3H+2Na–3Boc)$^+$: 241.

Intermediate H 4,6-Dichloro-5-fluoro-2-(fluoromethyl)pyrimidine

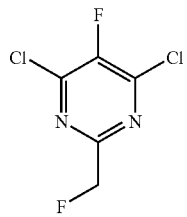

Part A:

5-Fluoro-2-(fluoromethyl)-6-hydroxy-4(1H)-pyrimidinone

2-Fluoro-acetamidine hydrochloride salt (11.2 g, 100 mmol) and dimethyl fluoromalonate (15 g, 100 mmol) in anhydrous methanol (300 mL) were treated with solid NaOMe (16.2 g, 300 mmol) and heated to 50° C. with stirring. When LCMS showed formation of the desired product, the solvent was evaporated to dryness, and the residue was neutralized with concentrated HCl (20 mL). The white precipitate was collected by filtration to give 5-fluoro-2-(fluoromethyl)-6-hydroxy-4(1H)-pyrimidinone (100% yield). LCMS: (M+H)$^+$: 163.1.

Part B:

4,6-Dichloro-5-fluoro-2-(fluoromethyl)pyrimidine

5-Fluoro-2-(fluoromethyl)-6-hydroxy-4(1H)-pyrimidinone (6 g, 37 mmol) was suspended in POCl$_3$ (20 mL, 222 mmol) and stirred at 120° C. for 2 h. After evaporation of the excess POCl$_3$, the residue was poured onto ice and the resulting mixture was extracted with CH$_2$Cl$_2$. The CH$_2$Cl$_2$ solution was passed through a silica gel pad, and the resulting filtrate was concentrated to provide the pure 4,6-dichloro-5-fluoro-2-(fluoromethyl)pyrimidine (6 g, 81%) as a colorless liquid. LCMS: (M+H)$^+$: not detected.

Intermediate I 4,6-Dichloro-2-(difluoromethyl)-5-fluoropyrimidine

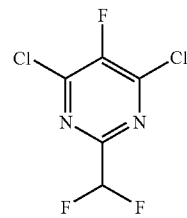

Part A 2,2-Difluoroethanimidamide.HCl

To a stirred suspension of ammonium chloride (5.1 g, 95 mmol) in toluene (150 mL) at 0° C. was added trimethyl aluminum (46 mL, 2M, 92 mmol), stirring until effervescence ceased. Methyl difluoroacetate (2.38 mL, 27 mmol) was added, and the resulting mixture was stirred overnight at 80° C. Upon cooling to 0° C., methanol was added slowly and the resulting solution was stirred for 90 minutes at reduced temperature, causing a solid to form. This was removed by filtration through Celite, and the filtrate was evaporated to yield 2,2-difluoroethanimidamide.HCl (1.7 g, 48 5%) as a yellow tinged solid.

Part B 2-(Difluoromethyl)-5-fluoro-6-hydroxy-4(1H)-pyrimidinone

Sodium metal (0.91 g, 40 mmol) was dissolved in MeOH (100 mL) to form sodium methoxide. 2,2-Difluoroethanimidamide.HCl (1.73 g, 13 mmol) was added followed by dimethyl fluoropropanedioate (2.0 g, 13 mmol). The resulting solution was stirred at 80° C. for 3 hours, then cooled to room temperature. Aqueous HCl (6 mL, 6M, 36 mmol) was added and the resulting mixture was concentrated in vacuo. The remaining solid was washed with cold water and filtered yielding 2-(difluoromethyl)-5-fluoro-6-hydroxy-4(1H)-pyrimidinone (1.43 g, 61%)

Part C 4,6-Dichloro-2-(difluoromethyl)-5-fluoropyrimidine

A mixture of 2-(difluoromethyl)-5-fluoro-6-hydroxy-4 (1H)-pyrimidinone (1.43 g, 8.0 mmol) and POCl$_3$ (6 mL) was heated at 110° C. for 2.5 hours. After cooling to room temperature, the reaction mixture was poured over ice and stirred for 30 min. The product was extracted into DCM and the combined organics were washed once with aqueous saturated sodium bicarbonate. The combined organics were dried over sodium sulfate and concentrated in vacuo. This yielded 4,6-dichloro-2-(difluoromethyl)-5-fluoropyrimidine (460 mg, 27%) as a yellow oil.

General Procedure A

Example 1

((2R)-2-(Cyclopentylmethyl)-3-{2-[5-fluoro-2-methyl-6-(1-pyrrolidinyl)-4-pyrimidinyl]hydrazino}-3-oxopropyl)hydroxyformamide

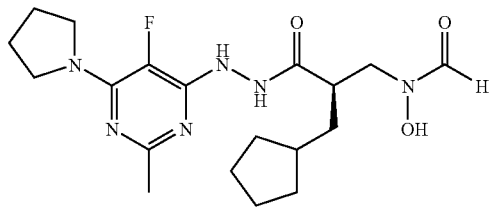

Part A:

5-Fluoro-4-hydrazino-2-methyl-6-(1-pyrrolidinyl)pyrimidine 4,6-Dichloro-5-fluoro-2-methylpyrimidine (100 mg, 0.55 mmol) was dissolved in 2 mL of DMSO and stirred at room temperature. Pyrrolidine (50 µL, 0.61 mmol) was added, followed by DIPEA (210 µL, 1.21 mmol). The resulting reaction mixture was stirred for 2 h, and then hydrazine was added (1.0 mL) and the contents were heated to 80° C. for 1 h. The reaction mixture was then cooled to room temperature and purified by RP-HPLC to provide 5-fluoro-4-hydrazino-2-methyl-6-(1-pyrrolidinyl)pyrimidine (69 mg, 59%).

Part B:

((2R)-2-(Cyclopentylmethyl)-3-{2-[5-fluoro-2-methyl-6-(1-pyrrolidinyl)-4-pyrimidinyl]hydrazino}-3-oxopropyl)[(phenylmethyl)oxy]formamide 5-Fluoro-4-hydrazino-2-methyl-6-(1-pyrrolidinyl)pyrimidine (69 mg, 0.33 mmol), (2R)-3-cyclopentyl-2-({formyl[(phenylmethyl)oxy]amino}methyl)propanoic acid (110 mg, 0.36 mmol), and HOAt (49 mg, 0.36 mmol) were dissolved in 2 mL of DMF. NMM (0.18 mL, 1.65 mmol) was added, followed by EDC (69 mg, 0.36 mmol). After stirring overnight at room temperature, the reaction mixture was purified by RP-HPLC to provide ((2R)-2-(cyclopentylmethyl)-3-{2-[5-fluoro-2-methyl-6-(1-pyrrolidinyl)-4-pyrimidinyl]hydrazino}-3-oxopropyl)[(phenylmethyl)oxy]formamide (90 mg, 55%).

Part C:

((2R)-2-(Cyclopentylmethyl)-3-{2-[5-fluoro-2-methyl-6-(1-pyrrolidinyl)-4-pyrimidinyl]hydrazino}-3-oxopropyl)hydroxyformamide ((2R)-2-(Cyclopentylmethyl)-3-{2-[5-fluoro-2-methyl-6-(1-pyrrolidinyl)-4-pyrimidinyl]hydrazino}-3-oxopropyl)[(phenylmethyl)oxy]formamide (90 mg, 0.18 mmol) was dissolved in 3 mL of MeOH, degassed and placed under argon. 10% Pd/C (18 mg) was added, and the contents were thoroughly degassed and placed under a hydrogen balloon for approximately 3 hrs. The contents were then degassed and filtered through Celite, and the Celite pad was washed with DCM and MeOH. The resulting filtrate was concentrated in vacuo to provide the pure ((2R)-2-(cyclopentylmethyl)-3-{2-[5-fluoro-2-methyl-6-(1-pyrrolidinyl)-4-pyrimidinyl]hydrazino}-3-oxopropyl)hydroxyformamide (42 mg, 57%). LCMS: (M+H)$^+$: 407.6.

General Procedure B

Example 2

[(2R)-3-{2-[6-(1-Azetidinyl)-2-ethyl-5-fluoro-4-pyrimidinyl]hydrazino}-2-(cyclopentylmethyl)-3-oxopropyl]hydroxyformamide

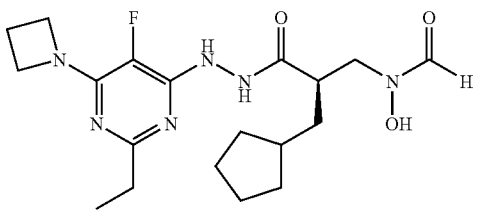

Part A:

6-Azetidinyl-2-ethyl-5-fluoro-4-hydrazinopyrimidine 4,6-Dichloro-2-ethyl-5-fluoropyrimidine (195 mg, 1.0 mmol) was dissolved in 3 mL of MeOH and stirred at room temperature. Azetidine (74 µL, 1.1 mmol) was added, followed by DIPEA (383 µL, 2.2 mmol). The resulting reaction mixture was stirred at room temperature until the azetidine displacement of one chlorine was complete as monitored by LCMS. Then, the MeOH was removed in vacuo, and the remaining residue was dissolved in a mixture of 2 mL DMSO and 1 mL of hydrazine. The resulting solution was heated at 40° C. for 1 h until the reaction was deemed complete by LCMS. The crude reaction mixture was purified by RP-HPLC to provide 4-(1-azetidinyl)-2-ethyl-5-fluoro-6-hydrazinopyrimidine (136 mg, 64%). LCMS: (M+H)$^+$: 212.1.

Part B:

[(2R)-3-{2-[6-(1-Azetidinyl)-2-ethyl-5-fluoro-4-pyrimidinyl]hydrazino}-2-(cyclopentylmethyl)-3-oxopropyl][(phenylmethyl)oxy]formamide 4-(1-Azetidinyl)-2-ethyl-5-fluoro-6-hydrazinopyrimidine (88 mg, 0.42 mmol), (2R)-3-cyclopentyl-2-({formyl[(phenylmethyl)oxy]amino}methyl)propanoic acid (140 mg, 0.46 mmol), and HOAt (56 mg, 0.42 mmol) were dissolved in 3 mL of DMF. Then, NMM (71 µL, 0.65 mmol) was added, followed by EDC (75 mg, 0.40 mmol). After stirring overnight at room temperature, the reaction mixture was purified by RP-HPLC to provide [(2R)-3-{2-[6-(1-azetidinyl)-2-ethyl-5-fluoro-4-pyrimidinyl]hydrazino}-2-(cyclopentylmethyl)-3-oxopropyl][(phenylmethyl)oxy]formamide (160 mg, 76%). LCMS: (M+H)$^+$: 499.4.

Part C:

[(2R)-3-{2-[6-(1-Azetidinyl)-2-ethyl-5-fluoro-4-pyrimidinyl]hydrazino}-2-(cyclopentylmethyl)-3-oxopropyl]hydroxyformamide

[(2R)-3-{2-[6-(1-Azetidinyl)-2-ethyl-5-fluoro-4-pyrimidinyl]hydrazino}-2-(cyclopentylmethyl)-3-oxopropyl][(phenylmethyl)oxy]formamide (160 mg, 0.32 mmol) was dissolved in 10 mL of MeOH, degassed and placed under argon. 5% Pd/C (40 mg) was added, and the contents were thoroughly degassed and stirred under a hydrogen balloon until the reaction was deemed complete by LCMS. The contents were then degassed and filtered through Celite, and the Celite pad was washed with DCM and MeOH. The resulting filtrate was concentrated in vacuo to provide [(2R)-3-{2-[6-(1-azetidinyl)-2-ethyl-5-fluoro-4-pyrimidinyl]hydrazino}-2-(cyclopentylmethyl)-3-oxopropyl]hydroxyformamide (100 mg, 76%). LCMS: (M+H)$^+$: 409.2.

General Procedure C

Example 3

[(2R)-3-{2-[6-(1-Azetidinyl)-5-fluoro-2-(methylthio)-4-pyrimidinyl]hydrazino}-2-(cyclopentylmethyl)-3-oxopropyl]hydroxyformamide

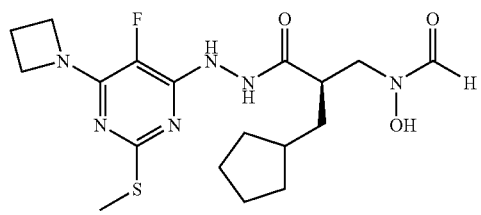

Part A:

[(2R)-3-{2-[6-(1-Azetidinyl)-5-fluoro-2-(methylthio)-4-pyrimidinyl]hydrazino}-2-(cyclopentylmethyl)-3-oxopropyl][(tetrahydro-2H-pyran-2-yloxy)formamide To a pressure tube was added [(2R)-3-{2-[6-chloro-5-fluoro-2-(methylthio)-4-pyrimidinyl]hydrazino}-2-(cyclopentylmethyl)-3-oxopropyl](tetrahydro-2H-pyran-2-yloxy)formamide (0.100 g, 0.204 mmol), azetidine hydrochloride (19.1 mg, 0.204 mmol), DIPEA (71.2 µL, 0.408 mmol) and DMSO (2 mL). The tube was sealed and was heated to 65-70° C. with stirring for 3 days. The reaction mixture was then cooled to RT and purified by RP-HPLC to afford [(2R)-3-{2-[6-(1-azetidinyl)-5-fluoro-2-(methylthio)-4-pyrimidinyl]hydrazino}-2-(cyclopentylmethyl)-3-oxopropyl](tetrahydro-2H-pyran-2-yloxy)formamide (68 mg, 65%). LCMS: (M+H)$^+$: 511.2.

Part B:

[(2R)-3-{2-[6-(1-Azetidinyl)-5-fluoro-2-(methylthio)-4-pyrimidinyl]hydrazino}-2-(cyclopentylmethyl)-3-oxopropyl]hydroxyformamide

[(2R)-3-{2-[6-(1-Azetidinyl)-5-fluoro-2-(methylthio)-4-pyrimidinyl]hydrazino}-2-(cyclopentylmethyl)-3-oxopropyl](tetrahydro-2H-pyran-2-yloxy)formamide (68 mg, 0.13 mmol) was dissolved in a mixture of AcOH/H$_2$O (20 mL, 4:1) and stirred at RT until LCMS indicated completion of the deprotection (overnight). The reaction mixture was concentrated to dryness under vacuum and purified by RP-HPLC to provide [(2R)-3-{2-[6-(1-azetidinyl)-5-fluoro-2-(methylthio)-4-pyrimidinyl]hydrazino}-2-(cyclopentylmethyl)-3-oxopropyl]hydroxyformamide (25 mg, 44%). LCMS: (M+H)$^+$: 427.2.

General Procedure D

Example 4

[(2R)-3-{2-[2-Chloro-5-fluoro-6-(4-methyl-1-piperazinyl)-4-pyrimidinyl]hydrazino}-2-(cyclopentylmethyl)-3-oxopropyl]hydroxyformamide

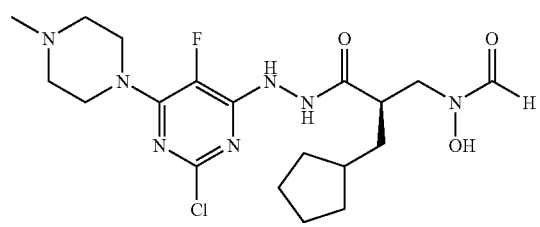

Part A:

2-Chloro-5-fluoro-4-hydrazino-6-(4-methyl-1-piperazinyl)pyrimidine

To a solution of 2,4,6-trichloro-5-fluoropyrimidine (402 mg, 2.0 mmol) in DMSO (3 mL) was added DIPEA (0.52 mL, 3.0 mmol), followed by N-methylpiperazine (0.24 mL, 2.2 mmol). The solution was stirred at room temperature. After 30 min, anhydrous hydrazine (1.29 mL, 99 mmol) was added, and the resulting mixture was heated at 80° C. for 30 min. After cooling to room temperature, the excess hydrazine was removed in vacuo, and the remaining solution was purified via RP-HPLC to provide the assumed 2-chloro-5-fluoro-4-hydrazino-6-(4-methyl-1-piperazinyl)pyrimidine (first eluent, 44 mg), as well as the assumed 6-chloro-5-fluoro-2-hydrazino-4-(4-methyl-1-piperazinyl)pyrimidine (second eluent, 30 mg). LCMS: (M+H)$^+$: 261.1.

Part B:

[(2R)-3-{2-[2-chloro-5-fluoro-6-(4-methyl-1-piperazinyl)-4-pyrimidinyl]hydrazino}-2-(cyclopentylmethyl)-3-oxopropyl](tetrahydro-2H-pyran-2-yloxy)formamide A mixture of 2-chloro-5-fluoro-4-hydrazino-6-(4-methyl-1-piperazinyl)pyrimidine (31 mg, 0.12 mmol), (2R)-3-cyclopentyl-2-{[formyl(tetrahydro-2H-pyran-2-yloxy)amino]methyl}propanoic acid (36 mg, 0.12 mmol), HOAt (20 mg, 0.144 mmol), EDC (28 mg, 0.144 mmol) and NMM (26 uL, 0.144 mmol) in DMF (2 mL) was stirred until the reaction was complete (2 h). The reaction mixture was then purified via RP-HPLC to provide [(2R)-3-{2-[2-chloro-5-fluoro-6-(4-methyl-1-piperazinyl)-4-pyrimidinyl]hydrazino}-2-(cyclopentylmethyl)-3-oxopropyl](tetrahydro-2H-pyran-2-yloxy)formamide (30 mg, 46%). LCMS: (M+H)$^+$: 542.3; (M+Na)$^+$: 564.3.

Part C:

[(2R)-3-{2-[2-Chloro-5-fluoro-6-(4-methyl-1-piperazinyl)-4-pyrimidinyl]hydrazino}-2-(cyclopentylmethyl)-3-oxopropyl]hydroxyformamide A solution of [(2R)-3-{2-[2-chloro-5-fluoro-6-(4-methyl-1-piperazinyl)-4-pyrimidinyl]hydrazino}-2-(cyclopentylmethyl)-3-oxopropyl](tetrahydro-2H-pyran-2-yloxy)formamide (30 mg) in 4:1 AcOH:water (4 mL) was stirred at room temperature overnight. The solvents were removed in vacuo, and the resulting crude product was purified by RP-HPLC to provide [(2R)-3-{2-[2-chloro-5-fluoro-6-(4-methyl-1-piperazinyl)-4-pyrimidinyl]hydrazino}-2-(cyclopentylmethyl)-3-oxopropyl]hydroxyformamide (12 mg, 47%). LCMS: (M+H)$^+$: 458.3.

General Procedure E

Example 5

[(2R)-3-(2-{2-Chloro-5-fluoro-6-[(1-methylethyl)amino]-4-pyrimidinyl}hydrazino)-2-(cyclopentylmethyl)-3-oxopropyl]hydroxyformamide

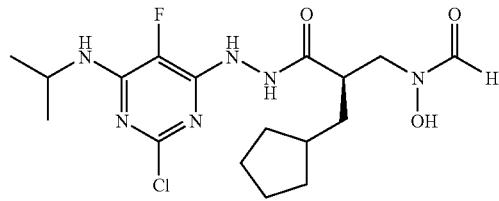

Part A:

Tris(1,1-dimethylethyl)2-{2-chloro-5-fluoro-6-[(1-methylethyl)amino]-4-pyrimidinyl}-1,1,2-hydrazinetricarboxylate To a vigorously stirred solution of isopropyl amine (83 µL, 1.21 mmol) in DMF (6 mL) at 0° C. was added DIPEA (0.24 mL, 1.33 mmol) followed immediately by tris(1,1-dimethylethyl)2-(2,6-dichloro-5-fluoro-4-pyrimidinyl)-1,1,2-hydrazinetricarboxylate (600 mg, 1.21 mmol). When the reaction was complete as determined by LCMS, the reaction mixture was diluted with diethyl ether (~40 mL) and washed with water (3×40 mL). The combined three aqueous layers were back-extracted once with diethyl ether, and then the combined organics were dried (Na$_2$SO$_4$) and concentrated in vacuo. This crude product was purified by flash chromatography (Combiflash, 5-60% ethyl acetate/hexanes, 1% triethylamine) to provide tris(1,1-dimethylethyl)2-{2-chloro-5-fluoro-6-[(1-methylethyl)amino]-4-pyrimidinyl}-1,1,2-hydrazinetricarboxylate (597 mg, 95%). LCMS: (M+H)$^+$: 520.2.

Part B:

2-Chloro-5-fluoro-6-hydrazino-N-(1-methylethyl)-4-pyrimidinamine

A solution of tris(1,1-dimethylethyl)2-{2-chloro-5-fluoro-6-[(1-methylethyl)amino]-4-pyrimidinyl}-1,1,2-hydrazinetricarboxylate (597 mg, 1.15 mmol) in MeOH (5 mL) and 4.0M HCl in dioxane (5 mL) was stirred at room temperature overnight. After filtering away the precipitate, the solvent was removed in vacuo, providing the crude 2-chloro-5-fluoro-6-hydrazino-N-(1-methylethyl)-4-pyrimidinamine, presumably as the tri-HCl salt. LCMS: (M+H)$^+$: 219.9.

Part C:

[(2R)-3-(2-{2-Chloro-5-fluoro-6-[(1-methylethyl)amino]-4-pyrimidinyl}hydrazino)-2-(cyclopentylmethyl)-3-oxopropyl][(phenylmethyl)oxy]formamide A mixture of (2R)-3-cyclopentyl-2-({formyl[(phenylmethyl)oxy]amino}methyl)propanoic acid (268 mg, 0.88 mmol), 2-chloro-5-fluoro-6-hydrazino-N-(1-methylethyl)-4-pyrimidinamine (assumed 253 mg of free base, 0.97 mmol), EDC (186 mg, 0.97 mmol), HOAt (132 mg, 0.97 mmol), and NMM (0.64 mL, 5.82 mmol) in DMF was stirred at room temperature overnight. The reaction mixture was then purified via reverse phase HPLC to provide [(2R)-3-(2-{2-chloro-5-fluoro-6-[(1-methylethyl)amino]-4-pyrimidinyl}hydrazino)-2-(cyclopentylmethyl)-3-oxopropyl][(phenylmethyl)oxy]formamide (74 mg, 17%). LCMS: (M+H)$^+$: 507.1.

Part D:

[(2R)-3-(2-{2-Chloro-5-fluoro-6-[(1-methylethyl)amino]-4-pyrimidinyl}hydrazino)-2-(cyclopentylmethyl)-3-oxopropyl]hydroxyformamide

[(2R)-3-(2-{2-Chloro-5-fluoro-6-[(1-methylethyl)amino]-4-pyrimidinyl}hydrazino)-2-(cyclopentylmethyl)-3-oxopropyl][(phenylmethyl)oxy]formamide (74 mg, 0.15 mmol) was dissolved in 5 mL of MeOH. Pd(OH)$_2$ (30 mg) was added, and the contents were stirred under a hydrogen balloon for approximately 90 min. The contents were then filtered to remove the catalyst, and the filtrate was concentrated in vacuo. The resulting crude product was purified via reverse phase HPLC to provide [(2R)-3-(2-{2-chloro-5-fluoro-6-[(1-methylethyl)amino]-4-pyrimidinyl}hydrazino)-2-(cyclopentylmethyl)-3-oxopropyl]hydroxyformamide (32 mg, 51%). LCMS: (M+H)$^+$: 417.0.

General Procedure F

Example 6

((2R)-2-(Cyclopentylmethyl)-3-{2-[6-(2,5-dihydro-1H-pyrrol-1-yl)-5-fluoro-2-methyl-4-pyrimidinyl]hydrazino}-3-oxopropyl)hydroxyformamide

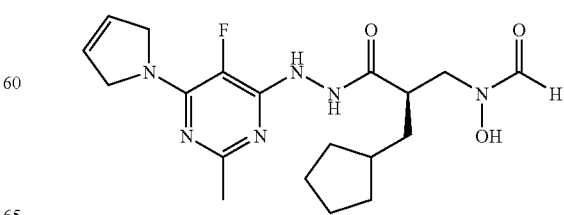

Part A:

4-(2,5-Dihydro-1H-pyrrol-1-yl)-5-fluoro-6-hydrazino-2-methylpyrimidine 4,6-Dichloro-5-fluoro-2-methylpyrimidine (181 mg, 1.0 mmol) was dissolved in 4 mL of DMSO and stirred at room temperature. 3-Pyrroline (71 mg, 1.05 mmol) was added, followed by DIPEA (244 µL, 1.4 mmol). The resulting reaction mixture was stirred until displacement of the first chloride was complete, and then hydrazine (350 µL) and MeOH (~2 mL) were added to the reaction mixture. The contents were then heated to 70° C. for 2 h, until displacement of the second chloride was complete. The reaction mixture was then cooled to room temperature and purified by RP-HPLC to provide 4-(2,5-dihydro-1H-pyrrol-1-yl)-5-fluoro-6-hydrazino-2-methylpyrimidine (142 mg, 68%).

Part B:

((2R)-2-(Cyclopentylmethyl)-3-{2-[6-(2,5-dihydro-1H-pyrrol-1-yl)-5-fluoro-2-methyl-4-pyrimidinyl]hydrazino}-3-oxopropyl)(tetrahydro-2H-pyran-2-yloxy)formamide 4-(2,5-Dihydro-1H-pyrrol-1-yl)-5-fluoro-6-hydrazino-2-methylpyrimidine (142 mg, 0.68 mmol), (2R)-3-cyclopentyl-2-{[formyl(tetrahydro-2H-pyran-2-yloxy)amino]methyl}propanoic acid (242 mg, 0.81 mmol), and HOAt (110 mg, 0.81 mmol) were dissolved in 4 mL of DMF. NMM (370 µL, 3.4 mmol) was added, followed by EDC (155 mg, 0.81 mmol). When the starting materials were consumed, the reaction mixture was purified by RP-HPLC to provide ((2R)-2-(cyclopentylmethyl)-3-{2-[6-(2,5-dihydro-1H-pyrrol-1-yl)-5-fluoro-2-methyl-4-pyrimidinyl]hydrazino}-3-oxopropyl)(tetrahydro-2H-pyran-2-yloxy)formamide (140 mg, 55%).

Part C:

((2R)-2-(Cyclopentylmethyl)-3-{2-[6-(2,5-dihydro-1H-pyrrol-1-yl)-5-fluoro-2-methyl-4-pyrimidinyl]hydrazino}-3-oxopropyl)hydroxyformamide A solution of ((2R)-2-(cyclopentylmethyl)-3-{2-[6-(2,5-dihydro-1H-pyrrol-1-yl)-5-fluoro-2-methyl-4-pyrimidinyl]hydrazino}-3-oxopropyl)(tetrahydro-2H-pyran-2-yloxy)formamide (140 mg) in 4:1 AcOH:water (2 mL) was stirred at room temperature until deprotection was complete. The solvents were removed in vacuo, and the resulting crude product was purified by RP-HPLC to provide ((2R)-2-(cyclopentylmethyl)-3-{2-[6-(2,5-dihydro-1H-pyrrol-1-yl)-5-fluoro-2-methyl-4-pyrimidinyl]hydrazino}-3-oxopropyl)hydroxyformamide (68 mg, 58%). LCMS: (M+H)$^+$: 407.3.

General Procedure G

Example 7

[(2R)-3-(2-{2-Chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl]hydroxyformamide

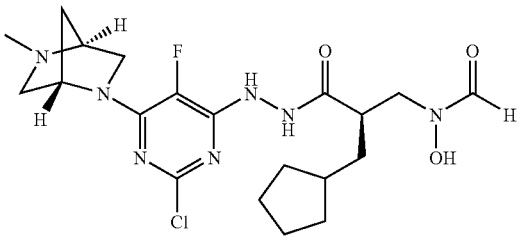

Part A:

(1S,4S)-2-(2-Chloro-5-fluoro-6-hydrazino-4-pyrimidinyl)-5-methyl-2,5-diazabicyclo[2.2.1]heptane 2,4,6-Trichloro-5-fluoropyrimidine (2.01 g, 10 mmol) was dissolved in 30 mL of DMSO and stirred at room temperature. Commercially-available (1S,4S)-2-methyl-2,5-diazabicyclo[2.2.1]heptane, dihydrobromide (2.74 g, 10 mmol) was added, followed by DIPEA (5.51 mL, 32 mmol). The resulting reaction mixture was stirred for 2.5 h, and then hydrazine was added (3.0 mL) and the contents were stirred at room temperature overnight. The reaction mixture was then purified by RP-HPLC to provide the assumed (1S,4S)-2-(2-chloro-5-fluoro-6-hydrazino-4-pyrimidinyl)-5-methyl-2,5-diazabicyclo[2.2.1]heptane (first eluent), as well as the assumed 4-chloro-5-fluoro-6-[(1S,4S)-5-methyl-2,5-diazabicyclo[2.2.1]hept-2-yl]-2(1H)-pyrimidinone hydrazone (second eluent).

Part B:

[(2R)-3-(2-{2-Chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl][(phenylmethyl)oxy]formamide (1S,4S)-2-(2-Chloro-5-fluoro-6-hydrazino-4-pyrimidinyl)-5-methyl-2,5-diazabicyclo[2.2.1]heptane (170 mg, 0.62 mmol), (2R)-3-cyclopentyl-2-({formyl[(phenylmethyl)oxy]amino}methyl)propanoic acid (190 mg, 0.62 mmol), and HOAt (93 mg, 0.68 mmol) were dissolved in 4 mL of DMF. NMM (0.27 mL, 2.5 mmol) was added, followed by EDC (131 mg, 0.36 mmol). After stirring overnight at room temperature, the reaction mixture was purified by RP-HPLC to provide [(2R)-3-(2-{2-chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl][(phenylmethyl)oxy]formamide (90 mg, 55%).

Part C:

[(2R)-3-(2-{2-Chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl]hydroxyformamide

[(2R)-3-(2-{2-chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl][(phenylmethyl)oxy]formamide (90 mg, 0.18 mmol) was dissolved in 3 mL of MeOH, degassed and placed under argon. 10% Pd/C (18 mg) was added, and the contents were thoroughly degassed and placed under a hydrogen balloon for approximately 3 hrs. The contents were then degassed and filtered through Celite, and the Celite pad was washed with DCM and MeOH. The resulting filtrate was concentrated in vacuo to provide the pure [(2R)-3-(2-{2-chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl]hydroxyformamide (42 mg, 57%). LCMS: (M+H)$^+$: 429.4.

Example 7 was also prepared in the following manner:
[(2R)-3-(2-{2-Chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl]hydroxyformamide was prepared according to General Procedure D, utilizing commercially-available (1S,4S)-2-methyl-2,5-diazabicyclo[2.2.1]heptane dihydrobromide in place of N-methylpiperazine in Part A, and using 3 equivalents of DIPEA in Part A.

General Procedure H

Example 8

((2R)-2-(Cyclopentylmethyl)-3-{2-[2-(difluoromethyl)-5-fluoro-6-(4-methyl-1-piperazinyl)-4-pyrimidinyl]hydrazino}-3-oxopropyl)hydroxyformamide

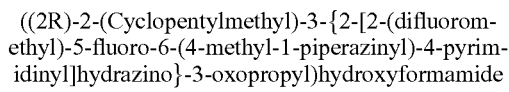

Part A:

2-(Difluoromethyl)-5-fluoro-4-hydrazino-6-(4-methyl-1-piperazinyl)pyrimidine 4,6-Dichloro-2-(difluoromethyl)-5-fluoropyrimidine (200 mg, 0.92 mmol) was dissolved in DMSO (5 mL) and stirred at room temperature. N-methylpiperazine (110 μL, 0.96 mmol) was added, followed by DIPEA (500 μL, 2.9 mmol). The resulting mixture was stirred at room temperature for 1 hour, until the N-methylpiperazine displacement of one chlorine was complete as determined by LCMS. Hydrazine (1 mL, 31 mmol) was added and the reaction was stirred overnight at room temperature. The crude reaction mixture was purified by RP-HPLC to provide 2-(difluoromethyl)-5-fluoro-4-hydrazino-6-(4-methyl-1-piperazinyl)pyrimidine (142 mg, 56%). LCMS: (M+H)$^+$: 277.0.

Part B:

((2R)-2-(Cyclopentylmethyl)-3-{2-[2-(difluoromethyl)-5-fluoro-6-(4-methyl-1-piperazinyl)-4-pyrimidinyl]hydrazino}-3-oxopropyl)hydroxyformamide 2-(Difluoromethyl)-5-fluoro-4-hydrazino-6-(4-methyl-1-piperazinyl)pyrimidine (142 mg, 0.51 mmol) was added to a solution of (2R)-3-cyclopentyl-2-({formyl[(phenylmethyl)oxy]amino}methyl)propanoic acid (156 mg, 0.51 mmol) in DMF (5 mL). To this mixture was added HOAt (83 mg, 6.1 mmol), EDC (117 mg, 6.1 mmol) and NMM (0.28 mL, 2.6 mmol). The reaction was stirred overnight and the resulting benzyl protected intermediate was isolated by RP-HPLC. This material was then dissolved in degassed MeOH (5 mL) and 10% Pd/C (20% w/w of the intermediate) was added. The resulting suspension was stirred under a hydrogen balloon for 3 hours, after which time the catalyst was removed by filtration. Concentration in vacuo yielded ((2R)-2-(cyclopentylmethyl)-3-{2-[2-(difluoromethyl)-5-fluoro-6-(4-methyl-1-piperazinyl)-4-pyrimidinyl]hydrazino}-3-oxopropyl)hydroxyformamide (78 mg, 32%). LCMS: (M+H)$^+$: 474.1

Example 9

[(2R)-3-{2-[6-(1-Azetidinyl)-5-fluoro-2-methyl-4-pyrimidinyl]hydrazino}-2-(cyclopentylmethyl)-3-oxopropyl]hydroxyformamide

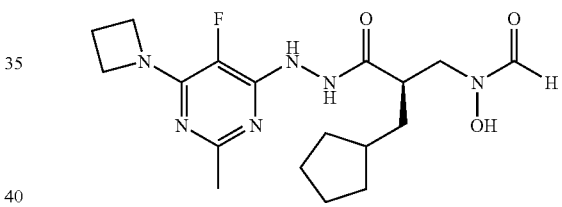

Part A:

4-Azetidino-6-hydrazino-5-fluoro-2-methylpyrimidine 4,6-Dichloro-5-fluoro-2-methylpyrimidine (6 g, 33 mmol) was dissolved in 50 mL of iPrOH and stirred at room temperature. Azetidine-HCl (3.25 g, 35 mmol) was added, followed by 14.4 mL of DIPEA. The resulting reaction mixture was stirred for 3 h, and then hydrazine monohydrate was added (4.0 mL, 82.5 mmol) and the contents were heated to 80° C. overnight. The reaction mixture was then cooled to room temperature and a precipitate formed. The precipitate was filtered, washed with iPrOH, and dried. The remaining filtrate was poured into 250 mL of water and extracted (5×100 mL) with EtOAc. The combined organic fractions were washed with water (2×100 mL) and brine (2×100 mL). The organics were dried over sodium sulfate, filtered, and concentrated in vacuo. This crude product was purified by flash chromatography on silica gel using 97.5/2.5/0.25 DCM/MeOH/NH$_4$OH as the eluent. The overall combined yield of 4-azetidino-6-hydrazino-5-fluoro-2-methylpyrimidine (precipitate+chromatographed product) was 3.6 g (55%). LCMS: (M+H)$^+$: 198.

Part B:

[(2R)-3-{2-[6-(1-azetidinyl)-5-fluoro-2-methyl-4-pyrimidinyl]hydrazino}-2-(cyclopentylmethyl)-3-oxopropyl][(phenylmethyl)oxy]formamide 4-Azetidino-6-hydrazino-5-fluoro-2-methylpyrimidine (2.3 g, 11.6 mmol), (2R)-3-cyclopentyl-2-({formyl[(phenylmethyl)oxy]amino}methyl)propanoic acid (3.54 g, 11.6 mmol), and HOAt (1.9 g, 13.9 mmol) were dissolved in 25 mL of DMF. DIPEA (6 mL, 34.8 mmol) was added, followed by EDC (2.75 g, 13.9 mmol). After stirring overnight at room temperature, the contents were poured into 400 mL of water (precipitate formed) and extracted with ethyl acetate (4×200 mL). The combined organic fractions were washed with water (2×200 mL) and brine (3×200 mL), and then dried over sodium sulfate, filtered and concentrated to dryness. The crude material was purified by flash chromatography on silica gel using 3% MeOH/DCM as the eluent, to provide [(2R)-3-{2-[6-(1-azetidinyl)-5-fluoro-2-methyl-4-pyrimidinyl]hydrazino}-2-(cyclopentylmethyl)-3-oxopropyl][(phenylmethyl)oxy]formamide (2.5 g, 44%). LCMS: (M+H)+: 485.

Part C:

[(2R)-3-{2-[6-(1-Azetidinyl)-5-fluoro-2-methyl-4-pyrimidinyl]hydrazino}-2-(cyclopentylmethyl)-3-oxopropyl]hydroxyformamide

[(2R)-3-{2-[6-(1-Azetidinyl)-5-fluoro-2-methyl-4-pyrimidinyl]hydrazino}-2-(cyclopentylmethyl)-3-oxopropyl][(phenylmethyl)oxy]formamide (3.9 g, 8.0 mmol) was dissolved in 50 mL of MeOH and degassed with argon. 10% Pd/C (400 mg) was added, and the contents were placed under a hydrogen balloon for 4.5 h. The contents were then degassed with argon and filtered through Celite, and the Celite pad was washed with DCM and MeOH. The resulting filtrate was concentrated in vacuo to provide the pure [(2R)-3-{2-[6-(1-azetidinyl)-5-fluoro-2-methyl-4-pyrimidinyl]hydrazino}-2-(cyclopentylmethyl)-3-oxopropyl]hydroxyformamide (3.1 g, 98%). LCMS: (M+H)+: 395.

Example 10

((2R)-2-(Cyclopentylmethyl)-3-{2-[5-fluoro-2-methyl-6-(4-morpholinyl)-4-pyrimidinyl]hydrazino}-3-oxopropyl)hydroxyformamide

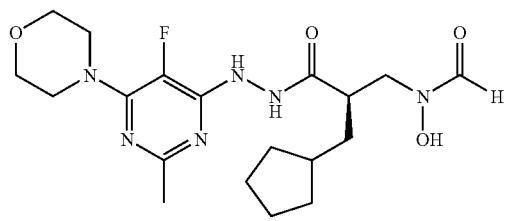

((2R)-2-(Cyclopentylmethyl)-3-{2-[5-fluoro-2-methyl-6-(4-morpholinyl)-4-pyrimidinyl]hydrazino}-3-oxopropyl)hydroxyformamide was prepared according to General Procedure A, utilizing commercially-available morpholine in place of pyrrolidine in Part A. LCMS: (M+H)+: 425.4.

Example 11

[(2R)-2-(Cyclopentylmethyl)-3-(2-{5-fluoro-2-methyl-6-[methyl(methyloxy)amino]-4-pyrimidinyl}hydrazino)-3-oxopropyl]hydroxyformamide

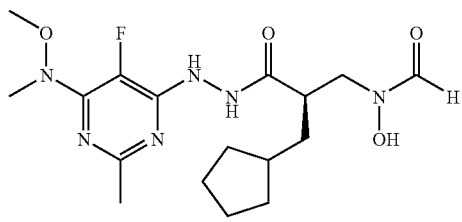

[(2R)-2-(Cyclopentylmethyl)-3-(2-{5-fluoro-2-methyl-6-[methyl(methyloxy)amino]-4-pyrimidinyl}hydrazino)-3-oxopropyl]hydroxyformamide was prepared according to General Procedure A, utilizing commercially-available N,O-dimethylhydroxylamine hydrochloride in place of pyrrolidine in Part A. LCMS: (M+H)+: 399.2.

Example 12

((2R)-2-(Cyclopentylmethyl)-3-{2-[5-fluoro-2-methyl-6-(1,3-thiazolidin-3-yl)-4-pyrimidinyl]hydrazino}-3-oxopropyl)hydroxyformamide

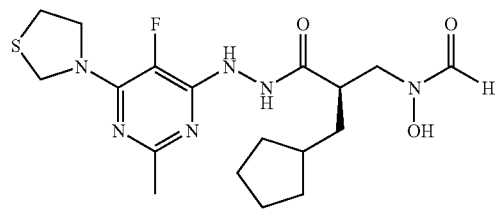

((2R)-2-(Cyclopentylmethyl)-3-{2-[5-fluoro-2-methyl-6-(1,3-thiazolidin-3-yl)-4-pyrimidinyl]hydrazino}-3-oxopropyl)hydroxyformamide was prepared according to General Procedure A, utilizing commercially-available thiazolidine in place of pyrrolidine in Part A. LCMS: (M+H)+: 427.4.

Example 13

[(2R)-2-(Cyclopentylmethyl)-3-(2-{5-fluoro-2-methyl-6-[3-(methyloxy)-1-azetidinyl]-4-pyrimidinyl}hydrazino)-3-oxopropyl]hydroxyformamide

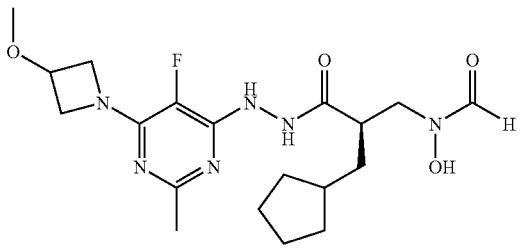

[(2R)-2-(Cyclopentylmethyl)-3-(2-{5-fluoro-2-methyl-6-[3-(methyloxy)-1-azetidinyl]-4-pyrimidinyl}hydrazino)-3-oxopropyl]hydroxyformamide was prepared according to General Procedure A, utilizing commercially-available 3-methoxyazetidine hydrochloride in place of pyrrolidine in Part A. LCMS: (M+H)$^+$: 425.2.

Example 14

[(2R)-2-(Cyclopentylmethyl)-3-(2-{5-fluoro-2-methyl-6-[(3R)-3-(methyloxy)-1-pyrrolidinyl]-4-pyrimidinyl}hydrazino)-3-oxopropyl]hydroxyformamide

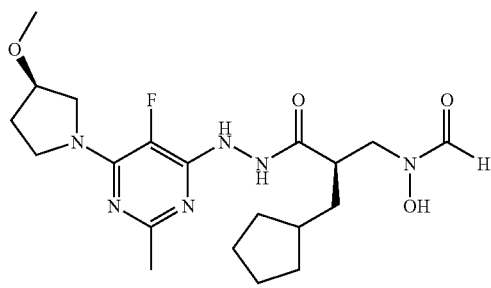

[(2R)-2-(Cyclopentylmethyl)-3-(2-{5-fluoro-2-methyl-6-[(3R)-3-(methyloxy)-1-pyrrolidinyl]-4-pyrimidinyl}hydrazino)-3-oxopropyl]hydroxyformamide was prepared according to General Procedure A, utilizing commercially-available (R)-3-hydroxypyrrolidine hydrochloride in place of pyrrolidine in Part A. LCMS: (M+H)$^+$: 439.2.

Example 15

[(2R)-2-(Cyclopentylmethyl)-3-(2-{5-fluoro-2-methyl-6-[(3S)-3-(methyloxy)-1-pyrrolidinyl]-4-pyrimidinyl}hydrazino)-3-oxopropyl]hydroxyformamide

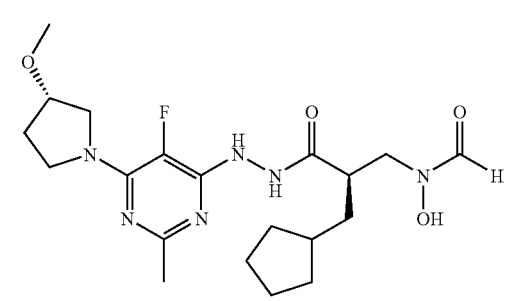

[(2R)-2-(Cyclopentylmethyl)-3-(2-{5-fluoro-2-methyl-6-[(3S)-3-(methyloxy)-1-pyrrolidinyl]-4-pyrimidinyl}hydrazino)-3-oxopropyl]hydroxyformamide was prepared according to General Procedure A, utilizing commercially-available (S)-3-hydroxypyrrolidine hydrochloride in place of pyrrolidine in Part A. LCMS: (M+H)$^+$: 439.2.

Example 16

[(2R)-2-(Cyclopentylmethyl)-3-(2-{5-fluoro-2-methyl-6-[(1-methylethyl)amino]-4-pyrimidinyl}hydrazino)-3-oxopropyl]hydroxyformamide

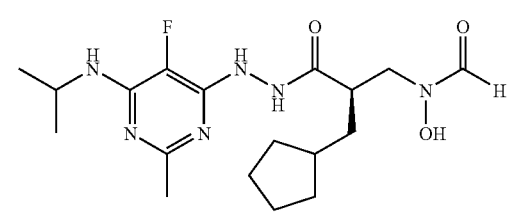

[(2R)-2-(Cyclopentylmethyl)-3-(2-{5-fluoro-2-methyl-6-[(1-methylethyl)amino]-4-pyrimidinyl}hydrazino)-3-oxopropyl]hydroxyformamide was prepared according to General Procedure A, utilizing commercially-available isopropylamine in place of pyrrolidine in Part A. LCMS: (M+H)$^+$: 397.4.

Example 17

{(2R)-2-(Cyclopentylmethyl)-3-[2-(5-fluoro-2-methyl-6-{methyl[2-(methyloxy)ethyl]amino}-4-pyrimidinyl)hydrazino]-3-oxopropyl}hydroxyformamide

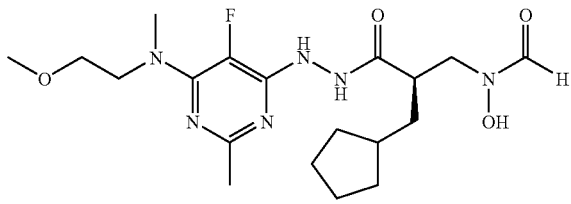

{(2R)-2-(Cyclopentylmethyl)-3-[2-(5-fluoro-2-methyl-6-{methyl[2-(methyloxy)ethyl]amino}-4-pyrimidinyl)hydrazino]-3-oxopropyl}hydroxyformamide was prepared according to General Procedure A, utilizing commercially-available N-(2-methoxyethyl)methylamine in place of pyrrolidine in Part A. LCMS: (M+H)$^+$: 427.2.

Example 18

[(2R)-2-(Cyclopentylmethyl)-3-(2-{6-[ethyl(methyl)amino]-5-fluoro-2-methyl-4-pyrimidinyl}hydrazino)-3-oxopropyl]hydroxyformamide

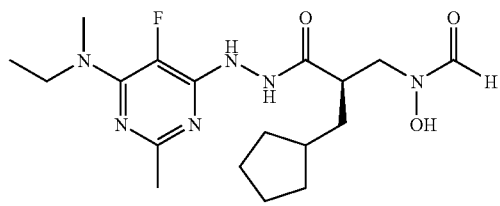

[(2R)-2-(Cyclopentylmethyl)-3-(2-{6-[ethyl(methyl)amino]-5-fluoro-2-methyl-4-pyrimidinyl}hydrazino)-3-oxopropyl]hydroxyformamide was prepared according to General Procedure A, utilizing commercially-available N-ethylmethylamine in place of pyrrolidine in Part A. LCMS: (M+H)$^+$: 397.4.

Example 19

[(2R)-2-(Cyclopentylmethyl)-3-(2-{5-fluoro-6-[(2S)-2-(hydroxymethyl)-1-pyrrolidinyl]-2-methyl-4-pyrimidinyl}hydrazino)-3-oxopropyl]hydroxyformamide

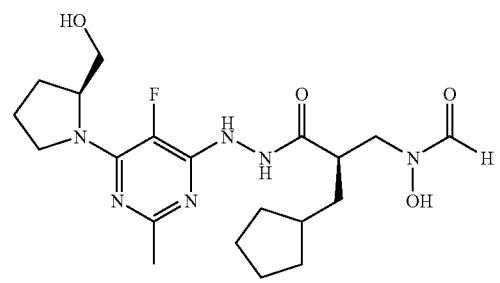

[(2R)-2-(Cyclopentylmethyl)-3-(2-{5-fluoro-6-[(2S)-2-(hydroxymethyl)-1-pyrrolidinyl]-2-methyl-4-pyrimidinyl}hydrazino)-3-oxopropyl]hydroxyformamide was prepared according to General Procedure A, utilizing commercially-available (S)-(+)-2-(hydroxymethyl)pyrrolidine in place of pyrrolidine in Part A. LCMS: (M+H)$^+$: 440.2.

Example 20

[(2R)-3-{2-[6-(Cyclobutylamino)-5-fluoro-2-methyl-4-pyrimidinyl]hydrazino}-2-(cyclopentylmethyl)-3-oxopropyl]hydroxyformamide

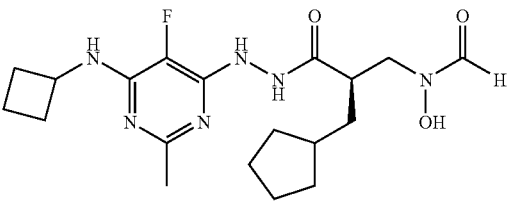

[(2R)-3-{2-[6-(Cyclobutylamino)-5-fluoro-2-methyl-4-pyrimidinyl]hydrazino}-2-(cyclopentylmethyl)-3-oxopropyl]hydroxyformamide was prepared according to General Procedure A, utilizing commercially-available cyclobutylamine in place of pyrrolidine in Part A. LCMS: (M+H)$^+$: 409.4.

Example 21

[(2R)-3-{2-[6-(Cyclopentylamino)-5-fluoro-2-methyl-4-pyrimidinyl]hydrazino}-2-(cyclopentylmethyl)-3-oxopropyl]hydroxyformamide

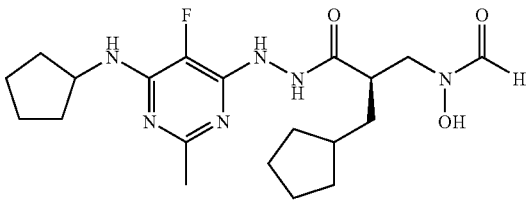

[(2R)-3-{2-[6-(Cyclopentylamino)-5-fluoro-2-methyl-4-pyrimidinyl]hydrazino}-2-(cyclopentylmethyl)-3-oxopropyl]hydroxyformamide was prepared according to General Procedure A, utilizing commercially-available cyclopentylamine in place of pyrrolidine in Part A. LCMS: (M+H)$^+$: 423.1.

Example 22

[(2R)-2-(Cyclopentylmethyl)-3-(2-{5-fluoro-6-[(3R)-3-(hydroxymethyl)-1-pyrrolidinyl]-2-methyl-4-pyrimidinyl}hydrazino)-3-oxopropyl]hydroxyformamide

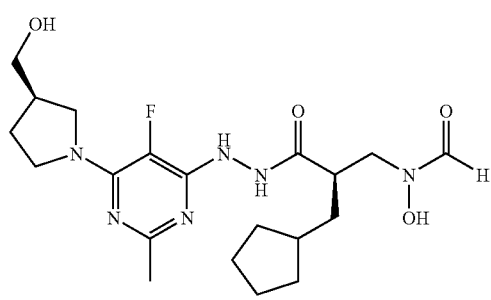

[(2R)-2-(Cyclopentylmethyl)-3-(2-{5-fluoro-6-[(3R)-3-(hydroxymethyl)-1-pyrrolidinyl]-2-methyl-4- pyrimidinyl}hydrazino)-3-oxopropyl]hydroxyformamide was prepared according to General Procedure A, utilizing 3(R)-pyrrolidinemethanol (J. of Med. Chem. 1987, 30, 1711-1715), in place of pyrrolidine in Part A. LCMS: (M+H)$^+$: 439.2.

Example 23

[(2R)-2-(Cyclopentylmethyl)-3-(2-{5-fluoro-6-[(3S)-3-(hydroxymethyl)-1-pyrrolidinyl]-2-methyl-4-pyrimidinyl}hydrazino)-3-oxopropyl]hydroxyformamide

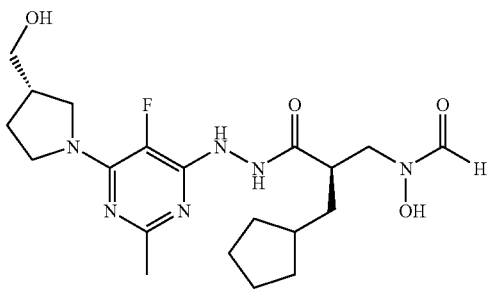

[(2R)-2-(Cyclopentylmethyl)-3-(2-{5-fluoro-6-[(3S)-3-(hydroxymethyl)-1-pyrrolidinyl]-2-methyl-4-pyrimidinyl}hydrazino)-3-oxopropyl]hydroxyformamide was prepared according to General Procedure A, utilizing 3(S)-pyrrolidinemethanol (J. of Med. Chem. 1987, 30, 1711-1715), in place of pyrrolidine in Part A. LCMS: (M+H)$^+$: 439.2.

Example 24

[(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl] hydroxyformamide

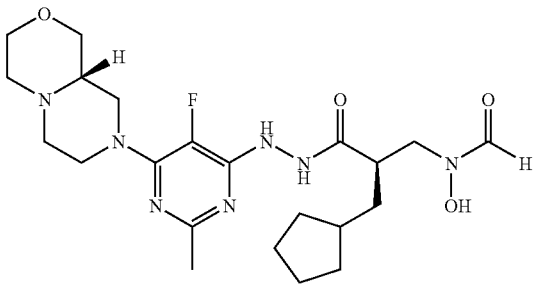

Part A:

N-(Phenylmethyl)-D-serine

As per the procedures of WO2005058245, a mixture of D-serine methyl ester hydrochloride (98.84 g, 635.3 mmol) in MeOH (280 mL) was cooled to 10° C. To the mixture was slowly added triethylamine (88.5 mL, 635.0 mmol). The mixture was warmed to room temperature and the resulting solution was cooled to 10° C. To the solution was added benzaldehyde (64 mL, 630.2 mmol), and the solution was stirred for 30 min. To the solution was added sodium borohydride (24.03 g, 635.2 mmol) portionwise over 30 min, and the mixture was stirred for a further 30 min. In a separate flask, MeOH (114 mL) was added to water (170 mL), and to this solution was added a solution of NaOH (77.25 g, 1931 mmol) in water (155 mL). The solution was cooled to 15° C., and the reductive amination mixture was slowly added to the NaOH-water-MeOH solution over 15 min. The solution was stirred and warmed to room temperature over 30 min, and water (170 mL) was added, followed by sufficient 6 N aqueous HCl to adjust the pH to 9.5. The solution was washed with EtOAc (2×60 mL), and sufficient 6 N aqueous HCl was added to adjust the pH to 6.5. The mixture was cooled to 0° C. and held overnight. The resulting solid was collected by vacuum filtration and washed with water (2×200 mL) followed by heptane (2×200 mL). The white solid was dried at 40° C. under high vacuum for 3 days to afford N-(phenylmethyl)-D-serine (79.51 g, 64%). LCMS: (M+H)$^+$: 196.1.

Part B:

(3R)-5-Oxo-4-(phenylmethyl)-3-morpholinecarboxylic acid

As per the procedures of WO2005058245, a solution of N-(phenylmethyl)-D-serine (79.51 g, 407.3 mmol) in THF (485 mL) was cooled to 0° C., and a precooled 0° C. solution of K$_2$CO$_3$ (168.87 g, 1222 mmol) in water (485 mL) was added. To the well-stirred mixture was added chloroacetyl chloride (45.4 mL, 570.0 mmol) slowly while keeping the internal temperature below 5° C. The mixture was vigorously stirred at 0° C. for 30 min, and then an additional portion of chloroacetyl chloride (4.54 mL, 57.0 mmol) was slowly added. The mixture was stirred for an additional 30 min at 0° C. To the mixture was added a sufficient quantity of precooled 0° C. aqueous NaOH (50% w/w) to adjust the pH>13.5 while keeping the internal temperature between 5° C. and 10° C. The mixture was stirred at 0° C. for 2 h, and then warmed to 20° C. The mixture was washed with heptane (165 mL) followed by a second portion of fresh heptane (240 mL). The aqueous phase was cooled to 0° C., and adjusted to pH<2 with concentrated aqueous HCl while keeping the internal temperature less than 10° C. The mixture was placed in a 0° C. freezer overnight, and the solid was collected by vacuum filtration. The solid was washed with water (2×300 mL) and dried in vacuo at 42° C. overnight. The resulting (3R)-5-oxo-4-(phenylmethyl)-3-morpholinecarboxylic acid (72.20 g, 75%) was isolated as a white solid. LCMS: (M+H)$^+$: 236.1.

Part C:

(3R)-5-Oxo-N,4-bis(phenylmethyl)-3-morpholinecarboxamide

A mixture of (3R)-5-oxo-4-(phenylmethyl)-3-morpholinecarboxylic acid (69.67 g, 296.2 mmol) and 1-hydroxybenzotriazole (48.01 g, 355.4 mmol) in DCM (990 mL) was cooled to 0° C. To the mixture was added 4-methylmorpholine (163 mL, 1483 mmol), benzyl amine (35.6 mL, 325.9 mmol), and EDC (62.46 g, 325.8 mmol). The yellow solution was stirred overnight at room temperature, and was then washed with water (500 mL), 6 N aqueous HCl (300 mL), and water (200 mL). The organic phase was dried over anhydrous Na$_2$SO$_4$, filtered, and concentrated in vacuo to give crude (3R)-5-oxo-N,4-bis(phenylmethyl)-3-morpholinecarboxamide (97.05 g, >100% crude yield) as a yellow foam. LCMS: (M+H)$^+$: 325.2.

Part D:

1-Phenyl-N-{[(3S)-4-(phenylmethyl)-3-morpholinyl]methyl}methanamine

To a 0° C. solution of (3R)-5-oxo-N,4-bis(phenylmethyl)-3-morpholinecarboxamide (assumed 96.07 g, 296.2 mmol) in PhMe (750 mL) was added Red-Al (65% w/w in PhMe, 645 mL) via addition funnel. After approximately 50 mL of Re-Al had been added, the resulting mixture was warmed to room temperature, and the remainder of the Red-Al was then added over 30 min. The mixture was then heated at 50° C. and stirred overnight. The solution was cooled to 0° C., and the reaction was quenched by the slow dropwise addition of 1 N aqueous NaOH (50 mL). An additional portion of 1 N aqueous NaOH (500 mL) was then added, followed by Et$_2$O (200 mL). The phases were separated, and the organic phase was washed with fresh 1 N aqueous NaOH (400 mL). The combined aqueous phase was extracted with fresh 4:1 PhMe-Et$_2$O (250 mL), and the combined organic phase was dried over anhydrous Na$_2$SO$_4$, filtered, and concentrated in vacuo to give 1-phenyl-N-{[(3S)-4-(phenylmethyl)-3-morpholinyl]methyl}methanamine as a yellow oil that was used without further purification. LCMS: (M+H)$^+$: 297.1.

Part E:

Ethyloxo((phenylmethyl){[(3S)-4-(phenylmethyl)-3 morpholinyl]methyl}amino)acetate A solution of 1-phenyl-N-{[(3S)-4-(phenylmethyl)-3-morpholinyl]methyl}methanamine (assumed 87.79 g, 296.2 mmol) and N,N-diisopropylethylamine (67.1 mL, 385.2 mmol) in THF (1000 mL) was cooled to 0° C. To the solution was added ethyl chloro(oxo)acetate (36.3 mL, 326.2 mmol) dropwise via addition funnel. The resulting mixture was allowed to stir and warm to room temperature for 1 h. The solvent was then removed in vacuo to approximately 20% volume, and the residue was partitioned between EtOAc (600 mL), water (100 mL) and sat. aqueous NaHCO$_3$ (500 mL). The aqueous phase was extracted with a fresh portion of EtOAc (200 mL), and the combined organic phase was dried over anhydrous Na$_2$SO$_4$, filtered, and concentrated in vacuo. The residue was then azeotroped with EtOH (100 mL) to provide ethyl oxo((phenylmethyl){[(3S)-4-(phenylmethyl)-3-morpholinyl]methyl}amino)acetate as a yellow oil that was used without further purification. LCMS: (M+H)$^+$: 397.2.

Part F:

(9aS)-8-(Phenylmethyl)hexahydropyrazino[2,1-c][1,4]oxazine-6,7-dione

To a solution of ethyl oxo((phenylmethyl){[(3S)-4-(phenylmethyl)-3-morpholinyl]methyl}amino)acetate (assumed 117.43 g, 296.2 mmol) in EtOH (1000 mL) was added 10% Pd/C (23 g). The resulting mixture was hydrogenated under balloon pressure for 5 days, and then filtered through a glass fiber filter with EtOH washes. The solution was then concentrated in vacuo and crystallized from EtOH-EtOAc to give approximately 15 g of a white solid. The Pd/C filter cake was then slurried with MeOH (600 mL), and the mixture was filtered through a glass fiber filter with MeOH washes. The solution was then concentrated in vacuo and crystallized from EtOH-EtOAc to give a white solid that was combined with the initial batch of solid. The combined mother liquors were then concentrated in vacuo and crystallized from EtOH-EtOAc to give a white solid that was combined with the first two batches of solid to afford (9aS)-8-(phenylmethyl)hexahydropyrazino[2,1-c][1,4]oxazine-6,7-dione (39.97 g, 52% yield for 4 steps). LCMS: (M+H)$^+$: 261.1.

Part G:

(9aS)-8-(Phenylmethyl)octahydropyrazino[2,1-c][1,4]oxazine

To a 0° C. mixture of two combined batches of (9aS)-8-(phenylmethyl)hexahydropyrazino[2,1-c][1,4]oxazine-6,7-dione (combined total 42.29 g, 162.5 mmol) in Et$_2$O (406 mL) was added 1 M LiAlH$_4$ in Et$_2$O (406 mL, 406 mmol) via dropping funnel over 40 min. The mixture was then warmed to 35° C. and stirred for 6 days. The mixture was then cooled to 0° C., and EtOAc (100 mL) was slowly added, followed by water (20 mL), 15% aqueous NaOH (20 mL), and water (60 mL). The mixture was vigorously stirred for 1 h, and then diluted with EtOAc (500 mL). The mixture was filtered, and the filter cake was diluted with 1 N aqueous NaOH (500 mL) and extracted with Et$_2$O (2×200 mL). The combined organic phase (filtrate and Et$_2$O extractions) was dried over anhydrous Na$_2$SO$_4$, filtered, concentrated in vacuo, azeotroped with MeOH (100 mL), and dried overnight under high vacuum. The resulting colorless oil was combined with a second batch of product prepared in the same fashion from (9aS)-8-(phenylmethyl)hexahydropyrazino[2,1-c][1,4]oxazine-6,7-dione (0.3047 g, 1.1 mmol) to give crude (9aS)-8-(phenylmethyl)octahydropyrazino[2,1-c][1,4]oxazine (combined total 38.59 g, >100% crude yield). LCMS: (M+H)$^+$: 233.1.

Part H:

(9aS)-Octahydropyrazino[2,1-c][1,4]oxazine dihydrochloride

To a solution of (9aS)-8-(phenylmethyl)octahydropyrazino[2,1-c][1,4]oxazine (assumed 38.02 g, 163.6 mmol) in MeOH (330 mL) was added 6 N aqueous HCl (55 mL, 330 mmol) and 10% Pd/C (3.80 g). The mixture was hydrogenated overnight, and then filtered through a glass fiber filter. The filter cake was washed with MeOH, and the combined solution was concentrated in vacuo and azeotroped with MeOH (4×150 mL) to provide (9aS)-octahydropyrazino[2,1-c][1,4]oxazine dihydrochloride (34.78 g, 99% yield for 2 steps) as a red oil that solidified under high vacuum. LCMS: (M+H)$^+$: 142.9.

Part I:

(9aS)-8-(6-Chloro-5-fluoro-2-methyl-4-pyrimidinyl) octahydropyrazino[2,1-c][1,4]oxazine To a mixture of (9aS)-octahydropyrazino[2,1-c][1,4]oxazine dihydrochloride (23.28 g, 108.2 mmol) in DCM (360 mL) was added 4,6-dichloro-5-fluoro-2-methylpyrimidine (19.59 g, 108.2 mmol) and N,N-diisopropylethylamine (68 mL, 390.4 mmol). The mixture was stirred for 2 h, and the resulting solution was diluted with DCM (100 mL) and washed with saturated aq. NaHCO$_3$ (200 mL). The aqueous phase was extracted with a fresh portion of DCM (100 mL), and this organic phase was washed with saturated aq. NaHCO$_3$ (50 mL). The combined organic phase was dried over anhydrous Na$_2$SO$_4$, filtered, and concentrated in vacuo to give (9aS)-8-(6-chloro-5-fluoro-2-methyl-4-pyrimidinyl) octahydropyrazino[2,1-c][1,4]oxazine as a light yellow oil that was used without further purification. LCMS: (M+H)$^+$: 287.1.

Part J:

(9aS)-8-(5-Fluoro-6-hydrazino-2-methyl-4-pyrimidinyl)octahydropyrazino[2,1-c][1,4]oxazine To a solution of (9aS)-8-(6-chloro-5-fluoro-2-methyl-4-pyrimidinyl)octahydropyrazino[2,1-c][1,4]oxazine (assumed 31.03 g, 108.2 mmol) in dioxane (430 mL) was added hydrazine monohydrate (31 mL). The mixture was heated and stirred at 80° C. overnight, and then at 85° C. for 7 h. The mixture was cooled to room temperature and concentrated in vacuo. The residue was dissolved in DCM (500 mL) and washed with saturated aq. NaHCO$_3$ (200 mL). The aqueous phase was extracted with a fresh portion of DCM (100 mL), and this organic phase was washed with saturated aq. NaHCO$_3$ (100 mL). The combined organic phase was dried over anhydrous Na$_2$SO$_4$, filtered, concentrated in vacuo, and dried under high vacuum overnight to provide (9aS)-8-(5-fluoro-6-hydrazino-2-methyl-4-pyrimidinyl)octahydropyrazino[2,1-c][1,4]oxazine (27.98 g, 92% yield for 2 steps) as a light yellow solid. LCMS: (M+H)$^+$: 283.3.

Part K:

[(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl][(phenylmethyl)oxy]formamide To a solution of (2R)-3-cyclopentyl-2-({formyl[(phenylmethyl)oxy]amino}methyl)propanoic acid, N,N-diisopropylethylamine salt, isopropanol solvate (33.64 g, 68.0 mmol) in DMF (230 mL) was added (9aS)-8-(5-fluoro-6-hydrazino-2-methyl-4-pyrimidinyl)octahydropyrazino[2,1-c][1,4]oxazine (20.16 g, 71.4 mmol), N-methylmorpholine (30 mL, 273 mmol), 1-hydroxy-7-azabenzotriazole (11.10 g, 81.6 mmol), and EDC (15.64 g, 81.6 mmol). The solution was stirred overnight and then diluted with Et$_2$O (500 mL). The mixture was washed with water (2×200 mL), and the combined aqueous phase was extracted with a fresh portion of Et$_2$O (100 mL). This Et$_2$O phase was then washed with water (50 mL). This extraction-wash procedure was repeated 6 times, and the total combined organic phase was then diluted with DCM (250 mL). The organic phase was then dried over anhydrous Na$_2$SO$_4$, filtered, and concentrated in vacuo to give crude [(2R)-2-(cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl][(phenylmethyl)oxy]formamide (42.32 g, >100% crude yield) as a light yellow foam. LCMS: (M+H)$^+$: 570.3.

Part L:

[(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide To a solution of [(2R)-2-(cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl][(phenylmethyl)oxy]formamide (assumed 38.74 g, 68.0 mmol) in methanol (225 mL) was added 10% Pd/C (5.81 g). The mixture was hydrogenated under balloon pressure for 4 h, and was then filtered through a glass fiber filter with MeOH washes. The resulting solution was concentrated in vacuo to approximately 10% volume, diluted with EtOAc (400 mL), and concentrated in vacuo to approximately 30% volume. The resulting solid was collected by vacuum filtration and washed with EtOAc. The mother liquor and EtOAc washings were concentrated in vacuo to approximately 10% volume, and the resulting solid was collected by vacuum filtration and washed with EtOAc. The two crops of solid were combined and dried at 50° C. for 16 h under high vacuum to afford [(2R)-2-(cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (25.48 g, 78% yield for 2 steps) as a white solid. LCMS: (M+H)$^+$: 480.1.

Alternative Procedure

To a solution of crude [(2R)-2-(cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl][(phenylmethyl)oxy]formamide (assumed 39.73 g, 69.74 mmol) in MeOH (350 mL) was added 10% Pd/C (50% water, 7.9 g). The suspension was hydrogenated under balloon pressure for 3 h, and was then filtered through two glass fiber filters with MeOH washings. The resulting solution was concentrated in vacuo to a volume of approximately 70 mL, and was then diluted with EtOAc (500 mL). The solution was concentrated in vacuo to remove approximately 100 mL of solvent. The resulting solid was collected by vacuum filtration, and washed well with EtOAc followed by hexanes. The mother liquor was concentrated in vacuo, and then diluted with EtOAc (200 mL). The mixture was concentrated in vacuo to approximately 50% volume, and the resulting solid was collected by vacuum filtration and washed well with EtOAc followed by hexanes. The two batches of solid were combined and placed under high vacuum overnight. To this material was then added approximately 466 mg of material prepared through a similar sequence, and the combined batch was heated at 50° C. under high vacuum overnight to afford [(2R)-2-(cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (28.27 g, 83% yield for 2 steps). LC/MS: (M+H)$^+$: 480.3. The resulting solid was analytically characterized and found to be polymorphic form, Form 1.

Example 25

((2R)-2-(Cyclopentylmethyl)-3-{2-[2-ethyl-5-fluoro-6-(4-methyl-1-piperazinyl)-4-pyrimidinyl]hydrazino}-3-oxopropyl)hydroxyformamide

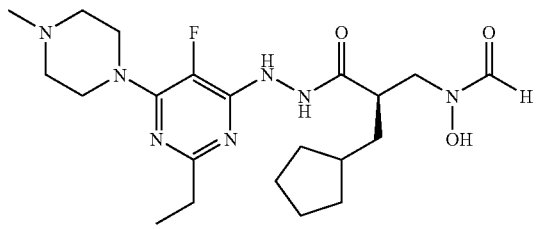

Part A:

2-Ethyl-5-fluoro-4-hydrazino-6-(4-methyl-1-piperazinyl)pyrimidine

To an ice-cold solution of 1,4-dioxane (10 mL) and MeOH (2 mL) was added 4,6-dichloro-2-ethyl-5-fluoropyrimidine (1.0 g, 5.13 mmol), N-methylpiperazine (626 uL, 5.64 mmol) and DIPEA (1.97 mL, 12.4 mmol) sequentially. The solution was then stirred at room temperature for 2 h. After the reaction was complete, anhydrous hydrazine (1.29 mL, 99 mmol) was added. The resulting suspension was heated at 90° C. in a oil bath for 2 h until the intermediate was consumed. Evaporation of the solvent gave a light yellow solid. The solid was dissolved in CH$_2$Cl$_2$ (100 mL) and washed with 1 N HCl. The aqueous phase was back-extracted with DCM (50 mL). The combined organic layers were dried over anhydrous Na₂SO₄. Evaporation of the solvent gave a light yellow residue as the desired product (890 mg, 69%).

Part B:

((2R)-2-(Cyclopentylmethyl)-3-{2-[2-ethyl-5-fluoro-6-(4-methyl-1-piperazinyl)-4-pyrimidinyl]hydrazino}-3-oxopropyl)[(phenylmethyl)oxy]formamide A solution of (2R)-3-cyclopentyl-2-({formyl[(phenylmethyl)oxy]amino}methyl)propanoic acid (12.4 g, 40.6 mmol) in DMF (120 mL) was added to a mixture of 2-ethyl-5-fluoro-4-hydrazino-6-(4-methyl-1-piperazinyl)pyrimidine (9.6 g, 37.8 mmol), HOAt (5.66 g, 41.58 mmol), and EDC (7.97 g, 41.58 mmol). The resulting solution was treated with NMM (9.1 mL, 83.2 mmol) and stirred at room temperature for 3 h. After the reaction was complete, 200 mL of water was added and the solution was extracted three times with 200 mL of ether. The combined organic layers were washed with water (200 mL) and brine (100 mL), and then dried over anhydrous Na₂SO₄. Evaporation of the solvent provided a light yellow glassy solid as the pure product (17.1 g, 84%).

Part C:

((2R)-2-(Cyclopentylmethyl)-3-{2-[2-ethyl-5-fluoro-6-(4-methyl-1-piperazinyl)-4-pyrimidinyl]hydrazino}-3-oxopropyl)hydroxyformamide A mixture of ((2R)-2-(cyclopentylmethyl)-3-{2-[2-ethyl-5-fluoro-6-(4-methyl-1-piperazinyl)-4-pyrimidinyl]hydrazino}-3-oxopropyl)[(phenylmethyl)oxy]formamide (17.1 g, 31.61 mmol) and 10% Pd/C (4 g) suspended in MeOH (400 mL) was stirred under a balloon of H₂ gas. After 2 h, and additional 2 g of fresh 10% Pd/C was added. The resulting suspension was stirred for another 1.5 h under a hydrogen atmosphere until the staring material was consumed. The Pd/C was removed by filtration through Celite, washing with MeOH and CH₂Cl₂. The filtrate was concentrated in vacuo. As the evaporation proceeded, the product crystallized out from the remaining solution. The evaporation continued until only ~50 mL of liquid remained. The crystals were then collected by filtration to provide the product as a white solid (10.0 g). The filtrate was further evaporated to give a second crop of crystals (1.5 g) as the pure product. In the same way, a third crop was collected. The combined yield of ((2R)-2-(cyclopentylmethyl)-3-{2-[2-ethyl-5-fluoro-6-(4-methyl-1-piperazinyl)-4-pyrimidinyl]hydrazino}-3-oxopropyl)hydroxyformamide was 86% (12.2 g). LCMS: (M+H)⁺: 452.1.

Example 26

N-[(2R)-2-(Cyclopentylmethyl)-3-{2-[2-ethyl-5-fluoro-6-(2-isoxazolidinyl)-4-pyrimidinyl]hydrazino}-3-oxopropyl]-N-hydroxyformamide

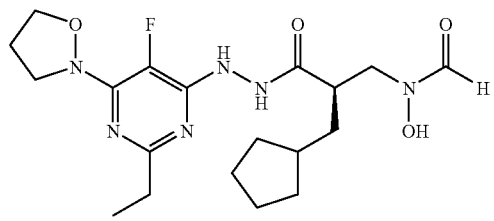

N-[(2R)-2-(Cyclopentylmethyl)-3-{2-[2-ethyl-5-fluoro-6-(2-isoxazolidinyl)-4-pyrimidinyl]hydrazino}-3-oxopropyl]-N-hydroxyformamide was prepared according to General Procedure B, utilizing commercially-available isoxazolidine in place of azetidine in Part A. LCMS: (M+H)⁺: 425.2.

Example 27

N-[(2R)-2-(Cyclopentylmethyl)-3-(2-{6-[(3R)-3-(dimethylamino)-1-pyrrolidinyl]-2-ethyl-5-fluoro-4-pyrimidinyl}hydrazino)-3-oxopropyl]-N-hydroxyformamide

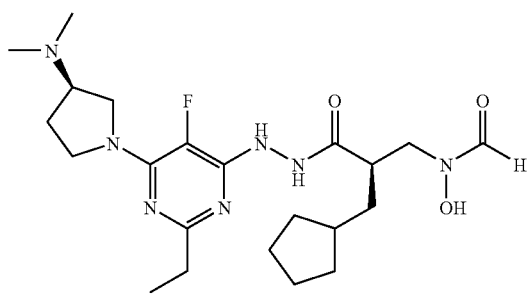

N-[(2R)-2-(Cyclopentylmethyl)-3-(2-{6-[(3R)-3-(dimethylamino)-1-pyrrolidinyl]-2-ethyl-5-fluoro-4-pyrimidinyl}hydrazino)-3-oxopropyl]-N-hydroxyformamide was prepared according to General Procedure B, utilizing commercially-available (3R)-(+)-3-(dimethylamino)pyrrolidine in place of azetidine in Part A. LCMS: (M+H)⁺: 466.2.

Example 28

N-[(2R)-2-(Cyclopentylmethyl)-3-(2-{6-[(3S)-3-(dimethylamino)-1-pyrrolidinyl]-2-ethyl-5-fluoro-4-pyrimidinyl}hydrazino)-3-oxopropyl]-N-hydroxyformamide

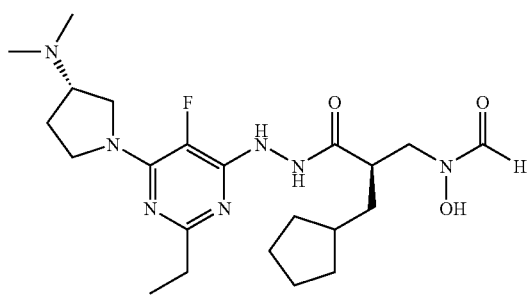

N-[(2R)-2-(Cyclopentylmethyl)-3-(2-{6-[(3S)-3-(dimethylamino)-1-pyrrolidinyl]-2-ethyl-5-fluoro-4-pyrimidinyl}hydrazino)-3-oxopropyl]-N-hydroxyformamide was prepared according to General Procedure B, utilizing commercially-available (3S)-(−)-3-(dimethylamino)pyrrolidine in place of azetidine in Part A. LCMS: (M+H)⁺: 466.2.

Example 29

N-[(2R)-2-(Cyclopentylmethyl)-3-(2-{2-ethyl-5-fluoro-6-[(3S)-3-hydroxy-1-pyrrolidinyl]-4-pyrimidinyl}hydrazino)-3-oxopropyl]-N-hydroxyformamide

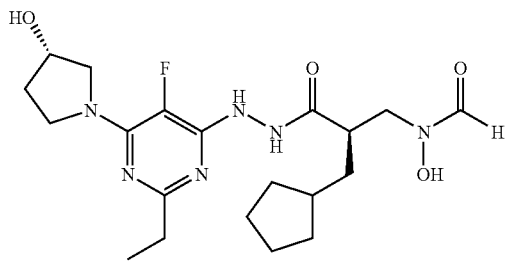

N-[(2R)-2-(Cyclopentylmethyl)-3-(2-{2-ethyl-5-fluoro-6-[(3S)-3-hydroxy-1-pyrrolidinyl]-4-pyrimidinyl}hydrazino)-3-oxopropyl]-N-hydroxyformamide was prepared according to General Procedure B, utilizing commercially-available (S)-3-hydroxypyrrolidine in place of azetidine in Part A. LCMS: (M+H)+: 439.2.

Example 30

N-[(2R)-2-(Cyclopentylmethyl)-3-(2-{2-ethyl-5-fluoro-6-[(3R)-3-hydroxy-1-pyrrolidinyl]-4-pyrimidinyl}hydrazino)-3-oxopropyl]-N-hydroxyformamide

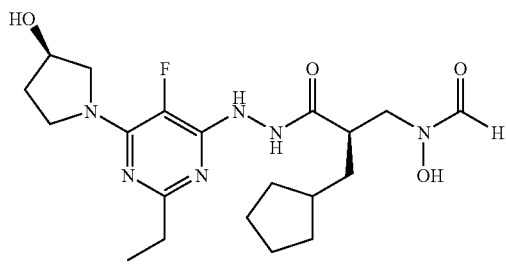

N-[(2R)-2-(Cyclopentylmethyl)-3-(2-{2-ethyl-5-fluoro-6-[(3R)-3-hydroxy-1-pyrrolidinyl]-4-pyrimidinyl}hydrazino)-3-oxopropyl]-N-hydroxyformamide was prepared according to General Procedure B, utilizing commercially-available (R)-3-hydroxypyrrolidine in place of azetidine in Part A. LCMS: (M+H)+: 439.0.

Example 31

N-[(2R)-2-(Cyclopentylmethyl)-3-{2-[6-(cyclopropylamino)-2-ethyl-5-fluoro-4-pyrimidinyl]hydrazino}-3-oxopropyl]-N-hydroxyformamide

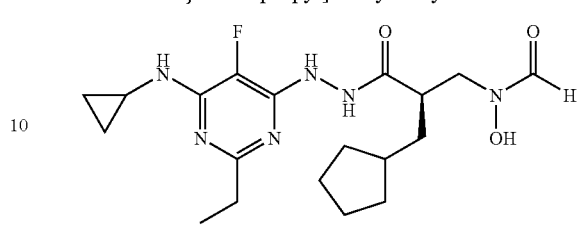

N-[(2R)-2-(Cyclopentylmethyl)-3-{2-[6-(cyclopropylamino)-2-ethyl-5-fluoro-4-pyrimidinyl]hydrazino}-3-oxopropyl]-N-hydroxyformamide was prepared according to General Procedure B, utilizing commercially-available cyclopropylamine in place of azetidine in Part A. LCMS: (M+H)+: 409.2.

Example 32

N-[(2R)-2-(Cyclopentylmethyl)-3-{2-[2-ethyl-6-(4-ethyl-1-piperazinyl)-5-fluoro-4-pyrimidinyl]hydrazino}-3-oxopropyl]-N-hydroxyformamide

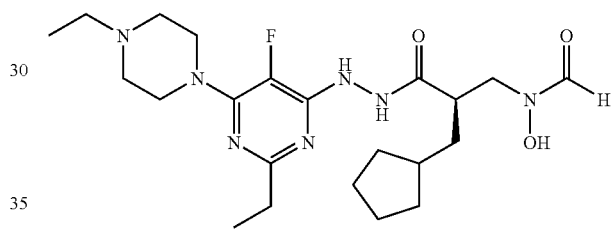

N-[(2R)-2-(Cyclopentylmethyl)-3-{2-[2-ethyl-6-(4-ethyl-1-piperazinyl)-5-fluoro-4-pyrimidinyl]hydrazino}-3-oxopropyl]-N-hydroxyformamide was prepared according to General Procedure B, utilizing commercially-available N-ethylpiperazine in place of azetidine in Part A. LCMS: (M+H)+: 466.5.

Example 33

N-[(2R)-2-(Cyclopentylmethyl)-3-(2-{2-ethyl-5-fluoro-6-[4-(2-hydroxyethyl)-1-piperazinyl]-4-pyrimidinyl}hydrazino)-3-oxopropyl]-N-hydroxyformamide

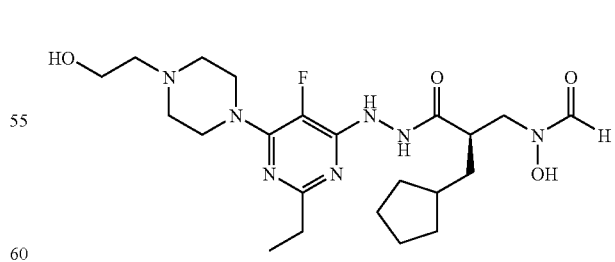

N-[(2R)-2-(Cyclopentylmethyl)-3-(2-{2-ethyl-5-fluoro-6-[4-(2-hydroxyethyl)-1-piperazinyl]-4-pyrimidinyl}hydrazino)-3-oxopropyl]-N-hydroxyformamide was prepared according to General Procedure B, utilizing commercially-available 1-(2-hydroxyethyl)piperazine in place of azetidine in Part A. LCMS: (M+H)+: 482.2.

Example 34

N-[(2R)-2-(Cyclopentylmethyl)-3-{2-[2-ethyl-5-fluoro-6-(methylamino)-4-pyrimidinyl]hydrazino}-3-oxopropyl]-N-hydroxyformamide

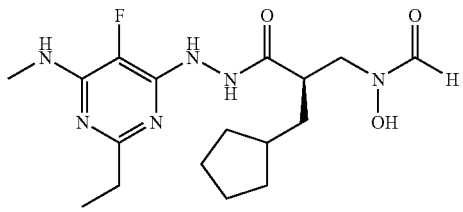

N-[(2R)-2-(Cyclopentylmethyl)-3-{2-[2-ethyl-5-fluoro-6-(methylamino)-4-pyrimidinyl]hydrazino}-3-oxopropyl]-N-hydroxyformamide was prepared according to General Procedure B, utilizing commercially-available methylamine in place of azetidine in Part A. LCMS: (M+H)$^+$: 383.4.

Example 35

N-[(2R)-2-(Cyclopentylmethyl)-3-{2-[2-ethyl-6-(ethylamino)-5-fluoro-4-pyrimidinyl]hydrazino}-3-oxopropyl]-N-hydroxyformamide

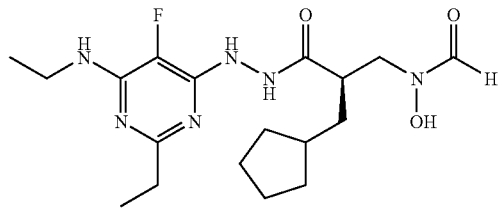

N-[(2R)-2-(Cyclopentylmethyl)-3-{2-[2-ethyl-6-(ethylamino)-5-fluoro-4-pyrimidinyl]hydrazino}-3-oxopropyl]-N-hydroxyformamide was prepared according to General Procedure B, utilizing commercially-available ethylamine in place of azetidine in Part A. LCMS: (M+H)$^+$: 397.4.

Example 36

N-[(2R)-2-(Cyclopentylmethyl)-3-(2-{2-ethyl-5-fluoro-6-[4-(1-methylethyl)-1-piperazinyl]-4-pyrimidinyl}hydrazino)-3-oxopropyl]-N-hydroxyformamide

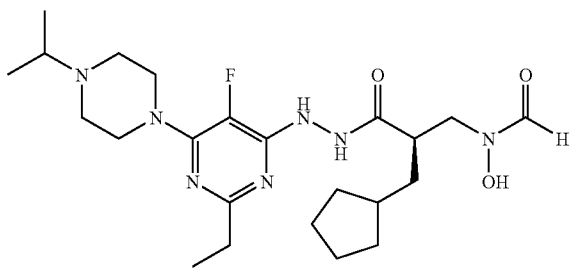

N-[(2R)-2-(Cyclopentylmethyl)-3-(2-{2-ethyl-5-fluoro-6-[4-(1-methylethyl)-1-piperazinyl]-4-pyrimidinyl}hydrazino)-3-oxopropyl]-N-hydroxyformamide was prepared according to General Procedure B, utilizing commercially-available 1-isopropylpiperazine in place of azetidine in Part A. LCMS: (M+H)$^+$: 480.

Example 37

1-(6-{2-[(2R)-3-Cyclopentyl-2-{[formyl(hydroxy)amino]methyl}propanoyl]hydrazino}-2-ethyl-5-fluoro-4-pyrimidinyl)-N,N-dimethyl-L-prolinamide

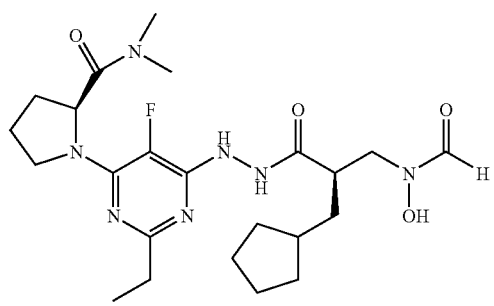

1-(6-{2-[(2R)-3-Cyclopentyl-2-{[formyl(hydroxy)amino]methyl}propanoyl]hydrazino}-2-ethyl-5-fluoro-4-pyrimidinyl)-N,N-dimethyl-L-prolinamide was prepared according to General Procedure B, utilizing commercially-available N,N-dimethyl-L-prolinamide in place of azetidine in Part A. LCMS: (M+H)$^+$: 494.2.

Example 38

N-{(2R)-2-(Cyclopentylmethyl)-3-[2-(6-{[2-(dimethylamino)ethyl](methyl)amino}-2-ethyl-5-fluoro-4-pyrimidinyl)hydrazino]-3-oxopropyl}-N-hydroxyformamide

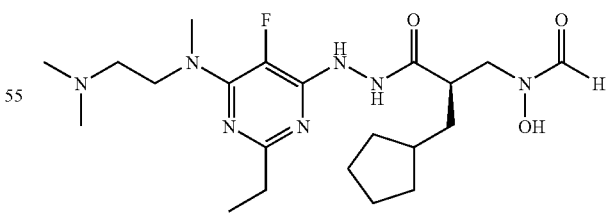

N-{(2R)-2-(Cyclopentylmethyl)-3-[2-(6-{[2-(dimethylamino)ethyl](methyl)amino}-2-ethyl-5-fluoro-4-pyrimidinyl)hydrazino]-3-oxopropyl}-N-hydroxyformamide was prepared according to General Procedure B, utilizing commercially-available N,N,N'-trimethylethylenediamine in place of azetidine in Part A. LCMS: (M+H)$^+$: 454.2.

Example 39

N-[(2R)-2-(Cyclopentylmethyl)-3-(2-{6-[(3R)-3,4-dimethyl-1-piperazinyl]-2-ethyl-5-fluoro-4-pyrimidinyl}hydrazino)-3-oxopropyl]-N-hydroxyformamide

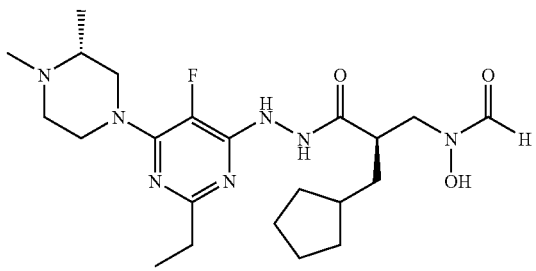

Part A:

(R)-1,2-Dimethylpiperazine, Dihydrochloride Salt

Commercially-available 1,1-dimethylethyl (3R)-3-methyl-1-piperazinecarboxylate (1.0 g, 5.0 mmol), sodium cyanoborohydride (1.57 g, 25 mmol), and formaldehyde (37% in H$_2$O, 2.25 mL, 30 mmol) were dissolved and stirred in MeOH (50 mL). Acetic acid (1.75 mL, 30 mmol) was added dropwise, and the resulting reaction mixture was stirred at room temperature for 2 h. After this time, the solvent was evaporated and the residue was taken up in aq. NaHCO$_3$ solution and extracted three times with diethyl ether. After removal of the solvent from the combined ether layers, the crude 1,1-dimethylethyl (3R)-3,4-dimethyl-1-piperazinecarboxylate was dissolved in ethanol and treated with 2 mL of concentrated HCl. A precipitate formed which was filtered and then recrystallized from ethanol and water to provide (R)-1,2-dimethylpiperazine, dihydrochloride salt (1.27 g).

Part B:

N-[(2R)-2-(Cyclopentylmethyl)-3-(2-{6-[(3R)-3,4-dimethyl-1-piperazinyl]-2-ethyl-5-fluoro-4-pyrimidinyl}hydrazino)-3-oxopropyl]-N-hydroxyformamide N-[(2R)-2-(Cyclopentylmethyl)-3-(2-{6-[(3R)-3,4-dimethyl-1-piperazinyl]-2-ethyl-5-fluoro-4-pyrimidinyl}hydrazino)-3-oxopropyl]-N-hydroxyformamide was prepared according to General Procedure B, utilizing (R)-1,2-dimethylpiperazine, dihydrochloride salt in place of azetidine, and using 3.5 equivalents of DIPEA in Part A. LCMS: (M+H)$^+$: 466.2.

Example 40

N-[(2R)-2-(Cyclopentylmethyl)-3-(2-{6-[(3S)-3,4-dimethyl-1-piperazinyl]-2-ethyl-5-fluoro-4-pyrimidinyl}hydrazino)-3-oxopropyl]-N-hydroxyformamide

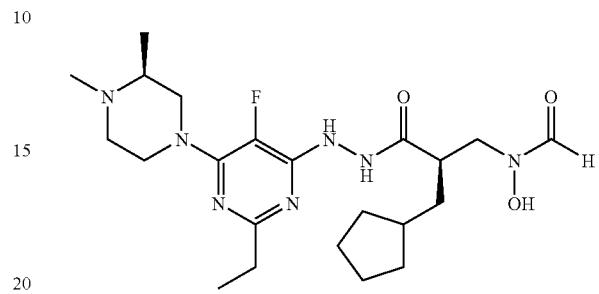

Part A:

(S)-1,2-Dimethylpiperazine, Dihydrochloride Salt (S)-1,2-Dimethylpiperazine dihydrochloride can be prepared in a similar fashion to (R)-1,2-dimethylpiperazine dihydrochloride, as described in Example 39.

Part B:

N-[(2R)-2-(Cyclopentylmethyl)-3-(2-{6-[(3S)-3,4-dimethyl-1-piperazinyl]-2-ethyl-5-fluoro-4-pyrimidinyl}hydrazino)-3-oxopropyl]-N-hydroxyformamide N-[(2R)-2-(Cyclopentylmethyl)-3-(2-{6-[(3S)-3,4-dimethyl-1-piperazinyl]-2-ethyl-5-fluoro-4-pyrimidinyl}hydrazino)-3-oxopropyl]-N-hydroxyformamide was prepared according to General Procedure B, utilizing (S)-1,2-dimethylpiperazine dihydrochloride in place of azetidine, and using 3.5 equivalents of DIPEA in Part A. LCMS: (M+H)$^+$: 466.2.

Example 41

((2R)-2-(Cyclopentylmethyl)-3-{2-[5-fluoro-6-(4-methyl-1-piperazinyl)-2-(methylthio)-4-pyrimidinyl]hydrazino}-3-oxopropyl)hydroxyformamide

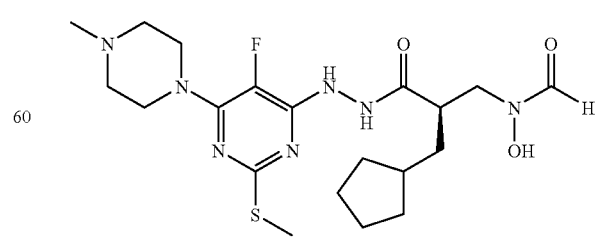

Part A:

((2R)-2-(Cyclopentylmethyl)-3-{2-[5-fluoro-6-(4-methyl-1-piperazinyl)-2-(methylthio)-4-pyrimidinyl]hydrazino}-3-oxopropyl)(tetrahydro-2H-pyran-2-yloxy)formamide In a sealed tube, {(2R)-2-(cyclopentylmethyl)-3-{2-[4-chloro-5-fluoro-2-(methylthio)-6-pyrimidinyl]hydrazine}-3-oxopropyl}(tetrahydro-2H-pyran-2-yloxy)formamide (11.60 g, 23.67 mmol), N-methyl piperazine (2.89 mL, 26.00 mmol, 1.1 eq) and N,N-diisopropyl ethylamine (4.95 mL, 28.40 mmol, 1.2 eq) were dissolved in dry DMSO (100 mL), and the mixture was heated to 68° C. with stirring for 3 days. The reaction mixture was cooled to RT, diluted with water (300 mL) and extracted with ethyl acetate/hexanes (2:1, 2×300 mL). The combined organic solution was washed with water (3×200 mL), dried (Na$_2$SO$_4$), and concentrated to provide ((2R)-2-(cyclopentylmethyl)-3-{2-[5-fluoro-6-(4-methyl-1-piperazinyl)-2-(methylthio)-4-pyrimidinyl]hydrazino}-3-oxopropyl)(tetrahydro-2H-pyran-2-yloxy)formamide as a red foamy solid (12.5 g, 95.4%).

Part B:

((2R)-2-(Cyclopentylmethyl)-3-{2-[5-fluoro-6-(4-methyl-1-piperazinyl)-2-(methylthio)-4-pyrimidinyl]hydrazino}-3-oxopropyl)hydroxyformamide ((2R)-2-(Cyclopentylmethyl)-3-(2-[5-fluoro-6-(4-methyl-1-piperazinyl)-2-(methylthio)-4-pyrimidinyl]hydrazino}-3-oxopropyl)(tetrahydro-2H-pyran-2-yloxy)formamide (2.5 g, 22.58 mmol) was dissolved in acetic acid/water (4:1, 1 L) and stirred at RT for 3 days. The reaction mixture was concentrated to dryness and co-evaporated with toluene (20 mL) followed by methanol (50 mL)/triethylamine (20 mL). The residue was dissolved in methanol (120 mL) and triethylamine (20 mL) and purified by Gilson HPLC (10-95% acetonitrile/water, 8 min gradient time) to provide ((2R)-2-(cyclopentylmethyl)-3-{2-[5-fluoro-6-(4-methyl-1-piperazinyl)-2-(methylthio)-4-pyrimidinyl]hydrazino}-3-oxopropyl)hydroxyformamide as a reddish foamy solid (6.90 g, 65.1%). LCMS: (M+H)$^+$: 470.2.

Example 42

((2R)-2-(Cyclopentylmethyl)-3-{2-[6-(ethylamino)-5-fluoro-2-(methylthio)-4-pyrimidinyl]hydrazino}-3-oxopropyl)hydroxyformamide

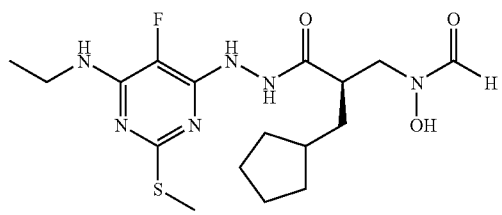

((2R)-2-(Cyclopentylmethyl)-3-{2-[6-(ethylamino)-5-fluoro-2-(methylthio)-4-pyrimidinyl]hydrazino}-3-oxopropyl)hydroxyformamide was prepared according to General Procedure C, utilizing commercially-available ethylamine in place of azetidine hydrochloride in Part A. LCMS: (M+H)$^+$: 415.2.

Example 43

((2R)-2-(Cyclopentylmethyl)-3-{2-[5-fluoro-6-(methylamino)-2-(methylthio)-4-pyrimidinyl]hydrazino}-3-oxopropyl)hydroxyformamide

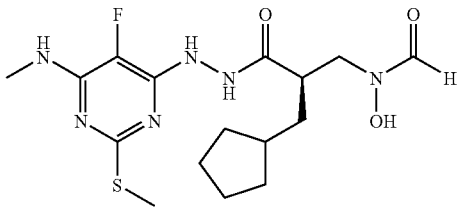

((2R)-2-(Cyclopentylmethyl)-3-{2-[5-fluoro-6-(methylamino)-2-(methylthio)-4-pyrimidinyl]hydrazino}-3-oxopropyl)hydroxyformamide was prepared according to General Procedure C, utilizing commercially-available methylamine in place of azetidine hydrochloride in Part A. LCMS: (M+H)$^+$: 401.1.

Example 44

((2R)-2-(Cyclopentylmethyl)-3-{2-[5-fluoro-6-[(3S)-3-hydroxy-1-pyrrolidinyl]-2-(methylthio)-4-pyrimidinyl]hydrazino}-3-oxopropyl)hydroxyformamide

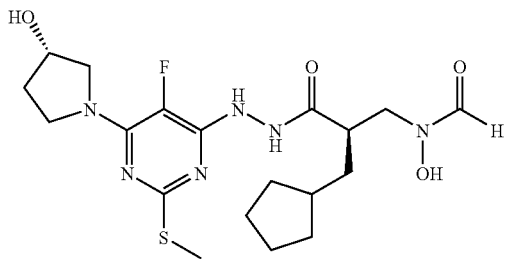

((2R)-2-(Cyclopentylmethyl)-3-{2-[5-fluoro-6-[(3S)-3-hydroxy-1-pyrrolidinyl]-2-(methylthio)-4-pyrimidinyl]hydrazino}-3-oxopropyl)hydroxyformamide was prepared according to General Procedure C, utilizing commercially-available (S)-3-hydroxypyrrolidine in place of azetidine hydrochloride in Part A. LCMS: (M+H)$^+$: 457.4.

Example 45

((2R)-2-(Cyclopentylmethyl)-3-{2-[6-(dimethylamino)-5-fluoro-2-(methylthio)-4-pyrimidinyl]hydrazino}-3-oxopropyl)hydroxyformamide

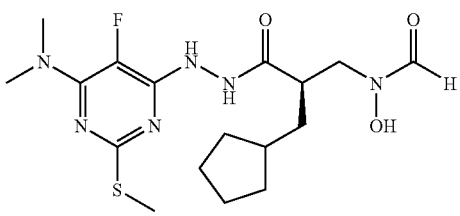

((2R)-2-(Cyclopentylmethyl)-3-{2-[6-(dimethylamino)-5-fluoro-2-(methylthio)-4-pyrimidinyl]hydrazino}-3-oxopropyl)hydroxyformamide was prepared according to General Procedure C, utilizing commercially-available dimethylamine in place of azetidine hydrochloride in Part A. LCMS: (M+H)$^+$: 415.5.

Example 46

((2R)-2-(Cyclopentylmethyl)-3-{2-[5-fluoro-2-(methylthio)-6-(propylamino)-4-pyrimidinyl]hydrazino}-3-oxopropyl)hydroxyformamide

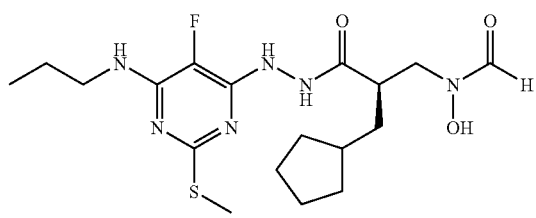

((2R)-2-(Cyclopentylmethyl)-3-{2-[5-fluoro-2-(methylthio)-6-(propylamino)-4-pyrimidinyl]hydrazino}-3-oxopropyl)hydroxyformamide was prepared according to General Procedure C, utilizing commercially-available N-propylamine in place of azetidine hydrochloride in Part A. LCMS: (M+H)$^+$: 429.3.

Example 47

((2R)-2-(Cyclopentylmethyl)-3-{2-[5-fluoro-6-{[2-(methyl oxy)ethyl]amino}-2-(methylthio)-4-pyrimidinyl]hydrazino}-3-oxopropyl)hydroxyformamide

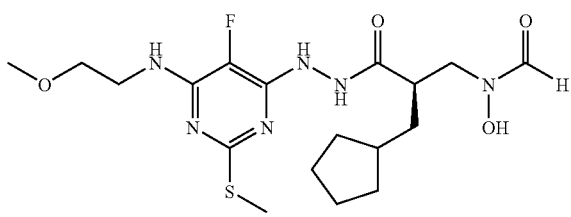

((2R)-2-(Cyclopentylmethyl)-3-{2-[5-fluoro-6-{[2-(methyloxy)ethyl]amino}-2-(methylthio)-4-pyrimidinyl]hydrazino}-3-oxopropyl)hydroxyformamide was prepared according to General Procedure C, utilizing commercially-available methoxyethylamine in place of azetidine hydrochloride in Part A. LCMS: (M+H)$^+$: 445.2.

Example 48

1-[6-[2-((2R)-3-Cyclopentyl-2-{[formyl(hydroxy)amino]methyl}propanoyl)hydrazino]-5-fluoro-2-(methylthio)-4-pyrimidinyl]-N,N-dimethyl-L-prolinamide

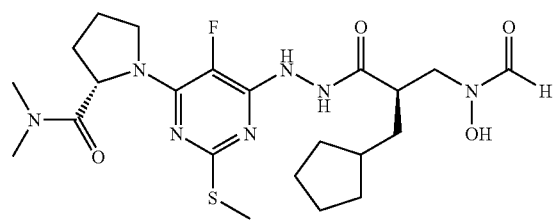

1-[6-[2-((2R)-3-Cyclopentyl-2-{[formyl(hydroxy)amino]methyl}propanoyl)hydrazino]-5-fluoro-2-(methylthio)-4-pyrimidinyl]-N,N-dimethyl-L-prolinamide was prepared according to General Procedure C, utilizing commercially-available N,N-dimethyl-L-prolinamide in place of azetidine hydrochloride in Part A. LCMS: (M+H)$^+$: 512.3.

Example 49

((2R)-2-(Cyclopentylmethyl)-3-{2-[5-fluoro-6-[(3R)-3-hydroxy-1-pyrrolidinyl]-2-(methylthio)-4-pyrimidinyl]hydrazino}-3-oxopropyl)hydroxyformamide

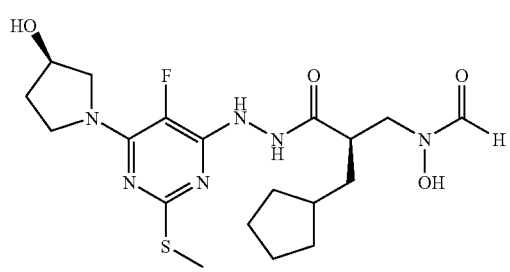

((2R)-2-(Cyclopentylmethyl)-3-{2-[5-fluoro-6-[(3R)-3-hydroxy-1-pyrrolidinyl]-2-(methylthio)-4-pyrimidinyl]hydrazino}-3-oxopropyl)hydroxyformamide was prepared according to General Procedure C, utilizing commercially-available (R)-3-hydroxypyrrolidine in place of azetidine hydrochloride in Part A. LCMS: (M+H)$^+$: 457.2.

Example 50

((2R)-2-(Cyclopentylmethyl)-3-{2-[6-[(3R)-3-(dimethylamino)-1-pyrrolidinyl]-5-fluoro-2-(methylthio)-4-pyrimidinyl]hydrazino}-3-oxopropyl)hydroxyformamide

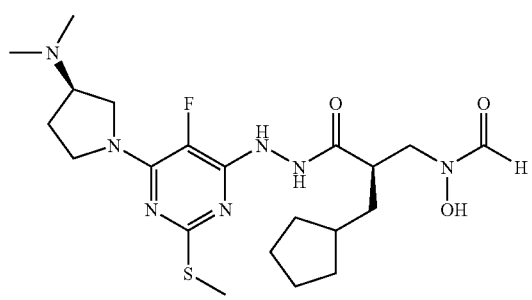

((2R)-2-(Cyclopentylmethyl)-3-{2-[6-[(3R)-3-(dimethylamino)-1-pyrrolidinyl]-5-fluoro-2-(methylthio)-4-pyrimidinyl]hydrazino}-3-oxopropyl)hydroxyformamide was prepared according to General Procedure C, utilizing commercially-available (3R)-(+)-3-(dimethylamino)pyrrolidine in place of azetidine hydrochloride in Part A. LCMS: (M+H)$^+$: 484.4.

Example 51

((2R)-2-(Cyclopentylmethyl)-3-{2-[6-(4-ethyl-1-piperazinyl)-5-fluoro-2-(methylthio)-4-pyrimidinyl]hydrazino}-3-oxopropyl)hydroxyformamide

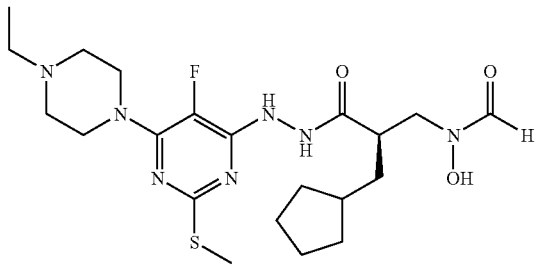

((2R)-2-(Cyclopentylmethyl)-3-{2-[6-(4-ethyl-1-piperazinyl)-5-fluoro-2-(methylthio)-4-pyrimidinyl]hydrazino}-3-oxopropyl)hydroxyformamide was prepared according to General Procedure C, utilizing commercially-available N-ethylpiperazine in place of azetidine hydrochloride in Part A. LCMS: (M+H)+: 484.2.

Example 52

[(2R)-3-{2-[2-Chloro-5-fluoro-6-(4-morpholinyl)-4-pyrimidinyl]hydrazino}-2-(cyclopentylmethyl)-3-oxopropyl]hydroxyformamide

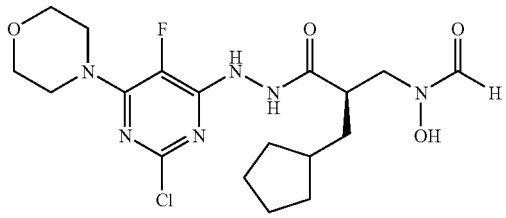

[(2R)-3-{2-[2-Chloro-5-fluoro-6-(4-morpholinyl)-4-pyrimidinyl]hydrazino}-2-(cyclopentylmethyl)-3-oxopropyl]hydroxyformamide was prepared according to General Procedure D, utilizing commercially-available morpholine in place of N-methylpiperazine in Part A. LCMS: (M+H)+: 445.2.

Example 53

[(2R)-3-{2-[6-(1-Azetidinyl)-2-chloro-5-fluoro-4-pyrimidinyl]hydrazino}-2-(cyclopentylmethyl)-3-oxopropyl]hydroxyformamide

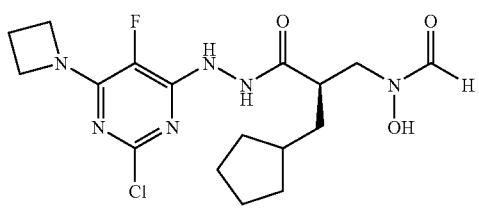

[(2R)-3-{2-[6-(1-Azetidinyl)-2-chloro-5-fluoro-4-pyrimidinyl]hydrazino}-2-(cyclopentylmethyl)-3-oxopropyl]hydroxyformamide was prepared according to General Procedure D, utilizing commercially-available azetidine hydrochloride in place of N-methylpiperazine in Part A. LCMS: (M+H)+: 415.2.

Example 54

[(2R)-3-{2-[2-Chloro-6-(4-ethyl-1-piperazinyl)-5-fluoro-4-pyrimidinyl]hydrazino}-2-(cyclopentylmethyl)-3-oxopropyl]hydroxyformamide

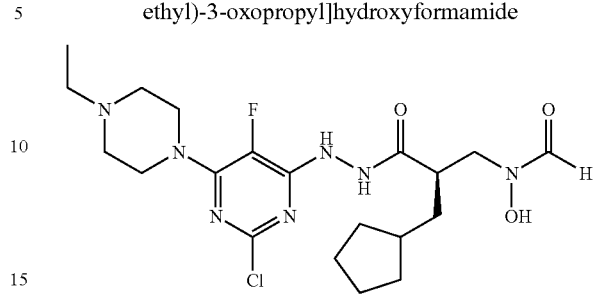

[(2R)-3-{2-[2-Chloro-6-(4-ethyl-1-piperazinyl)-5-fluoro-4-pyrimidinyl]hydrazino}-2-(cyclopentylmethyl)-3-oxopropyl]hydroxyformamide was prepared according to General Procedure D, utilizing commercially-available N-ethylpiperazine in place of N-methylpiperazine in Part A. LCMS: (M+H)+: 472.2.

Example 55

[(2R)-3-(2-{2-Chloro-5-fluoro-6-[(2-hydroxyethyl)(methyl)amino]-4-pyrimidinyl}hydrazino)-2-(cyclopentylmethyl)-3-oxopropyl]hydroxyformamide

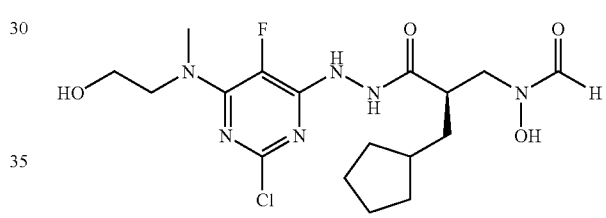

[(2R)-3-(2-{2-Chloro-5-fluoro-6-[(2-hydroxyethyl)(methyl)amino]-4-pyrimidinyl}hydrazino)-2-(cyclopentylmethyl)-3-oxopropyl]hydroxyformamide was prepared according to General Procedure D, utilizing commercially-available N-2-hydroxyethyl-N-methylamine in place of N-methylpiperazine in Part A. LCMS: (M+H)+: 433.6.

Example 56

[(2R)-3-(2-{2-Chloro-5-fluoro-6-[3-(methyloxy)-1-azetidinyl]-4-pyrimidinyl}hydrazino)-2-(cyclopentylmethyl)-3-oxopropyl]hydroxyformamide

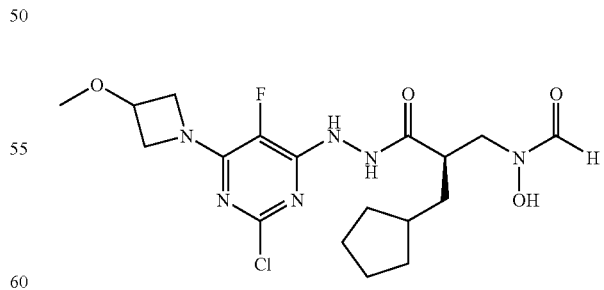

[(2R)-3-(2-{2-Chloro-5-fluoro-6-[3-(methyloxy)-1-azetidinyl]-4-pyrimidinyl}hydrazino)-2-(cyclopentylmethyl)-3-oxopropyl]hydroxyformamide was prepared according to General Procedure D, utilizing commercially-available 3-methoxyazetidine hydrochloride in place of N-methylpiperazine in Part A. LCMS: (M+H)+: 445.7.

Example 57

[(2R)-3-[2-(2-Chloro-5-fluoro-6-{methyl[2-(methyloxy)ethyl]amino}-4-pyrimidinyl)hydrazino]-2-(cyclopentylmethyl)-3-oxopropyl]hydroxyformamide

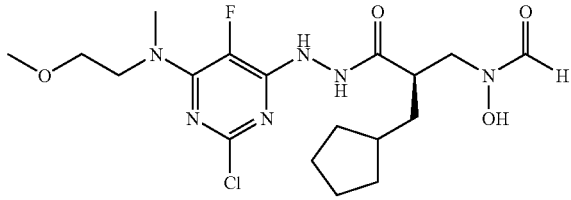

[(2R)-3-[2-(2-Chloro-5-fluoro-6-{methyl[2-(methyloxy)ethyl]amino}-4-pyrimidinyl)hydrazino]-2-(cyclopentylmethyl)-3-oxopropyl]hydroxyformamide was prepared according to General Procedure D, utilizing commercially-available N-methyl-2-(methyloxy)ethanamine in place of N-methylpiperazine in Part A. LCMS: (M+H)$^+$: 447.5.

Example 58

[(2R)-3-(2-{2-Chloro-5-fluoro-6-[(8aS)-hexahydropyrrolo[1,2-a]pyrazin-2(1H)-yl]-4-pyrimidinyl}hydrazino)-2-(cyclopentylmethyl)-3-oxopropyl]hydroxyformamide

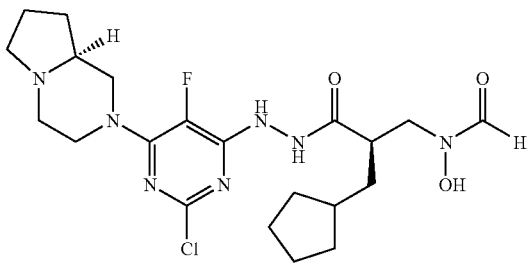

[(2R)-3-(2-{2-Chloro-5-fluoro-6-[(8aS)-hexahydropyrrolo[1,2-a]pyrazin-2(1H)-yl]-4-pyrimidinyl}hydrazino)-2-(cyclopentylmethyl)-3-oxopropyl]hydroxyformamide was prepared according to General Procedure D, utilizing commercially-available (8aS)-octahydropyrrolo[1,2-a]pyrazine in place of N-methylpiperazine in Part A. LCMS: (M+H)$^+$: 484.4.

Example 59

1-{6-Chloro-2-[2-((2R)-3-cyclopentyl-2-{[formyl(hydroxy)amino]methyl}propanoyl)hydrazino]-5-fluoro-4-pyrimidinyl}-N,N-dimethyl-L-prolinamide

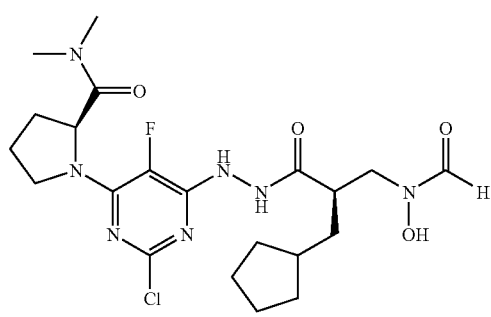

1-{6-Chloro-2-[2-((2R)-3-cyclopentyl-2-{[formyl(hydroxy)amino]methyl}propanoyl)hydrazino]-5-fluoro-4-pyrimidinyl}-N,N-dimethyl-L-prolinamide was prepared according to General Procedure D, utilizing commercially-available N,N-dimethyl-L-prolinamide in place of N-methylpiperazine in Part A. LCMS: (M+H)$^+$: 500.1.

Example 60

[(2R)-3-{2-[2-Chloro-5-fluoro-6-(propylamino)-4-pyrimidinyl]hydrazino}-2-(cyclopentylmethyl)-3-oxopropyl]hydroxyformamide

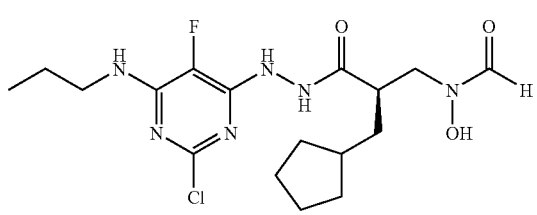

[(2R)-3-{2-[2-Chloro-5-fluoro-6-(propylamino)-4-pyrimidinyl]hydrazino}-2-(cyclopentylmethyl)-3-oxopropyl]hydroxyformamide was prepared according to General Procedure D, utilizing propylamine in place of N-methylpiperazine in Part A. LCMS: (M+H)$^+$: 417.1.

Example 61

[(2R)-3-(2-{2-Chloro-6-[(3S)-3,4-dimethyl-1-piperazinyl]-5-fluoro-4-pyrimidinyl}hydrazino)-2-(cyclopentylmethyl)-3-oxopropyl]hydroxyformamide

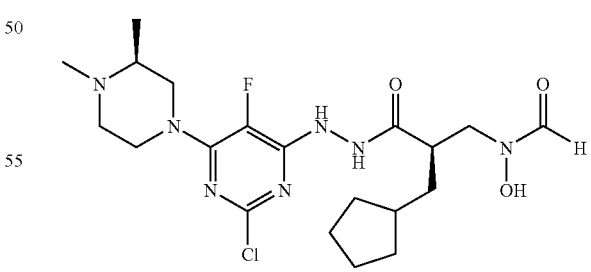

[(2R)-3-(2-{2-Chloro-6-[(3S)-3,4-dimethyl-1-piperazinyl]-5-fluoro-4-pyrimidinyl}hydrazino)-2-(cyclopentylmethyl)-3-oxopropyl]hydroxyformamide was prepared according to General Procedure D, utilizing (S)-1,2-dimethylpiperazine dihydrochloride (Example 40) in place of N-methylpiperazine in Part A. LCMS: (M+H)$^+$: 472.2.

Example 62

[(2R)-3-(2-{2-Chloro-6-[(3R)-3,4-dimethyl-1-piperazinyl]-5-fluoro-4-pyrimidinyl}hydrazino)-2-(cyclopentylmethyl)-3-oxopropyl]hydroxyformamide

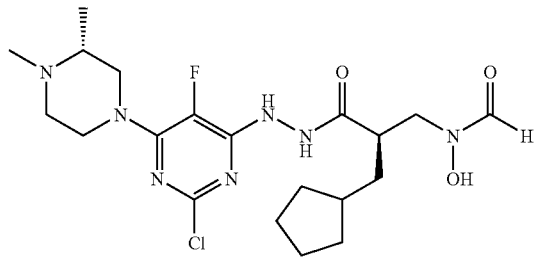

[(2R)-3-(2-{2-Chloro-6-[(3R)-3,4-dimethyl-1-piperazinyl]-5-fluoro-4-pyrimidinyl}hydrazino)-2-(cyclopentylmethyl)-3-oxopropyl]hydroxyformamide was prepared according to General Procedure D, utilizing (R)-1,2-dimethylpiperazine dihydrochloride (Example 39) in place of N-methylpiperazine in Part A. LCMS: (M+H)+: 472.2.

Example 63

[(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide

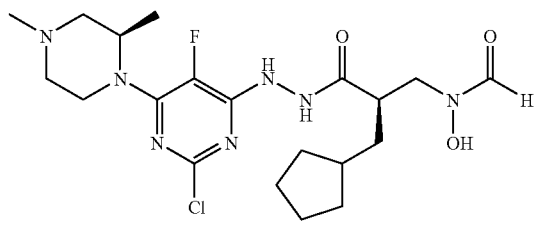

Part A:

Methyl N-{[(phenylmethyl)oxy]carbonyl}-D-alanyl-N-methylglycinate

To a mixture of N-{[(phenylmethyl)oxy]carbonyl}-D-alanine (133.53 g, 598.2 mmol) in DCM (1100 mL) was added powdered sarcosine methyl ester hydrochloride (83.49 g, 598.2 mmol), 1-hydroxybenzotriazole (80.81 g, 598.1 mmol), and 4-methylmorpholine (242 mL, 2201 mmol). The mixture was stirred for 10 min, and then EDC (114.68 g, 598.2 mmol) was added. The mixture was stirred overnight, and was then washed with water (500 mL), 1 N aqueous HCl (2×300 mL), and brine (300 mL). The organic phase was dried over anhydrous Na2SO4, filtered, and concentrated in vacuo to give crude methyl N-{[(phenylmethyl)oxy]carbonyl}-D-alanyl-N-methylglycinate (162.35 g, 88% yield) as a yellow oil. LCMS: (M+H)+: 309.0.

Part B:

(3R)-1,3-Dimethyl-2,5-piperazinedione

To a slurry of three combined batches of methyl N-{[(phenylmethyl)oxy]carbonyl}-D-alanyl-N-methylglycinate (combined total 489.09 g, 1586 mmol) in DCM (210 mL) was added MeOH (1000 mL) and 10% Pd/C (50 g). The mixture was hydrogenated at 50 psi overnight, and then an additional portion of 10% Pd/C (5 g) was added. The mixture was hydrogenated at 50 psi for an additional 6 h, and was then filtered and washed with MeOH and DCM. The resulting clear liquid was evaporated to give a clear oil, which subsequently solidified upon standing to afford (3R)-1,3-dimethyl-2,5-piperazinedione (214.0 g, 95% yield) as a pale yellow tinted solid. LCMS: (M+H)+: 143.0.

Part C:

(3R)-1,3-Dimethylpiperazine Dihydrochloride

To a 0° C. suspension of (3R)-1,3-dimethyl-2,5-piperazinedione (93.74 g, 659.4 mmol) in THF (660 mL) was added LiAlH4 (75.1 g, 1979 mmol) portionwise over 1 h. The mixture was then heated at 65° C. and stirred for 2.5 h. The mixture was then cooled to 0° C., and Na2SO4.10H2O (75 g) was slowly added, followed by slow addition of 1 N aqueous NaOH (1000 mL). The mixture was extracted with CHCl3 (6×1000 mL), and the combined organic phase was dried over anhydrous Na2SO4 and filtered. To the resulting solution was added 4 N HCl in dioxane (367 mL), and the mixture was stirred overnight. The mixture was then diluted with MeOH (2000 mL) and concentrated in vacuo. The residue was azeotroped with MeOH (2×1000 mL) and placed under high vacuum overnight to provide (3R)-1,3-dimethylpiperazine dihydrochloride (102.22 g, 83% yield) as a brown gum. LCMS: (M+H)+: 115.1.

Part D:

Tris(1,1-dimethylethyl)2-{2-chloro-6-[(2R)-2,4-dimethyl-1-piperazinyl]-5-fluoro-4-pyrimidinyl}-1,1,2-hydrazinetricarboxylate To (3R)-1,3-dimethylpiperazine dihydrochloride (102.22 g, 546.3 mmol) was added a solution of tris(1,1-dimethylethyl)2-(2,6-dichloro-5-fluoro-4-pyrimidinyl)-1,1,2-hydrazinetricarboxylate (271.71 g, 546.3 mmol) in DMF (900 mL). The mixture was cooled to 0° C., and N,N-diisopropylethylamine (295 mL, 1694 mmol) was added. The solution was stirred and warmed to room temperature overnight. The solution was then diluted with Et2O (1000 mL) and washed with water (1000 mL). The aqueous phase was extracted with a fresh portion of Et2O (1000 mL), and the combined organic phase was washed with water (2×500 mL). The organic phase was then diluted with DCM (1000 mL), dried over anhydrous Na2SO4, filtered, and concentrated in vacuo. The residue was filtered through a silica gel plug (30% EtOAc in hexanes; 1% Et3N). The solution was then concentrated in vacuo, and the residue was azeotroped with MeOH. The residue was diluted with MeOH (1000 mL), and crystallized by addition of water. The resulting solid was collected by vacuum filtration and washed with 10% MeOH in water. The resulting yellow solid was dried at 50° C. under high vacuum to give tris(1,1-dimethylethyl)2-{2-chloro-6-[(2R)-2,4-dimethyl-1-piperazinyl]-5-fluoro-4-pyrimidinyl}-1,1,2-hydrazinetricarboxylate (257.34 g, 82% yield) as a light yellow solid. LCMS: (M+H)+: 575.2.

Part E:

2-Chloro-4-[(2R)-2,4-dimethyl-1-piperazinyl]-5-fluoro-6-hydrazinopyrimidine trihydrochloride To a solution of tris(1,1-dimethylethyl)2-{2-chloro-6-[(2R)-2,4-dimethyl-1-piperazinyl]-5-fluoro-4-pyrimidinyl}-1,1,2-hydrazinetricarboxylate (215.28 g, 374.3 mmol) in DCM (1870 mL) was added 2 N HCl in $Et_2O$ (1870 mL, 3740 mmol). The solution was mechanically stirred for 64 h, and the resulting suspension was allowed to settle. Most of the solvent was then decanted, and the remaining solid was triturated with DCM (1000 mL) and collected by vacuum filtration. The solid was washed with DCM and dried under high vacuum to provide 2-chloro-4-[(2R)-2,4-dimethyl-1-piperazinyl]-5-fluoro-6-hydrazinopyrimidine, assumed trihydrochloride (138.22 g, 96% yield) as a light yellow powder. LCMS: $(M+H)^+$: 275.1.

Part F:

[(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl][(phenylmethyl)oxy]formamide To a 0° C. mixture of 2-chloro-4-[(2R)-2,4-dimethyl-1-piperazinyl]-5-fluoro-6-hydrazinopyrimidine, assumed trihydrochloride (126.70 g, 329.9 mmol) and (2R)-3-cyclopentyl-2-({formyl[(phenylmethyl)oxy]amino}methyl)propanoic acid, N,N-diisopropylethylamine salt, isopropanol solvate (155.42 g, 314.1 mmol) in DMF (630 mL) was added 4-methylmorpholine (240 mL, 2183 mmol), followed by 1-hydroxy-7-azabenzotriazole (51.31 g, 377.0 mmol) and EDC (72.27 g, 377.0 mmol). The mixture was stirred overnight, diluted with $Et_2O$ (1000 mL), and washed with water (1000 mL). The aqueous phase was extracted with a fresh portion of $Et_2O$ (1000 mL), and the combined organic phase was washed with water (3×300 mL). The combined aqueous phase was extracted with a fresh portion of $Et_2O$ (300 mL), and this $Et_2O$ phase was washed with water (200 mL). The total combined organic phase was diluted with DCM (1000 mL), dried over anhydrous $Na_2SO_4$, filtered, and concentrated in vacuo to give crude [(2R)-3-(2-{2-chloro-6-[(2R)-2,4-dimethyl-1-piperazinyl]-5-fluoro-4-pyrimidinyl}hydrazino)-2-(cyclopentylmethyl)-3-oxopropyl][(phenylmethyl)oxy]formamide (193.65 g, >100% crude yield) as a dark red foam. LCMS: $(M+H)^+$: 562.3.

Part G:

[(2R)-3-(2-{2-Chloro-6-[(2R)-2,4-dimethyl-1-piperazinyl]-5-fluoro-4-pyrimidinyl}hydrazino)-2-(cyclopentylmethyl)-3-oxopropyl]hydroxyformamide To a solution of crude [(2R)-3-(2-{2-chloro-6-[(2R)-2,4-dimethyl-1-piperazinyl]-5-fluoro-4-pyrimidinyl}hydrazino)-2-(cyclopentylmethyl)-3-oxopropyl][(phenylmethyl)oxy]formamide (assumed 176.57 g, 314.1 mmol) in MeOH (800 mL) was added 20% $Pd(OH)_2/C$ (14.13 g). The mixture was hydrogenated under balloon pressure with monitoring every 30 min until the reaction was judged to be complete (7 h). The mixture was then filtered through a glass fiber filter with MeOH washes. The resulting dark filtrate was concentrated in vacuo and purified by preparative reverse phase chromatography (Luna C18 (2) column; 10 microns; 101.6 mm×250 mm; 250 nm UV detection; 480 mL/min; 40 mg/mL sample concentration; 4 g injection mass; mobile phase A: 300 mmol aqueous ammonium formate at pH 4.0; mobile phase B: MeCN; method: 28% B for 9 min; 90% B for 9 min; 28% B for 5 min). The product solution fractions were combined and adjusted to pH 6.8 with aqueous $NH_4OH$, and then stirred with Darco (50% weight load based on crude product) for 30 min at room temperature. The solution was then filtered through Celite. The filtrate was concentrated to a volume of 3.5 L, and the pH was adjusted from 5.6 to 8.5 with $NH_4OH$, affording an orange precipitate. The aqueous phase was extracted 3 times with EtOAc, and then the combined organics were washed with water and brine. The organics were dried ($Na_2SO_4$), filtered, and concentrated in vacuo to a volume of 1 L, producing a tan precipitate. An equal volume of heptane (1 L) was added, and the mixture was cooled to 0° C. for 1 h. Then the product was isolated by filtration, washing with heptane, and dried under reduced pressure at 50° C. for 20 h to provide [(2R)-3-(2-{2-chloro-6-[(2R)-2,4-dimethyl-1-piperazinyl]-5-fluoro-4-pyrimidinyl}hydrazino)-2-(cyclopentylmethyl)-3-oxopropyl]hydroxyformamide (85.5 g, 57% yield for 2 steps) as a white solid. LCMS: $(M+H)^+$: 472.2.

Example 64

[(2R)-3-(2-{2-Chloro-6-[(2S)-2,4-dimethyl-1-piperazinyl]-5-fluoro-4-pyrimidinyl}hydrazino)-2-(cyclopentylmethyl)-3-oxopropyl]hydroxyformamide

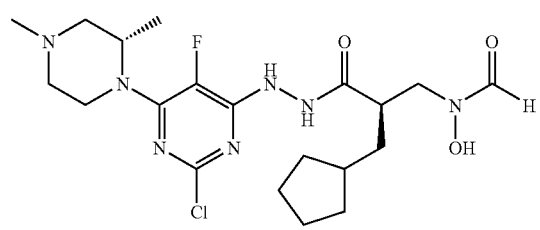

Part A:

(3S)-1,3-Dimethylpiperazine, Dihydrochloride (3S)-1,3-Dimethylpiperazine, dihydrochloride can be prepared in a manner similar to (3R)-1,3-dimethylpiperazine, dihydrochloride (Example 63), using CBZ-L-alanine in place of CBZ-D-alanine.

Part B:

[(2R)-3-(2-{2-Chloro-6-[(2S)-2,4-dimethyl-1-piperazinyl]-5-fluoro-4-pyrimidinyl}hydrazino)-2-(cyclopentylmethyl)-3-oxopropyl]hydroxyformamide was prepared according to General Procedure D, utilizing (S)-1,3-dimethylpiperazine in place of N-methylpiperazine in Part A. LCMS: $(M+H)^+$: 472.2.

Example 65

[(2R)-3-(2-{2-Chloro-5-fluoro-6-[(9aS)-hexahydropyrazino[2,1-c][1,4]oxazin-8(1H)-yl]-4-pyrimidinyl}hydrazino)-2-(cyclopentylmethyl)-3-oxopropyl]hydroxyformamide

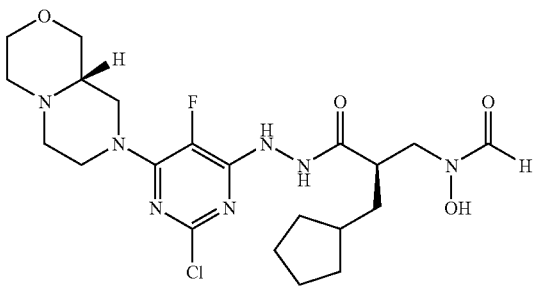

[(2R)-3-(2-{2-Chloro-5-fluoro-6-[(9aS)-hexahydropyrazino[2,1-c][1,4]oxazin-8(1H)-yl]-4-pyrimidinyl}hydrazino)-2-(cyclopentylmethyl)-3-oxopropyl]hydroxyformamide was prepared according to General Procedure E, utilizing (9aS)-octahydropyrazino[2,1-c][1,4]oxazine dihydrochloride (which may be prepared as described in Example 24, Parts A-H) in place of isopropyl amine in Part A, utilizing 2N HCl in ether in Part B, performing an extractive (ether/water) workup rather than HPLC purification in Part C, and purifying the final product in Part D by recrystallization from EtOAc/ether rather than HPLC. LCMS: (M+H)$^+$: 501.0.

Example 66

N-[(2R)-2-(Cyclopentylmethyl)-3-(2-{5-fluoro-6-[(2S)-2-(hydroxymethyl)-1-azetidinyl]-2-methyl-4-pyrimidinyl}hydrazino)-3-oxopropyl]-N-hydroxyformamide

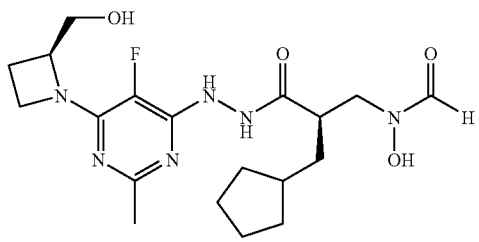

Part A:

(2S)-2-Azetidinylmethanol, TFA Salt

Commercially-available (S)-1-(t-butoxycarbonyl)-2-azetidinemethanol (100 mg, 5.3 mmol) was dissolved and stirred in dichloromethane (2 mL). Trifluoroacetic acid (1 mL) was added dropwise, and the resulting reaction mixture was stirred at room temperature until removal of the t-butoxycarbonyl group was complete. Then the solvent was evaporated and the crude, TFA salt of (2S)-2-azetidinylmethanol was used directly in the next step.

Part B:

N-[(2R)-2-(Cyclopentylmethyl)-3-(2-{5-fluoro-6-[(2S)-2-(hydroxymethyl)-1-azetidinyl]-2-methyl-4-pyrimidinyl}hydrazino)-3-oxopropyl]-N-hydroxyformamide N-[(2R)-2-(Cyclopentylmethyl)-3-(2-{5-fluoro-6-[(2S)-2-(hydroxymethyl)-1-azetidinyl]-2-methyl-4-pyrimidinyl}hydrazino)-3-oxopropyl]-N-hydroxyformamide was prepared according to General Procedure A, utilizing (2S)-2-azetidinylmethanol, TFA salt in place of pyrrolidine, and using 3 equivalents of DIPEA in Part A. LCMS: (M+H)$^+$: 425.4

Example 67

((2R)-2-(Cyclopentylmethyl)-3-{2-[6-(dimethylamino)-5-fluoro-2-(fluoromethyl)-4-pyrimidinyl]hydrazino}-3-oxopropyl)hydroxyformamide

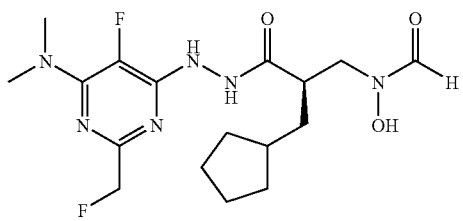

((2R)-2-(Cyclopentylmethyl)-3-{2-[6-(dimethylamino)-5-fluoro-2-(fluoromethyl)-4-pyrimidinyl]hydrazino}-3-oxopropyl)hydroxyformamide was prepared according to General Procedure A, utilizing dimethylamine in place of pyrrolidine, and 4,6-dichloro-5-fluoro-2-(fluoromethyl)pyrimidine in place of 4,6-dichloro-5-fluoro-2-methylpyrimidine in Part A. LCMS: (M+H)$^+$: 401.2.

Example 68

[(2R)-3-{2-[6-(Cyclobutylamino)-5-fluoro-2-(fluoromethyl)-4-pyrimidinyl]hydrazino}-2-(cyclopentylmethyl)-3-oxopropyl]hydroxyformamide

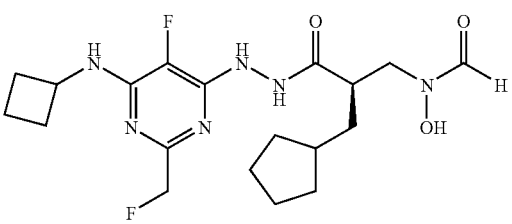

[(2R)-3-{2-[6-(Cyclobutylamino)-5-fluoro-2-(fluoromethyl)-4-pyrimidinyl]hydrazino}-2-(cyclopentylmethyl)-3-oxopropyl]hydroxyformamide was prepared according to General Procedure A, utilizing commercially-available cyclobutylamine in place of pyrrolidine, and 4,6-dichloro-5- fluoro-2-(fluoromethyl)pyrimidine in place of 4,6-dichloro-5-fluoro-2-methylpyrimidine in Part A. LCMS: (M+H)+: 427.2.

Example 69

N-{(2R)-2-(Cyclopentylmethyl)-3-[2-(5-fluoro-2-methyl-6-{[2-oxo-2-(1-pyrrolidinyl)ethyl]amino}-4-pyrimidinyl)hydrazino]-3-oxopropyl}-N-hydroxyformamide

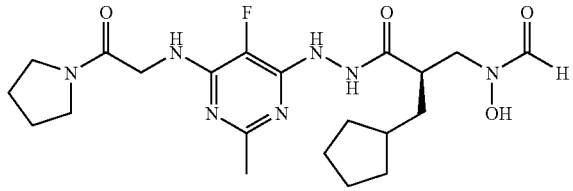

Part A:

Phenylmethyl [2-oxo-2-(1-pyrrolidinyl)ethyl]carbamate

Pyrrolidine (248 uL, 3 mmol), N-CBZ-glycine (628 mg, 3 mmol), and HOAt (408 mg, 3 mmol) were dissolved in 10 mL of dichloromethane. NMM (0.66 mL, 6 mmol) was added, followed by EDC (575 mg, 3 mmol). After stirring overnight at room temperature, the reaction mixture was diluted with dichloromethane, washed with water, saturated aqueous NaHCO3 solution, and saturated aqueous NH4Cl solution, then dried (Na2SO4) and evaporated to yield phenylmethyl [2-oxo-2-(1-pyrrolidinyl)ethyl]carbamate as a beige solid (782 mg, 100%). LCMS: (M+H)+: 263.1.

Part B:

2-Oxo-2-(1-Pyrrolidinyl)ethanamine, Hydrochloride Salt

Phenylmethyl [2-oxo-2-(1-pyrrolidinyl)ethyl]carbamate (782 mg, 3 mmol) was dissolved in 30 mL of MeOH, degassed and placed under argon. 10% Pd/C (117 mg) was added followed by 0.5 mL 6N HCl, and the contents were thoroughly degassed and placed under a hydrogen balloon for approximately 3 hrs. The contents were then degassed and filtered through Celite, and the Celite pad was washed with DCM and MeOH. The resulting filtrate was concentrated in vacuo to provide the 2-oxo-2-(1-pyrrolidinyl)ethanamine, hydrochloride salt (491 mg, 100%). LCMS: (M+H)+: 129.1.

Part C:

N-{(2R)-2-(Cyclopentylmethyl)-3-[2-(5-fluoro-2-methyl-6-{[2-oxo-2-(1-pyrrolidinyl)ethyl]amino}-4-pyrimidinyl)hydrazino]-3-oxopropyl}-N-hydroxyformamide N-{(2R)-2-(Cyclopentylmethyl)-3-[2-(5-fluoro-2-methyl-6-{[2-oxo-2-(1-pyrrolidinyl)ethyl]amino}-4-pyrimidinyl)hydrazino]-3-oxopropyl}-N-hydroxyformamide was prepared according to General Procedure A, utilizing 2-oxo-2-(1-pyrrolidinyl)ethanamine, hydrochloride salt in place of pyrrolidine, and using 2.3 equivalents of DIPEA in Part A. LCMS: (M+H)+: 466.2.

Example 70

N-{(2R)-2-(Cyclopentylmethyl)-3-[2-(2-ethyl-5-fluoro-6-{[(1R)-1-methyl-2-oxo-2-(1-pyrrolidinyl)ethyl]amino}-4-pyrimidinyl)hydrazino]-3-oxopropyl}-N-hydroxyformamide

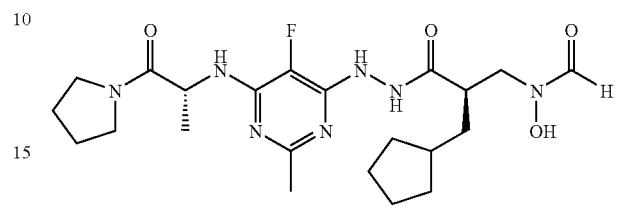

Part A:

Phenylmethyl [(1R)-1-methyl-2-oxo-2-(1-pyrrolidinyl)ethyl]carbamate

Pyrrolidine (1668 uL, 2 mmol), N-CBZ-D-alanine (446 mg, 2 mmol), and HOAt (272 mg, 2 mmol) were dissolved in 6 mL of dichloromethane. NMM (0.44 mL, 4 mmol) was added, followed by EDC (382 mg, 2 mmol). After stirring overnight at room temperature, the reaction mixture was diluted with EtOAc, washed with water, saturated aqueous NaHCO3 solution, and saturated aqueous NH4Cl solution, then dried (Na2SO4) and evaporated to yield phenylmethyl [(1R)-1-methyl-2-oxo-2-(1-pyrrolidinyl)ethyl]carbamate as a white solid (496 mg, 90%). LCMS: (M+H)+: 277.2.

Part B:

(2R)-1-Oxo-1-(1-pyrrolidinyl)-2-propanamine

Phenylmethyl [(1R)-1-methyl-2-oxo-2-(1-pyrrolidinyl) ethyl]carbamate (496 mg, 1.8 mmol) was dissolved in 20 mL of MeOH, degassed and placed under argon. 10% Pd/C (125 mg) was added, and the contents were thoroughly degassed and placed under a hydrogen balloon overnight. The contents were then degassed and filtered through Celite, and the Celite pad was washed with DCM and MeOH. The resulting filtrate was concentrated in vacuo to provide the (2R)-1-oxo-1-(1-pyrrolidinyl)-2-propanamine (235 mg, 91%). LCMS: (M+H)+: 143.1.

Part C:

N-{(2R)-2-(Cyclopentylmethyl)-3-[2-(2-ethyl-5-fluoro-6-{[(1R)-1-methyl-2-oxo-2-(1-pyrrolidinyl) ethyl]amino}-4-pyrimidinyl)hydrazino]-3-oxopropyl}-N-hydroxyformamide N-{(2R)-2-(Cyclopentylmethyl)-3-[2-(2-ethyl-5-fluoro-6-{[(1R)-1-methyl-2-oxo-2-(1-pyrrolidinyl)ethyl]amino}-4-pyrimidinyl)hydrazino]-3-oxopropyl}-N-hydroxyformamide was prepared according to General Procedure A, utilizing (2R)-1-oxo-1-(1-pyrrolidinyl)-2-propanamine in place of pyrrolidine in Part A. LCMS: (M+H)+: 494.2.

Example 71

[(2R)-2-(Cyclopentylmethyl)-3-(2-{5-fluoro-2-(fluoromethyl)-6-[(3S)-3-(methyloxy)-1-pyrrolidinyl]-4-pyrimidinyl}hydrazino)-3-oxopropyl]hydroxyformamide

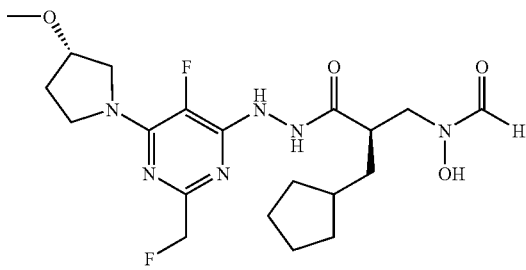

[(2R)-2-(Cyclopentylmethyl)-3-(2-{5-fluoro-2-(fluoromethyl)-6-[(3S)-3-(methyloxy)-1-pyrrolidinyl]-4-pyrimidinyl}hydrazino)-3-oxopropyl]hydroxyformamide was prepared according to General Procedure A, utilizing commercially-available (S)-3-methoxylpyrrolidine in place of pyrrolidine, and 4,6-dichloro-5-fluoro-2-(fluoromethyl)pyrimidine in place of 4,6-dichloro-5-fluoro-2-methylpyrimidine in Part A. LCMS: (M+H)+: 457.2.

Example 72

((2R)-2-(Cyclopentylmethyl)-3-{2-[5-fluoro-2-methyl-6-(propylamino)-4-pyrimidinyl]hydrazino}-3-oxopropyl)hydroxyformamide

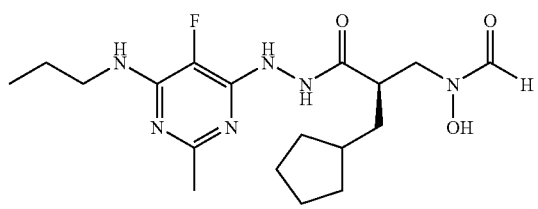

((2R)-2-(Cyclopentylmethyl)-3-{2-[5-fluoro-2-methyl-6-(propylamino)-4-pyrimidinyl]hydrazino}-3-oxopropyl)hydroxyformamide was prepared according to General Procedure A, utilizing propylamine in place of pyrrolidine in Part A. LCMS: (M+H)+: 494.2.

Example 73

((2R)-2-(Cyclopentylmethyl)-3-{2-[5-fluoro-2-(fluoromethyl)-6-(propylamino)-4-pyrimidinyl]hydrazino}-3-oxopropyl)hydroxyformamide

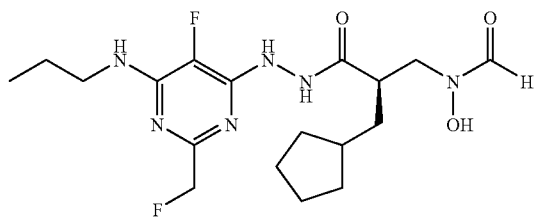

((2R)-2-(Cyclopentylmethyl)-3-{2-[5-fluoro-2-(fluoromethyl)-6-(propylamino)-4-pyrimidinyl]hydrazino}-3-oxopropyl)hydroxyformamide was prepared according to General Procedure A, utilizing commercially-available propylamine in place of pyrrolidine, and 4,6-dichloro-5-fluoro-2-(fluoromethyl)pyrimidine in place of 4,6-dichloro-5-fluoro-2-methylpyrimidine in Part A. LCMS: (M+H)+: 415.2.

Example 74

N2-(6-{2-[(2R)-3-Cyclopentyl-2-{[formyl(hydroxy)amino]methyl}propanoyl]hydrazino}-5-fluoro-2-methyl-4-pyrimidinyl)-N,N-dimethyl-D-alaninamide

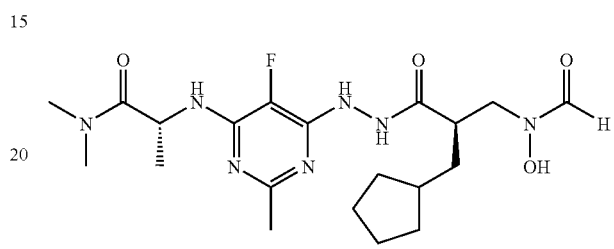

Part A:

N1,N1-dimethyl-D-alaninamide

N1,N1-dimethyl-D-alaninamide, hydrochloride salt was prepared in a manner similar to Example 69, utilizing N-CBZ-D-alanine in place of N-CBZ-glycine, utilizing dimethylamine, hydrochloride salt in place of pyrrolidine, and using 3 equivalents of NMM.

Part B:

N2-(6-{2-[(2R)-3-Cyclopentyl-2-{[formyl(hydroxy)amino]methyl}propanoyl]hydrazino}-5-fluoro-2-methyl-4-pyrimidinyl)-N,N-dimethyl-D-alaninamide N2-(6-{2-[(2R)-3-Cyclopentyl-2-{[formyl(hydroxy)amino]methyl}propanoyl]hydrazino}-5-fluoro-2-methyl-4-pyrimidinyl)-N,N-dimethyl-D-alaninamide was prepared according to General Procedure A, utilizing N1,N1-dimethyl-D-alaninamide, hydrochloride salt in place of pyrrolidine in Part A. LCMS: (M+H)+: 454.2.

Example 75

((2R)-2-(Cyclopentylmethyl)-3-{2-[6-(4-ethyl-1-piperazinyl)-5-fluoro-2-(methyloxy)-4-pyrimidinyl]hydrazino}-3-oxopropyl)hydroxyformamide

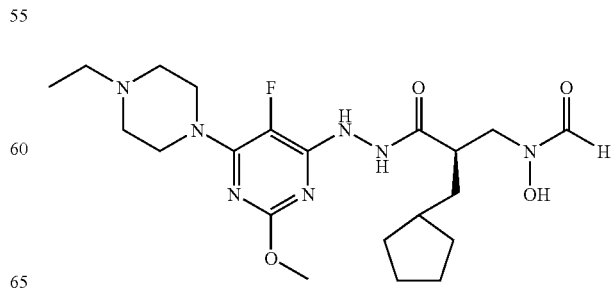

Part A:

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide can be prepared in a manner similar to Intermediate E, utilizing o-methylisourea sulphate in place of 2-methyl-2-thiopseudourea sulfate in Part A and (2R)-3-cyclopentyl-2-({formyl[(phenylmethyl)oxy]amino}methyl)propanoic acid in place of (2R)-3-cyclopentyl-2-{[formyl(tetrahydro-2H-pyran-2-yloxy)amino]methyl}propanoic acid in part D. LCMS: (M+H)$^+$: 480.1.

Part B:

((2R)-2-(Cyclopentylmethyl)-3-{2-[6-(4-ethyl-1-piperazinyl)-5-fluoro-2-(methyloxy)-4-pyrimidinyl]hydrazino}-3-oxopropyl)[(phenylmethyl)oxy]formamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide (0.150 g, 0.31 mmol), commercially available 1-ethylpiperazine (0.080 mL, 0.63 mmol) and diisopropylethylamine (0.054 mL, 0.31 mmol) were stirred in DMSO (2 mL) overnight at 65° C. The reaction mixture was then purified by RP-HPLC to provide ((2R)-2-(cyclopentylmethyl)-3-{2-[6-(4-ethyl-1-piperazinyl)-5-fluoro-2-(methyloxy)-4-pyrimidinyl]hydrazino}-3-oxopropyl)[(phenylmethyl)oxy]formamide as a red solid (0.145 g, 83%). LCMS: (M+H)$^+$=558.3.

Part C:

((2R)-2-(Cyclopentylmethyl)-3-{2-[6-(4-ethyl-1-piperazinyl)-5-fluoro-2-(methyloxy)-4-pyrimidinyl]hydrazino}-3-oxopropyl)hydroxyformamide A solution of ((2R)-2-(cyclopentylmethyl)-3-{2-[6-(4-ethyl-1-piperazinyl)-5-fluoro-2-(methyloxy)-4-pyrimidinyl]hydrazino}-3-oxopropyl)[(phenylmethyl)oxy]formamide (0.145 g, 0.26 mmol), and Pd(C) (0.030 g) in MeOH (10 mL) was run under standard hydrogenation conditions as in General Procedure A, Part C, to provide ((2R)-2-(cyclopentylmethyl)-3-{2-[6-(4-ethyl-1-piperazinyl)-5-fluoro-2-(methyloxy)-4-pyrimidinyl]hydrazino}-3-oxopropyl)hydroxyformamide as a red solid (0.119 g, 98%). LCMS: (M+H)$^+$=468.4.

Example 76

[(2R)-2-(Cyclopentylmethyl)-3-(2-{2-(difluoromethyl)-6-[(3R)-3-(dimethylamino)-1-pyrrolidinyl]-5-fluoro-4-pyrimidinyl}hydrazino)-3-oxopropyl]hydroxyformamide

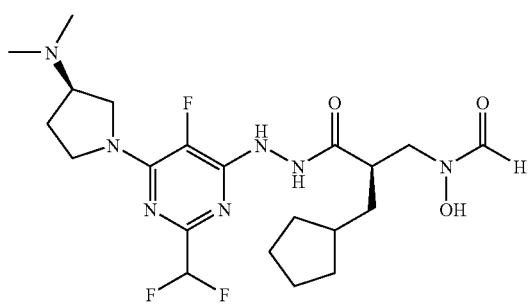

[(2R)-2-(Cyclopentylmethyl)-3-(2-{2-(difluoromethyl)-6-[(3R)-3-(dimethylamino)-1-pyrrolidinyl]-5-fluoro-4-pyrimidinyl}hydrazino)-3-oxopropyl]hydroxyformamide was prepared according to General Procedure H, utilizing commercially-available (3R)—N,N-dimethyl-3-pyrrolidinamine in place of N-methylpiperazine in Part A. LCMS: (M+H)$^+$: 488.1.

Example 77

N2-(6-{2-[(2R)-3-Cyclopentyl-2-{[formyl(hydroxy)amino]methyl}propanoyl]hydrazino}-2-ethyl-5-fluoro-4-pyrimidinyl)-N,N-dimethyl-D-alaninamide

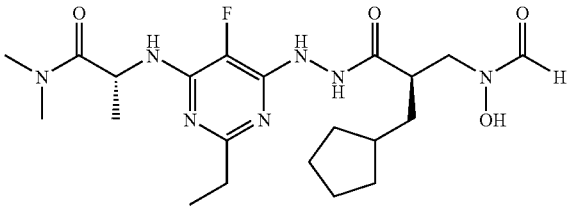

N2-(6-{2-[(2R)-3-Cyclopentyl-2-{[formyl(hydroxy)amino]methyl}propanoyl]hydrazino}-2-ethyl-5-fluoro-4-pyrimidinyl)-N,N-dimethyl-D-alaninamide was prepared according to General Procedure B, utilizing N$^1$,N$^1$-dimethyl-D-alaninamide (Example 74) in place of azetidine in Part A. LCMS: (M+H)$^+$: 468.1.

Example 78

N-[(2R)-3-{2-[6-(Butylamino)-5-fluoro-2-methyl-4-pyrimidinyl]hydrazino}-2-(cyclopentylmethyl)-3-oxopropyl]-N-hydroxyformamide

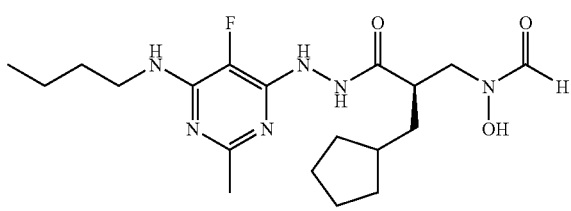

N-[(2R)-3-{2-[6-(Butylamino)-5-fluoro-2-methyl-4-pyrimidinyl]hydrazino}-2-(cyclopentylmethyl)-3-oxopropyl]-N-hydroxyformamide was prepared according to General Procedure A, utilizing commercially-available butylamine in place of pyrrolidine in Part A. LCMS: (M+H)+: 411.1.

Example 79

{(2R)-2-(Cyclopentylmethyl)-3-[2-(5-fluoro-2-(methyloxy)-6-{[(1S)-1-(1-pyrrolidinylcarbonyl)propyl]amino}-4-pyrimidinyl)hydrazino]-3-oxopropyl}hydroxyformamide

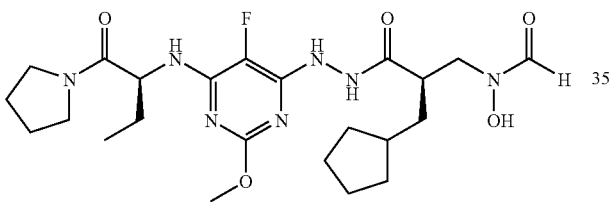

Part A:

[(1S)-1-(1-Pyrrolidinylcarbonyl)propyl]amine

Phenylmethyl [(1S)-1-(1-pyrrolidinylcarbonyl)propyl]carbamate (J. Med. Chem., 1991, 34, 3149-58) was dissolved in methanol (20 mL) (559 mg, 1.9 mmol). Pd(OH)$_2$ (140 mg) was added, and the resulting suspension was stirred under a hydrogen balloon until the deprotection was complete. Filtration of the catalyst and evaporation of the solvent yielded [(1S)-1-(1-pyrrolidinylcarbonyl)propyl]amine (291 mg, 97%).

Part B:

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide can be prepared in a manner similar to Intermediate E, utilizing o-methylisourea sulphate in place of 2-methyl-2-thiopseudourea sulfate in Part A and (2R)-3-cyclopentyl-2-({formyl[(phenylmethyl)oxy]amino}methyl)propanoic acid in place of (2R)-3-cyclopentyl-2-{[formyl(tetrahydro-2H-pyran-2-yloxy)amino]methyl}propanoic acid in part D LCMS: (M+H)+: 480.1.

Part C:

{(2R)-2-(Cyclopentylmethyl)-3-[2-(5-fluoro-2-(methyloxy)-6-{[(1S)-1-(1-pyrrolidinylcarbonyl)propyl]amino}-4-pyrimidinyl)hydrazino]-3-oxopropyl}hydroxyformamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide (70 mg, 0.15 mmol) was dissolved in DMSO (2 mL) and [(1S)-1-(1-pyrrolidinylcarbonyl)propyl]amine (46 mg, 0.29 mmol) was added, followed by DIPEA (26 μL, 0.15 mmol). The resulting mixture was stirred at 80° C. for 6 days. The reaction was purified directly by RP-HPLC yielding the benzyl protected intermediate which was subsequently dissolved in degassed MeOH (7 mL). To this solution was added 10% Pd/C (6.3 mg) and the combined mixture was stirred under a hydrogen balloon for 2 hours. Filtration of the catalyst and evaporation of the solvent yielded a crude residue which was purified by RP-HPLC. This yielded {(2R)-2-(cyclopentylmethyl)-3-[2-(5-fluoro-2-(methyloxy)-6-{[(1S)-1-(1-pyrrolidinylcarbonyl)propyl]amino}-4-pyrimidinyl)hydrazino]-3-oxopropyl}hydroxyformamide (15 mg, 20%).

Example 80

((2R)-2-(Cyclopentylmethyl)-3-{2-[6-[(3R)-3,4-dimethyl-1-piperazinyl]-5-fluoro-2-(methyloxy)-4-pyrimidinyl]hydrazino}-3-oxopropyl)hydroxyformamide

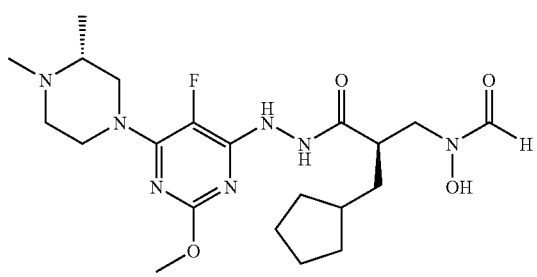

((2R)-2-(Cyclopentylmethyl)-3-{2-[6-[(3R)-3,4-dimethyl-1-piperazinyl]-5-fluoro-2-(methyloxy)-4-pyrimidinyl]hydrazino}-3-oxopropyl)hydroxyformamide was synthesized according to Example 79, utilizing (2R)-1,2-dimethylpiperazine (Example 39) in place of [(1S)-1-(1-pyrrolidinylcarbonyl)propyl]amine in part C. LCMS: (M+H)+: 468.3.

Example 81

[(2R)-2-(Cyclopentylmethyl)-3-(2-{2-(difluoromethyl)-6-[(3S)-3-(dimethylamino)-1-pyrrolidinyl]-5-fluoro-4-pyrimidinyl}hydrazino)-3-oxopropyl]hydroxyformamide

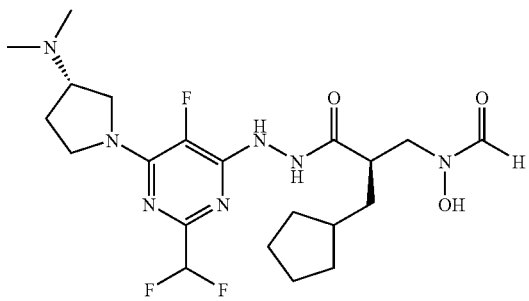

[(2R)-2-(Cyclopentylmethyl)-3-(2-{2-(difluoromethyl)-6-[(3S)-3-(dimethylamino)-1-pyrrolidinyl]-5-fluoro-4-pyrimidinyl}hydrazino)-3-oxopropyl]hydroxyformamide was prepared according to General Procedure H, utilizing commercially-available (3S)—N,N-dimethyl-3-pyrrolidinamine in place of N-methylpiperazine in Part A. LCMS: (M+H)$^+$: 488.3.

Example 82

((2R)-2-(Cyclopentylmethyl)-3-{2-[6-(cyclopropylamino)-2-(difluoromethyl)-5-fluoro-4-pyrimidinyl]hydrazino}-3-oxopropyl)hydroxyformamide

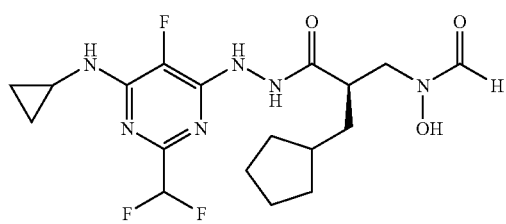

((2R)-2-(Cyclopentylmethyl)-3-{2-[6-(cyclopropylamino)-2-(difluoromethyl)-5-fluoro-4-pyrimidinyl]hydrazino}-3-oxopropyl)hydroxyformamide was prepared according to General Procedure H, utilizing cyclopropylamine in place of N-methylpiperazine in Part A. LCMS: (M+H)$^+$: 431.3.

Example 83

(2S)-2-[(6-{2-[(2R)-3-Cyclopentyl-2-{[formyl(hydroxy)amino]methyl}propanoyl]hydrazino}-5-fluoro-2-methyl-4-pyrimidinyl)amino]-N,N-dimethylbutanamide

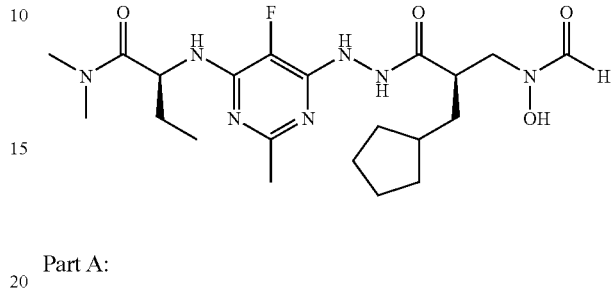

Part A:

(2S)-2-Amino-N,N-dimethylbutanamide, Hydrochloride Salt (2S)-2-Amino-N,N-dimethylbutanamide, hydrochloride salt was prepared in a manner similar to 2-oxo-2-(1-pyrrolidinyl)ethanamine, hydrochloride salt (Example 69), utilizing N-CBZ-L-2-aminobutyric acid in place of N-CBZ-glycine, utilizing dimethylamine, hydrochloride salt in place of pyrrolidine, and using 3 equivalents of NMM in Part A. (M+H)$^+$: 130.9.

Part B:

(2S)-2-[(6-{2-[(2R)-3-Cyclopentyl-2-{[formyl(hydroxy)amino]methyl}propanoyl]hydrazino}-5-fluoro-2-methyl-4-pyrimidinyl)amino]-N,N-dimethylbutanamide (2S)-2-[(6-{2-[(2R)-3-Cyclopentyl-2-{[formyl(hydroxy)amino]methyl}propanoyl]hydrazino}-5-fluoro-2-methyl-4-pyrimidinyl)amino]-N,N-dimethylbutanamide was prepared according to General Procedure A, utilizing (2S)-2-amino-N,N-dimethylbutanamide, hydrochloride salt in place of pyrrolidine in Part A. LCMS: (M+H)$^+$: 468.1.

Example 84

(2S)-2-[(6-{2-[(2R)-3-Cyclopentyl-2-{[formyl(hydroxy)amino]methyl}propanoyl]hydrazino}-2-ethyl-5-fluoro-4-pyrimidinyl)amino]-N,N-dimethylbutanamide

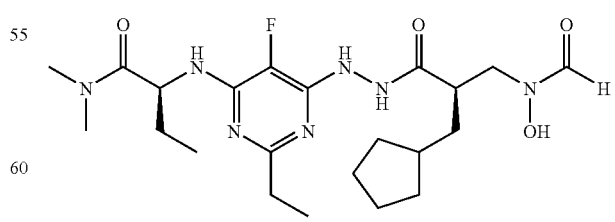

(2S)-2-[(6-{2-[(2R)-3-Cyclopentyl-2-{[formyl(hydroxy)amino]methyl}propanoyl]hydrazino}-2-ethyl-5-fluoro-4-pyrimidinyl)amino]-N,N-dimethylbutanamide was prepared according to General Procedure B, utilizing (2S)-2-amino-N, N-dimethylbutanamide, hydrochloride salt (Example 83) in place of azetidine in Part A. LCMS: (M+H)⁺: 482.1.

Example 85

{(2R)-2-(Cyclopentylmethyl)-3-[2-(5-fluoro-2-methyl-6-{[(3S)-1-methyl-2-oxohexahydro-1H-azepin-3-yl]amino}-4-pyrimidinyl)hydrazino]-3-oxopropyl}hydroxyformamide

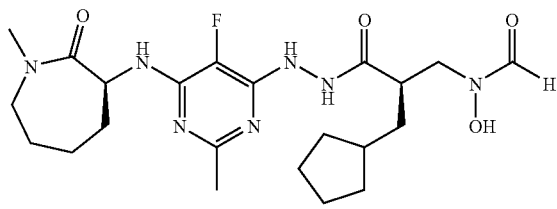

{(2R)-2-(Cyclopentylmethyl)-3-[2-(5-fluoro-2-methyl-6-{[(3S)-1-methyl-2-oxohexahydro-1H-azepin-3-yl]amino}-4-pyrimidinyl)hydrazino]-3-oxopropyl}hydroxyformamide was prepared according to General Procedure A, utilizing (3S)-3-amino-1-methylhexahydro-2H-azepin-2-one (Example 193) in place of pyrrolidine in Part A. LCMS: (M+H)⁺: 480.3.

Example 86

(2S)-2-{[6-[2-((2R)-3-Cyclopentyl-2-{[formyl(hydroxy)amino]methyl}propanoyl)hydrazino]-5-fluoro-2-(methyloxy)-4-pyrimidinyl]amino}-N,N-dimethylbutanamide

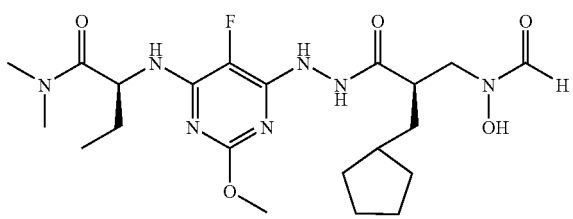

Part A:

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide can be prepared according to Intermediate E, utilizing o-methylisourea sulphate in place of 2-methyl-2-thiopseudourea sulfate in Part A and (2R)-3-cyclopentyl-2-({formyl[(phenylmethyl)oxy]amino}methyl)propanoic acid in place of (2R)-3-cyclopentyl-2-{[formyl(tetrahydro-2H-pyran-2-yloxy)amino]methyl}propanoic acid in part D. LCMS: (M+H)⁺: 480.1.

Part B:

(2S)-2-{[6-{2-[(2R)-3-Cyclopentyl-2-({formyl[(phenylmethyl)oxy]amino}methyl)propanoyl]hydrazino}-5-fluoro-2-(methyloxy)-4-pyrimidinyl]amino}-N,N-dimethylbutanamide

[(2R)-3-{2-[6-Chloro-5-fluoro-2-(methyloxy)-4-pyrimidinyl]hydrazino}-2-(cyclopentylmethyl)-3-oxopropyl][(phenylmethyl)oxy]formamide (0.133 g, 0.28 mmol), (2S)-2-amino-N,N-dimethylbutanamide, hydrochloride salt (Example 83) (0.075 g, 0.45 mmol) and diisopropylethylamine (0.1 mL, 0.62 mmol) were stirred in DMSO (2 mL) overnight at 65° C. Then additional diisopropylethylamine (0.2 mL) was added, and the reaction was stirred for 7 days at 80° C. Purified by RP-HPLC to provide (2S)-2-{[6-{2-[(2R)-3-cyclopentyl-2-({formyl[(phenylmethyl)oxy]amino}methyl)propanoyl]hydrazino}-5-fluoro-2-(methyloxy)-4-pyrimidinyl]amino}-N,N-dimethylbutanamide (0.036 g, 23%). LCMS: (M+H)⁺=574.3.

Part C:

(2S)-2-{[6-[2-((2R)-3-Cyclopentyl-2-{[formyl(hydroxy)amino]methyl}propanoyl)hydrazino]-5-fluoro-2-(methyloxy)-4-pyrimidinyl]amino}-N,N-dimethylbutanamide A solution of (2S)-2-{[6-{2-[(2R)-3-cyclopentyl-2-({formyl[(phenylmethyl)oxy]amino}methyl)propanoyl]hydrazino}-5-fluoro-2-(methyloxy)-4-pyrimidinyl]amino}-N,N-dimethylbutanamide (0.036 g, 0.063 mmol), and Pd(C) (0.008 g) in MeOH (10 mL) was run under standard hydrogenation conditions as in General Procedure A, Part C, to provide (2S)-2-{[6-[2-((2R)-3-cyclopentyl-2-{[formyl(hydroxy)amino]methyl}propanoyl)hydrazino]-5-fluoro-2-(methyloxy)-4-pyrimidinyl]amino}-N,N-dimethylbutanamide as an orange solid (0.019 g, 63%). LCMS: (M+H)⁺=484.4.

Example 87

((2R)-2-(Cyclopentylmethyl)-3-{2-[5-fluoro-2-methyl-6-(tetrahydro-5H-[1,3]dioxolo[4,5-c]pyrrol-5-yl)-4-pyrimidinyl]hydrazino}-3-oxopropyl)hydroxyformamide

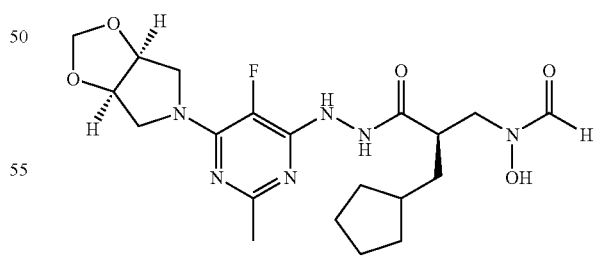

Part A:

Phenylmethyl (cis)-3,4-dihydroxy-1-pyrrolidinecarboxylate

Phenylmethyl 2,5-dihydro-1H-pyrrole-1-carboxylate (commercially-available) (5.07 g, 25 mmol) was dissolved in a mixture of acetone (25 mL) and water (10 mL). NMO (5.9 g, 50 mmol) was added followed by catalytic OsO₄. The reaction was stirred for 19 hours and then quenched by the addition of an aqueous solution of Na₂S₂O₃. A standard work-up followed by silica gel chromatography (3:1 Hexane: ethyl acetate to pure ethyl acetate to 9:1 DCM: MeOH) yielded phenylmethyl (cis)-3,4-dihydroxy-1-pyrrolidinecarboxylate (0.872 g, 15%) as a clear oil. LCMS: (M+H)⁺: 237.9.

Part B:

(cis)-Tetrahydro-3aH-[1,3]dioxolo[4,5-c]pyrrole

To a solution of phenylmethyl (3R,4S)-3,4-dihydroxy-1-pyrrolidinecarboxylate (0.872 g, 3.7 mmol) and dimethoxymethane (10 mL) in DCM (4 mL) was added 5 drops of triflic acid and the resulting solution was stirred until the reaction was judged to be complete by LCMS. Quenching the reaction with a saturated aqueous solution of sodium bicarbonate followed by a standard work-up and purification by RP-HPLC yielded the intermediate phenylmethyl (syn)-tetrahydro-5H-[1,3]dioxolo[4,5-c]pyrrole-5-carboxylate. This was immediately dissolved in degassed MeOH (5 mL), 10% Pd/C (25 mg) was added and the reaction was stirred under a hydrogen balloon until it was judged to be complete by LCMS. Filtration and concentration in vacuo yielded (cis)-tetrahydro-3aH-[1,3]dioxolo[4,5-c]pyrrole (88 mg, 21%). LCMS: (M+H)⁺: 116.1.

Part C:

((2R)-2-(Cyclopentylmethyl)-3-{2-[5-fluoro-2-methyl-6-(tetrahydro-5H-[1,3]dioxolo[4,5-c]pyrrol-5-yl)-4-pyrimidinyl]hydrazino}-3-oxopropyl)hydroxyformamide ((2R)-2-(Cyclopentylmethyl)-3-{2-[5-fluoro-2-methyl-6-(tetrahydro-5H-[1,3]dioxolo[4,5-c]pyrrol-5-yl)-4-pyrimidinyl]hydrazino}-3-oxopropyl)hydroxyformamide was prepared according to General Procedure A, utilizing (cis)-tetrahydro-3aH-[1,3]dioxolo[4,5-c]pyrrole in place of pyrrolidine in Part A. LCMS: (M+H)⁺: 453.3.

Example 88

[(2R)-3-{2-[2-Chloro-6-(dimethylamino)-5-fluoro-4-pyrimidinyl]hydrazino}-2-(cyclopentylmethyl)-3-oxopropyl]hydroxyformamide

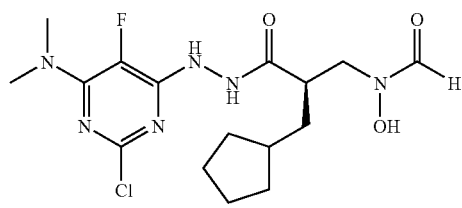

[(2R)-3-{2-[2-Chloro-6-(dimethylamino)-5-fluoro-4-pyrimidinyl]hydrazino}-2-(cyclopentylmethyl)-3-oxopropyl]hydroxyformamide was prepared according to General Procedure D, utilizing commercially-available dimethylamine in place of N-methylpiperazine in Part A. LCMS: (M+H)⁺: 403.

Example 89

[(2R)-2-(Cyclopentylmethyl)-3-(2-{6-[(trans)-3-(dimethylamino)-4-methyl-1-pyrrolidinyl]-5-fluoro-2-methyl-4-pyrimidinyl}hydrazino)-3-oxopropyl]hydroxyformamide (Mixture of Diastereomers)

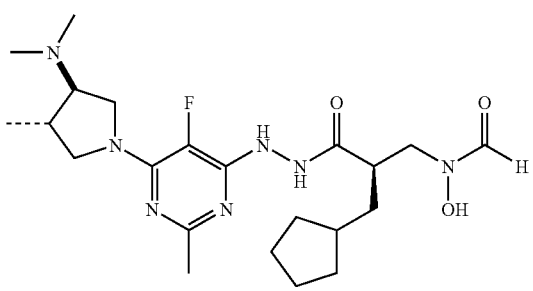

Part A:

(trans)-N,N,4-Trimethyl-3-pyrrolidinamine

A solution of commercially available 1,1-dimethylethyl (trans)-3-amino-4-methyl-1-pyrrolidinecarboxylate (1 g, 5 mmol) and formaldehyde (0.69 mL, 25 mmol, 37% in water) in THF (20 mL) was stirred at room temperature for 1 hour. NaBH(OAc)₃ (7.4 g, 35 mmol) was added and the reaction was stirred overnight. 1 M NaOH (20 mL) was added and the layers were allowed to separate. The aqueous phase was extracted with ether and the combined organics were dried over sodium sulfate, filtered and concentrated to yield a crude residue. This material was dissolved in 4 M HCl in dioxane (24 mL) and stirred for 3 hours. Evaporation of the solvent yielded (trans)-N,N,4-trimethyl-3-pyrrolidinamine in quantitative yield. LCMS: (M+H)⁺: 129.1.

Part B:

[(2R)-2-(Cyclopentylmethyl)-3-(2-{6-[(trans)-3-(dimethylamino)-4-methyl-1-pyrrolidinyl]-5-fluoro-2-methyl-4-pyrimidinyl}hydrazino)-3-oxopropyl]hydroxyformamide

[(2R)-2-(Cyclopentylmethyl)-3-(2-{6-[(trans)-3-(dimethylamino)-4-methyl-1-pyrrolidinyl]-5-fluoro-2-methyl-4-pyrimidinyl}hydrazino)-3-oxopropyl]hydroxyformamide was prepared as a mixture of diastereomers according to General Procedure A, utilizing trans-N,N,4-trimethyl-3-pyrrolidinamine in place of pyrrolidine in Part A. LCMS: (M+H)⁺: 466.4.

Example 90

(trans)-1-{6-[2-((2R)-3-Cyclopentyl-2-{[formyl(hydroxy)amino]methyl}propanoyl)hydrazino]-5-fluoro-2-methyl-4-pyrimidinyl}-N,N,4-trimethyl-3-pyrrolidinecarboxamide (Mixture of Diastereomers)

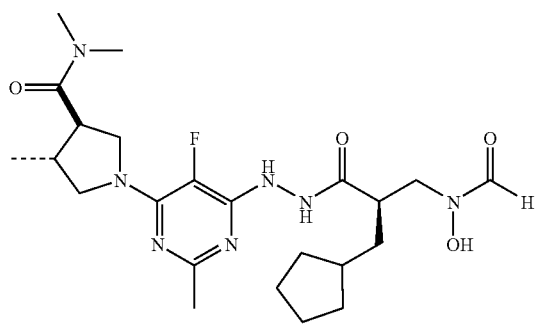

Part A:

(trans)-N,N,4-Trimethyl-3-pyrrolidinecarboxamide

A solution of commercially available phenylmethyl (trans)-3-[(dimethylamino)carbonyl]-4-methyl-1-pyrrolidinecarboxylate (1.06 g, 3.4 mmol), DMAP (0.63 g, 5.2 mmol), and EDC (1.0 g, 5.2 mmol) in DCM (18 mL) was stirred for 5 min and dimethylamine (1.9 mL, 3.8 mmol, 2M in THF) was added. The reaction was allowed to stir until it was judged to be complete by LCMS and was quenched with 1 M HCl. A standard work-up provided the desired amide intermediate. This material was immediately dissolved in degassed MeOH (20 mL) and 10% Pd/C (120 mg) was added. The reaction mixture was allowed to stir under a hydrogen balloon until complete deprotection was observed by LCMS. The catalyst was removed by filtration to yield (trans)-N,N,4-trimethyl-3-pyrrolidinecarboxamide. LCMS: (M+H)$^+$: 157.2.

Part B:

(trans)-1-{6-[2-((2R)-3-Cyclopentyl-2-{[formyl(hydroxy)amino]methyl}propanoyl)hydrazino]-5-fluoro-2-methyl-4-pyrimidinyl}-N,N,4-trimethyl-3-pyrrolidinecarboxamide (trans)-1-{6-[2-((2R)-3-Cyclopentyl-2-{[formyl(hydroxy)amino]methyl}propanoyl)hydrazino]-5-fluoro-2-methyl-4-pyrimidinyl}-N,N,4-trimethyl-3-pyrrolidinecarboxamide was prepared as a mixture of diastereisomers according to General Procedure A, utilizing (trans)-N,N,4-trimethyl-3-pyrrolidinecarboxamide in place of pyrrolidine in Part A. LCMS: (M+H)$^+$: 494.4.

Example 91

[(2R)-2-(Cyclopentylmethyl)-3-(2-{2-(difluoromethyl)-6-[(trans)-3-(dimethylamino)-4-methyl-1-pyrrolidinyl]-5-fluoro-4-pyrimidinyl}hydrazino)-3-oxopropyl]hydroxyformamide (Mixture of Diastereomers)

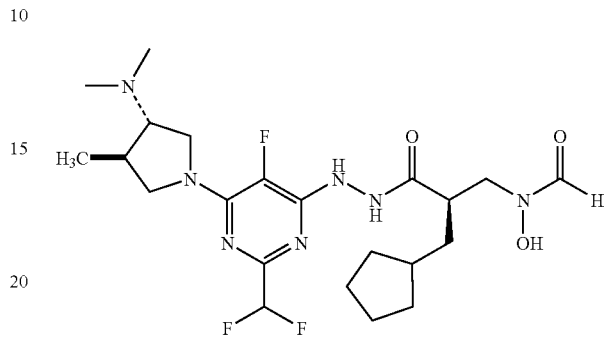

[(2R)-2-(Cyclopentylmethyl)-3-(2-{2-(difluoromethyl)-6-[(3S,4R)-3-(dimethylamino)-4-methyl-1-pyrrolidinyl]-5-fluoro-4-pyrimidinyl}hydrazino)-3-oxopropyl]hydroxyformamide was prepared as a 1:1 mixture of diastereoisomers according to General Procedure H, utilizing trans-N,N,4-trimethyl-3-pyrrolidinamine (Example 89) in place of N-methylpiperazine in Part A. LCMS: (M+H)$^+$: 502.4.

Example 92

[(2R)-2-(Cyclopentylmethyl)-3-(2-{6-[(trans)-3-(dimethylamino)-4-methyl-1-pyrrolidinyl]-2-ethyl-5-fluoro-4-pyrimidinyl}hydrazino)-3-oxopropyl]hydroxyformamide

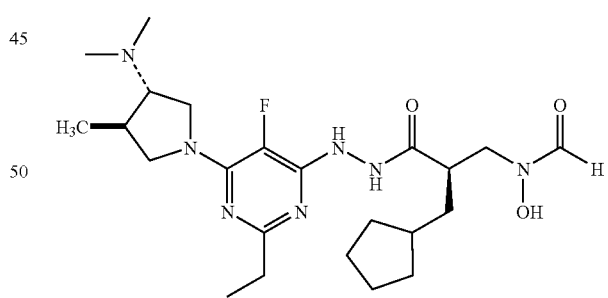

[(2R)-2-(Cyclopentylmethyl)-3-(2-{6-[(trans)-3-(dimethylamino)-4-methyl-1-pyrrolidinyl]-2-ethyl-5-fluoro-4-pyrimidinyl}hydrazino)-3-oxopropyl]hydroxyformamide was prepared as a 1:1 mixture of diastereoisomers according to General Procedure B, utilizing (trans)-N,N,4-trimethyl-3-pyrrolidinamine (Example 89) in place of azetidine in Part A. LCMS: (M+H)$^+$: 480.3.

Example 93

[(2R)-2-(Cyclopentylmethyl)-3-(2-{2-(difluoromethyl)-6-[(3R)-3,4-dimethyl-1-piperazinyl]-5-fluoro-4-pyrimidinyl}hydrazino)-3-oxopropyl]hydroxyformamide

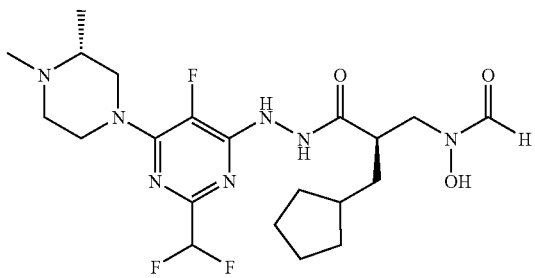

[(2R)-2-(Cyclopentylmethyl)-3-(2-{2-(difluoromethyl)-6-[(3R)-3,4-dimethyl-1-piperazinyl]-5-fluoro-4-pyrimidinyl}hydrazino)-3-oxopropyl]hydroxyformamide was prepared according to General Procedure H, utilizing (2R)-1,2-dimethylpiperazine dihydrochloride salt (Example 39) in place of N-methylpiperazine in Part A. LCMS: (M+H)$^+$: 488.7.

Example 94

{(2R)-2-(Cyclopentylmethyl)-3-[2-(5-fluoro-2-methyl-6-{[(3S)-1-methyl-2-oxo-2,3,4,7-tetrahydro-1H-azepin-3-yl]amino}-4-pyrimidinyl)hydrazino]-3-oxopropyl}hydroxyformamide

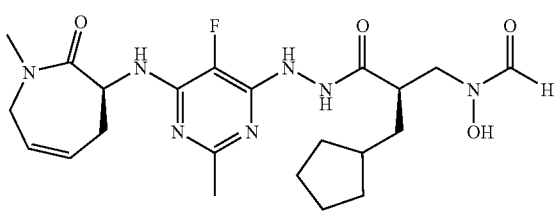

Part A:

(2S)-2-({[(1,1-Dimethylethyl)oxy]carbonyl}amino)-4-pentenoic acid

To a mixture of MeOH (60 mL) and water (70 mL) was added L-2-amino-4-pentanoic acid (2.02 g, 17.5 mmol), K$_2$CO$_3$ (12.12 g, 88 mmol) and di-tert-butyl dicarbonate (4.02 g, 18.4 mmol). This mixture was stirred for 12 hours before being cooled to 0° C. and acidified to pH 2 with 1 M HCl. Removal of the MeOH yielded an aqueous solution that was extracted with DCM. The combined organics were dried over sodium sulfate and concentrated yielding (2S)-2-({[(1,1-dimethylethyl)oxy]carbonyl}amino)-4-pentenoic acid (3.47 g, 92%). LCMS: (M+Na)$^+$: 238.1.

Part B:

1,1-Dimethylethyl {(1S)-1-[(2-propen-1-ylamino)carbonyl]-3-buten-1-yl}carbamate

To a stirred solution of (2S)-2-({[(1,1-dimethylethyl)oxy]carbonyl}amino)-4-pentenoic acid (2.82 g, 13 mmol), DMAP (1.9 g, 16 mmol) and EDC (3.1 g, 16 mmol) was added N-methylallylamine (1.38 mL, 14 mmol). The reaction was stirred for 72 hours before being quenched by the addition of 1 M HCl (15 mL). The resulting biphasic mixture was separated and the aqueous phase was extracted once with DCM. The combined organics were dried over sodium sulfate and concentrated to yield 1,1-dimethylethyl {(1S)-1-[(2-propen-1-ylamino)carbonyl]-3-buten-1-yl}carbamate (0.94 g, 28%). LCMS: (M−$^t$But)$^+$: 238.1.

Part C:

1,1-Dimethylethyl [(3S)-1-methyl-2-oxo-2,3,4,7-tetrahydro-1H-azepin-3-yl]carbamate 1,1-Dimethylethyl {(1S)-1-[(2-propen-1-ylamino)carbonyl]-3-buten-1-yl}carbamate (0.94 g, 3.9 mmol) was dissolved in DCM (350 mL) and 1,3-bis(2,4,6-trimethylphenyl)-2-imidazolidinylidene)dichloro(phenylmethylene)(tricyclohexylphosphine)ruthenium (0.3 g, 3.5 mmol) was added. The resulting solution was heated to 40° C. and stirred for 12 hours. The solvent was evaporated under reduced pressure and the crude product was purified by RP-HPLC yielding 1,1-dimethylethyl [(3S)-1-methyl-2-oxo-2,3,4,7-tetrahydro-1H-azepin-3-yl]carbamate (0.6 g, 63%). LCMS: (M+H)$^+$: 242.3.

Part D:

(3S)-3-Amino-1-methyl-1,3,4,7-tetrahydro-2H-azepin-2-one.HCl

To a solution of 1,1-dimethylethyl [(3S)-1-methyl-2-oxo-2,3,4,7-tetrahydro-1H-azepin-3-yl]carbamate (0.6 g, 2.5 mmol) in DCM (4 mL) was added HCl (6.2 mL, 25 mmol, 4M in dioxane) and the resulting mixture was stirred for 12 hours. Removal of the solvents under reduced pressure yielded (3S)-3-amino-1-methyl-1,3,4,7-tetrahydro-2H-azepin-2-one.HCl (500 mg, quantitative). LCMS: (M+H)$^+$: not detected.

Part E:

{(2R)-2-(Cyclopentylmethyl)-3-[2-(5-fluoro-2-methyl-6-{[(3S)-1-methyl-2-oxo-2,3,4,7-tetrahydro-1H-azepin-3-yl]amino}-4-pyrimidinyl)hydrazino]-3-oxopropyl}hydroxyformamide {(2R)-2-(Cyclopentylmethyl)-3-[2-(5-fluoro-2-methyl-6-{[(3S)-1-methyl-2-oxo-2,3,4,7-tetrahydro-1H-azepin-3-yl]amino}-4-pyrimidinyl)hydrazino]-3-oxopropyl}hydroxyformamide was prepared in a manner similar to Example 105, utilizing (3S)-3-amino-1-methyl-1,3,4,7-tetrahydro-2H-azepin-2-one.HCl in place of N-methyl-1-(4-pyrimidinyl)methanamine and using diisopropylethylamine in place of triethylamine. LCMS: (M+H)$^+$: 478.5.

Example 95

[(2R)-2-(Cyclopentylmethyl)-3-(2-{2-(difluoromethyl)-6-[(3S)-3,4-dimethyl-1-piperazinyl]-5-fluoro-4-pyrimidinyl}hydrazino)-3-oxopropyl]hydroxyformamide

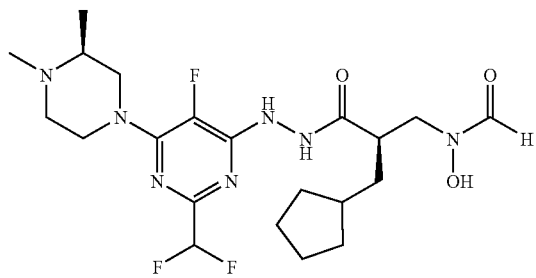

[(2R)-2-(Cyclopentylmethyl)-3-(2-{2-(difluoromethyl)-6-[(3S)-3,4-dimethyl-1-piperazinyl]-5-fluoro-4-pyrimidinyl}hydrazino)-3-oxopropyl]hydroxyformamide was prepared according to General Procedure H, utilizing (2S)-1,2-dimethylpiperazine dihydrochloride salt (Example 40) in place of N-methylpiperazine in Part A. LCMS: (M+H)$^+$: 488.6.

Example 96

[(2R)-2-(Cyclopentylmethyl)-3-(2-{2-(difluoromethyl)-6-[(2S)-2,4-dimethyl-1-piperazinyl]-5-fluoro-4-pyrimidinyl}hydrazino)-3-oxopropyl]hydroxyformamide

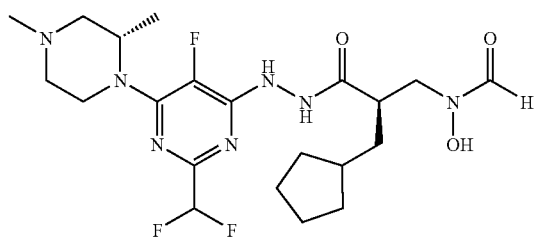

[(2R)-2-(Cyclopentylmethyl)-3-(2-{2-(difluoromethyl)-6-[(2S)-2,4-dimethyl-1-piperazinyl]-5-fluoro-4-pyrimidinyl}hydrazino)-3-oxopropyl]hydroxyformamide was prepared according to General Procedure H, utilizing (3S)-1,3-dimethylpiperazine (Example 64) in place of N-methylpiperazine in Part A. LCMS: (M+H)$^+$: 488.5.

Example 97

[(2R)-2-(Cyclopentylmethyl)-3-(2-{6-[(3S)-3,4-dimethyl-1-piperazinyl]-5-fluoro-2-methyl-4-pyrimidinyl}hydrazino)-3-oxopropyl]hydroxyformamide

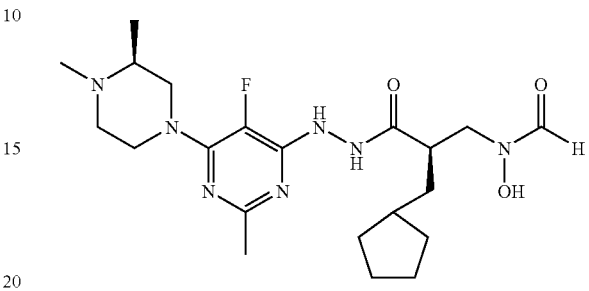

Part A:

1,1-Dimethylethyl (3S)-3,4-dimethyl-1-piperazinecarboxylate

Commercially available 1,1-dimethylethyl (3S)-3-methyl-1-piperazinecarboxylate (3.05 g, 15.23 mmol), formaldehyde (37% in water) (2.13 mL), sodium triacetoxy borohoydride (5.52 g, 26.04 mmol) and DCM (250 mL) were stirred overnight. The solvent was removed, and 1N NaOH was added to the residue. The mixture was extracted with dichloromethane, and the organics were dried (Na$_2$SO$_4$) and concentrated in vacuo to provide 1,1-dimethylethyl (3S)-3,4-dimethyl-1-piperazinecarboxylate as a clear oil (3.15 g, 97%). LCMS: (M+H)$^+$=215.3.

Part B:

(2S)-1,2-Dimethylpiperazine dihydrochloride 1,1-Dimethylethyl (3S)-3,4-dimethyl-1-piperazinecarboxylate (3.15 g, 14.7 mmol) in 1N HCl (40 mL) was stirred overnight. Then 4M HCl in 1,4-dioxane (25 mL) was added and the reaction was left to stir overnight. Removed volatiles in vacuo to provide (2S)-1,2-dimethylpiperazine dihydrochloride as a white solid (2.88 g). LCMS: (M+H)$^+$=115.1.

Part C:

4-Chloro-6-[(3S)-3,4-dimethyl-1-piperazinyl]-5-fluoro-2-methylpyrimidine

To a solution of 4,6-dichloro-5-fluoro-2-methylpyrimidine (0.181 g, 1.0 mmol) and (2S)-1,2-dimethylpiperazine dihydrochloride (0.189 g, 1.0 mmol) in THF (10 mL) was added triethylamine (0.42 mL, 3.0 mmol) at room temperature. MeOH (1 mL) was added to improve solubility. The reaction mixture was stirred overnight, and then the solvent was removed in vacuo. Ether, THF and water were added to the resulting residue. The organics were separated, dried (Na$_2$SO$_4$) and evaporated to provide 4-chloro-6-[(3S)-3,4-dimethyl-1-piperazinyl]-5-fluoro-2-methylpyrimidine as a yellow solid (0.254 g, 98%). LCMS: (M+H)$^+$=259.3.

Part D:

4-[(3S)-3,4-Dimethyl-1-piperazinyl]-5-fluoro-6-hydrazino-2-methylpyrimidine

To 4-chloro-6-[(3S)-3,4-dimethyl-1-piperazinyl]-5-fluoro-2-methylpyrimidine (0.254 g, 0.98 mmol) in DMSO (3 mL) was added hydrazine monohydrate (2 mL). The reaction was stirred at room temperature for 3 days. The volatiles were removed in vacuo, and the residue was purified by RP-HPLC to provide 4-[(3S)-3,4-dimethyl-1-piperazinyl]-5-fluoro-6-hydrazino-2-methylpyrimidine as a yellow solid (0.161 g, 64%). LCMS: $(M+H)^+=255.6$.

Part E:

[(2R)-2-(Cyclopentylmethyl)-3-(2-{6-[(3S)-3,4-dimethyl-1-piperazinyl]-5-fluoro-2-methyl-4-pyrimidinyl}hydrazino)-3-oxopropyl][(phenylmethyl)oxy]formamide (2R)-3-Cyclopentyl-2-({formyl[(phenylmethyl)oxy]amino}methyl)propanoic acid (0.184 g, 0.60 mmol), 4-[(3S)-3,4-dimethyl-1-piperazinyl]-5-fluoro-6-hydrazino-2-methylpyrimidine (0.161 g, 0.63 mmol), NMM (0.21 mL, 1.89 mmol), HOAt (0.086 g, 0.63 mmol), and EDC (0.121 g, 0.63 mmol) were dissolved in DMF (4 mL), and the reaction was stirred overnight. Purified by RP-HPLC to provide [(2R)-2-(cyclopentylmethyl)-3-(2-{6-[(3S)-3,4-dimethyl-1-piperazinyl]-5-fluoro-2-methyl-4-pyrimidinyl}hydrazino)-3-oxopropyl][(phenylmethyl)oxy]formamide (0.219 g, 64%). LCMS: $(M+H)^+=542.7$.

Part F:

[(2R)-2-(Cyclopentylmethyl)-3-(2-{6-[(3S)-3,4-dimethyl-1-piperazinyl]-5-fluoro-2-methyl-4-pyrimidinyl}hydrazino)-3-oxopropyl]hydroxyformamide A mixture of [(2R)-2-(cyclopentylmethyl)-3-(2-{6-[(3S)-3,4-dimethyl-1-piperazinyl]-5-fluoro-2-methyl-4-pyrimidinyl}hydrazino)-3-oxopropyl][(phenylmethyl)oxy]formamide (0.219 g, 0.40 mmol) and Pd(C) (0.042 g) in MeOH (10 mL) was run under standard hydrogenation conditions as in General Procedure A, Part C, to provide [(2R)-2-(cyclopentylmethyl)-3-(2-{6-[(3S)-3,4-dimethyl-1-piperazinyl]-5-fluoro-2-methyl-4-pyrimidinyl}hydrazino)-3-oxopropyl]hydroxyformamide as a white solid (0.172 g, 94%). LCMS: $(M+H)^+=452.3$.

Example 98

[(2R)-2-(Cyclopentylmethyl)-3-(2-{6-[(3R)-3,4-dimethyl-1-piperazinyl]-5-fluoro-2-methyl-4-pyrimidinyl}hydrazino)-3-oxopropyl]hydroxyformamide

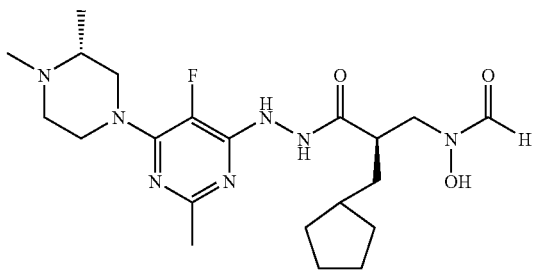

Part A:

1,1-Dimethylethyl (3R)-3,4-dimethyl-1-piperazinecarboxylate

Commercially available 1,1-dimethylethyl (3R)-3-methyl-1-piperazinecarboxylate (2.78 g, 13.88 mmol), formaldehyde (37% in water) (1.94 mL), sodium triacetoxy borohoydride (5.03 g, 23.73 mmol) and DCM (200 mL) were stirred overnight. The solvent was removed, and 1N NaOH was added to the residue. The mixture was extracted with dichloromethane, and the organics were dried ($Na_2SO_4$) and concentrated in vacuo to provide 1,1-dimethylethyl (3R)-3,4-dimethyl-1-piperazinecarboxylate as a clear oil (2.70 g, 91%). LCMS: $(M+H)^+=215.4$.

Part B:

(2R)-1,2-Dimethylpiperazine dihydrochloride 1,1-Dimethylethyl (3R)-3,4-dimethyl-1-piperazinecarboxylate (2.70 g, 12.6 mmol) in 1N HCl (25 mL) was stirred overnight. Then 4M HCl in 1,4-dioxane (25 mL) was added and the reaction was left to stir overnight. The volatiles were removed in vacuo to provide (2R)-1,2-dimethylpiperazine dihydrochloride as a white solid (2.53 g). LCMS: $(M+H)^+=115.1$.

Part C:

4-Chloro-6-[(3R)-3,4-dimethyl-1-piperazinyl]-5-fluoro-2-methylpyrimidine

To a solution of 4,6-dichloro-5-fluoro-2-methylpyrimidine (0.181 g, 1.0 mmol) and (2R)-1,2-dimethylpiperazine dihydrochloride (0.189 g, 1.0 mmol) in THF (10 mL) was added triethylamine (0.42 mL, 3.0 mmol). MeOH (1 mL) was added to improve solubility. Reaction left to stir overnight. The solvent was removed in vacuo, and THF and ether were added to the resulting residue, which was washed with water. The organics were dried ($Na_2SO_4$) and concentrated in vacuo to provide 4-chloro-6-[(3R)-3,4-dimethyl-1-piperazinyl]-5-fluoro-2-methylpyrimidine as a yellow oil (0.242 g, 94%). LCMS: $(M+H)^+=259.3$.

Part D:

4-[(3R)-3,4-Dimethyl-1-piperazinyl]-5-fluoro-6-hydrazino-2-methylpyrimidine

To 4-chloro-6-[(3R)-3,4-dimethyl-1-piperazinyl]-5-fluoro-2-methylpyrimidine (0.242 g, 0.94 mmol) in DMSO (3 mL) was added hydrazine monohydrate (2 mL). The reaction was stirred at room temperature for 3 days. Removed volatiles in vacuo and purified by RP-HPLC to provide 4-[(3R)-3,4-dimethyl-1-piperazinyl]-5-fluoro-6-hydrazino-2-methylpyrimidine as a yellow solid (0.079 g, 33%). LCMS: $(M+H)^+=255.3$.

Part E:

[(2R)-2-(Cyclopentylmethyl)-3-(2-{6-[(3R)-3,4-dimethyl-1-piperazinyl]-5-fluoro-2-methyl-4-pyrimidinyl}hydrazino)-3-oxopropyl][(phenylmethyl)oxy]formamide (2R)-3-Cyclopentyl-2-({formyl[(phenylmethyl)oxy]amino}methyl)propanoic acid (0.079 g, 0.30 mmol), 4-[(3R)-3,4-dimethyl-1-piperazinyl]-5-fluoro-6-hydrazino-2-methylpyrimidine (0.079 g, 0.31 mmol), NMM (0.10 mL, 0.90 mmol), HOAt (0.042 g, 0.31 mmol), and EDC (0.059 g, 0.31 mmol) were dissolved in DMF (4 mL) and treated in a manner similar to General Procedure A, Part B, to provide [(2R)-2-(cyclopentylmethyl)-3-(2-{6-[(3R)-3,4-dimethyl-1-piperazinyl]-5-fluoro-2-methyl-4-pyrimidinyl}hydrazino)-3-oxopropyl][(phenylmethyl)oxy]formamide (0.082 g, 49%). LCMS: (M+H)$^+$=542.7.

Part F:

[(2R)-2-(Cyclopentylmethyl)-3-(2-{6-[(3R)-3,4-dimethyl-1-piperazinyl]-5-fluoro-2-methyl-4-pyrimidinyl}hydrazino)-3-oxopropyl]hydroxyformamide A solution of [(2R)-2-(cyclopentylmethyl)-3-(2-{6-[(3R)-3,4-dimethyl-1-piperazinyl]-5-fluoro-2-methyl-4-pyrimidinyl}hydrazino)-3-oxopropyl][(phenylmethyl)oxy]formamide (0.082 g, 0.15 mmol), and Pd(C) (0.016 g) in MeOH (10 mL) was run under standard hydrogenation conditions as in General Procedure A, Part C, to provide [(2R)-2-(cyclopentylmethyl)-3-(2-{6-[(3R)-3,4-dimethyl-1-piperazinyl]-5-fluoro-2-methyl-4-pyrimidinyl}hydrazino)-3-oxopropyl]hydroxyformamide as a white solid (0.067 g, 99%). LCMS: (M+H)$^+$=452.4.

Example 99

((2R)-2-(Cyclopentylmethyl)-3-{2-[5-fluoro-2-methyl-6-(tetrahydro-1H-furo[3,4-c]pyrrol-5(3H)-yl)-4-pyrimidinyl]hydrazino}-3-oxopropyl)hydroxyformamide

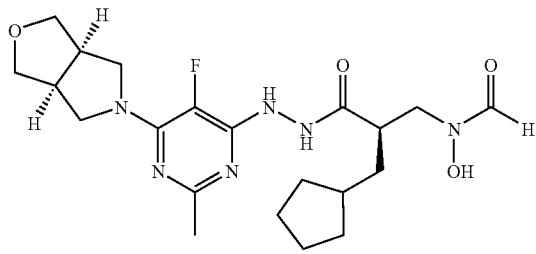

Part A:

[(cis)-1-(Phenylmethyl)-3,4-pyrrolidinediyl]dimethanol

Dimethyl (cis)-1-(phenylmethyl)-3,4-pyrrolidinedicarboxylate (Chem. Pharm. Bull. 1985 33; 896-898) (2.44 g, 8.8 mmol) was dissolved in THF (100 mL) and cooled to 0° C. LiAlH$_4$ (1 g, 26 mmol) was added in portions and the reaction was heated overnight at 60° C. Upon cooling to 0° C., wet ether was added followed by water (1 mL), 15 w/w NaOH (aq) (1 mL) and water (3 mL). The resulting mixture was stirred for 15 min and filtered through Celite yielding crude [(cis)-1-(phenylmethyl)-3,4-pyrrolidinediyl]dimethanol (2.5 g) which was used directly in the next reaction. LCMS: (M+H)$^+$: 222.3.

Part B:

(cis)-3,4-Pyrrolidinediyldimethanol

To a solution of crude [(cis)-1-(phenylmethyl)-3,4-pyrrolidinediyl]dimethanol (2.5 g) in MeOH (50 mL) was added conc HCl (0.2 mL) followed by Pearlmans catalyst (700 mg). The resulting suspension was hydrogenated for 48 hours at 50 psi on a Parr shaker, after which time a further 700 mg of the catalyst was added. Hydrogenation for another 72 hours at 50 psi resulted in completion of the reaction. Removal of the catalyst by filtration and evaporation of the solvents under reduced pressure yielded (cis)-3,4-pyrrolidinediyldimethanol (970 mg, 7.4 mmol). LCMS: (M+H)$^+$: Not detected.

Part C:

Phenylmethyl (cis)-3,4-bis(hydroxymethyl)-1-pyrrolidinecarboxylate (cis)-3,4-Pyrrolidinediyldimethanol (970 mg, 7.4 mmol) was dissolved in a mixture of MeOH (20 mL) and water (7 mL) and cooled to 0° C. Na$_2$CO$_3$ (1.96 g, 19 mmol) was added followed by benzyl chloroformate (1.15 mL, 8.1 mmol) and the resulting solution was stirred for 4 hours, maintaining the temperature at 0° C. The reaction was concentrated under reduced pressure to remove most of the methanol, and the remaining aqueous solution was extracted twice with EtOAc. The combined organics were washed with brine and dried over sodium sulfate before being concentrated in vacuo. RP-HPLC yielded phenylmethyl (cis)-3,4-bis(hydroxymethyl)-1-pyrrolidinecarboxylate (450 mg, 22%, 1.7 mmol). LCMS: (M+H)$^+$: 266.1.

Part D:

Phenylmethyl tetrahydro-1H-furo[3,4-c]pyrrole-5(3H)-carboxylate

To a mixture of DCM (3 mL) and pyridine (3 mL) was added phenylmethyl (cis)-3,4-bis(hydroxymethyl)-1-pyrrolidinecarboxylate (250 mg, 0.94 mmol) followed by tosylchloride (540 mg, 2.8 mmol) and the resulting solution was refluxed for 4 hours. The solvents were evaporated and the residue was azeotroped once with hexane before being purified by RP-HPLC. This yielded phenylmethyl tetrahydro-1H-furo[3,4-c]pyrrole-5(3H)-carboxylate (170 mg, 73%). LCMS: (M+H)$^+$: 248.4.

Part E:

Hexahydro-1H-furo[3,4-c]pyrrole

To a degassed solution of MeOH (5 mL) was added phenylmethyl tetrahydro-1H-furo[3,4-c]pyrrole-5(3H)-carboxylate (170 mg, 0.68 mmol) followed by Pd/C (40 mg). Stirring under a hydrogen balloon for 3 hours followed by filtration of the catalyst and evaporation of the solvent yielded hexahydro-1H-furo[3,4-c]pyrrole (70 mg, 91%). LCMS: (M+H)$^+$: Not detected.

Part F:

((2R)-2-(Cyclopentylmethyl)-3-{2-[5-fluoro-2-methyl-6-(tetrahydro-1H-furo[3,4-c]pyrrol-5(3H)-yl)-4-pyrimidinyl]hydrazino}-3-oxopropyl)hydroxyformamide ((2R)-2-(Cyclopentylmethyl)-3-{2-[5-fluoro-2-methyl-6-(tetrahydro-1H-furo[3,4-c]pyrrol-5(3H)-yl)-4-pyrimidinyl]hydrazino}-3-oxopropyl)hydroxyformamide was prepared according to General Procedure A, utilizing hexahydro-1H-furo[3,4-c]pyrrole in place of pyrrolidine in Part A. LCMS: (M+H)+: 451.3.

Example 100

[(2R)-2-(Cyclopentylmethyl)-3-(2-{6-[(3R,4S)-3-(dimethylamino)-4-methyl-1-pyrrolidinyl]-2-ethyl-5-fluoro-4-pyrimidinyl}hydrazino)-3-oxopropyl]hydroxyformamide (D1)

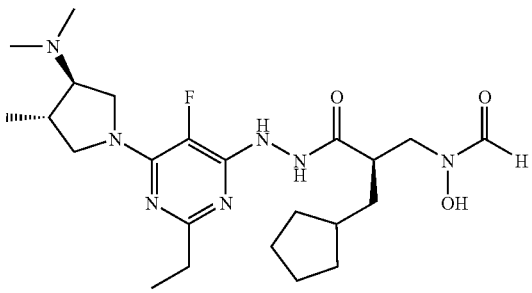

[(2R)-2-(Cyclopentylmethyl)-3-(2-{6-[(3R,4S)-3-(dimethylamino)-4-methyl-1-pyrrolidinyl]-2-ethyl-5-fluoro-4-pyrimidinyl}hydrazino)-3-oxopropyl]hydroxyformamide was prepared according to General Procedure B, utilizing trans-N,N,4-trimethyl-3-pyrrolidinamine (Example 89) in place of azetidine in Part A. Chiral chromatography of the product of part B yielded a single enantiomer which was deprotected according to Part C. The absolute stereochemistry of this compound is unknown and arbitrarily assigned on the pyrrolidine ring in the above structure. LCMS: (M+H)+: 480.6.

Example 101

[(2R)-2-(Cyclopentylmethyl)-3-(2-{6-[(3S,4R)-3-(dimethylamino)-4-methyl-1-pyrrolidinyl]-2-ethyl-5-fluoro-4-pyrimidinyl}hydrazino)-3-oxopropyl]hydroxyformamide (D2)

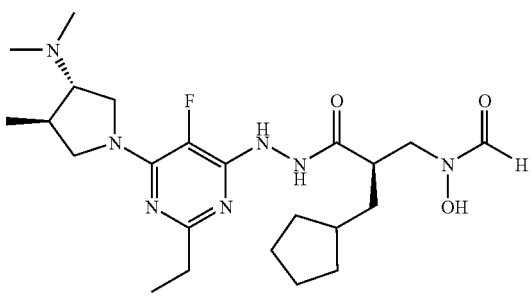

[(2R)-2-(Cyclopentylmethyl)-3-(2-{6-[(3S,4R)-3-(dimethylamino)-4-methyl-1-pyrrolidinyl]-2-ethyl-5-fluoro-4-pyrimidinyl}hydrazino)-3-oxopropyl]hydroxyformamide was prepared according to General Procedure B, utilizing trans-N,N,4-trimethyl-3-pyrrolidinamine (Example 89) in place of azetidine in Part A. Chiral chromatography of the product of part B yielded a single enantiomer which was deprotected according to Part C. The absolute stereochemistry of this compound is unknown and arbitrarily assigned on the pyrrolidine ring in the above structure. LCMS: (M+H)+: 480.4.

Example 102

[(2R)-3-(2-{2-Chloro-5-fluoro-6-[(trans)-3-(hydroxymethyl)-4-methyl-1-pyrrolidinyl]-4-pyrimidinyl}hydrazino)-2-(cyclopentylmethyl)-3-oxopropyl]hydroxyformamide (Imixture of Diastereomers)

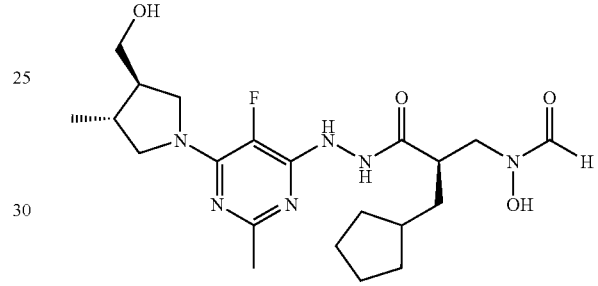

Part A:

Methyl rac-(trans)-4-methyl-1-(phenylmethyl)-3-pyrrolidinecarboxylate

To a solution of N-(methoxymethyl)-N-(trimethylsilylmethyl)benzylamine (1.8 mL, 7 mmol) and methyl crotonate (0.62 mL, 5.8 mmol) in DCM (25 mL) at 0° C. was added dropwise a solution of trifluoroacetic acid (0.045 mL, 0.58 mmol) in DCM (1 mL). The reaction was allowed to warm to room temperature and was stirred for 3 h. Saturated sodium bicarbonate solution was added and the phases were separated. The aqueous phase was extracted twice with DCM and the combined organics were dried over sodium sulfate and concentrated in vacuo. This yielded crude methyl rac-(trans)-4-methyl-1-(phenylmethyl)-3-pyrrolidinecarboxylate (1.58 g) which was used without further purification. LCMS: (M+H)+: 234.3.

Part B:

Rac-[(trans)-4-Methyl-3-pyrrolidinyl]methanol

[(trans)-4-Methyl-3-pyrrolidinyl]methanol was synthesized in accordance with Example 99 parts A and B, utilizing methyl rac-(trans)-4-methyl-1-(phenylmethyl)-3-pyrrolidinecarboxylate in place of dimethyl (cis)-1-(phenylmethyl)-3,4-pyrrolidinedicarboxylate in part A. LCMS: (M+H)+: Not detected.

Part C:

[(2R)-3-(2-{2-Chloro-5-fluoro-6-[(trans)-3-(hydroxymethyl)-4-methyl-1-pyrrolidinyl]-4-pyrimidinyl}hydrazino)-2-(cyclopentylmethyl)-3-oxopropyl]hydroxyformamide

[(2R)-3-(2-{2-Chloro-5-fluoro-6-[(trans)-3-(hydroxymethyl)-4-methyl-1-pyrrolidinyl]-4-pyrimidinyl}hydrazino)-2-(cyclopentylmethyl)-3-oxopropyl]hydroxyformamide was prepared according to General Procedure A, utilizing Rac-(trans) [(3R,4R)-4-methyl-3-pyrrolidinyl]methanol in place of pyrrolidine in Part A. The product was a mixture of diastereomers. LCMS: (M+H)$^+$: 453.3.

Example 103

[(2R)-2-(Cyclopentylmethyl)-3-(2-{5-fluoro-2-methyl-6-[(2-pyridinylmethyl)amino]-4-pyrimidinyl}hydrazino)-3-oxopropyl]hydroxyformamide

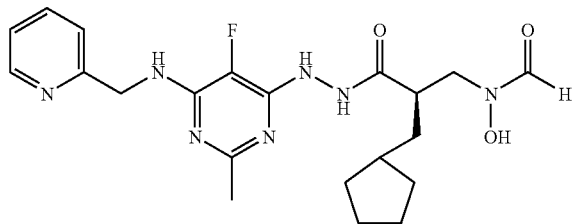

Part A:

6-Chloro-5-fluoro-2-methyl-N-(2-pyridinylmethyl)-4-pyrimidinamine 4,6-Dichloro-5-fluoro-2-methylpyrimidine (0.2 g, 1.111 mmol) was dissolved in THF (1 mL). To this solution was added triethylamine (0.17 mL, 1.22 mmol), followed by commercially available (2-pyridinylmethyl)amine (0.11 mL, 1.067 mmol), which was dissolved in THF (1 mL). The reaction was left to stir for 4 hours. The reaction mixture was diluted with water and extracted with ether. The organics were dried (MgSO$_4$) and concentrated to provide 6-chloro-5-fluoro-2-methyl-N-(2-pyridinylmethyl)-4-pyrimidinamine as a yellow wax (0.2517 g, 90%). LCMS: (M+H)$^+$=253.3.

Part B:

5-Fluoro-2-methyl-6-[(2-pyridinylmethyl)amino]-4(1H)-pyrimidinone hydrazone

6-Chloro-5-fluoro-2-methyl-N-(2-pyridinylmethyl)-4-pyrimidinamine (0.2517 g, 0.999 mmol) was dissolved in 2 mL of DMSO and 1 mL of hydrazine monohydrate. The resulting reaction mixture was stirred overnight. Then the reaction mixture was purified by RP-HPLC to provide 5-fluoro-2-methyl-6-[(2-pyridinylmethyl)amino]-4(1H)-pyrimidinone hydrazone as a beige solid (0.0954 g, 39%). LCMS: (M+H)$^+$= 249.3.

Part C:

[(2R)-2-(Cyclopentylmethyl)-3-(2-{5-fluoro-2-methyl-6-[(2-pyridinylmethyl)amino]-4-pyrimidinyl}hydrazino)-3-oxopropyl][(phenylmethyl)oxy]formamide 5-Fluoro-2-methyl-6-[(2-pyridinylmethyl)amino]-4(1H)-pyrimidinone hydrazone (0.0954 g, 0.3846 mmol) and (2R)-3-cyclopentyl-2-({formyl[(phenylmethyl)oxy]amino}methyl)propanoic acid (0.141 g, 0.4622 mmol) were dissolved in DMF (3 mL). NMM (0.13 mL, 1.1824 mmol) was added, followed by HOAt (0.063 g, 0.4632 mmol) and EDC (0.088 g, 0.459 mmol). After stirring overnight the reaction mixture was purified by RP-HPLC to provide [(2R)-2-(cyclopentylmethyl)-3-(2-{5-fluoro-2-methyl-6-[(2-pyridinylmethyl)amino]-4-pyrimidinyl}hydrazino)-3-oxopropyl][(phenylmethyl)oxy]formamide as a white solid (0.0999 g, 48%). LCMS: (M+H)$^+$=536.3.

Part D:

[(2R)-2-(Cyclopentylmethyl)-3-(2-{5-fluoro-2-methyl-6-[(2-pyridinylmethyl)amino]-4-pyrimidinyl}hydrazino)-3-oxopropyl]hydroxyformamide

[(2R)-2-(Cyclopentylmethyl)-3-(2-{5-fluoro-2-methyl-6-[(2-pyridinylmethyl)amino]-4-pyrimidinyl}hydrazino)-3-oxopropyl][(phenylmethyl)oxy]formamide (0.0999 g, 0.1867 mmol) was dissolved in 10 mL of MeOH, degassed and placed under nitrogen. Then 10% Pd(C) (0.025 g) was added and the contents were degassed and stirred under a hydrogen balloon for 2.75 h. The contents were then degassed and filtered through an Acrodisc (CR PTFE 0.45 μm). The resulting filtrate was concentrated and purified by RP-HPLC to provide [(2R)-2-(cyclopentylmethyl)-3-(2-{5-fluoro-2-methyl-6-[(2-pyridinylmethyl)amino]-4-pyrimidinyl}hydrazino)-3-oxopropyl]hydroxyformamide as a beige solid (0.0231 g, 28%). LCMS: (M+H)$^+$=446.5.

Example 104

[(2R)-2-(Cyclopentylmethyl)-3-(2-{2-ethyl-5-fluoro-6-[(8aS)-hexahydropyrrolo[1,2-a]pyrazin-2(1H)-yl]-4-pyrimidinyl}hydrazino)-3-oxopropyl]hydroxyformamide

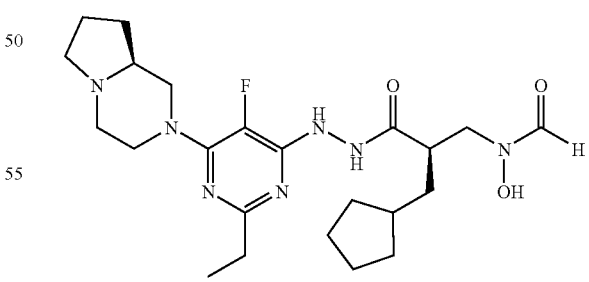

[(2R)-2-(Cyclopentylmethyl)-3-(2-{2-ethyl-5-fluoro-6-[(8aS)-hexahydropyrrolo[1,2-a]pyrazin-2(1H)-yl]-4-pyrimidinyl}hydrazino)-3-oxopropyl]hydroxyformamide was prepared according to General Procedure B, utilizing commercially-available (8aS)-octahydropyrrolo[1,2-a]pyrazine in place of azetidine and DMSO in place of MeOH in Part A.

Example 105

[(2R)-2-(Cyclopentylmethyl)-3-(2-{5-fluoro-2-methyl-6-[methyl(4-pyridinylmethyl)amino]-4-pyrimidinyl}hydrazino)-3-oxopropyl]hydroxyformamide

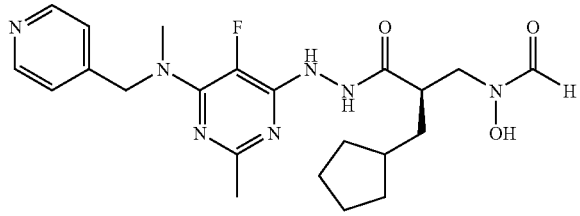

Part A:

5-Fluoro-6-hydrazino-N,2-dimethyl-N-(4-pyridinylmethyl)-4-pyrimidinamine 4,6-Dichloro-5-fluoro-2-methylpyrimidine (0.18 g, 0.99 mmol) was dissolved in DMSO (1 mL). To this solution was added triethylamine (0.15 mL, 1.08 mmol), followed by commercially available N-methyl-1-(4-pyridinyl)methanamine (0.122 g, 1.0 mmol). The reaction was left to stir for 3 hours. Then hydrazine monohydrate was added, and the resulting reaction mixture was stirred overnight at room temperature. The reaction mixture was heated to 60° C. for 90 minutes. After cooling, the reaction mixture was purified by RP-HPLC to provide 5-fluoro-6-hydrazino-N,2-dimethyl-N-(4-pyridinylmethyl)-4-pyrimidinamine (0.130 g, 49%). LCMS: $(M+H)^+=263.0$.

Part B:

[(2R)-2-(Cyclopentylmethyl)-3-(2-{5-fluoro-2-methyl-6-[methyl(4-pyridinylmethyl)amino]-4-pyrimidinyl}hydrazino)-3-oxopropyl](tetrahydro-2H-pyran-2-yloxy)formamide 5-Fluoro-6-hydrazino-N,2-dimethyl-N-(4-pyridinylmethyl)-4-pyrimidinamine (0.130 g, 0.496 mmol) and (2R)-3-cyclopentyl-2-{[formyl(tetrahydro-2H-pyran-2-yloxy)amino]methyl}propanoic acid, diisopropylamine salt, (0.238 g, 0.56 mmol) were dissolved in DMF (5 mL). NMM (0.272 mL, 2.4739 mmol) was added, followed by HOAt (0.081 g, 0.5955 mmol) and EDC (0.114 g, 0.5946 mmol). After stirring overnight, the reaction mixture was purified by RP-HPLC to provide [(2R)-2-(cyclopentylmethyl)-3-(2-{5-fluoro-2-methyl-6-[methyl (4-pyridinylmethyl)amino]-4-pyrimidinyl}hydrazino)-3-oxopropyl](tetrahydro-2H-pyran-2-yloxy)formamide as a beige solid (0.0979 g, 36%). LCMS: $(M+2H)^+=545.6$.

Part C:

[(2R)-2-(Cyclopentylmethyl)-3-(2-{5-fluoro-2-methyl-6-[methyl(4-pyridinylmethyl)amino]-4-pyrimidinyl}hydrazino)-3-oxopropyl]hydroxyformamide

[(2R)-2-(Cyclopentylmethyl)-3-(2-{5-fluoro-2-methyl-6-[methyl(4-pyridinylmethyl)amino]-4-pyrimidinyl}hydrazino)-3-oxopropyl](tetrahydro-2H-pyran-2-yloxy)formamide (0.0979 g, 0.1802 mmol) was dissolved in acetic acid (8 mL) and water (2 mL). The reaction was left to stir overnight. The volatiles were evaporated, and the resulting material was purified by RP-HPLC to provide [(2R)-2-(cyclopentylmethyl)-3-(2-{5-fluoro-2-methyl-6-[methyl(4-pyridinylmethyl)amino]-4-pyrimidinyl}hydrazino)-3-oxopropyl]hydroxyformamide as a beige solid (0.0273 g, 33%). LCMS: $(M+H)^+=460.7$.

Example 106

[(2R)-2-(Cyclopentylmethyl)-3-(2-{2-(difluoromethyl)-5-fluoro-6-[(8aS)-hexahydropyrrolo[1,2-a]pyrazin-2(1H)-yl]-4-pyrimidinyl}hydrazino)-3-oxopropyl]hydroxyformamide

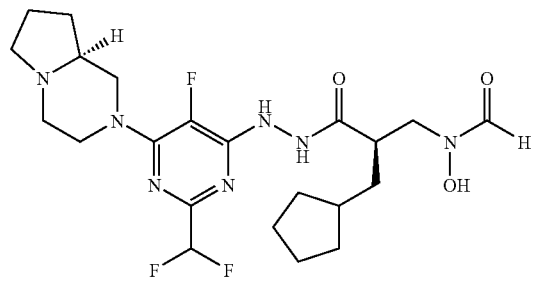

[(2R)-2-(Cyclopentylmethyl)-3-(2-{2-(difluoromethyl)-5-fluoro-6-[(8aS)-hexahydropyrrolo[1,2-a]pyrazin-2(1H)-yl]-4-pyrimidinyl}hydrazino)-3-oxopropyl]hydroxyformamide was prepared according to General Procedure H, utilizing commercially available (8aS)-octahydropyrrolo[1,2-a]pyrazine instead of N-methylpiperazine in Part A. LCMS: $(M+H)^+$: 500.3.

Example 107

N-[(2R)-2-(Cyclopentylmethyl)-3-(2-{5-fluoro-2-methyl-6-[(1,3-thiazol-2-ylmethyl)amino]-4-pyrimidinyl}hydrazino)-3-oxopropyl]-N-hydroxyformamide

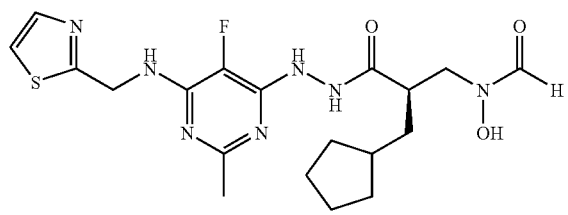

Part A:

5-Fluoro-4-hydrazino-2-methyl-6-[(1,3-thiazol-2-ylmethyl)amino]pyrimidine 4,6-Dichloro-5-fluoro-2-methylpyrimidine (180 mg, 1 mmol) was dissolved in 1 mL of DMSO and stirred at room temperature. (1,3-Thiazol-2-ylmethyl)amine (124 mg, 1.1 mmol) was added, followed by triethylamine (150 µL, 1.1 mmol). The resulting reaction mixture was stirred for 3 h, then hydrazine was added (1.0 mL), and the contents were heated to 60° C. for 1.5 h. The reaction mixture was then cooled to room temperature and purified by RP-HPLC to provide 5-fluoro-4-hydrazino-2-methyl-6-[(1,3-thiazol-2-yl-methyl)amino]pyrimidine (97 mg, 38%). LCMS: (M+H)$^+$: 255.2.

Part B:

[(2R)-2-(Cyclopentylmethyl)-3-(2-{5-fluoro-2-methyl-6-[(1,3-thiazol-2-ylmethyl)amino]-4-pyrimidinyl}hydrazino)-3-oxopropyl](tetrahydro-2H-pyran-2-yloxy)formamide 5-Fluoro-4-hydrazino-2-methyl-6-[(1,3-thiazol-2-ylmethyl)amino]pyrimidine (80 mg, 0.33 mmol), (2R)-3-cyclopentyl-2-{[formyl(tetrahydro-2H-pyran-2-yloxy)amino]methyl}propanoic acid (Hunigs base salt, 140 mg, 0.33 mmol), and HOAt (45 mg, 0.33 mmol) were dissolved in 3 mL of DMF. NMM (0.1 mL, 0.9 mmol) was added, followed by EDC (65 mg, 0.33 mmol). After stirring overnight at room temperature, the reaction mixture was purified by RP-HPLC to provide [(2R)-2-(cyclopentylmethyl)-3-(2-{5-fluoro-2-methyl-6-[(1,3-thiazol-2-ylmethyl)amino]-4-pyrimidinyl}hydrazino)-3-oxopropyl](tetrahydro-2H-pyran-2-yloxy)formamide (72 mg, 45%). LCMS: (M+H)$^+$: 536.2.

Part C:

[(2R)-2-(Cyclopentylmethyl)-3-(2-{5-fluoro-2-methyl-6-[(1,3-thiazol-2-ylmethyl)amino]-4-pyrimidinyl}hydrazino)-3-oxopropyl]hydroxyformamide

[(2R)-2-(Cyclopentylmethyl)-3-(2-{5-fluoro-2-methyl-6-[(1,3-thiazol-2-ylmethyl)amino]-4-pyrimidinyl}hydrazino)-3-oxopropyl](tetrahydro-2H-pyran-2-yloxy)formamide (67 mg, 0.13 mmol) in 4:1 AcOH:water (5 mL) was stirred at room temperature overnight. The solvents were removed in vacuo, and the resulting crude product was purified by RP-HPLC to provide [(2R)-2-(cyclopentylmethyl)-3-(2-{5-fluoro-2-methyl-6-[(1,3-thiazol-2-ylmethyl)amino]-4-pyrimidinyl}hydrazino)-3-oxopropyl]hydroxyformamide (30 mg, 51%). LCMS: (M+H)$^+$: 452.1.

Example 108

[(2R)-2-(Cyclopentylmethyl)-3-(2-{6-[(2S)-2,4-dimethyl-1-piperazinyl]-5-fluoro-2-methyl-4-pyrimidinyl}hydrazino)-3-oxopropyl]hydroxyformamide

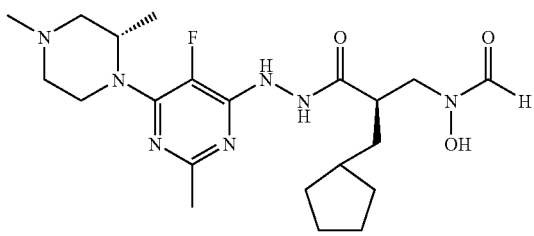

Part A:

4-Chloro-6-[(2S)-2,4-dimethyl-1-piperazinyl]-5-fluoro-2-methylpyrimidine

To 4,6-dichloro-5-fluoro-2-methylpyrimidine (0.309 g, 1.71 mmol) and triethylamine (0.83 mL, 5.98 mmol) in THF (6.0 mL) was added (3S)-1,3-dimethylpiperazine dihydrochloride (Example 64) (0.320 g, 1.71 mmol). MeOH (3 mL) was added to improve solubility and the reaction was stirred for 4 days at room temperature. The solvent was removed in vacuo, and ether, THF and water were added to the resulting residue. The organics were dried (Na$_2$SO$_4$) and concentrated in vacuo to provide 4-chloro-6-[(2S)-2,4-dimethyl-1-piperazinyl]-5-fluoro-2-methylpyrimidine as an orange solid (0.277 g, 63%). LCMS: (M+H)$^+$=259.3.

Part B:

4-[(2S)-2,4-Dimethyl-1-piperazinyl]-5-fluoro-6-hydrazino-2-methylpyrimidine

4-Chloro-6-[(2S)-2,4-dimethyl-1-piperazinyl]-5-fluoro-2-methylpyrimidine (0.277 g, 1.07 mmol), hydrazine monohydrate (0.5 mL) and DMSO (2.0 mL) were stirred at room temperature overnight. Then the reaction was heated to 50° C. and stirred for 7 hours. Purified by RP-HPLC to provide 4-[(2S)-2,4-dimethyl-1-piperazinyl]-5-fluoro-6-hydrazino-2-methylpyrimidine as an orange solid (0.118 g, 43%). LCMS: (M+H)$^+$=255.3.

Part C:

[(2R)-2-(Cyclopentylmethyl)-3-(2-{6-[(2S)-2,4-dimethyl-1-piperazinyl]-5-fluoro-2-methyl-4-pyrimidinyl}hydrazino)-3-oxopropyl][(phenylmethyl)oxy]formamide (2R)-3-Cyclopentyl-2-({formyl[(phenylmethyl)oxy]amino}methyl)propanoic acid (0.139 g, 0.45 mmol), 4-[(2S)-2,4-dimethyl-1-piperazinyl]-5-fluoro-6-hydrazino-2-methylpyrimidine (0.118 g, 0.46 mmol), NMM (0.15 mL, 1.38 mmol), HOAt (0.063 g, 0.46 mmol), and EDC (0.088 g, 0.46 mmol) were dissolved in DMF (2 mL). The reaction was stirred overnight. Purified by RP-HPLC to provide [(2R)-2-(cyclopentylmethyl)-3-(2-{6-[(2S)-2,4-dimethyl-1-piperazinyl]-5-fluoro-2-methyl-4-pyrimidinyl}hydrazino)-3-oxopropyl][(phenylmethyl)oxy]formamide as a white solid (0.118 g, 47%). LCMS: (M+H)$^+$=542.7.

Part D:

[(2R)-2-(Cyclopentylmethyl)-3-(2-{6-[(2S)-2,4-dimethyl-1-piperazinyl]-5-fluoro-2-methyl-4-pyrimidinyl}hydrazino)-3-oxopropyl]hydroxyformamide A solution of [(2R)-2-(cyclopentylmethyl)-3-(2-{6-[(2S)-2,4-dimethyl-1-piperazinyl]-5-fluoro-2-methyl-4-pyrimidinyl}hydrazino)-3-oxopropyl][(phenylmethyl)oxy]formamide (0.118 g, 0.22 mmol) and Pd(C) (0.018 g) in MeOH (10 mL) was treated as in General Procedure A, Part C, to provide [(2R)-2-(cyclopentylmethyl)-3-(2-{6-[(2S)-2,4-dimethyl-1-piperazinyl]-5-fluoro-2-methyl-4-pyrimidinyl}hydrazino)-3-oxopropyl]hydroxyformamide as a white solid (0.089 g, 91%). LCMS: (M+H)$^+$=452.4.

Example 109

[(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide

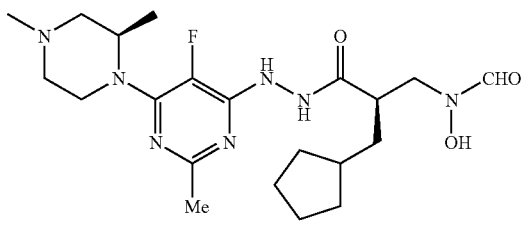

Part A:

4-Chloro-6-[(2R)-2,4-dimethyl-1-piperazinyl]-5-fluoro-2-methylpyrimidine

To a solution of (3R)-1,3-dimethylpiperazine dihydrochloride (Example 63) (5.88 g, 31.4 mmol) in dichloromethane (126 mL) was added N,N-diisopropylethylamine (18.11 mL, 104 mmol), and 4,6-dichloro-5-fluoro-2-methylpyrimidine (5.69 g, 31.4 mmol). The solution was heated at 35° C. and stirred for 3 days. The solution was cooled to room temperature, diluted with DCM (100 mL), and washed with sat. aq. NaHCO$_3$ (100 mL). The aqueous phase was extracted with a fresh portion of DCM (50 mL), and the combined organic phase was dried over anhydrous Na$_2$SO$_4$, filtered, and concentrated in vacuo to give crude 4-chloro-6-[(2R)-2,4-dimethyl-1-piperazinyl]-5-fluoro-2-methylpyrimidine (9.60 g, >100% yield) as a brown oil that was used without further purification. LCMS: (M+H)$^+$: 258.9.

Part B:

4-[(2R)-2,4-Dimethyl-1-piperazinyl]-5-fluoro-6-hydrazino-2-methylpyrimidine

To a solution of 4-chloro-6-[(2R)-2,4-dimethyl-1-piperazinyl]-5-fluoro-2-methylpyrimidine (9.6 g, assumed 31.4 mmol) in 1,4-dioxane (126 mL) was added hydrazine monohydrate (8.5 mL, 175 mmol). The mixture was heated at 85° C. and stirred for 24 h. The mixture was cooled to room temperature and then concentrated in vacuo. The residue was partitioned between DCM (200 mL) and sat. aq. NaHCO$_3$ (100 mL). The aqueous phase was extracted with a fresh portion of DCM (50 mL), and the combined organic phase was dried over anhydrous Na$_2$SO$_4$, filtered, and concentrated in vacuo to give crude 4-[(2R)-2,4-dimethyl-1-piperazinyl]-5-fluoro-6-hydrazino-2-methylpyrimidine (8.04 g, >100% crude yield) as a dark orange oil. LCMS: (M+H)$^+$: 254.9.

Part C:

[(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl][(phenylmethyl)oxy]formamide To a solution of 4-[(2R)-2,4-dimethyl-1-piperazinyl]-5-fluoro-6-hydrazino-2-methylpyrimidine (8.04 g, assumed 31.4 mmol) in N,N-dimethylformamide (125 mL) was added (2R)-3-cyclopentyl-2-({formyl[(phenylmethyl)oxy]amino}methyl)propanoic acid diisopropylethylamine salt, isopropanol solvate (15.48 g, 31.3 mmol), N-methylmorpholine (17.21 mL, 156 mmol), 1-hydroxy-7-azabenzotriazole (5.11 g, 37.6 mmol), and EDC (7.20 g, 37.6 mmol). The solution was stirred overnight, and then diluted with Et$_2$O (150 mL) and washed with water (2×100 mL). The combined aqueous phase was extracted with a fresh portion of Et$_2$O (150 mL), and this organic phase was washed with water (75 mL). The total combined aqueous phase was extracted with another fresh portion of Et$_2$O (150 mL), and this organic phase was washed with water (75 mL). The combined organic phase was diluted with DCM (100 mL), and dried over anhydrous Na$_2$SO$_4$. The mixture was filtered and concentrated in vacuo to give crude [(2R)-2-(cyclopentylmethyl)-3-(2-{6-[(2R)-2,4-dimethyl-1-piperazinyl]-5-fluoro-2-methyl-4-pyrimidinyl}hydrazino)-3-oxopropyl][(phenylmethyl)oxy]formamide (15.60 g, 28.8 mmol, 92% yield) as a light brown foam. LCMS: (M+H)$^+$: 541.7.

Part D:

[(2R)-2-(Cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide To a solution of [(2R)-2-(cyclopentylmethyl)-3-(2-{6-[(2R)-2,4-dimethyl-1-piperazinyl]-5-fluoro-2-methyl-4-pyrimidinyl}hydrazino)-3-oxopropyl][(phenylmethyl)oxy]formamide (15.60 g, 28.8 mmol) in methanol (115 mL) was added Pd/C (50% water, 3.1 g). The mixture was hydrogenated under balloon pressure for 2 h, and then filtered through a glass fiber filter. The solution was then concentrated in vacuo and azeotroped with EtOAc (100 mL). The resulting solid was triturated with 70% EtOAc in hexanes, and collected by vacuum filtration. The supernatant was concentrated in vacuo and crystallized from EtOAc-hexanes, and the solid was combined with the first crop of material. The combined solid was dried overnight under high vacuum to give [(2R)-2-(cyclopentylmethyl)-3-(2-{6-[(2R)-2,4-dimethyl-1-piperazinyl]-5-fluoro-2-methyl-4-pyrimidinyl}hydrazino)-3-oxopropyl]hydroxyformamide (8.15 g, 18.05 mmol, 62.7% yield) as a white solid. LCMS: (M+H)$^+$: 451.8.

Example 110

((2R)-2-(Cyclopentylmethyl)-3-{2-[6-[(3S,4R)-3-(dimethylamino)-4-methyl-1-pyrrolidinyl]-5-fluoro-2-(methylthio)-4-pyrimidinyl]hydrazino}-3-oxopropyl)hydroxyformamide (Mixture of Diastereomers)

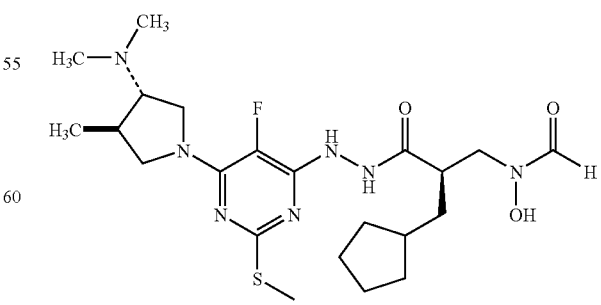

((2R)-2-(Cyclopentylmethyl)-3-{2-[6-[(3S,4R)-3-(dimethylamino)-4-methyl-1-pyrrolidinyl]-5-fluoro-2-(methylthio)-4-pyrimidinyl]hydrazino}-3-oxopropyl)hydroxyformamide was prepared as a 1:1 mixture of diastereoisomers according to General Procedure C, utilizing (trans)-N,N,4-trimethyl-3-pyrrolidinamine (Example 89) in place of azetidine hydrochloride in Part A. LCMS: (M+H)+ 498.5.

Example 111

((2R)-2-(Cyclopentylmethyl)-3-{2-[5-fluoro-6-[(8aS)-hexahydropyrrolo[1,2-a]pyrazin-2(1H)-yl]-2-(methylthio)-4-pyrimidinyl]hydrazino}-3-oxopropyl)hydroxyformamide

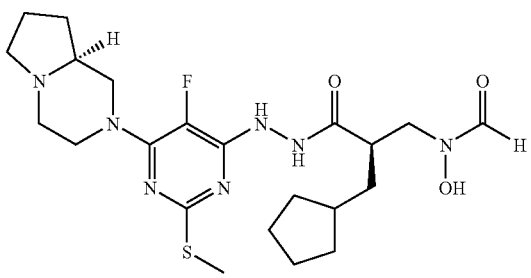

((2R)-2-(Cyclopentylmethyl)-3-{2-[5-fluoro-6-[(8aS)-hexahydropyrrolo[1,2-a]pyrazin-2(1H)-yl]-2-(methylthio)-4-pyrimidinyl]hydrazino}-3-oxopropyl)hydroxyformamide was prepared according to General Procedure C, utilizing commercially-available (8aS)-octahydropyrrolo[1,2-a]pyrazine in place of azetidine hydrochloride in Part A. LCMS: (M+H)+ 496.2.

Example 112

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (Diastereomeric Mixture)

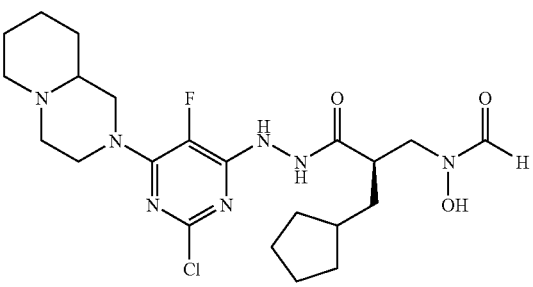

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide was prepared as a mixture of diastereomers according to General Procedure G, utilizing commercially-available (+/−)-1,4-diazabicyclo[4.4.0]decane in place of (1S,4S)-2-methyl-2,5-diazabicyclo[2.2.1]heptane, dihydrobromide in Part A, and using 1 equivalent of DIPEA. LCMS: (M+H)+: 498.3.

Example 113

[(2R)-3-(2-{6-[Syn-3,4-bis(dimethylamino)-1-pyrrolidinyl]-2-chloro-5-fluoro-4-pyrimidinyl}hydrazino)-2-(cyclopentylmethyl)-3-oxopropyl]hydroxyformamide

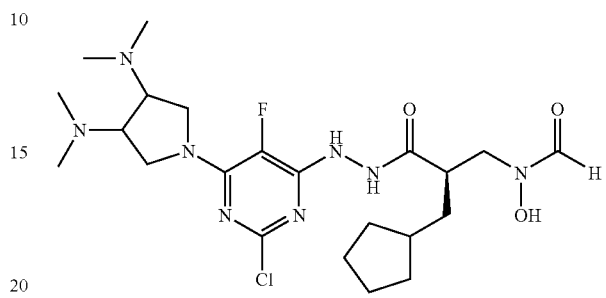

Part A:

Phenylmethyl 6-oxa-3-azabicyclo[3.1.0]hexane-3-carboxylate

To a 0° C. solution of phenylmethyl 2,5-dihydro-1H-pyrrole-1-carboxylate (10.30 g, 50.68 mmol) in DCM (250 mL) was added m-CPBA (wet; ca. 75%; 17.49 g). The solution was stirred and warmed to room temperature overnight. The solution was diluted with DCM and washed with 2×10% aq. NaHCO$_3$-1 N aq. NaOH (1:1). The organic phase was dried over anhydrous Na$_2$SO$_4$, filtered, concentrated in vacuo, and purified by silica gel chromatography (40% EtOAc in hexanes) to give phenylmethyl 6-oxa-3-azabicyclo[3.1.0]hexane-3-carboxylate (7.90 g, 71% yield) as a light yellow oil.

Part B:

Phenylmethyl syn-3,4-bis(dimethylamino)-1-pyrrolidinecarboxylate

To a solution of phenylmethyl 6-oxa-3-azabicyclo[3.1.0]hexane-3-carboxylate (1.0029 g, 4.574 mmol) in MeOH (4.6 mL) was added dimethylamine (2.0 M in THF, 4.6 mL, 9.2 mmol). The solution was heated at 140° C. under microwave irradiation for 1 h, and then cooled to room temperature. The solution was concentrated in vacuo, azeotroped with THF (40 mL), and then dissolved in THF (40 mL). To the solution was added DMAP (56 mg, 0.458 mmol), N,N-diisopropylethylamine (1.6 mL, 8.96 mmol), and MsCl (0.390 mL, 5.039 mmol). The mixture was stirred for 2 h, and then dimethylamine (2.0 M in THF, 4.6 mL, 9.2 mmol) was added. The mixture was stirred for 2 days, and then diluted with DCM (100 mL) and washed with 1 N aq. NaOH (20 mL). The organic phase was dried over anhydrous MgSO$_4$, filtered, and concentrated in vacuo. To a solution of the residue in MeOH (5 mL) was added dimethylamine (2.0 M in THF, 4.6 mL, 9.2 mmol), and the solution was heated at 140° C. for 30 min under microwave irradiation. The solution was concentrated in vacuo and purified directly by Gilson RPLC to afford racemic phenylmethyl syn-3,4-bis(dimethylamino)-1-pyrrolidinecarboxylate (911.4 mg, 68% yield) as a light yellow oil. LCMS: (M+H)+: 292.2.

Part C:

N,N,N',N'-Tetramethyl-syn-3,4-pyrrolidinediamine

To a solution of phenylmethyl syn-3,4-bis(dimethylamino)-1-pyrrolidinecarboxylate (911.4 mg, 3.128 mmol) in MeOH (30 mL) was added 10% Pd/C (50% water, 270 mg). The mixture was hydrogenated under balloon pressure for 1 h, and was then filtered and the resulting solution was concentrated in vacuo to provide crude racemic N,N,N',N'-tetramethyl-syn-3,4-pyrrolidinediamine (516.0 mg, >100% crude yield) as a bright yellow oil. LCMS: (M+H)$^+$: 158.1.

Part D:

1-(2-Chloro-5-fluoro-6-hydrazino-4-pyrimidinyl)-N,N,N',N'-tetramethyl-syn-3,4-pyrrolidinediamine To a solution of 2,4,6-trichloro-5-fluoropyrimidine (330 mg, 1.638 mmol) in DCM (5 mL) was added N,N-diisopropylethylamine (0.342 mL, 1.963 mmol) and N,N,N',N'-tetramethyl-syn-3,4-pyrrolidinediamine (257.4 mg, 1.637 mmol). The solution was stirred for 4 h at room temperature, and was then concentrated in vacuo. To a solution of the residue in MeOH (3 mL) was added hydrazine hydrate (0.5 mL). The solution was stirred and heated at 70° C. for 3 h, and was then cooled to room temperature. The solution was purified directly by Gilson RPLC (7% MeCN to 30% MeCN in water, 8 min gradient) to afford first racemic 1-(2-chloro-5-fluoro-6-hydrazino-4-pyrimidinyl)-N,N,N',N'-tetramethyl-syn-3,4-pyrrolidinediamine (118.3 mg) as an orange solid followed by racemic 4-[syn-3,4-bis(dimethylamino)-1-pyrrolidinyl]-6-chloro-5-fluoro-2(1H)-pyrimidinone hydrazone (194.6 mg, 60% combined yield for 2 steps) as an orange oil.

Part E:

[(2R)-3-(2-{6-[Syn-3,4-bis(dimethylamino)-1-pyrrolidinyl]-2-chloro-5-fluoro-4-pyrimidinyl}hydrazino)-2-(cyclopentylmethyl)-3-oxopropyl](tetrahydro-2H-pyran-2-yloxy)formamide To a solution of racemic 1-(2-chloro-5-fluoro-6-hydrazino-4-pyrimidinyl)-N,N,N',N'-tetramethyl-syn-3,4-pyrrolidinediamine (116.3 mg, 0.366 mmol) in DMF (3 mL) was added (2R)-3-cyclopentyl-2-{[formyl(tetrahydro-2H-pyran-2-yloxy)amino]methyl}propanoic acid, N,N-diisoproylethylamine salt (121.2 mg, 0.283 mmol), N-methylmorpholine (0.160 ml, 1.455 mmol), 1-hydroxy-7-azabenzotriazole (46 mg, 0.337 mmol), and EDC (65 mg, 0.339 mmol). The solution was stirred overnight and then purified directly by Gilson RPLC to afford [(2R)-3-(2-{6-[syn-3,4-bis(dimethylamino)-1-pyrrolidinyl]-2-chloro-5-fluoro-4-pyrimidinyl}hydrazino)-2-(cyclopentylmethyl)-3-oxopropyl](tetrahydro-2H-pyran-2-yloxy)formamide (133.4 mg, 78% yield) as a yellow oil. LCMS: (M+H)$^+$: 599.4.

Part F:

[(2R)-3-(2-{6-[Syn-3,4-bis(dimethylamino)-1-pyrrolidinyl]-2-chloro-5-fluoro-4-pyrimidinyl}hydrazino)-2-(cyclopentylmethyl)-3-oxopropyl]hydroxyformamide A solution of [(2R)-3-(2-{6-[syn-3,4-bis(dimethylamino)-1-pyrrolidinyl]-2-chloro-5-fluoro-4-pyrimidinyl}hydrazino)-2-(cyclopentylmethyl)-3-oxopropyl](tetrahydro-2H-pyran-2-yloxy)formamide (133.4 mg, 0.223 mmol) in 4:1 HOAc-H$_2$O (5 mL) was stirred at 30° C. for 18 h. The solution was concentrated in vacuo, and diluted with DCM (100 mL). The solution was washed with sat. aq. NaHCO$_3$ (50 mL), and the organic phase was dried over anhydrous Na$_2$SO$_4$, filtered, and concentrated in vacuo. The residue was purified by Gilson RPLC, and then crystallized from EtOAc-hexanes to provide [(2R)-3-(2-{6-[syn-3,4-bis(dimethylamino)-1-pyrrolidinyl]-2-chloro-5-fluoro-4-pyrimidinyl}hydrazino)-2-(cyclopentylmethyl)-3-oxopropyl]hydroxyformamide as a light yellow solid. LCMS: (M+H)$^+$: 515.2.

Example 114

[(2R)-2-(Cyclopentylmethyl)-3-(2-{5-fluoro-6-[(cis)-3-hydroxy-4-methyl-1-pyrrolidinyl]-2-methyl-4-pyrimidinyl}hydrazino)-3-oxopropyl]hydroxyformamide (Single Unknown Diastereomer)

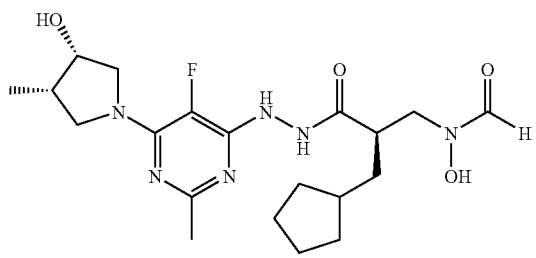

Part A:

Phenylmethyl (trans)-3-hydroxy-4-methyl-1-pyrrolidinecarboxylate

To a stirred suspension of CuI (10.2 g, 54 mmol) in ether (120 mL) at –10° C. was added dropwise MeLi (73 mL, 109 mmol, 1.5 M in ether) ensuring that the temperature remained below –5° C. The resulting solution was stirred at –10° C. for 20 min and a solution of phenylmethyl 6-oxa-3-azabicyclo[3.1.0]hexane-3-carboxylate (Example 113) (5 g, 23 mmol) in ether (50 mL) was added, maintaining the temperature below –2° C. The reaction was stirred at –10° C. for 1 hour after which time it was quenched with water and partitioned with DCM. A standard work up yielded phenylmethyl (trans)-3-hydroxy-4-methyl-1-pyrrolidinecarboxylate, which was purified and subjected to chiral chromatography, producing two enantiopure compounds of undetermined absolute stereochemistry. (Yield of E$_1$=1.55 g, yield of E$_2$=1.58 g).

Part B:

Phenylmethyl (cis)-3-methyl-4-{[(4-nitrophenyl)carbonyl]oxy}-1-pyrrolidinecarboxylate To a solution of enantiopure phenylmethyl (trans)-3-hydroxy-4-methyl-1-pyrrolidinecarboxylate (E1) (1 g, 4.25 mmol) in THF (21 mL) was added 4-nitrobenzoic acid (1.42 g, 8.5 mmol), triphenylphosphine (2.23 g, 8.5 mmol) and DIAD (1.7 mL, 8.5 mmol). The resulting solution was stirred overnight. Removal of the solvent under reduced pressure yielded the crude product which was purified by RP-HPLC yielding phenylmethyl (cis)-3-methyl-4-{[(4-nitrophenyl)carbonyl]oxy}-1-pyrrolidinecarboxylate (1.30 g, 79%). LCMS: (M+H)$^+$: 385.0 (single unknown enantiomer).

Part C:

(cis)-4-Methyl-3-pyrrolidinol

1 M NaOH (aq) (13 mL) was added dropwise to a solution of phenylmethyl (cis)-3-methyl-4-{[(4-nitrophenyl)carbonyl]oxy}-1-pyrrolidinecarboxylate (1.30 g, 3.4 mmol) in THF (13 mL) at 0° C. and the reaction was stirred overnight, allowing the ice bath to expire. Approximately half the reaction volume was removed under reduced pressure and chloroform was added. The phases were separated and the organic phase was washed with brine, dried over sodium sulfate and concentrated to yield the crude alcohol. This material was immediately dissolved in degassed MeOH and Pd/C (100 mg) was added. The reaction was stirred under a hydrogen balloon for 3.5 hours, the catalyst was removed by filtration and the solvents were removed by evaporation under reduced pressure to yield (cis)-4-methyl-3-pyrrolidinol (390 mg, quantitative yield). LCMS: (M+H)$^+$: 102.2 (single unknown enantiomer).

Part D:

[(2R)-2-(Cyclopentylmethyl)-3-(2-{5-fluoro-6-[(3S, 4S)-3-hydroxy-4-methyl-1-pyrrolidinyl]-2-methyl-4-pyrimidinyl}hydrazino)-3-oxopropyl]hydroxyformamide

[(2R)-2-(Cyclopentylmethyl)-3-(2-{5-fluoro-6-[(cis)-3-hydroxy-4-methyl-1-pyrrolidinyl]-2-methyl-4-pyrimidinyl}hydrazino)-3-oxopropyl]hydroxyformamide was prepared as a single diastereisomer (stereochemistry around the pyrrolidine ring is arbitrarily assigned) according to General Procedure A, utilizing (cis)-4-methyl-3-pyrrolidinol in place of pyrrolidine in Part A. LCMS: (M+H)$^+$: 439.2.

Example 115

[(2R)-3-(2-{2-Chloro-5-fluoro-6-[(4S)-4-hydroxy-3, 3-dimethyl-1-pyrrolidinyl]-4-pyrimidinyl}hydrazino)-2-(cyclopentylmethyl)-3-oxopropyl]hydroxyformamide

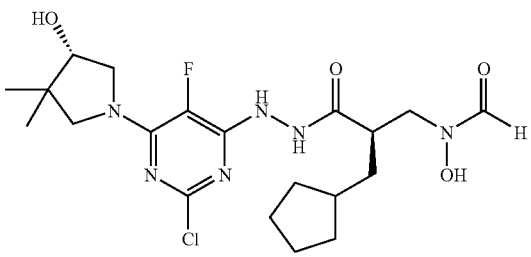

(3S)-4,4-Dimethyl-3-pyrrolidinol hydrochloride

To a solution of (3S)-4,4-dimethyl-1-(phenylmethyl)-3-pyrrolidinol (*J. Med. Chem.* 1992, 35, 4205-4213) (0.7738 g, 3.769 mmol) in MeOH (38 mL) was added 1 N aq. HCl (3.8 mL, 3.8 mmol) and 10% Pd/C (50% water, 230 mg). The mixture was hydrogenated under balloon pressure for 18 h, and was then filtered through a 0.2 μm filter tip syringe. The resulting solution was concentrated in vacuo and azeotroped with MeOH (2×50 mL) to afford (3S)-4,4-dimethyl-3-pyrrolidinol hydrochloride (0.5267 g, 93% yield) as a light orange solid. LCMS: (M+H)$^+$: 116.1.

Part B:

(3S)-1-(2-Chloro-5-fluoro-6-hydrazino-4-pyrimidinyl)-4,4-dimethyl-3-pyrrolidinol To a solution of 2,4,6-trichloro-5-fluoropyrimidine (0.3362 g, 1.669 mmol) in DCM (6 mL) was added (3S)-4, 4-dimethyl-3-pyrrolidinol hydrochloride (0.2530 g, 1.691 mmol) and N,N-diisopropylethylamine (0.640 mL, 3.674 mmol). The solution was stirred for 2 h, and was then concentrated in vacuo. To a solution of the residue in DMSO (4 mL) was added hydrazine hydrate (0.6 mL), and the solution was stirred overnight. The solution was then purified directly by Gilson RPLC to give first (3S)-1-(2-chloro-5-fluoro-6-hydrazino-4-pyrimidinyl)-4,4-dimethyl-3-pyrrolidinol (0.1464 g, 32% yield) as an orange solid, LCMS: (M+H)$^+$: 276.0, followed by 4-chloro-5-fluoro-6-[(4S)-4-hydroxy-3, 3-dimethyl-1-pyrrolidinyl]-2(1H)-pyrimidinone hydrazone (0.2149 g, 47% yield) as a light pink solid.

Part C:

[(2R)-3-(2-{2-Chloro-5-fluoro-6-[(4S)-4-hydroxy-3, 3-dimethyl-1-pyrrolidinyl]-4-pyrimidinyl}hydrazino)-2-(cyclopentylmethyl)-3-oxopropyl](tetrahydro-2H-pyran-2-yloxy)formamide To a solution of (3S)-1-(2-chloro-5-fluoro-6-hydrazino-4-pyrimidinyl)-4,4-dimethyl-3-pyrrolidinol (0.131 g, 0.475 mmol) in DMF (3 mL) was added added (2R)-3-cyclopentyl-2-{[formyl(tetrahydro-2H-pyran-2-yloxy)amino]methyl}propanoic acid (0.1181 g, 0.395 mmol), N-methylmorpholine (0.220 ml, 2.001 mmol), 1-hydroxy-7-azabenzotriazole (64 mg, 0.470 mmol), and EDC (91 mg, 0.475 mmol). The solution was stirred overnight and then purified directly by Gilson RPLC to afford [(2R)-3-(2-{2-chloro-5-fluoro-6-[(4S)-4-hydroxy-3,3-dimethyl-1-pyrrolidinyl]-4-pyrimidinyl}hydrazino)-2-(cyclopentylmethyl)-3-oxopropyl](tetrahydro-2H-pyran-2-yloxy)formamide (0.1294 g, 59% yield) as an orange oil. LCMS: (M+H)$^+$: 557.3.

Part D:

[(2R)-3-(2-{2-Chloro-5-fluoro-6-[(4S)-4-hydroxy-3, 3-dimethyl-1-pyrrolidinyl]-4-pyrimidinyl}hydrazino)-2-(cyclopentylmethyl)-3-oxopropyl]hydroxyformamide A solution of [(2R)-3-(2-{2-chloro-5-fluoro-6-[(4S)-4-hydroxy-3,3-dimethyl-1-pyrrolidinyl]-4-pyrimidinyl}hydrazino)-2-(cyclopentylmethyl)-3-oxopropyl](tetrahydro-2H-pyran-2-yloxy)formamide (0.1294 g, 0.232 mmol) in 4:1 HOAc-water (5 mL) was heated at 30° C. and stirred overnight. The solution was cooled to room temperature, concentrated in vacuo, and purified directly by Gilson RPLC to give [(2R)-3-(2-{2-chloro-5-fluoro-6-[(4S)-4-hydroxy-3,3-dimethyl-1-pyrrolidinyl]-4-pyrimidinyl}hydrazino)-2-(cyclopentylmethyl)-3-oxopropyl]hydroxyformamide (69.1 mg, 63% yield) as a yellow solid. LCMS: (M+H)$^+$: 473.2.

Example 116

[(2R)-2-(Cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl]hydroxyformamide

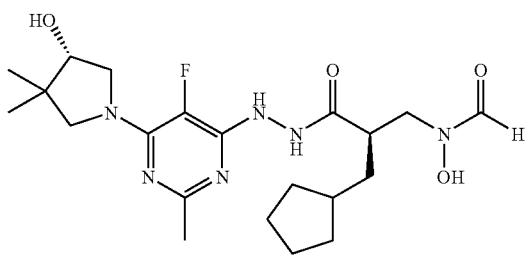

Part A:

(3S)-1-(5-Fluoro-6-hydrazino-2-methyl-4-pyrimidinyl)-4,4-dimethyl-3-pyrrolidinol To a solution of (3S)-4,4-dimethyl-3-pyrrolidinol hydrochloride (Example 115) (0.1370 g, 0.916 mmol) in MeOH (3 mL) was added 4,6-dichloro-5-fluoro-2-methylpyrimidine (0.1646 g, 0.909 mmol) and N,N-diisopropylethylamine (0.350 mL, 2.009 mmol). The solution was heated at 120° C. under microwave irradiation for 30 min, and then concentrated in vacuo. To a solution of the residue in DMSO (3 mL) was added hydrazine hydrate (0.5 mL), and the solution was heated at 50° C. and stirred for 24 h. The solution was then purified directly by Gilson RPLC to provide (3S)-1-(5-fluoro-6-hydrazino-2-methyl-4-pyrimidinyl)-4,4-dimethyl-3-pyrrolidinol (0.1560 g, 67% yield) as a light yellow foam. LCMS: (M+H)+: 256.2.

Part B:

[(2R)-2-(Cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl][(phenylmethyl)oxy]formamide To a solution of (3S)-1-(5-fluoro-6-hydrazino-2-methyl-4-pyrimidinyl)-4,4-dimethyl-3-pyrrolidinol (0.125 g, 0.490 mmol) in DMF (3 mL) was added (2R)-3-cyclopentyl-2-({formyl[(phenylmethyl)oxy]amino}methyl)propanoic acid (0.1246 g, 0.408 mmol), N-methylmorpholine (0.225 ml, 2.046 mmol), 1-hydroxy-7-azabenzotriazole (67 mg, 0.492 mmol), and EDC (94 mg, 0.490 mmol). The mixture was stirred overnight and then purified directly by Gilson RPLC to give [(2R)-2-(cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl][(phenylmethyl)oxy]formamide (0.1606 g, 73% yield) as a purple oil. LCMS: (M+H)+: 543.3.

Part C:

[(2R)-2-(Cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl]hydroxyformamide To a solution of [(2R)-2-(cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl][(phenylmethyl)oxy]formamide (0.1606 g, 0.296 mmol) in MeOH (5 mL) was added 10% Pd/C (50% water, 48 mg). The mixture was hydrogenated under balloon pressure for 1 h, and was then filtered. The solution was concentrated in vacuo and the residue was crystallized from EtOAc-hexanes to afford [(2R)-2-(cyclopentylmethyl)-3-(2-{5-fluoro-6-[(4S)-4-hydroxy-3,3-dimethyl-1-pyrrolidinyl]-2-methyl-4-pyrimidinyl}hydrazino)-3-oxopropyl]hydroxyformamide (0.1205 g, 90% yield) as a light pink solid. LCMS: (M+H)+: 453.3.

Example 117

((2R)-2-(Cyclopentylmethyl)-3-{2-[6-[(2R)-2,4-dimethyl-1-piperazinyl]-5-fluoro-2-(fluoromethyl)-4-pyrimidinyl]hydrazino}-3-oxopropyl)hydroxyformamide

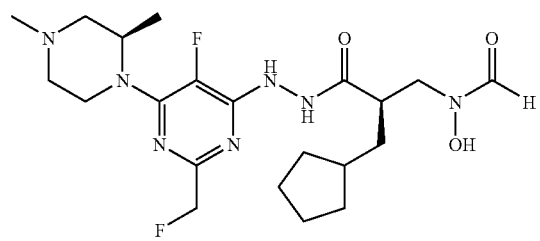

((2R)-2-(Cyclopentylmethyl)-3-{2-[6-[(2R)-2,4-dimethyl-1-piperazinyl]-5-fluoro-2-(fluoromethyl)-4-pyrimidinyl]hydrazino}-3-oxopropyl)hydroxyformamide was prepared according to General Procedure A, utilizing (3R)-1,3-dimethylpiperazine, dihydrochloride (Example 63) in place of pyrrolidine, and 4,6-dichloro-5-fluoro-2-(fluoromethyl) pyrimidine in place of 4,6-dichloro-5-fluoro-2-methylpyrimidine in Part A. LCMS: (M+H)+: 470.2.

Example 118

[(2R)-3-(2-{2-Chloro-6-[(3R)-3-(dimethylamino)-1-piperidinyl]-5-fluoro-4-pyrimidinyl}hydrazino)-2-(cyclopentylmethyl)-3-oxopropyl]hydroxyformamide

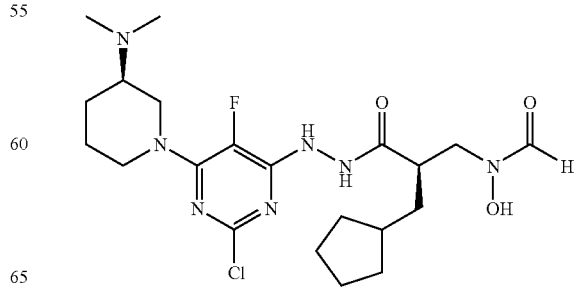

Part A:

(3R)—N,N-Dimethyl-3-piperidinamine a) Commercially-available (R)-tert-butyl 3-aminopiperidine-1-carboxylate, hydrochloride salt (5.0 g, 21.1 mmol), sodium triacetoxyborohydride (11.2 g, 52.8 mmol), and formaldehyde (37% in $H_2O$, 0.5 mL, 63.4 mmol) were dissolved and stirred in $CH_2Cl_2$ at 0° C. The reaction mixture was allowed to warm to room temperature and stirred for 3 h. After this time, the reaction mixture was diluted with additional $CH_2Cl_2$ (200 mL) and was washed with 1N NaOH (100 mL). The organic layer was separated, dried ($Na_2SO_4$), and evaporated to provide 1,1-dimethylethyl (3R)-3-(dimethylamino)-1-piperidinecarboxylate (5.0 g).

b) 1,1-Dimethylethyl (3R)-3-(dimethylamino)-1-piperidinecarboxylate (5.0 g crude, 21.12 assumed mmol) was dissolved and stirred in a mixture of $CH_2Cl_2$ (10 mL) and 4M HCl in dioxane (21 mL, 4 eqv.) A white precipitate formed. The reaction appeared to stall at approximately 70% completion, and therefore another 21 mL of 4M HCl in dioxane was added to the reaction mixture. After 4 h at room temperature, the solvent was evaporated, providing (3R)—N,N-dimethyl-3-piperidinamine, dihydrochloride as a white solid (3.5 g, 89% for two steps).

Part B:

[(2R)-3-(2-{2-Chloro-6-[(3R)-3-(dimethylamino)-1-piperidinyl]-5-fluoro-4-pyrimidinyl}hydrazino)-2-(cyclopentylmethyl)-3-oxopropyl]hydroxyformamide

[(2R)-3-(2-{2-Chloro-6-[(3R)-3-(dimethylamino)-1-piperidinyl]-5-fluoro-4-pyrimidinyl}hydrazino)-2-(cyclopentylmethyl)-3-oxopropyl]hydroxyformamide was prepared according to General Procedure D, utilizing (3R)—N,N-dimethyl-3-piperidinamine, dihydrochloride in place of N-methylpiperazine, and using 2 equivalents of DIPEA in Part A. LCMS: $(M+H)^+$: 486.3.

Example 119

N-[(2R)-3-[2-(6-{[(2-Amino-1,3-thiazol-4-yl)methyl](methyl)amino}-5-fluoro-2-methyl-4-pyrimidinyl)hydrazino]-2-(cyclopentylmethyl)-3-oxopropyl]-N-hydroxyformamide

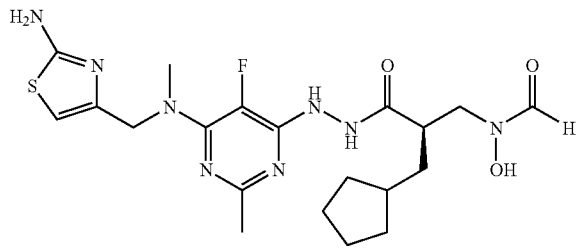

Part A:

4-[(Methylamino)methyl]-1,3-thiazol-2-amine 4-(Chloromethyl)-1,3-thiazol-2-amine (490 mg, 2.65 mmol) was stirred in 40% aqueous methylamine (25 ml) overnight. The reaction mixture was evaporated. The residue was diluted with 95:5 dichloromethane/methanol (25 ml), was dried over sodium sulfate, was filtered and was evaporated to provide 4-[(methylamino)methyl]-1,3-thiazol-2-amine that was used without purification. LCMS: $(M+H)^+$: 144.0.

Part B:

N-[(2-Amino-1,3-thiazol-4-yl)methyl]-6-chloro-5-fluoro-2-methyl-4-pyrimidinamine 4,6-Dichloro-5-fluoro-2-methylpyrimidine (480 mg, 2.65 mmol) was dissolved in 20 mL of THF and stirred at room temperature. (4-[(Methylamino)methyl]-1,3-thiazol-2-amine (2.65 mmol, theoretical) was added, followed by triethylamine (400 µL, 2.92 mmol). The resulting reaction mixture was stirred overnight and evaporated. The residue was stirred in water and the solid precipitate was collected by filtration and was dried in vacuo to provide N-[(2-amino-1,3-thiazol-4-yl)methyl]-6-chloro-5-fluoro-2-methyl-4-pyrimidinamine (450 mg, 59%) that was used without further purification. LCMS: $(M+H)^+$: 288.1.

Part C:

6-{[(2-Amino-1,3-thiazol-4-yl)methyl]amino}-5-fluoro-4-hydrazino-2-methylpyrimidine N-[(2-Amino-1,3-thiazol-4-yl)methyl]-6-chloro-5-fluoro-2-methyl-4-pyrimidinamine (450 mg, 1.56 mmol) was dissolved in 5 ml of DMSO and 5 ml of hydrazine monohydrate was added. The mixture was stirred overnight and was purified by RP-HPLC to provide 6-{[(2-amino-1,3-thiazol-4-yl)methyl]amino}-5-fluoro-4-hydrazino-2-methylpyrimidine (125 mg, 28%). LCMS: $(M+H)^+$: 284.1.

Part D:

[(2R)-3-[2-(6-{[(2-Amino-1,3-thiazol-4-yl)methyl]amino}-5-fluoro-2-methyl-4-pyrimidinyl)hydrazino]-2-(cyclopentylmethyl)-3-oxopropyl](tetrahydro-2H-pyran-2-yloxy)formamide 6-{[(2-Amino-1,3-thiazol-4-yl)methyl]amino}-5-fluoro-4-hydrazino-2-methylpyrimidine (125 mg, 0.44 mmol), (2R)-3-cyclopentyl-2-{[formyl(tetrahydro-2H-pyran-2-yloxy)amino]methyl}propanoic acid (130 mg, 0.44 mmol), and HOAt (65 mg, 0.48 mmol) were dissolved in 4 mL of DMF. NMM (0.15 mL, 1.32 mmol) was added, followed by EDC (96 mg, 0.48 mmol). After stirring overnight at room temperature, the reaction mixture was purified by RP-HPLC to provide [(2R)-3-[2-(6-{[(2-amino-1,3-thiazol-4-yl)methyl]amino}-5-fluoro-2-methyl-4-pyrimidinyl)hydrazino]-2-(cyclopentylmethyl)-3-oxopropyl](tetrahydro-2H-pyran-2-yloxy)formamide (114 mg, 46%). LCMS: $(M+H)^+$: 565.3.

Part E:

[(2R)-3-[2-(6-{[(2-Amino-1,3-thiazol-4-yl)methyl]amino}-5-fluoro-2-methyl-4-pyrimidinyl)hydrazino]-2-(cyclopentylmethyl)-3-oxopropyl]hydroxyformamide

[(2R)-3-[2-(6-{[(2-Amino-1,3-thiazol-4-yl)methyl]amino}-5-fluoro-2-methyl-4-pyrimidinyl)hydrazino]-2-(cyclopentylmethyl)-3-oxopropyl](tetrahydro-2H-pyran-2-yloxy)formamide (114 mg, 0.2 mmol) in 4:1 AcOH:water (5 mL) was stirred at room temperature overnight. The solvents were removed in vacuo, and the resulting crude product was purified by RP-HPLC to provide [(2R)-3-[2-(6-{[(2-amino-1,3-thiazol-4-yl)methyl]amino}-5-fluoro-2-methyl-4-pyrimidinyl)hydrazino]-2-(cyclopentylmethyl)-3-oxopropyl]hydroxyformamide (18 mg, 18%). LCMS: (M+H)+: 481.2.

Example 120

[(2R)-2-(Cyclopentylmethyl)-3-(2-{6-[(cis)-3-(dimethylamino)-4-methyl-1-pyrrolidinyl]-2-ethyl-5-fluoro-4-pyrimidinyl}hydrazino)-3-oxopropyl]hydroxyformamide (Single Unknown Diastereomer)

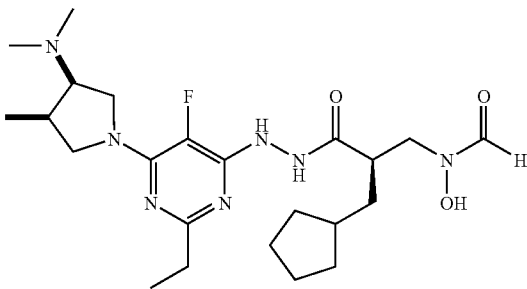

Part A:

(trans)-4-Methyl-3-pyrrolidinol

Phenylmethyl (trans)-3-hydroxy-4-methyl-1-pyrrolidinecarboxylate (E1, Example 114, Part A) (100 mg, 0.43 mmol) and 10% Pd/C (20 mg) were suspended in methanol (7 mL) and stirred under a hydrogen balloon for 19 h. Filtration of the catalyst and evaporation of the solvent provided (trans)-4-methyl-3-pyrrolidinol (single unknown enantiomer).

Part B:

1,1-Dimethylethyl (trans)-3-{[(4-chlorophenyl)sulfonyl]oxy}-4-methyl-1-pyrrolidinecarboxylate To a solution of (trans)-4-methyl-3-pyrrolidinol (single unknown enantiomer) (707 mg, 7 mmol) in a mixture of MeOH (10 mL), DCM (10 mL) and saturated aqueous potassium carbonate (20 mL) was added di-tert-butyl-dicarbonate (1.84 g, 8.42 mmol), and the resulting solution was stirred overnight. Water was added followed by chloroform and the phases were separated. The organic layer was washed with brine, dried over sodium sulfate, filtered and evaporated in vacuo to yield the crude Boc-protected alcohol (1.37 g). This was immediately dissolved in pyridine (10 mL) and p-toluenesulfonyl chloride (2.1 g, 11 mmol) was added. The reaction was stirred overnight, cooled to 0° C. and 1 M HCl was added. After stirring for 10 min at reduced temperature chloroform was added and the phases were separated. The aqueous phase was extracted twice with chloroform, and the combined organics were washed with brine, dried over sodium sulfate, filtered and concentrated in vacuo. This yielded 1,1-dimethylethyl (trans)-3-{[(4-chlorophenyl)sulfonyl]oxy}-4-methyl-1-pyrrolidinecarboxylate. LCMS: (M+Na)+: 378.1 (single unknown enantiomer).

Part C:

1,1-Dimethylethyl (cis)-3-amino-4-methyl-1-pyrrolidinecarboxylate

To a stirred solution of 1,1-dimethylethyl (trans)-3-{[(4-chlorophenyl)sulfonyl]oxy}-4-methyl-1-pyrrolidinecarboxylate 2.3 g, 6.5 mmol) in DMF (23 mL) was added NaN3 (4.2 g, 65 mmol). The resulting solution was stirred at 60° C. until LCMS showed the reaction to be complete. Upon cooling to r.t., the reaction was filtered to remove an insoluble precipitate and the solvent was removed in vacuo. The residual material was dissolved in EtOAc, washed with water, dried over sodium sulfate and concentrated in vacuo yielding 1.26 g of the crude intermediate. This crude azide was immediately dissolved in degassed MeOH (20 mL) and 10% Pd/C was added (126 mg). The resulting suspension was stirred under a hydrogen balloon overnight, after which time the catalyst was removed by filtration and the solvent was evaporated under reduced pressure. This yielded 1,1-dimethylethyl (cis)-3-amino-4-methyl-1-pyrrolidinecarboxylate (1.02 g, 70%). LCMS: (M−tBut)+: 145.1 (single unknown enantiomer).

Part D:

(cis)-N,N,4-Trimethyl-3-pyrrolidinamine.HCl 1,1-Dimethylethyl (cis)-3-amino-4-methyl-1-pyrrolidinecarboxylate (1.0 g, 5.0 mmol) was dissolved in THF (25 mL) and formaldehyde (4.1 mL, 50 mmol, 37% in water) was added. The resulting mixture was stirred for 40 min and sodium triacetoxyborohydride (14.8 g, 50.0 mmol) was added. The reaction was stirred for 72 hours and then quenched by the addition of 1 M NaOH (aq). Ether was added and the phases were separated. The combined organics were dried over sodium sulfate, filtered and evaporated to provide the intermediate dimethylated amine (1.65 g). This was dissolved in HCl (10 mL, 40 mmol, 4M in dioxane) and stirred overnight. Evaporation of the solvent and excess acid yielded (cis)-N,N,4-trimethyl-3-pyrrolidinamine.HCl (1.42 g). (Single Unknown Enantiomer)

Part E:

[(2R)-2-(Cyclopentylmethyl)-3-(2-{6-[(3R,4R)-3-(dimethylamino)-4-methyl-1-pyrrolidinyl]-2-ethyl-5-fluoro-4-pyrimidinyl}hydrazino)-3-oxopropyl]hydroxyformamide was prepared as a single unknown diastereisomer according to General Procedure B, utilizing (cis)-N,N,4-trimethyl-3-pyrrolidinamine.HCl in place of azetidine in Part A. LCMS: (M+H)+: 480.3.

Example 121

((2R)-2-(Cyclopentylmethyl)-3-{2-[6-[(3S)-3,4-dimethyl-1-piperazinyl]-5-fluoro-2-(methylthio)-4-pyrimidinyl]hydrazino}-3-oxopropyl)hydroxyformamide

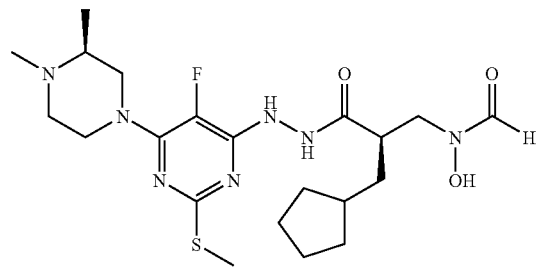

((2R)-2-(Cyclopentylmethyl)-3-{2-[6-[(3S)-3,4-dimethyl-1-piperazinyl]-5-fluoro-2-(methylthio)-4-pyrimidinyl]

hydrazino}-3-oxopropyl)hydroxyformamide was prepared according to General Procedure C, utilizing (2S)-1,2-dimethylpiperazine (Example 40) in place of azetidine hydrochloride in Part A. LCMS: (M+H)+ 484.4.

Example 122

[(2R)-3-(2-{2-Chloro-6-[(cis)-3-(dimethylamino)-4-methyl-1-pyrrolidinyl]-5-fluoro-4-pyrimidinyl}hydrazino)-2-(cyclopentylmethyl)-3-oxopropyl]hydroxyformamide (Single Unknown Diastereomer)

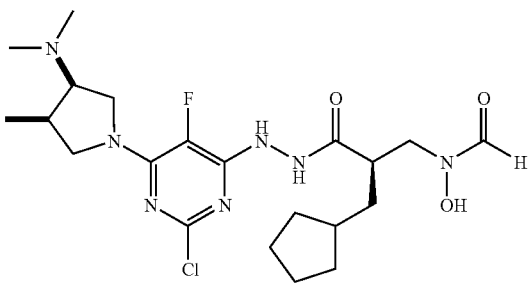

[(2R)-3-(2-{2-Chloro-6-[(cis)-3-(dimethylamino)-4-methyl-1-pyrrolidinyl]-5-fluoro-4-pyrimidinyl}hydrazino)-2-(cyclopentylmethyl)-3-oxopropyl]hydroxyformamide was prepared as a single unknown diastereisomer according to General Procedure D, utilizing enantiopure (cis)-N,N,4-trimethyl-3-pyrrolidinamine (Example 120) in place of N-methylpiperazine in Part A. LCMS: (M+H)+: 486.1/483.3.

Example 123

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (Single Unknown Diastereomer)

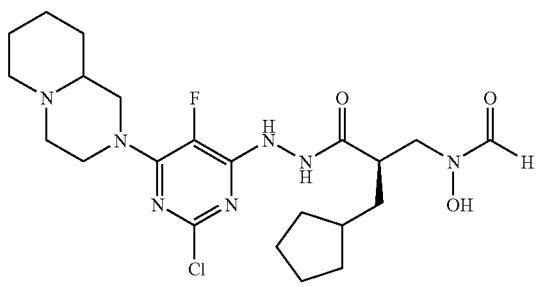

Part A:

[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 1)

[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (diastereomeric mixture) was prepared according to Part A and Part B of General Procedure G, utilizing commercially-available (+/−)-1,4-diazabicyclo[4.4.0]decane in place of (1S,4S)-2-methyl-2,5-diazabicyclo[2.2.1]heptane, dihydrobromide in Part A. [(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 1) was separated by chiral chromatography (Chiralpak AD-H 21.2× 250 mm). LCMS: (M+H)+: 588.3.

Part B:

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (Single Unknown Diastereomer)

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (single unknown diastereomer) was prepared according to Part C of General Procedure G, utilizing [(2R)-3-{2-[2-chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 1) in place of [(2R)-3-(2-{2-chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl][(phenylmethyl)oxy]formamide in Part C. LCMS: (M+H)+: 498.3.

Example 124

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (Single Unknown Diastereomer)

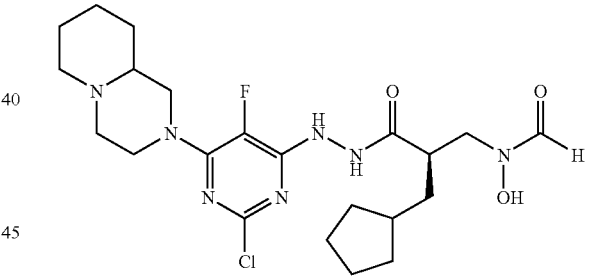

Part A:

[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 2)

[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (diastereomeric mixture) was prepared according to Part A and Part B General Procedure G, utilizing commercially-available (+/−)-1,4-diazabicyclo[4.4.0]decane in place of (1S,4S)-2-methyl-2,5-diazabicyclo[2.2.1]heptane, dihydrobromide in Part A. [(2R)-3-{2-[2-chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 2) was separated by chiral chromatography (Chiralpak AD-H 21.2× 250 mm). LCMS: (M+H)+: 588.3.

Part B:

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (Single Unknown Diastereomer)

N-[(2R)-3-{2-[2-Chloro-5-fluoro-6-(octahydro-2H-pyrido[1,2-a]pyrazin-2-yl)-4-pyrimidinyl]hydrazino}-2-(cyclopentylmethyl)-3-oxopropyl]-N-hydroxyformamide (single unknown diastereomer) was prepared according to Part C of General Procedure G, utilizing [(2R)-3-{2-[2-chloro-5-fluoro-6-(octahydro-2H-pyrido[1,2-a]pyrazin-2-yl)-4-pyrimidinyl]hydrazino}-2-(cyclopentylmethyl)-3-oxopropyl][(phenylmethyl)oxy]formamide (Diastereomer 2) in place of [(2R)-3-(2-{2-chloro-5-fluoro-6-[(1S,4S)-5-methyl-2,5-diazabicyclo[2.2.1]hept-2-yl]-4-pyrimidinyl}hydrazino)-2-(cyclopentylmethyl)-3-oxopropyl][(phenylmethyl)oxy]formamide in Part C. LCMS: (M+H)$^+$: 498.3.

Example 125

((2R)-2-(Cyclopentylmethyl)-3-{2-[6-[(3R)-3,4-dimethyl-1-piperazinyl]-5-fluoro-2-(methylthio)-4-pyrimidinyl]hydrazino}-3-oxopropyl)hydroxyformamide

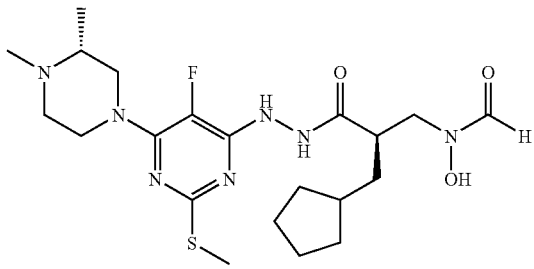

((2R)-2-(Cyclopentylmethyl)-3-{2-[6-[(3R)-3,4-dimethyl-1-piperazinyl]-5-fluoro-2-(methylthio)-4-pyrimidinyl]hydrazino}-3-oxopropyl)hydroxyformamide was prepared according to General Procedure C, utilizing (2R)-1,2-dimethylpiperazine (Example 39) in place of azetidine hydrochloride in Part A. LCMS: (M+H)$^+$ 484.5.

Example 126

((2R)-2-(Cyclopentylmethyl)-3-{2-[6-[(2S)-2,4-dimethyl-1-piperazinyl]-5-fluoro-2-(fluoromethyl)-4-pyrimidinyl]hydrazino}-3-oxopropyl)hydroxyformamide

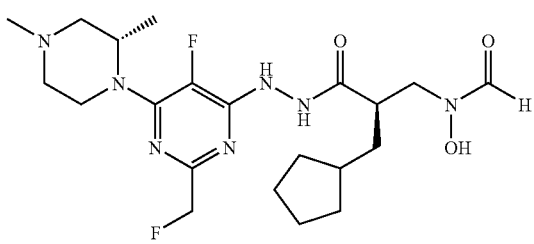

((2R)-2-(Cyclopentylmethyl)-3-{2-[6-[(2S)-2,4-dimethyl-1-piperazinyl]-5-fluoro-2-(fluoromethyl)-4-pyrimidinyl]hydrazino}-3-oxopropyl)hydroxyformamide was prepared according to General Procedure A, utilizing (3S)-1,3-dimethylpiperazine, dihydrochloride (Example 40) in place of pyrrolidine, and 4,6-dichloro-5-fluoro-2-(fluoromethyl)pyrimidine in place of 4,6-dichloro-5-fluoro-2-methylpyrimidine in Part A. LCMS: (M+H)$^+$: 470.2.

Example 127

[(2R)-3-{2-[2-Chloro-6-(cyclopropylamino)-5-fluoro-4-pyrimidinyl]hydrazino}-2-(cyclopentylmethyl)-3-oxopropyl]hydroxyformamide

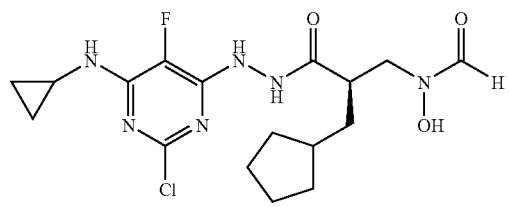

[(2R)-3-{2-[2-Chloro-6-(cyclopropylamino)-5-fluoro-4-pyrimidinyl]hydrazino}-2-(cyclopentylmethyl)-3-oxopropyl]hydroxyformamide was prepared according to General Procedure D, utilizing commercially-available cyclopropylamine in place of N-methylpiperazine in Part A. LCMS: (M+H)$^+$: 415.2.

Example 128

((2R)-2-(Cyclopentylmethyl)-3-{2-[5-fluoro-6-(7-hydroxy-5-azaspiro[2.4]hept-5-yl)-2-methyl-4-pyrimidinyl]hydrazino}-3-oxopropyl)hydroxyformamide

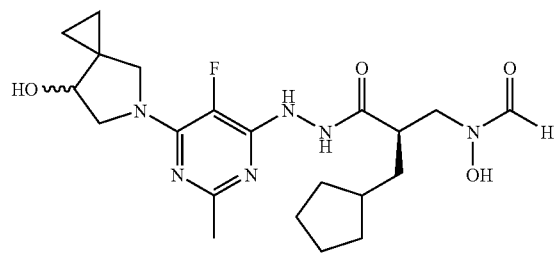

Part A:

Ethyl 1-acetylcyclopropanecarboxylate

To a stirred solution of ethyl 3-oxobutanoate (10 mL, 78.45 mmol) and 1,2-dibromoethane (6.5 mL, 78.45 mmol) in 150 mL of DMF was added potassium carbonate (22.7 g, 164.74 mmol). The resulting reaction mixture was stirred at room temperature for 2 days. The solution was diluted with 300 mL of water. The product was extracted into diethyl ether (2×200 mL), and the combined organic extracts were washed with water (1×1000 mL), and dried (MgSO$_4$). Filtration and atmospheric distillation of the ether provided the crude product, which was distilled under reduced pressure (10 mBar) to provide ethyl 1-acetylcyclopropanecarboxylate (6.4273 g, 52%). LCMS: (M+H)$^+$: not detected.

Part B:

5-(Phenylmethyl)-5-azaspiro[2.4]heptane-4,7-dione

Ethyl 1-acetylcyclopropanecarboxylate (6.4273 g, 41.153 mmol) was dissolved in 46 mL of EtOH. Bromine (2.32 mL, 45.2683 mmol) was slowly added to the solution. The resulting reaction mixture was stirred for 2 h, then concentrated in vacuo. The crude residue was dissolved in 46 mL of EtOH and the mixture was cooled to 0° C. with an ice water bath. To this solution was slowly added benzyl amine (11.2 mL 102.8825 mmol) and the reaction mixture was stirred at room temperature overnight, then concentrated in vacuo to dryness. The residue was dissolved in $CH_2Cl_2$ (200 mL) and 1N aq HCl (100 mL). The phases were separated, and the aqueous phase was extracted with $CH_2Cl_2$ (100 mL), the combined organic phase was dried over anhydrous $MgSO_4$, filtered, and concentrated in vacuo. Purification by chromatography on silica gel using an eluting system of hexane/EtOAc (60:40) provided 5-(phenylmethyl)-5-azaspiro[2.4]heptane-4,7-dione (2.4283 g 27%) as an orange solid. LCMS: $(M+H)^+$: not detected.

Part C:

5-(Phenylmethyl)-5-azaspiro[2.4]heptan-7-ol 5-(Phenylmethyl)-5-azaspiro[2.4]heptane-4,7-dione (997.4 mg, 4.63 mmol) was dissolved in 46 mL of THF and $LiAlH_4$ (997 mg) was added portion wise with stirring. The mixture was heated to 65° C. for 5 hours, then cooled to 0° C. The reaction was quenched with $Na_2SO_4.H_2O$ and was stirred at room temperature overnight. The contents were filtered through Celite, and the Celite pad was washed with EtOAc. The Celite filter cake was suspended in EtOAc (200 mL) and boiled for 5 min. The suspension was filtered, and the combined organic filtrates were then concentrated in vacuo to provide 5-(phenylmethyl)-5-azaspiro[2.4]heptan-7-ol (983 mg, >100%). LCMS: $(M+H)^+$: 204.1

Part D:

5-Azaspiro[2.4]heptan-7-ol hydrochloride 5-(Phenylmethyl)-5-azaspiro[2.4]heptan-7-ol (assumed 941.9 mg, 4.63 mmol) was dissolved in a solution of 4.6 mL of 1N aq HCl in 40 mL of MeOH, degassed and placed under argon. 10% Pd/C (280 mg) was added, and the contents were thoroughly degassed and placed under a hydrogen balloon overnight. The contents were then degassed and filtered through Celite, and the Celite pad was washed with MeOH. The resulting filtrate was concentrated in vacuo and azeotroped with MeOH (3×40 mL) to provide the pure 5-azaspiro[2.4]heptan-7-ol hydrochloride (685 mg, 99%). LCMS: $(M+H)^+$: not detected.

Part E:

5-(5-Fluoro-6-hydrazino-2-methyl-4-pyrimidinyl)-5-azaspiro[2.4]heptan-7-ol 4,6-Dichloro-5-fluoro-2-methylpyrimidine (110 mg, 0.636 mmol) was dissolved in 3 mL of MeOH then added 5-azaspiro[2.4]heptan-7-ol hydrochloride (685 mg, 0.668 mmol) was added, followed by DIPEA (243 µL, 1.4 mmol). The resulting reaction mixture was microwaved at 120° C. for 30 min, the voliailes were concentrated in vacuo, and the residue was dissolved in a mixture of DMSO (4 mL) and MeOH (1 mL). Then hydrazine monohydrate was added (600 µL), and the contents were heated to 60° C. overnight. The reaction mixture was then cooled to room temperature and purified by RP-HPLC to provide 5-(5-fluoro-6-hydrazino-2-methyl-4-pyrimidinyl)-5-azaspiro[2.4]heptan-7-ol (82 mg, 51%). LCMS: $(M+H)^+$: 254.

Part F:

((2R)-2-(Cyclopentylmethyl)-3-{2-[5-fluoro-6-(7-hydroxy-5-azaspiro[2.4]hept-5-yl)-2-methyl-4-pyrimidinyl]hydrazino}-3-oxopropyl)(tetrahydro-2H-pyran-2-yloxy)formamide 5-(5-Fluoro-6-hydrazino-2-methyl-4-pyrimidinyl)-5-azaspiro[2.4]heptan-7-ol (82 mg, 0.324 mmol), (2R)-3-cyclopentyl-2-{[formyl(tetrahydro-2H-pyran-2-yloxy)amino]methyl}propanoic acid (115 mg, 0.27 mmol), and HOAt (44 mg, 0.324 mmol) were dissolved in 2 mL of DMF. NMM (0.089 mL, 0.81 mmol) was added, followed by EDC (62 mg, 0.324 mmol). After stirring overnight at room temperature, the reaction mixture was purified by RP-HPLC to provide [(2R)-2-(cyclopentylmethyl)-3-(2-{5-fluoro-6-[(7S)-7-hydroxy-5-azaspiro[2.4]hept-5-yl]-2-methyl-4-pyrimidinyl}hydrazino)-3-oxopropyl](tetrahydro-2H-pyran-2-yloxy)formamide (91 mg, 63%). LCMS: $(M+H)^+$: 535.3.

Part G:

((2R)-2-(Cyclopentylmethyl)-3-{2-[5-fluoro-6-(7-hydroxy-5-azaspiro[2.4]hept-5-yl)-2-methyl-4-pyrimidinyl]hydrazino}-3-oxopropyl)hydroxyformamide

[(2R)-2-(Cyclopentylmethyl)-3-(2-{5-fluoro-6-[(7S)-7-hydroxy-5-azaspiro[2.4]hept-5-yl]-2-methyl-4-pyrimidinyl}hydrazino)-3-oxopropyl](tetrahydro-2H-pyran-2-yloxy)formamide (91 mg, 0.202 mmol) was dissolved in a mixture of $AcOH/H_2O$ (10 mL, 4:1) and stirred at RT until LCMS indicated completion of the deprotection (overnight). The reaction mixture was concentrated to dryness under vacuum and was purified by RP-HPLC to provide ((2R)-2-(cyclopentylmethyl)-3-{2-[5-fluoro-6-(7-hydroxy-5-azaspiro[2.4]hept-5-yl)-2-methyl-4-pyrimidinyl]hydrazino}-3-oxopropyl)hydroxyformamide (25 mg, 27%). LCMS: $(M+H)^+$: 451.2.

Example 129

[(2R)-2-(Cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl]hydroxyformamide (Mixture of Diastereomers)

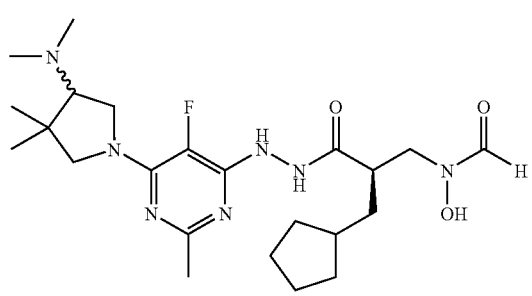

Part A:

(3R)-4,4-Dimethyl-3-pyrrolidinol hydrochloride

To a solution of (3R)-4,4-dimethyl-1-(phenylmethyl)-3-pyrrolidinol (*J. Med. Chem.* 1992, 35, 4205-4213) (1.8634 g, 9.076 mmol) in MeOH (45 mL) was added 1 N aq. HCl (9.1 mL, 9.1 mmol) and 10% Pd/C (50% water, 375 mg). The mixture was hydrogenated under balloon pressure for 2 days, and was then filtered. The solution was concentrated in vacuo and azeotroped with MeOH (4×20 mL) to give (3R)-4,4-dimethyl-3-pyrrolidinol hydrochloride (1.2654 g, 93% yield) as an amber solid. LCMS: $(M+H)^+$: 116.1.

Part B:

Phenylmethyl (4R)-4-hydroxy-3,3-dimethyl-1-pyrrolidinecarboxylate

To a mixture of (3R)-4,4-dimethyl-3-pyrrolidinol hydrochloride (0.9920 g, 6.630 mmol) in 1:1 DCM-1 N aq. NaOH (33 mL) was added benzyl chloroformate (0.994 mL, 6.963 mmol). The mixture was vigorously stirred overnight and then diluted with DCM (100 mL). The phases were partitioned, and the organic phase was dried over anhydrous MgSO$_4$, filtered, and concentrated in vacuo. The residue was then purified by silica gel chromatography (40% EtOAc in hexanes) to afford phenylmethyl (4R)-4-hydroxy-3,3-dimethyl-1-pyrrolidinecarboxylate (1.4654 g, 89% yield) as a colorless oil. LCMS: $(M+H)^+$: 250.1.

Part C:

Phenylmethyl 3,3-dimethyl-4-oxo-1-pyrrolidinecarboxylate

To a solution of phenylmethyl (4R)-4-hydroxy-3,3-dimethyl-1-pyrrolidinecarboxylate (1.4088 g, 5.651 mmol) in MeCN (50 mL) was added N-methylmorpholine-N-oxide (0.861 g, 7.350 mmol) and tetra-N-propylammonium perruthenate (0.099 g, 0.282 mmol). The solution was stirred for 90 min, concentrated in vacuo, and purified directly by silica gel chromatography (20% EtOAc in hexanes) to give phenylmethyl 3,3-dimethyl-4-oxo-1-pyrrolidinecarboxylate (1.1321 g, 79%) as a colorless oil. LCMS: $(M+Na)^+$: 270.4.

Part D:

Phenylmethyl (4Z)-3,3-dimethyl-4-[(methyloxy)imino]-1-pyrrolidinecarboxylate To a solution of phenylmethyl 3,3-dimethyl-4-oxo-1-pyrrolidinecarboxylate (0.9135 g, 3.694 mmol) in MeOH (37 mL) was added sodium acetate (0.606 g, 7.387 mmol) and O-methylhydroxylamine hydrochloride (0.620 g, 7.397 mmol). The solution was stirred for 3 h, and then concentrated in vacuo. The residue was partitioned between DCM (100 mL), water (5 mL), and sat. aq. NaHCO$_3$ (30 mL). The organic phase was dried over anhydrous MgSO$_4$, filtered, and concentrated in vacuo to provide phenylmethyl (4Z)-3,3-dimethyl-4-[(methyloxy)imino]-1-pyrrolidinecarboxylate (0.9124 g, 89% yield) as a pale yellow oil. LCMS: $(M+H)^+$: 277.0.

Part E:

Phenylmethyl 4-amino-3,3-dimethyl-1-pyrrolidinecarboxylate

To a solution of phenylmethyl (4Z)-3,3-dimethyl-4-[(methyloxy)imino]-1-pyrrolidinecarboxylate (0.7126 g, 2.579 mmol) in THF (26 mL) was added borane-THF complex (1.0 M in THF, 5.2 mL, 5.2 mmol). The solution was heated at 50° C. and stirred for 2 h. The solution was then cooled to room temperature and quenched by addition of 6 N aq. NaOH (2 mL). The mixture was diluted with brine and extracted with Et$_2$O (3×100 mL). The combined organic phase was dried over anhydrous MgSO$_4$, filtered, and concentrated in vacuo. To a solution of the residue in MeOH (20 mL) was added 50% aq. NH$_2$OH (5 mL), and the solution was heated at 60° C. and stirred overnight. The solution was then cooled to room temperature and concentrated in vacuo. The residue was partitioned between DCM (200 mL) and 1 N aq. NaOH (50 mL), and the organic phase was dried over anhydrous MgSO$_4$, filtered, and concentrated in vacuo to give racemic phenylmethyl 4-amino-3,3-dimethyl-1-pyrrolidinecarboxylate (0.5899 g, 92% yield) as a colorless oil. LCMS: $(M+H)^+$: 249.1.

Part F:

Phenylmethyl 4-(dimethylamino)-3,3-dimethyl-1-pyrrolidinecarboxylate

A solution of racemic phenylmethyl 4-amino-3,3-dimethyl-1-pyrrolidinecarboxylate (0.5899 g, 2.376 mmol) in formic acid (5 mL) and formalin (5 mL) was heated at 100° C. and stirred for 2 h. The solution was then cooled to room temperature and adjusted to pH 14 with 6 N. aq. NaOH. The mixture was then extracted with Et$_2$O (2×100 mL), and the combined organic phase was dried over anhydrous Na$_2$SO$_4$, filtered, and concentrated in vacuo. Two phases were observed to be present, and the MeOH soluble portion was collected and concentrated in vacuo to give crude, racemic phenylmethyl 4-(dimethylamino)-3,3-dimethyl-1-pyrrolidinecarboxylate (0.6862 g, >100% crude yield) as a colorless oil. LCMS: $(M+H)^+$: 277.2.

Part G:

N,N,4,4-Tetramethyl-3-pyrrolidinamine

To a solution of racemic phenylmethyl 4-(dimethylamino)-3,3-dimethyl-1-pyrrolidinecarboxylate (assumed 0.6565 g, 2.376 mmol) in MeOH was added 10% Pd/C (50% water, 195 mg). The mixture was hydrogenated under balloon pressure for 1 h, and then filtered. The solution was concentrated in vacuo to afford racemic N,N,4,4-tetramethyl-3-pyrrolidinamine (0.3479 g, quantitative yield) as an almost colorless oil. LCMS: $(M+H)^+$: 143.1.

Part H:

1-(5-Fluoro-6-hydrazino-2-methyl-4-pyrimidinyl)-N,N,4,4-tetramethyl-3-pyrrolidinamine To a solution of N,N,4,4-tetramethyl-3-pyrrolidinamine (0.0918 g, 0.645 mmol) in MeOH (3 mL) was added 4,6-dichloro-5-fluoro-2-methylpyrimidine (0.1088 g, 0.601 mmol) and N,N-diisopropylethylamine (0.130 mL, 0.746 mmol). The solution was heated at 120° C. under microwave irradiation and stirred for 30 min. The solution was then cooled to room temperature and concentrated in vacuo. To a solution of the residue in 4:1 DMSO-MeOH (5 mL) was added hydrazine hydrate (0.5 mL). The solution was heated at 65° C. and stirred overnight. The solution was then cooled to room temperature and diluted with DCM (50 mL). The mixture was washed with sat. aq. NaHCO₃ (20 mL), and the organic phase was dried over anhydrous Na₂SO₄, filtered, and concentrated in vacuo. The residue was purified by Gilson RPLC to afford racemic 1-(5-fluoro-6-hydrazino-2-methyl-4-pyrimidinyl)-N,N,4,4-tetramethyl-3-pyrrolidinamine (0.0617 g, 36%) as a light yellow solid. LCMS: (M+H)⁺: 283.2.

Part I:

[(2R)-2-(Cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl][(phenylmethyl)oxy]formamide To a solution of racemic 1-(5-fluoro-6-hydrazino-2-methyl-4-pyrimidinyl)-N,N,4,4-tetramethyl-3-pyrrolidinamine (0.0617 g, 0.219 mmol) in DMF (3 mL) was added (2R)-3-cyclopentyl-2-({formyl[(phenylmethyl)oxy]amino}methyl)propanoic acid (0.0637 g, 0.209 mmol), N-methylmorpholine (0.120 mL, 1.091 mmol), 1-hydroxy-7-azabenzotriazole (34 mg, 0.250 mmol), and EDC (48 mg, 0.250 mmol). The solution was stirred overnight and then purified directly by Gilson RPLC to give [(2R)-2-(cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl][(phenylmethyl)oxy]formamide (0.0775 g, 65% yield, mixture of diastereomers) as a pale yellow oil. LCMS: (M+H)⁺: 570.3.

Part J:

[(2R)-2-(Cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl]hydroxyformamide To a solution of [(2R)-2-(cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl][(phenylmethyl)oxy]formamide (0.0775 g, 0.136 mmol) in MeOH (5 mL) was added 10% Pd/C (50% water, 23 mg). The mixture was hydrogenated under balloon pressure for 1 h, and then filtered. The solution was concentrated in vacuo, and the residue was crystallized from EtOAc-hexanes to afford [(2R)-2-(cyclopentylmethyl)-3-(2-{6-[4-(dimethylamino)-3,3-dimethyl-1-pyrrolidinyl]-5-fluoro-2-methyl-4-pyrimidinyl}hydrazino)-3-oxopropyl]hydroxyformamide (0.0566 g, 87% yield, mixture of diastereomers) as an off-white solid. LCMS: (M+H)⁺: 480.1.

Example 130

[(2R)-3-{2-[2-Chloro-5-fluoro-6-(7-hydroxy-5-azaspiro[2.4]hept-5-yl)-4-pyrimidinyl]hydrazino}-2-(cyclopentylmethyl)-3-oxopropyl]hydroxyformamide (Mixture of Diastereomers)

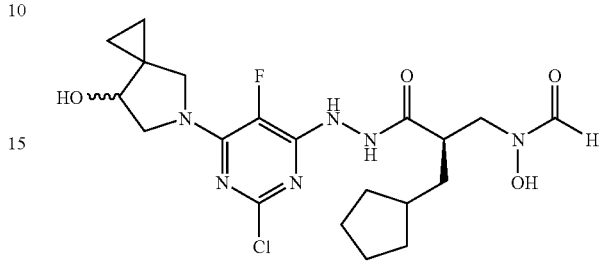

Part A:

5-(2-Chloro-5-fluoro-6-hydrazino-4-pyrimidinyl)-5-azaspiro[2.4]heptan-7-ol

To a solution of 2,4,6-trichloro-5-fluoropyrimidine (611 mg, 3.036 mmol) in DCM (5 mL) was added DIPEA (1.163 mL, 6.679 mmol), followed by 5-azaspiro[2.4]heptan-7-ol hydrochloride (Example 128) (477 mg, 3.188 mmol). The solution was stirred at room temperature. After 1 hour, the volatiles were concentrated in vacuo and the residue was dissolved in a mixture of DMSO (4 mL) and MeOH (1 mL). Hydrazine monohydrate was added (3.055 mL), and the contents were stirred at RT overnight. The excess hydrazine was removed in vacuo, and the remaining solution was purified via RP-HPLC to provide the assumed 5-(2-chloro-5-fluoro-6-hydrazino-4-pyrimidinyl)-5-azaspiro[2.4]heptan-7-ol (first eluent, 167 mg), as well as the assumed 6-chloro-5-fluoro-2-hydrazino-4-(4-methyl-1-piperazinyl)pyrimidine (second eluent, 312 mg). LCMS: (M+H)⁺: 274.0.

Part B:

[(2R)-3-{2-[2-Chloro-5-fluoro-6-(7-hydroxy-5-azaspiro[2.4]hept-5-yl)-4-pyrimidinyl]hydrazino}-2-(cyclopentylmethyl)-3-oxopropyl](tetrahydro-2H-pyran-2-yloxy)formamide 5-(2-Chloro-5-fluoro-6-hydrazino-4-pyrimidinyl)-5-azaspiro[2.4]heptan-7-ol (167 mg 0.610 mmol), (2R)-3-cyclopentyl-2-{[formyl(tetrahydro-2H-pyran-2-yloxy)amino]methyl}propanoic acid (217 mg, 0.508 mmol), and HOAt (83 mg, 0.610 mmol) were dissolved in 5 mL of DMF. NMM (0.167 mL, 1.525 mmol) was added, followed by EDC (117 mg, 0.6101 mmol). After stirring overnight at room temperature, the reaction mixture was purified by RP-HPLC to provide [(2R)-2-(cyclopentylmethyl)-3-(2-{5-fluoro-6-[(7S)-7-hydroxy-5-azaspiro[2.4]hept-5-yl]-2-methyl-4-pyrimidinyl}hydrazino)-3-oxopropyl](tetrahydro-2H-pyran-2-yloxy)formamide (223 mg, 79%). LCMS: (M+H)⁺: 555.3.

Part C:

[(2R)-3-{2-[2-Chloro-5-fluoro-6-(7-hydroxy-5-azaspiro[2.4]hept-5-yl)-4-pyrimidinyl]hydrazino}-2-(cyclopentylmethyl)-3-oxopropyl]hydroxyformamide

[(2R)-2-(Cyclopentylmethyl)-3-(2-{5-fluoro-6-[(7S)-7-hydroxy-5-azaspiro[2.4]hept-5-yl]-2-methyl-4-pyrimidinyl}hydrazino)-3-oxopropyl](tetrahydro-2H-pyran-2-yloxy)formamide (223 mg, 0.401 mmol) was dissolved in a mixture of AcOH/H₂O (20 mL, 4:1) and stirred at RT until LCMS indicated completion of the deprotection (overnight). The reaction mixture was concentrated to dryness under vacuum, and was purified by RP-HPLC to provide [(2R)-3-{2-[2-chloro-5-fluoro-6-(7-hydroxy-5-azaspiro[2.4]hept-5-yl)-4-pyrimidinyl]hydrazino}-2-(cyclopentylmethyl)-3-oxopropyl]hydroxyformamide (14 mg, 7%). LCMS: (M+H)⁺: 471.1.

Example 131

((2R)-2-(Cyclopentylmethyl)-3-{2-[6-[(2S)-2,4-dimethyl-1-piperazinyl]-5-fluoro-2-(methylthio)-4-pyrimidinyl]hydrazino}-3-oxopropyl)hydroxyformamide

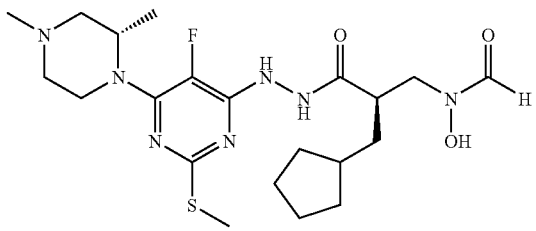

((2R)-2-(Cyclopentylmethyl)-3-{2-[6-[(2S)-2,4-dimethyl-1-piperazinyl]-5-fluoro-2-(methylthio)-4-pyrimidinyl]hydrazino}-3-oxopropyl)hydroxyformamide was prepared according to General Procedure C, utilizing (3S)-1,3-dimethylpiperazine (Example 64) in place of azetidine hydrochloride in Part A. LCMS: (M+H)⁺ 484.4.

Example 132

((2R)-2-(Cyclopentylmethyl)-3-{2-[6-[(3R)-3-(dimethylamino)-1-piperidinyl]-5-fluoro-2-(methylthio)-4-pyrimidinyl]hydrazino}-3-oxopropyl)hydroxyformamide

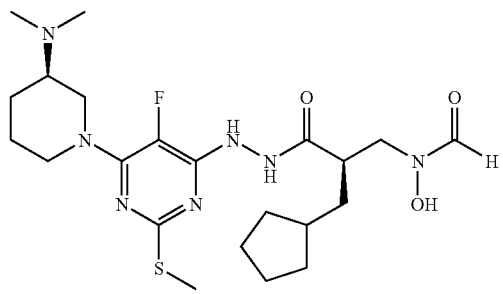

((2R)-2-(Cyclopentylmethyl)-3-{2-[6-[(3R)-3-(dimethylamino)-1-piperidinyl]-5-fluoro-2-(methylthio)-4-pyrimidinyl]hydrazino}-3-oxopropyl)hydroxyformamide was prepared according to General Procedure C, utilizing (3R)—N,N-dimethyl-3-piperidinamine (Example 118) in place of azetidine hydrochloride in Part A. LCMS: (M+H)⁺ 498.5.

Example 133

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl]hydroxyformamide (Mixture of Diastereomers)

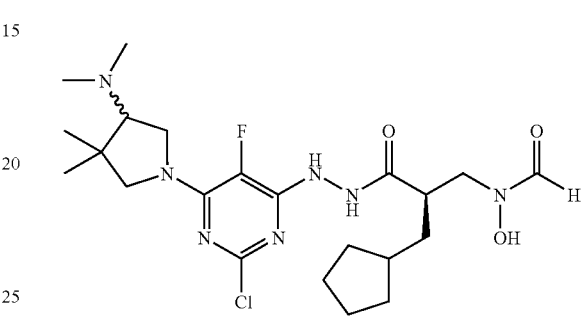

Part A:

1-(2-Chloro-5-fluoro-6-hydrazino-4-pyrimidinyl)-N,N,4,4-tetramethyl-3-pyrrolidinamine To a solution of racemic N,N,4,4-tetramethyl-3-pyrrolidinamine (0.1629 g, 1.145 mmol, prepared according to Example 129) in DCM (4 mL) was added 2,4,6-trichloro-5-fluoropyrimidine (0.2219 g, 1.102 mmol) and N,N-diisopropylethylamine (0.230 mL, 1.320 mmol). The solution was stirred at room temperature for 3 h, and was then concentrated in vacuo. To a solution of the residue in 4:1 DMSO-MeOH (5 mL) was added hydrazine hydrate (0.5 mL), and the solution was stirred overnight. The solution was diluted with DCM (50 mL) and washed with sat. aq. NaHCO₃ (20 mL). The organic phase was dried over anhydrous Na₂SO₄, filtered, and concentrated in vacuo. The residue was purified by Gilson RPLC to give first racemic 1-(2-chloro-5-fluoro-6-hydrazino-4-pyrimidinyl)-N,N,4,4-tetramethyl-3-pyrrolidinamine (0.0546 g, 16% yield) as a yellow/orange oil, LCMS: (M+H)⁺: 303.1, followed by racemic 4-chloro-6-[4-(dimethylamino)-3,3-dimethyl-1-pyrrolidinyl]-5-fluoro-2(1H)-pyrimidinone hydrazone (0.0859 g, 26% yield) as a yellow/orange oil.

Part B:

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl](tetrahydro-2H-pyran-2-yloxy)formamide To a solution of racemic 1-(2-chloro-5-fluoro-6-hydrazino-4-pyrimidinyl)-N,N,4,4-tetramethyl-3-pyrrolidinamine (0.0546 g, 0.180 mmol) in DMF (3 mL) was added (2R)-3-cyclopentyl-2-{[formyl(tetrahydro-2H-pyran-2-yloxy)amino]methyl}propanoic acid, N,N-diisoproylethylamine salt (71.1 mg, 0.166 mmol), N-methylmorpholine (0.100 mL, 0.910 mmol), 1-hydroxy-7-azabenzotriazole (27 mg, 0.198 mmol), and EDC (38 mg, 0.198 mmol). The solution was stirred overnight and was then purified directly by Gilson RPLC to give [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl](tetrahydro-2H-pyran-2-yloxy)formamide (0.0681 g, 70% yield, mixture of diastereomers) as a light yellow oil. LCMS: (M+H)$^+$: 584.4.

Part C:

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl]hydroxyformamide A solution of [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl](tetrahydro-2H-pyran-2-yloxy)formamide (0.0681 g, 0.117 mmol) in 4:1 HOAc-water (5 mL) was stirred for 56 h and then concentrated in vacuo. A solution of the residue in DCM (100 mL) was washed with sat. aq. NaHCO$_3$ (30 mL), and the organic phase was dried over anhydrous Na$_2$SO$_4$, filtered, and concentrated in vacuo. The residue was purified by Gilson RPLC and crystallized from EtOAc-hexanes to provide [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl]hydroxyformamide (0.0300 g, 51% yield, mixture of diastereomers) as a white solid. LCMS: (M+H)$^+$: 500.3.

Example 134

((2R)-2-(Cyclopentylmethyl)-3-{2-[5-fluoro-2-(methylthio)-6-(octahydro-2(1H)-isoquinolinyl)-4-pyrimidinyl]hydrazino}-3-oxopropyl)hydroxyformamide (Mixture of Diastereomers)

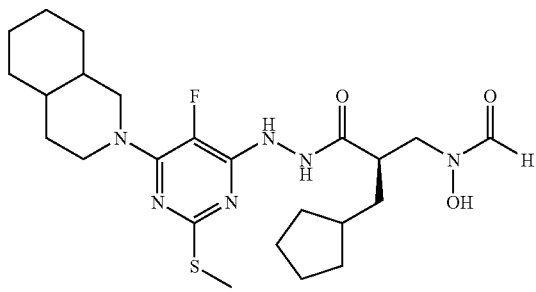

((2R)-2-(Cyclopentylmethyl)-3-{2-[5-fluoro-2-(methylthio)-6-(octahydro-2(1H)-isoquinolinyl)-4-pyrimidinyl]hydrazino}-3-oxopropyl)hydroxyformamide was prepared according to General Procedure C, utilizing commercially-available decahydroisoquinoline in place of azetidine hydrochloride in Part A. LCMS: (M+H)$^+$ 510.5.

Example 135

[(2R)-2-(Cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl]hydroxyformamide (Mixture of Diastereomers)

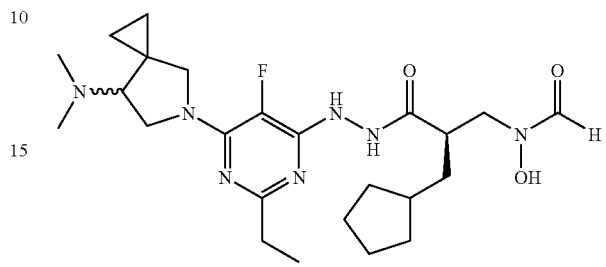

Part A:

5-(2-Ethyl-5-fluoro-6-hydrazino-4-pyrimidinyl)-N,N-dimethyl-5-azaspiro[2.4]heptan-7-amine To a solution of racemic N,N-dimethyl-5-azaspiro[2.4]heptan-7-amine dihydrochloride (0.163 g, 0.765 mmol, prepared according to the procedures of Example 136) in MeOH (3 mL) was added 4,6-dichloro-2-ethyl-5-fluoropyrimidine (0.1358 g, 0.696 mmol). The solution was heated at 120° C. under microwave irradiation for 30 min, and was then concentrated in vacuo. To a solution of the residue in 3:1 DMSO-MeOH (4 mL) was added hydrazine hydrate (0.5 mL). The solution was heated at 50° C. and stirred for 3 days. The solution was then cooled to room temperature and diluted with DCM (100 mL). The mixture was washed with sat. aq. NaHCO$_3$ (20 mL), and the aqueous phase was back extracted with a fresh portion of DCM (50 mL). The combined organic phase was dried over anhydrous Na$_2$SO$_4$, filtered, and concentrated in vacuo. The residue was purified by Gilson RPLC to give racemic 5-(2-ethyl-5-fluoro-6-hydrazino-4-pyrimidinyl)-N,N-dimethyl-5-azaspiro[2.4]heptan-7-amine (0.0818 g, 40% yield) as a light yellow oil. LCMS: (M+H)$^+$: 295.2.

Part B:

[(2R)-2-(Cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl][(phenylmethyl)oxy]formamide To a solution of racemic 5-(2-ethyl-5-fluoro-6-hydrazino-4-pyrimidinyl)-N,N-dimethyl-5-azaspiro[2.4]heptan-7-amine (0.0818 g, 0.278 mmol) in DMF (3 mL) was added (2R)-3-cyclopentyl-2-({formyl[(phenylmethyl)oxy]amino}methyl)propanoic acid (0.0778 g, 0.255 mmol), N-methylmorpholine (0.140 mL, 1.273 mmol), 1-hydroxy-7-azabenzotriazole (42 mg, 0.309 mmol), and EDC (59 mg, 0.308 mmol). The solution was stirred overnight and then purified directly by Gilson RPLC to give [(2R)-2-(cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl][(phenylmethyl)oxy]formamide (0.1058 g, 71% yield, mixture of diastereomers) as a yellow oil. LCMS: (M+H)$^+$: 582.3.

Part C:

[(2R)-2-(Cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl]hydroxyformamide To a solution of [(2R)-2-(cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl][(phenylmethyl)oxy]formamide (0.1058 g, 0.182 mmol) in MeOH (5 mL) was added 10% Pd/C (50% water, 32 mg). The mixture was hydrogenated under balloon pressure for 1 h, and then filtered. The solution was concentrated in vacuo, and the residue was azeotroped with EtOAc and crystallized from EtOAc-hexanes to afford [(2R)-2-(cyclopentylmethyl)-3-(2-{6-[7-(dimethylamino)-5-azaspiro[2.4]hept-5-yl]-2-ethyl-5-fluoro-4-pyrimidinyl}hydrazino)-3-oxopropyl]hydroxyformamide (0.0795 g, 89% yield, mixture of diastereomers) as a white solid. LCMS: (M+H)$^+$: 492.3.

Example 136

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide (Mixture of Diastereomers)

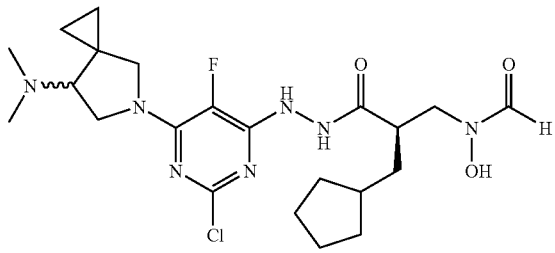

Part A:

Ethyl 1-acetylcyclopropanecarboxylate

To a solution of ethyl 3-oxobutanoate (10.0 g, 76.84 mmol) in DMF (150 mL) was added potassium carbonate (22.30 g, 161.3 mmol) and 1,2-dibromoethane (6.62 mL, 76.82 mmol). The mixture was stirred for 2 days, and then filtered. The solution was diluted with water (300 mL), and extracted with Et$_2$O (2×200 mL). The combined organic phase was washed with a fresh portion of water (100 mL), dried over anhydrous MgSO$_4$, filtered, and concentrated in vacuo. The residue was subjected to vacuum distillation at ca. 10 mbar, and the fraction boiling at 100° C. was collected to give ethyl 1-acetylcyclopropanecarboxylate (7.6482 g, 64%) as a colorless oil.

Part B:

5-(Phenylmethyl)-5-azaspiro[2.4]heptane-4,7-dione

To a solution of ethyl 1-acetylcyclopropanecarboxylate (7.6482 g, 48.97 mmol) in EtOH (54 mL) was slowly added bromine (2.76 mL, 53.87 mmol) via syringe. The orange solution was stirred for 2 h and then concentrated in vacuo. To a 0° C. solution of the residue in EtOH (54 mL) was added benzylamine (13.4 mL, 122.7 mmol) slowly via syringe, and the mixture was stirred and warmed to room temperature overnight. The mixture was concentrated in vacuo and partitioned between DCM (200 mL) and 1 N aq. HCl (100 mL). The aqueous phase was extracted with a fresh portion of DCM (100 mL), and the combined organic phase was dried over anhydrous MgSO$_4$, filtered, and concentrated in vacuo. The residue was purified by silica gel chromatography (40% EtOAc in hexanes) to afford 5-(phenylmethyl)-5-azaspiro[2.4]heptane-4,7-dione (2.7842 g, 26%) as a yellow solid. LCMS: (M+H)$^+$: 216.1.

Part C:

(7Z)-5-(Phenylmethyl)-5-azaspiro[2.4]heptane-4,7-dione 7-(O-methyloxime)

To a solution of 5-(phenylmethyl)-5-azaspiro[2.4]heptane-4,7-dione (2.7802 g, 12.92 mmol) in MeOH (65 mL) was added sodium acetate (2.12 g, 25.8 mmol) and O-methylhydroxylamine hydrochloride (2.16 g, 25.9 mmol). The mixture was stirred overnight, and then diluted with DCM (100 mL). The mixture was washed with sat. aq. NaHCO$_3$, and the organic phase was dried over anhydrous MgSO$_4$, filtered, and concentrated in vacuo to give crude (7Z)-5-(phenylmethyl)-5-azaspiro[2.4]heptane-4,7-dione 7-(O-methyloxime) (3.4094 g, >100% crude yield) as a yellow oil. LCMS: (M+H)$^+$: 245.1.

Part D:

5-(Phenylmethyl)-5-azaspiro[2.4]heptan-7-amine

To a solution of (7Z)-5-(phenylmethyl)-5-azaspiro[2.4]heptane-4,7-dione 7-(O-methyloxime) (assumed 3.1553 g, 12.92 mmol) in THF (130 mL) was added lithium aluminum hydride (1.58 g, 41.63 mmol). The mixture was heated at 65° C. and stirred for 3 h. The mixture was then cooled to 0° C., and Na$_2$SO$_4$.10H$_2$O was added. The mixture was stirred overnight, and then 1 N aq. NaOH (6 mL) was added. The mixture was vigorously stirred for 30 min, and then extracted with DCM (3×50 mL). The combined organic phase was dried over anhydrous MgSO$_4$, filtered, and concentrated in vacuo to provide racemic crude 5-(phenylmethyl)-5-azaspiro[2.4]heptan-7-amine (2.5355 g, 97% for 2 steps) as a light yellow oil. LCMS: (M+H)$^+$: 203.1.

Part E:

N,N-Dimethyl-5-(phenylmethyl)-5-azaspiro[2.4]heptan-7-amine

A solution of racemic 5-(phenylmethyl)-5-azaspiro[2.4]heptan-7-amine (2.5355 g, 12.53 mmol) in formic acid (20 mL) and formalin (20 mL) was heated at 100° C. and stirred for 3 h. The solution was then cooled to 0° C. and adjusted to pH 14 with 6 N aq. NaOH. The resulting suspension was extracted with Et$_2$O (2×200 mL), and the combined organic phase was dried over anhydrous Na$_2$SO$_4$. The mixture was filtered, and the solution was concentrated in vacuo. The MeOH soluble portion was then purified by Gilson RPLC to give racemic N,N-dimethyl-5-(phenylmethyl)-5-azaspiro[2.4]heptan-7-amine (1.7643 g, 61%) as an orange oil. LCMS: (M+H)$^+$: 231.1.

Part F:

N,N-Dimethyl-5-azaspiro[2.4]heptan-7-amine dihydrochloride

To a solution of racemic N,N-dimethyl-5-(phenylmethyl)-5-azaspiro[2.4]heptan-7-amine (0.8015 g, 3.479 mmol) in MeOH (18 mL) was added 1 N aq. HCl (6.96 mL, 6.96 mmol) and 10% Pd/C (50% water, 160 mg). The mixture was hydrogenated under balloon pressure overnight and then filtered. The solution was concentrated in vacuo to give crude racemic N,N-dimethyl-5-azaspiro[2.4]heptan-7-amine dihydrochloride (0.8060 g, >100% crude yield). LCMS: $(M+H)^+$: 141.1.

Part G:

5-(2-Chloro-5-fluoro-6-hydrazino-4-pyrimidinyl)-N,N-dimethyl-5-azaspiro[2.4]heptan-7-amine To a mixture of racemic N,N-dimethyl-5-azaspiro[2.4]heptan-7-amine dihydrochloride (0.4585 g, 2.151 mmol) in DCM (8 mL) was added 2,4,6-trichloro-5-fluoropyrimidine (0.3234 g, 1.606 mmol) and N,N-diisopropylethylamine (1.25 mL, 7.18 mmol). The solution was stirred for 3 h and then concentrated in vacuo. To a solution of the residue in 3:1 DMSO-MeOH was added hydrazine hydrate (1 mL), and the solution was stirred for 3 days, and then diluted with DCM (100 mL). The mixture was washed with sat. aq. NaHCO₃ (20 mL), and the aqueous phase was extracted with a fresh portion of DCM (50 mL). The combined organic phase was dried over anhydrous Na₂SO₄ and filtered. The solution was concentrated in vacuo and the residue was purified by Gilson RPLC to give first racemic 5-(2-chloro-5-fluoro-6-hydrazino-4-pyrimidinyl)-N,N-dimethyl-5-azaspiro[2.4]heptan-7-amine (0.0968 g, 20% yield) as an orange oil, LCMS: $(M+H)^+$: 301.1, followed by racemic 4-chloro-6-[7-(dimethylamino)-5-azaspiro[2.4]hept-5-yl]-5-fluoro-2(1H)-pyrimidinone hydrazone (0.1990 g, 41%) as an orange foam.

Part H:

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl](tetrahydro-2H-pyran-2-yloxy)formamide To a solution of racemic 5-(2-chloro-5-fluoro-6-hydrazino-4-pyrimidinyl)-N,N-dimethyl-5-azaspiro[2.4]heptan-7-amine (0.0968 g, 0.322 mmol) in DMF (3 mL) was added (2R)-3-cyclopentyl-2-{[formyl(tetrahydro-2H-pyran-2-yloxy)amino]methyl}propanoic acid, N,N-diisoproylethylamine salt (122.1 mg, 0.285 mmol), N-methylmorpholine (0.160 mL, 1.455 mmol), 1-hydroxy-7-azabenzotriazole (47 mg, 0.345 mmol), and EDC (66 mg, 0.344 mmol). The solution was stirred overnight and then purified directly by Gilson RPLC to afford [(2R)-3-(2-{2-chloro-6-[7-(dimethylamino)-5-azaspiro[2.4]hept-5-yl]-5-fluoro-4-pyrimidinyl}hydrazino)-2-(cyclopentylmethyl)-3-oxopropyl](tetrahydro-2H-pyran-2-yloxy)formamide (0.0961 g, 58%, mixture of diastereomers) as a light purple oil. LCMS: $(M+H)^+$: 582.3.

Part I:

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide A solution of [(2R)-3-(2-{2-chloro-6-[7-(dimethylamino)-5-azaspiro[2.4]hept-5-yl]-5-fluoro-4-pyrimidinyl}hydrazino)-2-(cyclopentylmethyl)-3-oxopropyl](tetrahydro-2H-pyran-2-yloxy)formamide (0.0961 g, 0.165 mmol) in 4:1 HOAc-water (5 mL) was stirred for 3 days. The solution was concentrated in vacuo and diluted with DCM (100 mL). The solution was washed with sat. aq. NaHCO₃ (25 mL), and the organic phase was dried over anhydrous MgSO₄, filtered, and concentrated in vacuo. The residue was purified by Gilson RPLC, and the desired fractions were concentrated in vacuo and azeotroped first with MeOH and then with EtOAc. The residue was crystallized from EtOAc-hexanes to provide [(2R)-3-(2-{2-chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide (0.0469 g, 57%, mixture of diastereomers) as a white solid. LCMS: $(M+H)^+$: 498.1.

Example 137

[(2R)-3-(2-{2-Chloro-5-fluoro-6-[methyl(4-pyridinylmethyl)amino]-4-pyrimidinyl}hydrazino)-2-(cyclopentylmethyl)-3-oxopropyl]hydroxyformamide

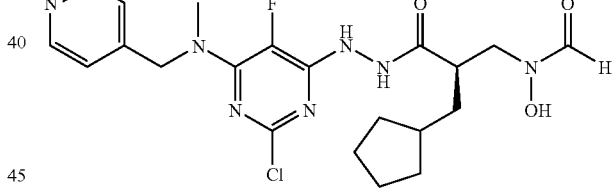

Part A:

2,6-Dichloro-5-fluoro-N-methyl-N-(4-pyridinylmethyl)-4-pyrimidinamine

Commercially available N-methyl-1-(4-pyridinyl)methanamine (0.305 g, 2.5 mmol) was dissolved in THF (5 mL). To this solution was added triethylamine (0.38 mL, 2.73 mmol), followed by 2,4,6-trichloro-5-fluoropyrimidine (0.5 g, 2.5 mmol), which was dissolved in THF (5 mL). The reaction was left to stir for 2.5 hours. The reaction mixture was diluted with water, then extracted with ether. The organics were dried (MgSO₄) and concentrated. The resulting material was purified via filtration over silica gel with a solvent mixture of 5% MeOH in 95% DCM as the mobile phase to provide 2,6-dichloro-5-fluoro-N-methyl-N-(4-pyridinylmethyl)-4-pyrimidinamine as a brown oily solid (0.3516 g, 49%). LCMS: $(M+H)^+$=287.0.

Part B:

2-Chloro-5-fluoro-6-hydrazino-N-methyl-N-(4-pyridinylmethyl)-4-pyrimidinamine 2,6-Dichloro-5-fluoro-N-methyl-N-(4-pyridinylmethyl)-4-pyrimidinamine (0.3516 g, 1.23 mmol) was dissolved in 5 mL of DMSO and hydrazine monohydrate (0.36 mL, 7.4229 mmol). The reaction vessel was pressure sealed and heated to 50° C. for 2.5 hours. The reaction mixture was then purified by RP-HPLC to provide 2-chloro-5-fluoro-6-hydrazino-N-methyl-N-(4-pyridinylmethyl)-4-pyrimidinamine as a wine colored solid (0.0803 g, 23%). LCMS: $(M+H)^+=283.0$.

Part C:

[(2R)-3-(2-{2-Chloro-5-fluoro-6-[methyl(4-pyridinylmethyl)amino]-4-pyrimidinyl}hydrazino)-2-(cyclopentylmethyl)-3-oxopropyl](tetrahydro-2H-pyran-2-yloxy)formamide 2-Chloro-5-fluoro-6-hydrazino-N-methyl-N-(4-pyridinylmethyl)-4-pyrimidinamine (0.0803 g, 0.2847 mmol) and (2R)-3-cyclopentyl-2-{[formyl(tetrahydro-2H-pyran-2-yloxy)amino]methyl}propanoic acid, diisopropylamine salt form (0.146 g, 0.3406 mmol) were dissolved in DMF (4 mL). NMM (0.16 mL, 1.4552 mmol) was added, followed by HOAt (0.046 g, 0.3382 mmol) and EDC (0.065 g, 0.339 mmol). After stirring overnight the reaction mixture was purified by RP-HPLC to provide [(2R)-3-(2-{2-chloro-5-fluoro-6-[methyl(4-pyridinylmethyl)amino]-4-pyrimidinyl}hydrazino)-2-(cyclopentylmethyl)-3-oxopropyl](tetrahydro-2H-pyran-2-yloxy)formamide as a beige solid (0.0958 g, 60%). LCMS: $(M+H)^+=564.3$.

Part D:

[(2R)-3-(2-{2-Chloro-5-fluoro-6-[methyl(4-pyridinylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[methyl(4-pyridinylmethyl)amino]-4-pyrimidinyl}hydrazino)-2-(cyclopentylmethyl)-3-oxopropyl](tetrahydro-2H-pyran-2-yloxy)formamide (0.0958 g, 0.1701 mmol) was dissolved in acetic acid (8 mL) and water (2 mL). This reaction mixture was left to stir overnight. The volatiles were evaporated, and the resulting material was purified by RP-HPLC to provide [(2R)-3-(2-{2-chloro-5-fluoro-6-[methyl(4-pyridinylmethyl)amino]-4-pyrimidinyl}hydrazino)-2-(cyclopentylmethyl)-3-oxopropyl]hydroxyformamide as a beige solid (0.0249 g, 31%). LCMS: $(M+H)^+=480.1$.

Example 138

[(2R)-3-(2-{2-Chloro-6-[(trans)-3-(dimethylamino)-4-methyl-1-pyrrolidinyl]-5-fluoro-4-pyrimidinyl}hydrazino)-2-(cyclopentylmethyl)-3-oxopropyl]hydroxyformamide

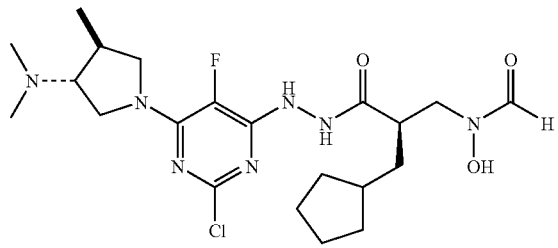

[(2R)-3-(2-{2-Chloro-6-[(trans)-3-(dimethylamino)-4-methyl-1-pyrrolidinyl]-5-fluoro-4-pyrimidinyl}hydrazino)-2-(cyclopentylmethyl)-3-oxopropyl]hydroxyformamide was prepared according to General Procedure D, utilizing (trans)-N,N,4-trimethyl-3-pyrrolidinamine (Example 89) in place of N-methylpiperazine in Part A. LCMS: $(M+H)^+$: 486.6.

Example 139

[(2R)-2-(Cyclopentylmethyl)-3-(2-{5-fluoro-6-[(2S,3R)-3-hydroxy-2-methyl-1-pyrrolidinyl]-2-methyl-4-pyrimidinyl}hydrazino)-3-oxopropyl]hydroxyformamide

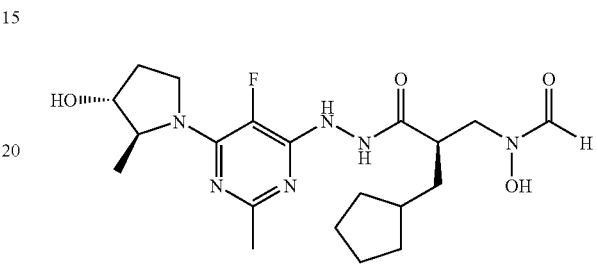

[(2R)-2-(Cyclopentylmethyl)-3-(2-{5-fluoro-6-[(2S,3R)-3-hydroxy-2-methyl-1-pyrrolidinyl]-2-methyl-4-pyrimidinyl}hydrazino)-3-oxopropyl]hydroxyformamide was prepared according to General Procedure A, utilizing (2S,3R)-2-methyl-3-pyrrolidinol (Tetrahedron, 1998, 54, 12547-12560) in place of pyrrolidine in Part A. LCMS: $(M+H)^+$: 439.2.

Example 140

[(2R)-3-{2-[2-Chloro-5-fluoro-6-(3-hydroxy-3-methyl-1-pyrrolidinyl)-4-pyrimidinyl]hydrazino}-2-(cyclopentylmethyl)-3-oxopropyl]hydroxyformamide (Mixture of Diastereomers)

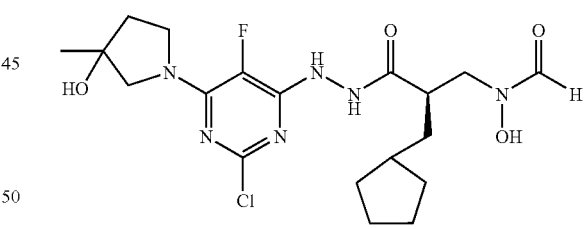

Part A:

3-Methyl-1-(phenylmethyl)-3-pyrrolidinol

To a solution of commercially available 1-(phenylmethyl)-3-pyrrolidinone (1.0 g, 5.71 mmol) in THF (30 mL) and ether (30 mL) at 0° C. was added MeMgBr (1.4 M solution in toluene:THF (3:1)) (6.1 mL, 8.65 mmol). The reaction was stirred at 0° C. for 1.5 hours, then quenched with water and extracted. Removed organic solvent in vacuo and extracted again with ether, dried organics (Na$_2$SO$_4$) and removed solvent in vacuo. Purified by RP-HPLC to provide racemic 3-methyl-1-(phenylmethyl)-3-pyrrolidinol as a yellow oil (0.501 g, 46%). LCMS: $(M+H)^+=192.3$.

Part B:

3-Methyl-3-pyrrolidinol

A solution of 3-methyl-1-(phenylmethyl)-3-pyrrolidinol (0.501 g, 2.62 mmol) and Pd(C) in MeOH (30 mL) was treated under standard hydrogenation conditions as in General Procedure A, Part C, for 3 days to provide 3-methyl-3-pyrrolidinol as an orange oil (0.239 g, 90%). LCMS: (M+H)$^+$= 102.1.

Part C:

1-(2,6-Dichloro-5-fluoro-4-pyrimidinyl)-3-methyl-3-pyrrolidinol

To a solution of 2,4,6-trichloro-5-fluoropyrimidine (0.476 g, 2.36 mmol) and triethylamine (0.36 mL, 2.60 mmol) in THF was added 3-methyl-3-pyrrolidinol (0.239 g, 2.36 mmol) in THF and MeOH (2 mL). The reaction was stirred at room temperature for 2.5 hours, and then the solvent was removed in vacuo. Water was added to the residue, and the mixture was extracted with ethyl acetate. The organics were dried (Na$_2$SO$_4$) and evaporated to provide 1-(2,6-dichloro-5-fluoro-4-pyrimidinyl)-3-methyl-3-pyrrolidinol as an orange solid (0.486 g, 77%). LCMS: (M+H)$^+$=266.1.

Part D:

1-(2-Chloro-5-fluoro-6-hydrazino-4-pyrimidinyl)-3-methyl-3-pyrrolidinol 1-(2,6-Dichloro-5-fluoro-4-pyrimidinyl)-3-methyl-3-pyrrolidinol (0.486 g, 1.83 mmol) and hydrazine monohydrate (0.53 mL, 10.96 mmol) in DMSO (5 mL) were heated at 50° C. until the reaction was deemed complete. Purification by RP-HPLC provided 1-(2-chloro-5-fluoro-6-hydrazino-4-pyrimidinyl)-3-methyl-3-pyrrolidinol as a brown solid (0.104 g, 21%). LCMS: (M+H)$^+$=262.1.

Part E:

[(2R)-3-{2-[2-Chloro-5-fluoro-6-(3-hydroxy-3-methyl-1-pyrrolidinyl)-4-pyrimidinyl]hydrazino}-2-(cyclopentylmethyl)-3-oxopropyl][(phenylmethyl)oxy]formamide (2R)-3-Cyclopentyl-2-({formyl[(phenylmethyl)oxy]amino}methyl)propanoic acid (0.122 g, 0.4 mmol), racemic 1-(2-chloro-5-fluoro-6-hydrazino-4-pyrimidinyl)-3-methyl-3-pyrrolidinol (0.104 g, 0.4 mmol), NMM (0.13 mL, 1.2 mmol), HOAt (0.054 g, 0.4 mmol), EDC (0.077 g, 0.4 mmol) and DMF (2 mL) were combined. When the reaction was complete, the mixture was purified by RP-HPLC to provide [(2R)-3-{2-[2-chloro-5-fluoro-6-(3-hydroxy-3-methyl-1-pyrrolidinyl)-4-pyrimidinyl]hydrazino}-2-(cyclopentylmethyl)-3-oxopropyl][(phenylmethyl)oxy]formamide as a mixture of diastereomers (0.035 g, 16%). LCMS: (M+H)$^+$= 549.5.

Part F:

[(2R)-3-{2-[2-Chloro-5-fluoro-6-(3-hydroxy-3-methyl-1-pyrrolidinyl)-4-pyrimidinyl]hydrazino}-2-(cyclopentylmethyl)-3-oxopropyl]hydroxyformamide A solution of [(2R)-3-{2-[2-chloro-5-fluoro-6-(3-hydroxy-3-methyl-1-pyrrolidinyl)-4-pyrimidinyl]hydrazino}-2-(cyclopentylmethyl)-3-oxopropyl][(phenylmethyl)oxy]formamide (0.035 g, 0.064 mmol), and Pd(C) (0.005 g) in MeOH (10 mL) was treated under standard hydrogenation conditions as in General Procedure A, Part C. Purification by RP-HPLC provided [(2R)-3-{2-[2-chloro-5-fluoro-6-(3-hydroxy-3-methyl-1-pyrrolidinyl)-4-pyrimidinyl]hydrazino}-2-(cyclopentylmethyl)-3-oxopropyl]hydroxyformamide as a white solid (Mixture of Diastereomers) (0.010 g, 34%). LCMS: (M+H)$^+$=459.4.

Example 141

((2R)-2-(Cyclopentylmethyl)-3-{2-[5-fluoro-6-[(3S)-3-(hydroxymethyl)-4-morpholinyl]-2-(methylthio)-4-pyrimidinyl]hydrazino}-3-oxopropyl)hydroxyformamide

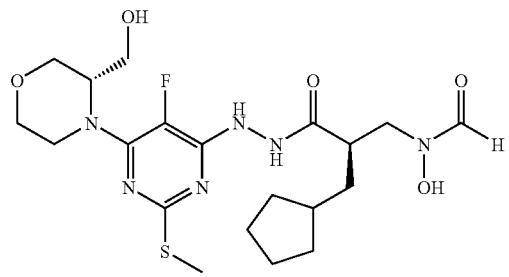

((2R)-2-(Cyclopentylmethyl)-3-{2-[5-fluoro-6-[(3S)-3-(hydroxymethyl)-4-morpholinyl]-2-(methylthio)-4-pyrimidinyl]hydrazino}-3-oxopropyl)hydroxyformamide was prepared according to General Procedure C, utilizing commercially-available (3S)-3-morpholinylmethanol in place of azetidine hydrochloride in Part A. LCMS: (M+H)$^+$ 487.5.

Example 142

N-[(2R)-3-{2-[2-Chloro-5-fluoro-6-(octahydropyrazino[1,2-a]azepin-2(1H)-yl)-4-pyrimidinyl]hydrazino}-2-(cyclopentylmethyl)-3-oxopropyl]-N-hydroxyformamide

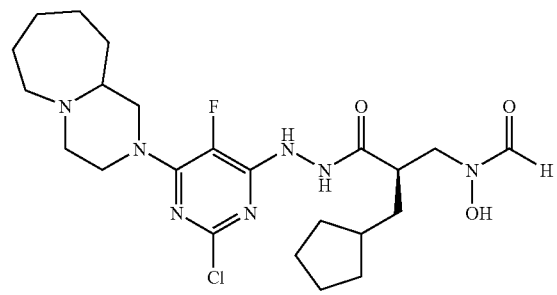

N-[(2R)-3-{2-[2-Chloro-5-fluoro-6-(octahydropyrazino[1,2-a]azepin-2(1H)-yl)-4-pyrimidinyl]hydrazino}-2-(cyclopentylmethyl)-3-oxopropyl]-N-hydroxyformamide was prepared according to General Procedure G, utilizing commercially-available decahydro-pyrazino[1,2-A]azepine in place of (1S,4S)-2-methyl-2,5-diazabicyclo[2.2.1]heptane, dihydrobromide in Part A, and using 1 equivalent of DIPEA. LCMS: (M+H)$^+$: 602.4.

Example 143

[(2R)-3-[2-(2-Chloro-5-fluoro-6-{[2-(4-morpholinyl)ethyl]amino}-4-pyrimidinyl)hydrazino]-2-(cyclopentylmethyl)-3-oxopropyl]hydroxyformamide

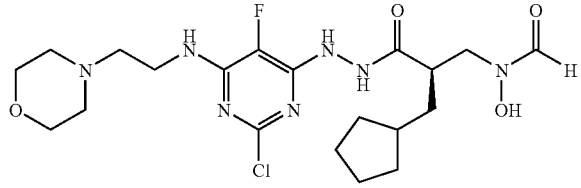

[(2R)-3-[2-(2-Chloro-5-fluoro-6-{[2-(4-morpholinyl)ethyl]amino}-4-pyrimidinyl)hydrazino]-2-(cyclopentylmethyl)-3-oxopropyl]hydroxyformamide was prepared according to General Procedure D, utilizing commercially-available 4-(2-aminoethyl)morpholine in place of N-methylpiperazine in Part A. LCMS: (M+H)+: 488.3.

Example 144

[(2R)-2-(Cyclopentylmethyl)-3-(2-{5-fluoro-6-[(2R)-2-(hydroxymethyl)-4-methyl-1-piperazinyl]-2-methyl-4-pyrimidinyl}hydrazino)-3-oxopropyl]hydroxyformamide

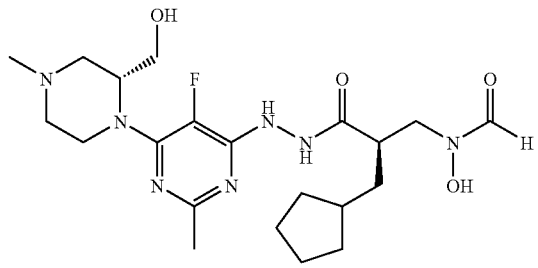

[(2R)-2-(Cyclopentylmethyl)-3-(2-{5-fluoro-6-[(2R)-2-(hydroxymethyl)-4-methyl-1-piperazinyl]-2-methyl-4-pyrimidinyl}hydrazino)-3-oxopropyl]hydroxyformamide was prepared according to General Procedure A, utilizing [(2R)-4-methyl-2-piperazinyl]methanol (Tetrahedron: Asymmetry, 1993, 4, 2389-2398) in place of pyrrolidine in Part A. LCMS: (M+H)+: 468.3.

Example 145

N-[(2R)-3-(2-{2-Chloro-5-fluoro-6-[(3R,5S)-3,4,5-trimethyl-1-piperazinyl]-4-pyrimidinyl}hydrazino)-2-(cyclopentylmethyl)-3-oxopropyl]-N-hydroxyformamide

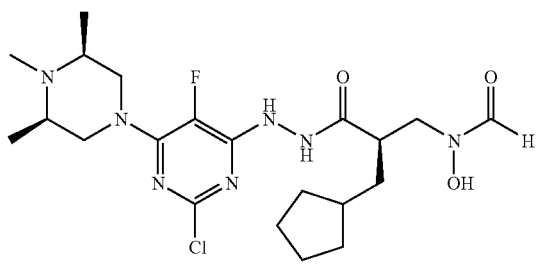

Part A:

1,1-Dimethylethyl (3R,5S)-3,5-dimethyl-1-piperazinecarboxylate

To a solution of cis-2,6-dimethylpiperazine (1.142 g, 10 mmol) in dichloromethane (25 mL) at 0° C. was added dropwise bis(1,1-dimethylethyl)dicarbonate (2.161 g, 9.9 mmol) in dichloromethane (6 mL). The reaction mixture was allowed to warm to room temperature and stirred overnight before being diluted with dichloromethane and washed with saturated aqueous $Na_2CO_3$ solution. The aqueous layer was back extracted with dichloromethane once. The combined organic layers were washed with brine, dried ($MgSO_4$) and evaporated to yield 1,1-dimethylethyl (3R,5S)-3,5-dimethyl-1-piperazinecarboxylate (2.04 g, 95%). LCMS: (M+H)+: 215.1.

Part B:

1,1-Dimethylethyl (3R,5S)-3,4,5-trimethyl-1-piperazinecarboxylate

To a solution of 1,1-dimethylethyl (3R,5S)-3,5-dimethyl-1-piperazinecarboxylate (2.04 g, 9.5 mmol) in dichloromethane (25 mL) at 0° C. was added formaldehyde (1.075 mL, 37% water solution, 14.3 mmol) followed by sodium triacetoxyborohydride (2.628 g, 12.4 mmol). The reaction mixture was allowed to warm to room temperature and stirred for 2 h before being diluted with dichloromethane and washed with 1N NaOH solution. The organics were then washed with brine, dried ($MgSO_4$) and evaporated to yield 1,1-dimethylethyl (3R,5S)-3,4,5-trimethyl-1-piperazinecarboxylate (2.06 g, 95%). LCMS: (M+H)+: 229.2.

Part C:

(2R,6S)-1,2,6-Trimethylpiperazine, TFA Salt 1,1-Dimethylethyl (3R,5S)-3,4,5-trimethyl-1-piperazinecarboxylate (253 mg, 1.1 mmol) was dissolved and stirred in dichloromethane (3 mL). Trifluoroacetic acid (1.2 mL) was added dropwise, and the resulting reaction mixture was stirred at room temperature for 2.5 h. Then the solvent was evaporated and the crude, TFA salt of (2R,6S)-1,2,6-trimethylpiperazine was used for the next step. LCMS: (M+H)+: 129.1.

Part D:

N-[(2R)-3-(2-{2-Chloro-5-fluoro-6-[(3R,5S)-3,4,5-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(3R,5S)-3,4,5-trimethyl-1-piperazinyl]-4-pyrimidinyl}hydrazino)-2-(cyclopentylmethyl)-3-oxopropyl]-N-hydroxyformamide was prepared according to General Procedure G, utilizing (2R,6S)-1,2,6-trimethylpiperazine, TFA salt in place of (1S,4S)-2-methyl-2,5-diazabicyclo[2.2.1]heptane, dihydrobromide in Part A. LCMS: (M+H)+: 486.3.

Example 146

[(2R)-2-(Cyclopentylmethyl)-3-(2-{6-[(2R,3R)-3-(dimethylamino)-2-methyl-1-pyrrolidinyl]-5-fluoro-2-methyl-4-pyrimidinyl}hydrazino)-3-oxopropyl]hydroxyformamide

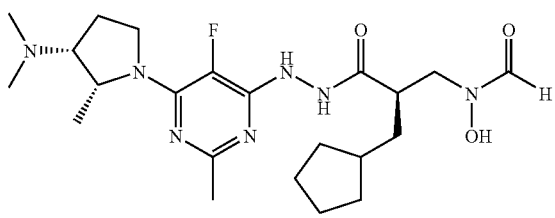

[(2R)-2-(Cyclopentylmethyl)-3-(2-{6-[(2R,3R)-3-(dimethylamino)-2-methyl-1-pyrrolidinyl]-5-fluoro-2-methyl-4-pyrimidinyl}hydrazino)-3-oxopropyl]hydroxyformamide was prepared according to General Procedure A, utilizing (2R,3R)—N,N,2-trimethyl-3-pyrrolidinamine (Tetrahedron, 1998, 54, 12547-12560) in place of pyrrolidine in Part A. LCMS: (M+H)$^+$: 466.4.

Example 147

[(2R)-3-{2-[2-Chloro-5-fluoro-6-(2,2,4-trimethyl-1-piperazinyl)-4-pyrimidinyl]hydrazino}-2-(cyclopentylmethyl)-3-oxopropyl]hydroxyformamide

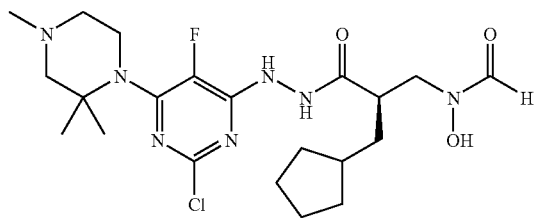

[(2R)-3-{2-[2-Chloro-5-fluoro-6-(2,2,4-trimethyl-1-piperazinyl)-4-pyrimidinyl]hydrazino}-2-(cyclopentylmethyl)-3-oxopropyl]hydroxyformamide was prepared according to General Procedure D, utilizing 1,3,3-trimethyl-piperazine (commercially-available) in place of N-methylpiperazine in Part A. LCMS: (M+H)$^+$: 486.3.

Example 148

[(2R)-3-{2-[2-Chloro-5-fluoro-6-(3,3,4-trimethyl-1-piperazinyl)-4-pyrimidinyl]hydrazino}-2-(cyclopentylmethyl)-3-oxopropyl]hydroxyformamide

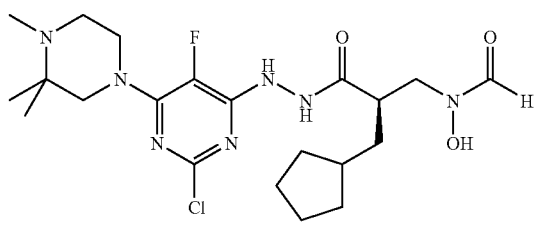

[(2R)-3-{2-[2-Chloro-5-fluoro-6-(3,3,4-trimethyl-1-piperazinyl)-4-pyrimidinyl]hydrazino}-2-(cyclopentylmethyl)-3-oxopropyl]hydroxyformamide was prepared according to General Procedure D, utilizing 1,2,2-trimethyl-piperazine (commercially-available) in place of N-methylpiperazine in Part A. LCMS: (M+H)$^+$: 486.3.

Example 149

N-[(2R)-2-(Cyclopentylmethyl)-3-(2-{5-fluoro-2-methyl-6-[(3R,5S)-3,4,5-trimethyl-1-piperazinyl]-4-pyrimidinyl}hydrazino)-3-oxopropyl]-N-hydroxyformamide

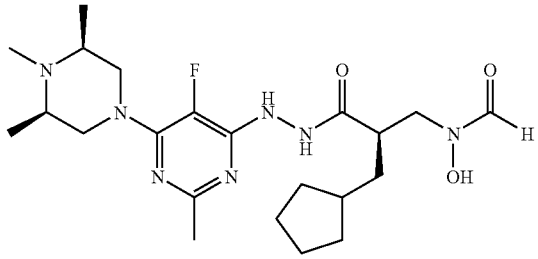

N-[(2R)-2-(Cyclopentylmethyl)-3-(2-{5-fluoro-2-methyl-6-[(3R,5S)-3,4,5-trimethyl-1-piperazinyl]-4-pyrimidinyl}hydrazino)-3-oxopropyl]-N-hydroxyformamide was prepared according to General Procedure A, utilizing (2R,6S)-1,2,6-trimethylpiperazine, TFA salt (Example 145) in place of pyrrolidine in Part A, and using 3 equivalents of DIPEA. LCMS: (M+H)$^+$: 466.4.

Example 150

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide (Single Unknown Diastereomer)

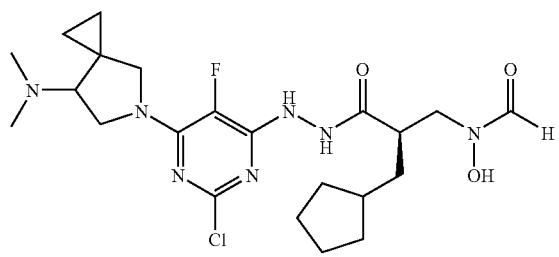

Part A:

(7Z)-5-(Phenylmethyl)-5-azaspiro[2.4]heptane-4,7-dione 7-(O-methyloxime)

5-(Phenylmethyl)-5-azaspiro[2.4]heptane-4,7-dione (Example 128) (2.8619 g, 13.29 mmol), sodium acetate (2.23 g, 26.59 mmol), and O-methylhydroxylamine hydrochloride (2.22 g, 26.59) was dissolved in 65 mL of MeOH. The mixture was stirred at room temperature overnight and then diluted with 300 mL of DCM. The mixture was washed with sat. aq. NaHCO$_3$ (200 mL), and the organics were dried over anhydrous MgSO₄, filtered, and concentrated in vacuo to provide (7Z)-5-(phenylmethyl)-5-azaspiro[2.4]heptane-4,7-dione 7-(O-methyloxime) (3.0864 g, 95%). LCMS: (M+H)⁺: 245.1.

Part B:

7-Amino-5-(phenylmethyl)-5-azaspiro[2.4]heptan-4-one

7-Amino-5-(phenylmethyl)-5-azaspiro[2.4]heptan-4-one was prepared according to Example 130, Part C, utilizing (7Z)-5-(phenylmethyl)-5-azaspiro[2.4]heptane-4,7-dione 7-(O-methyloxime) in place of 5-(phenylmethyl)-5-azaspiro[2.4]heptane-4,7-dione. LCMS: (M+H)⁺: 203.1.

Part C:

N,N-Dimethyl-5-(phenylmethyl)-5-azaspiro[2.4]heptan-7-amine

7-Amino-5-(phenylmethyl)-5-azaspiro[2.4]heptan-4-one (2.535 g, 12.28 mmol) was dissolved in a mixture of AcOH (20 mL) and aq. HCHO (20 mL) the contents were heated to 100° C. for 3 h and then cooled to 0° C. The solution was adjusted to pH 14 with 6 N aq. NaOH, and then extracted with Et₂O (2×200 mL). The combined organic phase was dried over anhydrous Na₂SO₄, filtered, concentrated in vacuo, and purified by RP-HPLC to provide N,N-dimethyl-5-(phenylmethyl)-5-azaspiro[2.4]heptan-7-amine (2.6062 g, 92.5%).

The enantiomeric mixture was separated by chiral LC. E1 (1.4 g) LCMS: (M+H)⁺: 231. E2 (1.5 g) LCMS: (M+H)⁺: 231.

Part E:

N,N-Dimethyl-5-azaspiro[2.4]heptan-7-amine

N,N-Dimethyl-5-(phenylmethyl)-5-azaspiro[2.4]heptan-7-amine (E1) (1.4 g, 0.18 mmol) was dissolved in a mixture of 12 mL of 1N aq HCl in 30 mL of MeOH, degassed and placed under argon. 10% Pd/C (280 mg) was added, and the contents were thoroughly degassed and placed under a hydrogen balloon overnight. The contents were then degassed and filtered through a 0.2 µm filter tip syringe. The resulting filtrate was concentrated in vacuo and the residue was adjusted to pH 14 with 1N aq. NaOH. The aqueous phase was extracted with CH₂Cl₂ (2×100 mL), the combined organic phase was dried over anhydrous Na₂SO₄, filtered, and concentrated in vacuo to provide the pure N,N-dimethyl-5-azaspiro[2.4]heptan-7-amine (718 mg, 84%). LCMS: (M+H)⁺: not detected.

Part F:

2-Chloro-5-fluoro-4,6-bis(phenylthio)pyrimidine

To a solution of 2,4,6-trichloro-5-fluoropyrimidine (10.0635 g, 49.96 mmol) in DCM (250 mL) at −30° C. was added phenyl hydrosulfide (10.26 mL, 99.93 mmol). To the solution was added DIEA (21.8 mL, 124.9 mmol) dropwise via an addition funnel, with vigorous stirring. The reaction mixture was stirred at room temperature for 1 h, then the volatiles were concentrated in vacuo, and the residue was dissolved in MeOH (100 mL) and water (200 mL). The resulting pale yellow solid precipitate was collected by filtration. The precipitate was washed with water (2×100 mL), and the resulting solid was dried in vacuo to provide 2-chloro-5-fluoro-4,6-bis(phenylthio)pyrimidine (17.4080 g, 99%). LCMS: (M+H)⁺: 349.0.

Part G:

2-Chloro-5-fluoro-4,6-bis(phenylsulfonyl)pyrimidine

2-Chloro-5-fluoro-4,6-bis(phenylthio)pyrimidine (3.0185 g, 8.652 mmol) was dissolved in a mixture of ACN (43 mL) and water (86 mL). To this solution was added sodium periodate (11.10 g, 51.916 mmol) followed by ruthenium(III) chloride (36 mg, 0.173 mmol). The mixture was vigorously stirred for 3.5 h. The reaction mixture was extracted with CH₂Cl₂ (2×100 mL), and the combined organic phase was dried over anhydrous Na₂SO₄, filtered, and concentrated in vacuo to provide the pure 2-chloro-5-fluoro-4,6-bis(phenylsulfonyl)pyrimidine (2.51 g, 70%). LCMS: (M+H)⁺: 413.0.

Part H:

5-(2-Chloro-5-fluoro-6-hydrazino-4-pyrimidinyl)-N,N-dimethyl-5-azaspiro[2.4]heptan-7-amine N,N-Dimethyl-5-azaspiro[2.4]heptan-7-amine (464 mg, 3.31 mmol) and DIEA (580 µL, 3.31 mmol) were dissolved in DCM (43 mL) and cooled to 0° C. A solution of 2-chloro-5-fluoro-4,6-bis(phenylsulfonyl)pyrimidine (1.2427 g, 3.01 mmol) in 30 mL DCM was added dropwise with vigorous stirring. The mixture was stirred for 30 min and then concentrated in vacuo. The residue was dissolved in MeOH (30 mL), hydrazine monohydrate was added (1.4 mL), and the contents were stirred at RT overnight and then concentrated in vacuo. The crude residue was dissolved in CH₂Cl₂ (100 mL), and the mixture was washed with NaHCO₃ (1×50 mL). The aqueous phase was extracted with CH₂Cl₂ (1×100 mL), and the combined organic phase was dried over anhydrous Na₂SO₄, filtered, and concentrated in vacuo. The resulting crude product was purified by RP-HPLC to provide 5-(2-chloro-5-fluoro-6-hydrazino-4-pyrimidinyl)-N,N-dimethyl-5-azaspiro[2.4]heptan-7-amine (465.5 mg, 53%). LCMS: (M+H)⁺: 301.2.

Part I:

[(2R)-3-(2-{5-Chloro-3-[7-(dimethylamino)-5-azaspiro[2.4]hept-5-yl]-2-fluorophenyl}hydrazino)-2-(cyclopentylmethyl)-3-oxopropyl][(phenylmethyl)oxy]formamide

[(2R)-3-(2-{5-Chloro-3-[7-(dimethylamino)-5-azaspiro[2.4]hept-5-yl]-2-fluorophenyl}hydrazino)-2-(cyclopentylmethyl)-3-oxopropyl][(phenylmethyl)oxy]formamide was prepared according to General Procedure E, Part C, utilizing 5-(2-chloro-5-fluoro-6-hydrazino-4-pyrimidinyl)-N,N-dimethyl-5-azaspiro[2.4]heptan-7-amine in place of (5-chloro-2-fluoro-3-hydrazinophenyl)(1-methylethyl)amine. LCMS: (M+H)⁺: 588.3.

Part J:

[(2R)-3-(2-{5-Chloro-3-[7-(dimethylamino)-5-azaspiro[2.4]hept-5-yl]-2-fluorophenyl}hydrazino)-2-(cyclopentylmethyl)-3-oxopropyl]hydroxyformamide

[(2R)-3-(2-{5-Chloro-3-[7-(dimethylamino)-5-azaspiro[2.4]hept-5-yl]-2-fluorophenyl}hydrazino)-2-(cyclopentylmethyl)-3-oxopropyl][(phenylmethyl)oxy]formamide (300 mg, 0.51 mmol) was dissolved in 5 mL of MeOH. 5% Rhodium on Alumina (240 mg) was added, and the contents were stirred under a hydrogen balloon overnight. The contents were then filtered to remove the catalyst, and the filtrate was concentrated in vacuo. The resulting crude product was purified via reverse phase HPLC to provide [(2R)-3-(2-{5-chloro-3-[7-(dimethylamino)-5-azaspiro[2.4]hept-5-yl]-2-fluorophenyl}hydrazino)-2-(cyclopentylmethyl)-3-oxopropyl]hydroxyformamide (single unknown diastereomer) (142 mg, 56%). LCMS: (M+H)+: 498.3.

Example 151

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide (Single Unknown Diastereomer)

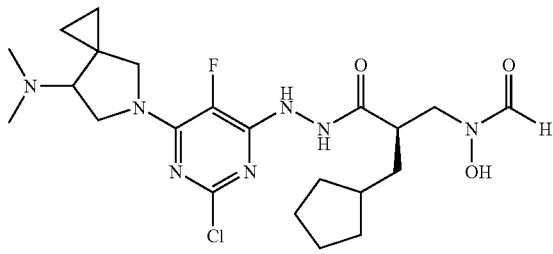

[(2R)-3-(2-{2-Chloro-6-[7-(dimethylamino)-5-azaspiro[2.4]hept-5-yl]-5-fluoro-4-pyrimidinyl}hydrazino)-2-(cyclopentylmethyl)-3-oxopropyl]hydroxyformamide (single unknown diastereomer) was prepared according to Example 150, utilizing the E2 enantiomer in place of the E1 enantiomer in Part E. LCMS: (M+H)+: 498.3.

Example 152

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (Mixture of Diastereomers)

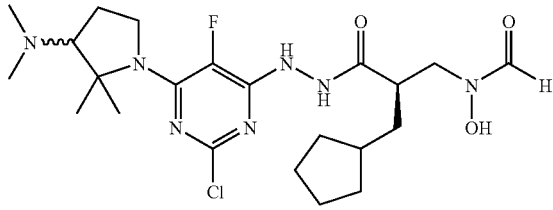

Part A:

Methyl 2-methyl-N-[3-(methyloxy)-3-oxopropyl]alaninate

A solution of N-(2-cyanoethyl)-2-methylalanine (*J. Am. Chem. Soc.* 1950, 72, 2599) (22.58 g) in 1.25 M methanolic HCl (460 mL) was heated at 75° C. and stirred overnight. The solution was then concentrated in vacuo and diluted with CHCl3 (200 mL). The mixture was filtered, and the solution was washed with sat. aq. NaHCO3. The organic phase was dried over anhydrous Na2SO4, filtered, and concentrated in vacuo to provide methyl 2-methyl-N-[3-(methyloxy)-3-oxopropyl]alaninate (11.71 g, 40% yield) as a colorless oil. LCMS: (M+H)+: 204.1.

Part B:

Methyl 2-methyl-N-[3-(methyloxy)-3-oxopropyl]-N-(phenylcarbonyl)alaninate

To a mixture of methyl 2-methyl-N-[3-(methyloxy)-3-oxopropyl]alaninate (11.71 g, 57.62 mmol) in 1:1 DCM-water (300 mL) was added NaHCO3 (9.68 g, 115.2 mmol) followed by benzoyl chloride (7.02 mL, 60.48 mmol). The mixture was vigorously stirred overnight, and the phases were then separated. The organic phase was dried over anhydrous MgSO4, filtered, and concentrated in vacuo. The residue was purified by silica gel chromatography (35% EtOAc in hexanes) to give methyl 2-methyl-N-[3-(methyloxy)-3-oxopropyl]-N-(phenylcarbonyl)alaninate (3.6787 g, 21% yield) as a colorless oil. LCMS: (M+H)+: 308.1.

Part C:

Methyl 5,5-dimethyl-4-oxo-1-(phenylcarbonyl)-3-pyrrolidinecarboxylate

To a solution of methyl 2-methyl-N-[3-(methyloxy)-3-oxopropyl]-N-(phenylcarbonyl)alaninate (3.5589 g, 11.58 mmol) in toluene (115 mL) was added MeOH (0.94 mL, 23.21 mmol), and NaOMe (1.25 g, 23.14 mmol). The mixture was heated at 60° C. and stirred for 2 h. An additional portion of MeOH (10 mL) was added, and the mixture was stirred for an additional 2 h at 60° C. The mixture was then concentrated in vacuo, and the residue was partitioned between DCM (200 mL) and 1 N aq. HCl (100 mL). The organic phase was dried over anhydrous MgSO4, filtered, and concentrated in vacuo to provide crude methyl 5,5-dimethyl-4-oxo-1-(phenylcarbonyl)-3-pyrrolidinecarboxylate (2.746 g, 86% yield) as a colorless oil. LCMS: (M+H)+: 276.1.

Part D:

2,2-Dimethyl-1-(phenylcarbonyl)-3-pyrrolidinone

A solution of methyl 5,5-dimethyl-4-oxo-1-(phenylcarbonyl)-3-pyrrolidinecarboxylate (2.5781 g, 9.364 mmol) in 10:1 HOAc-water (50 mL) was heated at 100° C. and stirred for 42 h. The solution was cooled to room temperature and concentrated in vacuo. The residue was dissolved in DCM (200 mL) and washed with sat. aq. NaHCO3. The organic phase was dried over anhydrous MgSO4, filtered, and concentrated in vacuo to afford crude 2,2-dimethyl-1-(phenylcarbonyl)-3-pyrrolidinone as a light yellow oil. LCMS: (M+H)+: 218.1.

Part E:

(3E)-2,2-Dimethyl-1-(phenylcarbonyl)-3-pyrrolidinone O-methyloxime

To a solution of 2,2-dimethyl-1-(phenylcarbonyl)-3-pyrrolidinone (2.0602 g, 9.482 mmol) in MeOH (50 mL) was added sodium acetate (0.956 g, 11.38 mmol) and methoxyamine hydrochloride (0.950 g, 11.37 mmol). The mixture was stirred overnight and then concentrated in vacuo. The residue was dissolved in DCM (200 mL) and washed with sat. aq. NaHCO3 (50 mL), water (50 mL), and brine (50 mL). The organic phase was dried over anhydrous Na2SO4, filtered, and concentrated in vacuo to afford (3E)-2,2-dimethyl-1-(phenylcarbonyl)-3-pyrrolidinone O-methyloxime (1.9567 g, 84% yield) as a light yellow oil that solidified under high vacuum. LCMS: (M+H)$^+$: 247.2.

Part F:

2,2-Dimethyl-1-(phenylmethyl)-3-pyrrolidinamine

To a solution of (3E)-2,2-dimethyl-1-(phenylcarbonyl)-3-pyrrolidinone O-methyloxime (1.9492 g, 7.914 mmol) in THF (80 mL) was added lithium aluminum hydride (0.900 g, 23.72 mmol), and the mixture was heated at 65° C. and stirred for 5 h. The mixture was cooled to 0° C., and Na$_2$SO$_4$.10H$_2$O (2 g) was added. The mixture was stirred for 30 min, and 1 N aq. NaOH (100 mL) was then added. The mixture was extracted with Et$_2$O (3×150 mL), and the combined organic phase was dried over anhydrous Na$_2$SO$_4$, filtered, and concentrated in vacuo to give crude racemic 2,2-dimethyl-1-(phenylmethyl)-3-pyrrolidinamine (1.8247 g, >100% crude yield) as a light yellow oil. LCMS: (M+H)$^+$: 205.2.

Part G:

N,N,2,2-Tetramethyl-1-(phenylmethyl)-3-pyrrolidinamine

A solution of racemic 2,2-dimethyl-1-(phenylmethyl)-3-pyrrolidinamine (assumed 1.6169 g, 7.914 mmol) in formic acid (15 mL) and formalin (15 mL) was heated at 100° C. and stirred for 3 h. The solution was then cooled to 0° C. and adjusted to pH 14 with 6 N aq. NaOH. The mixture was extracted with Et$_2$O (3×100 mL), and the combined organic phase was dried over anhydrous Na$_2$SO$_4$, filtered, and concentrated in vacuo. The residue was purified by Gilson RPLC to give racemic N,N,2,2-tetramethyl-1-(phenylmethyl)-3-pyrrolidinamine (0.5637 g, 31% yield for 2 steps) as an orange oil. LCMS: (M+H)$^+$: 233.3.

Part H:

N,N,2,2-Tetramethyl-3-pyrrolidinamine

To a solution of racemic N,N,2,2-tetramethyl-1-(phenylmethyl)-3-pyrrolidinamine (0.5637 g, 2.426 mmol) in MeOH (24 mL) was added 1 N aq. HCl (4.9 ml) and 10% Pd/C (50% water, 113 mg). The mixture was hydrogenated overnight, and then filtered through a 0.2 μM membrane. The resulting solution was concentrated in vacuo. The residue was diluted with 1 N aq. NaOH (20 mL) and extracted with DCM (2×100 mL). The combined organic phase was dried over anhydrous Na$_2$SO$_4$, filtered, and concentrated in vacuo to afford crude, racemic N,N,2,2-tetramethyl-3-pyrrolidinamine (0.2930 g, 85% yield) as a pale yellow oil. LCMS: (M+H)$^+$: 143.1.

Part I:

Tris(1,1-dimethylethyl)2-{2-chloro-6-[3-(dimethylamino)-2,2-dimethyl-1-pyrrolidinyl]-5-fluoro-4-pyrimidinyl}-1,1,2-hydrazinetricarboxylate To a solution of racemic N,N,2,2-tetramethyl-3-pyrrolidinamine (0.1466 g, 1.031 mmol) in DMF (6 mL) was added N,N-diisopropylethylamine (0.220 mL, 1.263 mmol) and tris (1,1-dimethylethyl)2-(2,6-dichloro-5-fluoro-4-pyrimidinyl)-1,1,2-hydrazinetricarboxylate (0.513 g, 1.031 mmol), and the solution was stirred overnight. The solution was partitioned between Et$_2$O (100 mL) and water (20 mL), and the organic phase was washed with a fresh portion of water (20 mL). The combined aqueous phase was extracted with a fresh portion of Et$_2$O (50 mL), and the combined organic phase was dried over anhydrous Na$_2$SO$_4$, filtered, and concentrated in vacuo. The residue was purified by gradient silica gel chromatography (0% to 100% EtOAc in hexanes) to give racemic tris(1,1-dimethylethyl)2-{2-chloro-6-[3-(dimethylamino)-2,2-dimethyl-1-pyrrolidinyl]-5-fluoro-4-pyrimidinyl}-1,1,2-hydrazinetricarboxylate (0.4647 g, 75% yield) as a white foam. LCMS: (M+H)$^+$: 603.3.

Part J:

1-(2-Chloro-5-fluoro-6-hydrazino-4-pyrimidinyl)-N,N,2,2-tetramethyl-3-pyrrolidinamine Pentahydrochloride To a solution of racemic tris(1,1-dimethylethyl)2-{2-chloro-6-[3-(dimethylamino)-2,2-dimethyl-1-pyrrolidinyl]-5-fluoro-4-pyrimidinyl}-1,1,2-hydrazinetricarboxylate (0.4618 g, 0.766 mmol) in MeOH (5 mL) was added 4 N HCl in dioxane (5 mL). The solution was stirred for 3 days, and then concentrated in vacuo to afford racemic 1-(2-chloro-5-fluoro-6-hydrazino-4-pyrimidinyl)-N,N,2,2-tetramethyl-3-pyrrolidinamine pentahydrochloride (0.3673 g, 99% yield) as an orange oil that crystallized under vacuum. LCMS: (M+H)$^+$: 303.1.

Part K:

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide To a solution of racemic 1-(2-chloro-5-fluoro-6-hydrazino-4-pyrimidinyl)-N,N,2,2-tetramethyl-3-pyrrolidinamine pentahydrochloride (0.3649 g, 0.752 mmol) in DMF (5 mL) was added (2R)-3-cyclopentyl-2-({formyl[(phenylmethyl)oxy]amino}methyl)propanoic acid (0.2140 g, 0.701 mmol), N-methylmorpholine (0.770 mL, 7.00 mmol), 1-hydroxy-7-azabenzotriazole (114 mg, 0.838 mmol), and EDC (161 mg, 0.840 mmol). The solution was stirred overnight and purified directly by Gilson RPLC to provide [(2R)-3-(2-{2-chloro-6-[3-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide (0.1755 g, 42% yield, mixture of diastereomers) as a brown oil. LCMS: (M+H)$^+$: 590.4.

Part L:

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide To a solution of [(2R)-3-(2-{2-chloro-6-[3-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide (0.1737 g, 0.294 mmol) in MeOH (10 mL) was added 5% Rh/C (175 mg). The mixture was hydrogenated at 50 psi overnight, and was then filtered through a 0.2 μM membrane and concentrated in vacuo. To a solution of the residue in MeOH (4 mL) was added 20% Pd(OH)$_2$/C (50% water, 5 mg). The mixture was hydrogenated under balloon pressure for 50 min. The mixture was then filtered though a 0.2 μM membrane, and the solution was concentrated in vacuo. The residue was purified by Gilson RPLC to give [(2R)-3-(2-{2-chloro-6-[3-(dimethylamino)-2, 2-dimethyl-1-pyrrolidinyl]-5-fluoro-4-pyrimidinyl}hydrazino)-2-(cyclopentylmethyl)-3-oxopropyl]hydroxyformamide (0.0670 g, 46% yield, mixture of diastereomers) as a while solid following crystallization from EtOAc-hexanes. LCMS: (M+H)+: 500.3.

Example 153

[(2R)-2-(Cyclopentylmethyl)-3-(2-{5-fluoro-2-methyl-6-[3-(3-pyridinyl)-1-pyrrolidinyl]-4-pyrimidinyl}hydrazino)-3-oxopropyl]hydroxyformamide (Mixture of Diastereomers)

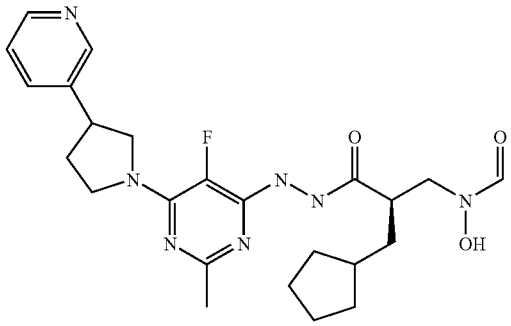

[(2R)-2-(Cyclopentylmethyl)-3-(2-{5-fluoro-2-methyl-6-[3-(3-pyridinyl)-1-pyrrolidinyl]-4-pyrimidinyl}hydrazino)-3-oxopropyl]hydroxyformamide was prepared according to General Procedure A, utilizing commercially-available 3-(3-pyrrolidinyl)pyridine in place of pyrrolidine in Part A. (Mixture of diastereomers) LCMS: (M+H)+ 486.3.

Example 154

((2R)-2-(Cyclopentylmethyl)-3-{2-[5-fluoro-6-[2-(hydroxymethyl)-4-morpholinyl]-2-(methylthio)-4-pyrimidinyl]hydrazino}-3-oxopropyl)hydroxyformamide

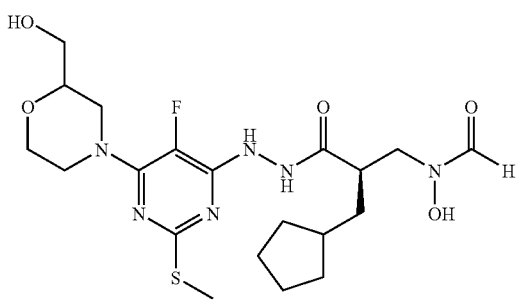

((2R)-2-(Cyclopentylmethyl)-3-{2-[5-fluoro-6-[2-(hydroxymethyl)-4-morpholinyl]-2-(methylthio)-4-pyrimidinyl]hydrazino}-3-oxopropyl)hydroxyformamide was prepared according to General Procedure C, utilizing commercially-available 2-morpholinylmethanol in place of azetidine hydrochloride in Part A. (Mixture of diastereomers) LCMS: (M+H)+ 487.5.

Example 155

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide (D1, Single Unknown Diastereomer)

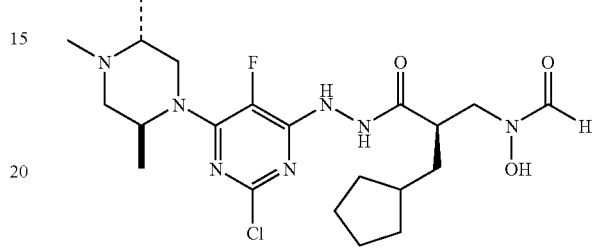

Part A:

Phenylmethyl (trans)-2,5-dimethyl-1-piperazinecarboxylate (Enantiomeric Mixture)

To a solution of (2R,5S)-2,5-dimethylpiperazine (commercially available) (3.495 g, 30 mmol) in dichloromethane (25 mL) at 0° C. was added triethylamine (3.76 mL, 27 mmol) followed by dropwise benzyl chloroformate (4.0 mL, 27 mmol). The reaction mixture was allowed to warm to room temperature and stirred overnight. The solvent was then evaporated to dryness. The residue was taken up in aqueous 1N HCl solution and washed with EtOAc. The organic layer was extracted with 1N HCl solution twice and the combined aqueous layers were basicified with 6N NaOH to ~pH 11. The resulting basic aqueous solution was extracted with EtOAc three times. The combined organic layers were washed with brine, dried (MgSO4) and evaporated to yield phenylmethyl trans-2,5-dimethyl-1-piperazinecarboxylate (enantiomeric mixture) (1.35 g, 18%). LCMS: (M+H)+: 249.1.

Part B:

Phenylmethyl trans-2,4,5-trimethyl-1-piperazinecarboxylate (Enantiomer 1)

To a solution of phenylmethyl trans-2,5-dimethyl-1-piperazinecarboxylate (enantiomeric mixture) (1.35 g, 5.43 mmol) in dichloromethane (40 mL) at 0° C. was added formaldehyde (0.817 mL, 37% water solution, 10.87 mmol) followed by sodium triacetoxyborohydride (1.726 g, 8.14 mmol). The reaction mixture was allowed to warm to room temperature and stirred for 2 h before being diluted with dichloromethane and washed with 1N NaOH solution. The organics were washed with brine, dried (MgSO4) and evaporated to yield phenylmethyl trans-2,4,5-trimethyl-1-piperazinecarboxylate (enantiomeric mixture) (1.42 g, 100%). Phenylmethyl trans-2,4,5-trimethyl-1-piperazinecarboxylate (enantiomer 1) (480 mg) and phenylmethyl trans-2,4,5-trimethyl-1-piperazinecarboxylate (enantiomer 2) (400 mg) were separated by chiral chromatography. LCMS: (M+H)+: 263.3.

Part C:

trans-1,2,5-Trimethylpiperazine, hydrochloride salt (Enantiomer 1)

Phenylmethyl trans-2,4,5-trimethyl-1-piperazinecarboxylate (Enantiomer 1) (480 mg, 1.83 mmol) was dissolved in 30 mL of MeOH, degassed and placed under argon. 10% Pd/C (96 mg) was added, and the contents were thoroughly degassed and placed under a hydrogen balloon for approximately 3 hrs. The contents were then degassed and filtered through Celite, and the Celite pad was washed with DCM and MeOH. 1N HCl (3.8 mL) was added to the resulting filtrate, which was concentrated in vacuo to provide the trans-1,2,5-trimethylpiperazine, hydrochloride salt (enantiomer 1) (370 mg, 100%). LCMS: (M+H)$^+$: 129.1.

Part D:

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide (D1, Single Unknown Diastereomer)

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide was prepared according to General Procedure G, utilizing trans-1,2,5-trimethylpiperazine, hydrochloride salt (enantiomer 1) in place of (1S,4S)-2-methyl-2,5-diazabicyclo[2.2.1]heptane, dihydrobromide in Part A. LCMS: (M+H)$^+$: 486.1.

Example 156

{(2R)-2-(Cyclopentylmethyl)-3-[2-(6-{(3R)-3-[(dimethylamino)methyl]-4-morpholinyl}-5-fluoro-2-methyl-4-pyrimidinyl)hydrazino]-3-oxopropyl}hydroxyformamide

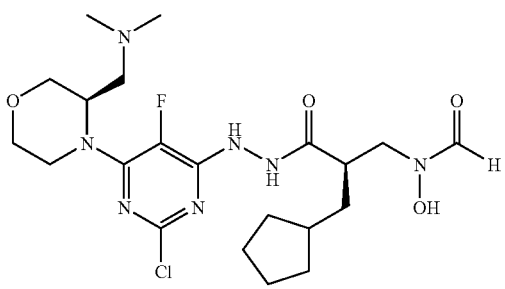

Part A:

(3S)—N,N-Dimethyl-5-oxo-4-(phenylmethyl)-3-morpholinecarboxamide

To a solution of (3S)-5-oxo-4-(phenylmethyl)-3-morpholinecarboxylic acid (1.5 g, 6.4 mmol) (J. Chem. Soc., Perkin Trans. 1, 1985, 2577-2580) in THF (50 mL) was added dimethylamine (3.8 mL, 7.6 mmol, 2M in THF), EDC (1.46 g, 7.7 mmol), HOAt (1.06 g, 7.7 mmol) and NMM (3.5 mL, 30 mmol). The reaction mixture was stirred overnight and the THF was evaporated, replacing it with EtOAc. 1 M HCl was added and the phases were separated. The aqueous layer was extracted twice with EtOAc and the combined organics were dried over sodium sulfate. Concentration in vacuo yielded (3S)—N,N-dimethyl-5-oxo-4-(phenylmethyl)-3 morpholinecarboxamide, which was purified by RP-HPLC. LCMS: (M+H)$^+$: 263.1.

Part B:

Dimethyl{[(3R)-4-(phenylmethyl)-3-morpholinyl]methyl}amine (3S)—N,N-Dimethyl-5-oxo-4-(phenylmethyl)-3 morpholinecarboxamide (390 mg, 1.5 mmol) was dissolved in THF (20 mL) and the solution was cooled to 0° C. LiAlH$_4$ (225 mg, 5.9 mmol) was added and the resulting mixture was refluxed overnight. Upon cooling to 0° C., water (1.4 mL) was added followed by 15% (w/w) NaOH (aq) (1.4 mL) and finally another portion of water (4.2 mL). Stirring for 30 min followed by filtration and concentration in vacuo yielded a crude mixture which was purified by RP-HPLC to provide dimethyl{[(3R)-4-(phenylmethyl)-3-morpholinyl]methyl}amine (510 mg, 41%). LCMS: (M+H)$^+$: 235.2.

Part C:

Dimethyl[(3R)-3-morpholinylmethyl]amine.HCl

To a solution of dimethyl{[(3R)-4-(phenylmethyl)-3-morpholinyl]methyl}amine (510 mg) in degassed MeOH and 4 drops of concentrated HCl was added 10% (Pd/C) (100 mg). The resulting mixture was hydrogenated at 50 psi on a Parr shaker for 3 hours before being filtered and concentrated in vacuo. This yielded dimethyl[(3R)-3-morpholinylmethyl] amine as the hydrochloride salt. LCMS: (M+H)$^+$: 145.2.

Part D:

{(2R)-2-(Cyclopentylmethyl)-3-[2-(6-{(3R)-3-[(dimethylamino)methyl]-4-morpholinyl}-5-fluoro-2-methyl-4-pyrimidinyl)hydrazino]-3-oxopropyl}hydroxyformamide {(2R)-2-(Cyclopentylmethyl)-3-[2-(6-{(3R)-3-[(dimethylamino)methyl]-4-morpholinyl}-5-fluoro-2-methyl-4-pyrimidinyl)hydrazino]-3-oxopropyl}hydroxyformamide was prepared according to General Procedure E, utilizing dimethyl[(3R)-3-morpholinylmethyl]amine hydrochloride in place of isopropyl amine in Part A. LCMS: (M+H)$^+$: 502.2.

Example 157

[(2R)-3-[2-(2-Chloro-5-fluoro-6-{[2-methyl-2-(4-morpholinyl)propyl]amino}-4-pyrimidinyl)hydrazino]-2-(cyclopentylmethyl)-3-oxopropyl]hydroxyformamide

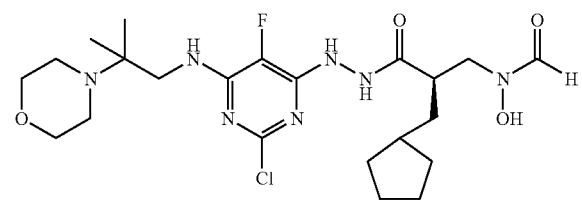

Part A:

Tris(1,1-dimethylethyl)2-(2-chloro-5-fluoro-6-{[2-methyl-2-(4-morpholinyl)propyl]amino}-4-pyrimidinyl)-1,1,2-hydrazinetricarboxylate To a stirred solution of commercially-available [2-methyl-2-(4-morpholinyl)propyl]amine (0.158 g, 1.00 mmol) in DMF (10 mL) under a nitrogen atmosphere at 0° C., was added diisopropylethylamine (0.19 mL, 1.1 mmol) followed immediately by tris(1,1-dimethylethyl)2-(2,6-dichloro-5-fluoro-4-pyrimidinyl)-1,1,2-hydrazinetricarboxylate (0.497 g, 1.00 mmol). The reaction was allowed to reach room temperature and was stirred overnight. Then ether was added, and the mixture was washed with water. The aqueous layer was back extracted with ether, and the combined organics were dried (Na$_2$SO$_4$) and concentrated in vacuo. The resulting residue was purified by silica gel chromatography (5-60% ethyl acetate in hexanes, 1% triethylamine) to provide tris(1,1-dimethylethyl)2-(2-chloro-5-fluoro-6-{[2-methyl-2-(4-morpholinyl)propyl]amino}-4-pyrimidinyl)-1,1,2-hydrazinetricarboxylate as a clear oil (0.578 g, 94%). LCMS: (M+H)$^+$=619.4.

Part B:

2-Chloro-5-fluoro-6-{[2-methyl-2-(4-morpholinyl)propyl]amino}-4(1H)-pyrimidinone hydrazone To a suspension of tris(1,1-dimethylethyl)2-(2-chloro-5-fluoro-6-{[2-methyl-2-(4-morpholinyl)propyl]amino}-4-pyrimidinyl)-1,1,2-hydrazinetricarboxylate (0.578 g, 0.94 mmol) in MeOH (8 mL) was added 4M HCl in 1,4-dioxane (8 mL), and the resulting mixture was stirred at room temperature overnight. The solvent was removed in vacuo, and the crude residue was treated with an aqueous K$_2$CO$_3$ extractive workup to provide 2-chloro-5-fluoro-6-{[2-methyl-2-(4-morpholinyl)propyl]amino}-4(1H)-pyrimidinone hydrazone as a brown oil (0.249 g). LCMS: (M+H)$^+$=319.2.

Part C:

[(2R)-3-[2-(2-Chloro-5-fluoro-6-{[2-methyl-2-(4-morpholinyl)propyl]amino}-4-pyrimidinyl)hydrazino]-2-(cyclopentylmethyl)-3-oxopropyl][(phenylmethyl)oxy]formamide (2R)-3-Cyclopentyl-2-({formyl[(phenylmethyl)oxy]amino}methyl)propanoic acid (0.238 g, 0.78 mmol), 2-chloro-5-fluoro-6-{[2-methyl-2-(4-morpholinyl)propyl]amino}-4(1H)-pyrimidinone hydrazone (0.249 g), NMM (0.26 mL, 2.35 mmol), HOAt (0.106 g, 0.78 mmol), EDC (0.150 g, 0.78 mmol) and DMF (4 mL) were combined, and the solution was stirred overnight. Purification by RP-HPLC provided [(2R)-3-[2-(2-chloro-5-fluoro-6-{[2-methyl-2-(4-morpholinyl)propyl]amino}-4-pyrimidinyl)hydrazino]-2-(cyclopentylmethyl)-3-oxopropyl][(phenylmethyl)oxy]formamide as a brown oil (0.169 g). LCMS: (M+H)$^+$=606.3.

Part D:

[(2R)-3-[2-(2-Chloro-5-fluoro-6-{[2-methyl-2-(4-morpholinyl)propyl]amino}-4-pyrimidinyl)hydrazino]-2-(cyclopentylmethyl)-3-oxopropyl]hydroxyformamide

[(2R)-3-[2-(2-Chloro-5-fluoro-6-{[2-methyl-2-(4-morpholinyl)propyl]amino}-4-pyrimidinyl)hydrazino]-2-(cyclopentylmethyl)-3-oxopropyl][(phenylmethyl)oxy]formamide (0.169 g, 0.28 mmol) and Pd(OH)$_2$ (0.017 g) were treated as described in General Procedure E, Part D, to provide [(2R)-3-[2-(2-chloro-5-fluoro-6-{[2-methyl-2-(4-morpholinyl)propyl]amino}-4-pyrimidinyl)hydrazino]-2-(cyclopentylmethyl)-3-oxopropyl]hydroxyformamide as a white solid (0.070 g, 49%). LCMS: (M+H)$^+$=516.3.

Example 158

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide (D2, Single Unknown Diastereomer)

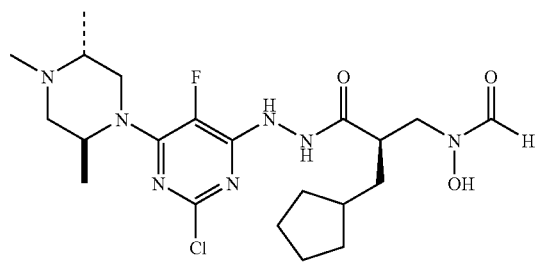

Part A:

trans-1,2,5-Trimethylpiperazine, hydrochloride salt (Enantiomer 2)

Phenylmethyl trans-2,4,5-trimethyl-1-piperazinecarboxylate (enantiomer 2) (Example 155, Part B) (400 mg, 1.52 mmol) was dissolved in 30 mL of MeOH, degassed and placed under argon. 10% Pd/C (80 mg) was added, and the contents were thoroughly degassed and placed under a hydrogen balloon for approximately 3 hrs. The contents were then degassed and filtered through Celite, and the Celite pad was washed with DCM and MeOH. 1N HCl (3.2 mL) was added to the resulting filtrate, which was concentrated in vacuo to provide the trans-1,2,5-trimethylpiperazine, hydrochloride salt (enantiomer 2) (370 mg, 100%). LCMS: (M+H)$^+$: 129.1.

Part B:

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide (D2, Single Unknown Diastereomer)

N-[(2R)-3-(2-{2-Chloro-5-fluoro-6-(trans-2,4,5-trimethyl-1-piperazinyl)-4-pyrimidinyl}hydrazino)-2-(cyclopentylmethyl)-3-oxopropyl]-N-hydroxyformamide was prepared according to General Procedure G, utilizing trans-1,2,5-trimethylpiperazine, hydrochloride salt (enantiomer 2) in place of (1S,4S)-2-methyl-2,5-diazabicyclo[2.2.1]heptane, dihydrobromide in Part A. LCMS: (M+H)$^+$: 486.1.

Example 159

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl]hydroxyformamide (D1, Single Unknown Diastereomer)

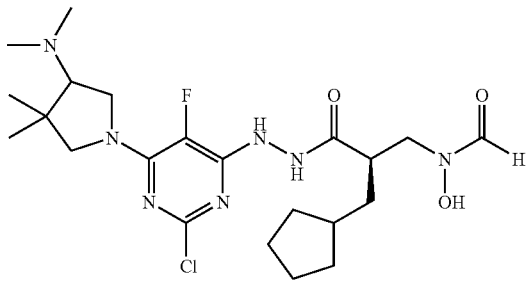

Part A:

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide To a solution of racemic 1-(2-chloro-5-fluoro-6-hydrazino-4-pyrimidinyl)-N,N,4,4-tetramethyl-3-pyrrolidinamine (7.37 g, 24.34 mmol, prepared according to the procedures of Example 133) in DMF (77 mL) was added (2R)-3-cyclopentyl-2-({formyl[(phenylmethyl)oxy]amino}methyl)propanoic acid (7.08 g, 23.18 mmol), N-methylmorpholine (12.75 mL, 116.0 mmol), 1-hydroxy-7-azabenzotriazole (3.79 g, 27.85 mmol), and EDC (5.33 g, 27.80 mmol). The solution was stirred overnight and was then diluted with Et₂O (100 mL) and washed with water (3×100 mL). The combined aqueous phase was extracted with a fresh portion of Et₂O (100 mL), and this organic phase was washed with a fresh portion of water (50 mL). The combined organic phase was dried over anhydrous Na₂SO₄, filtered, and concentrated in vacuo. The residue was diluted with EtOAc (200 mL), and the resulting solution was dried over anhydrous Na₂SO₄, filtered, and concentrated in vacuo to afford crude [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (12.52 g, 92% yield, mixture of diastereomers). LCMS: (M+H)⁺: 590.2.

The diastereomeric mixture was purified and separated by chiral preparative supercritical fluid chromatography (Chiralcel OJ-H 21.2×250 mm, 15% MeOH (0.5% isopropylamine) 85% CO₂, 70 mL/min, 35° C., 280 nM detection, 16 mg injection per cycle) to give both enantiomers in pure form.

Part B:

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (D1, Single Unknown Diastereomer)

To a solution of the first eluting enantiomer of [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (3.90 g, 6.61 mmol) in MeOH (66 mL) was added 20% Pd(OH)₂/C (50% water, 390 mg). The mixture was hydrogenated for 30 min under balloon pressure, and was then filtered through a 0.2 μM membrane. The solution was concentrated in vacuo and the residue was purified by Gilson RPLC. The desired fractions were combined, concentrated in vacuo, and azeotroped with MeOH. The residue was crystallized from EtOAc-hexanes to give [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (1.6820 g, 51% yield, single enantiomer, unknown relative configuration) as a light pink solid. LCMS: (M+H)⁺: 500.3.

Example 160

[(2R)-3-(2-{2-Chloro-6-[4-(dimethylamino)-3,3-dimethyl-1-pyrrolidinyl]-5-fluoro-4-pyrimidinyl}hydrazino)-2-(cyclopentylmethyl)-3-oxopropyl]hydroxyformamide (D2, Single Unknown Diastereomer)

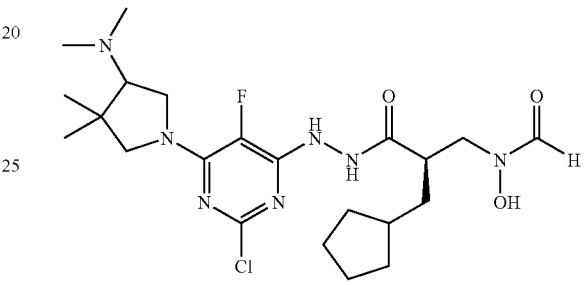

To a solution of the second eluting enantiomer of [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (3.1 g, 5.25 mmol, as per Example 159) in MeOH (50 mL) was added 20% Pd(OH)₂/C (50% water, 310 mg). The mixture was hydrogenated for 30 min under balloon pressure, and was then filtered. The solution was concentrated in vacuo and the residue was purified by Gilson RPLC. The desired fractions were combined, concentrated in vacuo, and azeotroped with MeOH followed by EtOAc. The residue was crystallized from EtOAc-hexanes to give [(2R)-3-(2-{2-chloro-6-[4-(dimethylamino)-3,3-dimethyl-1-pyrrolidinyl]-5-fluoro-4-pyrimidinyl}hydrazino)-2-(cyclopentylmethyl)-3-oxopropyl][(phenylmethyl)oxy]formamide (1.0294 g, 39% yield, single enantiomer, unknown relative configuration) as a light pink solid. LCMS: (M+H)⁺: 500.3.

Example 161

[(2R)-3-(2-{2-Chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl]hydroxyformamide (Mixture of Diastereomers)

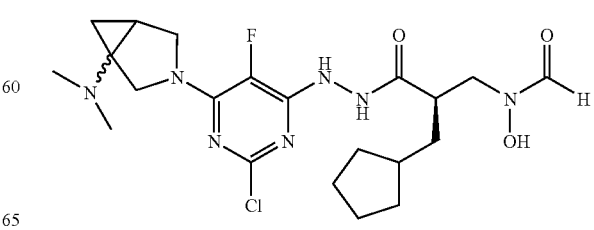

Part A:

N,N-Dimethyl-3-(phenylmethyl)-3-azabicyclo[3.1.0]hexan-1-amine

A solution of racemic 3-(phenylmethyl)-3-azabicyclo[3.1.0]hexan-1-amine (Tetrahedron Lett. 2003, 44, 2485) (0.5930 g, 3.150 mmol) in formic acid (6 mL) and formalin (6 mL) was heated at 100° C. and stirred for 2 h. The solution was then cooled to room temperature and adjusted to pH 14 with 6 N aq. NaOH. The mixture was extracted with Et$_2$O (2×100 mL), and the combined organic phase was dried over anhydrous Na$_2$SO$_4$, filtered, and concentrated in vacuo. The residue was purified by silica gel chromatography (4% MeOH in DCM, 1% Et$_3$N) to afford racemic N,N-dimethyl-3-(phenylmethyl)-3-azabicyclo[3.1.0]hexan-1-amine (0.5806 g, 85%) as a yellow oil. LCMS: (M+H)$^+$: 217.2.

Part B:

N,N-Dimethyl-3-azabicyclo[3.1.0]hexan-1-amine dihydrochloride

To a solution of racemic N,N-dimethyl-3-(phenylmethyl)-3-azabicyclo[3.1.0]hexan-1-amine (0.5800 g, 2.681 mmol) in MeOH (13 mL) was added 1 N aq. HCl (5.4 mL, 5.4 mmol) and 10% Pd/C (50% water, 120 mg). The mixture was hydrogenated under balloon pressure overnight, and then filtered. The solution was concentrated in vacuo and azeotroped with MeOH (4×50 mL) to give crude, racemic N,N-dimethyl-3-azabicyclo[3.1.0]hexan-1-amine dihydrochloride (0.5453 g, >100% crude yield) as a light yellow foam. LCMS: (M+H)$^+$: 127.2.

Part C:

Tris(1,1-dimethylethyl)2-{2-chloro-6-[1-(dimethylamino)-3-azabicyclo[3.1.0]hex-3-yl]-5-fluoro-4-pyrimidinyl}-1,1,2-hydrazinetricarboxylate To a solution of racemic N,N-dimethyl-3-azabicyclo[3.1.0]hexan-1-amine dihydrochloride (assumed 0.5339 g, 2.681 mmol) in DMF (13 mL) was added tris(1,1-dimethylethyl) 2-(2,6-dichloro-5-fluoro-4-pyrimidinyl)-1,1,2-hydrazinetricarboxylate (1.33 g, 2.674 mmol) and N,N-diisopropylethylamine (1.87 mL, 10.74 mmol). The solution was stirred overnight and then diluted with Et$_2$O (100 mL). The mixture was washed with water (2×50 mL), and the combined aqueous phase was extracted with a fresh portion of Et$_2$O (50 mL). The combined organic phase was dried over anhydrous Na$_2$SO$_4$, filtered, and concentrated in vacuo. The residue was purified by gradient silica gel chromatography (0% to 100% EtOAc in hexanes; 1% Et$_3$N) to afford racemic tris(1,1-dimethylethyl)2-{2-chloro-6-[1-(dimethylamino)-3-azabicyclo[3.1.0]hex-3-yl]-5-fluoro-4-pyrimidinyl}-1,1,2-hydrazinetricarboxylate (1.3261 g, 84%) as a white foam. LCMS: (M+H)$^+$: 587.3.

Part D:

3-(2-Chloro-5-fluoro-6-hydrazino-4-pyrimidinyl)-N,N-dimethyl-3-azabicyclo[3.1.0]hexan-1-amine To a solution of racemic tris(1,1-dimethylethyl)2-{2-chloro-6-[1-(dimethylamino)-3-azabicyclo[3.1.0]hex-3-yl]-5-fluoro-4-pyrimidinyl}-1,1,2-hydrazinetricarboxylate (1.3231 g, 2.254 mmol) in MeOH (13 mL) was added 4 N HCl in dioxane (13 mL). The solution was stirred for 3 days, and was then concentrated in vacuo. The residue was partitioned between 10% aq. K$_2$CO$_3$ and DCM, and the aqueous phase was extracted with a fresh portion of DCM. The combined organic phase was dried over anhydrous Na$_2$SO$_4$, filtered, and concentrated in vacuo to give racemic 3-(2-chloro-5-fluoro-6-hydrazino-4-pyrimidinyl)-N,N-dimethyl-3-azabicyclo[3.1.0]hexan-1-amine (0.3415 g, 53%) as a brown solid. LCMS: (M+H)$^+$: 287.1.

Part E:

[(2R)-3-(2-{2-Chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl][(phenylmethyl)oxy]formamide To a solution of racemic 3-(2-chloro-5-fluoro-6-hydrazino-4-pyrimidinyl)-N,N-dimethyl-3-azabicyclo[3.1.0]hexan-1-amine (0.3374 g, 1.177 mmol) in DMF (10 mL) was added (2R)-3-cyclopentyl-2-({formyl[(phenylmethyl)oxy]amino}methyl)propanoic acid (0.3257 g, 1.067 mmol), N-methylmorpholine (0.590 mL, 5.366 mmol), 1-hydroxy-7-azabenzotriazole (0.174 g, 1.278 mmol), and EDC (0.245 g, 1.278 mmol). The mixture was stirred overnight, and then diluted with Et$_2$O (100 mL). The mixture was washed with water (2×50 mL), and the combined aqueous phase was extracted with a fresh portion of Et$_2$O (50 mL). This organic phase was washed with a fresh portion of water (50 mL), and the combined organic phase was dried over anhydrous Na$_2$SO$_4$, filtered, and concentrated in vacuo. The residue was diluted with DCM (200 mL), and dried over anhydrous Na$_2$SO$_4$. The mixture was filtered and concentrated in vacuo to provide crude [(2R)-3-(2-{2-chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl][(phenylmethyl)oxy]formamide (0.6428 g, >100% crude yield, mixture of diastereomers) as an orange oil. LCMS: (M+H)$^+$: 574.2.

Part F:

[(2R)-3-(2-{2-Chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl]hydroxyformamide To a solution of [(2R)-3-(2-{2-chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl][(phenylmethyl)oxy]formamide (assumed 0.6123 g, 1.067 mmol) in MeOH (10 mL) was added 20% Pd(OH)$_2$/C (50% water, 61 mg). The mixture was hydrogenated for 6.5 h and then filtered. The filtrate was concentrated in vacuo and purified by Gilson RPLC to give [(2R)-3-(2-{2-chloro-6-[1-(dimethylamino)-3-azabicyclo[3.1.0]hex-3-yl]-5-fluoro-4-pyrimidinyl}hydrazino)-2-(cyclopentylmethyl)-3-oxopropyl]hydroxyformamide (0.2537 g, 49% yield for 2 steps, mixture of diastereomers) as a light pink solid. LCMS: (M+H)$^+$: 484.2.

Example 162

N-[(2R)-2-(Cyclopentylmethyl)-3-{2-[5-fluoro-2-methyl-6-(trans-2,4,5-trimethyl-1-piperazinyl)-4-pyrimidinyl]hydrazino}-3-oxopropyl]-N-hydroxyformamide (Single Unknown Diastereomer)

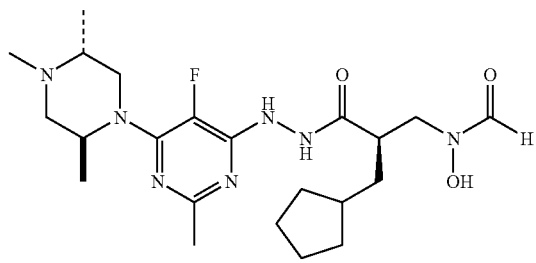

N-[(2R)-2-(Cyclopentylmethyl)-3-{2-[5-fluoro-2-methyl-6-(trans-2,4,5-trimethyl-1-piperazinyl)-4-pyrimidinyl]hydrazino}-3-oxopropyl]-N-hydroxyformamide (single unknown diastereomer) was prepared according to General Procedure A, utilizing trans-1,2,5-trimethylpiperazine, hydrochloride salt (enantiomer 2) (Example 158) in place of pyrrolidine in Part A, and using 3 equivalents of DIPEA. LCMS: (M+H)$^+$: 466.2.

Example 163

[(2R)-3-{2-[2-Chloro-6-(cyclopentylamino)-5-fluoro-4-pyrimidinyl]hydrazino}-2-(cyclopentylmethyl)-3-oxopropyl]hydroxyformamide

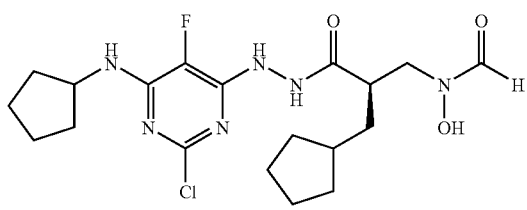

[(2R)-3-{2-[2-Chloro-6-(cyclopentylamino)-5-fluoro-4-pyrimidinyl]hydrazino}-2-(cyclopentylmethyl)-3-oxopropyl]hydroxyformamide was prepared according to General Procedure E, utilizing cyclopentylamine in place of isopropyl amine in Part A. LCMS: (M+H)$^+$: 443.2/445.4.

Example 164

[(2R)-3-(2-{2-Chloro-5-fluoro-6-[3-methyl-3-(4-morpholinyl)-1-azetidinyl]-4-pyrimidinyl}hydrazino)-2-(cyclopentylmethyl)-3-oxopropyl]hydroxyformamide

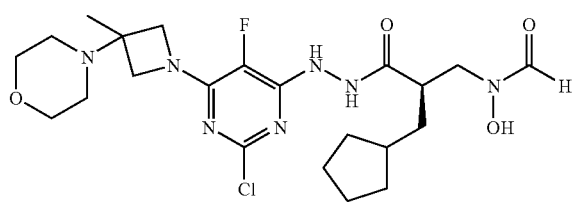

Part A:

4-[1-(Diphenylmethyl)-3-methyl-3-azetidinyl]morpholine 1-(Diphenylmethyl)-3-methyl-3-azetidinyl methanesulfonate was prepared according to reported procedure (J. Med. Chem., 1993, 36, 801-810). A mixture of this compound (1.50 g, 4.53 mmol) and morpholine (3.90 g, 45.3 mmol) in isopropanol (20 ml) was heated to 70° C. overnight. After cooling to room temperature, the mixture was concentrated to dryness in vacuo. Water (100 mL) was added, and the mixture was extracted with dichloromethane (2×100 mL). The combined organic solution was washed with brine (60 mL), dried (Na$_2$SO$_4$) and concentrated. The residue was purified via RP-HPLC to provide 4-[1-(diphenylmethyl)-3-methyl-3-azetidinyl]morpholine (1.05 g, 71.9%). LCMS: (M+H)$^+$ 323.3.

Part B:

4-(3-Methyl-3-azetidinyl)morpholine dihydrochloride

A mixture of 4-[1-(diphenylmethyl)-3-methyl-3-azetidinyl]morpholine (1.05 g, 3.26 mmol), 10% Pd(OH)$_2$ (0.12 g) in ethanol (30 ml) and 1N HCl (7 ml) was treated with H$_2$ at 60 psi overnight. The catalyst was removed by filtration, and the solvent was evaporated under vacuum. The residue was washed with benzene (3×5 ml) and dried under high vacuum to provide 4-(3-methyl-3-azetidinyl)morpholine dihydrochloride (0.52 g, 74.9%). LCMS: (M+H)$^+$ 156.9.

Part C:

[(2R)-3-(2-{2-Chloro-5-fluoro-6-[3-methyl-3-(4-morpholinyl)-1-azetidinyl]-4-pyrimidinyl}hydrazino)-2-(cyclopentylmethyl)-3-oxopropyl]hydroxyformamide

[(2R)-3-(2-{2-Chloro-5-fluoro-6-[3-methyl-3-(4-morpholinyl)-1-azetidinyl]-4-pyrimidinyl}hydrazino)-2-(cyclopentylmethyl)-3-oxopropyl]hydroxyformamide was prepared according to General Procedure D, utilizing 4-(3-methyl-3-azetidinyl)morpholine dihydrochloride in place of N-methylpiperazine in Part A. LCMS: (M+H)$^+$ 514.4.

Example 165

[(2R)-2-(Cyclopentylmethyl)-3-(2-{5-fluoro-2-methyl-6-[3-(4-pyridinyl)-1-pyrrolidinyl]-4-pyrimidinyl}hydrazino)-3-oxopropyl]hydroxyformamide

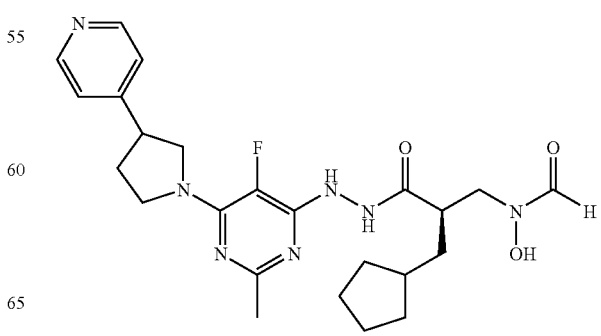

[(2R)-2-(Cyclopentylmethyl)-3-(2-{5-fluoro-2-methyl-6-[3-(4-pyridinyl)-1-pyrrolidinyl]-4-pyrimidinyl}hydrazino)-3-oxopropyl]hydroxyformamide was prepared in a manner similar to Example 182, utilizing 4-(3-pyrrolidinyl)pyridine in place of 1-(3-methyl-3-azetidinyl)pyrrolidine dihydrochloride in Part A. LCMS: (M+H)+ 486.2.

Example 166

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (D1, Single Unknown Diastereomer)

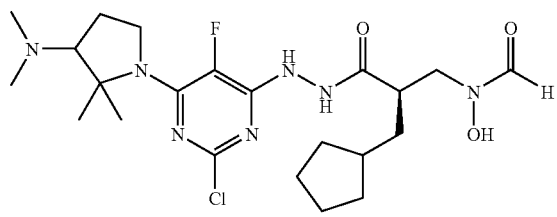

Part A:

2,2-Dimethyl-1-(phenylmethyl)-3-pyrrolidinamine

Racemic 2,2-dimethyl-1-(phenylmethyl)-3-pyrrolidinamine was prepared according the procedures described in Example 152. The enantiomers were separated by preparative LC (Chiralpak AD 20µ 100×250 mm column, 75:25:0.1 MeCN-MeOH-iPrNH₂, 400 mL/min, 254 nm detection) to provide the (+)- and (−)-enantiomers of 2,2-dimethyl-1-(phenylmethyl)-3-pyrrolidinamine.

Part B:

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide The (+)-enantiomer of 2,2-dimethyl-1-(phenylmethyl)-3-pyrrolidinamine was employed to prepare [(2R)-3-(2-{2-chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide according to the procedures of Example 152 as a single diastereomer with unknown relative configuration. LCMS: (M+H)+: 500.3.

Example 167

[(2R)-3-(2-{2-Chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (D2, Single Unknown Diastereomer)

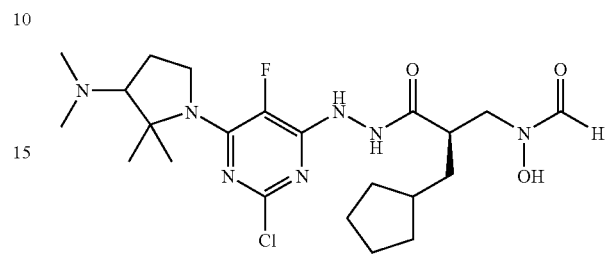

The (−)-enantiomer of 2,2-dimethyl-1-(phenylmethyl)-3-pyrrolidinamine, prepared according to the procedures of Example 166, was employed to prepare [(2R)-3-(2-{2-chloro-6-[3-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide as per Example 152 as a single diastereomer with unknown relative configuration. LCMS: (M+H)+: 500.3.

Example 168

[(2R)-3-{2-[2-Chloro-6-(cyclobutylamino)-5-fluoro-4-pyrimidinyl]hydrazino}-2-(cyclopentylmethyl)-3-oxopropyl]hydroxyformamide

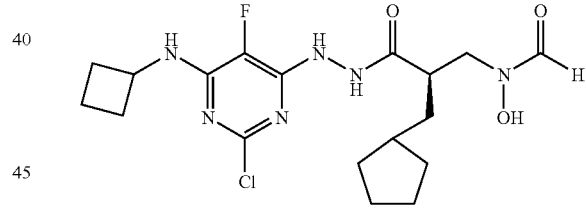

Part A:

Tris(1,1-dimethylethyl)2-[2-chloro-6-(cyclobutylamino)-5-fluoro-4-pyrimidinyl]-1,1,2-hydrazinetricarboxylate To a solution of tris(1,1-dimethylethyl)2-(2,6-dichloro-5-fluoro-4-pyrimidinyl)-1,1,2-hydrazinetricarboxylate (0.497 g, 1.0 mmol) in DMF (5 mL) at room temperature was added diisopropylethylamine (0.19 mL, 1.10 mmol) followed immediately by commercially available cyclobutylamine (0.085 mL, 1.0 mmol). The reaction was stirred for 4 days, then ether was added, and the mixture was washed with water and the aqueous layer was back extracted. The combined organics were dried (Na₂SO₄), concentrated in vacuo, and azeotroped once with MeOH to provide tris(1,1-dimethylethyl)2-[2-chloro-6-(cyclobutylamino)-5-fluoro-4-pyrimidinyl]-1,1,2-hydrazinetricarboxylate as a white solid.

Part B:

2-Chloro-6-(cyclobutylamino)-5-fluoro-4(1H)-pyrimidinone hydrazone

To a solution of tris(1,1-dimethylethyl)2-[2-chloro-6-(cyclobutylamino)-5-fluoro-4-pyrimidinyl]-1,1,2-hydrazinetricarboxylate (0.495 g, 0.96 mmol) in MeOH (10 mL) was added 4M HCl in 1,4-dioxane (10 mL). The reaction was stirred at room temperature overnight, then the solvent was evaporated, and the residue was treated with a standard $K_2CO_3$ aqueous workup to provide 2-chloro-6-(cyclobutylamino)-5-fluoro-4(1H)-pyrimidinone hydrazone as a reddish brown oil (0.225 g). LCMS: $(M+H)^+=232.0$.

Part C:

[(2R)-3-{2-[2-Chloro-6-(cyclobutylamino)-5-fluoro-4-pyrimidinyl]hydrazino}-2-(cyclopentylmethyl)-3-oxopropyl][(phenylmethyl)oxy]formamide To a stirred solution of (2R)-3-cyclopentyl-2-({formyl[(phenylmethyl)oxy]amino}methyl)propanoic acid (0.282 g, 0.92 mmol), 2-chloro-6-(cyclobutylamino)-5-fluoro-4(1H)-pyrimidinone hydrazone (0.225 g), HOAt (0.132 g, 0.97 mmol) and NMM (0.53 mL, 4.85 mmol) in DMF (5 mL) was added EDC (0.186 g, 0.97 mmol) and the reaction was stirred overnight. The mixture was diluted with ether, washed with water, and the aqueous layer was back extracted with ether. The organics were dried ($Na_2SO_4$) and concentrated in vacuo. The resulting residue was purified by RP-HPLC to provide [(2R)-3-{2-[2-chloro-6-(cyclobutylamino)-5-fluoro-4-pyrimidinyl]hydrazino}-2-(cyclopentylmethyl)-3-oxopropyl][(phenylmethyl)oxy]formamide as a brown oil (0.055 g). LCMS: $(M+H)^+=519.2$.

Part D:

[(2R)-3-{2-[2-Chloro-6-(cyclobutylamino)-5-fluoro-4-pyrimidinyl]hydrazino}-2-(cyclopentylmethyl)-3-oxopropyl]hydroxyformamide

[(2R)-3-{2-[2-Chloro-6-(cyclobutylamino)-5-fluoro-4-pyrimidinyl]hydrazino}-2-(cyclopentylmethyl)-3-oxopropyl][(phenylmethyl)oxy]formamide (0.055 g, 0.106 mmol) was dissolved in MeOH (5 mL) at room temperature. $Pd(OH)_2$ (0.006 g) was added and the contents were stirred under a hydrogen balloon for 4 hours. The contents were filtered to remove the catalyst, and the filtrate was concentrated in vacuo. The above procedure was repeated 3 more times. Twice $Pd(OH)_2$ (0.010 g) was used and the third time $Pd(OH)_2$ (0.015 g) was used and The reaction was stirred for 5.5 hours. The contents were filtered to remove the catalyst, and the filtrate was concentrated in vacuo. The resulting crude product was purified by RP-HPLC to provide [(2R)-3-{2-[2-chloro-6-(cyclobutylamino)-5-fluoro-4-pyrimidinyl]hydrazino}-2-(cyclopentylmethyl)-3-oxopropyl]hydroxyformamide as a tan solid (0.005 g, 11%). LCMS: $(M+H)^+=428.9$.

Example 169

[(2R)-3-(2-{2-Chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl]hydroxyformamide

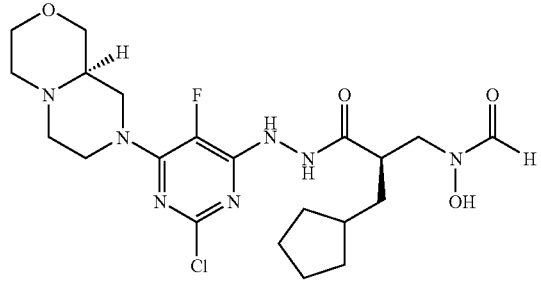

Part A:

(3S)-5-Oxo-4-(phenylmethyl)-3-morpholinecarboxylic acid

To a 0° C. solution of N-benzylserine (19.15 g, 105.7 mmol) in 2 N aq. NaOH (100 mL) was added chloroacetyl chloride (10.2 mL, 126.4 mmol) dropwise, and the solution was stirred for 45 min. To the solution was added 30% aq. NaOH (40 mL) dropwise, and the reaction was stirred for 1 h, and then stirred and warmed to room temperature for 72 h. The reaction was adjusted to pH 1 and extracted with three portions of EtOAc. The combined organic phase was dried over anhydrous $Na_2SO_4$, filtered, and concentrated in vacuo. The residue was washed with EtOAc/hexane to give (3S)-5-oxo-4-(phenylmethyl)-3-morpholinecarboxylic acid (4.61 g, 19% yield).

Part B:

(3S)-5-Oxo-N,4-bis(phenylmethyl)-3-morpholinecarboxamide

To a solution of (3S)-5-oxo-4-(phenylmethyl)-3-morpholinecarboxylic acid (4.611 g, 19.60 mmol) in DCM (65 mL) was added benzylamine (2.6 mL, 23.80 mmol), N-methylmorpholine (11 mL, 100.0 mmol), 1-hydroxy-7-azabenzotriazole (3.20 g, 23.51 mmol), and EDC (4.51 g, 23.53 mmol). The solution was stirred overnight and then diluted with DCM (100 mL). The solution was washed with 6 N aq. HCl (2×100 mL), and the organic phase was dried over anhydrous $MgSO_4$, filtered, and concentrated in vacuo to provide crude (3S)-5-oxo-N,4-bis(phenylmethyl)-3-morpholinecarboxamide (6.454 g, >100% crude yield) as a pale yellow foam. LCMS: $(M+H)^+$: 325.2.

Part C:

1-Phenyl-N-{[(3R)-4-(phenylmethyl)-3-morpholinyl]methyl}methanamine

To a solution of (3S)-5-oxo-N,4-bis(phenylmethyl)-3-morpholinecarboxamide (6.3109 g, 19.45 mmol) in 1,2-dimethoxyethane (100 mL) was added $LiAlH_4$ (2.6 g, 68.51 mmol). The mixture was heated at 100° C. and stirred for 6 h, and then cooled to 60° C. and stirred overnight. The mixture was cooled to 0° C. and quenched by slow addition of 1 N aq. NaOH (100 mL). The mixture was extracted with Et₂O (2×150 mL), and the combined organic phase was dried over anhydrous Na₂SO₄, filtered, and concentrated in vacuo. The residue was purified by gradient silica gel chromatography (1% to 5% MeOH in DCM) to give 1-phenyl-N-{[(3R)-4-(phenylmethyl)-3-morpholinyl]methyl}methanamine (3.8342 g, 66%) as a light yellow oil. LCMS: (M+H)⁺: 297.1.

Part D:

Methyl oxo((phenylmethyl){[(3R)-4-(phenylmethyl)-3-morpholinyl]methyl}amino)acetate To a solution of 1-phenyl-N-{[(3R)-4-(phenylmethyl)-3-morpholinyl]methyl}methanamine (3.3777 g, 11.40 mmol) in THF (114 mL) was added N,N-diisopropylethylamine (3 mL, 17.22 mmol). To the solution was added methyl chloro(oxo)acetate (1.15 mL, 12.50 mmol) dropwise via syringe, and the mixture was stirred for 3 h. The solvent was removed in vacuo, and the residue was dissolved in EtOAc (200 mL) and washed with sat. aq. NaHCO₃ followed by water. The organic phase was dried over anhydrous Na₂SO₄, filtered, and concentrated in vacuo to afford crude methyl oxo((phenylmethyl){[(3R)-4-(phenylmethyl)-3-morpholinyl]methyl}amino)acetate (4.6881 g, >100% crude yield) as a yellow oil. LCMS: (M+H)⁺: 383.1.

Part E:

(9aR)-8-(Phenylmethyl)hexahydropyrazino[2,1-c][1,4]oxazine-6,7-dione

To a solution of crude methyl oxo((phenylmethyl){[(3R)-4-(phenylmethyl)-3-morpholinyl]methyl}amino)acetate (assumed 4.3583 g, 11.40 mmol) in MeOH (114 mL) was added 10% Pd/C (50% water, 870 mg). The mixture was hydrogenated under balloon pressure for 16 h, and then filtered through a 0.2 μm membrane. The solution was concentrated in vacuo, and the residue was triturated with 20% EtOAc-hexanes. The resulting solid was collected by vacuum filtration and washed with hexanes to provide (9aR)-8-(phenylmethyl)hexahydropyrazino[2,1-c][1,4]oxazine-6,7-dione (2.5610 g, 86% for 2 steps) as a light yellow solid. LCMS: (M+H)⁺: 261.1.

Part F:

(9aR)-8-(Phenylmethyl)octahydropyrazino[2,1-c][1,4]oxazine

To a 0° C. solution of (9aR)-8-(phenylmethyl)hexahydropyrazino[2,1-c][1,4]oxazine-6,7-dione (2.5610 g, 9.84 mmol) in THF (100 mL) was added LiAlH₄ (1.12 g, 29.51 mmol) portionwise. The mixture was heated at 70° C. and stirred for 1 week. The mixture was then cooled to 0° C. and quenched by addition of Na₂SO₄·10H₂O (2 g) followed by 1 N aq. NaOH (100 mL). The mixture was extracted with Et₂O (2×150 mL), and the combined organic phase was dried over anhydrous Na₂SO₄, filtered, and concentrated in vacuo. The residue was dissolved in DCM (200 mL), dried over anhydrous Na₂SO₄, filtered, and concentrated in vacuo. The residue was purified by gradient silica gel chromatography (0% to 100% EtOAc in hexanes; 1% Et₃N) to give (9aR)-8-(phenylmethyl)octahydropyrazino[2,1-c][1,4]oxazine (1.8147 g, 79%) as a colorless oil. LCMS: (M+H)⁺: 233.1.

Part G:

(9aR)-Octahydropyrazino[2,1-c][1,4]oxazine dihydrochloride

To a solution of (9aR)-8-(phenylmethyl)octahydropyrazino[2,1-c][1,4]oxazine (1.8055 g, 7.77 mmol) in MeOH (80 mL) was added 1 N aq. HCl (15.5 mL, 15.5 mmol) and 10% Pd/C (50% water, 360 mg). The mixture was hydrogenated under balloon pressure overnight, and was then filtered through a 0.2 μm PTFE membrane. The solution was concentrated in vacuo and the residue was azeotroped with MeOH (3×50 mL) to provide crude (9aR)-octahydropyrazino[2,1-c][1,4]oxazine dihydrochloride (1.7185 g, >100% crude yield) as an orange solid. LCMS: (M+H)⁺: 142.9.

Part H:

Tris(1,1-dimethylethyl)2-{2-chloro-5-fluoro-6-[(9aR)-hexahydropyrazino[2,1-c][1,4]oxazin-8(1H)-yl]-4-pyrimidinyl}-1,1,2-hydrazinetricarboxylate To a solution of crude (9aR)-octahydropyrazino[2,1-c][1,4]oxazine dihydrochloride (1.7185 g, 7.99 mmol) in DMF (40 mL) was added tris(1,1-dimethylethyl)2-(2,6-dichloro-5-fluoro-4-pyrimidinyl)-1,1,2-hydrazinetricarboxylate (3.97 g, 7.98 mmol) and N,N-diisopropylethylamine (4.60 mL, 26.41 mmol). The solution was stirred overnight and then diluted with Et₂O (200 mL). The mixture was washed with water (2×100 mL), and the combined aqueous phase was extracted with a fresh portion of Et₂O (100 mL). The combined organic phase was washed with a fresh portion of water (50 mL), and then dried over anhydrous Na₂SO₄. The mixture was filtered, concentrated in vacuo, and the residue was dissolved in DCM (200 mL) and dried over anhydrous Na₂SO₄. The mixture was filtered, and the solution was concentrated in vacuo. The residue was purified by gradient silica gel chromatography (0% to 100% EtOAc in hexanes; 1% Et₃N) to afford tris(1,1-dimethylethyl)2-{2-chloro-5-fluoro-6-[(9aR)-hexahydropyrazino[2,1-c][1,4]oxazin-8(1H)-yl]-4-pyrimidinyl}-1,1,2-hydrazinetricarboxylate (4.34 g, 90%) as a white foam. LCMS: (M+H)⁺: 603.3.

Part I:

(9aR)-8-(2-Chloro-5-fluoro-6-hydrazino-4-pyrimidinyl)octahydropyrazino[2,1-c][1,4]oxazine To a solution of tris(1,1-dimethylethyl)2-{2-chloro-5-fluoro-6-[(9aR)-hexahydropyrazino[2,1-c][1,4]oxazin-8(1H)-yl]-4-pyrimidinyl}-1,1,2-hydrazinetricarboxylate (4.34 g, 7.20 mmol) in MeOH (18 mL) was added 4 N HCl in dioxane (18 mL, 72 mmol). The solution was stirred for 3 days, and then concentrated in vacuo. The residue was dissolved in water (50 mL) and the solution was adjusted to pH 10 with 20% aq. K₂CO₃. The mixture was extracted with DCM (2×100 mL), and the combined organic phase was dried over anhydrous Na₂SO₄, filtered, and concentrated in vacuo to give (9aR)-8-(2-chloro-5-fluoro-6-hydrazino-4-pyrimidinyl)octahydropyrazino[2,1-c][1,4]oxazine (1.41 g, 65%) as an orange solid. LCMS: (M+H)⁺: 303.1.

Part J:

[(2R)-3-(2-{2-Chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl][(phenylmethyl)oxy]formamide To a solution of (9aR)-8-(2-chloro-5-fluoro-6-hydrazino-4-pyrimidinyl)octahydropyrazino[2,1-c][1,4]oxazine (1.41 g, 4.66 mmol) in DMF (45 mL) was added (2R)-3-cyclopentyl-2-({formyl[(phenylmethyl)oxy]amino}methyl)propanoic acid (1.36 g, 4.45 mmol), N-methylmorpholine (2.45 mL, 22.3 mmol), 1-hydroxy-7-azabenzotriazole (0.730 g, 5.364 mmol), and EDC (1.02 g, 5.32 mmol). The solution was stirred overnight and was then diluted with Et$_2$O (200 mL). The mixture was washed with water (2×100 mL), and the combined aqueous phase was extracted with a fresh portion of Et$_2$O (100 mL). This Et$_2$O layer was washed with a fresh portion of water (50 mL), and the combined organic phase was dried over anhydrous Na$_2$SO$_4$, filtered, and concentrated in vacuo. The residue was dissolved in DCM (200 mL), dried over anhydrous Na$_2$SO$_4$, filtered, and concentrated in vacuo. The residue was azeotroped with MeOH (50 mL) to give [(2R)-3-(2-{2-chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl][(phenylmethyl)oxy]formamide (2.4027 g, 91% crude yield) as a red/orange oil. LCMS: (M+H)$^+$: 590.2.

Part K:

[(2R)-3-(2-{2-Chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl]hydroxyformamide To a solution of [(2R)-3-(2-{2-chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl][(phenylmethyl)oxy]formamide (2.3947 g, 4.058 mmol) in MeOH (40 mL) was added 20% Pd(OH)$_2$/C (50% water, 240 mg). The mixture was hydrogenated under balloon pressure for 2.5 h, and then filtered through a 0.2 μm membrane. The solution was concentrated in vacuo, and the residue was purified by Gilson RPLC (10% MeCN in water to 65% MeCN in water; 8 min gradient). The desired fractions were combined, and the MeCN was removed in vacuo. The resulting mixture was extracted with EtOAc (2×150 mL), and the combined organic phase was dried over anhydrous Na$_2$SO$_4$, filtered, and concentrated in vacuo. The residue was then crystallized from EtOAc-hexanes to provide [(2R)-3-(2-{2-chloro-5-fluoro-6-[(9aR)-hexahydropyrazino[2,1-c][1,4]oxazin-8(1H)-yl]-4-pyrimidinyl}hydrazino)-2-(cyclopentylmethyl)-3-oxopropyl]hydroxyformamide (1.2759 g, 63%) as a pale pink solid. LCMS: (M+H)$^+$: 500.1.

Example 170

[(2R)-3-(2-{2-Chloro-5-fluoro-6-[(3S)-4-methyl-3-(1-methylethyl)-1-piperazinyl]-4-pyrimidinyl}hydrazino)-2-(cyclopentylmethyl)-3-oxopropyl]hydroxyformamide

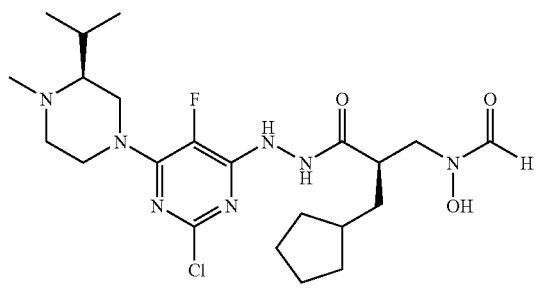

(2S)-1-Methyl-2-(1-methylethyl)piperazine, Dihydrochloride a) Commercially-available (S)—N-4-benzyl-2-isopropylpiperazine (2.0 g, 9.2 mmol), sodium triacetoxyborohydride (2.9 g, 13.8 mmol), and formaldehyde (37% in H$_2$O, 1.12 mL, 13.8 mmol) were dissolved and stirred in CH$_2$Cl$_2$ (40 mL) for 1 h at room temperature. After this time, the reaction mixture was diluted with additional CH$_2$Cl$_2$ and washed with 1 N NaOH (2×) and brine (1×). The combined organic extracts were dried (Na$_2$SO$_4$) and concentrated in vacuo to provide (2S)-1-methyl-2-(1-methylethyl)-4-(phenylmethyl)piperazine (2.14 g) as a colorless oil.

b) (2S)-1-Methyl-2-(1-methylethyl)-4-(phenylmethyl)piperazine (2.14 g crude, 9.2 assumed mmol) was dissolved in 20 mL of MeOH. 5% Pd/C (500 mg) was added, and the contents were thoroughly degassed and placed under a hydrogen balloon. The resulting reaction mixture was stirred overnight, and the contents were then degassed and filtered. 4 N HCl in dioxane (4.6 mL) was added to the filtrate, and the filtrate was concentrated in vacuo to provide (2S)-1-methyl-2-(1-methylethyl)piperazine, dihydrochloride salt.

[(2R)-3-(2-{2-Chloro-5-fluoro-6-[(3S)-4-methyl-3-(1-methylethyl)-1-piperazinyl]-4-pyrimidinyl}hydrazino)-2-(cyclopentylmethyl)-3-oxopropyl]hydroxyformamide

[(2R)-3-(2-{2-Chloro-5-fluoro-6-[(3S)-4-methyl-3-(1-methylethyl)-1-piperazinyl]-4-pyrimidinyl}hydrazino)-2-(cyclopentylmethyl)-3-oxopropyl]hydroxyformamide was prepared according to General Procedure D, utilizing (2S)-1-methyl-2-(1-methylethyl)piperazine, dihydrochloride in place of N-methylpiperazine, and using 2 equivalents of DIPEA in Part A. LCMS: (M+H)$^+$: 500.3.

Example 171

[(2R)-3-(2-{2-Chloro-5-fluoro-6-[(2S)-4-methyl-2-(1-methylethyl)-1-piperazinyl]-4-pyrimidinyl}hydrazino)-2-(cyclopentylmethyl)-3-oxopropyl]hydroxyformamide

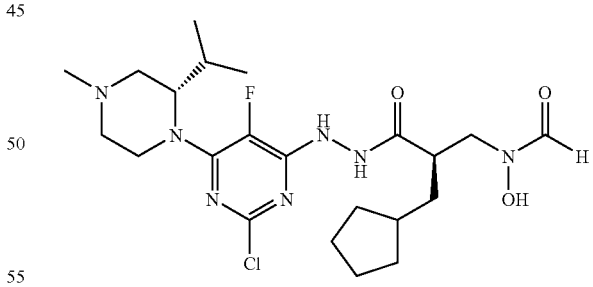

(3S)-1-Methyl-3-(1-methylethyl)piperazine, Dihydrochloride a) Commercially-available (S)—N-1-Boc-2-isopropylpiperazine (2.0 g, 8.76 mmol), sodium triacetoxyborohydride (2.76 g, 13 mmol), and formaldehyde (37% in H$_2$O, 1.06 mL, 13 mmol) were dissolved and stirred in CH$_2$Cl$_2$ (40 mL) overnight at room temperature. After this time, the reaction mixture was diluted with additional CH$_2$Cl$_2$ and washed with 1 N NaOH and brine. The combined organic extracts were dried (Na$_2$SO$_4$) and concentrated in vacuo to provide 1,1-dimethylethyl (2S)-4-methyl-2-(1-methylethyl)-1-piperazinecarboxylate (2.18 g) as a colorless oil.

b) 1,1-Dimethylethyl (2S)-4-methyl-2-(1-methylethyl)-1-piperazinecarboxylate (2.18 g crude, 8.76 assumed mmol) was dissolved in a mixture of MeOH (5 mL), CH$_2$Cl$_2$ (5 mL), and 4 N HCl in dioxane (8 mL). After stirring overnight at room temperature, another 8 mL of 4 N HCl in dioxane and 8 mL of MeOH were added, which dissolved the white precipitate that had formed and pushed the reaction to completion. Evaporation of the solvents in vacuo provided (3S)-1-methyl-3-(1-methylethyl)piperazine, dihydrochloride (1.97 g) as a white solid.

[(2R)-3-(2-{2-Chloro-5-fluoro-6-[(2S)-4-methyl-2-(1-methylethyl)-1-piperazinyl]-4-pyrimidinyl}hydrazino)-2-(cyclopentylmethyl)-3-oxopropyl]hydroxyformamide

[(2R)-3-(2-{2-Chloro-5-fluoro-6-[(2S)-4-methyl-2-(1-methylethyl)-1-piperazinyl]-4-pyrimidinyl}hydrazino)-2-(cyclopentylmethyl)-3-oxopropyl]hydroxyformamide was prepared according to General Procedure D, utilizing ((3S)-1-methyl-3-(1-methylethyl)piperazine, dihydrochloride in place of N-methylpiperazine, and using 2 equivalents of DIPEA in Part A. LCMS: (M+H)$^+$: 500.3.

Example 172

[(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide

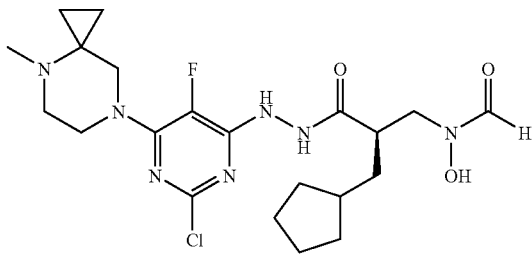

Part A:

Methyl 1-aminocyclopropanecarboxylate

1-Aminocyclopropanecarboxylic acid (13.1 g, 129.57 mmol) was dissolved in MeOH (200 mL), and the resulting mixture was cooled to 0° C. for 30 min. Then thionyl chloride (11.84 mL, 161.97 mmol) was added and the mixture was heated to 80° C. for 4 h. The mixture was allowed to cool to room temperature overnight. The volatiles were concentrated in vacuo, and the residue was dissolved in Et$_2$O (200 mL) and stirred vigorously for 30 min. The resulting white solid precipitate was collected by filtration to provide methyl 1-aminocyclopropanecarboxylate (15.83 g, 80%) LCMS: (M+H)$^+$: 116.1.

Part B:

Methyl 1-({[(phenylmethyl)oxy]carbonyl}amino)cyclopropanecarboxylate

Methyl 1-aminocyclopropanecarboxylate (15.83 g, 104.43 mmol) was dissolved in a mixture of CH$_2$Cl$_2$ (150 mL) and water (150 mL). To this mixture was added NaHCO$_3$ (35.09 g, 417.72 mmol) followed by benzyl chloroformate (15.43 mL, 109.64 mmol). The mixture was stirred vigorously for 2 hours, and after separation of the two layers, the aqueous layer was extracted with 100 mL of CH$_2$Cl$_2$. The combined organic layers were dried over MgSO$_4$, filtered, and concentrated in vacuo to provide methyl 1-({[(phenylmethyl)oxy]carbonyl}amino)cyclopropanecarboxylate (12.0 g, 46%). LCMS: (M+H)$^+$: 206.1.

Part C:

Methyl 1-(methyl{[(phenylmethyl)oxy]carbonyl}amino)cyclopropanecarboxylate

Sodium hydride (995 mg, 41.466 mmol) was taken up in DMF (50 mL) and was cooled to 0° C. for 30 min. Then a mixture of methyl 1-({[(phenylmethyl)oxy]carbonyl}amino)cyclopropanecarboxylate (6.46 g, 25.916 mmol) in DMF (25 mL) was slowly added over 10 min. The resulting mixture was allowed to stir for 45 min, and then iodomethane (4.84 mL, 77.74 mmol) was added, and the reaction was allowed to warm to room temperature overnight. The mixture was then carefully diluted with water (10 mL), and the aqueous layer was extracted with Et$_2$O (5×50 mL). The organic extracts were washed with water (5×50 mL), then dried over Na$_2$SO$_4$ and concentrated in vacuo. The crude residue was purified via Combiflash, utilizing a 0%-50 EtOAc/Hex gradient to provide methyl 1-(methyl{[(phenylmethyl)oxy]carbonyl}amino)cyclopropanecarboxylate (16.9 g, >100%) LCMS: (M+H)$^+$: 264.1.

Part D:

Methyl 1-(methylamino)cyclopropanecarboxylate

Methyl 1-(methyl{[(phenylmethyl)oxy]carbonyl}amino)cyclopropanecarboxylate (assumed 6.8 g, 25.91 mmol, 100% theoretical yield) was dissolved in 30 mL of MeOH, degassed and placed under argon. 10% Pd/C (2.04 g) was added, and the contents were thoroughly degassed and placed under a hydrogen balloon overnight. The contents were then degassed, and the Pd/C was removed by filtration through Celite, washing with MeOH. The filtrate was concentrated in vacuo to provide pure methyl 1-(methylamino)cyclopropanecarboxylate (1.53 g, 45% over two step). LCMS: (M+H)$^+$: 130.1.

Part E:

Methyl 1-[methyl(N-{[(phenylmethyl)oxy]carbonyl}glycyl)amino]cyclopropanecarboxylate To a solution of methyl 1-(methylamino)cyclopropanecarboxylate (1.53 g, 11.85 mmol) and HOBt (1.920 g, 14.21 mmol) in CH$_2$Cl$_2$ (30 mL) was added 4-methylmorpholine (5.2 mL, 47.40 mmol), N-{[(phenylmethyl)oxy]carbonyl}glycine (2.48 g, 11.85 mmol), and EDCI (2.73 g, 14.21 mmol). After stirring overnight, the solution was washed 6 N aq. HCl (100 mL) and water (100 mL). The aqueous layers were extracted with CH$_2$Cl$_2$ (1×100 mL), and the combined organic layers were washed with water (100 mL) and brine (100 mL), then dried over anhydrous MgSO$_4$ and concentrated in vacuo to provide pure methyl 1-[methyl(N-{[(phenylmethyl)oxy]carbonyl}glycyl)amino]cyclopropanecarboxylate (3.66 g, 97%). LCMS: (M+H)$^+$: 321.1.

Part F:

4-Methyl-4,7-diazaspiro[2.5]octane-5,8-dione

Methyl 1-[methyl(N-{[(phenylmethyl)oxy]carbonyl}glycyl)amino]cyclopropanecarboxylate (3.66 g, 11.42 mmol) was dissolved in 50 mL of MeOH, degassed and placed under argon. 10% Pd/C (2.04 g) was added, and the contents were thoroughly degassed and placed under a hydrogen balloon for 2 h. The contents were then degassed, and the Pd/C was removed by filtration through Celite, washing with MeOH. The filtrate was concentrated in vacuo. The residue was dissolved in MeOH (100 mL) and heated to 60° C. with stirring for 4 h. The solvent was removed in vacuo to provide pure 4-methyl-4,7-diazaspiro[2.5]octane-5,8-dione (1.76 g, 99%). LCMS: (M+H)$^+$: 155.1.

Part G:

4-Methyl-7-(phenylmethyl)-4,7-diazaspiro[2.5]octane-5,8-dione

Sodium hydride (302 mg, 12.62 mmol) was taken up in DMF (10 mL) and cooled to 0° C. for 30 min. Then a mixture 4-methyl-4,7-diazaspiro[2.5]octane-5,8-dione (1.769 g, 11.47 mmol) in DMF (5 mL) was slowly added over 10 min. This mixture was allowed to stir for 45 min, and then benzyl bromide (4.08 mL, 34.41 mmol) was added, and the reaction was stirred for 45 min further. The mixture was carefully diluted with water (10 mL) and concentrated in vacuo. The resulting crude product was purified via reverse phase HPLC to provide 4-methyl-7-(phenylmethyl)-4,7-diazaspiro[2.5]octane-5,8-dione (1.535 g, 54%). LCMS: (M+H)$^+$: 245.1.

Part H;

4-Methyl-7-(phenylmethyl)-4,7-diazaspiro[2.5]octane

4-Methyl-7-(phenylmethyl)-4,7-diazaspiro[2.5]octane-5,8-dione (1.535 g, 6.284 mmol) was dissolved in THF (100 mL) and the mixture was cooled to 0° C. Borane-THF complex (25.13 mL, 25.13 mmol) was added portionwise over 10 min. The mixture was heated to 60° C. for 4 h and was then checked by LCMS. If greater than 15% of the starting material remained, an additional portion of Borane-THF complex (12.56 mL, 12.56 mmol) was slowly added, and the reaction was allowed to stir for an additional 45 min. When the reaction was complete as determined by LCMS, the reaction mixture was cooled to room temperature. 1N HCl (25 mL) was added, and the mixture was heated to 80° C. for 1 h. The reaction mixture was then cooled to room temperature, and 6 N aq. NaOH was added to adjust the pH to 14. The mixture was extracted with CH$_2$Cl$_2$ (3×50 mL). The combined organic layers were dried over Na$_2$SO$_4$, filtered, and concentrated in vacuo. The resulting crude product was purified via reverse phase HPLC to provide 4-methyl-7-(phenylmethyl)-4,7-diazaspiro[2.5]octane (1.43 g, 94%). LCMS: (M+H)$^+$: 217.2.

Part I:

4-Methyl-4-aza-7-azoniaspiro[2.5]octane, Dihydrochloride

4-Methyl-7-(phenylmethyl)-4,7-diazaspiro[2.5]octane (1.43 g, 6.624 mmol) was dissolved in 10 mL of MeOH, degassed and placed under argon. Pd(OH)$_2$ (140 mg) was added, and the contents were hydrogenated for 4 h under 50 psi. The contents were then filtered to remove the catalyst, 1N HCl (14.57 mL, 14.57 mmol) was added to the filtrate, and the filtrate was concentrated in vacuo to provide pure 4-methyl-4-aza-7-azoniaspiro[2.5]octane, dihydrochloride (0.8 g, 60%). LCMS: (M+H)$^+$: 127.2.

Part J:

[(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide

[(2R)-3-{2-[2-Chloro-5-fluoro-6-(4-methyl-4,7-diazaspiro[2.5]oct-7-yl)-4-pyrimidinyl]hydrazino}-2-(cyclopentylmethyl)-3-oxopropyl]hydroxyformamide was prepared according to General Procedure E, utilizing 4-methyl-4-aza-7-azoniaspiro[2.5]octane, dihydrochloride in place of isopropyl amine, and using 3.5 equivalents of DIEA, in Part A. LCMS: (M+H)$^+$: 484.2.

Example 173

N-[(2R)-3-(2-{2-Chloro-5-fluoro-6-[(2R,3S)-2,3,4-trimethyl-1-piperazinyl]-4-pyrimidinyl}hydrazino)-2-(cyclopentylmethyl)-3-oxopropyl]-N-hydroxyformamide

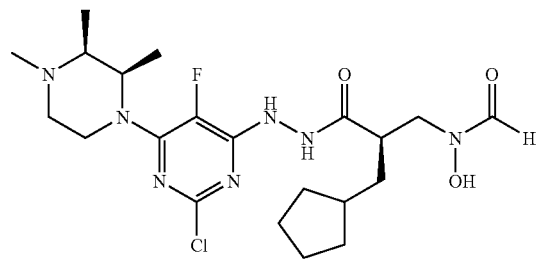

Part A:

(2S,3R)-1,2,3-Trimethylpiperazine, Hydrochloride Salt

Phenylmethyl (2R,3S)-2,3,4-trimethyl-1-piperazinecarboxylate (Example 175) (770 mg, 2.94 mmol) was dissolved in 40 mL of MeOH, degassed and placed under argon. 10% Pd/C (125 mg) was added, and the contents were thoroughly degassed and placed under a hydrogen balloon for approximately 3 hrs. The contents were then degassed and filtered through Celite, and the Celite pad was washed with DCM and MeOH. After 6.2 mL 1N HCl was added, the resulting filtrate was concentrated in vacuo to provide the dihydrochloride salt of (2S,3R)-1,2,3-trimethylpiperazine. LCMS: (M+H)$^+$: 129.1.

Part B:

N-[(2R)-3-(2-{2-Chloro-5-fluoro-6-[(2R,3S)-2,3,4-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(2R,3S)-2,3,4-trimethyl-1-piperazinyl]-4-pyrimidinyl}hydrazino)-2-(cyclopentylmethyl)-3-oxopropyl]-N-hydroxyformamide was prepared according to General Procedure O G, utilizing (2S,3R)-1,2,3-trimethylpiperazine, dihydrochloride salt in place of (1S,4S)-2-methyl-2,5-diazabicyclo[2.2.1]heptane, dihydrobromide in Part A. LCMS: (M+H)+: 486.1.

Example 174

[(2R)-3-(2-{2-Chloro-5-fluoro-6-[(8aR)-hexahydropyrrolo[1,2-a]pyrazin-2(1H)-yl]-4-pyrimidinyl}hydrazino)-2-(cyclopentylmethyl)-3-oxopropyl]hydroxyformamide

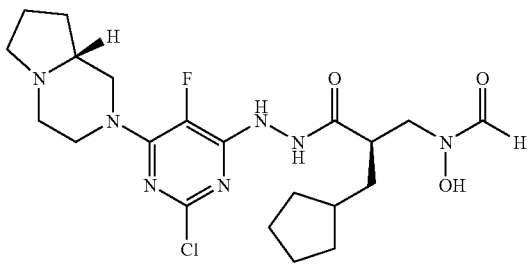

[(2R)-3-(2-{2-Chloro-5-fluoro-6-[(8aR)-hexahydropyrrolo[1,2-a]pyrazin-2(1H)-yl]-4-pyrimidinyl}hydrazino)-2-(cyclopentylmethyl)-3-oxopropyl]hydroxyformamide was prepared according to General Procedure D, utilizing (8aR)-octahydropyrrolo[1,2-a]pyrazine (J. Med. Chem. 1993, 36, 2311-20) (used as the di-HCl salt) in place of N-methylpiperazine in Part A, and using 3 equivalents of DIPEA in Part A. LCMS: (M+H)+: 484.2.

Example 175

N-[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]-N-hydroxyformamide

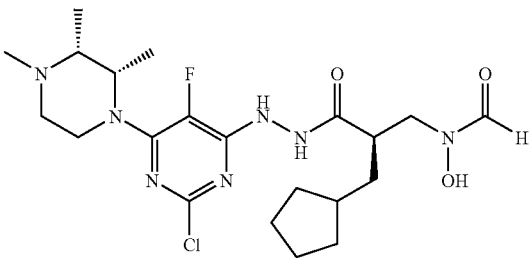

Part A:

Phenylmethyl cis-2,3-dimethyl-1-piperazinecarboxylate (enantiomeric mixture)

A 100 mL, three-necked round-bottom flask was charged with cis-2,3-dimethylpiperazine (Helvetica Chimica Acta, 1994, 77, 1057-64) (1.781 g, 15.6 mmol). The flask was cooled in an ice bath, and a solution of methanesulfonic acid (2.02 mL, 31.2 mmol) in 1.4 mL of water was added slowly, maintaining the temperature below 40° C. The solution was cooled to 20° C., and 2 mL of ethanol was added. The pH was adjusted to 4 with 60% aqueous potassium acetate, and then benzyl chloroformate (2.08 mL, 14.8 mmol in 1 mL of THF) and potassium acetate solutions were simultaneously added dropwise with adjustment of the rate to maintain the reaction solution at pH 4, with cooling to maintain the temperature at 25° C. After the mixture was stirred an additional hour, the organic solvents were removed and the remaining aqueous solution was washed with ethyl acetate. The ethyl acetate wash was extracted with 1 M HCl twice to recover the desired product. The acid extracts were combined with the original aqueous solution, and the pH was adjusted to 11 by the addition of 6 N NaOH, with cooling to maintain temperature below 40° C. The aqueous solution was extracted with ethyl acetate, and the combined extracts were dried over magnesium sulfate and concentrated in vacuo to provide phenylmethyl cis-2,3-dimethyl-1-piperazinecarboxylate (enantiomeric mixture) as a yellow oil (1.77 g, 46%). LCMS: (M+H)+: 249.1.

Part B:

Phenylmethyl (2S,3R)-2,3,4-trimethyl-1-piperazinecarboxylate and phenylmethyl (2R,3S)-2,3,4-trimethyl-1-piperazinecarboxylate To a solution of phenylmethyl cis-2,5-dimethyl-1-piperazinecarboxylate (enantiomeric mixture) (1.77 g, 7.1 mmol) in dichloromethane (50 mL) at 0° C. was added formaldehyde (0.803 mL, 37% water solution, 10.7 mmol) followed by sodium triacetoxyborohydride (1.964 g, 9.2 mmol). The reaction mixture was allowed to warm to room temperature and stirred for 2 h before being diluted with dichloromethane and washed with 1N NaOH solution. The organics were washed with brine, dried (MgSO4) and evaporated to yield phenylmethyl cis-2,3,4-trimethyl-1-piperazinecarboxylate (enantiomeric mixture) (1.72 g, 92%). Phenylmethyl (2S,3R)-2,3,4-trimethyl-1-piperazinecarboxylate (950 mg) and phenylmethyl (2R,3S)-2,3,4-trimethyl-1-piperazinecarboxylate (770 mg) were separated by chiral chromatography. Absolute configuration was assigned using Ab Initio vibrational circular dichroism. LCMS: (M+H)+: 263.3.

Part C:

(2R,3S)-1,2,3-Trimethylpiperazine, Dihydrochloride Salt

Phenylmethyl (2S,3R)-2,3,4-trimethyl-1-piperazinecarboxylate (950 mg, 3.62 mmol) was dissolved in 60 mL of MeOH, degassed and placed under argon. 10% Pd/C (160 mg) was added, and the contents were thoroughly degassed and placed under a hydrogen balloon for approximately 3 hrs. The contents were then degassed and filtered through Celite, and the Celite pad was washed with DCM and MeOH. After 7.6 mL 1N HCl was added, the resulting filtrate was concentrated in vacuo to provide the dihydrochloride salt of (2R,3S)-1,2,3-trimethylpiperazine (740 mg). LCMS: (M+H)+: 129.1.

Part D:

N-[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]-N-hydroxyformamide was prepared according to General Procedure G, utilizing (2R,3S)-1,2,3-trimethylpiperazine, dihydrochloride salt in place of (1S,4S)-2-methyl-2,5-diazabicyclo[2.2.1]heptane, dihydrobromide in Part A. LCMS: (M+H)⁺: 486.1.

Example 176

[(2R)-3-(2-{2-Chloro-5-fluoro-6-[3-methyl-3-(1-pyrrolidinyl)-1-azetidinyl]-4-pyrimidinyl}hydrazino)-2-(cyclopentylmethyl)-3-oxopropyl]hydroxyformamide

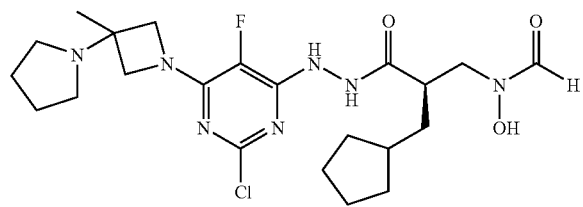

Part A:

1-[1-(Diphenylmethyl)-3-methyl-3-azetidinyl]pyrrolidine

A mixture of 1-(diphenylmethyl)-3-methyl-3-azetidinyl methanesulfonate (1.55 g, 4.68 mmol) (J. Med. Chem. 1993, 36, 801-810) and pyrrolidine (3.86 ml, 46.68 mmol) in isopropanol (15 ml) was heated to 70° C. overnight. After cooling to room temperature, the mixture was concentrated to dryness in vacuo. Water (100 ml) was added, and the mixture was extracted with dichloromethane (2×100 ml). The combined organic solution was washed with brine (60 ml), dried (Na₂SO₄) and concentrated. The residue was purified via RP-HPLC to provide 1-[1-(diphenylmethyl)-3-methyl-3-azetidinyl]pyrrolidine (0.94 g, 65%). LCMS: (M+H)⁺: 307.2.

Part B:

1-(3-Methyl-3-azetidinyl)pyrrolidine dihydrochloride

A mixture of 1-[1-(diphenylmethyl)-3-methyl-3-azetidinyl]pyrrolidine (0.94 g, 3.07 mmol) and 20% Pd(OH)₂ (0.11 g) in ethanol (30 ml) and 1N HCl (7 ml) was treated with H₂ at 60 psi overnight. The catalyst was removed by filtration, and the filtrate was evaporated under vacuum. The residue was washed with benzene (3×5 ml) and dried under high vacuum to provide 1-(3-methyl-3-azetidinyl)pyrrolidine dihydrochloride (0.76 g, presumed 86% pure). LCMS: (M+H)⁺: 141.0.

Part C:

Tris(1,1-dimethylethyl)2-{2-chloro-5-fluoro-6-[3-methyl-3-(1-pyrrolidinyl)-1-azetidinyl]-4-pyrimidinyl}-1,1,2-hydrazinetricarboxylate To a stirred solution of 1-(3-methyl-3-azetidinyl)pyrrolidine dihydrochloride (0.128 g, 86% pure, 0.52 mmol) in DMF (8 mL) at 0° C. was added DIPEA (0.34 mL, 1.94 mmol) followed immediately by tris(1,1-dimethylethyl)2-(2,6-dichloro-5-fluoro-4-pyrimidinyl)-1,1,2-hydrazinetricarboxylate (0.24, 0.49 mmol). The reaction was warmed up to rt and stirred overnight. The mixture was purified by RP-HPLC to provide tris(1,1-dimethylethyl)2-{2-chloro-5-fluoro-6-[3-methyl-3-(1-pyrrolidinyl)-1-azetidinyl]-4-pyrimidinyl}-1,1,2-hydrazinetricarboxylate (0.225 g, 77%). LCMS: (M+H)⁺: 601.2.

Part D:

2-Chloro-5-fluoro-4-hydrazino-6-[3-methyl-3-(1-pyrrolidinyl)-1-azetidinyl]pyrimidine A solution of tris(1,1-dimethylethyl)2-{2-chloro-5-fluoro-6-[3-methyl-3-(1-pyrrolidinyl)-1-azetidinyl]-4-pyrimidinyl}-1,1,2-hydrazinetricarboxylate (0.225 g, 0.37 mmol) in MeOH (6 mL) and 4.0M HCl in dioxane (4 mL) was stirred at room temperature for 3 days. The solvent was then removed in vacuo, providing the crude 2-chloro-5-fluoro-6-hydrazino-N-(1-methylethyl)-4-pyrimidinamine, presumably as the tri-HCl salt. LCMS: (M+H)⁺: 301.0.

Part E:

[(2R)-3-(2-{2-Chloro-5-fluoro-6-[3-methyl-3-(1-pyrrolidinyl)-1-azetidinyl]-4-pyrimidinyl}hydrazino)-2-(cyclopentylmethyl)-3-oxopropyl](tetrahydro-2H-pyran-2-yloxy)formamide A mixture of (2R)-3-cyclopentyl-2-{[formyl(tetrahydro-2H-pyran-2-yloxy)amino]methyl}propanoic acid (112 mg, 0.374 mmol), 2-chloro-5-fluoro-4-hydrazino-6-[3-methyl-3-(1-pyrrolidinyl)-1-azetidinyl]pyrimidine (assumed 112 mg of free base, 0.374 mmol), EDC (86 mg, 0.449 mmol), HOAt (56 mg, 0.411 mmol), and NMM (0.25 mL, 2.24 mmol) in DMF (5 ml) was stirred at room temperature overnight. The reaction mixture was then purified via RP-HPLC to provide [(2R)-3-(2-{2-chloro-5-fluoro-6-[3-methyl-3-(1-pyrrolidinyl)-1-azetidinyl]-4-pyrimidinyl}hydrazino)-2-(cyclopentylmethyl)-3-oxopropyl](tetrahydro-2H-pyran-2-yloxy)formamide (145 mg, 66%). LCMS: (M+H)⁺: 582.5.

Part F:

[(2R)-3-(2-{2-Chloro-5-fluoro-6-[3-methyl-3-(1-pyrrolidinyl)-1-azetidinyl]-4-pyrimidinyl}hydrazino)-2-(cyclopentylmethyl)-3-oxopropyl]hydroxyformamide A solution of [(2R)-3-(2-{2-chloro-5-fluoro-6-[3-methyl-3-(1-pyrrolidinyl)-1-azetidinyl]-4-pyrimidinyl}hydrazino)-2-(cyclopentylmethyl)-3-oxopropyl](tetrahydro-2H-pyran-2-yloxy)formamide (145 mg) in 4:1 AcOH:water (20 mL) was stirred at room temperature overnight. LCMS indicated ~45% completion of the deprotection. Another portion of the mixed solvents (4:1 AcOH:water, 20 mL) was added, and stirring continued overnight. The solvents were then removed in vacuo, and the resulting crude product was purified by RP-HPLC to provide [(2R)-3-(2-{2-chloro-5-fluoro-6-[3-methyl-3-(1-pyrrolidinyl)-1-azetidinyl]-4-pyrimidinyl}hydrazino)-2-(cyclopentylmethyl)-3-oxopropyl]hydroxyformamide (45 mg, 36%). LCMS: (M+H)⁺: 498.2.

Example 177

[(2R)-2-(Cyclopentylmethyl)-3-(2-{5-fluoro-6-[(8aR)-hexahydropyrrolo[1,2-a]pyrazin-2(1H)-yl]-2-methyl-4-pyrimidinyl}hydrazino)-3-oxopropyl]hydroxyformamide

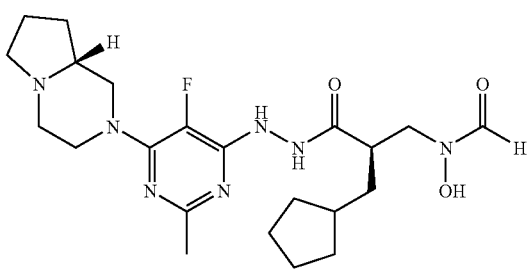

[(2R)-2-(Cyclopentylmethyl)-3-(2-{5-fluoro-6-[(8aR)-hexahydropyrrolo[1,2-a]pyrazin-2(1H)-yl]-2-methyl-4-pyrimidinyl}hydrazino)-3-oxopropyl]hydroxyformamide was prepared according to General Procedure A, utilizing (8aR)-octahydropyrrolo[1,2-a]pyrazine (J. Med. Chem. 1993, 36, 2311-20) (used as the di-HCl salt) in place of pyrrolidine in Part A. LCMS: (M+H)$^+$: 464.2.

Example 178

[(2R)-2-(Cyclopentylmethyl)-3-(2-{2-ethyl-5-fluoro-6-[(8aR)-hexahydropyrrolo[1,2-a]pyrazin-2(1H)-yl]-4-pyrimidinyl}hydrazino)-3-oxopropyl]hydroxyformamide

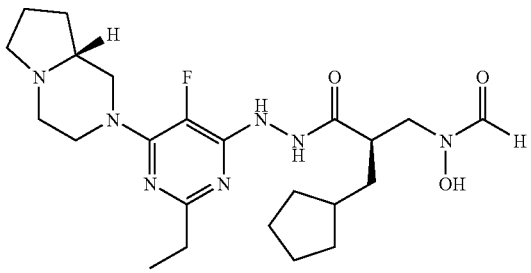

[(2R)-2-(Cyclopentylmethyl)-3-(2-{2-ethyl-5-fluoro-6-[(8aR)-hexahydropyrrolo[1,2-a]pyrazin-2(1H)-yl]-4-pyrimidinyl}hydrazino)-3-oxopropyl]hydroxyformamide was prepared according to General Procedure B, utilizing (8aR)-octahydropyrrolo[1,2-a]pyrazine (J. Med. Chem. 1993, 36, 2311-20) (used as the di-HCl salt) in place of pyrrolidine in Part A, using 4 equivalents of DIPEA, and using a mixed solvent system of 1:1 MeOH:DMSO in place of pure MeOH or pure DMSO.

Example 179

[(2R)-3-{2-[2-Chloro-5-fluoro-6-(tetrahydro-2H-pyran-4-ylamino)-4-pyrimidinyl]hydrazino}-2-(cyclopentylmethyl)-3-oxopropyl]hydroxyformamide

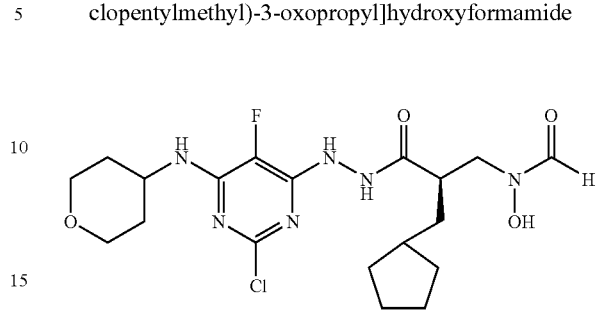

Part A:

Tris(1,1-dimethylethyl)2-[2-chloro-5-fluoro-6-(tetrahydro-2H-pyran-4-ylamino)-4-pyrimidinyl]-1,1,2-hydrazinetricarboxylate A solution of commercially available tetrahydro-2H-pyran-4-amine (0.122 g, 1.21 mmol) in DMF (6 mL) was cooled to 0° C. Then diisopropylethylamine (0.24 mL, 1.33 mmol) and tris(1,1-dimethylethyl)2-(2,6-dichloro-5-fluoro-4-pyrimidinyl)-1,1,2-hydrazinetricarboxylate (0.600 g, 1.21 mmol) were added. The resulting solution was left to reach room temperature and stir overnight. The mixture was extracted with ether and washed with water, and the resulting aqueous layer was extracted once with ether. The combined ether layers were dried (Na$_2$SO$_4$) and concentrated in vacuo. The resulting material was purified by silica gel chromatography with (5-60% ethyl acetate in hexanes, 1% triethylamine) to provide tris(1,1-dimethylethyl)2-[2-chloro-5-fluoro-6-(tetrahydro-2H-pyran-4-ylamino)-4-pyrimidinyl]-1,1,2-hydrazinetricarboxylate as a white solid (0.602 g, 89%). LCMS: (M+H−2Boc)$^+$=362.1.

Part B:

2-Chloro-5-fluoro-6-(tetrahydro-2H-pyran-4-ylamino)-4(1H)-pyrimidinone hydrazone To a solution of tris(1,1-dimethylethyl)2-[2-chloro-5-fluoro-6-(tetrahydro-2H-pyran-4-ylamino)-4-pyrimidinyl]-1,1,2-hydrazinetricarboxylate (0.602 g, 1.071 mmol) in MeOH (20 mL) was added 4M HCl in 1,4-dioxane (20 mL). After stirring at room temperature for 2 days, the solvent was evaporated and saturated NaHCO$_3$ was added. The aqueous layer was extracted, and the organics were dried (Na$_2$SO$_4$) and concentrated in vacuo to provide 2-chloro-5-fluoro-6-(tetrahydro-2H-pyran-4-ylamino)-4(1H)-pyrimidinone hydrazone as a red solid (0.199 g). LCMS: (M+H)$^+$=261.8.

Part C:

[(2R)-3-{2-[2-Chloro-5-fluoro-6-(tetrahydro-2H-pyran-4-ylamino)-4-pyrimidinyl]hydrazino}-2-(cyclopentylmethyl)-3-oxopropyl][(phenylmethyl)oxy]formamide (2R)-3-Cyclopentyl-2-({formyl[(phenylmethyl)oxy]amino}methyl)propanoic acid (0.220 g, 0.72 mmol), 2-chloro-5-fluoro-6-(tetrahydro-2H-pyran-4-ylamino)-4(1H)-pyrimidinone hydrazone (0.199 g), NMM (0.42 mL, 3.80 mmol), HOAt (0.103 g, 0.76 mmol), EDC (0.146 g, 0.76 mmol) were dissolved in DMF (5 mL). Reaction left to stir overnight. Added ether, washed with water, back extracted aqueous layers with ether, dried (Na$_2$SO$_4$) and concentrated in vacuo to provide [(2R)-3-{2-[2-chloro-5-fluoro-6-(tetrahydro-2H-pyran-4-ylamino)-4-pyrimidinyl]hydrazino}-2-(cyclopentylmethyl)-3-oxopropyl][(phenylmethyl)oxy]formamide as a dark brown solid (0.321 g). LCMS: (M+H)$^+$ =549.2.

Part D:

[(2R)-3-{2-[2-Chloro-5-fluoro-6-(tetrahydro-2H-pyran-4-ylamino)-4-pyrimidinyl]hydrazino}-2-(cyclopentylmethyl)-3-oxopropyl]hydroxyformamide

[(2R)-3-{2-[2-Chloro-5-fluoro-6-(tetrahydro-2H-pyran-4-ylamino)-4-pyrimidinyl]hydrazino}-2-(cyclopentylmethyl)-3-oxopropyl][(phenylmethyl)oxy]formamide (0.321 g, 0.58 mmol), Pd(OH)$_2$ (0.064 g) and MeOH (10 mL) were combined and treated as described in General Procedure E, Part D, for 4 hours. The reaction was not complete, and therefore the contents were filtered to remove the catalyst, and the filtrate was concentrated in vacuo. The resulting residue was redissolved in MeOH (10 mL), Pd(OH)$_2$ (0.080 g) was, and the contents were again stirred under hydrogenation conditions as described in General Procedure E, Part D, for 2.5 hours. The contents were then filtered to remove the catalyst, and the filtrate was concentrated in vacuo. The resulting crude product was purified by RP-HPLC to provide [(2R)-3-{2-[2-chloro-5-fluoro-6-(tetrahydro-2H-pyran-4-ylamino)-4-pyrimidinyl]hydrazino}-2-(cyclopentylmethyl)-3-oxopropyl]hydroxyformamide as an off-white solid (0.024 g, 9%). LCMS: (M+H)$^+$=459.5.

Example 180

N-[(2R)-2-(Cyclopentylmethyl)-3-(2-{5-fluoro-2-methyl-6-[(2S,3R)-2,3,4-trimethyl-1-piperazinyl]-4-pyrimidinyl}hydrazino)-3-oxopropyl]-N-hydroxyformamide

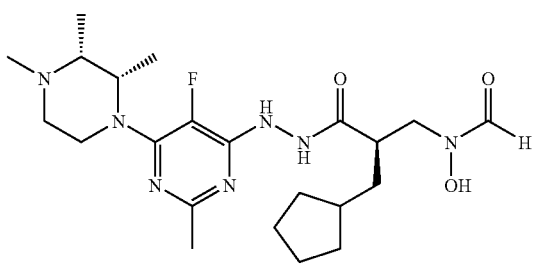

N-[(2R)-2-(Cyclopentylmethyl)-3-(2-{5-fluoro-2-methyl-6-[(2S,3R)-2,3,4-trimethyl-1-piperazinyl]-4-pyrimidinyl}hydrazino)-3-oxopropyl]-N-hydroxyformamide was prepared according to General Procedure A, utilizing (2R,3S)-1,2,3-trimethylpiperazine, dihydrochloride salt (Example 175) in place of pyrrolidine in Part A, and using 3 equivalents of DIPEA. LCMS: (M+H)$^+$: 466.2.

Example 181

N-[(2R)-2-(Cyclopentylmethyl)-3-(2-{5-fluoro-2-methyl-6-[(2R,3S)-2,3,4-trimethyl-1-piperazinyl]-4-pyrimidinyl}hydrazino)-3-oxopropyl]-N-hydroxyformamide

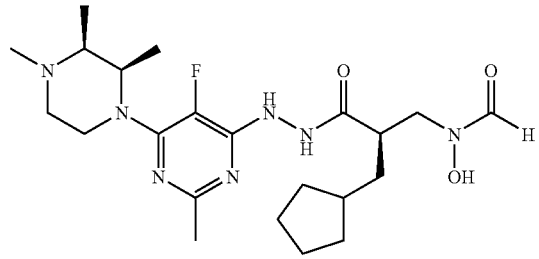

N-[(2R)-2-(Cyclopentylmethyl)-3-(2-{5-fluoro-2-methyl-6-[(2R,3S)-2,3,4-trimethyl-1-piperazinyl]-4-pyrimidinyl}hydrazino)-3-oxopropyl]-N-hydroxyformamide was prepared according to General Procedure A, utilizing (2S,3R)-1,2,3-trimethylpiperazine, dihydrochloride salt (Example 173) in place of pyrrolidine in Part A, and using 3 equivalents of DIPEA. LCMS: (M+H)$^+$: 466.2.

Example 182

[(2R)-2-(Cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl]hydroxyformamide

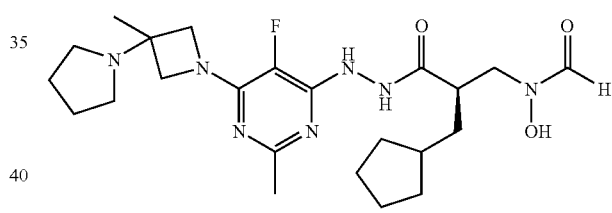

Part A:

5-Fluoro-4-hydrazino-2-methyl-6-[3-methyl-3-(1-pyrrolidinyl)-1-azetidinyl]pyrimidine To a mixture of 4,6-dichloro-5-fluoro-2-methylpyrimidine (90 mg, 0.50 mmol), 1-(3-methyl-3-azetidinyl)pyrrolidine dihydrochloride (Example 176) (131 mg, assumed 86% pure, 0.53 mmol) in 5 mL of DMSO was added DIPEA (0.345 mL, 1.98 mmol). The resulting reaction mixture was stirred at rt overnight, and then hydrazine monohydrate was added (0.5 mL) and the contents were heated to 80° C. for 4 h. The reaction mixture was then cooled to room temperature and purified by RP-HPLC to provide 5-fluoro-4-hydrazino-2-methyl-6-[3-methyl-3-(1-pyrrolidinyl)-1-azetidinyl]pyrimidine (100 mg, 71%). LCMS: (M+H)$^+$: 281.0.

Part B:

[(2R)-2-(Cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl](tetrahydro-2H-pyran-2-yloxy)formamide A mixture of (2R)-3-cyclopentyl-2-{[formyl(tetrahydro-2H-pyran-2-yloxy)amino]methyl}propanoic acid (107 mg, 0.357 mmol), 5-fluoro-4-hydrazino-2-methyl-6-[3-methyl-3-(1-pyrrolidinyl)-1-azetidinyl]pyrimidine (100 mg, 0.357 mmol), EDC (82 mg, 0.428 mmol), HOAt (53 mg, 0.393 mmol), and NMM (0.20 mL, 1.79 mmol) in DMF (5 ml) was stirred at room temperature overnight. The reaction mixture was then purified via RP-HPLC to provide [(2R)-2-(cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl](tetrahydro-2H-pyran-2-yloxy)formamide (118 mg, 58%). LCMS: (M+H)$^+$: 562.2.

Part C:

[(2R)-2-(Cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl]hydroxyformamide A solution of [(2R)-2-(cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl](tetrahydro-2H-pyran-2-yloxy)formamide (118 mg) in 4:1 AcOH:water (20 mL) was stirred at room temperature for 3 days. The solvents were removed in vacuo, and the resulting crude product was purified by RP-HPLC to provide [(2R)-2-(cyclopentylmethyl)-3-(2-{5-fluoro-2-methyl-6-[3-methyl-3-(1-pyrrolidinyl)-1-azetidinyl]-4-pyrimidinyl}hydrazino)-3-oxopropyl]hydroxyformamide (65 mg, 64%). LCMS: (M+H)$^+$: 478.1.

Example 183

{(2R)-2-[(2-{2-Chloro-6-[(2R)-2,4-dimethyl-1-piperazinyl]-5-fluoro-4-pyrimidinyl}hydrazino)carbonyl]hexyl}hydroxyformamide

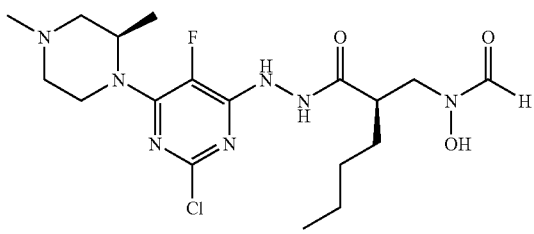

{(2R)-2-[(2-{2-Chloro-6-[(2R)-2,4-dimethyl-1-piperazinyl]-5-fluoro-4-pyrimidinyl}hydrazino)carbonyl]hexyl}hydroxyformamide was prepared according to General Procedure E, utilizing (R)-1,3-dimethylpiperazine dihydrochloride (Example 39) in place of isopropyl amine in Part A, 2.0 M HCl in ether with DCM as a solvent in Part B, and (2R)-2-{[formyl(hydroxy)amino]methyl}hexanoic acid (Example 201) in place of (2R)-3-cyclopentyl-2-({formyl[(phenylmethyl)oxy]amino}methyl)propanoic acid in Part C. LCMS: (M+H)$^+$: 446.1/448.2.

Example 184

[(2R)-3-{2-[2-Chloro-5-fluoro-6-(4,4,5-trimethyl hexahydropyrrolo[3,4-c]pyrrol-2(1H)-yl)-4-pyrimidinyl]hydrazino}-2-(cyclopentylmethyl)-3-oxopropyl]hydroxyformamide (Mixture of Diastereomers)

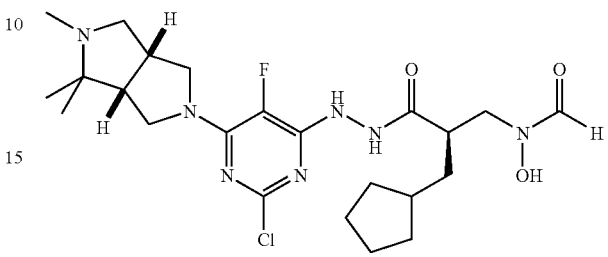

Part A:

(Rac)-cis-1,1,2-trimethyl-5-(phenylmethyl)octahydropyrrolo[3,4-c]pyrrole 4,4,5-Trimethyl-2-(phenylmethyl)tetrahydropyrrolo[3,4-c]pyrrole-1,3(2H,3aH)-dione (5.39 g, 20 mmol) (Bull. Chem. Soc. Jpn., 1987, 60, 4079-4089) was dissolved in THF (50 mL) and cooled to 0° C. LiAlH$_4$ (2.25 g, 59 mmol) was added portionwise and the resulting mixture was refluxed overnight. Upon cooling to 0° C., the reaction was quenched by the addition of water (2.25 mL), followed by 15% (w/w) NaOH (aq) (2.25 mL) and another portion of water (6.75 mL). The quenched reaction was stirred and then filtered through Celite, before being concentrated under reduced pressure. Purification by RP-HPLC yielded (rac)-cis-1,1,2-trimethyl-5-(phenylmethyl)octahydropyrrolo[3,4-c]pyrrole (1.44 g, 30%). LCMS: (M+H)$^+$: 245.2.

Part B:

(Rac)-cis-1,1,2-trimethyloctahydropyrrolo[3,4-c]pyrrole

To a degassed solution of (rac)-cis-1,1,2-trimethyl-5-(phenylmethyl)octahydropyrrolo[3,4-c]pyrrole (1.44 g, 6 mmol) in MeOH (30 mL) was added 1 M HCl (12.3 mL, 12 mmol) followed by 10% Pd/C (220 mg). The resulting mixture was stirred overnight under a hydrogen balloon. Filtration of the catalyst and evaporation of the solvents in vacuo yielded (rac)-cis-1,1,2-trimethyloctahydropyrrolo[3,4-c]pyrrole in quantitative yield as a hydrochloride salt. LCMS: (M+H)$^+$: 155.1.

Part C:

[(2R)-3-{2-[2-chloro-5-fluoro-6-(4,4,5-trimethyl hexahydropyrrolo[3,4-c]pyrrol-2(1H)-yl)-4-pyrimidinyl]hydrazino}-2-(cyclopentylmethyl)-3-oxopropyl]hydroxyformamide

[(2R)-3-{2-[2-chloro-5-fluoro-6-(4,4,5-trimethylhexahydropyrrolo[3,4-c]pyrrol-2(1H)-yl)-4-pyrimidinyl]hydrazino}-2-(cyclopentylmethyl)-3-oxopropyl]hydroxyformamide was prepared according to General Procedure E, utilizing rac-(cis)-1,1,2-trimethyloctahydropyrrolo[3,4-c]pyrrole in place of isopropyl amine in Part A. The product was a mixture of diastereomers. LCMS: (M+H)$^+$: 512.3/514.2.

Example 185

((2R)-2-(Cyclopentylmethyl)-3-{2-[6-[3-(dimethylamino)-3-methyl-1-azetidinyl]-5-fluoro-2-(methylthio)-4-pyrimidinyl]hydrazino}-3-oxopropyl)hydroxyformamide

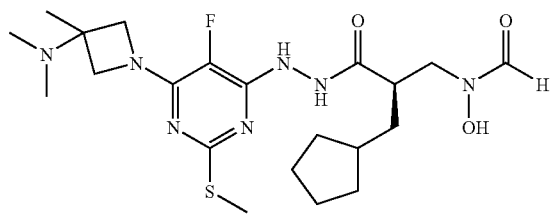

((2R)-2-(Cyclopentylmethyl)-3-{2-[6-[3-(dimethylamino)-3-methyl-1-azetidinyl]-5-fluoro-2-(methylthio)-4-pyrimidinyl]hydrazino}-3-oxopropyl)hydroxyformamide was prepared according to General Procedure C, utilizing N,N,3-trimethyl-3-azetidinamine (J. Med. Chem. 1993, 36, 801-810) in place of azetidine hydrochloride in Part A. LCMS: (M+H)+ 484.1.

Example 186

[(2R)-2-(Cyclopentylmethyl)-3-(2-{5-fluoro-2-methyl-6-[(cis)-10-oxa-4-azatricyclo[5.2.1.0$^{2,6}$]dec-4-yl]-4-pyrimidinyl}hydrazino)-3-oxopropyl]hydroxyformamide

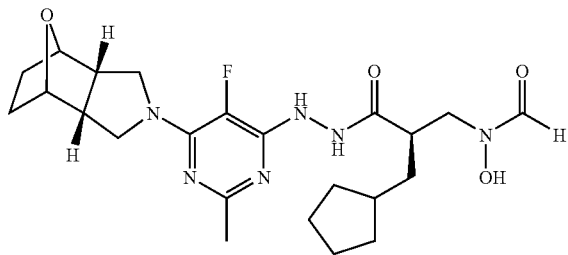

Part A:

(cis)-4-(Phenylmethyl)-10-oxa-4-azatricyclo[5.2.1.0$^{2,6}$]dec-8-ene-3,5-dione

Furan (6 mL, 83 mmol) was added to a solution of N-benzylmaleimide (3 g, 16 mmol) in ether (30 mL) in a sealed tube and the reaction was heated to 90° C. overnight. Evaporation of the solvent yielded a residue which was triturated with cold MeOH to give (cis)-4-(phenylmethyl)-10-oxa-4-azatricyclo[5.2.1.0$^{2,6}$]dec-8-ene-3,5-dione (2.72 g, 67%) as an off white solid. LCMS: (M+Na)+: 278.1.

Part B:

(cis)-4-(Phenylmethyl)-10-oxa-4-azatricyclo[5.2.1.0$^{2,6}$]decane-3,5-dione

To a degassed solution of (cis)-4-(phenylmethyl)-10-oxa-4-azatricyclo[5.2.1.0$^{2,6}$]dec-8-ene-3,5-dione (2.72 g, 10.1 mmol) in 1,2 DME (50 mL) was added 10% Pd/C (540 mg, 20% w/w). The resulting suspension was stirred under a hydrogen balloon for 1 hour. Removal of the catalyst by filtration and concentration of the filtrate in vacuo yielded (cis)-4-(phenylmethyl)-10-oxa-4-azatricyclo[5.2.1.0$^{2,6}$]decane-3,5-dione in quantitative yield. LCMS: (M+H)+: 258.1.

Part C:

(cis)-4-(Phenylmethyl)-10-oxa-4-azatricyclo[5.2.1.0$^{2,6}$]decane

To a solution of (cis)-4-(phenylmethyl)-10-oxa-4-azatricyclo[5.2.1.0$^{2,6}$]decane-3,5-dione (2.39 g, 9.2 mmol) in THF (93 mL) at 0° C. was added LiAlH$_4$ and the resulting solution was heated to 65° C. The reaction was allowed to stir at this temperature for 72 hours before being cooled to 0° C. and quenched with 1 M NaOH. The quenched reaction was then extracted with ether, the combined organics were dried over sodium sulfate and the solvent was removed in vacuo. The residual material was dissolved in DCM, dried over sodium sulfate, concentrated and purified by gradient silica gel chromatography (0-100% EtOAc in hexane, 1% Et$_3$N) yielding (cis)-4-(phenylmethyl)-10-oxa-4-azatricyclo[5.2.1.0$^{2,6}$]decane as a yellow oil (1.72 g, 67%). LCMS: (M+H)+: 230.1.

Part D:

(cis)-10-Oxa-4-azatricyclo[5.2.1.0$^{2,6}$]decane

To a degassed solution of (cis)-4-(phenylmethyl)-10-oxa-4-azatricyclo[5.2.1.0$^{2,6}$]decane (1.72 g, 7.5 mmol) in MeOH (40 mL) was added 1 M HCl (7.5 mL) followed by 10% Pd/C (344 mg, 20% w/w). Stirring under a hydrogen balloon for 72 hours followed by filtration and concentration in vacuo yielded the hydrochloride of (cis)-10-oxa-4-azatricyclo[5.2.1.0$^{2,6}$]decane (1.26 g, 96%) as a yellow foam. LCMS: (M+H)+: 140.1.

Part E:

[(2R)-2-(Cyclopentylmethyl)-3-(2-{5-fluoro-2-methyl-6-[(cis)-10-oxa-4-azatricyclo[5.2.1.0$^{2,6}$]dec-4-yl]-4-pyrimidinyl}hydrazino)-3-oxopropyl]hydroxyformamide

[(2R)-2-(Cyclopentylmethyl)-3-(2-{5-fluoro-2-methyl-6-[(cis)-10-oxa-4-azatricyclo[5.2.1.0$^{2,6}$]dec-4-yl]-4-pyrimidinyl}hydrazino)-3-oxopropyl]hydroxyformamide was prepared according to General Procedure A, utilizing (cis)-10-oxa-4-azatricyclo[5.2.1.0$^{2,6}$]decane in place of pyrrolidine in Part A. LCMS: (M+H)+: 477.3.

Example 187

[(2R)-3-(2-{2-Chloro-5-fluoro-6-[(cis)-10-oxa-4-azatricyclo[5.2.1.0$^{2,6}$]dec-4-yl]-4-pyrimidinyl}hydrazino)-2-(cyclopentylmethyl)-3-oxopropyl]hydroxyformamide

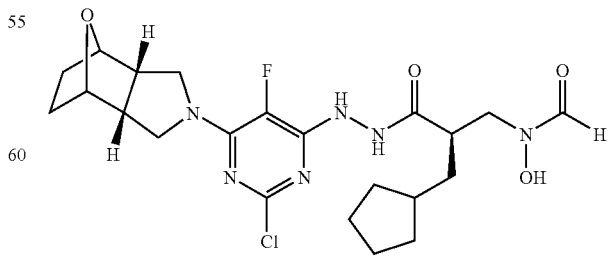

[(2R)-3-(2-{2-Chloro-5-fluoro-6-[(cis)-10-oxa-4-azatricyclo[5.2.1.0$^{2,6}$]dec-4-yl]-4-pyrimidinyl}hydrazino)-2-(cyclopentylmethyl)-3-oxopropyl]hydroxyformamide was prepared according to General Procedure E, utilizing (cis)-10-oxa-4-azatricyclo [5.2.1.0$^{2,6}$]decane (Example 186) in place of isopropyl amine in Part A and 2.0 M HCl in ether with DCM as a solvent in part B. LCMS: (M+H)$^+$: 497.1/499.2.

Example 188

[(2R)-2-(Cyclopentylmethyl)-3-(2-{5-fluoro-2-methyl-6-[(9aR)-octahydro-2H-pyrido[1,2-a]pyrazin-2-yl]-4-pyrimidinyl}hydrazino)-3-oxopropyl]hydroxyformamide

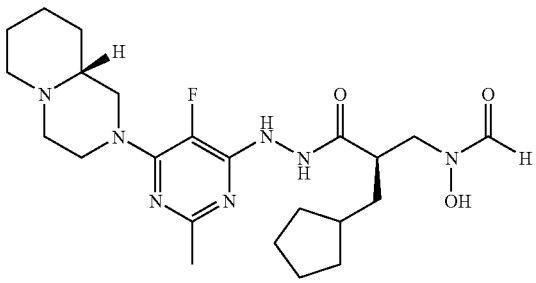

Part A:

Methyl (2R)-1-(N-{[(phenylmethyl)oxy]carbonyl}glycyl)-2-piperidinecarboxylate

To a solution of methyl (2R)-2-piperidinecarboxylate hydrochloride (1.0 g, 5.56 mmol) and HOBt (0.90 g, 6.67 mmol) in CH$_2$Cl$_2$ (20 mL) was added 4-methylmorpholine (2.44 mL, 22.24 mmol), N-{[(phenylmethyl)oxy]carbonyl}glycine (1.16 g, 5.56 mmol), and EDCI (1.28 g, 6.67 mmol). After stirring overnight, the solution was washed 6 N aq. HCl (100 mL) and water (100 mL). The aqueous layer was extracted with CH$_2$Cl$_2$ (3×50 mL). The combined organic layers were washed with water (50 mL) and brine (50 mL), and then dried over anhydrous MgSO$_4$ and concentrated in vacuo to provide methyl (2R)-1-(N-{[(phenylmethyl)oxy]carbonyl}glycyl)-2-piperidinecarboxylate (2.029 g, 99%). LCMS: (M+H)$^+$: 335.1.

Part B:

(9aR)-Tetrahydro-2H-pyrido[1,2-a]pyrazine-1,4(3H,6H)-dione

Methyl (2R)-1-(N-{[(phenylmethyl)oxy]carbonyl}glycyl)-2-piperidinecarboxylate (2.029 g, 6.068 mmol) was dissolved in MeOH (30 mL), degassed and placed under argon. 10% Pd/C (610 mg) was added, and the contents were thoroughly degassed and placed under a hydrogen balloon for 3 h. The contents were then degassed, and the Pd/C was removed by filtration through Celite, washing with MeOH. The filtrate was concentrated in vacuo to provide pure (9aR)-tetrahydro-2H-pyrido[1,2-a]pyrazine-1,4(3H,6H)-dione (779 mg, 76%). LCMS: (M+H)$^+$: 169.1.

Part C:

Phenylmethyl (9aR)-octahydro-2H-pyrido[1,2-a]pyrazine-2-carboxylate (9aR)-Tetrahydro-2H-pyrido[1,2-a]pyrazine-1,4(3H,6H)-dione (779 mg, 4.63 mmol) was dissolved in 46 mL of THF and cooled to 0° C. LiAlH$_4$ (352 mg, 9.57 mmol) was then added portion wise. The mixture was heated to 85° C. for 2 hours, then cooled to 0° C. The reaction was quenched with sodium sulphate decahydrate (704 mg, 9.27 mmol) and was stirred at 0° C. for 30 min. To this solution was added 1N aq. NaOH (5 mL) and the reaction mixture was stirred at 0° C. for 30 min. Then Et$_2$O (20 mL) was added, followed by benzyl chloroformate (0.783 mL, 5.563 mmol). The reaction mixture was stirred vigorously at 0° C. for 2 h, the phases were separated, and the aqueous phase was extracted with Et$_2$O (3×50 mL). The combined organic phase was dried over anhydrous MgSO$_4$, filtered, and concentrated in vacuo. The resulting crude product was purified by RP-HPLC to provide phenylmethyl (9aR)-octahydro-2H-pyrido[1,2-a]pyrazine-2-carboxylate (688 mg, 55%). LCMS: (M+H)$^+$: 275.1.

Part D:

(9aR)-Octahydro-2H-pyrido[1,2-a]pyrazine

Phenylmethyl (9aR)-octahydro-2H-pyrido[1,2-a]pyrazine-2-carboxylate (688 mg, 2.50 mmol) was dissolved in MeOH (15 mL), degassed and placed under argon. 10% Pd/C (206 mg) was added, and the contents were thoroughly degassed and placed under a hydrogen balloon for 2 h. The contents were then degassed, and the Pd/C was removed by filtration through Celite, washing with MeOH. The filtrate was concentrated in vacuo to provide pure (9aR)-octahydro-2H-pyrido[1,2-a]pyrazine (364 mg, 99%). LCMS: (M+H)$^+$: 141.1.

Part E:

[(2R)-2-(Cyclopentylmethyl)-3-(2-{5-fluoro-2-methyl-6-[(9aR)-octahydro-2H-pyrido[1,2-a]pyrazin-2-yl]-4-pyrimidinyl}hydrazino)-3-oxopropyl]hydroxyformamide

[(2R)-2-(Cyclopentylmethyl)-3-(2-{5-fluoro-2-methyl-6-[(9aR)-octahydro-2H-pyrido[1,2-a]pyrazin-2-yl]-4-pyrimidinyl}hydrazino)-3-oxopropyl]hydroxyformamide was prepared in a manner similar to Example 210, Part E and F, utilizing (9aR)-octahydro-2H-pyrido[1,2-a]pyrazine in place of 1-{1-[(2S)-2-pyrrolidinyl]cyclopropyl}pyrrolidine hydrochloride in Part E. LCMS: (M+H)$^+$: 478.4.

Example 189

[(2R)-3-[2-(2-Chloro-6-{(2S)-2-[1-(dimethylamino)cyclopropyl]-1-pyrrolidinyl}-5-fluoro-4-pyrimidinyl)hydrazino]-2-(cyclopentylmethyl)-3-oxopropyl]hydroxyformamide

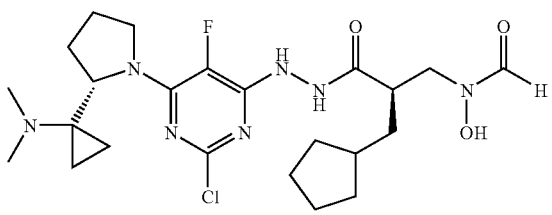

Part A:

N,N-Dimethyl-1-[(2S)-2-pyrrolidinyl]cyclopropanamine

N,N-Dimethyl-1-[(2S)-2-pyrrolidinyl]cyclopropanamine prepared according to Example 210, Part A through Part D, utilizing commercially-available dimethyl amine in place of pyrrolidine in Part B. LCMS: (M+H)+: not detected.

Part B:

[(2R)-3-[2-(2-Chloro-6-{(2S)-2-[1-(dimethylamino)cyclopropyl]-1-pyrrolidinyl}-5-fluoro-4-pyrimidinyl)hydrazino]-2-(cyclopentylmethyl)-3-oxopropyl]hydroxyformamide was prepared according to General Procedure E, utilizing N,N-dimethyl-1-[(2S)-2-pyrrolidinyl]cyclopropanamine in place of isopropyl amine in Part A. LCMS: (M+H)+: 512.3.

Example 190

N-{(2R)-2-(Cyclopentylmethyl)-3-[2-(5-fluoro-2-methyl-6-{methyl[2-(4-pyridinyl)ethyl]amino}-4-pyrimidinyl)hydrazino]-3-oxopropyl}-N-hydroxyformamide

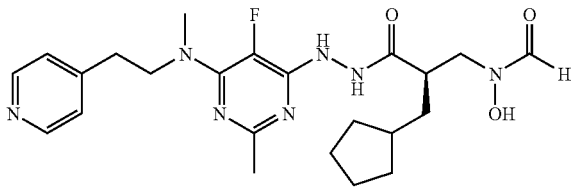

Part A:

6-Chloro-5-fluoro-N,2-dimethyl-N-[2-(4-pyridinyl)ethyl]-4-pyrimidinamine 4,6-Dichloro-5-fluoro-2-methylpyrimidine (280 mg, 1.54 mmol) was dissolved in 5 mL of THF and stirred at room temperature. Methyl[2-(4-pyridinyl)ethyl]amine (210 mg, 1.54 mmol) was added, followed by triethylamine (240 µL, 1.69 mmol). The resulting reaction mixture was stirred overnight. The reaction was diluted with EtOAc, washed with brine, was dried (sodium sulfate) and was evaporated to provide 6-chloro-5-fluoro-N,2-dimethyl-N-[2-(4-pyridinyl)ethyl]-4-pyrimidinamine (350 mg, 81%) that was used without further purification. LCMS: (M+H)+: 281.1.

Part B:

5-Fluoro-6-hydrazino-N,2-dimethyl-N-[2-(4-pyridinyl)ethyl]-4-pyrimidinamine

6-Chloro-5-fluoro-N,2-dimethyl-N-[2-(4-pyridinyl)ethyl]-4-pyrimidinamine (350 mg, 1.25 mmol) was dissolved in 4 ml of DMSO and 4 ml of hydrazine monohydrate was added. The mixture was stirred overnight and was purified by RP-HPLC to provide 5-fluoro-6-hydrazino-N,2-dimethyl-N-[2-(4-pyridinyl)ethyl]-4-pyrimidinamine (220 mg, 63%). LCMS: (M+H)+: 277.2.

Part C:

{(2R)-2-(Cyclopentylmethyl)-3-[2-(5-fluoro-2-methyl-6-{methyl[2-(4-pyridinyl)ethyl]amino}-4-pyrimidinyl)hydrazino]-3-oxopropyl}[(phenylmethyl)oxy]formamide A mixture of (2R)-3-cyclopentyl-2-({formyl[(phenylmethyl)oxy]amino}methyl)propanoic acid (230 mg, 0.76 mmol), 5-fluoro-6-hydrazino-N,2-dimethyl-N-[2-(4-pyridinyl)ethyl]-4-pyrimidinamine (210 mg, 0.76 mmol), EDC (180 mg, 0.91 mmol), HOAt (120 mg, 0.91 mmol), and NMM (0.25 mL, 2.28 mmol) in 5 ml DMF was stirred at room temperature overnight. The reaction mixture was then purified via reverse phase HPLC to provide {(2R)-2-(cyclopentylmethyl)-3-[2-(5-fluoro-2-methyl-6-{methyl[2-(4-pyridinyl)ethyl]amino}-4-pyrimidinyl)hydrazino]-3-oxopropyl}[(phenylmethyl)oxy]formamide (290 mg, 67%). LCMS: (M+H)+: 564.3.

Part D:

N-{(2R)-2-(Cyclopentylmethyl)-3-[2-(5-fluoro-2-methyl-6-{methyl[2-(4-pyridinyl)ethyl]amino}-4-pyrimidinyl)hydrazino]-3-oxopropyl}-N-hydroxyformamide {(2R)-2-(Cyclopentylmethyl)-3-[2-(5-fluoro-2-methyl-6-{methyl[2-(4-pyridinyl)ethyl]amino}-4-pyrimidinyl)hydrazino]-3-oxopropyl}[(phenylmethyl)oxy]formamide (290 mg, 0.51 mmol) was dissolved in 10 mL of MeOH. 10% Pd/carbon (60 mg) was added, and the contents were stirred under a hydrogen balloon for approximately 5 h. The contents were then filtered to remove the catalyst, and the filtrate was concentrated in vacuo to provide {(2R)-2-(cyclopentylmethyl)-3-[2-(5-fluoro-2-methyl-6-{methyl[2-(4-pyridinyl)ethyl]amino}-4-pyrimidinyl)hydrazino]-3-oxopropyl}hydroxyformamide (230 mg, 96%). LCMS: (M+H)+: 474.3.

Example 191

[(2R)-3-(2-{2-Chloro-5-fluoro-6-[(1,3-thiazol-2-ylmethyl)amino]-4-pyrimidinyl}hydrazino)-2-(cyclopentylmethyl)-3-oxopropyl]hydroxyformamide

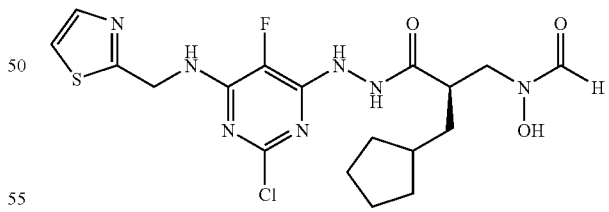

Part A:

Tris(1,1-dimethylethyl)2-{2-chloro-5-fluoro-6-[(1,3-thiazol-2-ylmethyl)amino]-4-pyrimidinyl}-1,1,2-hydrazinetricarboxylate Tris(1,1-dimethylethyl)2-(2,6-dichloro-5-fluoro-4-pyrimidinyl)-1,1,2-hydrazinetricarboxylate (0.988 g, 1.992 mmol) was dissolved in THF (10 mL). To this solution was added triethylamine (0.61 mL, 4.3765 mmol), followed by commercially available 2-aminomethyl thiazole hydrochloride (0.30 g, 1.992 mmol), which was suspended in THF (12 mL). The reaction was left to stir for 2 days during which time an additional 10 mL THF and 2-aminomethyl thiazole hydrochloride (0.061 g, 0.4049 mmol) were added to the reaction mixture. After 3 more days, the reaction mixture was diluted with water and extracted with ethyl acetate. The organics were dried ($Na_2SO_4$) and concentrated. The resulting crude material was purified by silica gel chromatography (0-100% ethyl acetate in hexanes) to provide tris(1,1-dimethylethyl)2-{2-chloro-5-fluoro-6-[(1,3-thiazol-2-ylmethyl)amino]-4-pyrimidinyl}-1,1,2-hydrazinetricarboxylate as a yellow oil (0.5826, 51%). LCMS: $(M+H–3\ Boc)^+=375.0$.

Part B:

2-Chloro-5-fluoro-6-[(1,3-thiazol-2-ylmethyl)amino]-4(1H)-pyrimidinone hydrazone dihydrochloride Tris(1,1-dimethylethyl)2-{2-chloro-5-fluoro-6-[(1,3-thiazol-2-ylmethyl)amino]-4-pyrimidinyl}-1,1,2-hydrazinetricarboxylate (0.5826, 1.015 mmol) was dissolved in MeOH (10 mL) and HCl (4M in 1,4-dioxane) (10 mL) at room temperature and stirred overnight. Removal of the solvents in vacuo provided 2-chloro-5-fluoro-6-[(1,3-thiazol-2-ylmethyl)amino]-4(1H)-pyrimidinone hydrazone, presumed dihydrochloride, as a beige solid (0.3507, 100%). LCMS: $(M+H)^+=274.8$.

Part C:

[(2R)-3-(2-{2-Chloro-5-fluoro-6-[(1,3-thiazol-2-ylmethyl)amino]-4-pyrimidinyl}hydrazino)-2-(cyclopentylmethyl)-3-oxopropyl](tetrahydro-2H-pyran-2-yloxy)formamide 2-Chloro-5-fluoro-6-[(1,3-thiazol-2-ylmethyl)amino]-4(1H)-pyrimidinone hydrazone dihydrochloride (0.3052 g, 0.882 mmol) and (2R)-3-cyclopentyl-2-{[formyl(tetrahydro-2H-pyran-2-yloxy)amino]methyl}propanoic acid (0.457 g, 1.059 mmol) were dissolved in DMF (8 mL). NMM (0.58 mL, 5.2753 mmol) was added, followed by HOAt (0.144 g, 1.059 mmol) and EDC (0.203 g, 1.059 mmol). After stirring overnight, the reaction mixture was purified by RP-HPLC to provide [(2R)-3-(2-{2-chloro-5-fluoro-6-[(1,3-thiazol-2-yl methyl)amino]-4-pyrimidinyl}hydrazino)-2-(cyclopentylmethyl)-3-oxopropyl](tetrahydro-2H-pyran-2-yloxy)formamide as a beige solid (0.3031 g, 62%). LCMS: $(M+H)^+=556.2$.

Part D:

[(2R)-3-(2-{2-Chloro-5-fluoro-6-[(1,3-thiazol-2-ylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[(1,3-thiazol-2-ylmethyl)amino]-4-pyrimidinyl}hydrazino)-2-(cyclopentylmethyl)-3-oxopropyl](tetrahydro-2H-pyran-2-yloxy)formamide (0.3031 g, 0.5461 mmol) was dissolved in acetic acid (8 mL) and water (2 mL). This reaction mixture was stirred overnight. The volatiles were evaporated and reaction mixture was purified by RP-HPLC to provide [(2R)-3-(2-{2-chloro-5-fluoro-6-[(1,3-thiazol-2-ylmethyl)amino]-4-pyrimidinyl}hydrazino)-2-(cyclopentylmethyl)-3-oxopropyl]hydroxyformamide as a white solid (0.1484 g, 58%). LCMS: $(M+H)^+=472.0$.

Example 192

[(2R)-3-(2-{2-Chloro-5-fluoro-6-[methyl(1,3-thiazol-2-ylmethyl)amino]-4-pyrimidinyl}hydrazino)-2-(cyclopentylmethyl)-3-oxopropyl]hydroxyformamide

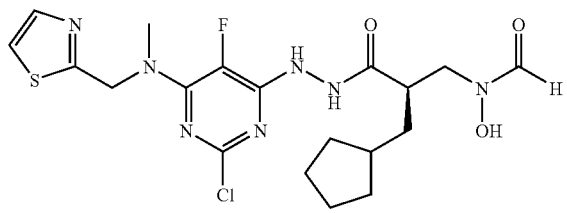

Part A:

N-Methyl-1-(1,3-thiazol-2-yl)methanamine

Commercially available 2-thiazole carboxaldehyde (3.61 g, 31.91 mmol) was dissolved in isopropanol (90 mL), and sieves (3.65 g) were added to reaction vessel. Then methylamine hydrochloride (17.28 g, 256 mmol), sodium acetate (7.85 g, 96 mmol) and sodium cyanoborohydride (3.07 g, 48.9 mmol) were added to the reaction mixture. The mixture was placed under argon and stirred for 3 days. The sieves were filtered away and rinsed with isopropanol. The filtrate was evaporated, and the resulting residue was dissolved in ethyl acetate. The organics were washed with saturated aqueous $NaHCO_3$ and brine. The combined aqueous layers were extracted with 1 L of 10% MeOH in chloroform solvent mixture, and the combined organics were dried ($Na_2SO_4$) and evaporated. The crude product was purified by silica gel chromatography (0-5% MeOH in dichloromethane) to produce N-methyl-1-(1,3-thiazol-2-yl)methanamine as a yellow oil (0.930 g, 23%). LCMS: $(M+H)^+=129.0$.

Part B:

Tris(1,1-dimethylethyl)2-{2-chloro-5-fluoro-6-[methyl(1,3-thiazol-2-ylmethyl)amino]-4-pyrimidinyl}-1,1,2-hydrazinetricarboxylate Tris(1,1-dimethylethyl)2-(2,6-dichloro-5-fluoro-4-pyrimidinyl)-1,1,2-hydrazinetricarboxylate (1.16 g, 2.339 mmol) was dissolved in THF (5 mL). To this solution was added triethylamine (0.39 mL, 2.8 mmol), followed by N-methyl-1-(1,3-thiazol-2-yl)methanamine (0.30 g, 2.3437 mmol) in THF (2 mL). The reaction was left to stir overnight. Then the reaction mixture was diluted with water, and the aqueous layer was extracted with ethyl acetate. The organics were dried ($Na_2SO_4$) and concentrated to produce tris(1,1-dimethylethyl)2-{2-chloro-5-fluoro-6-[methyl(1,3-thiazol-2-ylmethyl)amino]-4-pyrimidinyl}-1,1,2-hydrazinetricarboxylate as a white solid (1.51 g). LCMS: $(M+H–Boc)^+=489.1$.

Part C:

2-Chloro-5-fluoro-6-hydrazino-N-methyl-N-(1,3-thiazol-2-ylmethyl)-4-pyrimidinamine dihydrochloride Tris(1,1-dimethylethyl)2-{2-chloro-5-fluoro-6-[methyl(1,3-thiazol-2-ylmethyl)amino]-4-pyrimidinyl}-1,1,2-hydrazinetricarboxylate (1.51 g, 2.57 mmol) was dissolved in MeOH (25 mL) and HCl (4M in 1,4-dioxane) (25 mL) at room temperature. The reaction mixture was left to stir over 4 days and then evaporated to provide 2-chloro-5-fluoro-6-hydrazino-N-methyl-N-(1,3-thiazol-2-ylmethyl)-4-pyrimidinamine, assumed dihydrochloride, as a beige solid (0.9034 g, 98%). LCMS: $(M+H-2HCl)^+=289.0$.

Part D:

[(2R)-3-(2-{2-Chloro-5-fluoro-6-[methyl(1,3-thiazol-2-ylmethyl)amino]-4-pyrimidinyl}hydrazino)-2-(cyclopentylmethyl)-3-oxopropyl](tetrahydro-2H-pyran-2-yloxy)formamide 2-Chloro-5-fluoro-6-hydrazino-N-methyl-N-(1,3-thiazol-2-ylmethyl)-4-pyrimidinamine (assumed dihydrochloride) (0.9034 g, 2.509 mmol) and (2R)-3-cyclopentyl-2-{[formyl(tetrahydro-2H-pyran-2-yloxy)amino]methyl}propanoic acid (1.299 g, 3.01 mmol) were dissolved in DMF (13 mL). NMM (1.655 mL, 15.05 mmol) was added, followed by HOAt (0.4095 g, 3.01 mmol) and EDC (0.577 g, 3.01 mmol). After stirring overnight, the reaction mixture was purified by RP-HPLC to provide [(2R)-3-(2-{2-chloro-5-fluoro-6-[methyl(1,3-thiazol-2-ylmethyl)amino]-4-pyrimidinyl}hydrazino)-2-(cyclopentylmethyl)-3-oxopropyl](tetrahydro-2H-pyran-2-yloxy)formamide as a red sticky material. LCMS: $(M+H)^+=570.2$.

Part E:

[(2R)-3-(2-{2-Chloro-5-fluoro-6-[methyl(1,3-thiazol-2-ylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[methyl(1,3-thiazol-2-ylmethyl)amino]-4-pyrimidinyl}hydrazino)-2-(cyclopentylmethyl)-3-oxopropyl](tetrahydro-2H-pyran-2-yloxy)formamide was dissolved in acetic acid (8 mL) and water (2 mL). The reaction mixture was left to stir 2 days. The volatiles were evaporated, and the resulting residue was purified by RP-HPLC to provide [(2R)-3-(2-{2-chloro-5-fluoro-6-[methyl(1,3-thiazol-2-ylmethyl)amino]-4-pyrimidinyl}hydrazino)-2-(cyclopentylmethyl)-3-oxopropyl]hydroxyformamide as a beige solid (0.3469 g). LCMS: $(M+H)^+=486.1$.

Example 193

[(2R)-3-[2-(2-Chloro-5-fluoro-6-{[(3S)-1-methyl-2-oxohexahydro-1H-azepin-3-yl]amino}-4-pyrimidinyl)hydrazino]-2-(cyclopentylmethyl)-3-oxopropyl]hydroxyformamide

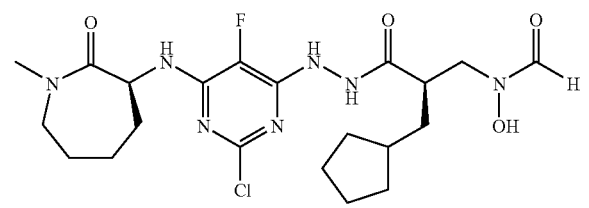

Part A:

1,1-Dimethylethyl [(3S)-1-methyl-2-oxohexahydro-1H-azepin-3-yl]carbamate

To a degassed solution of 1,1-dimethylethyl [(3S)-1-methyl-2-oxo-2,3,4,7-tetrahydro-1H-azepin-3-yl]carbamate (Example 94) (680 mg, 2.8 mmol) in MeOH (20 mL) was added 10% Pd/C (100 mg) and the resulting suspension was stirred overnight under a balloon of hydrogen. Filtration of the catalyst and concentration of the filtrate under reduced pressure yielded 1,1-dimethylethyl [(3S)-1-methyl-2-oxohexahydro-1H-azepin-3-yl]carbamate (470 mg, 88%). LCMS: $(M-{}^tBut)^+$: 186.2.

Part B:

(3S)-3-Amino-1-methylhexahydro-2H-azepin-2-one

To a solution of 1,1-dimethylethyl [(3S)-1-methyl-2-oxohexahydro-1H-azepin-3-yl]carbamate (470 mg, 1.9 mmol) in dioxane (5 mL) was added HCl (4.8 mL, 19 mmol, 4M in dioxane), and the reaction was stirred overnight. Evaporation of the solvent gave a quantitative yield of (3S)-3-amino-1-methylhexahydro-2H-azepin-2-one. LCMS: $(M+H)^+$: 143.1.

Part C:

[(2R)-3-[2-(2-Chloro-5-fluoro-6-{[(3S)-1-methyl-2-oxohexahydro-1H-azepin-3-yl]amino}-4-pyrimidinyl)hydrazino]-2-(cyclopentylmethyl)-3-oxopropyl]hydroxyformamide

[(2R)-3-[2-(2-Chloro-5-fluoro-6-{[(3S)-1-methyl-2-oxohexahydro-1H-azepin-3-yl]amino}-4-pyrimidinyl)hydrazino]-2-(cyclopentylmethyl)-3-oxopropyl]hydroxyformamide was prepared according to General Procedure E, utilizing (3S)-3-amino-1-methylhexahydro-2H-azepin-2-one in place of isopropyl amine in Part A, and 2.0 M HCl in ether with DCM as a solvent in Part B. LCMS: $(M+H)^+$: 500.1/502.2.

Example 194

[(2R)-3-[2-(2-Chloro-5-fluoro-6-{(2R)-2-[(methyloxy)methyl]-1-pyrrolidinyl}-4-pyrimidinyl)hydrazino]-2-(cyclopentylmethyl)-3-oxopropyl]hydroxyformamide

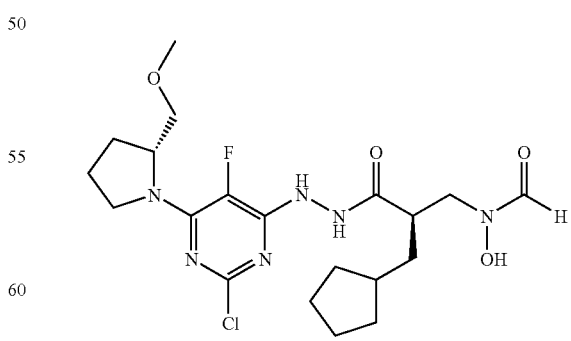

[(2R)-3-[2-(2-Chloro-5-fluoro-6-{(2R)-2-[(methyloxy)methyl]-1-pyrrolidinyl}-4-pyrimidinyl)hydrazino]-2-(cyclopentylmethyl)-3-oxopropyl]hydroxyformamide was prepared according to General Procedure E, utilizing commercially-available (S)-(+)-2-(methoxymethyl)pyrrolidine in place of isopropyl amine in Part A, and 2.0 M HCl in ether with DCM as a solvent in Part B. LCMS: (M+H)⁺: 473.2/475.2.

Example 195

[(2R)-3-(2-{2-Chloro-6-[4-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (D1, Single Unknown Diastereomer)

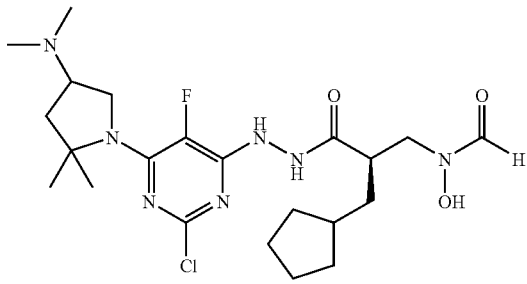

Part A:

Methyl 3-methyl-3-[(phenylmethyl)amino]butanoate

To a solution of benzylamine (10.0 mL, 91.6 mmol) in 95% MeOH-water (180 mL) was added methyl 3-methyl-2-butenoate (12.3 mL, 100.8 mmol). The solution was heated at 55° C. and stirred for 2 weeks. The solution was then cooled to room temperature, concentrated in vacuo, and the residue purified by gradient silica gel chromatography (0% to 100% EtOAc in hexanes; 1% Et₃N) to provide methyl 3-methyl-3-[(phenylmethyl)amino]butanoate (5.5893 g, 28%) as a pale yellow oil. LCMS: (M+H)⁺: 222.1.

Part B:

Methyl 3-methyl-3-[[(methyloxy)(oxo)acetyl](phenylmethyl)amino]butanoate

To a solution of methyl 3-methyl-3-[(phenylmethyl)amino]butanoate (5.5853 g, 25.24 mmol) in THF (125 mL) was added N,N-diisopropylethylamine (6.6 mL, 37.89 mmol). The solution was cooled to 0° C., and methyl chloro(oxo)acetate (2.55 mL, 27.73 mmol) was added dropwise. The mixture was then allowed to stir and warm to room temperature overnight. The mixture was diluted with EtOAc (200 mL) and washed with 1 N aq. HCl (100 mL), followed by sat. aq. NaHCO₃ (100 mL). The organic phase was dried over anhydrous MgSO₄, filtered, and concentrated in vacuo. The residue was crystallized from EtOAc—hexanes to give a white solid that was collected by vacuum filtration and washed with hexanes. The resulting methyl 3-methyl-3-[[(methyloxy)(oxo)acetyl](phenylmethyl)amino]butanoate (7.0709 g, 91%) was obtained as a white solid. LCMS: (M+H)⁺: 308.1.

Part C:

Methyl 2,2-dimethyl-4,5-dioxo-1-(phenylmethyl)-3-pyrrolidinecarboxylate

To a mixture of methyl 3-methyl-3-[[(methyloxy)(oxo)acetyl](phenylmethyl)amino]butanoate (6.9702 g, 22.68 mmol) in toluene (110 mL) was added 25% w/w NaOMe in MeOH (14 mL). The mixture was heated at 80° C. and stirred for 2 h. The solution was then cooled to room temperature and concentrated in vacuo to ca. ½ volume. The residue was partitioned between DCM (200 mL) and 1 N aq. HCl (200 mL). The aqueous phase was extracted with a fresh portion of DCM (100 mL), and the combined organic phase was dried over anhydrous MgSO₄, filtered, and concentrated in vacuo. The resulting white solid was triturated with hexanes and collected by vacuum filtration to afford methyl 2,2-dimethyl-4,5-dioxo-1-(phenylmethyl)-3-pyrrolidinecarboxylate (5.5965 g, 88%) as a white solid. LCMS: (M+H)⁺: 276.1.

Part D:

5,5-Dimethyl-1-(phenylmethyl)-2,3-pyrrolidinedione

A solution of methyl 2,2-dimethyl-4,5-dioxo-1-(phenylmethyl)-3-pyrrolidinecarboxylate (5.6429 g, 20.50 mmol) in 10:1 HOAc-water (100 mL) was heated at 100° C. and stirred for 2 days. The solution was cooled to room temperature and concentrated in vacuo. The residue was partitioned between DCM (200 mL) and sat. aq. NaHCO₃ (100 mL). The aqueous phase was extracted with a fresh portion of DCM (50 mL), and the combined organic phase was dried over anhydrous MgSO₄, filtered, and concentrated in vacuo to give crude 5,5-dimethyl-1-(phenylmethyl)-2,3-pyrrolidinedione (3.9096 g, 88% crude yield) as a light orange solid. LCMS: (M+H)⁺: 218.1.

Part E:

(3E)-5,5-Dimethyl-1-(phenylmethyl)-2,3-pyrrolidinedione 3-(O-methyloxime)

To a solution of 5,5-dimethyl-1-(phenylmethyl)-2,3-pyrrolidinedione (3.9036 g, 17.97 mmol) in MeOH (90 mL) was added sodium acetate (1.81 g, 21.54 mmol) and methoxyamine hydrochloride (1.80 g, 21.55 mmol). The solution was stirred overnight and the solvent was then removed in vacuo. The residue was partitioned between DCM (200 mL), sat. aq. NaHCO₃, and water. The aqueous phase was extracted with a fresh portion of DCM (50 mL), and the combined organic phase was dried over anhydrous Na₂SO₄, filtered, and concentrated in vacuo to provide crude (3E)-5,5-dimethyl-1-(phenylmethyl)-2,3-pyrrolidinedione 3-(O-methyloxime) (4.5282 g, >100% crude yield) as a yellow/orange oil. LCMS: (M+H)⁺: 247.1.

Part F:

5,5-Dimethyl-1-(phenylmethyl)-3-pyrrolidinamine

To a 0° C. solution of (3E)-5,5-dimethyl-1-(phenylmethyl)-2,3-pyrrolidinedione 3-(O-methyloxime) (4.2872 g, 17.41 mmol) in THF (90 mL) was added LiAlH₄ (2.64 g, 69.57 mmol) portionwise. The mixture was heated at 70° C. and stirred for 6.5 h. The mixture was then cooled to room temperature and quenched by addition of Na₂SO₄.10H₂O (3 g), followed by 1 N aq. NaOH (100 mL). The mixture was extracted with Et₂O (2×150 mL), and the combined organic phase was dried over anhydrous Na₂SO₄, filtered, and concentrated in vacuo. The residue was diluted with DCM (200 mL), and the mixture was dried over anhydrous Na₂SO₄, filtered, and concentrated in vacuo to give crude racemic 5,5-dimethyl-1-(phenylmethyl)-3-pyrrolidinamine (3.2293 g, 86%) as a light yellow oil. LCMS: (M+H)⁺: 205.2.

Part G:

N,N,5,5-Tetramethyl-1-(phenylmethyl)-3-pyrrolidinamine

A solution of racemic 5,5-dimethyl-1-(phenylmethyl)-3-pyrrolidinamine (3.2293 g, 15.81 mmol) in formic acid (20 mL) and formalin (20 mL) was heated at 100° C. and stirred for 1 h. The solution was then cooled to 0° C. and adjusted to pH 14 with 6 N aq. NaOH. The mixture was extracted with Et₂O (2×150 mL), and the combined organic phase was dried over anhydrous Na₂SO₄, filtered, and concentrated in vacuo. The residue was diluted with DCM (200 mL), and the solution was dried over anhydrous Na₂SO₄, filtered, and concentrated in vacuo. The residue was purified by gradient silica gel chromatography (0% to 100% EtOAc in hexanes; 1% Et₃N) to give racemic N,N,5,5-tetramethyl-1-(phenylmethyl)-3-pyrrolidinamine (2.8158 g, 77%) as an orange oil. LCMS: (M+H)⁺: 232.9. This material was separated into its two constitutive enantiomers by preparative chiral supercritical fluid chromatography (Chiralpak AD-H 20×250 mm; 6% MeOH (0.1% Et₂NH), 94% CO₂; 50 mL/min; 230 nm detection; 50 mg injection/cycle).

Part H:

N,N,5,5-Tetramethyl-3-pyrrolidinamine dihydrochloride

To a solution of the first eluting enantiomer of N,N,5,5-tetramethyl-1-(phenylmethyl)-3-pyrrolidinamine (1.0607 g, 4.569 mmol) in MeOH (40 mL) was added 1 N aq. HCl (9.1 mL, 9.1 mmol) and 10% Pd/C (50% water, 265 mg). The mixture was hydrogenated overnight and was then filtered through a 0.2 μm PTFE membrane. The solution was concentrated in vacuo, and the residue was azeotroped with MeOH (5×50 mL) to give crude N,N,5,5-tetramethyl-3-pyrrolidinamine dihydrochloride (1.0206 g, >100% crude yield) as a white foam. LCMS: (M+H)⁺: 143.1.

Part I:

Tris(1,1-dimethylethyl)2-{2-chloro-6-[4-(dimethylamino)-2,2-dimethyl-1-pyrrolidinyl]-5-fluoro-4-pyrimidinyl}-1,1,2-hydrazinetricarboxylate To a solution of N,N,5,5-tetramethyl-3-pyrrolidinamine dihydrochloride (assumed 0.9831 g, 4.569 mmol) in DMF (23 mL) was added tris(1,1-dimethylethyl)2-(2,6-dichloro-5-fluoro-4-pyrimidinyl)-1,1,2-hydrazinetricarboxylate (2.27 g, 4.564 mmol) and N,N-diisopropylethylamine (2.63 mL, 15.10 mmol). The solution was stirred overnight and then diluted with Et₂O (100 mL). The mixture was washed with water (2×50 mL), and the combined aqueous phase was extracted with a fresh portion of Et₂O (50 mL). This organic phase was washed with a fresh portion of water (20 mL), and the combined organic phase was dried over anhydrous Na₂SO₄, filtered, and concentrated in vacuo.

The residue was purified by gradient silica gel chromatography (0% to 100% EtOAc in hexanes; 1% Et₃N) to give tris(1,1-dimethylethyl)2-{2-chloro-6-[4-(dimethylamino)-2,2-dimethyl-1-pyrrolidinyl]-5-fluoro-4-pyrimidinyl}-1,1,2-hydrazinetricarboxylate (2.2034 g, 80%) as a light yellow foam. LCMS: (M+H)⁺: 603.3.

Part J:

1-(2-Chloro-5-fluoro-6-hydrazino-4-pyrimidinyl)-N,N,5,5-tetramethyl-3-pyrrolidinamine To a solution of tris(1,1-dimethylethyl)2-{2-chloro-6-[4-(dimethylamino)-2,2-dimethyl-1-pyrrolidinyl]-5-fluoro-4-pyrimidinyl}-1,1,2-hydrazinetricarboxylate (2.2004 g, 3.648 mmol) in MeOH (22 mL) was added 4 N HCl in dioxane (22 mL). The solution was stirred for 3 days and then concentrated in vacuo. The residue was azeotroped with MeOH (50 mL), and then partitioned between DCM (100 mL) and sat. aq. NaHCO₃ (100 mL). The aqueous phase was extracted with fresh DCM (2×50 mL), and the combined organic phase was dried over anhydrous Na₂SO₄, filtered, and concentrated in vacuo to give 1-(2-chloro-5-fluoro-6-hydrazino-4-pyrimidinyl)-N,N,5,5-tetramethyl-3-pyrrolidinamine (1.0552 g, 96%) as an orange foam. LCMS: (M+H)⁺: 303.1.

Part K:

[(2R)-3-(2-{2-Chloro-6-[4-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide To a solution of 1-(2-chloro-5-fluoro-6-hydrazino-4-pyrimidinyl)-N,N,5,5-tetramethyl-3-pyrrolidinamine (1.0502 g, 3.469 mmol) in DMF (16 mL) was added (2R)-3-cyclopentyl-2-({formyl[(phenylmethyl)oxy]amino}methyl)propanoic acid (1.0075 g, 3.299 mmol), N-methylmorpholine (1.8 mL, 16.37 mmol), 1-hydroxy-7-azabenzotriazole (0.540 g, 3.968 mmol), and EDC (0.760 g, 3.964 mmol). The solution was stirred overnight and then diluted with Et₂O (100 mL). The mixture was washed with water (3×50 mL), and the combined aqueous phase was extracted with a fresh portion of Et₂O (50 mL). This organic phase was washed with a fresh portion of water (25 mL), and the combined organic phase was dried over anhydrous Na₂SO₄, filtered, and concentrated in vacuo. The residue was dissolved in DCM (150 mL), dried over anhydrous Na₂SO₄, filtered, and concentrated in vacuo to provide crude [(2R)-3-(2-{2-chloro-6-[4-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide (1.6539 g, 85% crude yield) as a dark red foam. LCMS: (M+H)⁺: 590.2.

Part L:

[(2R)-3-(2-{2-Chloro-6-[4-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide To a solution of [(2R)-3-(2-{2-chloro-6-[4-(dimethylamino)-2,2-dimethyl-1-pyrrolidinyl]-5-fluoro-4-pyrimidinyl}hydrazino)-2-(cyclopentylmethyl)-3-oxopropyl][(phenylmethyl)oxy]formamide (1.6493 g, 2.795 mmol) in MeOH (28 mL) was added 20% Pd(OH)₂/C (50% water, 165 mg). The mixture was hydrogenated for 3.5 h, and then filtered. The solution was concentrated in vacuo, and the residue was purified by Gilson RPLC to provide [(2R)-3-(2-{2-chloro-6-[4-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (0.7580 g, 54%, single unknown diastereomer) as a pink solid following crystallization from EtOAc-hexanes. LCMS: (M+H)+: 500.3.

Example 196

[(2R)-3-(2-{2-Chloro-6-[4-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide (D2, Single Unknown Diastereomer)

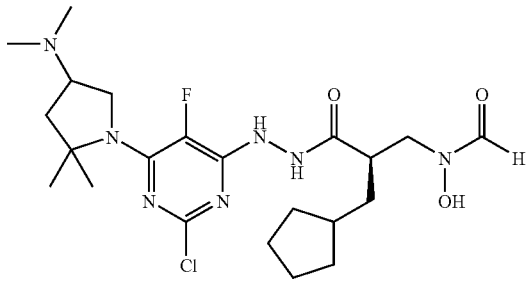

The second eluting enantiomer of N,N,5,5-tetramethyl-1-(phenylmethyl)-3-pyrrolidinamine was employed to prepare [(2R)-3-(2-{2-chloro-6-[4-(dimethylamino)-2,2-dimethyl-1-pyrrolidinyl]-5-fluoro-4-pyrimidinyl}hydrazino)-2-(cyclopentylmethyl)-3-oxopropyl]hydroxyformamide according to the procedures of Example 195. LCMS: (M+H)+: 500.3.

Example 197

[(2R)-3-[2-(2-Chloro-6-{3-[2-(dimethylamino)-1,1-dimethylethyl]-1-pyrrolidinyl}-5-fluoro-4-pyrimidinyl)hydrazino]-2-(cyclopentylmethyl)-3-oxopropyl]hydroxyformamide (Mixture of Diastereomers)

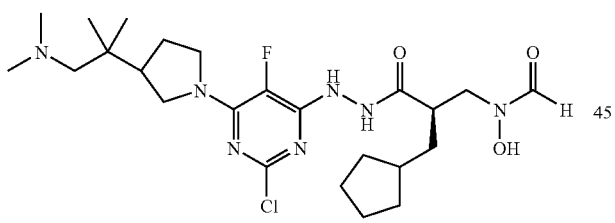

Part A:

{1-Methyl-1-[1-(phenylmethyl)-3-pyrrolidinyl]ethyl}amine

{1-Methyl-1-[1-(phenylmethyl)-3-pyrrolidinyl]ethyl}amine can be prepared according to literature procedure (J. Org. Chem. 2000, 65, 1016-1021). LCMS: (M+H)+: 219.1.

Part B:

N,N-Dimethyl-2-[1-(phenylmethyl)-3-pyrrolidinyl]-2-propanamine

{1-Methyl-1-[1-(phenylmethyl)-3-pyrrolidinyl]ethyl}amine (1.0726 mg, 4.912 mmol) was dissolved in a mixture of formaldehyde (30 mL) and formic acid (30 mL), and then heated to 100° C. for 2 hours. After cooling to 0° C., 6 N aq. NaOH was added to adjust the pH to 14. The aqueous layer was then extracted with Et2O (3×50 mL), and the combined organic phase was dried over anhydrous MgSO4, filtered, and concentrated in vacuo to provide N,N-dimethyl-2-[1-(phenylmethyl)-3-pyrrolidinyl]-2-propanamine (1.85 g, 99%). LCMS: (M+H)+: 247.2.

Part C:

N,N-Dimethyl-2-(3-pyrrolidinyl)-2-propanamine hydrochloride

N,N-Dimethyl-2-[1-(phenylmethyl)-3-pyrrolidinyl]-2-propanamine (2.089 g, 8.47 mmol) was dissolved in a mixture of MeOH (50 mL) and 1N HCl (18.65 mL, 18.65 mmol), degassed and placed under argon. 10% Pd/C (625 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure N,N-dimethyl-2-(3-pyrrolidinyl)-2-propanamine hydrochloride (1.245 g, 76%). LCMS: (M+H)+: 157.2.

Part D:

[(2R)-3-[2-(2-Chloro-6-{3-[2-(dimethylamino)-1,1-dimethylethyl]-1-pyrrolidinyl}-5-fluoro-4-pyrimidinyl)hydrazino]-2-(cyclopentylmethyl)-3-oxopropyl]hydroxyformamide

[(2R)-3-[2-(2-Chloro-6-{3-[2-(dimethylamino)-1,1-dimethylethyl]-1-pyrrolidinyl}-5-fluoro-4-pyrimidinyl)hydrazino]-2-(cyclopentylmethyl)-3-oxopropyl]hydroxyformamide was prepared as a mixture of diastereomers according to General Procedure E, utilizing N,N-dimethyl-2-(3-pyrrolidinyl)-2-propanamine hydrochloride in place of isopropyl amine in Part A. LCMS: (M+H)+: 514.2.

Example 198

N-[(2R)-3-(2-{2-Chloro-5-fluoro-6-[(2R,3R)-2,3,4-trimethyl-1-piperazinyl]-4-pyrimidinyl}hydrazino)-2-(cyclopentylmethyl)-3-oxopropyl]-N-hydroxyformamide

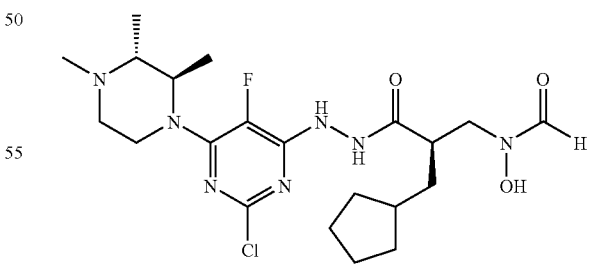

Part A:

Phenylmethyl 2,3-dimethyl-1-piperazinecarboxylate

A 100 mL, three-necked round-bottom flask was charged with a mixture of trans-2,3-dimethylpiperazine and cis-2,3- dimethylpiperazine (Yakugaku Zasshi, 1958, 78, 229-232) (3.571 g, 31.1 mmol). The flask was cooled in an ice bath, and a solution of methanesulfonic acid (3.95 mL, 60.9 mmol) in 2.7 mL of water was added slowly, maintaining the temperature below 40° C. The solution was cooled to 20° C., and 4 mL of ethanol was added. The pH was adjusted to 4 with 60% aqueous potassium acetate, and then benzyl chloroformate (3.86 mL, 27.4 mol in 2 mL of THF) and potassium acetate solutions were simultaneously added dropwise with adjustment of the rate to maintain the reaction solution at pH 4, with cooling to maintain the temperature at 25° C. After the mixture was stirred an additional hour, the organic solvents were removed, and the remaining aqueous solution was washed with ethyl acetate. The ethyl acetate wash was extracted with 1 M HCl twice to recover the desired product. The acid extracts were combined with the original aqueous solution, and the pH was adjusted to 11 by addition of 6 N NaOH, with cooling to maintain the temperature below 40° C. The aqueous solution was then extracted with ethyl acetate, and the ethyl acetate extraction was dried over magnesium sulfate. Filtration and removal of the solvent provided all four stereoisomers of phenylmethyl 2,3-dimethyl-1-piperazinecarboxylate as a dark brown oil (3.11 g, 41%). LCMS: (M+H)+: 249.1.

Part B:

Phenylmethyl (2R,3R)-2,3,4-trimethyl-1-piperazinecarboxylate and phenylmethyl (2S,3S)-2,3,4-trimethyl-1-piperazinecarboxylate To a solution of phenylmethyl 2,3-dimethyl-1-piperazinecarboxylate (mixture of four stereoisomers) (3.105 g, 12.5 mmol) in dichloromethane (90 mL) at 0° C. was added formaldehyde (1.409 mL, 37% water solution, 18.75 mmol) followed by sodium triacetoxyborohydride (3.445 g, 16.26 mmol). The reaction mixture was allowed to warm to room temperature and stirred for 2 h before being diluted with dichloromethane and washed with 1N NaOH solution. The organics were washed with brine, dried (MgSO4) and evaporated to yield phenylmethyl 2,3,4-trimethyl-1-piperazinecarboxylate (mixture of all four stereoisomers) (3.04 g, 93%). Phenylmethyl (2R,3R)-2,3,4-trimethyl-1-piperazinecarboxylate (365 mg) and phenylmethyl (2S,3S)-2,3,4-trimethyl-1-piperazinecarboxylate (420 mg) were separated out by a combination of preparative and chiral chromatography. Absolute configuration was assigned using Ab Initio vibrational circular dichroism. LCMS: (M+H)+: 263.3.

Part C:

(2R,3R)-1,2,3-Trimethylpiperazine, Hydrochloride Salt

Phenylmethyl (2R,3R)-2,3,4-trimethyl-1-piperazinecarboxylate (328 mg, 1.25 mmol) was dissolved in 20 mL of MeOH, degassed and placed under argon. 10% Pd/C (81 mg) was added, and the contents were thoroughly degassed and placed under a hydrogen balloon for approximately 3 hrs. The contents were then degassed and filtered through Celite, and the Celite pad was washed with DCM and MeOH. After 2.75 mL 1N HCl was added, the resulting filtrate was concentrated in vacuo to provide the hydrochloride salt of (2R,3R)-1,2,3-trimethylpiperazine (251 mg, 100%). LCMS: (M+H)+: 129.1.

Part D:

N-[(2R)-3-(2-{2-Chloro-5-fluoro-6-[(2R,3R)-2,3,4-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]-N-hydroxyformamide was prepared according to General Procedure E, utilizing (2R,3R)-1,2,3-trimethylpiperazine, hydrochloride salt in place of isopropyl amine in Part A, and using 3 equivalents of DIPEA. LCMS: (M+H)+: 486.1.

Example 199

[(2R)-3-{2-[2-Chloro-6-(3-ethyl-3-hydroxy-1-azetidinyl)-5-fluoro-4-pyrimidinyl]hydrazino}-2-(cyclopentylmethyl)-3-oxopropyl]hydroxyformamide

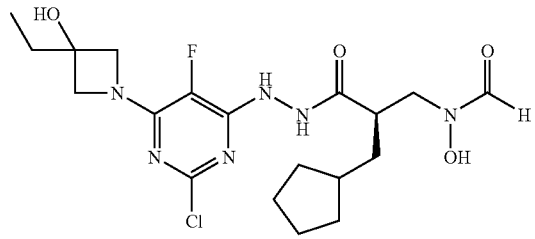

Part A:

3-Ethyl-3-azetidinol hydrochloride

A mixture of 1-(diphenylmethyl)-3-ethyl-3-azetidinol (0.200 g, 0.75 mmol) (J. Med. Chem. 1993, 36, 801-810) and 20% Pd(OH)2 (200 mg) in ethanol (30 ml) and 1N HCl (5 ml) was treated with H2 at 55 psi overnight. Standard work-up provided 3-ethyl-3-azetidinol hydrochloride. LCMS: (M+H)+ 102.2.

Part B:

[(2R)-3-{2-[2-Chloro-6-(3-ethyl-3-hydroxy-1-azetidinyl)-5-fluoro-4-pyrimidinyl]hydrazino}-2-(cyclopentylmethyl)-3-oxopropyl]hydroxyformamide

[(2R)-3-{2-[2-Chloro-6-(3-ethyl-3-hydroxy-1-azetidinyl)-5-fluoro-4-pyrimidinyl]hydrazino}-2-(cyclopentylmethyl)-3-oxopropyl]hydroxyformamide was prepared according to General Procedure D, utilizing 3-ethyl-3-azetidinol hydrochloride in place of N-methylpiperazine in Part A. LCMS: (M+H)+ 459.1.

Example 200

[(2R)-3-{2-[2-Chloro-5-fluoro-6-(tetrahydro-1H-furo[3,4-c]pyrrol-5(3H)-yl)-4-pyrimidinyl]hydrazino}-2-(cyclopentylmethyl)-3-oxopropyl]hydroxyformamide

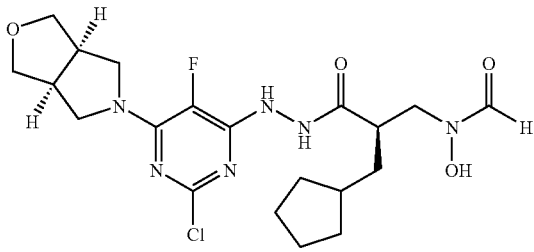

([(2R)-3-{2-[2-Chloro-5-fluoro-6-(tetrahydro-1H-furo[3,4-c]pyrrol-5(3H)-yl)-4-pyrimidinyl]hydrazino}-2-(cyclopentylmethyl)-3-oxopropyl]hydroxyformamide was prepared according to General Procedure E, utilizing hexahydro-1H-furo[3,4-c]pyrrole (Example 99) in place of isopropyl amine in Part A. LCMS: (M+H)$^+$: 471.1/473.1.

Example 201

{(2R)-2-[(2-{2-Chloro-5-fluoro-6-[(9aR)-octahydro-2H-pyrido[1,2-a]pyrazin-2-yl]-4-pyrimidinyl}hydrazino)carbonyl]hexyl}hydroxyformamide

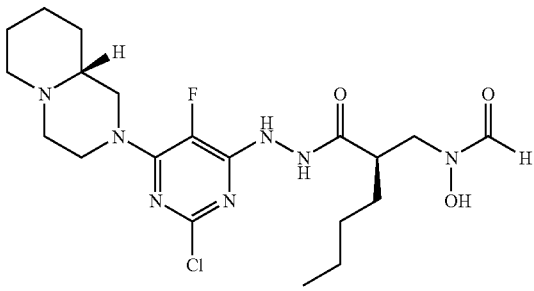

Part A:

(2R)-2-({Formyl[(phenylmethyl)oxy]amino}methyl)hexanoic acid (2R)-2-({Formyl[(phenylmethyl)oxy]amino}methyl)hexanoic acid was prepared in a manner similar to Intermediate A, utilizing hexanoyl chloride in place of 3-cyclopentylpropionyl chloride in Part A. LCMS: (M+H)$^+$: 280.2.

Part B:

{(2R)-2-[(2-{2-Chloro-5-fluoro-6-[(9aR)-octahydro-2H-pyrido[1,2-a]pyrazin-2-yl]-4-pyrimidinyl}hydrazino)carbonyl]hexyl}hydroxyformamide {(2R)-2-[(2-{2-Chloro-5-fluoro-6-[(9aR)-octahydro-2H-pyrido[1,2-a]pyrazin-2-yl]-4-pyrimidinyl}hydrazino)carbonyl]hexyl}hydroxyformamide was prepared according to General Procedure E, utilizing (9aR)-octahydro-2H-pyrido[1,2-a]pyrazine (J. Med. Chem. 1993, 36, 2311-2320) in place of isopropyl amine in Part A, 2.0 M HCl in ether with DCM as a solvent in Part B, and (2R)-2-({formyl[(phenylmethyl)oxy]amino}methyl)hexanoic acid in place of (2R)-3-cyclopentyl-2-({formyl[(phenylmethyl)oxy]amino}methyl)propanoic acid in Part C. LCMS: (M+H)$^+$: 472.2/474.1.

Example 202

N-[(2R)-2-(Cyclopentylmethyl)-3-(2-{5-fluoro-2-methyl-6-[(2S,3S)-2,3,4-trimethyl-1-piperazinyl]-4-pyrimidinyl}hydrazino)-3-oxopropyl]-N-hydroxyformamide

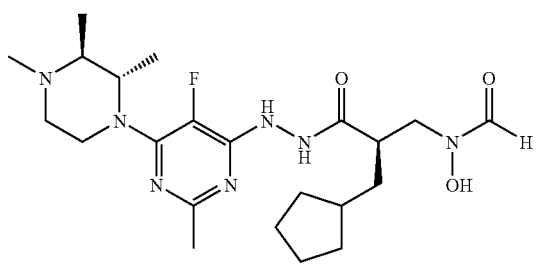

Part A:

(2S,3S)-1,2,3-Trimethylpiperazine, Hydrochloride Salt

Phenylmethyl (2S,3S)-2,3,4-trimethyl-1-piperazinecarboxylate (323 mg, 1.23 mmol) (Example 198) was dissolved in 20 mL of MeOH, degassed and placed under argon. 10% Pd/C (81 mg) was added, and the contents were thoroughly degassed and placed under a hydrogen balloon for approximately 3 hrs. The contents were then degassed and filtered through Celite, and the Celite pad was washed with DCM and MeOH. After 2.70 mL 1N HCl was added, the resulting filtrate was concentrated in vacuo to provide the hydrochloride salt of (2S,3S)-1,2,3-trimethylpiperazine (246 mg, 100%). LCMS: (M+H)$^+$: 129.1.

Part B:

N-[(2R)-2-(Cyclopentylmethyl)-3-(2-{5-fluoro-2-methyl-6-[(2S,3S)-2,3,4-trimethyl-1-piperazinyl]-4-pyrimidinyl}hydrazino)-3-oxopropyl]-N-hydroxyformamide N-[(2R)-2-(Cyclopentylmethyl)-3-(2-{5-fluoro-2-methyl-6-[(2S,3S)-2,3,4-trimethyl-1-piperazinyl]-4-pyrimidinyl}hydrazino)-3-oxopropyl]-N-hydroxyformamide was prepared according to General Procedure A, utilizing (2S,3S)-1,2,3-trimethylpiperazine, hydrochloride salt in place of pyrrolidine in Part A, and using 3 equivalents of DIPEA. LCMS: (M+H)$^+$: 466.2.

Example 203

N-[(2R)-2-(Cyclopentylmethyl)-3-(2-{5-fluoro-2-methyl-6-[(2R,3R)-2,3,4-trimethyl-1-piperazinyl]-4-pyrimidinyl}hydrazino)-3-oxopropyl]-N-hydroxyformamide

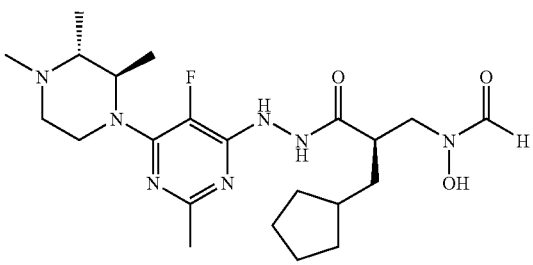

N-[(2R)-2-(Cyclopentylmethyl)-3-(2-{5-fluoro-2-methyl-6-[(2R,3R)-2,3,4-trimethyl-1-piperazinyl]-4-pyrimidinyl}hydrazino)-3-oxopropyl]-N-hydroxyformamide was prepared according to General Procedure A, utilizing (2R,3R)-1,2,3-trimethylpiperazine, hydrochloride salt (Example 198) in place of pyrrolidine in Part A, and using 3 equivalents of DIPEA. LCMS: (M+H)+: 466.2.

Example 204

[(2R)-3-(2-{2-Chloro-5-fluoro-6-[(3-thienylmethyl)amino]-4-pyrimidinyl}hydrazino)-2-(cyclopentylmethyl)-3-oxopropyl]hydroxyformamide

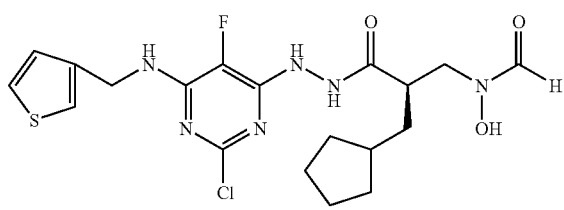

Tris(1,1-dimethylethyl)2-{2-chloro-5-fluoro-6-[(3-thienylmethyl)amino]-4-pyrimidinyl}-1,1,2-hydrazinetricarboxylate Tris(1,1-dimethylethyl)2-(2,6-dichloro-5-fluoro-4-pyrimidinyl)-1,1,2-hydrazinetricarboxylate (1.413 g, 2.85 mmol) was dissolved in THF (5 mL). To this solution was added triethylamine (0.48 mL, 3.4438 mmol), followed by commercially available (3-thienylmethyl)amine (0.322 g, 2.85 mmol) which was dissolved in THF (1 mL). After stirring, the reaction mixture was diluted with water, and the aqueous layer was extracted with ethyl acetate. The organics were dried (Na2SO4) and concentrated to produce tris(1,1-dimethylethyl)2-{2-chloro-5-fluoro-6-[(3-thienylmethyl)amino]-4-pyrimidinyl}-1,1,2-hydrazinetricarboxylate as a white solid (1.6214 g, 99%). LCMS: (M+H−3Boc)+=374.1.

2-Chloro-5-fluoro-6-[(3-thienylmethyl)amino]-4(1H)-pyrimidinone hydrazone dihydrochloride Tris(1,1-dimethylethyl)2-{2-chloro-5-fluoro-6-[(3-thienylmethyl)amino]-4-pyrimidinyl}-1,1,2-hydrazinetricarboxylate (1.6214 g, 2.83 mmol) was dissolved in MeOH (28 mL) and HCl (4M in 1,4-dioxane) (28 mL). The reaction mixture was left to stir overnight and then evaporated to provide 2-chloro-5-fluoro-6-[(3-thienylmethyl)amino]-4(1H)-pyrimidinone hydrazone, presumed dihydrochloride, as a wine colored solid (1.0828 g). LCMS: (M+H−2HCl)+= 273.9.

[(2R)-3-(2-{2-Chloro-5-fluoro-6-[(3-thienylmethyl)amino]-4-pyrimidinyl}hydrazino)-2-(cyclopentylmethyl)-3-oxopropyl](tetrahydro-2H-pyran-2-yloxy)formamide 2-Chloro-5-fluoro-6-[(3-thienylmethyl)amino]-4(1H)-pyrimidinone hydrazone dihydrochloride (1.0828 g) and (2R)-3-cyclopentyl-2-{[formyl(tetrahydro-2H-pyran-2-yloxy)amino]methyl}propanoic acid diisopropyl amine salt form (1.63 g, 3.8 mmol) were dissolved in DMF (9 mL). NMM (2.1 mL, 19.1 mmol) was added, followed by HOAt (0.512 g, 3.76 mmol) and EDC (0.722 g, 3.77 mmol). After stirring overnight, the reaction mixture was purified by RP-HPLC to provide [(2R)-3-(2-{2-chloro-5-fluoro-6-[(3-thienylmethyl)amino]-4-pyrimidinyl}hydrazino)-2-(cyclopentylmethyl)-3-oxopropyl](tetrahydro-2H-pyran-2-yloxy)formamide as a reddish brown solid (0.7045 g). LCMS: (M+H−THP)+= 471.1.

[(2R)-3-(2-{2-Chloro-5-fluoro-6-[(3-thienylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[(3-thienylmethyl)amino]-4-pyrimidinyl}hydrazino)-2-(cyclopentylmethyl)-3-oxopropyl](tetrahydro-2H-pyran-2-yloxy)formamide (0.7045 g, 1.272 mmol) was dissolved in acetic acid (8 mL) and water (2 mL). The reaction mixture was stirred overnight. The volatiles were evaporated, and the resulting residue was purified by RP-HPLC to provide [(2R)-3-(2-{2-chloro-5-fluoro-6-[(3-thienylmethyl)amino]-4-pyrimidinyl}hydrazino)-2-(cyclopentylmethyl)-3-oxopropyl]hydroxyformamide as a beige solid (0.2284 g, 38%). LCMS: (M+H)+=471.0.

Example 205

((2R)-2-(Cyclopentylmethyl)-3-{2-[5-fluoro-6-[methyl(1,3-thiazol-2-ylmethyl)amino]-2-(methylthio)-4-pyrimidinyl]hydrazino}-3-oxopropyl)hydroxyformamide

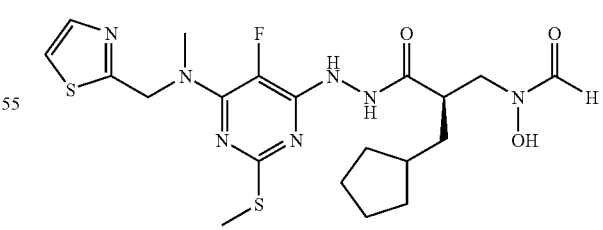

Part A:

N-Methyl-1-(1,3-thiazol-2-yl)methanamine

Commercially available 2-thiazole carboxaldehyde (3.61 g, 31.91 mmol) was dissolved in isopropanol (90 mL), and sieves (3.65 g) were added to reaction vessel. Then methylamine hydrochloride (17.28 g, 256 mmol), sodium acetate (7.85 g, 96 mmol) and sodium cyanoborohydride (3.07 g, 48.9 mmol) were added to the reaction mixture. The mixture was placed under argon and stirred for 3 days. The sieves were filtered away and rinsed with isopropanol. The filtrate was evaporated, and the resulting residue was dissolved in ethyl acetate. The organics were washed with saturated aqueous NaHCO$_3$ and brine. The combined aqueous layers were extracted with 1 L of 10% MeOH in chloroform solvent mixture, and the combined organics were dried (Na$_2$SO$_4$) and evaporated. The crude product was purified by silica gel chromatography (0-5% MeOH in dichloromethane) to produce N-methyl-1-(1,3-thiazol-2-yl)methanamine as a yellow oil (0.930 g, 23%). LCMS: (M+H)$^+$=129.0.

Part B:

6-Chloro-5-fluoro-N-methyl-2-(methylthio)-N-(1,3-thiazol-2-ylmethyl)-4-pyrimidinamine 4,6-Dichloro-5-fluoro-2-(methylthio)pyrimidine (see Intermediate E) (0.3313 g, 1.563 mmol), N-methyl-1-(1,3-thiazol-2-yl)methanamine (0.200 g, 1.5625 mmol), and triethylamine (0.26 mL, 1.8654 mmol) were dissolved in THF (5 mL) and left to stir overnight. Then the reaction mixture was diluted with water and the aqueous layer was extracted with ethyl acetate. The organics were dried (Na$_2$SO$_4$) and concentrated to produce 6-chloro-5-fluoro-N-methyl-2-(methylthio)-N-(1,3-thiazol-2-ylmethyl)-4-pyrimidinamine as a yellow oil (0.4928 g). LCMS: (M+H)$^+$=305.0.

Part C:

5-Fluoro-6-hydrazino-N-methyl-2-(methylthio)-N-(1,3-thiazol-2-ylmethyl)-4-pyrimidinamine 6-Chloro-5-fluoro-N-methyl-2-(methylthio)-N-(1,3-thiazol-2-ylmethyl)-4-pyrimidinamine (0.4928 g, 1.621 mmol) was dissolved in 5 mL of DMSO and hydrazine monohydrate (0.63 mL, 12.96 mmol). The reaction vessel was pressure sealed and heated to 80° C. for 2 hours. The reaction mixture was purified by RP-HPLC to provide 5-fluoro-6-hydrazino-N-methyl-2-(methylthio)-N-(1,3-thiazol-2-ylmethyl)-4-pyrimidinamine as a beige solid (0.2112 g, 43%). LCMS: (M+H)$^+$=301.0.

Part D:

((2R)-2-(Cyclopentylmethyl)-3-{2-[5-fluoro-6-[methyl(1,3-thiazol-2-ylmethyl)amino]-2-(methylthio)-4-pyrimidinyl]hydrazine}-3-oxopropyl)(tetrahydro-2H-pyran-2-yloxy)formamide 5-Fluoro-6-hydrazino-N-methyl-2-(methylthio)-N-(1,3-thiazol-2-ylmethyl)-4-pyrimidinamine (0.2112 g, 0.704 mmol), and (2R)-3-cyclopentyl-2-{[formyl(tetrahydro-2H-pyran-2-yloxy)amino]methyl}propanoic acid (0.365 g, 0.846 mmol) were dissolved in DMF (5 mL). NMM (0.31 mL, 2.8195 mmol) was added, followed by HOAt (0.115 g, 0.846 mmol) and EDC (0.162 g, 0.845 mmol). After stirring overnight, the reaction mixture was purified by RP-HPLC to provide ((2R)-2-(cyclopentylmethyl)-3-{2-[5-fluoro-6-[methyl(1,3-thiazol-2-yl)amino]-2-(methylthio)-4-pyrimidinyl]hydrazine}-3-oxopropyl)(tetrahydro-2H-pyran-2-yloxy)formamide as a beige-orange solid (0.2601 g, 63%). LCMS: (M+H)$^+$=582.2.

Part E:

((2R)-2-(Cyclopentylmethyl)-3-{2-[5-fluoro-6-[methyl(1,3-thiazol-2-ylmethyl)amino]-2-(methylthio)-4-pyrimidinyl]hydrazine}-3-oxopropyl)hydroxyformamide ((2R)-2-(Cyclopentylmethyl)-3-{2-[5-fluoro-6-[methyl(1,3-thiazol-2-ylmethyl)amino]-2-(methylthio)-4-pyrimidinyl]hydrazine}-3-oxopropyl)(tetrahydro-2H-pyran-2-yloxy)formamide (0.2601 g, 0.448 mmol) was dissolved in acetic acid (8 mL) and water (2 mL). This reaction mixture was stirred for 3 days. The volatiles were evaporated, and the resulting residue was purified by RP-HPLC to provide ((2R)-2-(cyclopentylmethyl)-3-{2-[5-fluoro-6-[methyl(1,3-thiazol-2-ylmethyl)amino]-2-(methylthio)-4-pyrimidinyl]hydrazine}-3-oxopropyl)hydroxyformamide as a beige solid (0.1396 g, 63%). LCMS: (M+H)$^+$=498.1.

Example 206

[(2R)-2-(Cyclopentylmethyl)-3-(2-{5-fluoro-2-(methylthio)-6-[(1,3-thiazol-2-ylmethyl)amino]-4-pyrimidinyl}hydrazino)-3-oxopropyl]hydroxyformamide

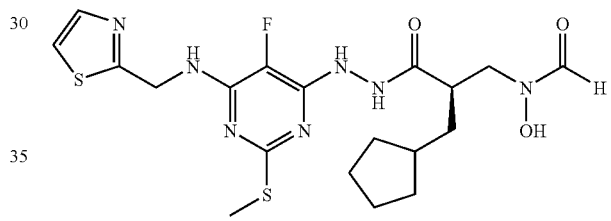

Part A:

6-Chloro-5-fluoro-2-(methylthio)-N-(1,3-thiazol-2-ylmethyl)-4-pyrimidinamine 4,6-Dichloro-5-fluoro-2-(methylthio)pyrimidine (see Intermediate E) (0.422 g, 1.991 mmol), commercially available (1,3-thiazol-2-ylmethyl)amine hydrochloride (0.300 g, 1.992 mmol) and triethylamine (0.61 mL, 4.3765 mmol) were dissolved in THF (3 mL) and left to stir for 4 days. The reaction mixture was diluted with water, and the aqueous layer was extracted with ethyl acetate. The organics were dried (MgSO$_4$) and concentrated to produce 6-chloro-5-fluoro-2-(methylthio)-N-(1,3-thiazol-2-ylmethyl)-4-pyrimidinamine as a yellow-orange solid (0.6773 g). LCMS: (M+H)$^+$=291.0.

Part B:

5-Fluoro-2-(methylthio)-6-[(1,3-thiazol-2-ylmethyl)amino]-4(1H)-pyrimidinone hydrazone 6-Chloro-5-fluoro-2-(methylthio)-N-(1,3-thiazol-2-ylmethyl)-4-pyrimidinamine (0.6773 g, 2.336 mmol) was dissolved in DMSO (7 mL) and hydrazine monohydrate (0.91 mL, 18.72 mmol). The reaction vessel was pressure sealed and heated to 80° C. for 2 hours. The reaction mixture was purified by RP-HPLC to provide 5-fluoro-2-(methylthio)-6-

[(1,3-thiazol-2-ylmethyl)amino]-4(1H)-pyrimidinone hydrazone as an orange solid (0.1958 g, 29%). LCMS: (M+H)+=287.1.

Part C:

[(2R)-2-(Cyclopentylmethyl)-3-(2-{5-fluoro-2-(methylthio)-6-[(1,3-thiazol-2-ylmethyl)amino]-4-pyrimidinyl}hydrazino)-3-oxopropyl](tetrahydro-2H-pyran-2-yloxy)formamide 5-Fluoro-2-(methylthio)-6-[(1,3-thiazol-2-ylmethyl)amino]-4(1H)-pyrimidinone hydrazone (0.1958 g, 0.685 mmol) and (2R)-3-cyclopentyl-2-{[formyl(tetrahydro-2H-pyran-2-yloxy)amino]methyl}propanoic acid (0.355 g, 0.823 mmol) were dissolved in DMF (5 mL). NMM (0.30 mL, 2.7286 mmol) was added, followed by HOAt (0.112 g, 0.824 mmol) and EDC (0.157 g, 0.819 mmol). After stirring overnight, the reaction mixture was purified by RP-HPLC to provide [(2R)-2-(cyclopentylmethyl)-3-(2-{5-fluoro-2-(methylthio)-6-[(1,3-thiazol-2-ylmethyl)amino]-4-pyrimidinyl}hydrazino)-3-oxopropyl](tetrahydro-2H-pyran-2-yloxy)formamide as an orange solid (0.2197 g, 57%). LCMS: (M+H)+=568.2.

Part D:

[(2R)-2-(Cyclopentylmethyl)-3-(2-{5-fluoro-2-(methylthio)-6-[(1,3-thiazol-2-ylmethyl)amino]-4-pyrimidinyl}hydrazino)-3-oxopropyl]hydroxyformamide

[(2R)-2-(Cyclopentylmethyl)-3-(2-{5-fluoro-2-(methylthio)-6-[(1,3-thiazol-2-ylmethyl)amino]-4-pyrimidinyl}hydrazino)-3-oxopropyl](tetrahydro-2H-pyran-2-yloxy)formamide (0.2197 g, 0.387 mmol) was dissolved in acetic acid (8 mL) and water (2 mL). This reaction mixture was left to stir over 3 days. The volatiles were evaporated, and the resulting residue was purified by RP-HPLC to provide [(2R)-2-(cyclopentylmethyl)-3-(2-{5-fluoro-2-(methylthio)-6-[(1,3-thiazol-2-ylmethyl)amino]-4-pyrimidinyl}hydrazino)-3-oxopropyl]hydroxyformamide as a beige solid (0.0878 g, 47%). LCMS: (M+H)+=484.2.

Example 207

[(2R)-3-(2-{2-Chloro-5-fluoro-6-[(2-furanyl methyl)(methyl)amino]-4-pyrimidinyl}hydrazino)-2-(cyclopentylmethyl)-3-oxopropyl]hydroxyformamide

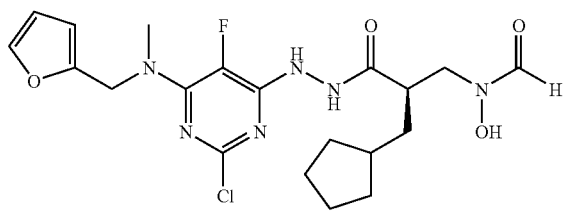

Part A:

Tris(1,1-dimethylethyl)2-{2-chloro-5-fluoro-6-[(2-furanyl methyl)(methyl)amino]-4-pyrimidinyl}-1,1,2-hydrazinetricarboxylate Tris(1,1-dimethylethyl)2-(2,6-dichloro-5-fluoro-4-pyrimidinyl)-1,1,2-hydrazinetricarboxylate (6.22 g, 12.54 mmol) was dissolved in THF (15 mL). To this solution was added triethylamine (2.1 mL, 15.0667 mmol), followed by commercially available (2-furanylmethyl)methylamine (1.394 g, 12.32 mmol) which was dissolved in THF (3 mL). The reaction was left to stir overnight. Then the reaction mixture was diluted with water, and the aqueous layer was extracted with ethyl acetate. The organics were dried (Na2SO4) and concentrated to produce tris(1,1-dimethylethyl)2-{2-chloro-5-fluoro-6-[(2-furanylmethyl)(methyl)amino]-4-pyrimidinyl}-1,1,2-hydrazinetricarboxylate as a beige solid (7.1439 g). LCMS: (M+H)+=572.3.

Part B:

2-Chloro-5-fluoro-N-(2-furanylmethyl)-6-hydrazino-N-methyl-4-pyrimidinamine

Tris(1,1-dimethylethyl)2-{2-chloro-5-fluoro-6-[(2-furanylmethyl)(methyl)amino]-4-pyrimidinyl}-1,1,2-hydrazinetricarboxylate (7.1439 g, 12.51 mmol) was dissolved in MeOH (65 mL) and HCl (4M in 1,4-dioxane) (65 mL). The reaction mixture was left to stir 5 hours, evaporated and purified by RP-HPLC to provide 2-chloro-5-fluoro-N-(2-furanylmethyl)-6-hydrazino-N-methyl-4-pyrimidinamine as an orange solid (0.8561 g). LCMS: (M+H)+=272.1.

Part C:

[(2R)-3-(2-{2-Chloro-5-fluoro-6-[(2-furanyl methyl)(methyl)amino]-4-pyrimidinyl}hydrazino)-2-(cyclopentylmethyl)-3-oxopropyl](tetrahydro-2H-pyran-2-yloxy)formamide 2-Chloro-5-fluoro-N-(2-furanylmethyl)-6-hydrazino-N-methyl-4-pyrimidinamine (0.400 g) and (2R)-3-cyclopentyl-2-{[formyl(tetrahydro-2H-pyran-2-yloxy)amino]methyl}propanoic acid (0.764 g, 1.770 mmol) were dissolved in DMF. NMM (0.65 mL, 5.912 mmol) was added, followed by HOAt (0.241 g, 1.772 mmol) and EDC (0.3396 g, 1.771 mmol). After stirring overnight, the reaction mixture was purified by RP-HPLC to provide [(2R)-3-(2-{2-chloro-5-fluoro-6-[(2-furanylmethyl)(methyl)amino]-4-pyrimidinyl}hydrazino)-2-(cyclopentylmethyl)-3-oxopropyl](tetrahydro-2H-pyran-2-yloxy)formamide as an orange solid (0.6318 g). LCMS: (M+H)+=553.2.

Part D:

[(2R)-3-(2-{2-Chloro-5-fluoro-6-[(2-furanyl methyl)(methyl)amino]-4-pyrimidinyl}hydrazino)-2-(cyclopentylmethyl)-3-oxopropyl]hydroxyformamide

[(2R)-3-(2-{2-Chloro-5-fluoro-6-[(2-furanylmethyl)(methyl)amino]-4-pyrimidinyl}hydrazino)-2-(cyclopentylmethyl)-3-oxopropyl](tetrahydro-2H-pyran-2-yloxy)formamide (0.6318 g, 1.145 mmol) was dissolved in acetic acid (8 mL) and water (2 mL). This reaction mixture was left to stir overnight. The volatiles were evaporated, and the resulting residue was purified by RP-HPLC to provide [(2R)-3-(2-{2-chloro-5-fluoro-6-[(2-furanylmethyl)(methyl)amino]-4- pyrimidinyl}hydrazino)-2-(cyclopentylmethyl)-3-oxopropyl]hydroxyformamide as a beige solid (0.3182 g, 59%). LCMS: (M+H)+=469.2.

Example 208

[(2R)-3-(2-{2-Chloro-5-fluoro-6-[4-(2-hydroxyethyl)-1-piperazinyl]-4-pyrimidinyl}hydrazino)-2-(cyclopentylmethyl)-3-oxopropyl]hydroxyformamide

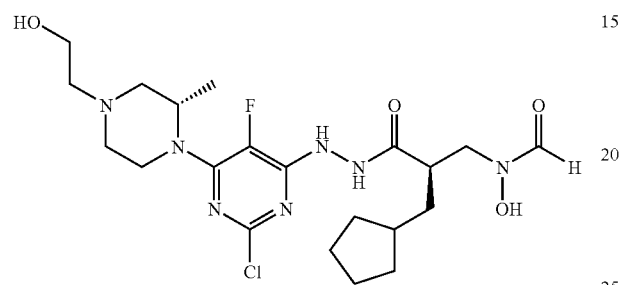

Part A:

Phenylmethyl (2S)-2-methyl-4-{2-[(phenylmethyl)oxy]ethyl}-1-piperazinecarboxylate A solution of phenylmethyl (2S)-2-methyl-1-piperazinecarboxylate (commercially available) (1 g, 4.3 mmol) and benzyloxyacetaldehyde (0.9 mL, 6.4 mmol) in DCM (50 mL) was stirred for 30 minutes, and then NaBH(OAc)₃ (1.36 g, 6.4 mmol) was added. The reaction was stirred overnight before being quenched with 1 M NaOH. The phases were separated and the aqueous layer was extracted with DCM. The combined organics were washed with brine, dried over sodium sulfate and concentrated to a crude residue, which was purified by silica gel chromatography (5-95% EtOAc in hexane) yielding phenylmethyl (2S)-2-methyl-4-{2-[(phenylmethyl)oxy]ethyl}-1-piperazinecarboxylate (0.93 g, 58%). LCMS: (M+H)+: 369.1

Part B:

2-[(3S)-3-Methyl-1-piperazinyl]ethanol

To a degassed solution of phenylmethyl (2S)-2-methyl-4-{2-[(phenylmethyl)oxy]ethyl}-1-piperazinecarboxylate (0.93 g, 2.5 mmol) in MeOH (30 mL) was added Pd/C (200 mg). The resulting suspension was stirred overnight underneath a balloon of hydrogen, but LCMS showed only loss of the CBZ-group. The catalyst was removed by filtration and the solvent was removed under reduced pressure. The remaining residue was dissolved in MeOH and another 200 mg of Pd/C was added, as well as 5 drops of concentrated HCl. This mixture was hydrogenated at 50 psi on a Parr shaker for 96 hours, after which time the catalyst was removed by filtration. Concentration of the filtrate under reduced pressure yielded 2-[(3S)-3-methyl-1-piperazinyl]ethanol hydrochloride in quantitative yield. LCMS: (M+H)+: 145.1.

Part C:

[(2R)-3-(2-{2-Chloro-5-fluoro-6-[4-(2-hydroxyethyl)-1-piperazinyl]-4-pyrimidinyl}hydrazino)-2-(cyclopentylmethyl)-3-oxopropyl]hydroxyformamide

[(2R)-3-(2-{2-Chloro-5-fluoro-6-[4-(2-hydroxyethyl)-1-piperazinyl]-4-pyrimidinyl}hydrazino)-2-(cyclopentylmethyl)-3-oxopropyl]hydroxyformamide was prepared according to General Procedure E, utilizing 2-[(3S)-3-methyl-1-piperazinyl]ethanol hydrochloride in place of isopropyl amine in Part A. LCMS: (M+H)+: 502.2.

Example 209

[(2R)-3-(2-{2-Chloro-5-fluoro-6-[(2R)-4-(2-hydroxyethyl)-2-methyl-1-piperazinyl]-4-pyrimidinyl}hydrazino)-2-(cyclopentylmethyl)-3-oxopropyl]hydroxyformamide

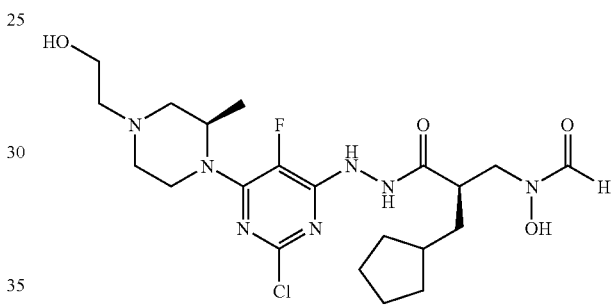

[(2R)-3-(2-{2-Chloro-5-fluoro-6-[(2R)-4-(2-hydroxyethyl)-2-methyl-1-piperazinyl]-4-pyrimidinyl}hydrazino)-2-(cyclopentylmethyl)-3-oxopropyl]hydroxyformamide was prepared according to General Procedure E, utilizing 2-[(R)-3-methyl-1-piperazinyl]ethanol hydrochloride (prepared according to Example 208, Parts A and B, using phenylmethyl (2R)-2-methyl-1-piperazinecarboxylate in place of phenylmethyl (2S)-2-methyl-1-piperazinecarboxylate) in place of isopropyl amine in Part A. LCMS: (M+H)+: 502.1

Example 210

{(2R)-2-(Cyclopentylmethyl)-3-[2-(5-fluoro-2-methyl-6-{(2S)-2-[1-(1-pyrrolidinyl)cyclopropyl]-1-pyrrolidinyl}-4-pyrimidinyl)hydrazino]-3-oxopropyl}hydroxyformamide

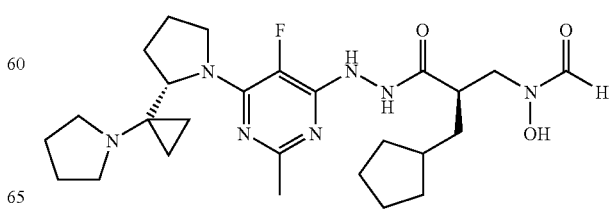

Part A:

1-(Phenylmethyl)-L-proline hydrochloride

Ethyl 1-(phenylmethyl)-L-prolinate (13.20 g, 56.57 mmol) was dissolved in a mixture of THF (40 mL), EtOH (40 mL) and $H_2O$ (16 mL). To this solution was added solid sodium hydroxide (6.789 g, 169.73 mmol), and the mixture was stirred at room temperature overnight. The solution was adjusted to pH 2 with 1N aq. HCl and then extracted with $CH_2Cl_2$ (3×50 mL). The combined organic layers were dried over $Na_2SO_4$, filtered, and concentrated in vacuo, and the resulting crude product was 1-(phenylmethyl)-L-proline hydrochloride (0.8 g). The aqueous layers were concentrated in vacuo, the residue was suspended in MeOH, and the resulting solid precipitate was collected by filtration and combined with the product from the organic extracts to provide 1-(phenylmethyl)-L-proline hydrochloride (13.30 g, 97%). LCMS: $(M+H)^+$: 206.1

Part B:

(2S)-1-(Phenylmethyl)-2-(1-pyrrolidinylcarbonyl)pyrrolidine 1-(Phenylmethyl)-L-proline hydrochloride (2.0 g, 8.247 mmol) and HOBt (1.34 g, 9.928 mmol) were dissolved in $CH_2Cl_2$ (50 mL), and 4-methylmorpholine (3.63 mL, 33.09 mmol), pyrrolidine (0.760 mL, 9.101 mmol), and EDCI (1.906 g, 9.928 mmol) were added. The solution was stirred overnight, and was then washed with water (50 mL). The aqueous layer was extracted with $CH_2Cl_2$ (3×50 mL), and the combined organic layers were dried over anhydrous $MgSO_4$ and concentrated in vacuo. This crude product was purified by flash chromatography (Combiflash, 0-100% ethyl acetate/hexanes, 1% triethylamine) to provide (2S)-1-(phenylmethyl)-2-(1-pyrrolidinylcarbonyl)pyrrolidine (1.619 g, 76%). LCMS: $(M+H)^+$: 259.2

Part C:

(2S)-1-(Phenylmethyl)-2-[1-(1-pyrrolidinyl)cyclopropyl]pyrrolidine

To a stirred solution of THF (50 mL) cooled to −78° C. was added ethyl magnesium bromide (11.6 mL, 34.8 mmol) followed by titanium(IV) isopropoxide (2.042 mL, 6.96 mmol) and then (2S)-1-(phenylmethyl)-2-(1-pyrrolidinylcarbonyl)pyrrolidine (1.619 g, 6.96 mmol). The mixture was allowed to warm to room temperature and stir for 2 h, and was then checked by LCMS. Greater than 40% of the starting material remained, and so the mixture was stirred overnight, and then checked by LCMS again. Greater than 20% of the starting material remained, and therefore an additional portion of ethyl magnesium bromide (5.8 mL, 17.4 mmol) was added, and the mixture was allowed to stir for 2 h and was checked by LCMS again. Greater than 5% of the starting material remained, and an additional portion of ethyl magnesium bromide (2.32 mL, 6.96 mmol) was added and the mixture was allowed to stir for 2 h. When the reaction was complete as determined by LCMS, the reaction mixture was diluted with sat. aq. $NH_4Cl$ (150 mL) and water (50 mL), and the resulting white solid precipitate was filtered off. The pH of the filtrate was adjusted to >12 with 6 N aq. NaOH. The aqueous solution was extracted with $Et_2O$ (3×100 mL), and the combined organic layers were dried over $MgSO_4$ and concentrated in vacuo. This crude product was purified by flash chromatography (Combiflash, 0-100% ethyl acetate/hexanes, 1% triethylamine) to provide (2S)-1-(phenylmethyl)-2-[1-(1-pyrrolidinyl)cyclopropyl]pyrrolidine (1.0837 g, 57%). LCMS: $(M+H)^+$: 271.2.

Part D:

1-{1-[(2S)-2-Pyrrolidinyl]cyclopropyl}pyrrolidine hydrochloride (2S)-1-(Phenylmethyl)-2-[1-(1-pyrrolidinyl)cyclopropyl]pyrrolidine (1.083 g, 4.00 mmol) was dissolved in a mixture of MeOH (30 mL) and 1N HCl (8.8 mL), degassed and placed under argon. 10% Pd/C (325 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure 1-{1-[(2S)-2-pyrrolidinyl]cyclopropyl}pyrrolidine hydrochloride (0.978 g, >99%). LCMS: $(M+H)^+$: 181.2.

Part E:

5-Fluoro-4-hydrazino-2-methyl-6-{(2S)-2-[1-(1-pyrrolidinyl)cyclopropyl]-1-pyrrolidinyl}pyrimidine 4,6-Dichloro-5-fluoro-2-methylpyrimidine (428 mg, 2.368 mmol) was dissolved in 3 mL of MeOH, and then 1-{1-[(2S)-2-pyrrolidinyl]cyclopropyl}pyrrolidine hydrochloride (489 mg, 2.256 mmol) was added, followed by DIPEA (1.572 mL, 9.024 mmol). The resulting reaction mixture was microwaved at 120° C. for 30 min, the volatiles were concentrated in vacuo, and the residue was dissolved in a mixture of DMSO (4 mL) and MeOH (1 mL). Hydrazine monohydrate was added (2.44 mL), and the contents were heated to 60° C. overnight. The reaction mixture was then cooled to room temperature and purified by RP-HPLC to provide 5-fluoro-4-hydrazino-2-methyl-6-{(2S)-2-[1-(1-pyrrolidinyl)cyclopropyl]-1-pyrrolidinyl}pyrimidine (69 mg, 10%). LCMS: $(M+H)^+$: 321.2.

Part F:

{(2R)-2-(Cyclopentylmethyl)-3-[2-(5-fluoro-2-methyl-6-{(2S)-2-[1-(1-pyrrolidinyl)cyclopropyl]-1-pyrrolidinyl}-4-pyrimidinyl)hydrazino]-3-oxopropyl}hydroxyformamide {(2R)-2-(Cyclopentylmethyl)-3-[2-(5-fluoro-2-methyl-6-{(2S)-2-[1-(1-pyrrolidinyl)cyclopropyl]-1-pyrrolidinyl}-4-pyrimidinyl)hydrazino]-3-oxopropyl}hydroxyformamide was prepared according to General Procedure A, Parts B and C, utilizing 5-fluoro-4-hydrazino-2-methyl-6-{(2S)-2-[1-(1-pyrrolidinyl)cyclopropyl]-1-pyrrolidinyl}pyrimidine in place of 5-fluoro-4-hydrazino-2-methyl-6-(1-pyrrolidinyl)pyrimidine in Part B. LCMS: $(M+H)^+$: 518.4.

Example 211

[(2R)-3-(2-{2-Chloro-6-[3-(dimethylamino)-3-ethyl-1-azetidinyl]-5-fluoro-4-pyrimidinyl}hydrazino)-2-(cyclopentylmethyl)-3-oxopropyl]hydroxyformamide

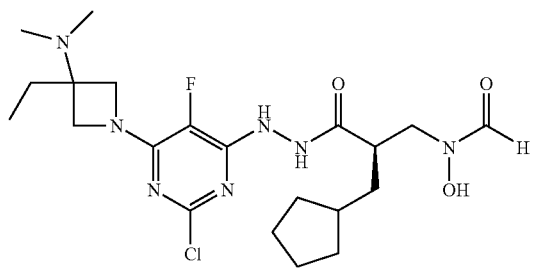

Part A:

1-(Diphenylmethyl)-3-ethyl-N,N-dimethyl-3-azetidinamine

A mixture of 1-(diphenylmethyl)-3-ethyl-3-azetidinyl methanesulfonate (1.00 g, 2.89 mmol) (Ellsworth, Edmund Lee; Hoyer, Denton Wade; Hutchings, Kim Marie; Kendall, Jackie Diane; Murphy, Sean Timothy; Starr, Jeremy Tyson; Tran, Tuan Phong. WO 2005049605), dimethylamine (2 M in THF, 14.45 ml, 28.9 mmol) and TEA (0.80 ml, 5.78 mmol) in isopropanol was heated to 70° C. overnight. Standard work-up followed by RP-HPLC provided 1-(diphenylmethyl)-3-ethyl-N,N-dimethyl-3-azetidinamine (0.215 g, 25.3%). LCMS: (M+H)$^+$ 295.2.

Part B:

3-Ethyl-N,N-dimethyl-3-azetidinamine dihydrochloride 1-(Diphenylmethyl)-3-ethyl-N,N-dimethyl-3-azetidinamine (0.215 g, 0.73 mmol) in 1 N HCl (5 ml) and ethanol (30 ml) was treated with H$_2$ at 60 psi in the presence of Pd(OH)$_2$ on carbon (100 mg). Standard work-up afforded 3-ethyl-N,N-dimethyl-3-azetidinamine dihydrochloride (0.165 g, 112.2%). LCMS: (M+H)$^+$ 129.1.

Part C:

[(2R)-3-(2-{2-Chloro-6-[3-(dimethylamino)-3-ethyl-1-azetidinyl]-5-fluoro-4-pyrimidinyl}hydrazino)-2-(cyclopentylmethyl)-3-oxopropyl]hydroxyformamide

[(2R)-3-(2-{2-Chloro-6-[3-(dimethylamino)-3-ethyl-1-azetidinyl]-5-fluoro-4-pyrimidinyl}hydrazino)-2-(cyclopentylmethyl)-3-oxopropyl]hydroxyformamide was prepared according to Example 176, utilizing 3-ethyl-N,N-dimethyl-3-azetidinamine dihydrochloride in place of 1-(3-methyl-3-azetidinyl)pyrrolidine dihydrochloride in Part C. LCMS: (M+H)$^+$ 486.2.

Example 212

((2R)-2-(Cyclopentylmethyl)-3-{2-[6-[3-(dimethylamino)-3-ethyl-1-azetidinyl]-5-fluoro-2-(methylthio)-4-pyrimidinyl]hydrazino}-3-oxopropyl)hydroxyformamide

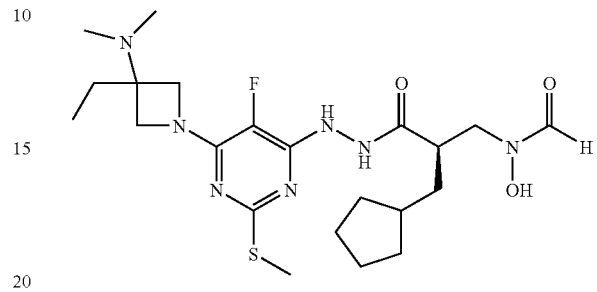

((2R)-2-(Cyclopentylmethyl)-3-{2-[6-[3-(dimethylamino)-3-ethyl-1-azetidinyl]-5-fluoro-2-(methylthio)-4-pyrimidinyl]hydrazino}-3-oxopropyl)hydroxyformamide was prepared according to General Procedure C, utilizing 3-ethyl-N,N-dimethyl-3-azetidinamine hydrochloride (Example 211) in place of azetidine hydrochloride in Part A. LCMS: (M+H)$^+$ 498.3.

Example 213

[(2R)-3-{2-[2-Chloro-6-(3-cyclopropyl-3-hydroxy-1-azetidinyl)-5-fluoro-4-pyrimidinyl]hydrazino}-2-(cyclopentylmethyl)-3-oxopropyl]hydroxyformamide

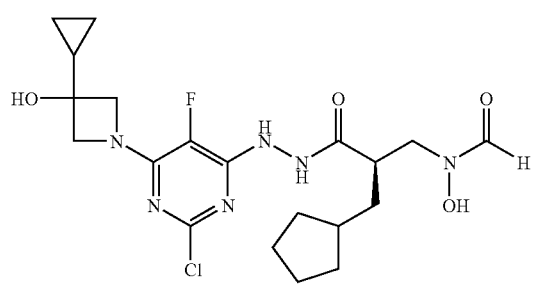

[(2R)-3-{2-[2-Chloro-6-(3-cyclopropyl-3-hydroxy-1-azetidinyl)-5-fluoro-4-pyrimidinyl]hydrazino}-2-(cyclopentylmethyl)-3-oxopropyl]hydroxyformamide was prepared according to General Procedure D, utilizing 3-cyclopropyl-3-azetidinol hydrochloride (Ellsworth, Edmund Lee; Hutchings, Kim Marie; Murphy, Sean Timothy; Powell, Sharon Anne; Sciotti, Richard John; Tran, Tuan Phong. WO 2005026146) in place of N-methylpiperazine in Part A. LCMS: (M+H)$^+$ 471.0.

Example 214

N-[(2R)-3-(2-{2-Chloro-5-fluoro-6-[(2R,5R)-2,4,5-trimethyl-1-piperazinyl]-4-pyrimidinyl}hydrazino)-2-(cyclopentylmethyl)-3-oxopropyl]-N-hydroxyformamide

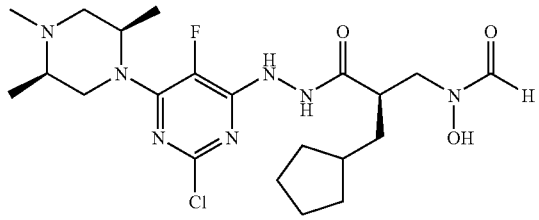

Part A:

(2R,5R)-1,2,5-Trimethyl-4-(phenylmethyl)piperazine

To a solution of (2R,5R)-2,5-dimethyl-1-(phenylmethyl)piperazine (prepared according to J. Med. Chem. 2006, 49, 716-726, utilizing N-Boc-D-alanine in place of N-Boc-L-alanine) (667 mg, 3.26 mmol) in dichloromethane (25 mL) at 0° C. was added formaldehyde (0.367 mL, 37% water solution, 4.89 mmol) followed by sodium triacetoxyborohydride (900 mg, 4.24 mmol). The reaction mixture was allowed to warm to room temperature and stirred for 2 h before being diluted with dichloromethane and washed with 1N NaOH solution. The organics were washed with brine, dried (MgSO$_4$) and evaporated to yield (2R,5R)-1,2,5-trimethyl-4-(phenylmethyl)piperazine (680 mg, 96%). LCMS: (M+H)$^+$: 219.1.

Part B:

(2R,5R)-1,2,3-Trimethylpiperazine, Hydrochloride Salt (2R,5R)-1,2,5-Trimethyl-4-(phenylmethyl)piperazine (680 mg, 3.11 mmol) was dissolved in 50 mL of MeOH, degassed and placed under argon. 10% Pd/C (170 mg) was added, and the contents were thoroughly degassed and placed under a hydrogen balloon for approximately 3 hrs. The contents were then degassed and filtered through Celite, and the Celite pad was washed with DCM and MeOH. After 6.5 mL 1N HCl was added, the resulting filtrate was concentrated in vacuo to provide the hydrochloride salt of (2R,5R)-1,2,5-trimethylpiperazine (251 mg, 100%). LCMS: (M+H)$^+$: 129.1.

Part C:

N-[(2R)-3-(2-{2-Chloro-5-fluoro-6-[(2R,5R)-2,4,5-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(2R,5R)-2,4,5-trimethyl-1-piperazinyl]-4-pyrimidinyl}hydrazino)-2-(cyclopentylmethyl)-3-oxopropyl]-N-hydroxyformamide was prepared according to General Procedure G, utilizing (2R,5R)-1,2,5-trimethylpiperazine, hydrochloride salt in place of (1S,4S)-2-methyl-2,5-diazabicyclo[2.2.1]heptane, dihydrobromide in Part A. LCMS: (M+H)$^+$: 486.1.

Example 215

N-[(2R)-2-(Cyclopentylmethyl)-3-(2-{5-fluoro-2-methyl-6-[(2R,5R)-2,4,5-trimethyl-1-piperazinyl]-4-pyrimidinyl}hydrazino)-3-oxopropyl]-N-hydroxyformamide

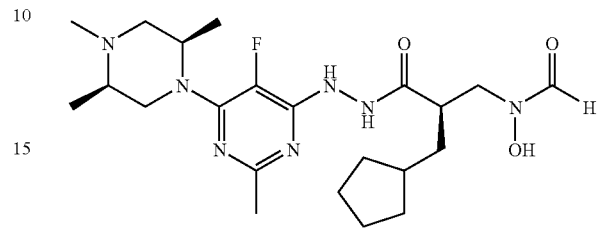

N-[(2R)-2-(Cyclopentylmethyl)-3-(2-{5-fluoro-2-methyl-6-[(2R,5R)-2,4,5-trimethyl-1-piperazinyl]-4-pyrimidinyl}hydrazino)-3-oxopropyl]-N-hydroxyformamide was prepared according to General Procedure A, utilizing (2R,5R)-1,2,5-trimethylpiperazine, hydrochloride salt (Example 214) in place of pyrrolidine in Part A, and using 3 equivalents of DIPEA. LCMS: (M+H)$^+$: 466.4.

Example 216

[(2R)-2-(Cyclopentylmethyl)-3-(2-{5-fluoro-2-(fluoromethyl)-6-[(9aS)-hexahydropyrazino[2,1-c][1,4]oxazin-8(1H)-yl]-4-pyrimidinyl}hydrazino)-3-oxopropyl]hydroxyformamide

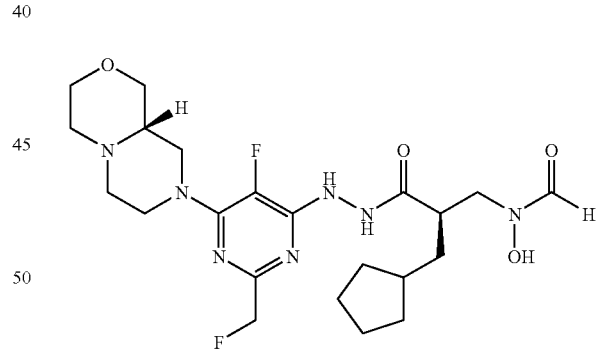

[(2R)-2-(Cyclopentylmethyl)-3-(2-{5-fluoro-2-(fluoromethyl)-6-[(9aS)-hexahydropyrazino[2,1-c][1,4]oxazin-8(1H)-yl]-4-pyrimidinyl}hydrazino)-3-oxopropyl]hydroxyformamide was prepared according to General Procedure A, utilizing (9aS)-octahydropyrazino[2,1-c][1,4]oxazine dihydrochloride (Example 22) in place of pyrrolidine, using 4,6-dichloro-5-fluoro-2-(fluoromethyl)pyrimidine in place of 4,6-dichloro-5-fluoro-2-methylpyrimidine, and using 3 equivalents of DIPEA in Part A. LCMS: (M+H)$^+$: 498.3.

Example 217

((2R)-2-(Cyclopentylmethyl)-3-{2-[6-(3-cyclopropyl-3-hydroxy-1-azetidinyl)-5-fluoro-2-(methylthio)-4-pyrimidinyl]hydrazino}-3-oxopropyl)hydroxyformamide

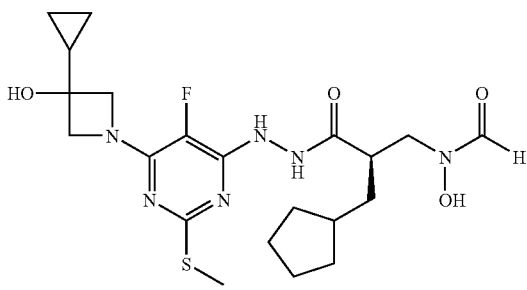

((2R)-2-(Cyclopentylmethyl)-3-{2-[6-(3-cyclopropyl-3-hydroxy-1-azetidinyl)-5-fluoro-2-(methylthio)-4-pyrimidinyl]hydrazino}-3-oxopropyl)hydroxyformamide was prepared according to General Procedure C, utilizing 3-cyclopropyl-3-azetidinol hydrochloride (Ellsworth, Edmund Lee; Hutchings, Kim Marie; Murphy, Sean Timothy; Powell, Sharon Anne; Sciotti, Richard John; Tran, Tuan Phong. WO 2005026146) in place of azetidine hydrochloride in Part A. LCMS: (M+H)⁺ 483.1.

Example 218

((2R)-2-(Cyclopentylmethyl)-3-{2-[6-[3-ethyl-3-(1-pyrrolidinyl)-1-azetidinyl]-5-fluoro-2-(methylthio)-4-pyrimidinyl]hydrazino}-3-oxopropyl)hydroxyformamide

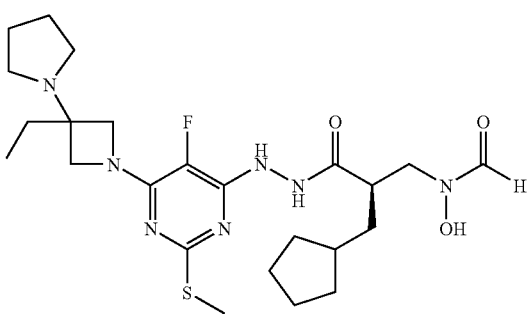

Part A:

1-(3-Ethyl-3-azetidinyl)pyrrolidine dihydrochloride 1-(3-Ethyl-3-azetidinyl)pyrrolidine dihydrochloride was prepared according to the procedure described for the preparation of 3-ethyl-N,N-dimethyl-3-azetidinamine dihydrochloride (Example 211), utilizing pyrrolidine in place of dimethylamine in Part A. LCMS: (M+H)⁺ 155.1.

Part B:

((2R)-2-(Cyclopentylmethyl)-3-{2-[6-[3-ethyl-3-(1-pyrrolidinyl)-1-azetidinyl]-5-fluoro-2-(methylthio)-4-pyrimidinyl]hydrazino}-3-oxopropyl)hydroxyformamide ((2R)-2-(Cyclopentylmethyl)-3-{2-[6-[3-ethyl-3-(1-pyrrolidinyl)-1-azetidinyl]-5-fluoro-2-(methylthio)-4-pyrimidinyl]hydrazino}-3-oxopropyl)hydroxyformamide was prepared according to General Procedure C, utilizing 1-(3-ethyl-3-azetidinyl)pyrrolidine dihydrochloride in place of azetidine hydrochloride in Part A. LCMS: (M+H)⁺ 524.3.

Example 219

[(2R)-3-(2-{2-Chloro-6-[(cyclopropylmethyl)amino]-5-fluoro-4-pyrimidinyl}hydrazino)-2-(cyclopentylmethyl)-3-oxopropyl]hydroxyformamide

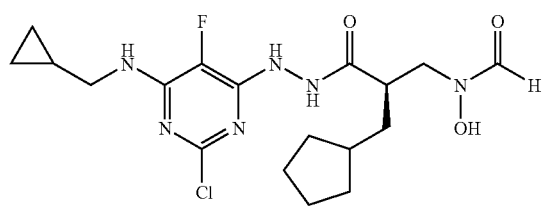

[(2R)-3-(2-{2-Chloro-6-[(cyclopropylmethyl)amino]-5-fluoro-4-pyrimidinyl}hydrazino)-2-(cyclopentylmethyl)-3-oxopropyl]hydroxyformamide was prepared in a manner similar to Example 176, utilizing 1-cyclopropylmethanamine in place of 1-(3-methyl-3-azetidinyl)pyrrolidine dihydrochloride in Part C. LCMS: (M+H)⁺ 429.1.

Example 220

[(2R)-3-[2-(2-Chloro-5-fluoro-6-{[2-(3-thienyl)ethyl]amino}-4-pyrimidinyl)hydrazino]-2-(cyclopentylmethyl)-3-oxopropyl]hydroxyformamide

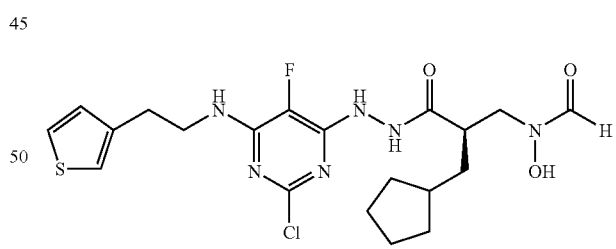

Part A:

2-(3-Thienyl)acetamide

Commercially available 3-thiophene acetic acid (2.0 g, 14.07 mmol) was dissolved in DCM (45 mL) under nitrogen. Then oxalyl chloride (1.35 mL, 15.48 mmol) was added and the reaction was stirred overnight. Then ammonium hydroxide (30% as NH₃ solution) (8.22 mL) was added dropwise with stirring. The reaction mixture was evaporated to provide 2-(3-thienyl)acetamide as a beige solid (3.2082 g). LCMS: (M+H)⁺=142.1.

Part B:

[2-(3-Thienyl)ethyl]amine

Lithium aluminum hydride was placed in THF (10 mL) at 0° C. in an ice bath under argon. Then 2-(3-thienyl)acetamide (0.9828 g, 6.97 mmol) was added as a suspension in THF (30 mL). The reaction mixture was heated at 65° C. overnight, then cooled to ambient temperature and placed in an ice bath. The reaction was quenched with water (10 mL), 3N NaOH (10 mL), and additional water (10 mL). The mixture was filtered over Celite, and the filtrate was washed with saturated NaCl solution, dried (MgSO$_4$) and evaporated to provide [2-(3-thienyl)ethyl]amine as a yellow oil (0.470 g, 53%). LCMS: (M+H)$^+$=128.1.

Part C:

Tris(1,1-dimethylethyl)2-(2-chloro-5-fluoro-6-{[2-(3-thienyl)ethyl]amino}-4-pyrimidinyl)-1,1,2-hydrazinetricarboxylate Tris(1,1-dimethylethyl)2-(2,6-dichloro-5-fluoro-4-pyrimidinyl)-1,1,2-hydrazinetricarboxylate (1.84 g, 3.71 mmol) was dissolved in THF (5 mL). To this solution was added triethylamine (0.62 mL, 4.4482 mmol), followed by [2-(3-thienyl)ethyl]amine (0.470 g, 3.70 mmol) which was semi-suspended in THF (15 mL). The reaction was left to stir overnight, then diluted with water and saturated NaCl. The aqueous layer was extracted with ethyl acetate. The organics were dried (MgSO$_4$) and concentrated to produce tris(1,1-dimethylethyl)2-(2-chloro-5-fluoro-6-{[2-(3-thienyl)ethyl]amino}-4-pyrimidinyl)-1,1,2-hydrazinetricarboxylate as an orange oil (2.389 g). LCMS: (M+H)$^+$=588.3.

Part D:

2-Chloro-5-fluoro-6-{[2-(3-thienyl)ethyl]amino}-4(1H)-pyrimidinone hydrazone Tris(1,1-dimethylethyl)2-(2-chloro-5-fluoro-6-{[2-(3-thienyl)ethyl]amino}-4-pyrimidinyl)-1,1,2-hydrazinetricarboxylate (2.389 g, 4.07 mmol) was dissolved in MeOH (25 mL) and HCl (4M in 1,4-dioxane) (25 mL) at room temperature. The reaction mixture was left to stir over 3 days, evaporated and purified by RP-HPLC to provide 2-chloro-5-fluoro-6-{[2-(3-thienyl)ethyl]amino}-4(1H)-pyrimidinone hydrazone as a brown sticky solid (0.1401 g). LCMS: (M+H)$^+$=288.0.

Part E:

[(2R)-3-[2-(2-Chloro-5-fluoro-6-{[2-(3-thienyl)ethyl]amino}-4-pyrimidinyl)hydrazino]-2-(cyclopentylmethyl)-3-oxopropyl](tetrahydro-2H-pyran-2-yloxy)formamide 2-Chloro-5-fluoro-6-{[2-(3-thienyl)ethyl]amino}-4(1H)-pyrimidinone hydrazone as a brown sticky solid (0.1401 g) and (2R)-3-cyclopentyl-2-{[formyl(tetrahydro-2H-pyran-2-yloxy)amino]methyl}propanoic acid (0.253 g, 0.586 mmol) were dissolved in DMF (7 mL). NMM (0.27 mL, 2.90 mmol) was added, followed by HOAt (0.080 g, 0.588 mmol) and EDC (0.112 g, 0.584 mmol). After stirring overnight, the reaction mixture was purified by RP-HPLC to provide [(2R)-3-[2-(2-Chloro-5-fluoro-6-{[2-(3-thienyl)ethyl]amino}-4-pyrimidinyl)hydrazino]-2-(cyclopentylmethyl)-3-oxopropyl](tetrahydro-2H-pyran-2-yloxy)formamide as an orange solid (0.1677 g). LCMS: (M+H)$^+$=569.3.

Part F:

[(2R)-3-[2-(2-Chloro-5-fluoro-6-{[2-(3-thienyl)ethyl]amino}-4-pyrimidinyl)hydrazino]-2-(cyclopentylmethyl)-3-oxopropyl]hydroxyformamide

[(2R)-3-[2-(2-Chloro-5-fluoro-6-{[2-(3-thienyl)ethyl]amino}-4-pyrimidinyl)hydrazino]-2-(cyclopentylmethyl)-3-oxopropyl](tetrahydro-2H-pyran-2-yloxy)formamide (0.1677, 0.295 mmol) was dissolved in acetic acid (8 mL) and water (2 mL). This reaction mixture was left to stir overnight. The volatiles were evaporated, and the resulting residue was purified by RP-HPLC to provide [(2R)-3-[2-(2-chloro-5-fluoro-6-{[2-(3-thienyl)ethyl]amino}-4-pyrimidinyl)hydrazino]-2-(cyclopentylmethyl)-3-oxopropyl]hydroxyformamide as a beige solid (0.0715 g, 50%). LCMS: (M+H)$^+$=485.1.

Example 221

[(2R)-3-{2-[2-Chloro-5-fluoro-6-(4-methyloctahydro-1(2H)-quinoxalinyl)-4-pyrimidinyl]hydrazino}-2-(cyclopentylmethyl)-3-oxopropyl]hydroxyformamide

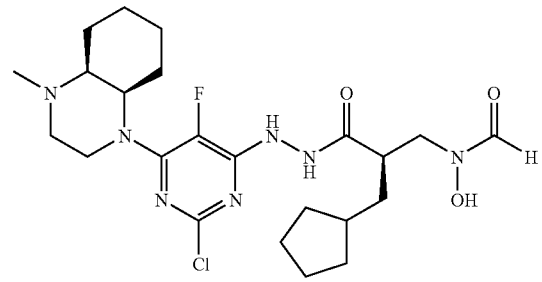

Part A:

(4aR,8aS)-Octahydro-2,3-quinoxalinedione

To a solution of cis-1,2-diaminocyclohexane (4.8 g, 42 mmol) in dimethoxy ethylene (100 mL) was added slowly diethyl oxalate (28.5 mL, 210 mmol). The reaction mixture was stirred at room temperature for 0.5 h and at 100° C. for 2 h. After the suspension was cooled down to room temperature, the resulting white solid precipitate was collected by filtration. The precipitate was washed with diethyl ether and dried to yield (4aR,8aS)-octahydro-2,3-quinoxalinedione (4.6 g, 66%). LCMS: (M+H)$^+$: 169.1.

Part B:

(4aR,8aS)-Decahydroquinoxaline (4aR,8aS)-Octahydro-2,3-quinoxalinedione (4.67 g, 27.8 mmol) was added portion wise to 1M LAH (111 mL, 111 mmol) in diethyl ether (30 mL). The reaction was allowed to heated to reflux and stirred at reflux for 4 h. After cooling to room temperature, the reaction was quenched by the sequential addition of H$_2$O (4.2 mL), 15% NaOH (4.2 mL), and H$_2$O (12.6 mL). The mixture was stirred for 0.5 h, and the solids were filtered off and washed with excess EtOAc. The combined filtrates were concentrated under reduced pressure to provide (4aR,8aS)-decahydroquinoxaline as a white solid (3.6 g, 92%). LCMS: (M+H)$^+$: 141.1.

Part C:

Phenylmethyl octahydro-1(2H)-quinoxalinecarboxylate (Enantiomeric Mixture, Cis)

To (4aR,8aS)-decahydroquinoxaline (1.4 g, 10 mmol) in dichloromethane (50 mL) was added triethylamine (1.7 mL, 12 mmol) followed by dropwise benzyl chloroformate (1.71 g, 10 mmol). The reaction mixture was stirred at room temperature for 2 h before being diluted with dichloromethane and washed with 1N NaOH followed by sat. aq. NH$_4$Cl. The combined organic layers were washed with brine, dried (MgSO$_4$) and concentrated to provide the crude product, which was purified via Combiflash to yield phenylmethyl octahydro-1(2H)-quinoxalinecarboxylate (enantiomeric mixture, cis) (2.32 g, 85%). LCMS: (M+H)$^+$: 275.1.

Part D:

Phenylmethyl (4aS,8aR)-4-methyloctahydro-1(2H)-quinoxalinecarboxylate, Phenylmethyl (4aR,8aS)-4-methyloctahydro-1(2H)-quinoxalinecarboxylate To a solution of phenylmethyl octahydro-1(2H)-quinoxalinecarboxylate (enantiomeric mixture) (2.32 g, 8.5 mmol) in dichloromethane (80 mL) at 0° C. was added formaldehyde (0.76 mL, 37% water solution, 10.2 mmol) followed by sodium triacetoxyborohydride (2.7 g, 12.75 mmol). The reaction mixture was allowed to warm to room temperature and stirred for 1 h before being diluted with dichloromethane and washed with 1N NaOH solution. The organics were washed with brine, dried (Na$_2$SO$_4$) and evaporated to yield 2.3 g of phenylmethyl 4-methyloctahydro-1(2H)-quinoxalinecarboxylate (enantiomeric mixture, cis) (2.3 g), which was separated by chiral LC to afford phenylmethyl (4aS,8aR)-4-methyloctahydro-1(2H)-quinoxalinecarboxylate, and phenylmethyl (4aR,8aS)-4-methyloctahydro-1(2H)-quinoxalinecarboxylate. Absolute configuration was assigned using Ab Initio vibrational circular dichroism. LCMS: (M+H)$^+$: 289.2.

Part E:

(4aR,8aS)-1-Methyldecahydroquinoxaline, Hydrochloride Salt

Phenylmethyl (4aS,8aR)-4-methyloctahydro-1(2H)-quinoxalinecarboxylate (2.7 g, 9.4 mmol) was dissolved in 140 mL of MeOH, degassed and placed under argon. 10% Pd/C (400 mg) was added, and the contents were thoroughly degassed and placed under a hydrogen balloon for approximately 2 hrs. The contents were then degassed and filtered through Celite, and the Celite pad was washed with DCM and MeOH. After 19.6 mL 1N HCl was added, the resulting filtrate was concentrated in vacuo to provide the hydrochloride salt of (4aR,8aS)-1-methyldecahydroquinoxaline (2.1 g, 100%). LCMS: (M+H)$^+$: 155.1.

Part F:

[(2R)-3-{2-[2-Chloro-5-fluoro-6-(4-methyloctahydro-1(2H)-quinoxalinyl)-4-pyrimidinyl]hydrazino}-2-(cyclopentylmethyl)-3-oxopropyl]hydroxyformamide

[(2R)-3-{2-[2-Chloro-5-fluoro-6-(4-methyloctahydro-1(2H)-quinoxalinyl)-4-pyrimidinyl]hydrazino}-2-(cyclopentylmethyl)-3-oxopropyl]hydroxyformamide was prepared according to General Procedure G, utilizing (4aR,8aS)-1-methyldecahydroquinoxaline, hydrochloride salt in place of (1S,4S)-2-methyl-2,5-diazabicyclo[2.2.1]heptane, dihydrobromide in Part A. LCMS: (M+H)$^+$: 512.3.

Example 222

((2R)-2-(Cyclopentylmethyl)-3-{2-[5-fluoro-2-methyl-6-(4-methyloctahydro-1(2H)-quinoxalinyl)-4-pyrimidinyl]hydrazino}-3-oxopropyl)hydroxyformamide

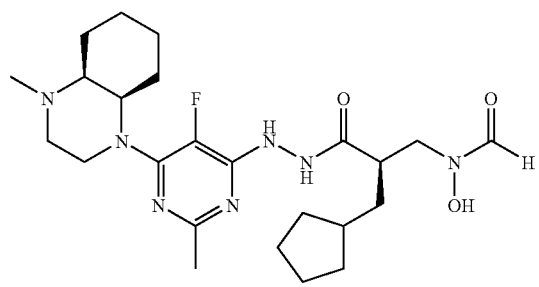

((2R)-2-(Cyclopentylmethyl)-3-{2-[5-fluoro-2-methyl-6-(4-methyloctahydro-1(2H)-quinoxalinyl)-4-pyrimidinyl]hydrazino}-3-oxopropyl)hydroxyformamide was prepared according to General Procedure A, utilizing (4aR,8aS)-1-methyldecahydroquinoxaline (preparation see Example 221) in place of pyrrolidine in Part A, and using 3 equivalents of DIPEA. LCMS: (M+H)$^+$: 492.3.

Example 223

N-[(2R)-3-[2-(6-{[(2-Amino-1,3-thiazol-4-yl)methyl](methyl)amino}-2-chloro-5-fluoro-4-pyrimidinyl)hydrazino]-2-(cyclopentylmethyl)-3-oxopropyl]-N-hydroxyformamide

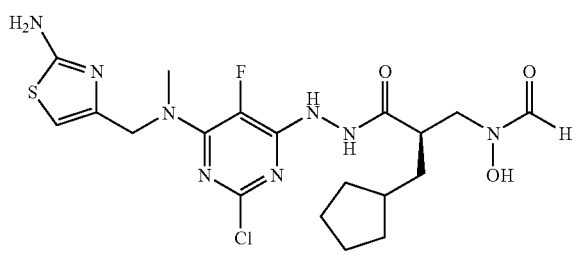

Part A:

4-[(Methylamino)methyl]-1,3-thiazol-2-amine 4-(Chloromethyl)-1,3-thiazol-2-amine (490 mg, 2.65 mmol) was stirred in 40% aqueous methylamine (25 ml) overnight. The reaction mixture was evaporated. The residue was then purified via reverse phase HPLC to provide 4-[(methylamino)methyl]-1,3-thiazol-2-amine (55 mg, 15%). LCMS: (M+H)$^+$: 144.0.

Part B:

Tris(1,1-dimethylethyl)2-{6-[[(2-amino-1,3-thiazol-4-yl)methyl](methyl)amino]-2-chloro-5-fluoro-4-pyrimidinyl}-1,1,2-hydrazinetricarboxylate 4-[(Methylamino)methyl]-1,3-thiazol-2-amine (55 mg, 0.38 mmol) was dissolved in THF (3 mL). Triethylamine (0.06 mL, 0.42 mmol) was added, followed immediately by tris(1,1-dimethylethyl)2-(2,6-dichloro-5-fluoro-4-pyrimidinyl)-1,1,2-hydrazinetricarboxylate (180 mg, 0.38 mmol). The reaction mixture was stirred overnight, was diluted with EtOAc, was dried (sodium sulfate) and was evaporated to provide tris(1,1-dimethylethyl)2-{6-[[(2-amino-1,3-thiazol-4-yl)methyl](methyl)amino]-2-chloro-5-fluoro-4-pyrimidinyl}-1,1,2-hydrazinetricarboxylate (230 mg, 100%). LCMS: (M+H)$^+$: 604.2.

Part C:

6-[[(2-Amino-1,3-thiazol-4-yl)methyl](methyl)amino]-2-chloro-5-fluoro-4(1H)-pyrimidinone hydrazone trihydrochloride Tris(1,1-dimethylethyl)2-{6-[[(2-amino-1,3-thiazol-4-yl)methyl](methyl)amino]-2-chloro-5-fluoro-4-pyrimidinyl}-1,1,2-hydrazinetricarboxylate (220 mg, 0.36 mmol) was dissolved in 10 mL of methanol and stirred. To this solution, 5 mL of 4M HCl in dioxane was slowly added. The mixture was stirred for 3 days and was evaporated to provide 6-[[(2-amino-1,3-thiazol-4-yl)methyl](methyl)amino]-2-chloro-5-fluoro-4(1H)-pyrimidinone hydrazone trihydrochloride (150 mg, 83%). LCMS: (M+H)$^+$: 303.9.

Part D:

[(2R)-3-(2-{6-[[(2-Amino-1,3-thiazol-4-yl)methyl](methyl)amino]-2-chloro-5-fluoro-4-pyrimidinyl}hydrazino)-2-(cyclopentylmethyl)-3-oxopropyl](tetrahydro-2H-pyran-2-yloxy)formamide 6-[[(2-Amino-1,3-thiazol-4-yl)methyl](methyl)amino]-2-chloro-5-fluoro-4(1H)-pyrimidinone hydrazone trihydrochloride (150 mg, 0.29 mmol), (2R)-3-cyclopentyl-2-{[formyl(tetrahydro-2H-pyran-2-yloxy)amino]methyl}propanoic acid (120 mg, 0.4 mmol), and HOAt (59 mg, 0.43 mmol) were dissolved in 10 mL of DMF. NMM (0.2 mL, 1.8 mmol) was added, followed by EDC (85 mg, 0.43 mmol). After stirring overnight at room temperature, the reaction mixture was purified by RP-HPLC [(2R)-3-(2-{6-[[(2-amino-1,3-thiazol-4-yl)methyl](methyl)amino]-2-chloro-5-fluoro-4-pyrimidinyl}hydrazino)-2-(cyclopentylmethyl)-3-oxopropyl](tetrahydro-2H-pyran-2-yloxy)formamide (110 mg, 52%). LCMS: (M+H)$^+$: 585.2.

Part E:

N-[(2R)-3-[2-(6-{[(2-Amino-1,3-thiazol-4-yl)methyl](methyl)amino}-2-chloro-5-fluoro-4-pyrimidinyl)hydrazino]-2-(cyclopentylmethyl)-3-oxopropyl]-N-hydroxyformamide

[(2R)-3-(2-{6-[[(2-Amino-1,3-thiazol-4-yl)methyl](methyl)amino]-2-chloro-5-fluoro-4-pyrimidinyl}hydrazino)-2-(cyclopentylmethyl)-3-oxopropyl](tetrahydro-2H-pyran-2-yloxy)formamide (110 mg, 0.19 mmol) in 4:1 AcOH:water (5 mL) was stirred at room temperature for 2 days. The solvents were removed in vacuo, and the resulting crude product was purified by RP-HPLC to provide N-[(2R)-3-[2-(6-{[(2-amino-1,3-thiazol-4-yl)methyl](methyl)amino}-2-chloro-5-fluoro-4-pyrimidinyl)hydrazino]-2-(cyclopentylmethyl)-3-oxopropyl]-N-hydroxyformamide (20 mg, 21%). LCMS: (M+H)$^+$: 501.1.

Example 224

[(2R)-3-(2-{2-Chloro-5-fluoro-6-[(2S)-2-(1-pyrrolidinylmethyl)-1-pyrrolidinyl]-4-pyrimidinyl}hydrazino)-2-(cyclopentylmethyl)-3-oxopropyl]hydroxyformamide

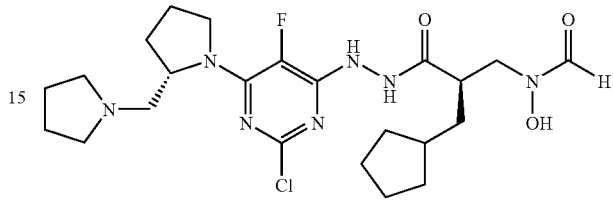

[(2R)-3-(2-{2-Chloro-5-fluoro-6-[(2S)-2-(1-pyrrolidinylmethyl)-1-pyrrolidinyl]-4-pyrimidinyl}hydrazino)-2-(cyclopentylmethyl)-3-oxopropyl]hydroxyformamide was prepared according to General Procedure E, utilizing commercially-available 1-[(2S)-2-pyrrolidinylmethyl]pyrrolidine in place of isopropyl amine in Part A. LCMS: (M+H)$^+$: 512.3

Example 225

((2R)-2-(Cyclopentylmethyl)-3-{2-[5-fluoro-2-methyl-6-(phenylamino)-4-pyrimidinyl]hydrazino}-3-oxopropyl)hydroxyformamide

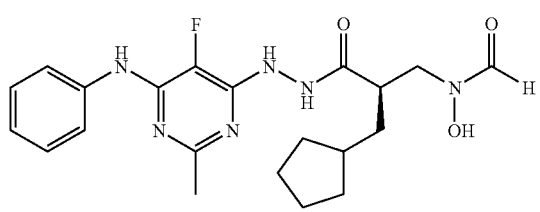

((2R)-2-(Cyclopentylmethyl)-3-{2-[5-fluoro-2-methyl-6-(phenylamino)-4-pyrimidinyl]hydrazino}-3-oxopropyl)hydroxyformamide was prepared according to General Procedure A, utilizing aniline in place of pyrrolidine in Part A. LCMS: (M+H)$^+$: 451.2.

Example 226

[(2R)-3-{2-[2-Chloro-5-fluoro-6-(4-methyloctahydro-1(2H)-quinoxalinyl)-4-pyrimidinyl]hydrazino}-2-(cyclopentylmethyl)-3-oxopropyl]hydroxyformamide

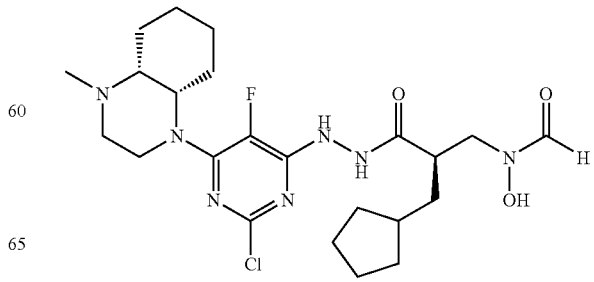

Part A:

(4aS,8aR)-1-Methyldecahydroquinoxaline, Hydrochloride Salt

Phenylmethyl (4aR,8aS)-4-methyloctahydro-1(2H)-quinoxalinecarboxylate (Example 221) (2.58 g, 9.0 mmol) was dissolved in 120 mL of MeOH, degassed and placed under argon. 10% Pd/C (380 mg) was added, and the contents were thoroughly degassed and placed under a hydrogen balloon for approximately 2 hrs. The contents were then degassed and filtered through Celite, and the Celite pad was washed with DCM and MeOH. After 19.0 mL 1N HCl was added, the resulting filtrate was concentrated in vacuo to provide the hydrochloride salt of (4aS,8aR)-1-methyldecahydroquinoxaline (2.0 g, 100%). LCMS: (M+H)$^+$: 155.1.

Part B:

[(2R)-3-{2-[2-Chloro-5-fluoro-6-(4-methyloctahydro-1(2H)-quinoxalinyl)-4-pyrimidinyl]hydrazino}-2-(cyclopentylmethyl)-3-oxopropyl]hydroxyformamide

[(2R)-3-{2-[2-Chloro-5-fluoro-6-(4-methyloctahydro-1 (2H)-quinoxalinyl)-4-pyrimidinyl]hydrazino}-2-(cyclopentylmethyl)-3-oxopropyl]hydroxyformamide was prepared according to General Procedure G, utilizing (4aS,8aR)-1-methyldecahydroquinoxaline, hydrochloride salt in place of (1S,4S)-2-methyl-2,5-diazabicyclo[2.2.1]heptane, dihydrobromide in Part A. LCMS: (M+H)$^+$: 512.3.

Example 227

((2R)-2-(Cyclopentylmethyl)-3-{2-[5-fluoro-2-methyl-6-(4-methyloctahydro-1(2H)-quinoxalinyl)-4-pyrimidinyl]hydrazino}-3-oxopropyl)hydroxyformamide

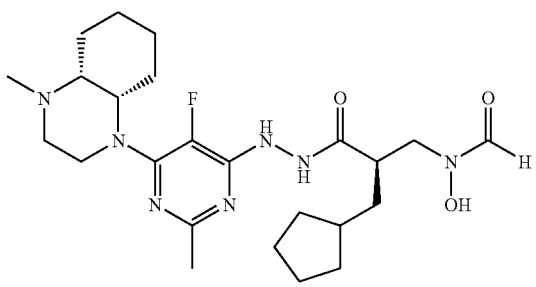

((2R)-2-(Cyclopentylmethyl)-3-{2-[5-fluoro-2-methyl-6-(4-methyloctahydro-1(2H)-quinoxalinyl)-4-pyrimidinyl]hydrazino}-3-oxopropyl)hydroxyformamide was prepared according to General Procedure A, utilizing (4aS,8aR)-1-methyldecahydroquinoxaline, hydrochloride salt (Example 226) in place of pyrrolidine in Part A, and using 3 equivalents of DIPEA. LCMS: (M+H)$^+$: 492.3.

Example 228

[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]hydroxyformamide

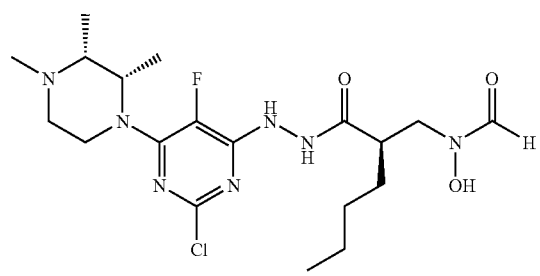

[(2R)-3-(2-{2-Chloro-5-fluoro-6-[(2S,3R)-2,3,4-trimethyl-1-piperazinyl]-4-pyrimidinyl}hydrazino)-2-(cyclopentylmethyl)-3-oxopropyl]hydroxyformamide was prepared according to General Procedure E, utilizing (2R,3S)-1,2,3-trimethylpiperazine dihydrochloride (Example 175) in place of isopropyl amine in Part A, 2.0 M HCl in ether with DCM as a solvent in Part B, and (2R)-2-({formyl[(phenylmethyl)oxy]amino}methyl)hexanoic acid (Example 201) in place of (2R)-3-cyclopentyl-2-({formyl[(phenylmethyl)oxy]amino}methyl)propanoic acid in Part C. LCMS: (M+H)$^+$: 460.2./462.1.

Example 229

[(2R)-3-(2-{2-Chloro-5-fluoro-6-[(2R)-2-(4-morpholinylmethyl)-1-pyrrolidinyl]-4-pyrimidinyl}hydrazino)-2-(cyclopentylmethyl)-3-oxopropyl]hydroxyformamide

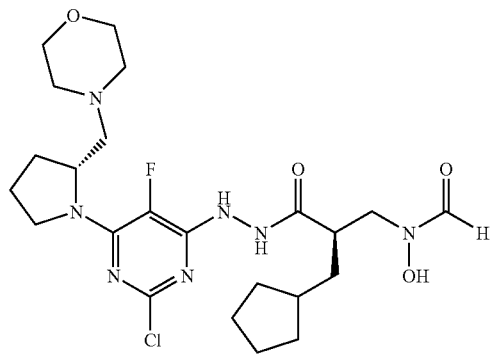

[(2R)-3-(2-{2-Chloro-5-fluoro-6-[(2R)-2-(4-morpholinylmethyl)-1-pyrrolidinyl]-4-pyrimidinyl}hydrazino)-2-(cyclopentylmethyl)-3-oxopropyl]hydroxyformamide was prepared according to General Procedure E, utilizing (S)-2-(morpholin-4-ylmethyl)-pyrrolidine (Bull. Chem. Soc. 1990, 63, 721-727) in place of isopropyl amine in Part A, and 2.0 M HCl in ether with DCM as a solvent in Part B. LCMS: (M+H)$^+$: 528.2/530.2.

Example 230

[(2R)-3-[2-(2-Chloro-6-{3-ethyl-3-[ethyl(methyl)amino]-1-azetidinyl}-5-fluoro-4-pyrimidinyl)hydrazino]-2-(cyclopentylmethyl)-3-oxopropyl]hydroxyformamide

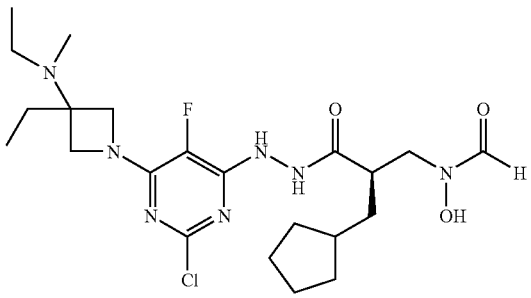

Part A:

N,3-Diethyl-N-methyl-3-azetidinamine dihydrochloride

N,3-Diethyl-N-methyl-3-azetidinamine dihydrochloride was prepared according to procedure described for the preparation of 3-ethyl-N,N-dimethyl-3-azetidinamine dihydrochloride (Example 211), utilizing N-methylethanamine in place of dimethylamine in Part A. LCMS: (M+H)$^+$ 144.1.

Part B:

[(2R)-3-[2-(2-Chloro-6-{3-ethyl-3-[ethyl(methyl)amino]-1-azetidinyl}-5-fluoro-4-pyrimidinyl)hydrazino]-2-(cyclopentylmethyl)-3-oxopropyl]hydroxyformamide

[(2R)-3-[2-(2-Chloro-6-{3-ethyl-3-[ethyl(methyl)amino]-1-azetidinyl}-5-fluoro-4-pyrimidinyl)hydrazino]-2-(cyclopentylmethyl)-3-oxopropyl]hydroxyformamide was prepared in a manner similar to Example 176, utilizing N,3-diethyl-N-methyl-3-azetidinamine dihydrochloride in place of 1-(3-methyl-3-azetidinyl)pyrrolidine dihydrochloride in Part C. LCMS: (M+H)$^+$ 500.3.

Example 231

((2R)-2-(Cyclopentylmethyl)-3-{2-[5-fluoro-6-[(9aS)-hexahydropyrazino[2,1-c][1,4]oxazin-8(1H)-yl]-2-(methylthio)-4-pyrimidinyl]hydrazino}-3-oxopropyl)hydroxyformamide

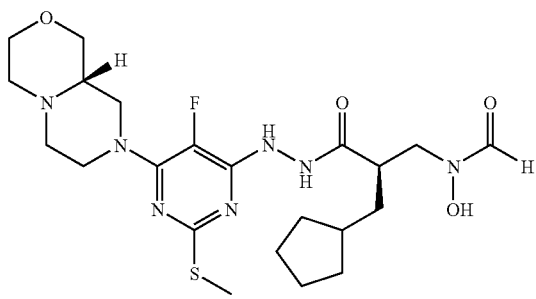

((2R)-2-(Cyclopentylmethyl)-3-{2-[5-fluoro-6-[(9aS)-hexahydropyrazino[2,1-c][1,4]oxazin-8(1H)-yl]-2-(methylthio)-4-pyrimidinyl]hydrazino}-3-oxopropyl)hydroxyformamide was prepared according to General Procedure C, utilizing (9aS)-octahydropyrazino[2,1-c][1,4]oxazine dihydrochloride (Example 22) in place of azetidine hydrochloride in Part A. LCMS: (M+H)$^+$ 512.2.

Example 232

[(2R)-3-[2-(2-Chloro-6-{(2S)-2-[(dimethylamino)methyl]-1-pyrrolidinyl}-5-fluoro-4-pyrimidinyl)hydrazino]-2-(cyclopentylmethyl)-3-oxopropyl]hydroxyformamide

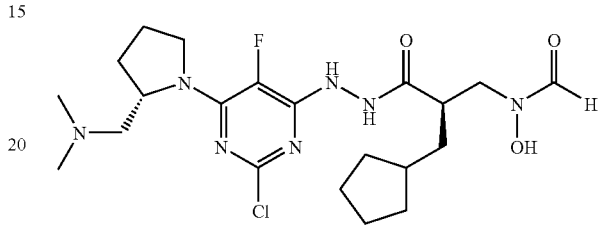

Part A:

N,N-Dimethyl-1-(phenylcarbonyl)-L-prolinamide

N,N-Dimethyl-L-prolinamide (2.50 g, 17.58 mmol) was dissolved in a mixture of CH$_2$Cl$_2$ (50 mL) and water (50 mL), then solid sodium bicarbonate (2.95 g, 35.16 mmol) was added, followed by benzoyl chloride (2.1 mL, 18.45 mmol). After stirring overnight, the phases were separated, and the aqueous phase was extracted with CH$_2$Cl$_2$ (3×50 mL). The combined organic phase was dried over anhydrous Na$_2$SO$_4$, filtered, and concentrated in vacuo to provide N,N-dimethyl-1-(phenylcarbonyl)-L-prolinamide (4.502 g, >99%). LCMS: (M+H)$^+$: 247.2.

Part B:

N,N-Dimethyl-1-[(2S)-1-(phenylmethyl)-2-pyrrolidinyl]methanamine

N,N-Dimethyl-1-(phenylcarbonyl)-L-prolinamide (4.50 g, 18.269 mmol) was dissolved in 100 mL of THF, cooled to 0° C., and then LiAlH$_4$ (1.386 mg, 36.54 mmol) was added portion wise. The mixture was heated to 80° C. for 2 h, then allowed to cool to RT. The reaction was quenched in succession with H$_2$O (1.5 mL), 15% aq. NaOH (1.5 mL) and H$_2$O (4.5 mL) and was stirred at room temperature overnight. The contents were filtered, and the filtrate was concentrated in vacuo to provide N,N-dimethyl-1-[(2S)-1-(phenylmethyl)-2-pyrrolidinyl]methanamine (3.7305 g, 94%). LCMS: (M+H)$^+$: 219.1.

Part C:

N,N-Dimethyl-1-[(2S)-2-pyrrolidinyl]methanamine hydrochloride

N,N-Dimethyl-1-[(2S)-1-(phenylmethyl)-2-pyrrolidinyl]methanamine (3.730 g, 17.08 mmol) was dissolved in a mixture of MeOH (100 mL) and 1N HCl (35 mL, 34.16 mmol), degassed and placed under argon. 10% Pd/C (1.119 g) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure N,N-dimethyl-1-[(2S)-2-pyrrolidinyl]methanamine hydrochloride (3.3701 g, >99%). LCMS: (M+H)+: 129.1.

Part D:

[(2R)-3-[2-(2-Chloro-6-{(2S)-2-[(dimethylamino)methyl]-1-pyrrolidinyl}-5-fluoro-4-pyrimidinyl)hydrazino]-2-(cyclopentylmethyl)-3-oxopropyl]hydroxyformamide

[(2R)-3-[2-(2-Chloro-6-{(2S)-2-[(dimethylamino)methyl]-1-pyrrolidinyl}-5-fluoro-4-pyrimidinyl)hydrazino]-2-(cyclopentylmethyl)-3-oxopropyl]hydroxyformamide was prepared according to General Procedure E, utilizing N,N-dimethyl-1-[(2S)-2-pyrrolidinyl]methanamine hydrochloride in place of isopropyl amine in Part A. LCMS: (M+H)+: 486.0.

Example 233

[(2R)-3-(2-{2-Chloro-5-fluoro-6-[(1,3-thiazol-4-ylmethyl)amino]-4-pyrimidinyl}hydrazino)-2-(cyclopentylmethyl)-3-oxopropyl]hydroxyformamide

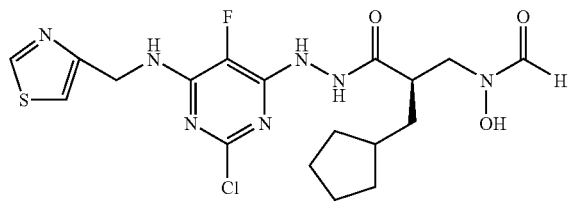

Part A:

2-(3-Bromo-2-oxopropyl)-1H-isoindole-1,3(2H)-dione

Commercially available phthalimidoacetone (2.0 g, 9.8522 mmol), under a nitrogen atmosphere, was taken up in diethylene glycol (13 mL) and cooled to 0° C. in an ice bath. Bromine (0.51 mL, 9.9242 mmol) was added dropwise. The reaction was shielded from light, allowed to reach ambient temperature, and stirred overnight. LCMS: (M+H)+=282.0.

Part B:

2-(1,3-Thiazol-4-ylmethyl)-1H-isoindole-1,3(2H)-dione

Ether (7.5 mL) was added to the above solution of 2-(3-bromo-2-oxopropyl)-1H-isoindole-1,3(2H)-dione and cooled to 0° C. in an ice/NaCl salt bath. Then thioformamide (European Journal of Medicinal Chemistry, 2004, 39, 867-872.) (1.20 g) in EtOH (8 mL) was added, and the reaction was stirred overnight. The solvents were evaporated and the reaction mixture was purified by RP-HPLC to provide 2-(1,3-thiazol-4-ylmethyl)-1H-isoindole-1,3(2H)-dione as a white solid. LCMS: (M+H)+=245.1.

Part C:

(1,3-Thiazol-4-ylmethyl)amine 2-(1,3-Thiazol-4-ylmethyl)-1H-isoindole-1,3(2H)-dione (0.6556 g, 2.69 mmol) dissolved in EtOH (15 mL) and hydrazine monohydrate (0.145 mL, 2.98 mmol) was placed in a sealed round bottom and heated to 70° C. for 2.5 hours, then stirred at ambient temperature overnight. After diluting with EtOH, the solids were filtered off, washed with EtOH, and the filtrate was evaporated to provide (1,3-thiazol-4-ylmethyl)amine as a beige solid (0.1491 g, 49%). LCMS: (M+H)+ =115.1.

Part D:

Tris(1,1-dimethylethyl)2-{2-chloro-5-fluoro-6-[(1,3-thiazol-4-ylmethyl)amino]-4-pyrimidinyl}-1,1,2-hydrazinetricarboxylate To a suspension of (1,3-thiazol-4-ylmethyl)amine (0.1491 g, 1.308 mmol) in THF (10 mL) was added a solution of tris(1,1-dimethylethyl)2-(2,6-dichloro-5-fluoro-4-pyrimidinyl)-1,1,2-hydrazinetricarboxylate (0.649 g, 1.308 mmol) and triethylamine (0.22 mL, 1.5784 mmol) in THF (2 mL). Additional THF (3 mL) was added, and the reaction was stirred overnight. Then the reaction mixture was diluted with water, and the aqueous layer was extracted with ethyl acetate. The organics were dried (Na2SO4) and concentrated. The resulting crude material was purified by silica gel chromatography (0-100% ethyl acetate in hexanes) to produce tris(1,1-dimethylethyl)2-{2-chloro-5-fluoro-6-[(1,3-thiazol-4-ylmethyl)amino]-4-pyrimidinyl}-1,1,2-hydrazinetricarboxylate as a yellow oil (0.51 g, 68%). LCMS: (M-2Boc)=375.0.

Part E:

2-Chloro-5-fluoro-6-[(1,3-thiazol-4-ylmethyl)amino]-4(1H)-pyrimidinone hydrazone Tris(1,1-dimethylethyl)2-{2-chloro-5-fluoro-6-[(1,3-thiazol-4-ylmethyl)amino]-4-pyrimidinyl}-1,1,2-hydrazinetricarboxylate (0.51 g, 0.8868 mmol) was dissolved in MeOH (5 mL) and HCl (4M in 1,4-dioxane) (5 mL). The reaction mixture was left to stir overnight, then evaporated and purified by RP-HPLC to provide 2-chloro-5-fluoro-6-[(1,3-thiazol-4-ylmethyl)amino]-4(1H)-pyrimidinone hydrazone as an orange oil (0.105 g). LCMS: (M+H)+=275.0.

Part F:

[(2R)-3-(2-{2-Chloro-5-fluoro-6-[(1,3-thiazol-4-ylmethyl)amino]-4-pyrimidinyl}hydrazino)-2-(cyclopentylmethyl)-3-oxopropyl](tetrahydro-2H-pyran-2-yloxy)formamide 2-Chloro-5-fluoro-6-[(1,3-thiazol-4-ylmethyl)amino]-4(1H)-pyrimidinone hydrazone (0.105 g) and (2R)-3-cyclopentyl-2-{[formyl(tetrahydro-2H-pyran-2-yloxy)amino]methyl}propanoic acid (0.182 g, 0.422 mmol) were dissolved in DMF (5 mL). NMM (0.21 mL, 1.91 mmol) was added, followed by HOAt (0.063 g, 0.463 mmol) and EDC (0.088 g, 0.459 mmol). After stirring for 2 days, the reaction mixture was purified by RP-HPLC to provide [(2R)-3-(2-{2-chloro-5-fluoro-6-[(1,3-thiazol-4-ylmethyl)amino]-4-pyrimidinyl}hydrazino)-2-(cyclopentylmethyl)-3-oxopropyl](tetrahydro-2H-pyran-2-yloxy)formamide as a maroon solid (0.1133 g). LCMS: (M+H)+=556.0.

Part G:

[(2R)-3-(2-{2-Chloro-5-fluoro-6-[(1,3-thiazol-4-ylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[(1,3-thiazol-4-ylmethyl)amino]-4-pyrimidinyl}hydrazino)-2-(cyclopentylmethyl)-3-oxopropyl](tetrahydro-2H-pyran-2-yloxy)formamide (0.1133 g, 0.204 mmol) was dissolved in acetic acid (8 mL) and water (2 mL). This reaction mixture was left to stir overnight. The volatiles were evaporated, and the resulting residue was purified by RP-HPLC to provide [(2R)-3-(2-{2-chloro-5-fluoro-6-[(1,3-thiazol-4-ylmethyl)amino]-4-pyrimidinyl}hydrazino)-2-(cyclopentylmethyl)-3-oxopropyl]hydroxyformamide (0.0497 g, 52%). LCMS: (M+H)$^+$ =472.1.

Example 234

[(2R)-3-(2-{2-Chloro-5-fluoro-6-[(2R)-2-(fluoromethyl)-1-pyrrolidinyl]-4-pyrimidinyl}hydrazino)-2-(cyclopentylmethyl)-3-oxopropyl]hydroxyformamide

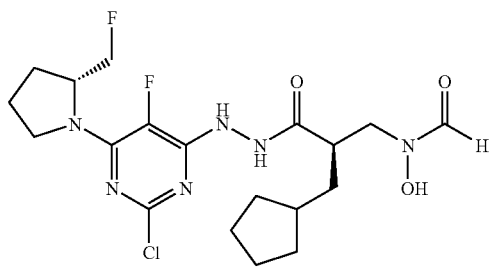

[(2R)-3-(2-{2-Chloro-5-fluoro-6-[(2R)-2-(fluoromethyl)-1-pyrrolidinyl]-4-pyrimidinyl}hydrazino)-2-(cyclopentylmethyl)-3-oxopropyl]hydroxyformamide was prepared according to General Procedure E, utilizing (2R)-fluoromethylpyrrolidine (Bioorg. Med. Chem. Lett. 2007, 17, 1443-1446) in place of isopropyl amine in Part A and 2.0 M HCl in ether with DCM as a solvent in Part B. LCMS: (M+H)$^+$: 461.1/463.0.

Example 235

{(2R)-2-(Cyclopentylmethyl)-3-[2-(6-{(2S)-2-[(dimethylamino)methyl]-1-pyrrolidinyl}-5-fluoro-2-methyl-4-pyrimidinyl)hydrazino]-3-oxopropyl}hydroxyformamide

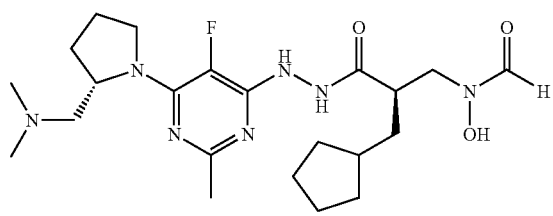

{(2R)-2-(Cyclopentylmethyl)-3-[2-(6-{(2S)-2-[(dimethylamino)methyl]-1-pyrrolidinyl}-5-fluoro-2-methyl-4-pyrimidinyl)hydrazino]-3-oxopropyl}hydroxyformamide was prepared according to General Procedure A, utilizing N,N-dimethyl-1-[(2S)-2-pyrrolidinyl]methanamine hydrochloride in place of pyrrolidine in Part A. LCMS: (M+H)$^+$: 466.2.

Example 236

[(2R)-3-(2-{2-Chloro-5-fluoro-6-[(3R)-3-methyl-4-morpholinyl]-4-pyrimidinyl}hydrazino)-2-(cyclopentylmethyl)-3-oxopropyl]hydroxyformamide

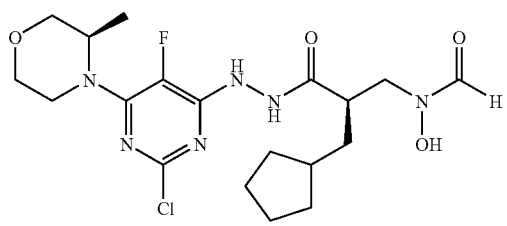

(2R)-2-Amino-1-propanol was employed to prepare [(2R)-3-(2-{2-chloro-5-fluoro-6-[(3R)-3-methyl-4-morpholinyl]-4-pyrimidinyl}hydrazino)-2-(cyclopentylmethyl)-3-oxopropyl]hydroxyformamide according to the procedures of Example 241.

Example 237

N-[(2R)-3-(2-{2-Chloro-5-fluoro-6-[(2S,5S)-2,4,5-trimethyl-1-piperazinyl]-4-pyrimidinyl}hydrazino)-2-(cyclopentylmethyl)-3-oxopropyl]-N-hydroxyformamide

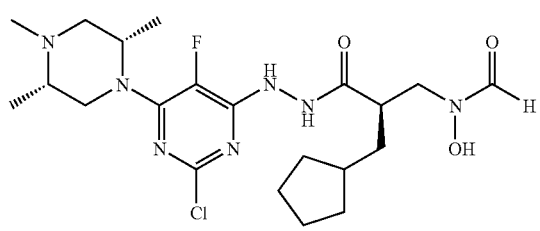

Part A:

(2S,5S)-1,2,5-Trimethyl-4-(phenylmethyl)piperazine

To a solution of (2S,5S)-2,5-dimethyl-1-(phenylmethyl)piperazine (J. Med. Chem. 2006, 49, 716-726) (770 mg, 3.77 mmol) in dichloromethane (25 mL) at 0° C. was added formaldehyde (0.396 mL, 37% water solution, 5.28 mmol) followed by sodium triacetoxyborohydride (959 mg, 4.52 mmol). The reaction mixture was allowed to warm to room temperature and stirred for 2 h before being diluted with dichloromethane and washed with 1N NaOH solution. The organics were washed with brine, dried (MgSO$_4$) and evaporated to yield (2S,5S)-1,2,5-trimethyl-4-(phenylmethyl)piperazine (782 mg, 95%). LCMS: (M+H)$^+$: 219.1.

Part B:

(2S,5S)-1,2,3-Trimethylpiperazine, Hydrochloride Salt (2S,5S)-1,2,5-Trimethyl-4-(phenylmethyl)piperazine (782 mg, 3.58 mmol) was dissolved in 50 mL of MeOH, degassed and placed under argon. 10% Pd/C (200 mg) was added, and the contents were thoroughly degassed and placed under a hydrogen balloon for approximately 3 hrs. The contents were then degassed and filtered through Celite, and the Celite pad was washed with DCM and MeOH. After 7.5 mL 1N HCl was added, the resulting filtrate was concentrated in vacuo to provide the hydrochloride salt of (2S,5S)-1,2,5-trimethylpiperazine (715 mg, 100%). LCMS: $(M+H)^+$: 129.1.

Part C:

N-[(2R)-3-(2-{2-Chloro-5-fluoro-6-[(2S,5S)-2,4,5-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(2S,5S)-2,4,5-trimethyl-1-piperazinyl]-4-pyrimidinyl}hydrazino)-2-(cyclopentylmethyl)-3-oxopropyl]-N-hydroxyformamide was prepared according to General Procedure G, utilizing (2S,5S)-1,2,5-trimethylpiperazine, hydrochloride salt in place of (1S,4S)-2-methyl-2,5-diazabicyclo[2.2.1]heptane, dihydrobromide in Part A. LCMS: $(M+H)^+$: 486.1.

Example 238

[(2R)-2-(Cyclopentylmethyl)-3-(2-{5-fluoro-6-[(5-fluoro-2-pyridinyl)amino]-2-methyl-4-pyrimidinyl}hydrazino)-3-oxopropyl]hydroxyformamide

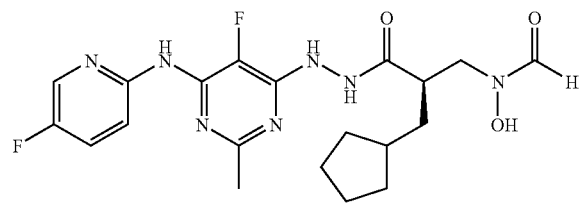

Part A:

5-Fluoro-6-[(5-fluoro-2-pyridinyl)amino]-2-methyl-4(1H)-pyrimidinone hydrazone

A solution of 2-amino-5-fluoropyrimidine (110 mg, 1 mmol) in THF (5 mL) was cooled to 0° C. and NaH (60% dispersion in oil) (72 mg, 1.8 mmol) was added. The reaction mixture was stirred at reduced temperature for 10 min, and room temperature for 20 mins before once again being cooled to 0° C. 4,6-Dichloro-5-fluoro-2-methylpyrimidine (180 mg, 1 mmol) was added and the reaction was warmed to room temperature and stirred for 1.5 hours. Water was then added and the solution was extracted with EtOAc. The combined organics were dried over sodium sulfate and concentrated, yielding crude material. This was dissolved in DMSO (4 mL) and hydrazine (1 mL) was added. The resulting mixture was heated to 60° C. and stirred for 5 hours. Upon cooling 5-fluoro-6-[(5-fluoro-2-pyridinyl)amino]-2-methyl-4(1H)-pyrimidinone hydrazone (63 mg, 25%) precipitated and was isolated by filtration. LCMS: $(M+H)^+$: 253.1.

Part B:

[(2R)-2-(Cyclopentylmethyl)-3-(2-{5-fluoro-6-[(5-fluoro-2-pyridinyl)amino]-2-methyl-4-pyrimidinyl}hydrazino)-3-oxopropyl]hydroxyformamide

[(2R)-2-(Cyclopentylmethyl)-3-(2-{5-fluoro-6-[(5-fluoro-2-pyridinyl)amino]-2-methyl-4-pyrimidinyl}hydrazino)-3-oxopropyl]hydroxyformamide was prepared according to General Procedure A, Parts B and C, utilizing 5-fluoro-6-[(5-fluoro-2-pyridinyl)amino]-2-methyl-4(1H)-pyrimidinone hydrazone in place of 5-fluoro-4-hydrazino-2-methyl-6-(1-pyrrolidinyl)pyrimidine in Part B. LCMS: $(M+H)^+$: 450.1.

Example 239

[(2R)-3-(2-{2-Chloro-6-[(2-cyanoethyl)(cyclopropyl)amino]-5-fluoro-4-pyrimidinyl}hydrazino)-2-(cyclopentylmethyl)-3-oxopropyl]hydroxyformamide

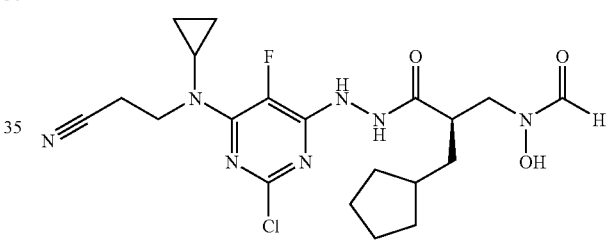

[(2R)-3-(2-{2-Chloro-6-[(2-cyanoethyl)(cyclopropyl)amino]-5-fluoro-4-pyrimidinyl}hydrazino)-2-(cyclopentylmethyl)-3-oxopropyl]hydroxyformamide was prepared according to General Procedure D, utilizing commercially-available 3-(cyclopropylamino)propanenitrile in place of N-methylpiperazine in Part A. LCMS: $(M+H)^+$ 468.1.

Example 240

[(2R)-2-(Cyclopentylmethyl)-3-(2-{5-fluoro-2-methyl-6-[(3S)-3-methyl-4-morpholinyl]-4-pyrimidinyl}hydrazino)-3-oxopropyl]hydroxyformamide

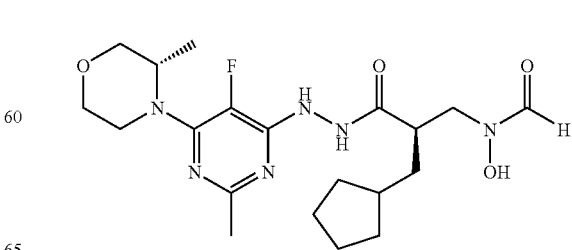

Part A:

(3S)-4-(5-Fluoro-6-hydrazino-2-methyl-4-pyrimidinyl)-3-methylmorpholine

To a solution of (3S)-3-methylmorpholine hydrochloride (0.1591 g, 1.156 mmol, prepared according to the procedures of Example 241) in MeOH (3 mL) was added N,N-diisopropylethylamine (0.440 mL, 2.526 mmol) and 4,6-dichloro-5-fluoro-2-methylpyrimidine (0.2085 g, 1.152 mmol). The solution was heated at 140° C. under microwave irradiation for 30 min, and then concentrated in vacuo. The resulting solid was triturated with water, collected by vacuum filtration, and washed with water. To a solution of the resulting solid in dioxane (11 mL) was added hydrazine hydrate (0.210 mL). The mixture was heated and stirred at 80° C. overnight, and then cooled to room temperature and concentrated in vacuo. The residue was partitioned between DCM (100 mL) and sat. aq. NaHCO$_3$ (30 mL). The organic phase was dried over anhydrous Na$_2$SO$_4$, filtered, and concentrated in vacuo to give (3S)-4-(5-fluoro-6-hydrazino-2-methyl-4-pyrimidinyl)-3-methylmorpholine (0.2148 g, 77% yield) as a yellow oil. LCMS: (M+H)$^+$: 242.1.

Part B:

[(2R)-2-(Cyclopentylmethyl)-3-(2-{5-fluoro-2-methyl-6-[(3S)-3-methyl-4-morpholinyl]-4-pyrimidinyl}hydrazino)-3-oxopropyl]hydroxyformamide To a solution of (3S)-4-(5-fluoro-6-hydrazino-2-methyl-4-pyrimidinyl)-3-methylmorpholine (0.2123 g, 0.880 mmol) in DMF (4 mL) was added (2R)-3-cyclopentyl-2-({formyl[(phenylmethyl)oxy]amino}methyl)propanoic acid, N,N-diisopropylethylamine salt, isopropanol solvate (327.1 mg, 0.661 mmol), N-methylmorpholine (0.290 ml, 2.64 mmol), 1-hydroxy-7-azabenzotriazole (0.108 g, 0.794 mmol), and EDC (0.152 g, 0.793 mmol). The solution was stirred overnight, and then purified directly by Gilson RPLC. To a solution of the residue in MeOH (7 mL) was added 10% Pd/C (50% water, 88 mg). The mixture was hydrogenated under balloon pressure for 1 h, and then filtered through a PTFE membrane. The resulting solution was concentrated in vacuo, dissolved in EtOAc, and concentrated in vacuo. The solid was collected by vacuum filtration and washed with hexanes to give [(2R)-2-(cyclopentylmethyl)-3-(2-{5-fluoro-2-methyl-6-[(3S)-3-methyl-4-morpholinyl]-4-pyrimidinyl}hydrazino)-3-oxopropyl]hydroxyformamide (0.2326 g, 80% yield) as a white solid. LCMS: (M+H)$^+$: 439.2.

Example 241

[(2R)-3-(2-{2-Chloro-5-fluoro-6-[(3S)-3-methyl-4-morpholinyl]-4-pyrimidinyl}hydrazino)-2-(cyclopentylmethyl)-3-oxopropyl]hydroxyformamide

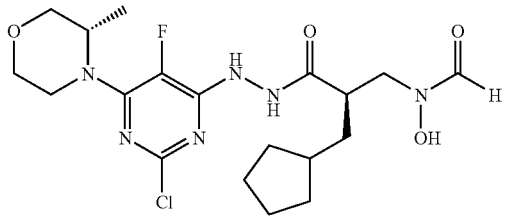

Part A:

(2S)-2-[(Phenylmethyl)amino]-1-propanol

To a solution of (2S)-2-amino-1-propanol (5.01 g, 66.70 mmol) in toluene (130 mL) was added benzaldehyde (7.08 mL, 70.05 mmol). The flask was fitted with a Dean-Stark trap, and the solution was heated at 150° C. for 2 h. The solution was then cooled to room temperature and concentrated in vacuo. To a 0° C. solution of the residue in EtOH (130 mL) was added NaBH$_4$ (6.31 g, 166.8 mmol) and sufficient 4 N HCl in dioxane to adjust the pH to ca. 2. The mixture was stirred overnight and then concentrated in vacuo. The residue was partitioned between 1 N aq. HCl (200 mL) and DCM (100 mL). The aqueous phase was washed with a fresh portion of DCM (100 mL), and then adjusted to pH>13 with 6 N aq. NaOH. The aqueous phase was extracted with DCM (2×150 mL), and the combined organic phase was dried over anhydrous Na$_2$SO$_4$, filtered, and concentrated in vacuo to provide (2S)-2-[(phenylmethyl)amino]-1-propanol (10.52 g, 95%) as a colorless oil. LCMS: (M+H)$^+$: 166.1.

Part B:

(5S)-5-Methyl-4-(phenylmethyl)-3-morpholinone

To a solution of (2S)-2-[(phenylmethyl)amino]-1-propanol (10.52 g, 63.67 mmol) in THF (65 mL) was added a solution of K$_2$CO$_3$ (26.40 g, 191.0 mmol) in water (65 mL). The vigorously stirred mixture was cooled to 0° C., and chloroacetyl chloride (7.10 mL, 89.14 mmol) was added dropwise over 20 min. The mixture was stirred for 1 h, and then an additional portion of chloroacetyl chloride (0.500 mL, 6.278 mmol) was added dropwise. The mixture was stirred for 1 h, and then the mixture was adjusted to pH>13 with 50% aq. NaOH (ca. 20 mL). The mixture was stirred and warmed to room temperature overnight, and then extracted with DCM (250 mL). The organic phase was washed with 1 N aq. HCl, followed by water. The organic phase was dried over anhydrous Na$_2$SO$_4$, filtered, and concentrated in vacuo to give (5S)-5-methyl-4-(phenylmethyl)-3-morpholinone (12.74 g, 97%) as a colorless oil. LCMS: (M+H)$^+$: 206.1.

Part C:

(3S)-3-Methyl-4-(phenylmethyl)morpholine

To a 0° C. solution of (5S)-5-methyl-4-(phenylmethyl)-3-morpholinone (12.74 g, 62.07 mmol) in toluene (150 mL) was added Red-Al (65% w/w in PhMe, 38 mL) dropwise via addition funnel. The resulting solution was heated at 60° C. and stirred for 4 h, then cooled to 40° C. and stirred overnight. The solution was then cooled to 0° C. and quenched by dropwise addition of 1 N aq. NaOH (15 mL). The mixture was diluted with Et$_2$O (100 mL) and washed with 1 N aq. NaOH (100 mL) followed by brine (50 mL). The organic phase was dried over anhydrous Na$_2$SO$_4$, filtered, concentrated in vacuo, and azeotroped with MeOH (50 mL) to provide (3S)-3-methyl-4-(phenylmethyl)morpholine (11.33 g, 95%) as a faintly pink oil. LCMS: (M+H)$^+$: 192.2.

Part D:

(3S)-3-Methylmorpholine hydrochloride

To a solution of (3S)-3-methyl-4-(phenylmethyl)morpholine (11.33 g, 59.24 mmol) in MeOH (150 mL) was added 6 N aq. HCl (9.9 mL, 59.4 mmol) and 10% Pd/C (50% water, 1.13 g). The suspension was hydrogenated under balloon pressure overnight, and then filtered through a glass fiber filter. The resulting yellow solution was concentrated in vacuo and azeotroped with MeOH (4×150 mL) to afford (3S)-3-methylmorpholine hydrochloride (8.17 g, quantitative yield) as a yellow oil that solidified under high vacuum. LCMS: (M+H)$^+$: 102.2.

Part E:

Tris(1,1-dimethylethyl)2-{2-chloro-5-fluoro-6-[(3S)-3-methyl-4-morpholinyl]-4-pyrimidinyl}-1,1,2-hydrazinetricarboxylate To a solution of (3S)-3-methylmorpholine hydrochloride (0.2059 g, 1.496 mmol) in DMF (7.5 mL) was added tris(1,1-dimethylethyl)2-(2,6-dichloro-5-fluoro-4-pyrimidinyl)-1,1,2-hydrazinetricarboxylate (0.7451 g, 1.498 mmol), and N,N-diisopropylethylamine (0.575 mL, 3.301 mmol). The solution was stirred overnight, and then diluted with Et$_2$O (150 mL). The mixture was washed with water (2×50 mL), and the combined aqueous phase was extracted with a fresh portion of Et$_2$O (50 mL). This Et$_2$O layer was washed with a fresh portion of water (50 mL), and the combined organic phase was diluted with DCM (50 mL), dried over anhydrous Na$_2$SO$_4$, filtered, concentrated in vacuo, and azeotroped with EtOAc. The solid was collected by vacuum filtration and washed with hexanes. The supernatant was concentrated in vacuo, and purified by gradient silica gel chromatography (0% to 100% EtOAc in hexanes; 1% Et$_3$N). The desired fractions were concentrated in vacuo, and the resulting solid was collected by vacuum filtration, washed with hexanes, and combined with the first crop of solid to give tris(1,1-dimethylethyl)2-{2-chloro-5-fluoro-6-[(3S)-3-methyl-4-morpholinyl]-4-pyrimidinyl}-1,1,2-hydrazinetricarboxylate (0.6610 g, 79%) as a white solid. LCMS: (M+H)$^+$: 562.2.

Part F:

(3S)-4-(5-Fluoro-6-hydrazino-2-methyl-4-pyrimidinyl)-3-methylmorpholine dihydrochloride To a solution of tris(1,1-dimethylethyl)2-{2-chloro-5-fluoro-6-[(3S)-3-methyl-4-morpholinyl]-4-pyrimidinyl}-1,1,2-hydrazinetricarboxylate (0.6552 g, 1.166 mmol) in DCM (12 mL) was added 2 N HCl in Et$_2$O (12 mL, 24 mmol). The solution was stirred for 2 days, and the resulting mixture was concentrated in vacuo. The solid was triturated with Et$_2$O and collected by vacuum filtration to afford (3S)-4-(5-fluoro-6-hydrazino-2-methyl-4-pyrimidinyl)-3-methylmorpholine dihydrochloride (0.2543 g, 65%) as a yellow solid. LCMS: (M+H)$^+$: 262.0.

Part G:

[(2R)-2-(Cyclopentylmethyl)-3-(2-{5-fluoro-2-methyl-6-[(3S)-3-methyl-4-morpholinyl]-4-pyrimidinyl}hydrazino)-3-oxopropyl][(phenylmethyl)oxy]formamide To a solution of (3S)-4-(5-fluoro-6-hydrazino-2-methyl-4-pyrimidinyl)-3-methyl morpholine dihydrochloride (251.5 mg, 0.752 mmol) in DMF (6 mL) was added (2R)-3-cyclopentyl-2-({formyl[(phenylmethyl)oxy]amino}methyl)propanoic acid, N,N-diisopropylethylamine salt, isopropanol solvate (306.1 mg, 0.619 mmol), N-methylmorpholine (0.410 ml, 3.73 mmol), 1-hydroxy-7-azabenzotriazole (0.101 g, 0.742 mmol), and EDC (0.142 g, 0.741 mmol). The solution was allowed to stir overnight, and was then purified directly by Gilson RPLC to give [(2R)-2-(cyclopentylmethyl)-3-(2-{5-fluoro-2-methyl-6-[(3S)-3-methyl-4-morpholinyl]-4-pyrimidinyl}hydrazino)-3-oxopropyl][(phenylmethyl)oxy]formamide (314.6 mg, 93%) as an orange foam. LCMS: (M+H)$^+$: 549.2.

Part H:

[(2R)-2-(Cyclopentylmethyl)-3-(2-{5-fluoro-2-methyl-6-[(3S)-3-methyl-4-morpholinyl]-4-pyrimidinyl}hydrazino)-3-oxopropyl]hydroxyformamide To a solution of [(2R)-2-(cyclopentylmethyl)-3-(2-{5-fluoro-2-methyl-6-[(3S)-3-methyl-4-morpholinyl]-4-pyrimidinyl}hydrazino)-3-oxopropyl][(phenylmethyl)oxy]formamide (309.1 mg, 0.563 mmol) in methanol (6 mL) was added 20% Pd(OH)$_2$/C (50% water, 62 mg). The suspension was hydrogenated for 1 h and then filtered through a PTFE membrane. The resulting solution was concentrated in vacuo and purified by Gilson RPLC to give [(2R)-2-(cyclopentylmethyl)-3-(2-{5-fluoro-2-methyl-6-[(3S)-3-methyl-4-morpholinyl]-4-pyrimidinyl}hydrazino)-3-oxopropyl]hydroxyformamide (94.0 mg, 36%) as a white solid following crystallization from EtOAc-Et$_2$O. LCMS: (M+H)$^+$: 459.1.

Example 242

N-[(2R)-3-(2-{2-Chloro-5-fluoro-6-[(3S,5S)-3,4,5-trimethyl-1-piperazinyl]-4-pyrimidinyl}hydrazino)-2-(cyclopentylmethyl)-3-oxopropyl]-N-hydroxyformamide

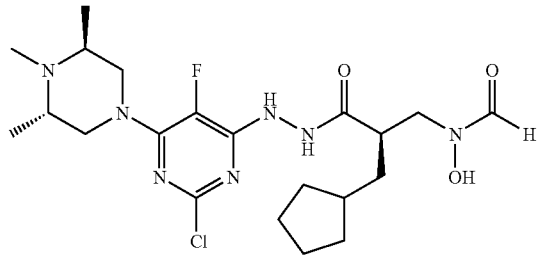

Part A:

(3S,5S)-3,5-Dimethyl-2-piperazinone

A mixture of methyl N-{(1S)-2-[bis(phenylmethyl)amino]-1-methylethyl}-L-alaninate (J. Org. Chem. 1995, 60, 4177-4183) (2.156 g, 6.33 mmol), concentrated hydrochloric acid 37% (0.805 mL), 5% palladium on carbon (0.863 g), and EtOH (40 mL) was hydrogenated under a hydrogen balloon for 48 h. The mixture was filtered through Celite, and the solids were washed with MeOH and CH$_2$Cl$_2$. The filtrates were combined and concentrated under reduced pressure. The residue was redissolved in EtOH (55 mL), p-toluenesulfonic acid (0.344 g) was added, and the mixture was heated at reflux for 16 h. The mixture was concentrated under reduced pressure and partitioned between CH$_2$Cl$_2$ and NaHCO$_3$. The aqueous layer was back extracted with CH$_2$Cl$_2$, and the combined organic layers were dried (MgSO$_4$), filtered, and concentrated under reduced pressure. The residue was purified by flash chromatography (9:1, CH₂Cl₂:MeOH) to provide methyl N-{(1S)-1-methyl-2-[(phenylmethyl)amino]ethyl}-L-alaninate (685 mg, 50%). LCMS: (M+H)⁺: 129.1. The leftover aqueous layer was extracted further with 40% isopropanol in CHCl₃ twice, and the combined organic layers were dried (Na₂SO₄), filtered, and concentrated to yield (3S,5S)-3,5-dimethyl-2-piperazinone (306 mg, 38%). LCMS: (M+H)⁺: 129.1.

Part B:

(3S,5S)-3,4,5-Trimethyl-2-piperazinone

To a solution of (3S,5S)-3,5-dimethyl-2-piperazinone in methanol (12 mL) at room temperature was added formaldehyde (0.345 mL, 37% water solution, 4.6 mmol) followed by sodium borohydride (261 mg, 6.9 mmol). The reaction mixture was stirred for 2 h before being diluted with dichloromethane and washed with 1N NaOH solution. The aqueous layer was back extracted with CH₂Cl₂ three times, and the combined organic layers were washed with brine, dried (MgSO₄) and evaporated to yield (3S,5S)-3,4,5-trimethyl-2-piperazinone (128 mg, 39%). LCMS: (M+H)⁺: 143.1.

Part C:

(2S,6S)-1,2,6-Trimethylpiperazine, Hydrochloride Salt

1M LAH in THF (3 mL, 3 mmol) was added dropwise to (3S,5S)-3,4,5-trimethyl-2-piperazinone (123 mg, 0.86 mmol). The reaction was allowed to warm to room temperature, then stirred at room temperature for 40 min and at reflux for an additional 5 h. After cooling to room temperature, the reaction was quenched by the sequential addition of H₂O (0.114 mL), 15% NaOH (0.114 mL), and H₂O (0.342 mL). The mixture was stirred for 0.5 h, and the solids were filtered off and washed with excess THF. To the combined filtrates was added 1.8 mL 1N HCl, followed by concentration under reduced pressure to provide the hydrochloride salt of (2S,6S)-1,2,6-trimethylpiperazine (162 mg, 93%). LCMS: (M+H)⁺: 129.1.

Part D:

N-[(2R)-3-(2-{2-Chloro-5-fluoro-6-[(3S,5S)-3,4,5-trimethyl-1-piperazinyl]-4-pyrimidinyl}hydrazino)-2-(cyclopentylmethyl)-3-oxopropyl]-N-hydroxyformamide N-[(2R)-3-(2-{2-Chloro-5-fluoro-6-[(3S,5S)-3,4,5-trimethyl-1-piperazinyl]-4-pyrimidinyl}hydrazino)-2-(cyclopentylmethyl)-3-oxopropyl]-N-hydroxyformamide was prepared according to General Procedure G, utilizing (2S,6S)-1,2,6-trimethylpiperazine, hydrochloride salt in place of (1S,4S)-2-methyl-2,5-diazabicyclo[2.2.1]heptane, dihydrobromide in Part A. LCMS: (M+H)⁺: 486.1.

Example 243

[(2R)-2-(Cyclopentylmethyl)-3-(2-{5-fluoro-2-methyl-6-[(2S)-2-(4-morpholinyl methyl)-1-pyrrolidinyl]-4-pyrimidinyl}hydrazino)-3-oxopropyl]hydroxyformamide

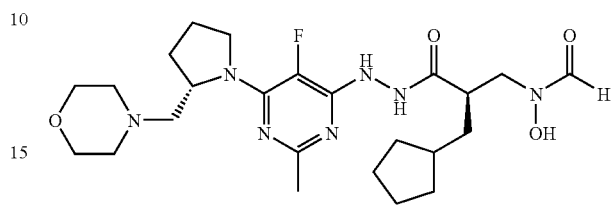

Part A:

4-[(2S)-2-Pyrrolidinylmethyl]morpholine hydrochloride

4-[(2S)-2-Pyrrolidinylmethyl]morpholine hydrochloride was prepared according to Example 264, Part A through Part C, utilizing commercially-available morpholine in place of piperidine in Part A. LCMS: (M+H)⁺: 171.1.

Part B:

4-{[(2S)-1-(5-Fluoro-6-hydrazino-2-methyl-4-pyrimidinyl)-2-pyrrolidinyl]methyl}morpholine 4-{[(2S)-1-(5-Fluoro-6-hydrazino-2-methyl-4-pyrimidinyl)-2-pyrrolidinyl]methyl}morpholine was prepared in a manner similar to Example 210, Part E and Part F, utilizing 4-[(2S)-2-pyrrolidinylmethyl]morpholine hydrochloride in place of 1-{1-[(2S)-2-pyrrolidinyl]cyclopropyl}pyrrolidine hydrochloride in Part E. LCMS: (M+H)⁺: 508.2.

Example 244

[(2R)-3-{2-[2-Chloro-5-fluoro-6-(3-fluoro-1-azetidinyl)-4-pyrimidinyl]hydrazino}-2-(cyclopentylmethyl)-3-oxopropyl]hydroxyformamide

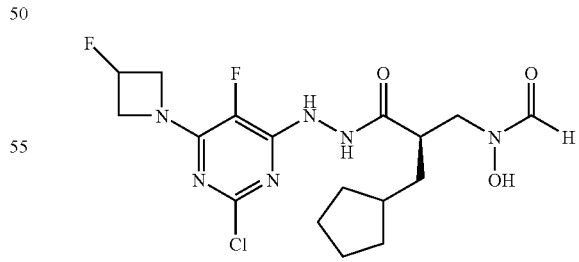

[(2R)-3-{2-[2-Chloro-5-fluoro-6-(3-fluoro-1-azetidinyl)-4-pyrimidinyl]hydrazino}-2-(cyclopentylmethyl)-3-oxopropyl]hydroxyformamide was prepared according to General Procedure D, utilizing 3-fluoroazetidine hydrochloride (Hulin, Bernard; Piotrowski, David W. US 2005256310) in place of N-methylpiperazine in Part A. LCMS: (M+H)⁺ 433.0.

Example 245

[(2R)-3-(2-{2-Chloro-5-fluoro-6-[(2S)-2-(hydroxymethyl)-1-pyrrolidinyl]-4-pyrimidinyl}hydrazino)-2-(cyclopentylmethyl)-3-oxopropyl]hydroxyformamide

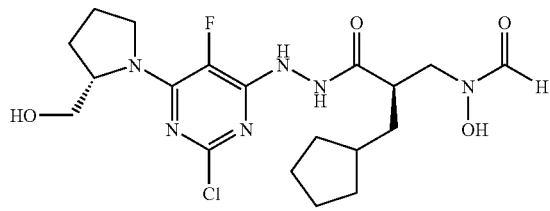

[(2R)-3-(2-{2-Chloro-5-fluoro-6-[(2S)-2-(hydroxymethyl)-1-pyrrolidinyl]-4-pyrimidinyl}hydrazino)-2-(cyclopentylmethyl)-3-oxopropyl]hydroxyformamide was prepared according to General Procedure E, utilizing commercially-available (2S)-2-pyrrolidinylmethanol in place of isopropyl amine in Part A. LCMS: (M+H)$^+$: 459.1.

Example 246

[(2R)-3-{2-[2-Chloro-5-fluoro-6-(2-methyl-1-pyrazolidinyl)-4-pyrimidinyl]hydrazino}-2-(cyclopentylmethyl)-3-oxopropyl]hydroxyformamide

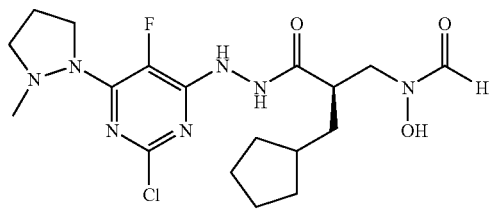

Part A:

1,1-Dimethylethyl 3-oxo-1-pyrazolidinecarboxylate

To a mixture of 3-pyrazolidinone hydrochloride (3.84 g, 31.33 mmol) in water (50 ml) and dioxane (10 ml) was added slowly sodium carbonate (6.64 g, 62.66 mmol), followed by a solution of bis(1,1-dimethylethyl)dicarbonate in dioxane (20 ml). The mixture was stirred at rt for 1 h. Water (50 ml) was added, and the mixture was extracted with dichloromethane (2×150 ml). The combined organic solution was washed with water (2×50 ml), dried (Na$_2$SO$_4$) and concentrated to provide 1,1-dimethylethyl 3-oxo-1-pyrazolidinecarboxylate (4.00 g, 68.6%). LCMS: (M+H)$^+$ 186.9.

Part B:

1,1-Dimethylethyl 2-methyl-3-oxo-1-pyrazolidinecarboxylate

To a mixture of 1,1-dimethylethyl 3-oxo-1-pyrazolidinecarboxylate (1.00 g, 5.37 mmol) and potassium carbonate (0.89 g, 6.44 mmol) in DMF (10 ml) was added iodomethane (2 M in MTBE, 3.22 ml, 6.44 mmol). The reaction mixture was stirred at rt for 2 h. LCMS indicated completion of the reaction. The mixture was diluted with ethyl acetate/hexanes (1:1, 150 ml) and washed with water (5×50 ml), brine (50 ml), dried (Na$_2$SO$_4$) and concentrated to provide 1,1-dimethylethyl 2-methyl-3-oxo-1-pyrazolidinecarboxylate (0.57 g, 53.0%). LCMS: (M+H)$^+$ 201.0.

Part C:

1,1-Dimethylethyl 2-methyl-1-pyrazolidinecarboxylate

To a solution of 1,1-dimethylethyl 2-methyl-3-oxo-1-pyrazolidinecarboxylate (0.98 g, 4.89 mmol) in dry dichloromethane was added borane dimethyl sulfide complex (1.16 ml, 12.24 mmol). The mixture was stirred at rt overnight. LCMS indicated ~40% starting material left. Another portion of borane dimethyl sulfide complex (0.5 ml, 5.28 mmol) was added, and stirring continued overnight. Methanol was added dropwise to the reaction mixture until bubbling ceased. Water (1 ml) was then added, and the mixture was refluxed for 1 h. After cooling to rt, the mixture was concentrated to dryness under vacuum. The residue was taken up in water (30 ml) and dichloromethane (45 ml), the organic layer was separated, and the aqueous layer was extracted with dichloromethane (45 ml). The combined organic solution was dried (Na$_2$SO$_4$), filtered and concentrated to provide 1,1-dimethylethyl 2-methyl-1-pyrazolidinecarboxylate (0.48 g, 52.7%). LCMS: (2M+H)$^+$ 372.9.

Part D:

1-Methylpyrazolidine Hydrochloride

A solution of 1,1-dimethylethyl 2-methyl-1-pyrazolidinecarboxylate (0.48 g, 2.58 mmol) in 4N HCl in dioxane (5 ml) was stirred at rt overnight. LCMS indicated completion of the reaction. Removal of the volatiles under vacuum afforded 1-methylpyrazolidine hydrochloride (0.41 g, presumed 77% pure) as a white solid.

Part E:

[(2R)-3-{2-[2-Chloro-5-fluoro-6-(2-methyl-1-pyrazolidinyl)-4-pyrimidinyl]hydrazino}-2-(cyclopentylmethyl)-3-oxopropyl]hydroxyformamide

[(2R)-3-{2-[2-Chloro-5-fluoro-6-(2-methyl-1-pyrazolidinyl)-4-pyrimidinyl]hydrazino}-2-(cyclopentylmethyl)-3-oxopropyl]hydroxyformamide was prepared in a manner similar to Example 176, utilizing 1-methylpyrazolidine hydrochloride in place of 1-(3-methyl-3-azetidinyl)pyrrolidine dihydrochloride in Part C. LCMS: (M+H)$^+$ 444.1.

Example 247

[(2R)-2-(Cyclopentylmethyl)-3-(2-{5-fluoro-6-[(2S)-2-(2-hydroxyethyl)-1-pyrrolidinyl]-2-methyl-4-pyrimidinyl}hydrazino)-3-oxopropyl]hydroxyformamide

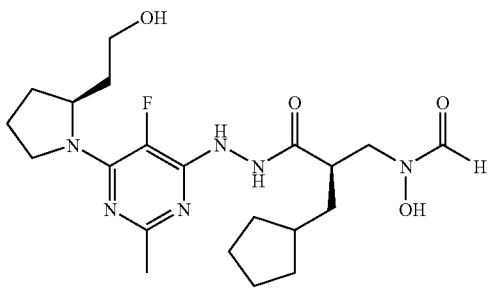

Part A:

2-[(2S)-2-Pyrrolidinyl]ethanol

2-[(2S)-2-Pyrrolidinyl]ethanol was prepared according to literature procedure (WO9748681, 1997), utilizing (S)-2-pyrrolidine methanol in place of the (R) enantiomer.

Part B:

[(2R)-2-(Cyclopentylmethyl)-3-(2-{5-fluoro-6-[(2S)-2-(2-hydroxyethyl)-1-pyrrolidinyl]-2-methyl-4-pyrimidinyl}hydrazino)-3-oxopropyl]hydroxyformamide

[(2R)-2-(Cyclopentylmethyl)-3-(2-{5-fluoro-6-[(2S)-2-(2-hydroxyethyl)-1-pyrrolidinyl]-2-methyl-4-pyrimidinyl}hydrazino)-3-oxopropyl]hydroxyformamide was prepared according to General Procedure A, utilizing 2-[(2S)-2-pyrrolidinyl]ethanol in place of pyrrolidine in Part A. LCMS: (M+H)$^+$: 453.1.

Example 248

[(2R)-3-(2-{2-Chloro-5-fluoro-6-[(2S)-2-(2-hydroxyethyl)-1-pyrrolidinyl]-4-pyrimidinyl}hydrazino)-2-(cyclopentylmethyl)-3-oxopropyl]hydroxyformamide

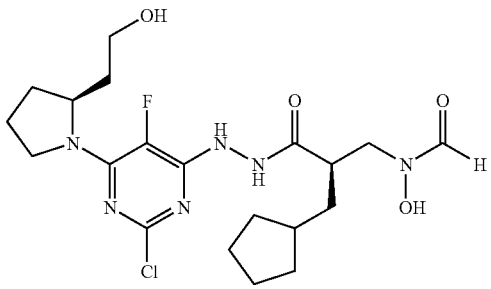

[(2R)-3-(2-{2-Chloro-5-fluoro-6-[(2S)-2-(2-hydroxyethyl)-1-pyrrolidinyl]-4-pyrimidinyl}hydrazino)-2-(cyclopentylmethyl)-3-oxopropyl]hydroxyformamide was prepared according to General Procedure E, utilizing 2-[(2S)-2-pyrrolidinyl]ethanol (Example 247) in place of isopropyl amine in Part A, and 2.0 M HCl in ether with DCM as a solvent in part B. LCMS: (M+H)$^+$: 473.1/475.2.

Example 249

[(2R)-3-{2-[2-Chloro-5-fluoro-6-((2S)-2-{[(2-hydroxyethyl)(methyl)amino]methyl}-1-pyrrolidinyl)-4-pyrimidinyl]hydrazino}-2-(cyclopentylmethyl)-3-oxopropyl]hydroxyformamide

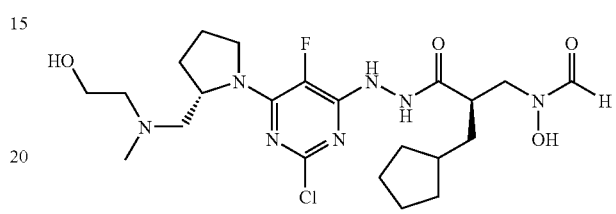

[(2R)-3-{2-[2-Chloro-5-fluoro-6-((2S)-2-{[(2-hydroxyethyl)(methyl)amino]methyl}-1-pyrrolidinyl)-4-pyrimidinyl]hydrazino}-2-(cyclopentylmethyl)-3-oxopropyl]hydroxyformamide was prepared in a manner similar to Example 264, utilizing commercially-available 2-(methylamino)ethanol in place of piperidine in Part A. LCMS: (M+H)$^+$: 517.0.

Example 250

[(2R)-3-(2-{2-Chloro-5-fluoro-6-[(2S)-2-({methyl[2-(methyloxy)ethyl]amino}methyl)-1-pyrrolidinyl]-4-pyrimidinyl}hydrazino)-2-(cyclopentylmethyl)-3-oxopropyl]hydroxyformamide

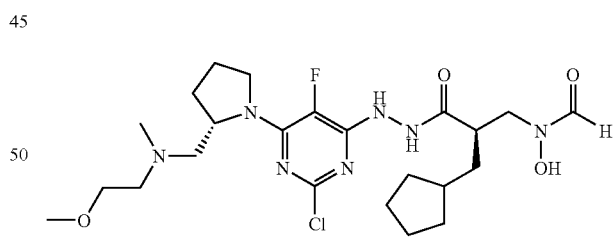

[(2R)-3-(2-{2-Chloro-5-fluoro-6-[(2S)-2-({methyl[2-(methyloxy)ethyl]amino}methyl)-1-pyrrolidinyl]-4-pyrimidinyl}hydrazino)-2-(cyclopentylmethyl)-3-oxopropyl]hydroxyformamide was prepared in a manner similar to Example 264, utilizing commercially-available N-methyl-2-(methyloxy)ethanamine in place of piperidine in Part A. LCMS: (M+H)$^+$: 530.1.

Example 251

[(2R)-3-{2-[2-Chloro-6-(3,3-difluoro-1-azetidinyl)-5-fluoro-4-pyrimidinyl]hydrazino}-2-(cyclopentylmethyl)-3-oxopropyl]hydroxyformamide

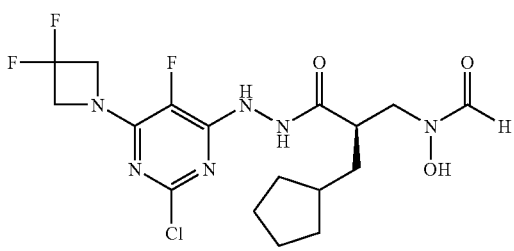

[(2R)-3-{2-[2-Chloro-6-(3,3-difluoro-1-azetidinyl)-5-fluoro-4-pyrimidinyl]hydrazino}-2-(cyclopentylmethyl)-3-oxopropyl]hydroxyformamide was prepared in a manner similar to Example 176, utilizing 3,3-difluoroazetidine hydrochloride (Carling, William Robert; Mitchinson, Andrew; Russell, Michael Geoffrey Neil; Street, Leslie Joseph. WO 2000047582) in place of 1-(3-methyl-3-azetidinyl)pyrrolidine dihydrochloride in Part C. LCMS: (M+H)$^+$ 450.9.

Example 252

[(2R)-3-(2-{6-[(2S)-2-Cyano-1-pyrrolidinyl]-5-fluoro-2-methyl-4-pyrimidinyl}hydrazino)-2-(cyclopentylmethyl)-3-oxopropyl]hydroxyformamide

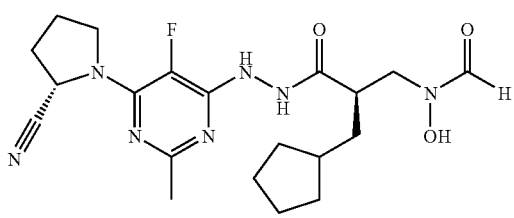

[(2R)-3-(2-{6-[(2S)-2-Cyano-1-pyrrolidinyl]-5-fluoro-2-methyl-4-pyrimidinyl}hydrazino)-2-(cyclopentylmethyl)-3-oxopropyl]hydroxyformamide was prepared according to General Procedure F, utilizing commercially-available (2S)-2-pyrrolidinecarbonitrile hydrochloride in place of 3-pyrroline in Part A. LCMS: (M+H)$^+$: 434.1.

Example 253

((2R)-2-(Cyclopentylmethyl)-3-{2-[6-((2S)-2-{[ethyl(methyl)amino]methyl}-1-pyrrolidinyl)-5-fluoro-2-methyl-4-pyrimidinyl]hydrazino}-3-oxopropyl)hydroxyformamide

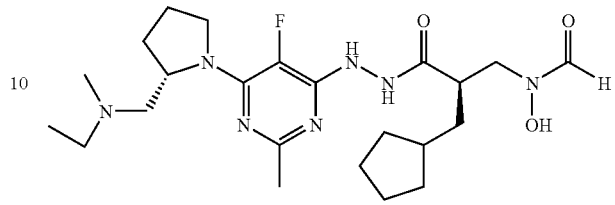

((2R)-2-(Cyclopentylmethyl)-3-{2-[6-((2S)-2-{[ethyl(methyl)amino]methyl}-1-pyrrolidinyl)-5-fluoro-2-methyl-4-pyrimidinyl]hydrazino}-3-oxopropyl)hydroxyformamide was prepared in a manner similar to Example 243, utilizing commercially-available ethyl(methyl)amine in place of morpholine in Part A. LCMS: (M+H)$^+$: 480.3.

Example 254

{(2R)-2-(Cyclopentylmethyl)-3-[2-(6-{(2S)-2-[(diethylamino)methyl]-1-pyrrolidinyl}-5-fluoro-2-methyl-4-pyrimidinyl)hydrazino]-3-oxopropyl}hydroxyformamide

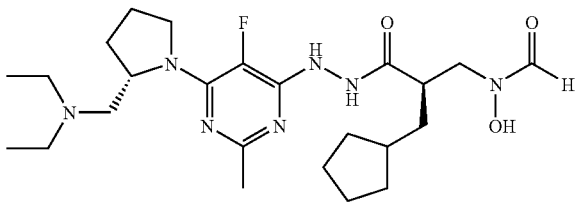

{(2R)-2-(Cyclopentylmethyl)-3-[2-(6-{(2S)-2-[(diethylamino)methyl]-1-pyrrolidinyl}-5-fluoro-2-methyl-4-pyrimidinyl)hydrazino]-3-oxopropyl}hydroxyformamide was prepared in a manner similar to Example 243, utilizing commercially-available diethylamine in place of morpholine in Part A. LCMS: (M+H)$^+$: 494.4.

Example 255

[(2R)-3-{2-[2-Chloro-6-((2S)-2-{[ethyl(methyl)amino]methyl}-1-pyrrolidinyl)-5-fluoro-4-pyrimidinyl]hydrazino}-2-(cyclopentylmethyl)-3-oxopropyl]hydroxyformamide

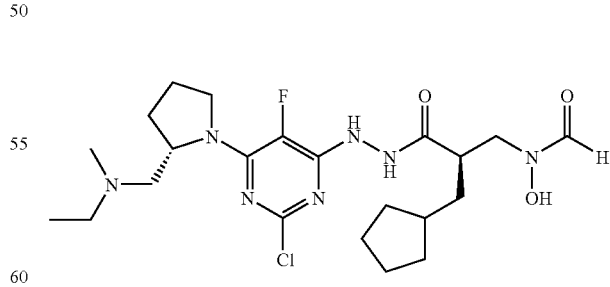

[(2R)-3-{2-[2-Chloro-6-((2S)-2-{[ethyl(methyl)amino]methyl}-1-pyrrolidinyl)-5-fluoro-4-pyrimidinyl]hydrazino}-2-(cyclopentylmethyl)-3-oxopropyl]hydroxyformamide was prepared in a manner similar to Example 197, utilizing commercially-available ethyl(methyl)amine in place of piperidine in Part A. LCMS: (M+H)$^+$: 500.1.

Example 256

[(2R)-3-[2-(2-Chloro-6-{(2S)-2-[(diethylamino)methyl]-1-pyrrolidinyl}-5-fluoro-4-pyrimidinyl)hydrazino]-2-(cyclopentylmethyl)-3-oxopropyl]hydroxyformamide

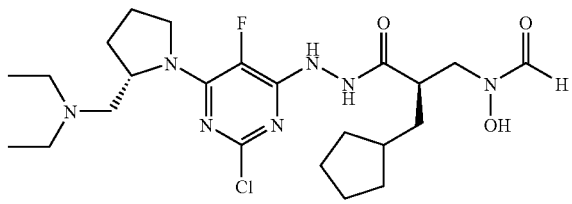

[(2R)-3-[2-(2-Chloro-6-{(2S)-2-[(diethylamino)methyl]-1-pyrrolidinyl}-5-fluoro-4-pyrimidinyl)hydrazino]-2-(cyclopentylmethyl)-3-oxopropyl]hydroxyformamide was prepared in a manner similar to Example 264, utilizing commercially-available diethylamine in place of piperidine in Part A. LCMS: (M+H)$^+$: 514.0.

Example 257

[(2R)-3-(2-{2-Chloro-6-[(2S)-2-cyano-1-pyrrolidinyl]-5-fluoro-4-pyrimidinyl}hydrazino)-2-(cyclopentylmethyl)-3-oxopropyl]hydroxyformamide

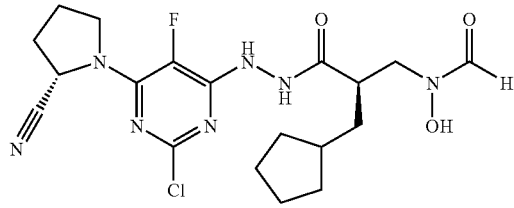

[(2R)-3-(2-{2-Chloro-6-[(2S)-2-cyano-1-pyrrolidinyl]-5-fluoro-4-pyrimidinyl}hydrazino)-2-(cyclopentylmethyl)-3-oxopropyl]hydroxyformamide was prepared according to General Procedure D, utilizing commercially-available (2S)-2-pyrrolidinecarbonitrile hydrochloride in place of N-methylpiperazine in Part A. LCMS: (M+H)$^+$: 454.0.

Example 258

[(2R)-2-(Cyclopentylmethyl)-3-(2-{5-fluoro-6-[(2S)-2-(hydroxymethyl)-1-piperidinyl]-2-methyl-4-pyrimidinyl}hydrazino)-3-oxopropyl]hydroxyformamide

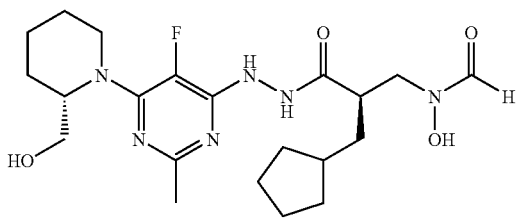

Part A:

Phenylmethyl (2S)-2-(hydroxymethyl)-1-piperidinecarboxylate (2S)-1-{[(Phenylmethyl)oxy]carbonyl}-2-piperidinecarboxylic acid (1.0 g, 3.798 mmol) in THF (5 mL) was cooled to −18° C. and borane-THF complex (3.798 mL, 3.798 mmol) was added over 10 min. The mixture was allowed to warm to room temperature with stirring overnight, then cooled to 0° C., and water (4 mL) was added, followed by K$_2$CO$_3$ (1.4 g). The phases were separated, and the aqueous phase was extracted with Et$_2$O (3×25 mL). The combined organic phase was washed with brine (1×25 mL) and dried over anhydrous MgSO$_4$, filtered, and concentrated in vacuo to provide phenylmethyl (2S)-2-(hydroxymethyl)-1-piperidinecarboxylate (815 mg, 86%). LCMS: (M+H)$^+$: 250.2.

Part B:

(2S)-2-Piperidinecarboxylic acid hydrochloride

Phenylmethyl (2S)-2-(hydroxymethyl)-1-piperidinecarboxylate (815 mg, 3.26 mmol) was dissolved in a mixture of MeOH (30 mL) and 1N HCl (7.19 mL, 7.19 mmol), degassed and placed under argon. 10% Pd/C (225 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure N,N-dimethyl-2-(3-pyrrolidinyl)-2-propanamine hydrochloride (492 mg, 99%). LCMS: (M+H)$^+$: 116.1

Part C:

[(2R)-2-(Cyclopentylmethyl)-3-(2-{5-fluoro-6-[(2S)-2-(hydroxymethyl)-1-piperidinyl]-2-methyl-4-pyrimidinyl}hydrazino)-3-oxopropyl]hydroxyformamide

[(2R)-2-(Cyclopentylmethyl)-3-(2-{5-fluoro-6-[(2S)-2-(hydroxymethyl)-1-piperidinyl]-2-methyl-4-pyrimidinyl}hydrazino)-3-oxopropyl]hydroxyformamide was prepared in a manner similar to Example 210, Part E and Part F, utilizing N,N-dimethyl-2-(3-pyrrolidinyl)-2-propanamine hydrochloride in place of 1-{1-[(2S)-2-pyrrolidinyl]cyclopropyl}pyrrolidine hydrochloride in Part E. LCMS: (M+H)$^+$: 453.3.

Example 259

[(2R)-3-{2-[2-Chloro-5-fluoro-6-(2-ethyl-1-pyrazolidinyl)-4-pyrimidinyl]hydrazino}-2-(cyclopentylmethyl)-3-oxopropyl]hydroxyformamide

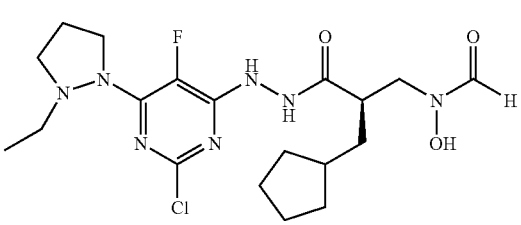

Part A:

1-Ethylpyrazolidine Hydrochloride

1-Ethylpyrazolidine hydrochloride was prepared according to procedure described for the preparation of 1-methylpyrazolidine hydrochloride (Example 246), utilizing iodoethane in place of iodomethane in Part B. LCMS: (M+H)+ 102.2.

Part B:

[(2R)-3-{2-[2-Chloro-5-fluoro-6-(2-ethyl-1-pyrazolidinyl)-4-pyrimidinyl]hydrazino}-2-(cyclopentylmethyl)-3-oxopropyl]hydroxyformamide

[(2R)-3-{2-[2-Chloro-5-fluoro-6-(2-ethyl-1-pyrazolidinyl)-4-pyrimidinyl]hydrazino}-2-(cyclopentylmethyl)-3-oxopropyl]hydroxyformamide was prepared in a manner similar to Example 176, utilizing 1-ethylpyrazolidine hydrochloride in place of 1-(3-methyl-3-azetidinyl)pyrrolidine dihydrochloride in Part C. LCMS: (M+H)+ 458.3.

Example 260

1-{2-Chloro-6-[2-((2R)-3-cyclopentyl-2-{[formyl(hydroxy)amino]methyl}propanoyl)hydrazino]-5-fluoro-4-pyrimidinyl}-N,N-dimethyl-L-prolinamide Part A:

N,N-Diethyl-1-(phenylmethyl)-L-prolinamide

N,N-Diethyl-1-(phenylmethyl)-L-prolinamide was prepared in a manner similar to Example 210, Part A through Part B, utilizing commercially-available dimethyl amine in place of pyrrolidine in Part B. LCMS: (M+H)+: 261.1.

Part B:

N,N-Diethyl-L-prolinamide hydrochloride

N,N-Diethyl-1-(phenylmethyl)-L-prolinamide (1.603 g, 6.156 mmol) was dissolved in a mixture of MeOH (50 mL) and 1N HCl (14 mL, 14 mmol), degassed and placed under argon. 10% Pd/C (480 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure N,N-diethyl-L-prolinamide hydrochloride (1.658 g, >99%). LCMS: (M+H)+: 171.1.

Part C:

1-{2-Chloro-6-[2-((2R)-3-cyclopentyl-2-{[formyl(hydroxy)amino]methyl}propanoyl)hydrazino]-5-fluoro-4-pyrimidinyl}-N,N-dimethyl-L-prolinamide 1-{2-Chloro-6-[2-((2R)-3-cyclopentyl-2-{[formyl(hydroxy)amino]methyl}propanoyl)hydrazino]-5-fluoro-4-pyrimidinyl}-N,N-dimethyl-L-prolinamide was prepared according to General Procedure E, utilizing N,N-diethyl-L-prolinamide hydrochloride in place of isopropyl amine in Part A. LCMS: (M+H)+: 528.3.

Example 261

N-[(2R)-3-(2-{2-Chloro-6-[(2R,5R)-5-ethyl-2,4-dimethyl-1-piperazinyl]-5-fluoro-4-pyrimidinyl}hydrazino)-2-(cyclopentylmethyl)-3-oxopropyl]-N-hydroxyformamide

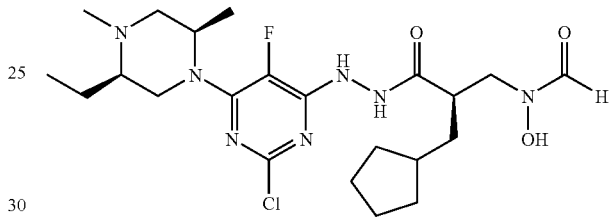

Part A:

(2R,5R)-2-Ethyl-1,5-dimethyl-4-(phenylmethyl)piperazine

To a solution of (2R,5R)-5-ethyl-2-methyl-1-(phenylmethyl)piperazine (prepared according to procedures in J. Med. Chem. 2006, 49, 716-726, utilizing Boc-D-2-aminobutyric acid in place of N-Boc-L-alanine) (902 mg, 4.13 mmol) in dichloromethane (25 mL) at 0° C. was added formaldehyde (0.435 mL, 37% water solution, 5.78 mmol) followed by sodium triacetoxyborohydride (1050 mg, 4.96 mmol). The reaction mixture was allowed to warm to room temperature and stirred for 2 h before being diluted with dichloromethane and washed with 1N NaOH solution. The organics were washed with brine, dried (MgSO4) and evaporated to yield (2R,5R)-2-ethyl-1,5-dimethyl-4-(phenylmethyl)piperazine (875 mg, 91%). LCMS: (M+H)+: 233.3.

Part B:

(2R,5R)-2-Ethyl-1,5-dimethylpiperazine, Hydrochloride Salt (2R,5R)-2-Ethyl-1,5-dimethyl-4-(phenylmethyl)piperazine (873 mg, 3.76 mmol) was dissolved in 50 mL of MeOH, degassed and placed under argon. 10% Pd/C (175 mg) was added, and the contents were thoroughly degassed and placed under a hydrogen balloon for approximately 3 hrs. The contents were then degassed and filtered through Celite, and the Celite pad was washed with DCM and MeOH. After 7.9 mL 1N HCl was added, the resulting filtrate was concentrated in vacuo to provide the hydrochloride salt of (2R,5R)-2-ethyl-1,5-dimethylpiperazine (800 mg, 100%). LCMS: (M+H)+: 143.1.

Part C:

N-[(2R)-3-(2-{2-Chloro-6-[(2R,5R)-5-ethyl-2,4-dimethyl-1-piperazinyl]-5-fluoro-4-pyrimidinyl}hydrazino)-2-(cyclopentylmethyl)-3-oxopropyl]-N-hydroxyformamide N-[(2R)-3-(2-{2-Chloro-6-[(2R,5R)-5-ethyl-2,4-dimethyl-1-piperazinyl]-5-fluoro-4-pyrimidinyl}hydrazino)-2-(cyclopentylmethyl)-3-oxopropyl]-N-hydroxyformamide was prepared according to General Procedure G, utilizing (2R,5R)-2-ethyl-1,5-dimethylpiperazine, hydrochloride salt in place of (1S,4S)-2-methyl-2,5-diazabicyclo[2.2.1]heptane, dihydrobromide in Part A. LCMS: (M+H)+: 500.3.

Example 262

N-[(2R)-2-(Cyclopentylmethyl)-3-(2-{6-[(2R,5R)-5-ethyl-2,4-dimethyl-1-piperazinyl]-5-fluoro-2-methyl-4-pyrimidinyl}hydrazino)-3-oxopropyl]-N-hydroxyformamide

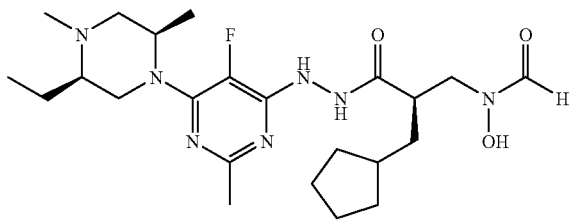

N-[(2R)-2-(Cyclopentylmethyl)-3-(2-{6-[(2R,5R)-5-ethyl-2,4-dimethyl-1-piperazinyl]-5-fluoro-2-methyl-4-pyrimidinyl}hydrazino)-3-oxopropyl]-N-hydroxyformamide was prepared according to General Procedure A, utilizing (2R,5R)-2-ethyl-1,5-dimethylpiperazine, hydrochloride salt (Example 261) in place of pyrrolidine in Part A, and using 3 equivalents of DIPEA. LCMS: (M+H)+: 480.1.

Example 263

((2R)-2-(Cyclopentylmethyl)-3-{2-[5-fluoro-2-methyl-6-(3-methyl-1-azetidinyl)-4-pyrimidinyl]hydrazino}-3-oxopropyl)hydroxyformamide

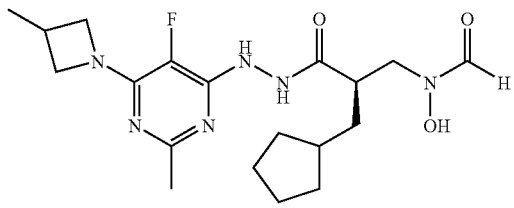

((2R)-2-(Cyclopentylmethyl)-3-{2-[5-fluoro-2-methyl-6-(3-methyl-1-azetidinyl)-4-pyrimidinyl]hydrazino}-3-oxopropyl)hydroxyformamide was prepared in a manner similar to Example 182, utilizing 3-methylazetidine hydrochloride (Journal of Heterocyclic Chemistry, 1971, 8, 961-6), in place of 1-(3-methyl-3-azetidinyl)pyrrolidine dihydrochloride in Part A. LCMS: (M+H)+ 409.1.

Example 264

[(2R)-3-(2-{2-Chloro-5-fluoro-6-[(2S)-2-(1-piperidinylmethyl)-1-pyrrolidinyl]-4-pyrimidinyl}hydrazino)-2-(cyclopentylmethyl)-3-oxopropyl]hydroxyformamide Part A:

(2S)-1-(Phenylmethyl)-2-(1-pyrrolidinylcarbonyl)pyrrolidine 1-(Phenylmethyl)-L-proline hydrochloride (2.0 g, 8.247 mmol) and HOBt (1.34 g, 9.928 mmol) were dissolved in CH₂Cl₂ (50 mL), and 4-methylmorpholine (2.72 mL, 24.822 mmol), piperidine (0.981 mL, 9.929 mmol), and EDCI (1.906 g, 9.928 mmol) were added to this solution. After stirring overnight, the solution was washed with water (50 mL), and the aqueous layer was extracted with CH₂Cl₂ (3×50 mL). The combined organic layers were dried over anhydrous MgSO₄ and concentrated in vacuo to provide (2S)-1-(phenylmethyl)-2-(1-pyrrolidinylcarbonyl)piperidine (0.901 g, 40%). LCMS: (M+H)+: 273.1.

Part B:

1-{[(2S)-1-(Phenylmethyl)-2-pyrrolidinyl]methyl}piperidine (2S)-1-(Phenylmethyl)-2-(1-pyrrolidinylcarbonyl)piperidine (901 mg, 3.307 mmol) was dissolved in 20 mL of THF, cooled to 0° C., and then LiAlH₄ (251 mg, 6.615 mmol) was added portion wise. The mixture was heated to 80° C. for 2 h, then allowed to cool to RT. The reaction was quenched in succession with H₂O (0.300 mL), 15% aq. NaOH (0.300 mL) and H₂O (0.900 mL) and was stirred at room temperature overnight. The contents were filtered, and the filtrate was concentrated in vacuo to provide 1-{[(2S)-1-(phenylmethyl)-2-pyrrolidinyl]methyl}piperidine (710 mg, 83%).

Part C:

1-[(2S)-2-Pyrrolidinylmethyl]piperidine hydrochloride

1-{[(2S)-1-(Phenylmethyl)-2-pyrrolidinyl]methyl}piperidine (710 mg, 2.747 mmol) was dissolved in a mixture of MeOH (20 mL) and 1N HCl (6 mL, 6.044 mmol), degassed and placed under argon. 10% Pd/C (213 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure 1-[(2S)-2-pyrrolidinylmethyl]piperidine hydrochloride (692 mg, >99%). LCMS: (M+H)+: 169.2.

Part D:

[(2R)-3-(2-{2-Chloro-5-fluoro-6-[(2S)-2-(1-piperidinylmethyl)-1-pyrrolidinyl]-4-pyrimidinyl}hydrazino)-2-(cyclopentylmethyl)-3-oxopropyl]hydroxyformamide

[(2R)-3-(2-{2-Chloro-5-fluoro-6-[(2S)-2-(1-piperidinylmethyl)-1-pyrrolidinyl]-4-pyrimidinyl}hydrazino)-2-(cyclopentylmethyl)-3-oxopropyl]hydroxyformamide was prepared according to General Procedure E, utilizing 1-[(2S)-2-pyrrolidinylmethyl]piperidine hydrochloride in place of isopropyl amine in Part A. LCMS: (M+H)+: 581.4.

Example 265

((2R)-2-(Cyclopentylmethyl)-3-{2-[5-fluoro-2-methyl-6-(2-methyl-1-azetidinyl)-4-pyrimidinyl]hydrazino}-3-oxopropyl)hydroxyformamide (Mixture of Diastereomers)

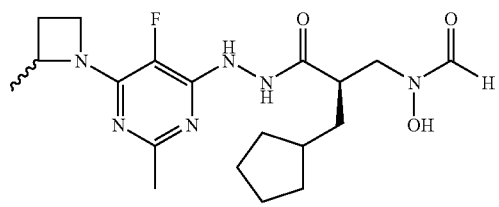

((2R)-2-(Cyclopentylmethyl)-3-{2-[5-fluoro-2-methyl-6-(2-methyl-1-azetidinyl)-4-pyrimidinyl]hydrazino}-3-oxopropyl)hydroxyformamide was prepared as a mixture of diastereomers in a manner similar to Example 182, utilizing 2-methylazetidine hydrochloride (J. Org. Chem. 1961, 26, 138-144) in place of 1-(3-methyl-3-azetidinyl)pyrrolidine dihydrochloride in Part A. LCMS: (M+H)+ 409.2.

Example 266

[(2R)-3-{2-[2-Chloro-5-fluoro-6-(2-methyl-1-azetidinyl)-4-pyrimidinyl]hydrazino}-2-(cyclopentylmethyl)-3-oxopropyl]hydroxyformamide (Mixture of Diastereomers)

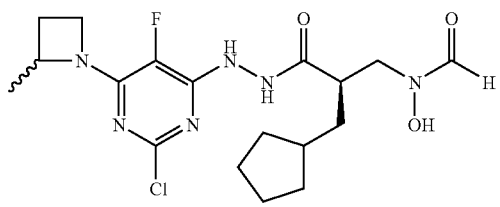

[(2R)-3-{2-[2-Chloro-5-fluoro-6-(2-methyl-1-azetidinyl)-4-pyrimidinyl]hydrazino}-2-(cyclopentylmethyl)-3-oxopropyl]hydroxyformamide was prepared as a mixture of diastereomers according to General Procedure D, utilizing 2-methylazetidine hydrochloride (J. Org. Chem. 1961, 26, 138-144) in place of N-methylpiperazine in Part A. LCMS: (M+H)+ 429.1.

Example 267

[(2R)-3-[2-(2-Chloro-6-{(2S)-2-[(dimethylamino)methyl]-1-piperidinyl}-5-fluoro-4-pyrimidinyl)hydrazino]-2-(cyclopentylmethyl)-3-oxopropyl]hydroxyformamide

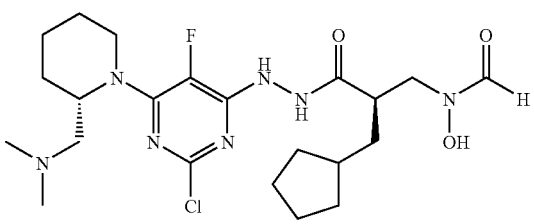

Part A:

Phenylmethyl (2S)-2-[(dimethylamino)carbonyl]-1-piperidinecarboxylate (2S)-1-{[(Phenylmethyl)oxy]carbonyl}-2-piperidinecarboxylic acid (2.0 g, 7.595 mmol) and HOBt (1.231 g, 9.114 mmol) were dissolved in CH$_2$Cl$_2$ (40 mL), and 4-methylmorpholine (2.5 mL, 22.78 mmol), 2.0 M solution of dimethyl amine in THF (4.55 mL, 9.114 mmol), and EDCI (1.750 g, 9.114 mmol) were added. This solution was stirred overnight, and was then washed with 1 N HCl (25 mL) and the aqueous layer was extracted with CH$_2$Cl$_2$ (3×25 mL). The combined organic layers were dried over anhydrous MgSO$_4$ and concentrated in vacuo. This crude product was purified by flash chromatography (Combiflash, 0-100% ethyl acetate/hexanes) to provide phenylmethyl (2S)-2-[(dimethylamino)carbonyl]-1-piperidinecarboxylate (1.919 g, 87%). LCMS: (M+H)+: 291.1.

Part B:

(2S)—N,N-Dimethyl-2-piperidinecarboxamide hydrochloride

Phenylmethyl (2S)-2-[(dimethylamino)carbonyl]-1-piperidinecarboxylate (1.918 g, 6.609 mmol) was dissolved in a mixture of MeOH (40 mL) and 1N HCl (14.53 mL, 14.53 mmol), degassed and placed under argon. 10% Pd/C (575 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure (2S)—N,N-dimethyl-2-piperidinecarboxamide hydrochloride (1.483 g, >99%). LCMS: (M+H)+: 157.2.

Part C:

(2S)—N,N-Dimethyl-1-(phenylcarbonyl)-2-piperidinecarboxamide (2S)—N,N-Dimethyl-2-piperidinecarboxamide hydrochloride (880 mg, 4.567 mmol) was dissolved in a mixture of CH$_2$Cl$_2$ (15 mL) and water (15 mL), and then solid sodium bicarbonate (1.534 g, 18.268 mmol) was added, followed by benzoyl chloride (0.556 mL, 4.795 mmol). After stirring overnight, the phases were separated, and the aqueous phase was extracted with CH$_2$Cl$_2$ (3×50 mL). The combined organic phase was dried over anhydrous MgSO₄, filtered, and concentrated in vacuo. This crude product was purified by flash chromatography (Combiflash, 0-10% methanol/dichloromethane) to provide (2S)—N,N-dimethyl-1-(phenylcarbonyl)-2-piperidinecarboxamide (883 mg, 74%). LCMS: (M+H)⁺: not detected.

Part D:

N,N-Dimethyl-1-[(2S)-1-(phenylmethyl)-2-piperidinyl]methanamine (2S)—N,N-Dimethyl-1-(phenylcarbonyl)-2-piperidinecarboxamide (883 mg, 3.396 mmol) was dissolved in 20 mL of THF, cooled to 0° C., and then LiAlH₄ (1.386 mg, 36.54 mmol) was added portion wise. The mixture was heated to 80° C. for 2 h, then allowed to cool to RT. The reaction was quenched in succession with H₂O (1.0 mL), 15% aq. NaOH (1.0 mL) and H₂O (3.0 mL), and was stirred at room temperature overnight. The contents were filtered, and the filtrate was concentrated in vacuo to provide N,N-dimethyl-1-[(2S)-1-(phenylmethyl)-2-piperidinyl]methanamine (590 mg, 75%). LCMS: (M+H)⁺: 233.1.

Part E:

N,N-Dimethyl-1-[(2S)-2-piperidinyl]methanamine hydrochloride

N,N-Dimethyl-1-[(2S)-1-(phenylmethyl)-2-piperidinyl]methanamine (590 mg, 2.539 mmol) was dissolved in a mixture of MeOH (20 mL) and 1N HCl (5.5 mL, 5.5 mmol), degassed and placed under argon. 10% Pd/C (117 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure N,N-dimethyl-1-[(2S)-2-piperidinyl]methanamine hydrochloride (425 mg, 78%). LCMS: (M+H)⁺: not detected.

Part F:

[(2R)-3-[2-(2-Chloro-6-{(2S)-2-[(dimethylamino)methyl]-1-piperidinyl}-5-fluoro-4-pyrimidinyl)hydrazino]-2-(cyclopentylmethyl)-3-oxopropyl]hydroxyformamide

[(2R)-3-[2-(2-Chloro-6-{(2S)-2-[(dimethylamino)methyl]-1-piperidinyl}-5-fluoro-4-pyrimidinyl)hydrazino]-2-(cyclopentylmethyl)-3-oxopropyl]hydroxyformamide was prepared according to General Procedure E, utilizing N,N-dimethyl-1-[(2S)-2-piperidinyl]methanamine hydrochloride in place of isopropyl amine in Part A. LCMS: (M+H)⁺: 501.1.

Example 268

[(2R)-3-(2-{2-Chloro-5-fluoro-6-[(2S)-2-phenyl-1-pyrrolidinyl]-4-pyrimidinyl}hydrazino)-2-(cyclopentylmethyl)-3-oxopropyl]hydroxyformamide

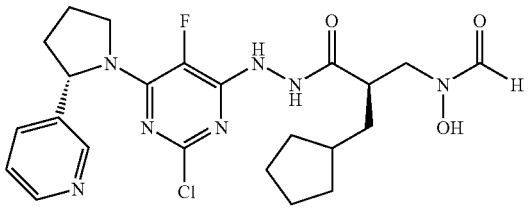

[(2R)-3-(2-{2-Chloro-5-fluoro-6-[(2S)-2-phenyl-1-pyrrolidinyl]-4-pyrimidinyl}hydrazino)-2-(cyclopentylmethyl)-3-oxopropyl]hydroxyformamide was prepared according to General Procedure E, utilizing (S)-nornicotine (J. Org. Chem. 2001, 66, 6305-6312) in place of isopropyl amine in Part A, and 2.0 M HCl in ether with DCM as a solvent in Part B. LCMS: (M+H)⁺: 506.2/508.2.

Example 269

[(2R)-3-{2-[2-Chloro-5-fluoro-6-((2S)-2-{[methyl(1-methylethyl)amino]methyl}-1-pyrrolidinyl)-4-pyrimidinyl]hydrazino}-2-(cyclopentylmethyl)-3-oxopropyl]hydroxyformamide

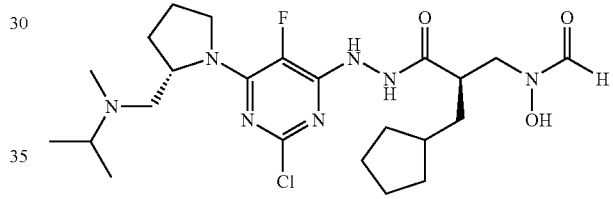

[(2R)-3-{2-[2-Chloro-5-fluoro-6-((2S)-2-{[methyl(1-methylethyl)amino]methyl}-1-pyrrolidinyl)-4-pyrimidinyl]hydrazino}-2-(cyclopentylmethyl)-3-oxopropyl]hydroxyformamide was prepared in a manner similar to Example 264, utilizing commercially-available methyl(1-methylethyl)amine in place of piperidine in Part A. LCMS: (M+H)⁺: 514.3.

Example 270

((2R)-2-(Cyclopentylmethyl)-3-{2-[5-fluoro-2-methyl-6-((2S)-2-{[methyl(1-methylethyl)amino]methyl}-1-pyrrolidinyl)-4-pyrimidinyl]hydrazino}-3-oxopropyl)hydroxyformamide

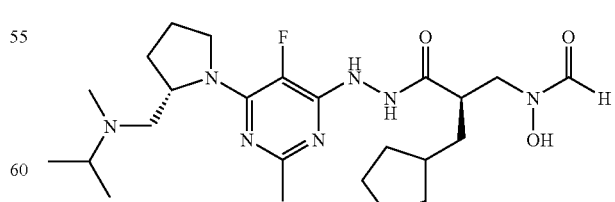

{(2R)-2-(Cyclopentylmethyl)-3-[2-(6-{(2S)-2-[(dimethylamino)methyl]-1-pyrrolidinyl}-5-fluoro-2-methyl-4-pyrimidinyl)hydrazino]-3-oxopropyl}hydroxyformamide was prepared in a manner similar to Example 243, utilizing commercially-available methyl(1-methylethyl)amine in place of morpholine in Part A. LCMS: (M+H)+: 494.2.

Example 271

((2R)-2-(Cyclopentylmethyl)-3-{2-[5-fluoro-2-methyl-6-((2S)-2-{[methyl(propyl)amino]methyl}-1-pyrrolidinyl)-4-pyrimidinyl]hydrazino}-3-oxopropyl)hydroxyformamide

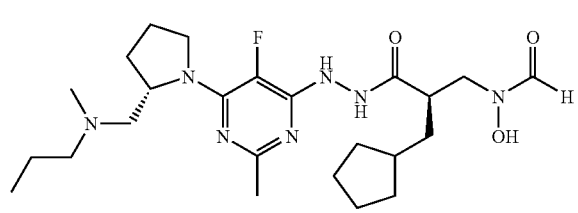

((2R)-2-(Cyclopentylmethyl)-3-{2-[5-fluoro-2-methyl-6-((2S)-2-{[methyl(propyl)amino]methyl}-1-pyrrolidinyl)-4-pyrimidinyl]hydrazino}-3-oxopropyl)hydroxyformamide was prepared in a manner similar to Example 243, utilizing commercially-available N-methyl-1-propanamine in place of morpholine in Part A. LCMS: (M+H)+: 494.4.

Example 272

[(2R)-3-{2-[2-Chloro-5-fluoro-6-((2S)-2-{[methyl(propyl)amino]methyl}-1-pyrrolidinyl)-4-pyrimidinyl]hydrazino}-2-(cyclopentylmethyl)-3-oxopropyl]hydroxyformamide

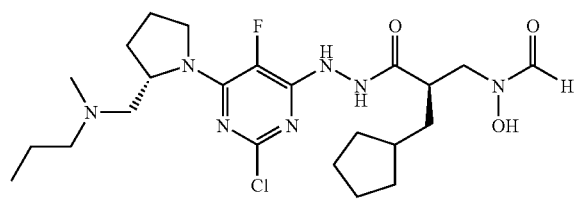

[(2R)-3-{2-[2-Chloro-5-fluoro-6-((2S)-2-{[methyl(propyl)amino]methyl}-1-pyrrolidinyl)-4-pyrimidinyl]hydrazino}-2-(cyclopentylmethyl)-3-oxopropyl]hydroxyformamide was prepared in a manner similar to Example 264, utilizing commercially-available N-methyl-1-propanamine in place of piperidine in Part A. LCMS: (M+H)+: 514.3.

Example 273

[(2R)-3-(2-{2-Chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl]hydroxyformamide

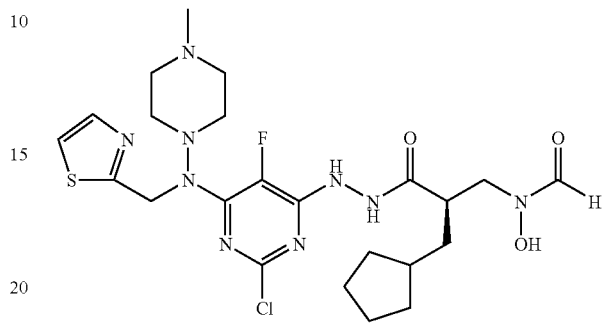

Part A:

4-Methyl-N-(1,3-thiazol-2-ylmethyl)-1-piperazinamine

Commercially available 1,3-thiazole-2-carbaldehyde (0.388 mL, 4.42 mmol) and commercially available 4-methyl-1-piperazinamine (0.532 mL, 4.42 mmol) were dissolved in MeOH (20 mL) and cooled to 0° C. Then methyl orange indicator and enough 4M HCl in dioxane was added to keep the reaction mixture acidic and a light pinkish color. Then sodium cyanoborohydride (0.555 g, 8.84 mmol) was added and the reaction was left to stir. The reaction mixture was evaporated to provide crude 4-methyl-N-(1,3-thiazol-2-ylmethyl)-1-piperazinamine as a beige-yellow solid (2.2168 g). LCMS: (M+H)+=213.0.

Part B:

Tris(1,1-dimethylethyl)2-{2-chloro-5-fluoro-6-[(4-methyl-1-piperazinyl)(1,3-thiazol-2-ylmethyl)amino]-4-pyrimidinyl}-1,1,2-hydrazinetricarboxylate 4-Methyl-N-(1,3-thiazol-2-ylmethyl)-1-piperazinamine (2.2169 g, 10.44 mmol) was dissolved in THF (30 mL) and triethylamine (4.37 ml, 31.3 mmol). Then tris(1,1-dimethylethyl)2-(2,6-dichloro-5-fluoro-4-pyrimidinyl)-1,1,2-hydrazinetricarboxylate (3.89 g, 7.83 mmol) and DMSO (5 mL) were added. The reaction was left to stir overnight. The THF was evaporated away, and the mixture was diluted with water. The aqueous layer was extracted with ethyl acetate, and the organics were dried (Na2SO4) and evaporated. Purification by silica gel chromatography and RP-HPLC provided tris(1,1-dimethylethyl) 2-{2-chloro-5-fluoro-6-[(4-methyl-1-piperazinyl)(1,3-thiazol-2-ylmethyl)amino]-4-pyrimidinyl}-1,1,2-hydrazinetricarboxylate (0.2014 g, 3%). LCMS: (M+H)+=674.6.

Part C:

2-Chloro-5-fluoro-6-hydrazino-N-(4-methyl-1-piperazinyl)-N-(1,3-thiazol-2-ylmethyl)-4-pyrimidinamine Tris(1,1-dimethylethyl)2-{2-chloro-5-fluoro-6-[(4-methyl-1-piperazinyl)(1,3-thiazol-2-ylmethyl)amino]-4-pyrimidinyl}-1,1,2-hydrazinetricarboxylate (0.2014 g, 0.299 mmol) was dissolved in DCM (20 mL) under a nitrogen atmosphere. Then 2M HCl (2.99 mL, 5.98 mmol) was added, and the reaction was stirred overnight. The reaction mixture was evaporated to provide crude 2-chloro-5-fluoro-6-hydrazino-N-(4-methyl-1-piperazinyl)-N-(1,3-thiazol-2-ylmethyl)-4-pyrimidinamine as a yellow solid (0.1683 g). LCMS: (M+H)$^+$=373.0.

Part D:

[(2R)-3-(2-{2-Chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl](tetrahydro-2H-pyran-2-yloxy)formamide (2R)-4-Ethyl-2-{[formyl(tetrahydro-2H-pyran-2-yloxy)amino]methyl}heptanoic acid (0.3764 g, 1.257 mmol), 2-chloro-5-fluoro-6-hydrazino-N-(4-methyl-1-piperazinyl)-N-(1,3-thiazol-2-ylmethyl)-4-pyrimidinamine (0.1683 g), NMM (0.298 mL, 2.71 mmol), HOAt (0.074 g, 0.542 mmol), and EDC (0.104 g, 0.542 mmol) were dissolved in DMF (10 mL). The reaction was left to stir overnight. Purification by RP-HPLC provided [(2R)-3-(2-{2-chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl](tetrahydro-2H-pyran-2-yloxy)formamide as a brown oily solid (0.1688 g). LCMS: (M+H)$^+$=655.4.

Part E:

[(2R)-3-(2-{2-Chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl]hydroxyformamide

[(2R)-3-(2-{2-Chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl](tetrahydro-2H-pyran-2-yloxy)formamide (0.1688 g, 0.258 mmol) was taken up in water (2 mL) and acetic acid (8 mL). The reaction was left to stir overnight. Purification by RP-HPLC provided [(2R)-3-(2-{2-chloro-5-fluoro-6-[(4-methyl-1-piperazinyl)(1,3-thiazol-2-ylmethyl)amino]-4-pyrimidinyl}hydrazino)-2-(cyclopentylmethyl)-3-oxopropyl]hydroxyformamide as a beige solid (0.0483 g, 25%). LCMS: (M+H)$^+$=571.2.

Example 274

[(2R)-3-(2-{2-Chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl]hydroxyformamide

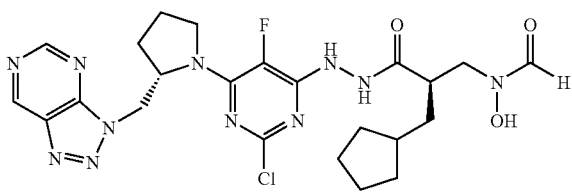

Part A:

1,1-Dimethylethyl (2S)-2-({[2-chloro-5-(dihydroxyamino)-4-pyrimidinyl]amino}methyl)-1-pyrrolidinecarboxylate 2,4-Dichloro-5-(dihydroxyamino)pyrimidine (2.5 g, 12.75 mmol), 1,1-dimethylethyl (2S)-2-(aminomethyl)-1-pyrrolidinecarboxylate (1.277 g, 6.38 mmol), and DIEA (1.114 mL, 6.38 mmol) were dissolved in DCM (75 mL). The mixture was stirred for 1 h, and when the reaction was complete as determined by LCMS, the solution was concentrated in vacuo. This crude product was purified by flash chromatography (Combiflash, 0-100% ethyl acetate/hexanes) to provide 1,1-dimethylethyl (2S)-2-({[2-chloro-5-(dihydroxyamino)-4-pyrimidinyl]amino}methyl)-1-pyrrolidinecarboxylate (1.6362 g, 71%). LCMS: (M+H)$^+$: 357.8.

Part B:

1,1-Dimethylethyl (2S)-2-{[(5-amino-4-pyrimidinyl)amino]methyl}-1-pyrrolidinecarboxylate 1,1-Dimethylethyl (2S)-2-({[2-chloro-5-(dihydroxyamino)-4-pyrimidinyl]amino}methyl)-1-pyrrolidinecarboxylate (2.064 g, 5.74 mmol) was dissolved in MeOH (40 mL), degassed and placed under argon. 10% Pd/C (619 mg) was added, and the contents were thoroughly degassed and placed under a hydrogen balloon for 2 h. The contents were then degassed, and the Pd/C was removed by filtration through a fiberglass filter, washing with MeOH. The filtrate was concentrated in vacuo to provide pure 1,1-dimethylethyl (2S)-2-{[(5-amino-4-pyrimidinyl)amino]methyl}-1-pyrrolidinecarboxylate (1.589 g, 94%). LCMS: (M+H)$^+$: 294.1.

Part C:

1,1-Dimethylethyl (2S)-2-(3H-[1,2,3]triazolo[4,5-d]pyrimidin-3-ylmethyl)-1-pyrrolidinecarboxylate 1,1-Dimethylethyl (2S)-2-{[(5-amino-4-pyrimidinyl)amino]methyl}-1-pyrrolidinecarboxylate (1.6633 g, 5.67 mmol) and sodium nitrite (469 mg, 6.80 mmol) were dissolved in a mixture of acetic acid (5 mL) and water (8 mL), and the mixture was stirred vigorously for 1 h. The solution was concentrated in vacuo to provide 1,1-dimethylethyl (2S)-2-(3H-[1,2,3]triazolo[4,5-d]pyrimidin-3-ylmethyl)-1-pyrrolidinecarboxylate (1.98 g, >99%). LCMS: (M+H)$^+$: 305.2.

Part D:

3-[(2S)-2-Pyrrolidinylmethyl]-3H-[1,2,3]triazolo[4,5-d]pyrimidine 1,1-Dimethylethyl (2S)-2-(3H-[1,2,3]triazolo[4,5-d]pyrimidin-3-ylmethyl)-1-pyrrolidinecarboxylate (1.98 g, 6.54 mmol) was dissolved in a mixture of CH$_2$Cl$_2$ (10 mL) and TFA (2.5 mL) and allowed to stir at room temperature overnight. When the reaction was complete as determined by LCMS, the solution was concentrated in vacuo, and the residue was dissolved in CH$_2$Cl$_2$ (5 mL) and washed with 1 N aq. NaOH (30 mL). The aqueous layer was extracted with CH$_2$Cl$_2$ (3×20 mL). The combined organic layers were dried over anhydrous MgSO$_4$ and concentrated in vacuo to provide 3-[(2S)-2-pyrrolidinylmethyl]-3H-[1,2,3]triazolo[4,5-d]pyrimidine (758 mg, 57%). LCMS: (M+H)$^+$: 205.1.

Part E:

2,4-Dichloro-5-fluoro-6-hydrazinopyrimidine

To hydrazine monohydrate (289 µL, 5.96 mmol) and triethylamine (830 µL, 5.96 mmol) in MeOH (15 mL) was added a solution of 2,4,6-trichloro-5-fluoropyrimidine (1.0 g, 4.96 mmol) in MeOH (15 mL), and the mixture was stirred overnight. When the reaction was complete as determined by LCMS, the solution was concentrated in vacuo, and the resulting crude product was purified by RP-HPLC to provide 2,4-dichloro-5-fluoro-6-hydrazinopyrimidine (358 mg, 32%). LCMS: (M+H)$^+$: 196.9.

Part F:

{(2R)-2-(Cyclopentylmethyl)-3-[2-(2,6-dichloro-5-fluoro-4-pyrimidinyl)hydrazino]-3-oxopropyl}[(phenylmethyl)oxy]formamide 2,4-Dichloro-5-fluoro-6-hydrazinopyrimidine (358 mg 1.817 mmol), (2R)-3-cyclopentyl-2-({formyl[(phenylmethyl)oxy]amino}methyl)propanoic acid (746 mg, 1.508 mmol), and HOAt (247 mg, 1.817 mmol) were dissolved in 15 mL of DMF. NMM (0.798 mL, 7.27 mmol) was added, followed by EDC (348 mg, 1.817 mmol). After stirring overnight at room temperature, the reaction mixture was purified by RP-HPLC to provide {(2R)-2-(cyclopentylmethyl)-3-[2-(2,6-dichloro-5-fluoro-4-pyrimidinyl)hydrazino]-3-oxopropyl}[(phenylmethyl)oxy]formamide (442 mg, 50%). LCMS: (M+H)$^+$: 483.6.

Part G:

[(2R)-3-(2-{2-Chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl][(phenylmethyl)oxy]formamide {(2R)-2-(Cyclopentylmethyl)-3-[2-(2,6-dichloro-5-fluoro-4-pyrimidinyl)hydrazino]-3-oxopropyl}[(phenylmethyl)oxy]formamide (136 mg, 0.278 mmol) and 3-[(2S)-2-pyrrolidinylmethyl]-3H-[1,2,3]triazolo[4,5-d]pyrimidine (63 mg, 0.308 mmol) were dissolved in DMSO (5 mL), then DIEA (59 µL, 0.308 mmol) was added, and the solution was heated at 65° C. overnight. When the reaction was complete as determined by LCMS, the solution was concentrated in vacuo, and the resulting crude product was purified by RP-HPLC to provide [(2R)-3-(2-{2-chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl][(phenylmethyl)oxy]formamide (43 mg, 21%). LCMS: (M+H)$^+$: 651.6.

Part H:

[(2R)-3-(2-{2-Chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl]hydroxyformamide

[(2R)-3-(2-{2-Chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl]hydroxyformamide was prepared according to General Procedure E, Part D, utilizing [(2R)-3-(2-{2-chloro-5-fluoro-6-[(2S)-2-(3H-[1,2,3]triazolo[4,5-d]pyrimidin-3-ylmethyl)-1-pyrrolidinyl]-4-pyrimidinyl}hydrazino)-2-(cyclopentylmethyl)-3-oxopropyl][(phenylmethyl)oxy]formamide in place of [(2R)-3-(2-{2-chloro-5-fluoro-6-[(1-methylethyl)amino]-4-pyrimidinyl}hydrazino)-2-(cyclopentylmethyl)-3-oxopropyl][(phenylmethyl)oxy]formamide in Part D. LCMS: (M+H)$^+$: 562.2.

Example 275

((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide

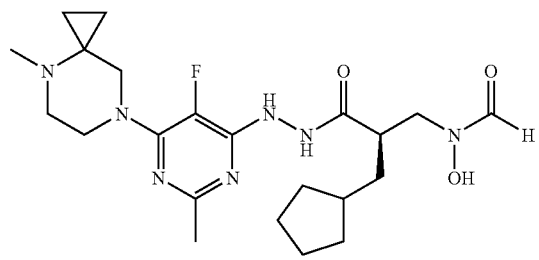

((2R)-2-(Cyclopentylmethyl)-3-{2-[5-fluoro-2-methyl-6-(4-methyl-4,7-diazaspiro[2.5]oct-7-yl)-4-pyrimidinyl]hydrazino}-3-oxopropyl)hydroxyformamide was prepared in a manner similar to Example 210, Part E and Part F, utilizing 4-methyl-4,7-diazaspiro[2.5]octane dihydrochloride (Example 172) in place of 1-{1-[(2S)-2-pyrrolidinyl]cyclopropyl}pyrrolidine hydrochloride in Part E. LCMS: (M+H)$^+$: 463.8.

Example 276

[(2R)-3-(2-{2-Chloro-6-[(2R)-2,4-dimethyl-1-piperazinyl]-5-fluoro-4-pyrimidinyl}hydrazino)-2-(cyclobutylmethyl)-3-oxopropyl]hydroxyformamide

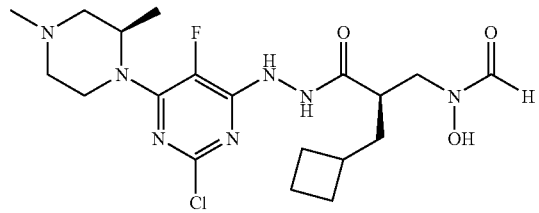

Part A:

(2R)-3-Cyclobutyl-2-({formyl[(phenylmethyl)oxy]amino}methyl)propanoic Acid (2R)-3-Cyclobutyl-2-({formyl[(phenylmethyl)oxy]amino}methyl)propanoic acid can be prepared in a manner similar to Intermediate A, utilizing bromomethyl cyclobutane in place of 3-cyclopentylpropionyl chloride in Part A.

Part B:

[(2R)-3-(2-{2-Chloro-6-[(2R)-2,4-dimethyl-1-piperazinyl]-5-fluoro-4-pyrimidinyl}hydrazino)-2-(cyclobutylmethyl)-3-oxopropyl]hydroxyformamide

[(2R)-3-(2-{2-Chloro-6-[(2R)-2,4-dimethyl-1-piperazinyl]-5-fluoro-4-pyrimidinyl}hydrazino)-2-(cyclobutylmethyl)-3-oxopropyl]hydroxyformamide was prepared in a manner similar to Example 63, utilizing (2R)-3-cyclobutyl-2-({formyl[(phenylmethyl)oxy]amino}methyl)propanoic acid in place of (2R)-3-cyclopentyl-2-({formyl[(phenylmethyl)oxy]amino}methyl)propanoic acid in Part F. LCMS: (M+H)$^+$: 457.6.

Example 277

[(2R)-3-(2-{2-Chloro-5-fluoro-6-[(9aS)-hexahydropyrazino[2,1-c][1,4]oxazin-8(1H)-yl]-4-pyrimidinyl}hydrazino)-2-(cyclobutylmethyl)-3-oxopropyl]hydroxyformamide

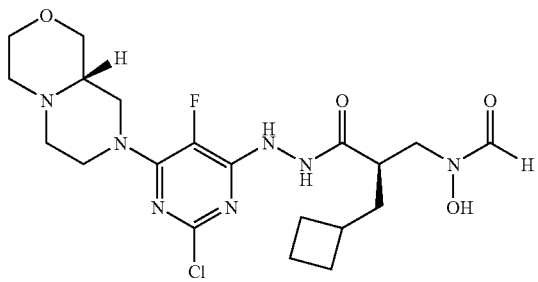

[(2R)-3-(2-{2-Chloro-5-fluoro-6-[(9aS)-hexahydropyrazino[2,1-c][1,4]oxazin-8(1H)-yl]-4-pyrimidinyl}hydrazino)-2-(cyclobutylmethyl)-3-oxopropyl]hydroxyformamide was prepared in a manner similar to Example 64, utilizing (2R)-3-cyclobutyl-2-({formyl[(phenylmethyl)oxy]amino}methyl)propanoic acid (Example 281) in place of (2R)-3-cyclopentyl-2-({formyl[(phenylmethyl)oxy]amino}methyl)propanoic acid in Part F. LCMS: (M+H)$^+$: 465.8.

Example 278

Methyl ((3S)-1-{2-chloro-6-[2-((2R)-3-cyclopentyl-2-{[formyl(hydroxy)amino]methyl}propanoyl)hydrazino]-5-fluoro-4-pyrimidinyl}-3-pyrrolidinyl)carbamate

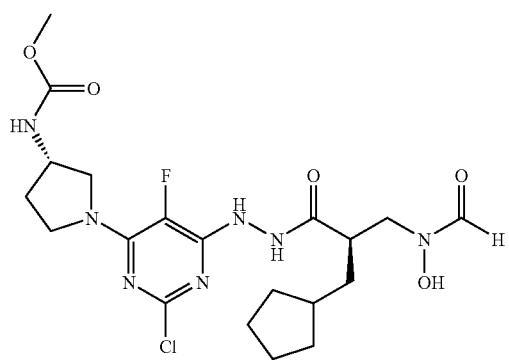

Part A:

Phenylmethyl (3S)-3-{[(methyloxy)carbonyl]amino}-1-pyrrolidinecarboxylate

Sodium bicarbonate (2.073 g, 24.68 mmol) was dissolved in a mixture of water (20.00 mL) and DCM (20 mL), and phenylmethyl (3S)-3-amino-1-pyrrolidinecarboxylate (2.88 g, 11.22 mmol) was added followed by methylchloroformate (0.953 mL, 12.34 mmol). This mixture was stirred for 6 h. The biphasic mixture was then separated, and the aqueous phase was extracted once with DCM. The combined organics were dried over sodium sulfate, filtered and evaporated. The residual material was then purified via silica gel chromatography (0-100% EtoAc in hexane) yielding phenylmethyl (3S)-3-{[(methyloxy)carbonyl]amino}-1-pyrrolidinecarboxylate (2 g, 64%) as a clear oil. LCMS: (M+H)$^+$: 278.9.

Part B:

Methyl (3S)-3-pyrrolidinylcarbamate

Phenylmethyl (3S)-3-{[(methyloxy)carbonyl]amino}-1-pyrrolidinecarboxylate (2.00 g, 7.19 mmol) was dissolved in degassed methanol (20 mL) and Pd/C (0.4 g, 0.376 mmol) was added. The reaction vessel was evacuated and back-filled with hydrogen via a balloon. The reaction was stirred for 2 h after which time the catalyst was removed by filtration through Celite. Evaporation of the solvent yielded methyl (3S)-3-pyrrolidinylcarbamate (0.99 g, 76%) as a clear oil.

Part C:

Methyl ((3S)-1-{2-chloro-6-[2-((2R)-3-cyclopentyl-2-{[formyl(hydroxy)amino]methyl}propanoyl)hydrazino]-5-fluoro-4-pyrimidinyl}-3-pyrrolidinyl)carbamate Methyl ((3S)-1-{2-chloro-6-[2-((2R)-3-cyclopentyl-2-{[formyl(hydroxy)amino]methyl}propanoyl)hydrazino]-5-fluoro-4-pyrimidinyl}-3-pyrrolidinyl)carbamate was prepared according to General Procedure E, utilizing methyl (3S)-3-pyrrolidinylcarbamate in place of isopropyl amine in Part A, and 2.0 M HCl in ether with DCM as a solvent in part B. LCMS: (M+H)$^+$: 502.2/504.1.

Example 279

[(2R)-3-(2-{2-Chloro-5-fluoro-6-[(2S)-2-(3H-[1,2,3]triazolo[4,5-b]pyridin-3-ylmethyl)-1-pyrrolidinyl]-4-pyrimidinyl}hydrazino)-2-(cyclopentylmethyl)-3-oxopropyl]hydroxyformamide

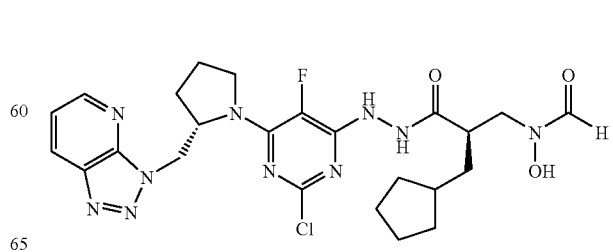

Part A:

3-[(2S)-2-Pyrrolidinylmethyl]-3H-[1,2,3]triazolo[4,5-b]pyridine

3-[(2S)-2-Pyrrolidinylmethyl]-3H-[1,2,3]triazolo[4,5-b]pyridine was prepared in a manner similar to Example 279, Part A through Part D, utilizing commercially-available 2-chloro-3-(dihydroxyamino)pyridine in place of 2,4-dichloro-5-(dihydroxyamino)pyrimidine in Part A. LCMS: (M+H)$^+$: 204.1.

Part B:

[(2R)-3-(2-{2-Chloro-5-fluoro-6-[(2S)-2-(3H-[1,2,3]triazolo[4,5-b]pyridin-3-ylmethyl)-1-pyrrolidinyl]-4-pyrimidinyl}hydrazino)-2-(cyclopentylmethyl)-3-oxopropyl]hydroxyformamide

[(2R)-3-(2-{2-Chloro-5-fluoro-6-[(2S)-2-(3H-[1,2,3]triazolo[4,5-b]pyridin-3-ylmethyl)-1-pyrrolidinyl]-4-pyrimidinyl}hydrazino)-2-(cyclopentylmethyl)-3-oxopropyl]hydroxyformamide was prepared according to General Procedure E, utilizing 3-[(2S)-2-pyrrolidinylmethyl]-3H-[1,2,3]triazolo[4,5-b]pyridine in place of isopropyl amine in Part A. LCMS: (M+H)$^+$: 561.2.

Example 280

[(2R)-3-[2-(2-Chloro-5-fluoro-6-{[2-(2-furanyl)ethyl]amino}-4-pyrimidinyl)hydrazino]-2-(cyclopentylmethyl)-3-oxopropyl]hydroxyformamide

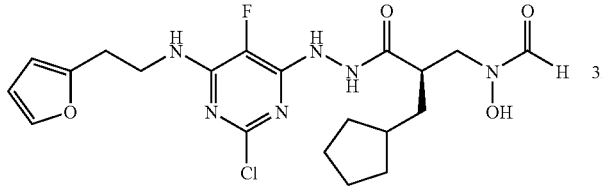

[(2R)-3-[2-(2-Chloro-5-fluoro-6-{[2-(2-furanyl)ethyl]amino}-4-pyrimidinyl)hydrazino]-2-(cyclopentylmethyl)-3-oxopropyl]hydroxyformamide was prepared according to General Procedure E, utilizing [2-(2-furanyl)ethyl]amine (WO9611210, 1996) in place of isopropyl amine in Part A, and 2.0 M HCl in ether with DCM as a solvent in Part B. LCMS: (M+H)$^+$: 469.2/471.1.

Example 281

[(2R)-3-[2-(2-Chloro-5-fluoro-6-{[2-(3-furanyl)ethyl]amino}-4-pyrimidinyl)hydrazino]-2-(cyclopentylmethyl)-3-oxopropyl]hydroxyformamide

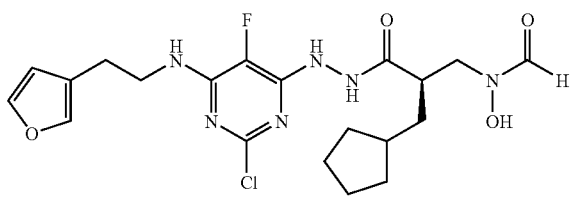

[(2R)-3-[2-(2-Chloro-5-fluoro-6-{[2-(3-furanyl)ethyl]amino}-4-pyrimidinyl)hydrazino]-2-(cyclopentylmethyl)-3-oxopropyl]hydroxyformamide was prepared according to General Procedure E, utilizing [2-(3-furanyl)ethyl]amine (WO9611210, 1996) in place of isopropyl amine in Part A, and 2.0 M HCl in ether with DCM as a solvent in Part B. LCMS: (M+H)$^+$: 469.2/471.1.

Polymorph Examples

Example 1P

Polymorphic Form 1 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide Form 1 was prepared by following the general procedure of Example 24, Part L, alternative procedure.

Alternative Procedure

Ethyl Acetate (0.5 mL) was added to crystalline [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (Form 1, 30.8 mg). The resulting slurry was temperature-cycled from 0-40° C. 16 times over ~48 hours. The solid in the slurry was the ethyl acetate solvate at this point. The resulting solids and supernatant were separated by filtration at room temperature. The solids were vacuum dried under ambient laboratory conditions for one hour, which desolvates the solvate to Form 1.

Example 2P

Polymorphic Form 2 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide 5.3 mg of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (Form 1) was slurried in 500 uL of water. The sample was mildly heated with a heat gun to increase solubility, but solid never completely dissolved. The solids were vacuum dried under ambient laboratory conditions and the resulting solid was analytically characterized and found to be Form 2.

Alternative Procedure

A reactor was charged with [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (Form 1, 1.0 eq) and water (20 vol). The suspension was stirred at T=20° C. over ~60 hours. The suspension was filtered and washed twice with 2.5 vol water. The material was dried under reduced pressure at T=60° C. and it was milled (Quadro Comil, stainless steel, mesh size: 1 mm). [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide Form 2 was obtained as a white solid.

Example 3P

Polymorphic Form 3 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide 1-propanol (0.5 mL) was added to crystalline [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide (Form 1, 30.8 mg). The resulting slurry was temperature-cycled from 0-40° C. 16 times over ~48 hours. The resulting solids and supernatant were separated by filtration at room temperature. The solids were vacuum dried under ambient laboratory conditions for one hour. The resulting solid was analytically characterized and found to be Form 3.

Analysis of Polymorphic Forms of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide Form 1 and Form 2 were analyzed by FT-IR, FT-Raman, XRPD, DSC, and TGA. Form 3 was analyzed by FT-Raman, XRPD, DSC, and TGA. Samples used for analyses were prepared by methods standard in the art and under ambient conditions. Generally 1-5 mg of dry Form 1, Form 2, or Form 3 was placed on the instrument/sample holder. The following instruments and parameters were used.

FT-IR

Instrument: Thermo Magna MidIR System

Key Operating Parameters:
  Number of sample scans: 64
  Resolution: 4.000 $cm^{-1}$
  Levels of zero filling: 2
  Apodization: Happ-Genzel
  Phase correction: Mertz
  Number of background scans: 64
  Detector: DTGS
  Beamsplitter: KBr
  Sampling Accessory Thermo Smart DuraScope ATR, diamond ATR element FT-Raman Instrument: Thermo FT-Raman System 960 Spectrometer Key Operating Parameters:
  Detector: Liquid Nitrogen-Cooled Germanium
  Beamsplitter: CaF2
  Sample scans: 64
  Resolution: 4.0 $cm^{-1}$
  Levels of zero filling: 2
  Apodization: Happ-Genzel
  Phase Correction Power spectrum
  Raman laser frequency: 9393.6416 $cm^{-1}$

XRPD

Instrument: Bruker AXS PXRD General Area Detector Diffraction System

Key Operating Parameters:
  Scan range: 3-42 degrees two-theta
  Generator power: 40 kV, 40 mA
  Radiation Source Cu Ka
  Scan type: Coupled scan
  Number of frames: 3 frames
  Time per frame: 5 min
  Sample Oscillation: 0.1-0.5 mm oscillation depending on sample size
  Detector Distance: 25 cm
  Filter/monochrometer: Single Goebel Mirror
  Detector Type General Area Detector Diffraction Thermal Analysis Instrument: TA Instruments Thermal Analysis System, Model DSC Q100

Key Operating Parameters:
  Module—DSC Standard Cell FC
  Method—Ramp
  Pan: Closed aluminum
  Purge gas: N2, 40 mL/min
  Cell# FC-00615
  Method
    1: Equilibrate at 30.00° C.
    2: Ramp 15.00° C./min to 350.00° C.

Instrument: TA Instruments Thermal Analysis System, Model TGA Q500

Key Operating Parameters:
  Method—Ramp
  Purge gas: N2, 40 mL/min
  Balance gas: N2, 40 mL/min
  Method 1: Ramp 15.00° C./min to 300.00° C.

What is claimed is:

1. [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide of formula

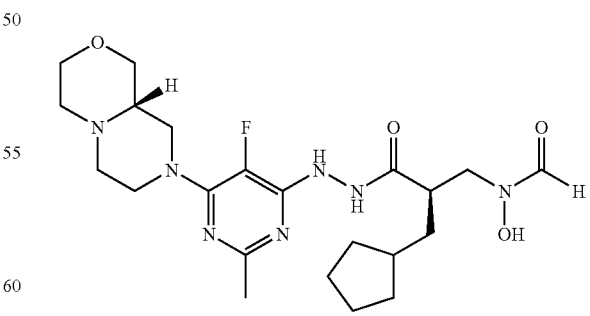

or a salt thereof.

2. [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide of formula

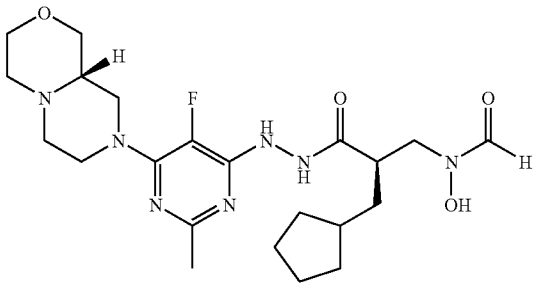

or a pharmaceutically acceptable salt thereof.

3. A pharmaceutical composition comprising [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide, or a pharmaceutically acceptable salt thereof, and a pharmaceutically acceptable excipient.

4. The pharmaceutical composition according to claim 3 formulated for oral administration.

5. The pharmaceutical composition according to claim 4 formulated as a tablet.

6. The pharmaceutical composition according to claim 4 formulated as a liquid.

7. The pharmaceutical composition according to claim 3 formulated for parenteral administration.

8. A method for the treatment of a bacterial infection in humans comprising administration of an effective amount of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide, or a pharmaceutically acceptable salt thereof, to a human in need thereof.

9. The method according to claim 8 wherein the bacterial infection is caused by *Streptococcus, Staphylococcus, Moraxella, Haemophilus, Neisseria, Mycoplasma, Legionella, Chlamydia, Bacteroides, Clostridium, Fusobacterium, Propionibacterium,* or *Peptostreptococcus*.

10. The method according to claim 8 wherein the bacterial infection is an ear infection, sinusitis, upper respiratory tract infection, lower respiratory tract infection, genital infection, skin and soft tissue infection, or bacterial endocarditis.

11. The method according to claim 10 wherein the bacterial infection is an upper respiratory tract infection.

12. The method according to claim 10 wherein the bacterial infection is a lower respiratory tract infection.

13. A method according to claim 10 wherein the bacterial infection is a skin and soft tissue infection.

14. [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide of formula

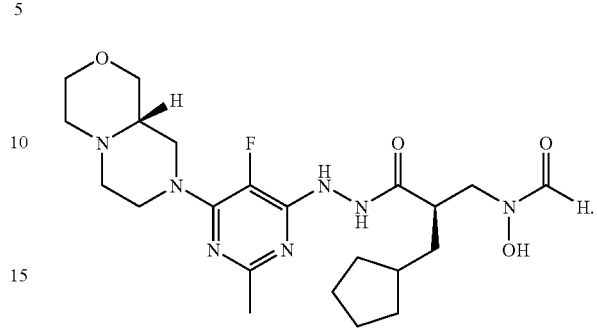

15. A pharmaceutical composition comprising [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide and a pharmaceutically acceptable excipient.

16. The pharmaceutical composition according to claim 15 formulated for oral administration.

17. The pharmaceutical composition according to claim 16 formulated as a tablet.

18. The pharmaceutical composition according to claim 16 formulated as a liquid.

19. The pharmaceutical composition according to claim 15 formulated for parenteral administration.

20. A method for the treatment of a bacterial infection in humans comprising administration of an effective amount of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide to a human in need thereof.

21. The method according to claim 20 wherein the bacterial infection is caused by *Streptococcus, Staphylococcus, Moraxella, Haemophilus, Neisseria, Mycoplasma, Legionella, Chlamydia, Bacteroides, Clostridium, Fusobacterium, Propionibacterium,* or *Peptostreptococcus*.

22. A method according to claim 20 wherein the bacterial infection is an ear infection, sinusitis, upper respiratory tract infection, lower respiratory tract infection, genital infection, skin and soft tissue infection, or bacterial endocarditis.

23. A method according to claim 22 wherein the bacterial infection is an upper respiratory tract infection.

24. A method according to claim 22 wherein the bacterial infection is a lower respiratory tract infection.

25. A method according to claim 22 wherein the bacterial infection is a skin and soft tissue infection.

26. A polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide substantially shown in at least one of the FT-IR spectrum of FIG. 1, FT-Raman spectrum of FIG. 3, X-ray powder diffraction pattern of FIG. 6, DSC thermogram of FIG. 9, and the TGA trace of FIG. 12.

27. The polymorphic form, Form 1, according to claim 26 which is of substantially pure crystalline form.

28. A polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, wherein:
  a. said X-ray diffraction pattern comprises a peak at 4.1+/−0.1°; or
  b. said X-ray diffraction pattern comprises a peak at 4.1+/−0.1° and 6.1+/−0.1°; or
  c. said X-ray diffraction pattern comprises a peak at 4.1+/−0.1°, 6.1+/−0.1°, and 6.9+/−0.1°; or
  d. said X-ray diffraction pattern comprises a peak at 4.1+/−0.1°, 6.1+/−0.1°, 6.9+/−0.1°, and 8.1+/−0.1°; or
  e. said X-ray diffraction pattern comprises a peak at 4.1+/−0.1°, 6.1+/−0.1°, 6.9+/−0.1°, 8.1+/−0.1°, and 9.5+/−0.1°; or
  f. said X-ray diffraction pattern comprises a peak at 4.1+/−0.1°, 6.1+/−0.1°, 6.9+/−0.1°, 8.1+/−0.1°, 9.5+/−0.1°, and 11.2+/−0.1°; or
  g. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, and 12.9+/−0.1°; or
  h. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, and 13.8+/−0.1°; or
  i. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, 13.8+/−0.1°, and 15.6+/−0.1°; or
  j. said X-ray diffraction pattern comprises a peak at 4.1+/−0.1°, 6.1+/−0.1°, 6.9+/−0.1°, 8.1+/−0.1°, 9.5+/−0.1°, 11.2+/−0.1°, 12.9+/−0.1°, 13.8+/−0.1°, 15.6+/−0.1°, and 18.3+/−0.1°.

29. A polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, at four or more positions selected from the group consisting of 4.1+/−0.1, 6.1+/−0.1, 6.9+/−0.1, 8.1+/−0.1, 9.5+/−0.1, 11.2+/−0.1, 12.9+/−0.1, 13.8+/−0.1, 15.6+/−0.1, and 18.3+/−0.1 degrees.

30. A pharmaceutical composition comprising polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide and a pharmaceutically acceptable excipient.

31. The pharmaceutical composition according to claim 30 formulated for oral administration.

32. The pharmaceutical composition according to claim 31 formulated as a tablet.

33. The pharmaceutical composition according to claim 31 formulated as a liquid.

34. The pharmaceutical composition according to claim 30 formulated for parenteral administration.

35. A method for the treatment of a bacterial infection in humans comprising administration of an effective amount of a polymorphic form, Form 1, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide to a human in need thereof.

36. The method according to claim 35 wherein the bacterial infection is caused by Streptococcus, Staphylococcus, Moraxella, Haemophilus, Neisseria, Mycoplasma, Legionella, Chlamydia, Bacteroides, Clostridium, Fusobacterium, Propionibacterium, or Peptostreptococcus.

37. The method according to claim 35 wherein the bacterial infection is an ear infection, sinusitis, upper respiratory tract infection, lower respiratory tract infection, genital infection, skin and soft tissue infection, or bacterial endocarditis.

38. The method according to claim 37 wherein the bacterial infection is an upper respiratory tract infection.

39. The method according to claim 37 wherein the bacterial infection is a lower respiratory tract infection.

40. The method according to claim 37 wherein the bacterial infection is a skin and soft tissue infection.

41. A polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide substantially shown in at least one of the FT-IR spectrum of FIG. 2, FT-Raman spectrum of FIG. 4, X-ray powder diffraction pattern of FIG. 7, DSC thermogram of FIG. 10, and the TGA trace of FIG. 13.

42. The polymorphic form, Form 2 according to claim 41 which is of substantially pure crystalline form.

43. A polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, wherein:
  k. said X-ray diffraction pattern comprises a peak at 7.8+/−0.1°; or
  l. said X-ray diffraction pattern comprises a peak at 7.8+/−0.1° and 9.5+/−0.1°; or
  m. said X-ray diffraction pattern comprises a peak at 7.8+/−0.1°, 9.5+/−0.1°, and 12.3+/−0.1°; or
  n. said X-ray diffraction pattern comprises a peak at 7.8+/−0.1°, 9.5+/−0.1°, 12.3+/−0.1°, and 13.2+/−0.1°; or
  o. said X-ray diffraction pattern comprises a peak at 7.8+/−0.1°, 9.5+/−0.1°, 12.3+/−0.1°, 13.2+/−0.1°, and 15.6+/−0.1°; or
  p. said X-ray diffraction pattern comprises a peak at 7.8+/−0.1°, 9.5+/−0.1°, 12.3+/−0.1°, 13.2+/−0.1°, 15.6+/−0.1°, and 18.3+/−0.1°; or
  q. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, and 19.0+/−0.1°; or
  r. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, and 20.6+/−0.1°; or
  s. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, and 21.4+/−0.1°; or
  t. said X-ray diffraction pattern comprises a peak at 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, 21.4+/−0.1°, and 26.7+/−0.1°.

44. A polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, at four or more positions selected from the group consisting of 7.8+/−0.1°, 9.5+/−0.1°, 12.3+/−0.1°, 13.2+/−0.1°, 15.6+/−0.1°, 18.3+/−0.1°, 19.0+/−0.1°, 20.6+/−0.1°, 21.4+/−0.1°, and 26.7+/−0.1°.

45. A pharmaceutical composition comprising polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide and a pharmaceutically acceptable excipient.

46. The pharmaceutical composition according to claim 45 formulated for oral administration.

47. The pharmaceutical composition according to claim 46 formulated as a tablet.

48. The pharmaceutical composition according to claim 46 formulated as a liquid.

49. The pharmaceutical composition according to claim 45 formulated for parenteral administration.

50. A method for the treatment of a bacterial infection in humans comprising administration of an effective amount of a polymorphic form, Form 2, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide to a human in need thereof.

51. The method according to claim 50 wherein the bacterial infection is caused by *Streptococcus, Staphylococcus, Moraxella, Haemophilus, Neisseria, Mycoplasma, Legionella, Chlamydia, Bacteroides, Clostridium, Fusobacterium, Propionibacterium*, or *Peptostreptococcus*.

52. The method according to claim 50 wherein the bacterial infection is an ear infection, sinusitis, upper respiratory tract infection, lower respiratory tract infection, genital infection, skin and soft tissue infection, or bacterial endocarditis.

53. The method according to claim 52 wherein the bacterial infection is an upper respiratory tract infection.

54. The method according to claim 52 wherein the bacterial infection is a lower respiratory tract infection.

55. The method according to claim 52 wherein the bacterial infection is a skin and soft tissue infection.

56. A polymorphic form, Form 3, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide substantially shown in at least one of the, FT-Raman spectrum of FIG. 5, X-ray powder diffraction pattern of FIG. 8, the DSC thermogram of FIG. 11, and the TGA trace of FIG. 14.

57. The polymorphic form, Form 3 according to claim 56 which is of substantially pure crystalline form.

58. A polymorphic form, Form 3, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, wherein:

a. said X-ray diffraction pattern comprises a peak at 6.1+/−0.1°; or b. said X-ray diffraction pattern comprises a peak at 6.1+/−0.1° and 7.5+/−0.1°; or c. said X-ray diffraction pattern comprises a peak at 6.1+/−0.1°, 7.5+/−0.1°, and 8.2+/−0.1°; or d. said X-ray diffraction pattern comprises a peak at 6.1+/−0.1°, 7.5+/−0.1°, 8.2+/−0.1°, and 9.1+/−0.1°; or e. said X-ray diffraction pattern comprises a peak at 6.1+/−0.1°, 7.5+/−0.1°, 8.2+/−0.1°, 9.1+/−0.1°, and 12.0+/−0.1°; or f. said X-ray diffraction pattern comprises a peak at 6.1+/−0.1°, 7.5+/−0.1°, 8.2+/−0.1°, 9.1+/−0.1°, 12.0+/−0.1°, and 12.8+/−0.1°; or g. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, and 13.4+/−0.1°; or h. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, and 16.0+/−0.1°; or i. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, and 23.3+/−0.1°; or j. said X-ray diffraction pattern comprises a peak at 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, 23.3+/−0.1°, and 27.6+/−0.1°.

59. A polymorphic form, Form 3 of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide wherein said polymorphic form is characterized by an X-ray diffraction pattern comprising peaks, expressed in terms of 2 theta angles, at four or more positions selected from the group consisting of 6.1+/−0.1°, 7.5+/−0.1°, 8.2+/−0.1°, 9.1+/−0.1°, 12.0+/−0.1°, 12.8+/−0.1°, 13.4+/−0.1°, 16.0+/−0.1°, 23.3+/−0.1°, and 27.6+/−0.1°.

60. A pharmaceutical composition comprising polymorphic form, Form 3, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide and a pharmaceutically acceptable excipient.

61. The pharmaceutical composition according to claim 60 formulated for oral administration.

62. The pharmaceutical composition according to claim 61 formulated as a tablet.

63. The pharmaceutical composition according to claim 61 formulated as a liquid.

64. The pharmaceutical composition according to claim 60 formulated for parenteral administration.

65. A method for the treatment of a bacterial infection in humans comprising administration of an effective amount of a polymorphic form, Form 3, of [(2R)-2-(Cyclopentylmethyl)-3-(2-{5-fluoro-6-[(9aS)-hexahydropyrazino[2,1-c][1,4]oxazin-8(1H)-yl]-2-methyl-4-pyrimidinyl}hydrazino)-3-oxopropyl]hydroxyformamide to a human in need thereof.

66. The method according to claim 64 wherein the bacterial infection is caused by *Streptococcus, Staphylococcus, Moraxella, Haemophilus, Neisseria, Mycoplasma, Legionella, Chlamydia, Bacteroides, Clostridium, Fusobacterium, Propionibacterium*, or *Peptostreptococcus*.

67. The method according to claim 65 wherein the bacterial infection is an ear infection, sinusitis, upper respiratory tract infection, lower respiratory tract infection, genital infection, skin and soft tissue infection, or bacterial endocarditis.

68. The method according to claim 67 wherein the bacterial infection is an upper respiratory tract infection.

69. The method according to claim 67 wherein the bacterial infection is a lower respiratory tract infection.

70. The method according to claim 67 wherein the bacterial infection is a skin and soft tissue infection.

* * * * *